US012415995B2

(12) United States Patent
Satchell et al.

(10) Patent No.: US 12,415,995 B2

(45) Date of Patent: Sep. 16, 2025

(54) BACTERIAL TOXINS AND USES THEREOF AS Ras SPECIFIC PROTEASES FOR TREATING CELL PROLIFERATION DISEASES AND DISORDERS

(71) Applicant: Northwestern University, Evanston, IL (US)

(72) Inventors: Karla J. F. Satchell, Evanston, IL (US); Irena Antic, Chicago, IL (US); Marco Biancucci, Chicago, IL (US)

(73) Assignee: Northwestern University, Evanston, IL (US)

( * ) Notice: Subject to any disclaimer, the term of this patent is extended or adjusted under 35 U.S.C. 154(b) by 560 days.

(21) Appl. No.: 17/746,952

(22) Filed: May 17, 2022

(65) Prior Publication Data

US 2023/0045284 A1 Feb. 9, 2023

Related U.S. Application Data

(63) Continuation-in-part of application No. 17/093,628, filed on Nov. 9, 2020, now abandoned, which is a continuation of application No. 15/957,396, filed on Apr. 19, 2018, now Pat. No. 10,829,752, and a continuation-in-part of application No. 14/816,724, filed on Aug. 3, 2015, now abandoned.

(60) Provisional application No. 62/487,217, filed on Apr. 19, 2017, provisional application No. 62/172,432, filed on Jun. 8, 2015, provisional application No. 62/032,330, filed on Aug. 1, 2014, provisional application No. 63/190,779, filed on May 19, 2021.

(51) Int. Cl.
*C12N 9/52* (2006.01)
*A61K 38/48* (2006.01)
*A61P 35/02* (2006.01)

(52) U.S. Cl.
CPC ................ *C12N 9/52* (2013.01); *A61K 38/48* (2013.01); *A61P 35/02* (2018.01); *A61K 2300/00* (2013.01); *C12Y 304/22* (2013.01)

(58) Field of Classification Search
CPC ...... C12N 9/52; A61K 38/48; A61K 2300/00; A61P 35/02; C12Y 304/22
See application file for complete search history.

(56) References Cited

U.S. PATENT DOCUMENTS

| | | | | |
|---|---|---|---|---|
| 4,897,355 | A | 1/1990 | Eppstein | |
| 4,946,787 | A | 8/1990 | Eppstein | |
| 5,049,386 | A | 9/1991 | Eppstein | |
| 5,599,665 | A | 2/1997 | Barbieri | |
| 7,396,664 | B2 | 7/2008 | Daly | |
| 8,257,946 | B2 | 9/2012 | Satchell | |
| 8,470,313 | B2 | 6/2013 | Guo | |
| 9,730,993 | B2 * | 8/2017 | Leysath ............ | A61K 47/6415 |

FOREIGN PATENT DOCUMENTS

| | | | |
|---|---|---|---|
| EP | 0877622 | B1 | 11/1998 |
| KR | 10-2004-0098202 | | 11/2004 |
| WO | 2008058944 | A1 | 5/2008 |

OTHER PUBLICATIONS

Janssen Research & Development (2019) First-in-Human Study of JNJ-74699157 in Participants With Tumors Harboring the KRAS G12C Mutation—Full Text View—ClinicalTrials.gov.

Jen, E. Y. et al., FDA Approval Summary: Tagraxofusp-erzs For Treatment of Blastic Plasmacytoid Dendritic Cell Neoplasm. Clinical cancer research: an official journal of the American Association for Cancer Research 26, 532-536 (2020).

Jiao, D, and Yang, S (2020). Overcoming Resistance to Drugs Targeting KRAS(G12C) Mutation. Innovation (N Y) 1.

Kerkhoff, E. and U.R. Rapp, Induction of cell proliferation in quiescent NIH 3T3 cells by oncogenic c-Raf-1. Mol Cell Biol, 1997. 17(5): p. 2576-86.

Kobrin, MS, Funatomi, H, Friess, H, Buchler, MW, Stathis, P, and Korc, M (1994). Induction and expression of heparin-binding EGF-like growth factor in human pancreatic cancer. Biochem Biophys Res Commun 202: 1705-1709.

Kreitman, RJ, and Pastan, I (2020). Development of Recombinant Immunotoxins for Hairy Cell Leukemia. Biomolecules 10.

Kwong, L.N., et al., Oncogenic NRAS signaling differentially regulates survival and proliferation in melanoma. Nat Med, 2012. 18(10): p. 1503-10.

Lanfredini, S, Thapa, A, and O'Neill, E (2019). RAS in pancreatic cancer. Biochemical Society transactions 47: 961-972.

Lim, S., et al., Exquisitely Specific anti-KRAS Biodegraders Inform on the Cellular Prevalence of Nucleotide-Loaded States. ACS Cent Sci, 2021. 7(2): p. 274-291.

Loftis, A.R., et al., Anthrax Protective Antigen Retargeted with Single-Chain Variable Fragments Delivers Enzymes to Pancreatic Cancer Cells. Chembiochem, 2020. 21(19): p. 2772-2776.

Mandell, J. W., Phosphorylation state-specific antibodies: applications in investigative and diagnostic pathology. The American journal of pathology 163, 1687-1698 (2003).

McCormick, F., KRAS as a Therapeutic Target. Clinical cancer research: an official journal of the American Association for Cancer Research 21, 1797-1801 (2015).

Metzger-Filho, O. et al., Dissecting the Heterogeneity of Triple-Negative Breast Cancer. 30, 1879-1887 (2012).

Miglio, U, Oldani, A, Mezzapelle, R, Veggiani, C, Paganotti, A, Garavoglia, M, et al. (2014). KRAS mutational analysis in ductal adenocarcinoma of the pancreas and its clinical significance. Pathol Res Pract 210: 307-311.

Mirati Therapeutics Inc. (2019) Phase 1/2 Study of MRTX849 in Patients With Cancer Having a KRAS G12C Mutation—Full Text View—https://clinicaltrials.gov/study/NCT03785249.

Mirati Therapeutics Inc. (2021). Phase 3 Study of MRTX849 With Cetuximab vs Chemotherapy in Patients With Advanced Colorectal Cancer With KRAS G12C Mutation (KRYSTAL-10)—Full Text View—ClinicalTrials.gov https://clinicaltrials.gov/ct2/show/NCT04793958.

(Continued)

*Primary Examiner* — Ganapathirama Raghu

(74) *Attorney, Agent, or Firm* — Quarles & Brady LLP

(57) ABSTRACT

Disclosed are bacterial toxins and uses thereof as specific proteases for Ras sarcoma oncoproteins (Ras proteins). The bacterial toxins may be modified for use as pharmaceutical agents for treating Ras-dependent diseases and disorders including cell proliferation diseases and disorders such as cancer.

6 Claims, 165 Drawing Sheets

Specification includes a Sequence Listing.

(56) References Cited

OTHER PUBLICATIONS

Mitamura, T., S. Higashiyama, N. Taniguchi, M. Klagsbrun, E. Mekada, Diphtheria toxin binds to the epidermal growth factor (EGF)-like domain of human heparin-binding EGF-like growth factor/diphtheria toxin receptor and inhibits specifically its mitogenic activity. The Journal of biological chemistry 270, 1015-1019 (1995).
Mokhlis, H. A. et al., The Modulatory Role of MicroRNA-873 in the Progression of KRAS-Driven Cancers. Mol Ther Nucleic Acids 14, 301-317 (2019).
N. Cancer Genome Atlas, Comprehensive molecular portraits of human breast tumours. Nature 490, 61-70 (2012).
Nam, S. O. et al., Anti-tumor Effect of Intravenous Administration of CRM197 for Triple-negative Breast Cancer Therapy. Anticancer Res 36, 3651-3657 (2016).
Neoptolemos, JP, Kleeff, J, Michl, P, Costello, E, Greenhalf, W, and Palmer, DH (2018). Therapeutic developments in pancreatic cancer: current and future perspectives. Nature reviews Gastroenterology & hepatology 15: 333-348.
Nevala-Plagemann, C, Hidalgo, M, and Garrido-Laguna, I (2020). From state-of-the-art treatments to novel therapies for advanced-stage pancreatic cancer. Nat Rev Clin Oncol 17: 108-123.
Novartis Pharmaceuticals (2021). Study of JDQ443 in Patients With Advanced Solid Tumors Harboring the KRAS G12C Mutation—Full Text View—ClinicalTrials.gov https://clinicaltrials.gov/ct2/show/NCT04699188.
O'Bryan, J. P., Pharmacological targeting of RAS: Recent success with direct inhibitors. Pharmacol Res 139, 503-511 (2019).
Ozdemir, BC, Pentcheva-Hoang, T, Carstens, JL, Zheng, X, Wu, CC, Simpson, TR, et al. (2014). Depletion of carcinoma-associated fibroblasts and fibrosis induces immunosuppression and accelerates pancreas cancer with reduced survival. Cancer cell 25: 719-734.
Palmiter, R., Interrogation by toxin. Nat Biotechnol 19, 731-732 (2001).
Papke, B., C. J. Der, Drugging RAS: Know the enemy. Science 355, 1158-1163 (2017).
Park, M. et al., Intracellular Delivery of Human Purine Nucleoside Phosphorylase by Engineered Diphtheria Toxin Rescues Function in Target Cells. Mol Pharm 15, 5217-5226 (2018).
Patel, RA, Forinash, KD, Pireddu, R, Sun, Y, Sun, N, Martin, MP, et al. (2012). RKI-1447 is a potent inhibitor of the Rho-associated ROCK kinases with anti-invasive and antitumor activities in breast cancer. Cancer research 72: 5025-5034.
Patricelli, M.P., et al., Selective Inhibition of Oncogenic KRAS Output with Small Molecules Targeting the Inactive State. Cancer Discov, 2016. 6(3): p. 316-29.
Pezzilli, R, Fabbri, D, and Imbrogno, A (2012). Pancreatic ductal adenocarcinoma screening: new perspectives. World J Gastroenterol 18: 4973-4977.
Prince, H. M. et al., Phase III placebo-controlled trial of denileukin diftitox for patients with cutaneous T-cell lymphoma. J Clin Oncol 28, 1870-1877 (2010).
Pruitt, K., R.G. Pestell, and C.J. Der, Ras inactivation of the retinoblastoma pathway by distinct mechanisms in NIH 3T3 fibroblast and RIE-1 epithelial cells. J Biol Chem, 2000. 275(52): p. 40916-24.
Ray, KC, Moss, ME, Franklin, JL, Weaver, CJ, Higginbotham, J, Song, Y, et al. (2014). Heparin-binding epidermal growth factor-like growth factor eliminates constraints on activated Kras to promote rapid onset of pancreatic neoplasia. Oncogene 33: 823-831.
Rhim, AD, Oberstein, PE, Thomas, DH, Mirek, ET, Palermo, CF, Sastra, SA, et al. (2014). Stromal elements act to restrain, rather than support, pancreatic ductal adenocarcinoma. Cancer cell 25: 735-747.
Romero-Calvo, I, Weber, CR, Ray, M, Brown, M, Kirby, K, Nandi, RK, et al. (2019). Human Organoids Share Structural and Genetic Features with Primary Pancreatic Adenocarcinoma Tumors. Mol Cancer Res 17: 70-83.
Ross, J. S. et al., Comprehensive genomic profiling of epithelial ovarian cancer by next generation sequencing-based diagnostic assay reveals new routes to targeted therapies. Gynecol Oncol 130, 554-559 (2013).
Roth, S., et al., Targeting Endogenous K-RAS for Degradation through the Affinity-Directed Protein Missile System. Cell Chem Biol, 2020. 27(9): p. 1151-1163 e6.
Satchell, K.J.F., Multifunctional-autoprocessing repeats-in-toxin (MARTX) Toxins of Vibrios. Microbiol Spectr, 2015. 3 (3).
Schiappacassi, M., et al., Role of T198 modification in the regulation of p27(Kip1) protein stability and function. PLoS One, 2011. 6(3): p. e17673.
Scholl, C. et al., Synthetic lethal interaction between oncogenic KRAS dependency and STK33 suppression in human cancer cells. Cell 137, 821-834 (2009).
Schreiber, M., et al., Comparison of the effectiveness of adenovirus vectors expressing cyclin kinase inhibitors p16INK4A, p18INK4C, p19INK4D, p21(WAF1/CIP1) and p27KIP1 in inducing cell cycle arrest, apoptosis and inhibition of tumorigenicity. Oncogene, 1999. 18(9): p. 1663-76.
Siegel, RL, Miller, KD, and Jemal, A (2020). Cancer statistics, 2020. CA Cancer J Clin 70: 7-30.
Simpson, LM, Macartney, TJ, Nardin, A, Fulcher, LJ, Roth, S, Testa, A, et al. (2020). Inducible Degradation of Target Proteins through a Tractable Affinity-Directed Protein Missile System. Cell Chem Biol 27: 1164-1180 e1165.
Singh, A, Greninger, P, Rhodes, D, Koopman, L, Violette, S, Bardeesy, N, et al. (2009). A gene expression signature associated with "K-Ras addiction" reveals regulators of EMT and tumor cell survival. Cancer cell 15: 489-500.
Skoulidis, F, Li, BT, Dy, GK, Price, TJ, Falchook, GS, Wolf, J, et al. (2021). Sotorasib for Lung Cancers with KRAS p. G12C Mutation. New England Journal of Medicine.
Solit, D.B., et al., BRAF mutation predicts sensitivity to MEK inhibition. Nature, 2006. 439(7074): p. 358-62.
Stubbs, CK, Biancucci, M, Vidimar, V, and Satchell, KJF (2021). RAS specific protease induces irreversible growth arrest via p27 in several KRAS mutant colorectal cancer cell lines. Sci Rep 11: 17925.
Teng, KW, Tsai, ST, Hattori, T, Fedele, C, Koide, A, Yang, C, et al. (2021). Selective and noncovalent targeting of RAS mutants for inhibition and degradation. Nat Commun 12: 2656.
U.S. Food and Drug Administration (2021). FDA grants accelerated approval to sotorasib for KRAS G12C mutated NSCLC. fda.gov/drugs/drug-approvals-and-databases/fda-grants-accelerated-approval-sotorasib-kras-g12c-mutated- nsclc.
Ganesan AK, Vincent TS, Olson JC, Barbieri JT: Pseudomonas aeruginosa exoenzyme S disrupts Ras-mediated signal transduction by inhibiting guanine nucleotide exchange factor-catalyzed nucleotide exchange. The Journal of biological chemistry 1999, 274(31):21823-21829.
Ganesan, A. K. et al. Pseudomonas aeruginosa exoenzyme S, a double ADPribosyltransferase, resembles vertebrate mono-ADP-ribosyltransferases. J. Biol. Chem. 274, 9503-9508 (1999).
Geissler B, Ahrens S, Satchell KJ: Plasma membrane association of three classes of bacterial toxins is mediated by a basic-hydrophobic motif. Cellular microbiology 2012, 14(2):286-298.
Geissler B, Bonebrake A, Sheahan KL, Walker ME, Satchell KJ. Genetic determination of essential residues of the Vibrio cholerae actin cross-linking domain reveals functional similarity with glutamine synthetases. Molecular microbiology 2009;73(5):858-868.
Geissler B, Tungekar R, Satchell KJ. Identification of a conserved membrane localization domain within numerous large bacterial protein toxins. Proceedings of the National Academy of Sciences of the United States of America 2010;107(12):5581-5586.
Genth, H. & Just, I. Functional implications of lethal toxin-catalysed glucosylation of (H/K/N)Ras and Rac1 in Clostridium sordellii-associated disease. Eur. J. Cell Biol. 90, 959-965 (2011).
Grdisa, M., "The Delivery of Biologically Active (Therapeutic) Peptides and Proteins into Cells," Cell-penetrating peptides (CPPS), Current Medicinal Chemistry, 2011. vol. 18.
Guttenberg G, Hornei S, Jank T, Schwan C, Lu W, Einsle O, Papatheodorou P, Aktories K: Molecular characteristics of Clostridium

(56) References Cited

OTHER PUBLICATIONS perfringens TpeL toxin and consequences of mono-O-GlcNAcylation of Ras in living cells. The Journal of biological chemistry 2012, 287(30):24929-24940.
Hamer, P. J et al. Production and characterization of anti-RAS p21 monoclonal antibodies. Hybridoma 9, 573-587 (1990).
Hoffman, R. V. and Kim, H. O. J. Org. Chem., 1995, 60, 5107.
International Preliminary Report on Patentability for PCT/US2015/043439 dated Feb. 16, 2017.
International Search Report for PCT/US2015/043439 dated Nov. 26, 2015.
Jank, T., Giesemann, T. & Aktories, K. Clostridium difficile glucosyltransferase toxin B-essential amino acids for substrate binding. J. Biol. Chem. 282, 35222-35231 (2007).
Jank, T., Pack, U., Giesemann, T., Schmidt, G. & Aktories, K. Exchange of a single amino acid switches the substrate properties of RhoA and RhoD toward glucosylating and transglutaminating toxins. J. Biol. Chem. 281, 19527-19535 (2006).
Jeong HG, Satchell KJ: Additive function of Vibrio vulnificus MARTX(Vv) and VvhA cytolysins promotes rapid growth and epithelial tissue necrosis during intestinal infection. PLoS pathogens 2012, 8(3):e1002581.
Just I, Selzer J, Hofmann F, Green GA, Aktories K: Inactivation of Ras by Clostridium sordellii lethal toxin-catalyzed glucosylation. The Journal of biological chemistry 1996, 271(17):10149-10153.
Just, I. et al. Glucosylation of Rho proteins by Clostridium difficile toxin B. Nature 375, 500-503 (1995).
Kamitani S, Kitadokoro K, Miyazawa M, Toshima H, Fukui A, Abe H, Miyake M, Horiguchi Y: Characterization of the membrane-targeting C1 domain in Pasteurella multocida toxin. The Journal of biological chemistry 2010, 285 (33):25467-25475.
Kashimoto, T. et al. Vibrio vulnificus detected in the spleen leads to fatal outcome in a mouse oral infection model. FEMS Microbiol. Lett. 362, fnv005 (2015).
Khvalevsky, E. Z. et al. Mutant KRAS is a druggable target for pancreatic cancer. Proc. Natl Acad. Sci. USA 110, 20723-20728 (2013).
Kim YR, et al., Vibrio vulnificus RTX toxin kills host cells only after contact of the bacteria with host cells. Cellular microbiology 2008, 10(4):848-862.
Kitadokoro K, et al., Crystal structures reveal a thiol protease-like catalytic triad in the C-terminal region of Pasteurella multocida toxin. Proceedings of the National Academy of Sciences of the United States of America 2007, 104(12):5139-5144.
Krogsgaard, Larsen, Liljefors and Madsen "Drug Design and Development", Chapter 14, (Eds) 1996, Norwood Acad. Pub.
Kudryashov DS, et al. Connecting actin monomers by isopeptide bond is a toxicity mechanism of the Vibrio cholerae MARTX toxin. Proceedings of the National Academy of Sciences of the United States of America 2008; 105(47): 18537-18542.
Kudryashova E, Heisler D, Zywiec A, Kudryashov DS: Thermodynamic properties of the effector domains of MARTX toxins suggest their unfolding for translocation across the host membrane. Molecular microbiology 2014.
Kurzawa et al., "PEP and CADY-mediated delivery of fluorescent peptides and proteins into living cells," Biochimica et a Biophysica Acta (BBA)—Biomembranes vol. 1798, Issue 12, Dec. 2010 2274-2285.
Kwak JS, Jeong HG, Satchell KJ: Vibrio vulnificus rtxA1 gene recombination generates toxin variants with altered potency during intestinal infection. Proceedings of the National Academy of Sciences of the United States of America 2011, 108(4):1645-1650.
Lavielle, S. et al., Int. J. Peptide Protein Res., 1993, 42, 270.
Lee, J. H. et al. Identification and characterization of the Vibrio vulnificus rtxA essential for cytotoxicity in vitro and virulence in mice. J. Microbiol. 45, 146-152 (2007).
Lemichez, E. & Aktories, K. Hijacking of Rho GTPases during bacterial infection. Exp. Cell. Res. 319, 2329-2336 (2013).
Liu, M., Alice, A. F., Naka, H. & Crosa, J. H. The HlyU protein is a positive regulator of rtxA1, a gene responsible for cytotoxicity and virulence in the human pathogen Vibrio vulnificus. Infect. Immun. 75, 3282-3289 (2007).
Lo, H. R. et al. RTX toxin enhances the survival of Vibrio vulnificus during infection by protecting the organism from phagocytosis. J. Infect. Dis. 203, 1866-1874 (2011).
Luisi, G. et al. Tetrahedron Lett. 1993, 34, 2391.
Makkerh et al. (1996) Curr Biol 6(8):1025-1027.
Malumbres M, Barbacid M: RAS oncogenes: the first 30 years. Nature reviews Cancer 2003, 3(6):459-465.
Maresso AW, Baldwin MR, Barbieri JT: Ezrin/radixin/moesin proteins are high affinity targets for ADP-ribosylation by Pseudomonas aeruginosa ExoS. The Journal of biological chemistry 2004, 279(37):38402-38408.
Maresso, A. W., Deng, Q., Pereckas, M. S., Wakim, B. T. & Barbieri, J. T. Pseudomonas aeruginosa ExoS ADP-ribosyltransferase inhibits ERM phosphorylation. Cell Microbiol. 9, 97-105 (2007).
Mattoo S, Durrant E, Chen MJ, Xiao J, Lazar CS, Manning G, Dixon JE, Worby CA: Comparative analysis of Histophilus somni immunoglobulin-binding protein A (lbpA) with other fic domain-containing enzymes reveals differences in substrate and nucleotide specificities. The Journal of biological chemistry 2011, 286(37):32834-32842.
McCluskey, A. J., Olive, A. J., Starnbach, M. N. & Collier, R. J. Targeting HER2-positive cancer cells with receptor-redirected anthrax protective antigen. Mol. Oncol. 7, 440-451 (2013).
Mechaly, A., McCluskey, A. J. & Collier, R. J. Changing the receptor specificity of anthrax toxin. mBio 3, e00088-12 (2012).
Mendoza, et al., The Ras-ERK and PI3K-mTOR pathways: cross-talk and compensation. Trends Biol. Sci. 36, 320-328 (2011).
Moon, E. Y. & Pyo, S. Lipopolysaccharide stimulates Epac1-mediated Rap1/NFkappaB pathway in Raw 264.7 murine macrophages. Immunol. Lett. 110, 121-125 (2007).
Morris et al., "A Peptide Carrier for the Delivery of Biologically Active Proteins into Mammalian Cells: Application to the Delivery of Antibodies and Therapeutic Proteins," Cell Biology, vol. 204, Part 20A, Chapter 2, 2006.
Nagahama M, Ohkubo A, Oda M, Kobayashi K, Amimoto K, Miyamoto K, Sakurai J: Clostridium perfringens TpeL glycosylates the Rac and Ras subfamily proteins. Infection and immunity 2011, 79(2):905-910.
Okada, T. et al. The strength of interaction at the Raf cysteine-rich domain is a critical determinant of response of Raf to Ras family small GTPases. Mol. Cell. Biol. 19, 6057-6064 (1999).
Orth JH, Fester I, Siegert P, Weise M, Lanner U, Kamitani S, Tachibana T, Wilson BA, Schlosser A, Horiguchi Y, Aktories K. Substrate specificity of Pasteurella multocida toxin for alpha subunits of heterotrimeric G proteins. FASEB J 2013;27(2):832-842.
Orth JH, Preuss I, Fester I, Schlosser A, Wilson BA, Aktories K: Pasteurella multocida toxin activation of heterotrimeric G proteins by deamidation. Proceedings of the National Academy of Sciences of the United States of America 2009, 106(17):179-7184.
Ostrem, J. M., Peters, U., Sos, M. L., Wells, J. A. & Shokat, K. M. K-Ras(G12C) inhibitors allosterically control GTP affinity and effector interactions. Nature 503, 548-551 (2013).
Pai, E. F. et al. Refined crystal-structure of the triphosphate conformation of H-Ras P21 at 1.35 a resolution-implications for the mechanism of GTP hydrolysis. EMBO J. 9, 2351-2359 (1990).
Pauillac, S. et al. Characterization of the enzymatic activity of Clostridium perfringens TpeL. Toxicon 75, 136-143 (2013).
Popoff, M. R. et al. Ras, Rap, and Rac small GTP-binding proteins are targets for Clostridium sordellii lethal toxin glucosylation. J. Biol. Chem. 271, 10217-10224 (1996).
Potala et al., Targeted therapy of cancer using diptheria toxin-derived immunotoxins. Drug Discovery, 2008, vol. 13 (17/18): 807-815. (Year: 2008).
Prior, I. A., Lewis, P. D. & Mattos, C. A comprehensive survey of Ras mutations in cancer. Cancer Res. 72, 2457-2467 (2012).
Prochazkova K, Satchell KJ: Structure-function analysis of inositol hexakisphosphate-induced autoprocessing of the Vibrio cholerae multifunctional autoprocessing RTX toxin. The Journal of biological chemistry 2008, 283 (35):23656-23664.

(56) References Cited

OTHER PUBLICATIONS

Prochazkova K, Shuvalova LA, Minasov G, Voburka Z, Anderson WF, Satchell KJ: Structural and molecular mechanism for autoprocessing of MARTX toxin of Vibrio cholerae at multiple sites. The Journal of biological chemistry 2009, 284(39):26557-26568.
Puck, T. T. & Marcus, P. I. A rapid method for viable cell titration and clone production with Hela cells in tissue culture—the use of X-irradiated cells to supply conditioning factors. Proc. Natl Acad. Sci. USA 41, 432-437 (1955).
Pullinger GD, Sowdhamini R, Lax AJ. Localization of functional domains of the mitogenic toxin of Pasteurella multocida. Infect Immun 2001;69(12):7839-7850.
Raaijmakers, J. H. & Bos, J. L. Specificity in Ras and Rap signaling. J. Biol. Chem. 284, 10995-10999 (2009).
Rangel, S. M., Logan, L. K. & Hauser, A. R. The ADP-ribosyltransferase domain of the effector protein ExoS inhibits phagocytosis of Pseudomonas aeruginosa during pneumonia. mBio 5, e01080-e01014 (2014).
Riese, M. J., Wittinghofer, A. & Barbieri, J. T. ADP ribosylation of Arg41 of Rap by ExoS inhibits the ability of Rap to interact with its guanine nucleotide exchange factor, C3G. Biochemistry 40, 3289-3294 (2001).
Roig F.J. G-C, F. and Amaro C. : Domain organization and evolution of multifunctional autoprocessing repeats-in-toxin (MARTX) toxin in Vibrio vulnificus. Appl Environ Microbiol 2011, 77:657-668.
Rubinfeld, H. & Seger, R. The ERK cascade: a prototype of MAPK signaling. Mol. Biotechnol. 31, 151-174 (2005).
Russo, M., Di Nicolantonio, F. & Bardelli, A. Climbing RAS, the everest of oncogenes. Cancer Discov. 4, 19-21 (2014).
Sali A, Potterton L, Yuan F, van Vlijmen H, Karplus M. Evaluation of comparative protein modeling by MODELLER. Proteins 1995;23(3):318-326.
Sanchez-Pulido L, Ponting C: Tiki, at the head of a new superfamily of enzymes. Bioinformatics 2013;29(19):2371-2374.
Santos, E. et al. Malignant activation of a K-ras oncogene in lung carcinoma but not in normal tissue of the same patient. Science 223, 661-664 (1984).
Sasaki, Y and Abe, J. Chem. Pharm. Bull. 1997 45, 13.
Satchell KJ:MARTX, multifunctional autoprocessing repeats-in-toxin toxins. Infection and immunity 2007, 75 (11):5079-5084.
Satchell KH:Structure and function of MARTX toxins and other large repetitive RTX proteins. Annual review of microbiology 2011, 65:71-90.
Schmidt, R. et al., Int. J. Peptide Protein Res., 1995, 46,47.
Schubbert et al., "Hyperactive Ras in developmental disorders and cancer," Nature Reviews Cancer 7, 295-308 (Jan. 2007).
Seffernick et al., Melamine deaminase and Atrazine chlorohydrolase: 98 percent identical but functionally different. J. Bacteriol., 2001, vol. 183 (8): 2405-2410. (Year: 2001).
Seger, R. & Krebs, E. G. The MAPK signaling cascade. Faseb J. 9, 726-735 (1995).
Sen et al., Developments in directed evolution for improving enzyme functions. Appl. Biochem. Biotechnol., 2007, vol. 143: 212-223. (Year: 2007).
Sen'Kova et al., "Ribonuclease binase decreases destructive changes of the liver and restores its regeneration potential in mouse lung carcinoma model," Biochimie, Jun. 2014, 101:256-259.
Shapira A, Benhar I: Toxin-based therapeutic approaches. Toxins 2010, 2(11):2519-2583.
Sheahan KL, Cordero CL, Satchell KJ. Identification of a domain within the multifunctional Vibrio cholerae RTX toxin that covalently cross-links actin. Proc Natl Acad Sci USA 2004; 101(26):9798-9803.
Sheahan KL, Satchell KJ: Inactivation of small Rho GTPases by the multifunctional RTX toxin from Vibrio cholerae. Cellular microbiology 2007, 9(5):1324-1335.
Shen A, Lupardus PJ, Albrow VE, Guzzetta A, Powers JC, Garcia KC, Bogyo M. Mechanistic and structural insights into the proteolytic activation of Vibrio cholera MARTX toxin. Nat Chem Biol 2009;5(7):469-478.
Sherman D. B. and Spatola, A. F. J. Am. Chem. Soc., 1990, 112, 433.
Shima, F. et al. In silico discovery of small-molecule Ras inhibitors that display antitumor activity by blocking the Ras-effector interaction. Proc. Natl Acad. Sci. USA 110, 8182-8187 (2013).
Shimizu K, Goldfarb M, Perucho M, Wigler M: Isolation and preliminary characterization of the transforming gene of a human neuroblastoma cell line. Proceedings of the National Academy of Sciences of the United States of America 1983, 80(2):383-387.
Simon NC, Barbieri JT: Exoenzyme S ADP-ribosylates Rab5 effector sites to uncouple intracellular trafficking. Infection and immunity 2014, 82(1):21-28.
Simon, N. C., Aktories, K. & Barbieri, J. T. Novel bacterial ADP-ribosylating toxins: structure and function. Nat. Rev. Microbiol. 12, 599-611 (2014).
Soding J, Biegert A, Lupas AN. The HHpred interactive server for protein homology detection and structure prediction. Nucleic acids research 2005;33(Web Server issue):W244-248.
Spatola, A. F., Methods Neurosci, 1993, 13, 19.
Spoemer, M., Herrmann, C., Vetter, I. R., Kalbitzer, H. R. & Wittinghofer, A. Dynamic properties of the Ras switch I region and its importance for binding to effectors. Proc. Natl Acad. Sci. USA 98, 4944-4949 (2001).
Spyres L, Qa'Dan M, Meader A, Tomasek J, Howeard E, Ballard J: Cytosolic delivery and characterization of the TcdB glycosylating domain by using a heterologous fusion protein. Infection and Immunity 2001; 69(1)599-601.
Steelman LS, Franklin RA, Abrams SL, Chappell W, Kempf CR, Basecke J, Stivala F, Donia M, Fagone P, Nicoletti F et al: Roles of the Ras/Raf/MEK/ERK pathway in leukemia therapy. Leukemia 2011, 25(7):1080-1094.
Stols L, Gu M, Dieckman L, Raffen R, Collart FR, Donnelly MI: A new vector for high-throughput, ligation-independent cloning encoding a tobacco etch virus protease cleavage site. Protein expression and purification 2002, 25(1):8-15.
Tatusova, Tatiana A., Thomas L. Madden (1999), "Blast 2 sequences—a new tool for comparing protein and nucleotide sequences", FEMS Microbiol Lett. 174:247-250.
Thiaville, P. C. et al. Genotype is correlated with but does not predict virulence of Vibrio vulnificus biotype 1 in subcutaneously inoculated, iron dextrantreated mice. Infect. Immun. 79, 1194-1207 (2011).
Torchilin, "Intracellular deliver of protein and peptide therapeutics," Drug Discovery Today: Technologies, Protein Therapeutics, 2009.
U.S. Appl. No. 62/032,330, filed Aug. 1, 2014.
Van Dessel, N. et al. Potent and tumor specific: arming bacteria with therapeutic proteins. Ther. Deliv. 6, 385-399 (2015).
Vidimar et al., "Inhibtion of tumor growth by a novel engineered chimeric toxin that cleaves activated mutant and wild-type RAS," bioRxiv, Dec. 18, 2019).
Vogelstein, B. et al. Cancer genome landscapes. Science 339, 1546-1558 (2013).
Von Moltke J, Trinidad NJ, Moayeri M, Kintzer AF, Wang SB, van Rooijen N, Brown CR, Krantz BA, Leppla SH, Gronert K, Vance RE: Rapid induction of inflammatory lipid mediators by the inflammasome in vivo. Nature 2012;490 (7418)107-11.
Walev et al., "Delivery of proteins into living cells by reversible membrane permeabilization with steptolysin-O," PNAS, Mar. 13, 2001, vol. 98, No. 6, 3185-3190.
Weill et al., "A practical approach for intracellular protein delivery," Cytotechnology. Jan. 20089; 56(1) 41-48.
Wesche J, Elliott JL, Falnes PO, Olsnes S, Collier RJ. Characterization of membrane translocation by anthrax protective antigen. Biochemistry 1998;37(45):15737-15746.
Whisstock et al., Prediction of protein function from protein sequence. Q. Rev. Biophysics., 2003, vol. 36 (3): 307-340. (Year: 2003).
Wilkinson P, et al., Comparative genomics of the emerging human pathogen Photorhabdus asymbiotica with the insect pathogen Photorhabdus luminescens. BMC Genomics 2009;10:302.
Willhite, D. C. & Blanke, S. R. Soluble expression and one-step purification of recombinant Bacillus anthracis protective antigen. Protein Peptide Lett. 5, 273-278 (1998).

(56) References Cited

OTHER PUBLICATIONS

Witkowski et al., Conversion of b-ketoacyl synthase to a Malonyl Decarboxylase by replacement of the active cysteine with glutamine. Biochemistry, 1999, vol. 38: 11643-11650. (Year: 1999).
Written Opinion for PCT/US2015/043439 dated Nov. 26, 2015.
Young, A., Lou, D. & McCormick, F. Oncogenic and wild-type Ras play divergent roles in the regulation of mitogen-activated protein kinase signaling. Cancer Discov. 3, 112-123 (2013).
Zeiser J, Gerhard R, Just I, Pich A: Substrate specificity of clostridial glucosylating toxins and their function on colonocytes analyzed by proteomics techniques. Journal of Proteomics Research 2013, 12(4)1604-1608.
Ziolo KJ, Jeong HG, Kwak JS, Yang S, Lavker RM, Satchell KJ: Vibrio vulnificus biotype 3 multifunctional autoprocessing RTX toxin is an adenylate cyclase toxin essential for virulence in mice. Infection and immunity 2014, 82 (5):2148-2157.
Adeyinka, A. et al., Activated mitogen-activated protein kinase expression during human breast tumorigenesis and breast cancer progression. Clinical cancer research: an official journal of the American Association for Cancer Research 8, 1747-1753 (2002).
Ahmed, D. et al., Epigenetic and genetic features of 24 colon cancer cell lines. Oncogenesis 2, e71 (2013).
Alexander, K. and P. W. Hinds, Requirement for p27(KIP1) in retinoblastoma protein-mediated senescence. Mol Cell Biol, 2001. 21(11): p. 3616-31.
Amgen (2019) A Phase 1/2, Study Evaluating the Safety, Tolerability, PK, and Efficacy of AMG 510 in Subjects With Solid Tumors With a Specific KRAS Mutation.https://clinicaltrials.gov/study/NCT03600883.
Amgen, FDA Approves LUMAKRAS (Sotorasib), The First And Only Targeted Treatment For patients With KRAS G12C-Mutated Locally Advanced Or Metastatic Non-Small Cell Lung Cancer. 2021.
Antic, I., et al., Site-specific processing of Ras and Rap1 Switch I by a MARTX toxin effector domain. Nat Commun, 2015. 6: p. 7396.
Apte, MV, Pirola, RC, and Wilson, JS (2012). Pancreatic stellate cells: a starring role in normal and diseased pancreas. Front Physiol 3: 344.
Auger, A. et al., Efficient Delivery of Structurally Diverse Protein Cargo into Mammalian Cells by a Bacterial Toxin. Mol Pharm 12, 2962-2971 (2015).
Bernard, V, Fleming, J, and Maitra, A (2016). Molecular and Genetic Basis of Pancreatic Carcinogenesis: Which Concepts May be Clinically Relevant? Surg Oncol Clin N Am 25: 227-238.
Bery, N., A. Miller, and T. Rabbitts, A potent KRAS macromolecule degrader specifically targeting tumours with mutant KRAS. Nat Commun, 2020. 11(1): p. 3233.
Biancucci, M. et al., Substrate Recognition of MARTX Ras/Rap1-Specific Endopeptidase. Biochemistry 56, 2747-2757 (2017).
Bond, M.J., et al., Targeted Degradation of Oncogenic KRAS(G12C) by VHL-Recruiting PROTACs. ACS Cent Sci, 2020. 6(8): p. 1367-1375.
Bos, J. L., H. Rehmann, A. Wittinghofer, GEFs and GAPs: critical elements in the control of small G proteins. Cell 129, 865-877 (2007).
Bos, J.L., J. de Rooij, and K.A. Reedquist, Rap1 signalling: adhering to new models. Nat Rev Mol Cell Biol, 2001. 2(5): p. 369-77.
Bos, J.L., Linking Rap to cell adhesion. Curr Opin Cell Biol, 2005. 17(2): p. 123-8.
Broude, E.V., et al., p21(Waf1/Cip1/Sdi1) mediates retinoblastoma protein degradation. Oncogene, 2007. 26(48): p. 6954-8.
Bryant, KL, Mancias, JD, Kimmelman, AC, and Der, CJ (2014). KRAS: feeding pancreatic cancer proliferation. Trends in biochemical sciences 39: 91-100.
Canon, J. et al., The clinical KRAS(G12C) inhibitor AMG 510 drives anti-tumour immunity. Nature 575, 217-223 (2019).
Cha, J. H., M. Y. Chang, J. A. Richardson, L. Eidels, Transgenic mice expressing the diphtheria toxin receptor are sensitive to the toxin. Mol Microbiol 49, 235-240 (2003).
Chabner, B.A., NCI-60 Cell Line Screening: A Radical Departure in its Time. J Natl Cancer Inst, 2016. 108(5).
Chen, J., et al., Tumor suppression and inhibition of aneuploid cell accumulation in human brain tumor cells by ectopic overexpression of the cyclin-dependent kinase inhibitor p27KIP1. J Clin Invest, 1996. 97(8): p. 1983-8.
Chen, Y., et al., Engineering subtilisin proteases that specifically degrade active RAS. Commun Biol, 2021. 4(1): p. 299.
Childs, B.G., et al., Senescence and apoptosis: dueling or complementary cell fates? EMBO Rep, 2014. 15(11): p. 1139-53.
Collins, M.A., et al., Metastatic pancreatic cancer is dependent on oncogenic Kras in mice. PLoS One, 2012. 7(12): p. e49707.
Crowe, AR, and Yue, W (2019). Semi-quantitative Determination of Protein Expression using Immunohistochemistry Staining and Analysis: An Integrated Protocol. Bio Protoc 9.
Dao, V.T., et al., Dynamic changes in Rap1 activity are required for cell retraction and spreading during mitosis. J Cell Sci, 2009. 122(Pt 16): p. 2996-3004.
Drosten, M., et al., Genetic analysis of Ras signalling pathways in cell proliferation, migration and survival. EMBO J, 2010. 29(6): p. 1091-104.
Dulak, A. M. et al., Gastrointestinal adenocarcinomas of the esophagus, stomach, and colon exhibit distinct patterns of genome instability and oncogenesis. Cancer research 72, 4383-4393 (2012).
Eckert, L. B. et al., Involvement of Ras activation in human breast cancer cell signaling, invasion, and anoikis. Cancer research 64, 4585-4592 (2004).
Ferlay, J. et al., Cancer incidence and mortality worldwide: sources, methods and major patterns in GLOBOCAN 2012. Int J Cancer 136, E359-386 (2015).
Ferreira, L. P., V. M. Gaspar, J. F. Mano, Design of spherically structured 3D in vitro tumor models—Advances and prospects. Acta Biomater 75, 11-34 (2018).
Fisher, G.H., et al., Induction and apoptotic regression of lung adenocarcinomas by regulation of a K-Ras transgene in the presence and absence of tumor suppressor genes. Genes Dev, 2001. 15(24): p. 3249-62.
Fleming, J. M., T. C. Miller, M. J. Meyer, E. Ginsburg, B. K. Vonderhaar, Local regulation of human breast xenograft models. J Cell Physiol 224, 795-806 (2010).
Gallolu Kankanamalage, S., A.S. Karra, and M.H. Cobb, WNK pathways in cancer signaling networks. Cell Commun Signal, 2018. 16(1): p. 72.
Garcia, PL, Miller, AL, and Yoon, KJ (2020). Patient-Derived Xenograft Models of Pancreatic Cancer: Overview and Comparison with Other Types of Models. Cancers (Basel) 12.
Gavin, H.E. and K.J.F. Satchell, RRSP and RID Effector Domains Dominate the Virulence Impact of Vibrio vulnificus MARTX Toxin. J Infect Dis, 2019. 219(6): p. 889-897.
Gavin, H.E., N.T. Beubier, and K.J. Satchell, The Effector Domain Region of the Vibrio vulnificus MARTX Toxin Confers Biphasic Epithelial Barrier Disruption and Is Essential for Systemic Spread from the Intestine. PLoS Pathog, 2017. 13(1): p. e1006119.
Genentech, I (2020). A Study to Evaluate the Safety, Pharmacokinetics, and Activity of GDC-6036 Alone or in Combination in Participants With Advanced or Metastatic Solid Tumors With a KRAS G12C Mutation—Full Text View—ClinicalTrials.gov https://clinicaltrials.gov/ct2/show/NCT04449874.
Giltnane, J. M., J. M. Balko, Rationale for targeting the Ras/MAPK pathway in triple-negative breast cancer. Discov Med 17, 275-283 (2014).
Goebel, L., et al., KRasG12C inhibitors in clinical trials: a short historical perspective. Rsc Medicinal Chemistry, 2020. 11(7): p. 760-770.
Hallin, J. et al., The KRASG12C Inhibitor, MRTX849, Provides Insight Toward Therapeutic Susceptibility of KRAS Mutant Cancers in Mouse Models and Patients. Cancer discovery 10.1158/2159-8290.CD-19-1167 (2019).
Hassan, S., A. Esch, T. Liby, J. W. Gray, L. M. Heiser, Pathway-Enriched Gene Signature Associated with 53BP1 Response to PARP Inhibition in Triple-Negative Breast Cancer. Molecular cancer therapeutics 16, 2892-2901 (2017).

(56) References Cited

OTHER PUBLICATIONS

Hengst, L. and S.I. Reed, Inhibitors of the Cip/Kip family. Curr Top Microbiol Immunol, 1998. 227: p. 25-41.
Hezel, AF, Kimmelman, AC, Stanger, BZ, Bardeesy, N, and Depinho, RA (2006). Genetics and biology of pancreatic ductal adenocarcinoma. Genes & development 20: 1218-1249.
Hoa, M., S. L. Davis, S. J. Ames, R. A. Spanjaard, Amplification of wild-type K-ras promotes growth of head and neck squamous cell carcinoma. Cancer research 62, 7154-7156 (2002).
Hobbs, G.A., C.J. Der, and K.L. Rossman, RAS isoforms and mutations in cancer at a glance. J Cell Sci, 2016. 129(7): p. 1287-92.
Hunter, J.C., et al., Biochemical and Structural Analysis of Common Cancer-Associated KRAS Mutations. Mol Cancer Res, 2015. 13(9): p. 1325-35.
Iovanna, J, Mallmann, MC, Goncalves, A, Turrini, O, and Dagorn, JC (2012). Current knowledge on pancreatic cancer. Front Oncol 2: 6.
Jain, R, Fischer, S, Serra, S, and Chetty, R (2010). The use of Cytokeratin 19 (CK19) immunohistochemistry in lesions of the pancreas, gastrointestinal tract, and liver. Appl Immunohistochem Mol Morphol 18: 9-15.
Janes, M. R. et al., Targeting KRAS Mutant Cancers with a Covalent G12C-Specific Inhibitor. Cell 172, 578-589 e517 (2018).
Ahrens S. et al: Identification of small Rho GTPases by the multifunctional RTX toxin from Vibrio cholerae. The Journal of biological chemistry 2013, 288:1397-1408.
Aktories, K. & Schmidt, G. in Ras Superfamily Small G Proteins: Biology and Mechanisms 1. (ed. Wittinghofer, A.) 65-97 (Springer-Verlag Wein, 2014).
Allmendinger, T. et al., Tetrahydron Lett., 1990, 31, 7297.
Altschul SF, Gish W, Miller W, Myers EW, Lipman DJ. Basic local alignment search tool. J Mol Biol 1990;215 (3):403-410.
Aminova LR, Luo S, Bannai Y, Ho M, Wilson BA. The C3 domain of Pasteurella multocida toxin is the minimal domain responsible for activation of Gq-dependent calcium and mitogenic signaling. Protein Sci 2008; 17(5):945-949.
Antic et al., "Site-specific processing of Ras and Rap1 Switch 1 by a MARTX toxin effector domain," Nature Comm. 6:7396, Jun. 8, 2015).
Antic et al., Cytotoxicity of the Vibrio vulnificus MARTX toxin effector DUF5 is linked to the C2A subdoamin. Proteins, 2014, vol. 82: 2643-2656. (Year: 2014).
Antic I., Identification and characterization of Ras and Rap 1A specific protease domain from Vibrio vulnificus MARTX toxin. A Dissertation, Northwestern Univ., PhD., Thesis, submitted Dec. 2014: 200 pages. (Year: 2014).
Antignani A, Fitzgerald D: Immunotoxins: the role of the toxin. Toxins 2013, 5(8):1486-1502.
Baines et al., "Inhibition of Ras for cancer treatment: the search continues," Future Med. Chem. Oct. 2011; 3(14): 1787-1808.
Baldwin MR, Lakey JH, Lax AJ. Identification and characterization of the Pasteurella multocida toxin translocation domain. Molecular microbiology 2004;54(1):239-250.
Ballard J, Doling A, Beauregard K, Collier R, Starnbach M: Anthrax toxin-mediated delivery in vivo and in vitro of a cytotoxic T-lymphocyte epitope from ovalbumin. Infection and Immunity 1998 66(2)615-619.
Bazan J, Macdonald B, He X: The TIKI/TraB/PrgY family: a common protease fold for cell signaling from bacteria to metazoa? Developmental Cell 2013;25(3):225-227.
Bell, J. & McFadden, G. Viruses for tumor therapy. Cell. Host Microbe 15, 260-265 (2014).
Biancucci et al., "The bacterial Ras/Rap1 site-specific endopeptidase cleaves Ras through an atypical mechanism to disrupt Ras-ERK signaling," Sci. Signa. 11, eaat8335 (2018) Oct. 2, 2018).
Bos, J. L., "Ras Oncogenes in Human Cancer: A Review," Cancer Research 49, 4682-4689, Sep. 1, 1989.
Brothers MC, Geissler B, Hisao GS, Wilson BA, Satchell KJ, Rienstra CM: Backbone and side-chain assignments of an effector membrane localization domain from Vibrio vulnificus MARTX toxin. Biomolecular NMR assignments 2013.
Brothers MC, Geissler B., Hisao G. S., Satchell K.J., Wilson B. A. and Rienstra C.M.: Backbone and side-chain resonance assignments of the membrane localization domain from Pasteurella multocida toxin. Biomolecular NMR assignments 2013.
Broun et al., Catalytic plasticity of fatty acid modification enzymes underlying chemical diversity of plant lipids. Science, 1998, vol. 282: 1315-1317. (Year: 1998).
Buhrman, G., Holzapfel, G., Fetics, S. & Mattos, C. Allosteric modulation of Ras positions Q61 for a direct role in catalysis. Proc. Natl Acad. Sci. USA 107, 4931-4936 (2010).
Burns, M. C. et al. Approach for targeting Ras with small molecules that activate SOS-mediated nucleotide exchange. Proc. Natl Acad. Sci. USA 111, 3401-3406 (2014).
Busch C, Orth J, Djouder N, Aktories K. Biological activity of a C-terminal fragment of Pasteurella multocida toxin. Infect Immun 2001;69(6):3628-3634.
Caron, E., Self, A. J. & Hall, A. The GTPase Rap1 controls functional activation of macrophage integrin alphaMbeta2 by LPS and other inflammatory mediators. Curr. Biol. 10, 974-978 (2000).
Chang F, Steelman LS, Lee JT, Shelton JG, Navolanic PM, Blalock WL, Franklin RA, McCubrey JA: Signal transduction mediated by the Ras/Raf/MEK/ERK pathway from cytokine receptors to transcription factors: potential targeting for therapeutic intervention. Leukemia 2003, 17(7):1263-1293.
Cherry, J. M. et al. *Saccharomyces* genome database: the genomics resource of budding yeast. Nucleic Acid Res. 40, D700-D705 (2012).
Chica et al., Semi-rational approaches to engineering enzyme activity: combining the benefits of directed evolution and rational design. Curr. Opi. Biotechnol., 2005, vol. 16: 378-384. (Year: 2005).
Chorev, M and Goodman, M., Acc. Chem. Res, 1993, 26, 266.
Chung KJ, Cho EJ, Kim MK, Kim YR, Kim SH, Yang HY, Chung KC, Lee SE, Rhee JH, Choy HE et al: RtxA1-induced expression of the small GTPase Rac2 plays a key role in the pathogenicity of Vibrio vulnificus. The Journal of infectious diseases 2010, 201(1):97-105.
Coburn, J. & Gill, D. M. ADP-ribosylation of p21ras and related proteins by Pseudomonas aeruginosa exoenzyme S. Infect. Immun. 59, 4259-4262 (1991).
Coburn, J., Dillon, S. T., Iglewski, B. H. & Gill, D. M. Exoenzyme S of Pseudomonas aeruginosa ADP-ribosylates the intermediate filament protein vimentin. Infect. Immun. 57, 996-998 (1989).
Cordero C, Kudryahov D, Reisler E, Satchell K: The actin crosslinking domain of the Vibrio cholerae RTX toxin directly catalyzes the covalent cross-linking of actin. The Journal of Biological Chemistry 2006; 283(43)32366-32374.
Cox, A. D. & Der, C. J. Ras history: the saga continues. Small GTPases 1, 2-27 (2010).
Cox, A. D., Fesik, S. W., Kimmelman, A. C., Luo, J. & Der, C. J. Drugging the undruggable RAS: Mission Possible? Nat. Rev. Drug Discov. 13, 828-851 (2014).
Cronican et al., "Naturally supercharged human proteins (NSHPs)," Chemistry & Biology 18, 833-838, Jul. 29, 2011.
Database NCBI: WP_011081430, Jun. 18, 2013.
David, M. D., Cochrane, C. L., Duncan, S. K. & Schrader, J. W. Pure lipopolysaccharide or synthetic lipid a induces activation of p21Ras in primary macrophages through a pathway dependent on Src family kinases and PI3K. J. Immunol. 175, 8236-8241 (2005).
Davies, H. et al. Mutations of the BRAF gene in human cancer. Nature 417, 949-954 (2002).
Devos et al., Practical limits of function prediction. Proteins: Structure, Function, and Genetics. 2000, vol. 41: 98-107. (Year: 2000).
Dolores, Analysis of Vibrio cholerae genome sequences reveals unique rtxA variants in environmental strains and an rtxA-null mutation in recent altered El Tor isolates. mBio 2013, 4:e00624-00612.
Downward J: Targeting Ras signalling pathways in cancer therapy. Nature reviews Cancer 2003, 3(1):11-22.

(56) References Cited

OTHER PUBLICATIONS

Dreger, S. C. et al. Killing of rat basophilic leukemia cells by lethal toxin from Clostridium sordellii: critical role of phosphatidylinositide 3'-OH kinase/Akt signaling. Biochemistry 48, 1785-1792 (2009).
Egerer M, Satchell KJ: Inositol hexakisphosphate-induced autoprocessing of large bacterial protein toxins. PLoS pathogens 2010, 6(7):e1000942.
Eisenberg, S. et al. The role of palmitoylation in regulating Ras localization and function. Biochem. Soc. Trans. 41, 79-83 (2013).
Fan JJ, Shao CP, Ho YC, Yu CK, Hor LI: Isolation and characterization of a Vibrio vulnificus mutant deficient in both extracellular metalloprotease and cytolysin. Infection and immunity 2001, 69(9):5943-5948.
Fernandez-Medarde et al., "Ras in Cancer and Developmental Diseases," Mar. 2011, vol. 2, No. 3: 344-358.
Ffrench-Constant R, Waterfield N, Dabom P, Joyce S, Bennett H, Au C, Dowling A, Boundy S, Reynolds S, Clarke D. Photorhabdus: towards a functional genomic analysis of a symbiont and pathogen. FEMS Microbiol Rev 2003;26(5):433-456.
Fraylick, J. E., Rucks, E. A., Greene, D. M., Vincent, T. S. & Olson, J. C. Eukaryotic cell determination of ExoS ADP-ribosyltransferase substrate specificity. Biochem. Biophys. Res. Commun. 291, 91-100 (2002).
Fuentes, et al., "Sravnitelnaya tsitotoksichnostbinazy po otnosheniu k opuxolevym i normalnym kletkam," Uchenye zapiski Kazanskogo universiteta, 2010, 152(3):143-148.
Fullner KJ, Mekalanos JJ. In vivo covalent crosslinking of actin by the RTX toxin of Vibrio cholerae. EMBO J 2000;19:5315-5323.
Futami et al. "Intracellular delivery of proteins into mammalian living cells by polyethylenimine-cationization," J Bioscience and Bioengineering, vol. 99, Iss 2, Feb. 2005 95-103.
Vidimar V, Park M, Stubbs CK, Ingram NK, Qiang W, Zhang S, Gursel D, Melnyk RA, Satchell KJF. Proteolytic pan-RAS Cleavage Leads to Tumor Regression in Patient-derived Pancreatic Cancer Xenografts. Mol Cancer Ther. May 4, 2022;21(5):810-820.
Vidimar, V. et al., The AKT/BCL-2 Axis Mediates Survival of Uterine Leiomyoma in a Novel 3D Spheroid Model. Endocrinology 159, 1453-1462 (2018).
Vidimar, V., et al., An engineered chimeric toxin that cleaves activated mutant and wild-type RAS inhibits tumor growth. Proc Natl Acad Sci U S A, 2020. 117(29): p. 16938-16948.
Vigil, D., et al., Ras superfamily GEFs and GAPs: validated and tractable targets for cancer therapy? Nat Rev Cancer, 2010. 10(12): p. 842-57.
Vitari, A.C., et al., WNK1, the kinase mutated in an inherited high-blood-pressure syndrome, is a novel PKB (protein kinase B)/Akt substrate. Biochem J, 2004. 378(Pt 1): p. 257-68.
Waddell, N, Pajic, M, Patch, AM, Chang, DK, Kassahn, KS, Bailey, P, et al. (2015). Whole genomes redefine the mutational landscape of pancreatic cancer. Nature 518: 495-501.
Wang, X., et al., The Photorhabdus Virulence Cassettes RRSP-Like Effector Interacts With Cyclin-Dependent Kinase 1 and Causes Mitotic Defects in Mammalian Cells. Front Microbiol, 2020. 11: p. 366.
Yeh, J.J., et al., KRAS/BRAF mutation status and ERK1/2 activation as biomarkers for MEK1/2 inhibitor therapy in colorectal cancer. Mol Cancer Ther, 2009. 8(4): p. 834-43.
Mng, H., et al., Oncogenic Kras maintains pancreatic tumors through regulation of anabolic glucose metabolism. Cell, 2012. 149(3): p. 656-70.
Zapata, M, Cohen, C, and Siddiqui, MT (2007). Immunohistochemical expression of SMAD4, CK19, and CA19-9 in fine needle aspiration samples of pancreatic adenocarcinoma: Utility and potential role. Cytojournal 4: 13.
Zhou, B., C. J. Der, A. D. Cox, The role of wild type RAS isoforms in cancer. Semin Cell Dev Biol 58, 60-69 (2016).

* cited by examiner

```
1    MTEYKLVVVG AGGVGKSALT IQLIQNHFVD EYDPTIEDSY RKQVVIDGET CLLDILDTAG
61   QEEYSAMRDQ YMRTGEGFLC VFAINNTKSF EDIHQYREQI KRVKDSDDVP MVLVGNKCDL
121  AARTVESRQA QDLARSYGIP YIETSAKTRQ GVEDAFYTLV REIRQHKLRK LNPPDESGPG
181  CMSCKCVLSN (SEQ ID NO:57)
```

FIG. 6B

H-RAS 17 S A L T I Q L I Q N H F V E D Y D P T I E D S Y R K (SEQ ID NO:57, amino acids 17-42)
K-RAS 17 S A L T I Q L I Q N H F V E D Y D P T I E D S Y R K (SEQ ID NO:57, amino acids 17-42)
N-RAS 17 S A L T I Q L I Q N H F V E D Y D P T I E D S Y R K (SEQ ID NO:57, amino acids 17-42)

32 ↓ 33

Cleavage site definted by Edman degradation

V. vulnificus MARTX
5206 a.a.
DUF1
RID
ABH
Mcf
DUF5
CPD
C1
C2A
C2B
P. multocida ToxA
1285 a.a.
C1/C2
C3
deamidase EGFP-positive cells rounded (%)
100
50
0
EGFP
DUF5Vv-EGFP
C1C2pm-EGFP EGFP
DUF5Vv-EGFP
C1C2pm-EGFP
85
60
25
EGFP fusion
EGFP DUF5-Vv – SEQ ID NO:1, amino acids 91-330
DUF5-Vs – SEQ ID NO:9, amino acids 91-331
DUF5-Ah – SEQ ID NO:15, amino acids 95-334
DUF5-Xn – SEQ ID NO:19, amino acids 103-342
Plu2400-Pl – SEQ ID NO:21, amino acids 149-388
DUF5-Yk – SEQ ID NO:25, amino acids 84-326
PMT – SEQ ID NO:27, amino acids 85-337

DUF5-Vv – SEQ ID NO:1, amino acids 331-500
DUF5-Vs – SEQ ID NO:9, amino acids 332-501
DUF5-Ah – SEQ ID NO:15, amino acids 335-504
DUF5-Xn – SEQ ID NO:19, amino acids 343-512
Plu2400-Pl – SEQ ID NO:21, amino acids 389-560
DUF5-Yk – SEQ ID NO:25, amino acids 327-492
PMT – SEQ ID NO:27, amino acids 338-510 hr
24
48

SEQ ID NO:57

FIG. 29A HeLa / 24 hr / 3 nM toxin
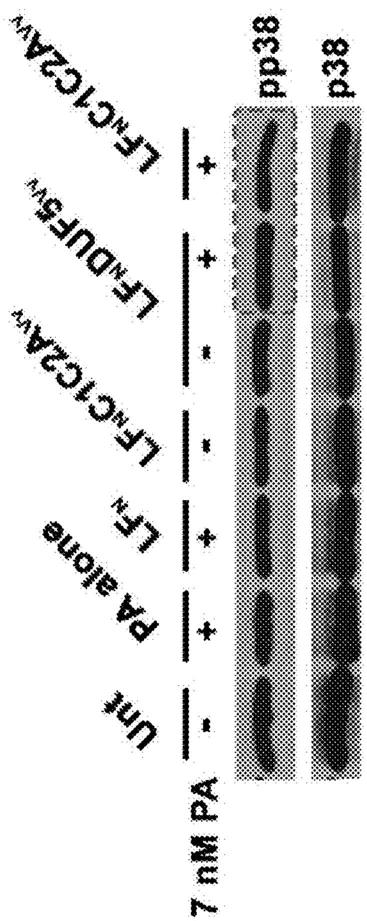
FIG. 29B HeLa / 24 hr / 3 nM toxin
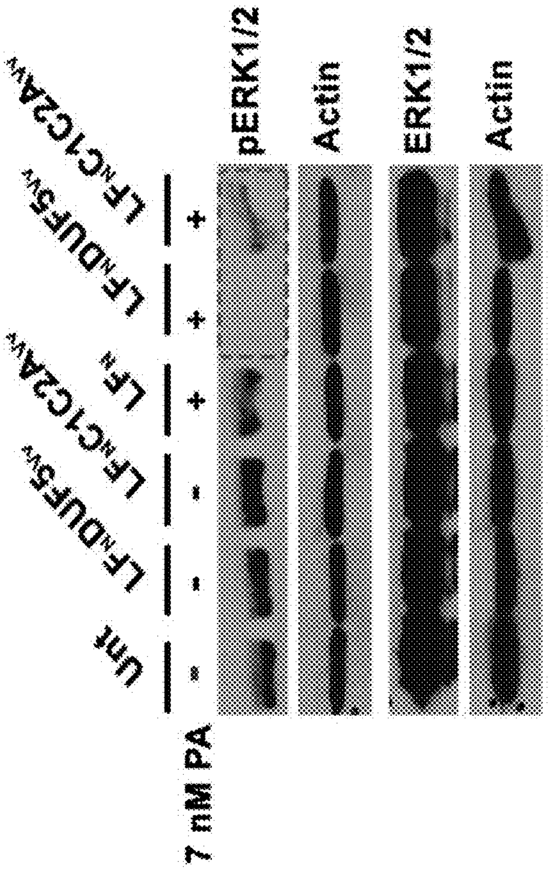

Raw data used for bar graph of EGFP-GTPase from Fig. 3e

| | EGFP | | HRas | | Rap1A | | Rit2 | |
|---|---|---|---|---|---|---|---|---|
| $LF_NDUF5_{Vv}$ | - | + | - | + | - | + | - | + |
| | 0 | 0 | 0 | 69.3 | 0 | 90.3 | 0 | 31.8 |
| | 0 | 0 | 23.6 | 95.2 | 0 | 100 | 0 | 86.7 |
| | 0 | 0 | 0 | 93.7 | 0 | 98.7 | 0 | 0 |
| | RalA | | RheB2A | | RhoB | | Arf1 | |
| $LF_NDUF5_{Vv}$ | - | + | - | + | - | + | - | + |
| | 33.6 | 52.3 | 10.4 | 12.1 | 0 | 0 | 0 | 0 |
| | 26 | 24.2 | 0 | 0 | 0 | 0 | 0 | 0 |
| | 0 | 6.1 | 0 | 0 | 0 | 0 | 0 | 0 |

FIG. 34A-C

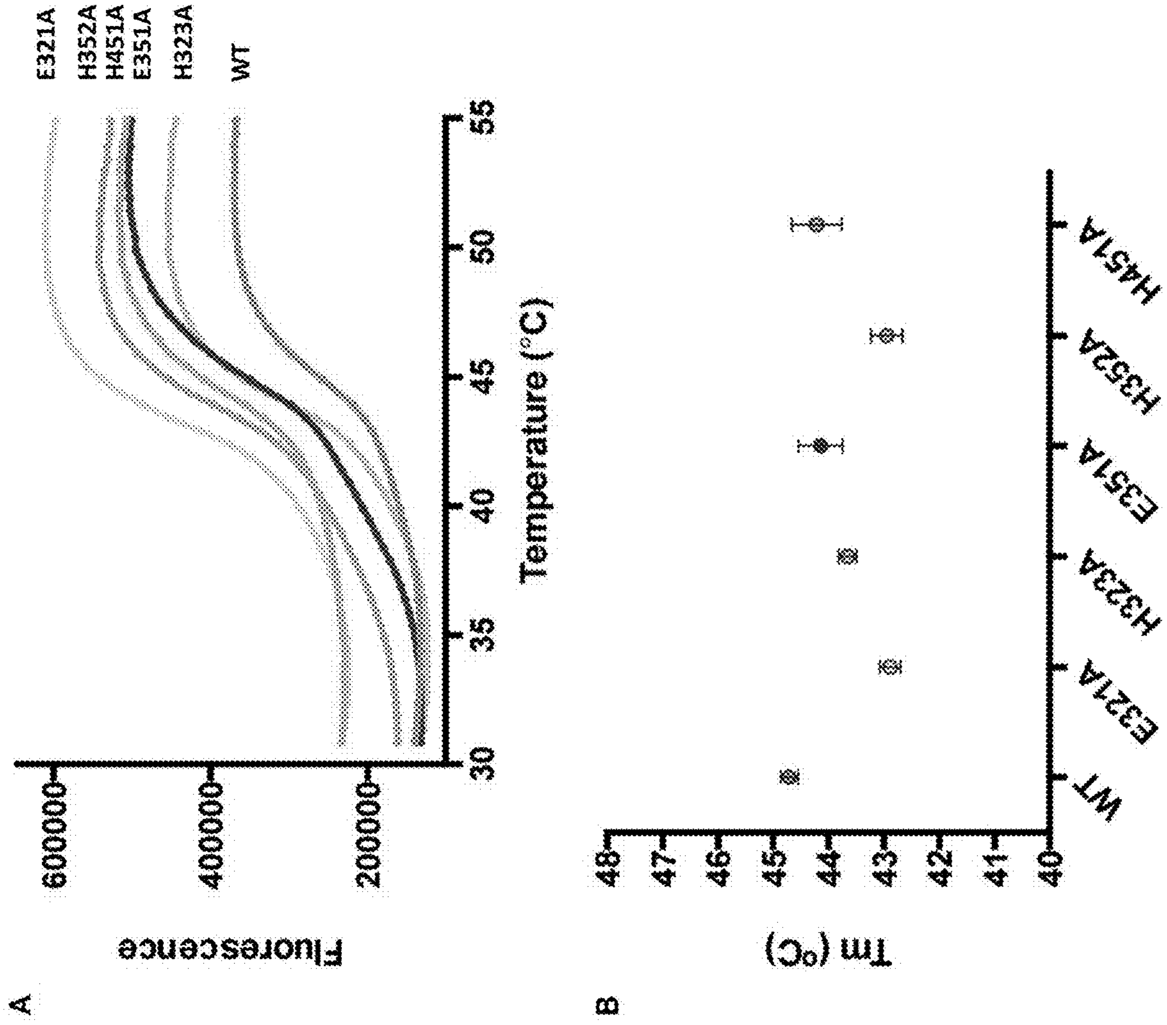
FIG. 41A-B

| Cell line | *KRAS* | $IC_{50}$ (nM) |
|---|---|---|
| **YAPC** | *G12V* | 0.03±0.01 |
| **SUIT-2** | *G12D* | 0.28±0.19 |
| **KP-1N** | *G12D* | 0.010±0.001 |
| **KP-4** | *G12D* | 0.03±0.01 |
| **PANC-1** | *G12D* | 0.04±0.01 |

| Cell line | *KRAS* | RRSP-DT$_B$ IC$_{50}$ (nM) |
|---|---|---|
| **YAPC** | *G12V* | 0.063±0.008 |
| **SUIT-2** | *G12D* | 0.181±0.023 |
| **KP-1N** | *G12D* | undefined |
| **KP-4** | *G12D* | undefined |
| **PANC-1** | *G12D* | undefined |

PDX2

E

H a

| Cell Line | KRAS Status |
|---|---|
| HCT-116 | $KRAS^{G13D/+}$ |
| SW1463 | $KRAS^{G12C/G12C}$ |
| SW620 | $KRAS^{G12V/G12V}$ |
| GP5d | $KRAS^{G12D/+}$ |

f a

FIG. 85A- 85G
a
| Cell Line | KRAS/RAF Status |
| --- | --- |
| BRAF-dependent MEFs | No RAS ; $BRAF^{V600E}$ |
| HT-29 | $KRAS^{+/+}$ ; $BRAF^{V600E/+}$ |
b
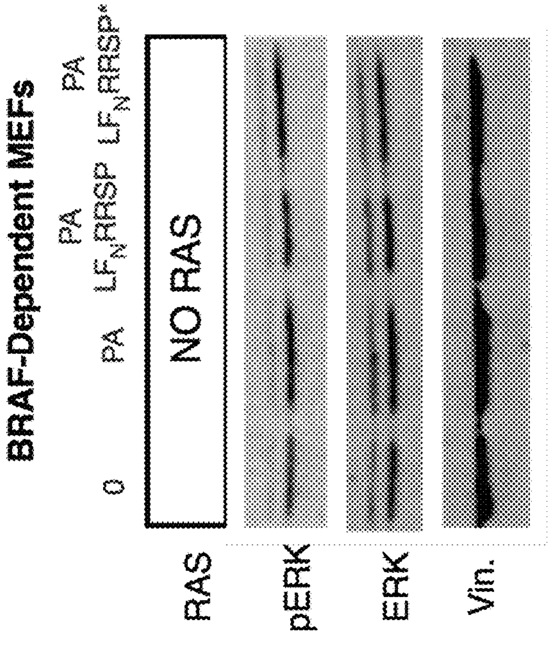
c
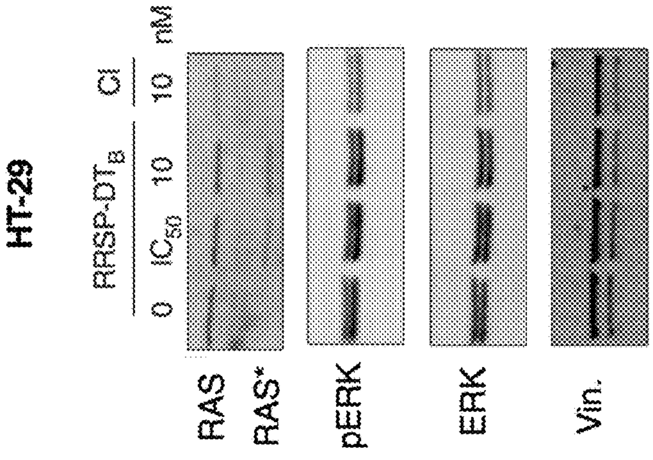

SEQUENCE LISTING

```
<160> NUMBER OF SEQ ID NOS: 73

<210> SEQ ID NO 1
<211> LENGTH: 510
<212> TYPE: PRT
<213> ORGANISM: Vibrio vulnificus

<400> SEQUENCE: 1

Gly Asp Lys Thr Lys Val Val Val Asp Leu Ala Gln Ile Phe Thr Val
1               5                   10                  15

Gln Glu Leu Lys Glu Arg Ala Lys Val Phe Ala Lys Pro Ile Gly Ala
            20                  25                  30

Ser Tyr Gln Gly Ile Leu Asp Gln Leu Asp Leu Val His Gln Ala Lys
        35                  40                  45

Gly Arg Asp Gln Ile Ala Ala Ser Phe Glu Leu Asn Lys Lys Ile Asn
    50                  55                  60

Asp Tyr Ile Ala Glu His Pro Thr Ser Gly Arg Asn Gln Ala Leu Thr
65                  70                  75                  80

Gln Leu Lys Glu Gln Val Thr Ser Ala Leu Phe Ile Gly Lys Met Gln
                85                  90                  95

Val Ala Gln Ala Gly Ile Asp Ala Ile Ala Gln Thr Arg Pro Glu Leu
            100                 105                 110

Ala Ala Arg Ile Phe Met Val Ala Ile Glu Glu Ala Asn Gly Lys His
        115                 120                 125

Val Gly Leu Thr Asp Met Met Val Arg Trp Ala Asn Glu Asp Pro Tyr
    130                 135                 140

Leu Ala Pro Lys His Gly Tyr Lys Gly Glu Thr Pro Ser Asp Leu Gly
145                 150                 155                 160

Phe Asp Ala Lys Tyr His Val Asp Leu Gly Glu His Tyr Ala Asp Phe
                165                 170                 175

Lys Gln Trp Leu Glu Thr Ser Gln Ser Asn Gly Leu Leu Ser Lys Ala
            180                 185                 190

Thr Leu Asp Glu Ser Thr Lys Thr Val His Leu Gly Tyr Ser Tyr Gln
        195                 200                 205
```

```
Glu Leu Gln Asp Leu Thr Gly Ala Glu Ser Val Gln Met Ala Phe Tyr
    210                 215                 220

Phe Leu Lys Glu Ala Ala Lys Lys Ala Asp Pro Ile Ser Gly Asp Ser
225                 230                 235                 240

Ala Glu Met Ile Leu Leu Lys Lys Phe Ala Asp Gln Ser Tyr Leu Ser
                245                 250                 255

Gln Leu Asp Ser Asp Arg Met Asp Gln Ile Glu Gly Ile Tyr Arg Ser
            260                 265                 270

Ser His Glu Thr Asp Ile Asp Ala Trp Asp Arg Arg Tyr Ser Gly Thr
        275                 280                 285

Gly Tyr Asp Glu Leu Thr Asn Lys Leu Ala Ser Ala Thr Gly Val Asp
    290                 295                 300

Glu Gln Leu Ala Val Leu Leu Asp Asp Arg Lys Gly Leu Leu Ile Gly
305                 310                 315                 320

Glu Val His Gly Ser Asp Val Asn Gly Leu Arg Phe Val Asn Glu Gln
                325                 330                 335

Met Asp Ala Leu Lys Lys Gln Gly Val Thr Val Ile Gly Leu Glu His
            340                 345                 350

Leu Arg Ser Asp Leu Ala Gln Pro Leu Ile Asp Arg Tyr Leu Ala Thr
        355                 360                 365

Gly Val Met Ser Ser Glu Leu Ser Ala Met Leu Lys Thr Lys His Leu
    370                 375                 380

Asp Val Thr Leu Phe Glu Asn Ala Arg Ala Asn Gly Met Arg Ile Val
385                 390                 395                 400

Ala Leu Asp Ala Asn Ser Ser Ala Arg Pro Asn Val Gln Gly Thr Glu
                405                 410                 415

His Gly Leu Met Tyr Arg Ala Gly Ala Ala Asn Asn Ile Ala Val Glu
            420                 425                 430

Val Leu Gln Asn Leu Pro Asp Gly Glu Lys Phe Val Ala Ile Tyr Gly
        435                 440                 445

Lys Ala His Leu Gln Ser His Lys Gly Ile Glu Gly Phe Val Pro Gly
    450                 455                 460

Ile Thr His Arg Leu Asp Leu Pro Ala Leu Lys Val Ser Asp Ser Asn
465                 470                 475                 480

Gln Phe Thr Val Glu Gln Asp Asp Val Ser Leu Arg Val Val Tyr Asp
                485                 490                 495

Asp Val Ala Asn Lys Pro Lys Ile Thr Phe Lys Gly Ser Leu
            500                 505                 510


<210> SEQ ID NO 2
<211> LENGTH: 186
<212> TYPE: PRT
<213> ORGANISM: Vibrio vulnificus

<400> SEQUENCE: 2

Phe Ile Gly Lys Met Gln Val Ala Gln Ala Gly Ile Asp Ala Ile Ala
1               5                   10                  15

Gln Thr Arg Pro Glu Leu Ala Ala Arg Ile Phe Met Val Ala Ile Glu
            20                  25                  30

Glu Ala Asn Gly Lys His Val Gly Leu Thr Asp Met Met Val Arg Trp
        35                  40                  45

Ala Asn Glu Asp Pro Tyr Leu Ala Pro Lys His Gly Tyr Lys Gly Glu
    50                  55                  60

Thr Pro Ser Asp Leu Gly Phe Asp Ala Lys Tyr His Val Asp Leu Gly
```

-continued

```
65                  70                  75                  80

Glu His Tyr Ala Asp Phe Lys Gln Trp Leu Glu Thr Ser Gln Ser Asn
                85                  90                  95

Gly Leu Leu Ser Lys Ala Thr Leu Asp Glu Ser Thr Lys Thr Val His
            100                 105                 110

Leu Gly Tyr Ser Tyr Gln Glu Leu Gln Asp Leu Thr Gly Ala Glu Ser
        115                 120                 125

Val Gln Met Ala Phe Tyr Phe Leu Lys Glu Ala Ala Lys Lys Ala Asp
    130                 135                 140

Pro Ile Ser Gly Asp Ser Ala Glu Met Ile Leu Leu Lys Lys Phe Ala
145                 150                 155                 160

Asp Gln Ser Tyr Leu Ser Gln Leu Asp Ser Asp Arg Met Asp Gln Ile
                165                 170                 175

Glu Gly Ile Tyr Arg Ser Ser His Glu Thr
            180                 185


<210> SEQ ID NO 3
<211> LENGTH: 510
<212> TYPE: PRT
<213> ORGANISM: Vibrio harveyi

<400> SEQUENCE: 3

Gly Asp Lys Thr Lys Val Val Val Asp Leu Ala Gln Ile Phe Thr Val
1               5                   10                  15

Gln Glu Leu Lys Glu Arg Ala Lys Val Phe Ala Lys Pro Ile Gly Ala
            20                  25                  30

Ser Tyr Gln Gly Ile Leu Asp Gln Leu Asp Leu Val His Gln Ala Lys
        35                  40                  45

Gly Arg Asp Gln Ile Ala Ala Ser Phe Glu Leu Asn Lys Lys Ile Asn
    50                  55                  60

Asp Tyr Ile Ala Glu His Pro Thr Ser Gly Arg Asn Gln Ala Leu Thr
65                  70                  75                  80

Gln Leu Lys Glu Gln Val Thr Ser Ala Leu Phe Ile Gly Lys Met Gln
                85                  90                  95

Val Ala Gln Ala Gly Ile Asp Ala Ile Ala Gln Thr Arg Pro Glu Leu
            100                 105                 110

Ala Ala Arg Ile Phe Met Val Ala Ile Glu Glu Ala Asn Gly Lys His
        115                 120                 125

Val Gly Leu Thr Asp Met Met Val Arg Trp Ala Asn Glu Asp Pro Tyr
    130                 135                 140

Leu Ala Pro Lys His Gly Tyr Lys Gly Glu Thr Pro Ser Asp Leu Gly
145                 150                 155                 160

Phe Asp Ala Lys Tyr His Val Asp Leu Gly Glu His Tyr Ala Asp Phe
                165                 170                 175

Lys Gln Trp Leu Glu Thr Ser Gln Ser Asn Gly Leu Leu Ser Lys Ala
            180                 185                 190

Thr Leu Asp Glu Ser Thr Lys Thr Val His Leu Gly Tyr Ser Tyr Gln
        195                 200                 205

Glu Leu Gln Asp Leu Thr Gly Ala Glu Ser Val Gln Met Ala Phe Tyr
    210                 215                 220

Phe Leu Lys Glu Ala Ala Lys Lys Ala Asp Pro Ile Ser Gly Asp Ser
225                 230                 235                 240

Val Glu Met Ile Leu Leu Lys Lys Phe Ala Asp Gln Ser Tyr Leu Ser
                245                 250                 255
```

```
Gln Leu Asp Ser Asp Arg Met Asp Gln Ile Glu Gly Ile Tyr Arg Ser
            260                 265                 270

Ser His Glu Thr Asp Ile Asp Ala Trp Asp Arg Arg Tyr Ser Gly Thr
        275                 280                 285

Gly Tyr Asp Glu Leu Thr Asn Lys Leu Ala Ser Ala Thr Gly Val Asp
    290                 295                 300

Glu Gln Leu Ala Val Leu Leu Asp Asp Arg Lys Gly Leu Leu Ile Gly
305                 310                 315                 320

Glu Val His Gly Ser Asp Val Asn Gly Leu Arg Phe Val Asn Glu Gln
                325                 330                 335

Met Asp Ala Leu Lys Lys Gln Gly Val Thr Val Ile Gly Leu Glu His
            340                 345                 350

Leu Arg Ser Asp Leu Ala Gln Pro Leu Ile Asp Arg Tyr Leu Ala Thr
        355                 360                 365

Gly Val Met Ser Ser Glu Leu Ser Ala Met Leu Lys Thr Lys His Leu
    370                 375                 380

Asp Val Thr Leu Phe Glu Asn Ala Arg Ala Asn Gly Met Arg Ile Val
385                 390                 395                 400

Ala Leu Asp Ala Asn Ser Ser Ala Arg Pro Asn Val Gln Gly Thr Glu
                405                 410                 415

His Gly Leu Met Tyr Arg Ala Gly Ala Ala Asn Asn Ile Ala Val Glu
            420                 425                 430

Val Leu Gln Asn Leu Pro Asp Gly Glu Lys Phe Val Ala Ile Tyr Gly
        435                 440                 445

Lys Ala His Leu Gln Ser His Lys Gly Ile Glu Gly Phe Val Pro Gly
    450                 455                 460

Ile Thr His Arg Leu Asp Leu Pro Ala Leu Lys Val Ser Asp Ser Asn
465                 470                 475                 480

Gln Phe Thr Val Glu Gln Asp Asp Val Ser Leu Arg Val Val Tyr Asp
                485                 490                 495

Asp Val Ala Asn Lys Pro Lys Ile Thr Phe Lys Asp Ser Leu
            500                 505                 510


<210> SEQ ID NO 4
<211> LENGTH: 186
<212> TYPE: PRT
<213> ORGANISM: Vibrio harveyi

<400> SEQUENCE: 4

Phe Ile Gly Lys Met Gln Val Ala Gln Ala Gly Ile Asp Ala Ile Ala
1               5                   10                  15

Gln Thr Arg Pro Glu Leu Ala Ala Arg Ile Phe Met Val Ala Ile Glu
            20                  25                  30

Glu Ala Asn Gly Lys His Val Gly Leu Thr Asp Met Met Val Arg Trp
        35                  40                  45

Ala Asn Glu Asp Pro Tyr Leu Ala Pro Lys His Gly Tyr Lys Gly Glu
    50                  55                  60

Thr Pro Ser Asp Leu Gly Phe Asp Ala Lys Tyr His Val Asp Leu Gly
65                  70                  75                  80

Glu His Tyr Ala Asp Phe Lys Gln Trp Leu Glu Thr Ser Gln Ser Asn
                85                  90                  95

Gly Leu Leu Ser Lys Ala Thr Leu Asp Glu Ser Thr Lys Thr Val His
            100                 105                 110

Leu Gly Tyr Ser Tyr Gln Glu Leu Gln Asp Leu Thr Gly Ala Glu Ser
        115                 120                 125
```

```
Val Gln Met Ala Phe Tyr Phe Leu Lys Glu Ala Ala Lys Lys Ala Asp
    130                 135                 140

Pro Ile Ser Gly Asp Ser Val Glu Met Ile Leu Leu Lys Lys Phe Ala
145                 150                 155                 160

Asp Gln Ser Tyr Leu Ser Gln Leu Asp Ser Asp Arg Met Asp Gln Ile
                165                 170                 175

Glu Gly Ile Tyr Arg Ser Ser His Glu Thr
            180                 185


<210> SEQ ID NO 5
<211> LENGTH: 510
<212> TYPE: PRT
<213> ORGANISM: Vibrio ordalii

<400> SEQUENCE: 5

Gly Asp Lys Thr Lys Val Val Val Asp Leu Ala Gln Ile Phe Thr Val
1               5                   10                  15

Gln Glu Leu Lys Glu Arg Ala Lys Val Phe Ala Lys Pro Ile Gly Ala
            20                  25                  30

Ser Tyr Gln Gly Ile Leu Asp Gln Leu Asp Leu Val His Gln Ala Lys
        35                  40                  45

Gly Arg Asp Gln Ile Ala Ala Ser Phe Glu Leu Asn Lys Lys Ile Asn
    50                  55                  60

Ala Tyr Ile Ala Glu His Pro Thr Ser Gly Arg Asn Gln Ala Leu Thr
65                  70                  75                  80

Gln Leu Lys Glu Gln Val Thr Ser Ala Leu Phe Ile Gly Lys Met Gln
                85                  90                  95

Ile Ala Gln Ala Gly Ile Asp Ala Ile Ala Gln Thr Arg Pro Glu Leu
            100                 105                 110

Ala Ala Arg Ile Phe Met Val Ala Ile Glu Glu Ala Asn Gly Lys His
        115                 120                 125

Val Gly Leu Thr Asp Met Met Val Arg Trp Ala Asn Glu Asp Pro Tyr
    130                 135                 140

Leu Ala Pro Lys His Gly Tyr Lys Gly Glu Thr Pro Ser Asp Leu Gly
145                 150                 155                 160

Phe Asp Ala Lys Tyr His Val Asp Leu Ser Glu His Tyr Ala Asp Phe
                165                 170                 175

Lys Gln Trp Leu Glu Thr Ser Gln Ser Asn Gly Leu Leu Ser Lys Ala
            180                 185                 190

Met Leu Asp Glu Ser Thr Lys Thr Val His Leu Gly Tyr Ser Tyr Gln
        195                 200                 205

Glu Leu Gln Asp Leu Thr Gly Val Glu Ser Val Gln Met Ala Phe Tyr
    210                 215                 220

Phe Leu Lys Glu Ala Ala Lys Lys Ala Asp Pro Ile Ser Gly Asp Ser
225                 230                 235                 240

Ala Glu Met Ile Leu Leu Lys Lys Phe Ala Asp Gln Ser Tyr Leu Ser
                245                 250                 255

Gln Leu Asp Ser Asp Arg Met Asp Gln Ile Glu Gly Ile Tyr Arg Ser
            260                 265                 270

Ser His Glu Thr Asp Val Asp Ala Trp Asp Arg Arg Tyr Ser Gly Lys
        275                 280                 285

Gly Tyr Asp Glu Leu Thr Asn Lys Leu Ala Ser Ala Thr Gly Val Asp
    290                 295                 300

Glu Gln Leu Ser Val Leu Leu Asp Asp Arg Lys Gly Leu Leu Ile Gly
```

-continued

```
305                 310                 315                 320

Glu Val His Gly Ser Asp Val Asn Gly Leu Arg Phe Val Asn Glu Gln
                325                 330                 335

Met Asp Ala Leu Lys Lys Gln Gly Val Thr Val Ile Gly Leu Glu His
            340                 345                 350

Leu Arg Ser Asp Leu Ala Gln Pro Leu Ile Asp Arg Tyr Leu Ala Thr
        355                 360                 365

Gly Val Met Ser Ser Glu Leu Ser Ala Met Leu Lys Thr Lys His Leu
    370                 375                 380

Asp Val Ala Leu Phe Glu Asn Ala Arg Ala His Gly Met Arg Ile Val
385                 390                 395                 400

Ala Leu Asp Ala Asn Ser Ser Ala Arg Pro Asn Val Gln Gly Thr Glu
                405                 410                 415

His Gly Leu Met Tyr Arg Ala Gly Ala Ala Asn Asn Ile Ala Val Glu
            420                 425                 430

Val Leu Gln Asn Leu Pro Asp Gly Glu Lys Phe Val Ala Ile Tyr Gly
        435                 440                 445

Lys Ala His Leu Gln Ser His Lys Gly Ile Glu Gly Phe Val Pro Gly
    450                 455                 460

Ile Thr His Arg Leu Asp Leu Pro Ala Leu Lys Val Ser Asp Ser Asn
465                 470                 475                 480

Gln Phe Thr Val Glu Gln Asp Asp Val Ser Leu Arg Val Val Tyr Asp
                485                 490                 495

Asp Val Ala Asn Lys Pro Lys Ile Thr Phe Lys Asp Ser Leu
            500                 505                 510


<210> SEQ ID NO 6
<211> LENGTH: 186
<212> TYPE: PRT
<213> ORGANISM: Vibrio ordalii

<400> SEQUENCE: 6

Phe Ile Gly Lys Met Gln Ile Ala Gln Ala Gly Ile Asp Ala Ile Ala
1               5                   10                  15

Gln Thr Arg Pro Glu Leu Ala Ala Arg Ile Phe Met Val Ala Ile Glu
            20                  25                  30

Glu Ala Asn Gly Lys His Val Gly Leu Thr Asp Met Met Val Arg Trp
        35                  40                  45

Ala Asn Glu Asp Pro Tyr Leu Ala Pro Lys His Gly Tyr Lys Gly Glu
    50                  55                  60

Thr Pro Ser Asp Leu Gly Phe Asp Ala Lys Tyr His Val Asp Leu Ser
65                  70                  75                  80

Glu His Tyr Ala Asp Phe Lys Gln Trp Leu Glu Thr Ser Gln Ser Asn
                85                  90                  95

Gly Leu Leu Ser Lys Ala Met Leu Asp Glu Ser Thr Lys Thr Val His
            100                 105                 110

Leu Gly Tyr Ser Tyr Gln Glu Leu Gln Asp Leu Thr Gly Val Glu Ser
        115                 120                 125

Val Gln Met Ala Phe Tyr Phe Leu Lys Glu Ala Ala Lys Lys Ala Asp
    130                 135                 140

Pro Ile Ser Gly Asp Ser Ala Glu Met Ile Leu Leu Lys Lys Phe Ala
145                 150                 155                 160

Asp Gln Ser Tyr Leu Ser Gln Leu Asp Ser Asp Arg Met Asp Gln Ile
                165                 170                 175
```

```
Glu Gly Ile Tyr Arg Ser Ser His Glu Thr
            180                 185


<210> SEQ ID NO 7
<211> LENGTH: 511
<212> TYPE: PRT
<213> ORGANISM: Vibrio cholerae

<400> SEQUENCE: 7

Ser Gly Asn Lys Ala Lys Val Ala Val Asp Leu Ala Gln Ile Phe Thr
1               5                   10                  15

Val Gln Glu Leu Lys Glu Arg Ala Lys Val Phe Ala Lys Pro Ile Gly
            20                  25                  30

Ala Ser Tyr Gln Gly Ile Leu Asp Gln Leu Asp Leu Val His Gln Ala
        35                  40                  45

Lys Gly Arg Tyr Gln Ile Ala Ala Ser Phe Glu Leu Asn Lys Lys Ile
    50                  55                  60

Asn Asp Tyr Ile Ala Glu His Pro Thr Ser Gly Arg Asn Gln Ala Leu
65                  70                  75                  80

Thr Gln Leu Lys Glu Gln Val Thr Ser Ala Leu Phe Ile Gly Lys Met
                85                  90                  95

Gln Val Ala Gln Ala Gly Ile Asp Ala Ile Ala Gln Thr Arg Pro Glu
            100                 105                 110

Leu Ala Thr Arg Ile Phe Met Val Ala Ile Glu Glu Ala Asn Gly Lys
        115                 120                 125

His Val Gly Leu Thr Asp Met Met Leu Arg Trp Ala Asn Glu Asp Pro
    130                 135                 140

Tyr Leu Ala Pro Lys His Gly Tyr Lys Gly Glu Met Pro Ser Asp Leu
145                 150                 155                 160

Gly Phe Asp Ala Lys Tyr His Val Asp Leu Gly Glu His Tyr Ala Asp
                165                 170                 175

Phe Lys Gln Trp Leu Glu Thr Ser Gln Ser Asn Gly Leu Leu Ser Lys
            180                 185                 190

Ala Thr Leu Asp Glu Ser Thr Lys Thr Val His Leu Gly Tyr Ser Tyr
        195                 200                 205

Gln Glu Leu Gln Asp Leu Thr Gly Ala Glu Ser Val Gln Met Ala Phe
    210                 215                 220

Tyr Phe Leu Lys Glu Ala Ala Lys Lys Ala Asp Pro Ile Ser Gly Asp
225                 230                 235                 240

Ser Ala Glu Met Ile Leu Leu Lys Lys Phe Ala Asp Gln Asn Tyr Leu
                245                 250                 255

Ser Gln Leu Asp Ser Asp Arg Met Asp Gln Ile Glu Gly Ile Tyr Arg
            260                 265                 270

Ser Ser His Glu Thr Asp Val Asp Ala Trp Asp Arg Arg Tyr Ser Gly
        275                 280                 285

Lys Gly Tyr Asp Glu Leu Thr Asn Met Leu Ala Ser Ala Thr Gly Val
    290                 295                 300

Asp Glu Gln Leu Ser Val Leu Leu Asp Asp Arg Lys Gly Leu Leu Ile
305                 310                 315                 320

Gly Glu Val His Gly Ser Asp Val Asn Gly Leu Arg Phe Val Asn Glu
                325                 330                 335

Gln Met Glu Ala Leu Lys Lys Gln Gly Val Thr Val Ile Gly Leu Glu
            340                 345                 350

His Leu Arg Ser Asp Leu Ala Gln Pro Leu Ile Asp Arg Tyr Leu Ala
        355                 360                 365
```

```
Thr Gly Val Met Ser Ser Glu Leu Ser Ala Met Leu Lys Thr Lys His
    370                 375                 380

Leu Asp Val Thr Leu Phe Glu Asn Ala Arg Val Asn Gly Met Arg Ile
385                 390                 395                 400

Val Ala Leu Asp Ala Asn Ser Ser Ala Arg Pro Asn Val Gln Gly Thr
                405                 410                 415

Glu His Gly Leu Met Tyr Arg Ala Gly Ala Ala Asn Asn Ile Ala Val
            420                 425                 430

Glu Val Leu Gln Asn Leu Pro Asp Gly Glu Lys Phe Val Ala Ile Tyr
        435                 440                 445

Gly Lys Ala His Leu Gln Ser His Lys Gly Ile Glu Gly Phe Val Pro
    450                 455                 460

Gly Ile Thr His Arg Leu Asp Leu Pro Ala Leu Lys Val Ser Asp Ser
465                 470                 475                 480

Asn Gln Phe Thr Val Glu Gln Asp Asp Val Ser Leu Arg Val Val Tyr
                485                 490                 495

Asp Asp Val Ala Asn Lys Pro Lys Ile Thr Phe Lys Gly Ser Leu
            500                 505                 510


<210> SEQ ID NO 8
<211> LENGTH: 186
<212> TYPE: PRT
<213> ORGANISM: Vibrio cholerae

<400> SEQUENCE: 8

Phe Ile Gly Lys Met Gln Val Ala Gln Ala Gly Ile Asp Ala Ile Ala
1               5                   10                  15

Gln Thr Arg Pro Glu Leu Ala Thr Arg Ile Phe Met Val Ala Ile Glu
            20                  25                  30

Glu Ala Asn Gly Lys His Val Gly Leu Thr Asp Met Met Leu Arg Trp
        35                  40                  45

Ala Asn Glu Asp Pro Tyr Leu Ala Pro Lys His Gly Tyr Lys Gly Glu
    50                  55                  60

Met Pro Ser Asp Leu Gly Phe Asp Ala Lys Tyr His Val Asp Leu Gly
65                  70                  75                  80

Glu His Tyr Ala Asp Phe Lys Gln Trp Leu Glu Thr Ser Gln Ser Asn
                85                  90                  95

Gly Leu Leu Ser Lys Ala Thr Leu Asp Glu Ser Thr Lys Thr Val His
            100                 105                 110

Leu Gly Tyr Ser Tyr Gln Glu Leu Gln Asp Leu Thr Gly Ala Glu Ser
        115                 120                 125

Val Gln Met Ala Phe Tyr Phe Leu Lys Glu Ala Ala Lys Lys Ala Asp
    130                 135                 140

Pro Ile Ser Gly Asp Ser Ala Glu Met Ile Leu Leu Lys Lys Phe Ala
145                 150                 155                 160

Asp Gln Asn Tyr Leu Ser Gln Leu Asp Ser Asp Arg Met Asp Gln Ile
                165                 170                 175

Glu Gly Ile Tyr Arg Ser Ser His Glu Thr
            180                 185


<210> SEQ ID NO 9
<211> LENGTH: 511
<212> TYPE: PRT
<213> ORGANISM: Vibrio splendidus

<400> SEQUENCE: 9
```

```
Gly Asn Lys Thr Lys Leu Val Val Asp Leu Ser Thr Ile Met Thr Lys
1               5                   10                  15

Gln Glu Leu Lys Asp Gly Gly Lys Val Phe Ala Lys Pro Ile Gly Ala
            20                  25                  30

Ser Tyr Gln Ala Ile Leu Asp Gln Val Glu Leu Val His Ser Ser Ile
        35                  40                  45

Gly Arg Asp Gln Val Gly Ala Ser Phe Glu Leu Asn Lys Gln Ile Asn
    50                  55                  60

Asn Tyr Leu Ala Glu His Pro Thr Ser Gly Arg Asn Leu Ala Leu Thr
65                  70                  75                  80

Thr Leu Lys Glu Gln Val Asn Thr Ala Leu Phe Ser Gly Lys Met Lys
                85                  90                  95

Val Thr Gln Glu Ser Ile Asp Ala Ile Ala Gln Thr Arg Thr Asp Leu
            100                 105                 110

Ala Ala Arg Ile Tyr Val Val Ala Met Glu Glu Ala Asn Gly Glu His
        115                 120                 125

Val Gly Leu Thr Asp Met Met Val Arg Trp Ala Asn Glu Asp Pro Tyr
    130                 135                 140

Leu Ser Pro Lys Gln Gly Tyr Ala Gly Glu Thr Pro Ser Asp Leu Gly
145                 150                 155                 160

Phe Asp Ala Lys Tyr His Ile Glu Leu Gly Glu Gln Tyr Ser Asp Phe
                165                 170                 175

Lys Leu Trp Leu Glu Lys Ser Gln Ser Ala Asp Leu Leu Ser Lys Ala
            180                 185                 190

Ala Leu Asp Glu Ala Thr Lys Thr Val His Leu Gly Tyr Ser Tyr Gln
        195                 200                 205

Glu Leu Gln Asp Leu Thr Gly Val Glu Ser Val Gln Met Ala Phe Tyr
    210                 215                 220

Phe Leu Lys Glu Ala Ala Lys Lys Ser Asp Ser Thr Thr Ser Asp Ser
225                 230                 235                 240

Ala Glu Met Ile Leu Leu Lys Lys Phe Ala Asp Gln Gly Tyr Ile Ser
                245                 250                 255

Gln Leu Glu Thr Asp Arg Met Asp His Ile Glu Gly Ile Tyr Arg Ser
            260                 265                 270

Ser His Glu Thr Asp Val Asp Asn Trp Asp Arg Arg Tyr Ser Gly Ala
        275                 280                 285

Gly Tyr Asp Glu Leu Ser Asp Lys Leu Ala Gly Ala Asn Gly Gly Val
    290                 295                 300

Glu Glu Gln Leu Ser Val Leu Leu Asn Glu Arg Lys Gly Leu Leu Ile
305                 310                 315                 320

Gly Glu Val His Gly Ser Asp Val Asn Gly Leu Arg Phe Val Asn Glu
                325                 330                 335

Gln Met Asp Ala Leu Lys Lys Gln Gly Val Thr Val Ile Gly Leu Glu
            340                 345                 350

His Leu Arg Ser Asp Leu Ala Gln Pro Leu Ile Asp Asn Tyr Leu Ser
        355                 360                 365

Thr Gly Ile Met Ser Ser Glu Leu Ser Ala Met Ile Lys Thr Lys His
    370                 375                 380

Leu Asp Ile Thr Leu Phe Glu Asn Ala Arg Ala Asn Gly Met Arg Ile
385                 390                 395                 400

Leu Ala Leu Asp Ala Asn Ser Thr Ala Arg Pro Thr Val Gln Gly Thr
                405                 410                 415
```

-continued

```
Glu His Gly Leu Met Tyr Arg Ala Gly Ala Ala Asn Asn Val Ala Val
            420                 425                 430

Asp Ala Leu Gln Ala Leu Pro Asp Gly Glu Lys Phe Val Ala Ile Tyr
        435                 440                 445

Gly Lys Ala His Leu Gln Ser His Lys Gly Ile Glu Ser Phe Val Pro
    450                 455                 460

Gly Ile Thr His Arg Leu Gly Leu Pro Ala Leu Lys Val Ser Ala Ser
465                 470                 475                 480

Asp Gln Phe Val Ile Glu Gln Asp Asp Lys Thr Leu Arg Thr Val Tyr
                485                 490                 495

Asp Asp Val Ala Asn Lys Pro Lys Ile Glu Phe Arg Ala Ser Leu
            500                 505                 510


<210> SEQ ID NO 10
<211> LENGTH: 186
<212> TYPE: PRT
<213> ORGANISM: Vibrio splendidus

<400> SEQUENCE: 10

Phe Ser Gly Lys Met Lys Val Thr Gln Glu Ser Ile Asp Ala Ile Ala
1               5                   10                  15

Gln Thr Arg Thr Asp Leu Ala Ala Arg Ile Tyr Val Val Ala Met Glu
            20                  25                  30

Glu Ala Asn Gly Glu His Val Gly Leu Thr Asp Met Met Val Arg Trp
        35                  40                  45

Ala Asn Glu Asp Pro Tyr Leu Ser Pro Lys Gln Gly Tyr Ala Gly Glu
    50                  55                  60

Thr Pro Ser Asp Leu Gly Phe Asp Ala Lys Tyr His Ile Glu Leu Gly
65                  70                  75                  80

Glu Gln Tyr Ser Asp Phe Lys Leu Trp Leu Glu Lys Ser Gln Ser Ala
                85                  90                  95

Asp Leu Leu Ser Lys Ala Ala Leu Asp Glu Ala Thr Lys Thr Val His
            100                 105                 110

Leu Gly Tyr Ser Tyr Gln Glu Leu Gln Asp Leu Thr Gly Val Glu Ser
        115                 120                 125

Val Gln Met Ala Phe Tyr Phe Leu Lys Glu Ala Ala Lys Lys Ser Asp
    130                 135                 140

Ser Thr Thr Ser Asp Ser Ala Glu Met Ile Leu Leu Lys Lys Phe Ala
145                 150                 155                 160

Asp Gln Gly Tyr Ile Ser Gln Leu Glu Thr Asp Arg Met Asp His Ile
                165                 170                 175

Glu Gly Ile Tyr Arg Ser Ser His Glu Thr
            180                 185


<210> SEQ ID NO 11
<211> LENGTH: 510
<212> TYPE: PRT
<213> ORGANISM: Moritella dasanensis

<400> SEQUENCE: 11

Gly Asn Lys Ala Lys Gln Ser Ala Asp Leu Ser Glu Val Phe Thr Lys
1               5                   10                  15

Asp Gln Leu Lys Lys Asn Ala Lys Val Phe Ala Lys Pro Ile Gly Val
            20                  25                  30

Ser Tyr Gln Arg Ile Leu Asp Gln Val Gly Leu Val His Ser Thr Thr
        35                  40                  45
```

```
Gly Arg Asp Gln Ile Ala Ala Ser Phe Glu Leu Asn Lys Gln Ile Asp
    50                  55                  60

Ala Tyr Val Glu Ala Asn Pro Ala Ser Gly Arg Asn Gln Ala Phe Asn
65                  70                  75                  80

Gln Leu Lys Gly Gln Ile Thr Asn Ala Leu Phe Asn Gly Asp Ile Gln
                85                  90                  95

Val Ala Lys Glu Gly Ile Ser Glu Ile Ala Gln Thr Arg Pro Glu Leu
            100                 105                 110

Ala Ala Arg Ile Tyr Ile Ile Ala Gln Glu Glu Ala Asn Gly Lys Asn
        115                 120                 125

Leu Gly Leu Thr Asp Leu Met Val Arg Trp Ala Lys Glu Asp Pro Tyr
    130                 135                 140

Leu Ser Ala Lys Asn Gly Tyr Gln Gly Asp Ile Pro Ser Asp Leu Gly
145                 150                 155                 160

Phe Glu Ala Lys Phe His Val Glu Leu Gly Ser Gln Tyr Ala Asp Phe
                165                 170                 175

Lys Gln Thr Leu Glu Lys Ala Gln Val Glu Gly Leu Leu Thr Lys Ala
            180                 185                 190

Val Ile Asp Glu Ser Thr Lys Thr Val His Leu Gly Tyr Thr Tyr Gln
        195                 200                 205

Glu Leu Gln Asp Gln Thr Gly Thr Glu Ser Val Gln Met Ala Ala Tyr
    210                 215                 220

Phe Leu Lys Glu Ala Ala Lys Lys Ser Asp Pro Thr Ser Ala Asp Ser
225                 230                 235                 240

Ala Glu Met Ile Leu Leu Asn Lys Phe Ala Asp Lys Asn Tyr Ile Thr
                245                 250                 255

Glu Leu Glu Arg Gln Arg Ile Asp Gln Ile Glu Ser Ile Tyr Arg Ser
            260                 265                 270

Ser His Asp Thr Asp Ile Ala Gly Trp Asp Lys Arg Tyr Ser Gly Thr
        275                 280                 285

Ala Leu Asn Glu Leu Asn Ser Gln Leu Gly Ala Ala Thr Ser Val Glu
    290                 295                 300

Ala Gln Leu Ala Leu Leu Leu Glu Lys Arg Asn Gly Leu Leu Ile Gly
305                 310                 315                 320

Glu Ser His Gly Ser Asp Val Asn Gly Leu Arg Phe Val Asn Glu Gln
                325                 330                 335

Met Asp Ala Leu Lys Ala Gln Gly Val Ser Val Ile Gly Leu Glu His
            340                 345                 350

Leu Arg Ala Asp Leu Ala Gln Pro Leu Ile Asp Ser Tyr Leu Ser Ser
        355                 360                 365

Gly Asp Met Ser Ser Glu Leu Arg Ile Met Leu Lys Thr Lys His Leu
    370                 375                 380

Asp Ile Ser Leu Phe Glu Asn Ala Arg Ala Lys Gly Leu Arg Ile Val
385                 390                 395                 400

Ala Leu Asp Ala Asn Ser Thr Thr Arg Pro Thr Ile Gln Gly Thr Glu
                405                 410                 415

His Gly Leu Met Tyr Arg Ala Gly Ala Ala Asn Asn Val Ala Val Glu
            420                 425                 430

Thr Leu Ser Gly Leu Pro Ala Gly Glu Lys Phe Val Ala Ile Tyr Gly
        435                 440                 445

Asn Ala His Leu Gln Ser His Lys Gly Ile Glu Gly Phe Val Pro Gly
    450                 455                 460

Ile Thr His Arg Leu Asp Leu Pro Gly Leu Lys Ile Ser Glu Thr Asn
```

465 470 475 480

Gln Phe Lys Ala Gln Ala Asp Asp Leu Ser Gln Arg Val Ile Tyr Gly
485 490 495

Asp Val Leu Asn Lys Ala Lys Ile Glu Phe Thr Asn Ser Leu
500 505 510

<210> SEQ ID NO 12
<211> LENGTH: 186
<212> TYPE: PRT
<213> ORGANISM: Moritella dasanensis

<400> SEQUENCE: 12

Phe Asn Gly Asp Ile Gln Val Ala Lys Glu Gly Ile Ser Glu Ile Ala
1 5 10 15

Gln Thr Arg Pro Glu Leu Ala Ala Arg Ile Tyr Ile Ile Ala Gln Glu
20 25 30

Glu Ala Asn Gly Lys Asn Leu Gly Leu Thr Asp Leu Met Val Arg Trp
35 40 45

Ala Lys Glu Asp Pro Tyr Leu Ser Ala Lys Asn Gly Tyr Gln Gly Asp
50 55 60

Ile Pro Ser Asp Leu Gly Phe Glu Ala Lys Phe His Val Glu Leu Gly
65 70 75 80

Ser Gln Tyr Ala Asp Phe Lys Gln Thr Leu Glu Lys Ala Gln Val Glu
85 90 95

Gly Leu Leu Thr Lys Ala Val Ile Asp Glu Ser Thr Lys Thr Val His
100 105 110

Leu Gly Tyr Thr Tyr Gln Glu Leu Gln Asp Gln Thr Gly Thr Glu Ser
115 120 125

Val Gln Met Ala Ala Tyr Phe Leu Lys Glu Ala Ala Lys Lys Ser Asp
130 135 140

Pro Thr Ser Ala Asp Ser Ala Glu Met Ile Leu Leu Asn Lys Phe Ala
145 150 155 160

Asp Lys Asn Tyr Ile Thr Glu Leu Glu Arg Gln Arg Ile Asp Gln Ile
165 170 175

Glu Ser Ile Tyr Arg Ser Ser His Asp Thr
180 185

<210> SEQ ID NO 13
<211> LENGTH: 509
<212> TYPE: PRT
<213> ORGANISM: Aeromonas salmonicida

<400> SEQUENCE: 13

Pro Gly Lys Val Val Ala Gln Glu Arg Ala Ser Ser Leu Phe Ala Asp
1 5 10 15

Ala Tyr Ser Pro Asp Glu Leu Lys Lys Ala Ala Gln Val Phe Ala Lys
20 25 30

Pro Ile Gly Glu Ser Tyr Gln Gly Ile Leu Asp Gln Leu Ala Val Leu
35 40 45

His Gly Ala Thr Gly Gln Val Gln Val Glu Ala Ala Leu Arg Leu Asn
50 55 60

Lys Leu Ile Asp Asp Tyr Gln Ala Arg His Glu Gly Ser Gly Arg Asn
65 70 75 80

Pro Ala Leu Ser Lys Leu Gln Ser Gln Leu Asn Gly Gly Leu Tyr His
85 90 95

Gly Glu Leu Ala Ser Leu Gln Ala Asp Val Ala Ala Leu Ala Lys Ser

-continued

```
            100                 105                 110

Arg Pro Asp Leu Ala Ala Leu Val Ile Gly Lys Ala Ala Glu Glu Ala
        115                 120                 125

Lys Gly Gln His Pro Gly Leu Thr Gln Met Leu Leu Arg Trp Ala Ala
    130                 135                 140

Gln Asp Pro Tyr Leu Ala Ala Lys Gly Gly Tyr Gln Gly Gln Ala Pro
145                 150                 155                 160

Ala Asp Leu Pro Phe Asp Ala Ser Phe His Val Val Leu Gly Glu Gln
                165                 170                 175

Tyr Gly Glu Leu Lys Arg Trp Leu Ala Asp Ala Gln Ser Lys Gly Leu
            180                 185                 190

Leu Ser Lys Ala Val Leu Asp Glu Thr Gly Lys Val Leu His Leu Gly
        195                 200                 205

Tyr Ser Tyr Gln Glu Leu Gln Asp Met Thr Gly Asp Gln Ser Ala Gln
    210                 215                 220

Met Thr Val Tyr Phe Ile Lys Glu Ala Ala Lys Gln Ala Ala Pro Gly
225                 230                 235                 240

Ser Glu Leu Ser Ala Glu Met Ile Met Leu Asp Lys Phe Ala Asp Arg
                245                 250                 255

Arg Tyr Leu Gly Glu Leu Gly Ser Arg Arg Leu Glu Gln Val Glu Ser
            260                 265                 270

Ile Tyr Arg Ser Ser Lys Gln Thr Asp Val Ala Ala Trp Asp Ala Arg
        275                 280                 285

Tyr Ala Gly Asn Ala Leu Arg Asp Leu Asn Asp Gln Val Ala Gln Glu
    290                 295                 300

Ser Thr Leu Ala Gly Gln Leu Ser Arg Leu Leu Glu Asn Arg Asn Gly
305                 310                 315                 320

Leu Leu Ile Gly Glu Thr His Gly Ser Asp Val Asn Gly Leu Arg Phe
                325                 330                 335

Val Asn Glu Gln Met Asp Val Leu Lys Ala Gln Gly Val Thr Val Ile
            340                 345                 350

Gly Leu Glu His Leu Arg Gly Glu Leu Ala Gln Pro Leu Ile Asp Arg
        355                 360                 365

Tyr Leu Ala Gly Gly Asp Met Ser Pro Glu Leu Ala Thr Met Leu Lys
    370                 375                 380

Thr Lys His Leu Asp Pro Ser Leu Phe Glu Arg Ala Arg Glu Lys Gly
385                 390                 395                 400

Leu Arg Ile Val Ala Leu Asp Asp Gly Ser Thr Ala Arg Pro Ala Ile
                405                 410                 415

Ala Gly Thr Glu His Gly Leu Met Tyr Arg Ala Gly Ala Ala Asn Asn
            420                 425                 430

Val Ala Val Asp Val Leu Gly Lys Leu Pro Ala Gly Glu Lys Phe Val
        435                 440                 445

Ala Ile Tyr Gly Ser Ala His Leu Ala Ser His Lys Gly Ile Glu Gly
    450                 455                 460

Phe Val Pro Gly Ile Thr His Arg Leu Gly Leu Pro Ala Leu Lys Val
465                 470                 475                 480

Asp Ala Asp Asn Arg Phe Arg Leu Gln Glu Asp Asp Thr Ser Gln Arg
                485                 490                 495

Val Glu Tyr Gly Asp Val Ala Arg Lys Trp Thr Pro Leu
            500                 505
```

<210> SEQ ID NO 14

```
<211> LENGTH: 186
<212> TYPE: PRT
<213> ORGANISM: Aeromonas salmonicida

<400> SEQUENCE: 14

Tyr His Gly Glu Leu Ala Ser Leu Gln Ala Asp Val Ala Ala Leu Ala
1               5                   10                  15

Lys Ser Arg Pro Asp Leu Ala Ala Leu Val Ile Gly Lys Ala Ala Glu
            20                  25                  30

Glu Ala Lys Gly Gln His Pro Gly Leu Thr Gln Met Leu Leu Arg Trp
        35                  40                  45

Ala Ala Gln Asp Pro Tyr Leu Ala Ala Lys Gly Gly Tyr Gln Gly Gln
    50                  55                  60

Ala Pro Ala Asp Leu Pro Phe Asp Ala Ser Phe His Val Val Leu Gly
65                  70                  75                  80

Glu Gln Tyr Gly Glu Leu Lys Arg Trp Leu Ala Asp Ala Gln Ser Lys
                85                  90                  95

Gly Leu Leu Ser Lys Ala Val Leu Asp Glu Thr Gly Lys Val Leu His
            100                 105                 110

Leu Gly Tyr Ser Tyr Gln Glu Leu Gln Asp Met Thr Gly Asp Gln Ser
        115                 120                 125

Ala Gln Met Thr Val Tyr Phe Ile Lys Glu Ala Ala Lys Gln Ala Ala
    130                 135                 140

Pro Gly Ser Glu Leu Ser Ala Glu Met Ile Met Leu Asp Lys Phe Ala
145                 150                 155                 160

Asp Arg Arg Tyr Leu Gly Glu Leu Gly Ser Arg Arg Leu Glu Gln Val
                165                 170                 175

Glu Ser Ile Tyr Arg Ser Ser Lys Gln Thr
            180                 185


<210> SEQ ID NO 15
<211> LENGTH: 512
<212> TYPE: PRT
<213> ORGANISM: Aeromonas hydrophila

<400> SEQUENCE: 15

Pro Gly Lys Thr Gly Val Thr Glu Arg Thr Ala Arg Leu Phe Ala Asp
1               5                   10                  15

Val Tyr Ser Pro Asp Glu Leu Lys Lys Ala Ala Gln Val Phe Ala Lys
            20                  25                  30

Pro Ile Gly Glu Ser Tyr Gln Gln Ile Leu Asp Gln Leu Ala Thr Leu
        35                  40                  45

His Gly Ala Ser Gly Gln Ala Lys Val Glu Ala Ala Leu Arg Leu Asn
    50                  55                  60

Asn Leu Ile Asp Asp Tyr Leu Val Lys His Glu Gly Ser Gly Arg Asn
65                  70                  75                  80

Pro Ala Leu Ser Lys Leu Gln Ser Gln Leu His Gly Asn Leu Tyr Arg
                85                  90                  95

Gly Glu Leu Ala Ser Leu Gln Ala Glu Val Thr Ala Leu Ala Lys Thr
            100                 105                 110

Arg Pro Asp Leu Ala Ala Ile Val Ile Gly Lys Ala Ala Glu Glu Ala
        115                 120                 125

Gln Gly Gln His Pro Gly Leu Thr Gln Met Val Leu Arg Trp Ala Ala
    130                 135                 140

Gln Asp Pro Tyr Leu Ala Ala Lys Ala Gly Tyr Gln Gly Val Val Pro
145                 150                 155                 160
```

```
Ala Asp Leu Pro Phe Asp Ala Arg Phe His Ile Ala Leu Gly Glu Gln
                165                 170                 175

His Asp Asp Leu Lys Lys Trp Leu Thr Glu Ala Gln Gly Lys Gly Leu
            180                 185                 190

Leu Asn Arg Ala Val Leu Asp Asp Thr Arg Lys Val Leu His Leu Gly
        195                 200                 205

Tyr Ser Tyr Gln Glu Leu Gln Asp Met Thr Gly Glu Gln Ser Ala Gln
    210                 215                 220

Met Ala Val Tyr Phe Ile Lys Glu Ala Ala Lys Gln Ala Ala Pro Gly
225                 230                 235                 240

Ser Glu Leu Ser Ala Glu Leu Ile Met Leu Asp Lys Phe Gly Asp Arg
                245                 250                 255

Arg Tyr Leu Gly Glu Leu Glu Ser Arg Arg Ile Ala Gln Ile Glu Asn
            260                 265                 270

Ile Tyr His Ser Ser Lys Gln Thr Asp Val Ala Ala Trp Asp Ala Arg
        275                 280                 285

Tyr Gly Gly Asp Ala Leu Arg Thr Leu Asn Asn Gln Leu Asp Gly Glu
    290                 295                 300

Ser Thr Leu Ala Gly Gln Leu Ser Arg Leu Leu Asp Asn Arg Asn Gly
305                 310                 315                 320

Leu Leu Ile Gly Glu Thr His Gly Ser Asp Val Asn Gly Leu Arg Phe
                325                 330                 335

Val Asn Glu Gln Met Asp Ala Leu Lys Ile Gln Gly Val Thr Val Ile
            340                 345                 350

Ala Leu Glu His Leu Arg Ser Glu Leu Ala Gln Pro Leu Ile Asp Arg
        355                 360                 365

Tyr Leu Ala Gly Gly Glu Met Ser Pro Glu Leu Thr Ser Met Leu Lys
    370                 375                 380

Asn Lys His Leu Glu Pro Ser Leu Phe Glu Arg Ala Arg Glu Arg Gly
385                 390                 395                 400

Met Arg Ile Val Ala Leu Asp Asp Gly Ser Thr Ala Arg Pro Ala Ile
                405                 410                 415

Ala Gly Thr Glu His Gly Leu Met Tyr Arg Ala Gly Ala Ala Asn Asn
            420                 425                 430

Val Ala Val Glu Val Leu Gly Lys Leu Pro Ala Gly Glu Lys Phe Val
        435                 440                 445

Ala Ile Tyr Gly Ser Ala His Leu Gly Ser His Lys Gly Ile Glu Gly
    450                 455                 460

Phe Val Pro Gly Ile Thr His Arg Leu Gly Leu Pro Ala Leu Lys Val
465                 470                 475                 480

Asp Ala Asp Asn Arg Phe His Leu Gln Ala Asp Asp Val Ser Gln Arg
                485                 490                 495

Val Glu Tyr Ala Asp Val Gly Arg Lys Trp Thr Pro Val Ala Ala Leu
            500                 505                 510


<210> SEQ ID NO 16
<211> LENGTH: 186
<212> TYPE: PRT
<213> ORGANISM: Aeromonas hydrophila

<400> SEQUENCE: 16

Tyr Arg Gly Glu Leu Ala Ser Leu Gln Ala Glu Val Thr Ala Leu Ala
1               5                   10                  15

Lys Thr Arg Pro Asp Leu Ala Ala Ile Val Ile Gly Lys Ala Ala Glu
```

```
            20                  25                  30

Glu Ala Gln Gly Gln His Pro Gly Leu Thr Gln Met Val Leu Arg Trp
        35                  40                  45

Ala Ala Gln Asp Pro Tyr Leu Ala Ala Lys Ala Gly Tyr Gln Gly Val
    50                  55                  60

Val Pro Ala Asp Leu Pro Phe Asp Ala Arg Phe His Ile Ala Leu Gly
65                  70                  75                  80

Glu Gln His Asp Asp Leu Lys Lys Trp Leu Thr Glu Ala Gln Gly Lys
                85                  90                  95

Gly Leu Leu Asn Arg Ala Val Leu Asp Asp Thr Arg Lys Val Leu His
            100                 105                 110

Leu Gly Tyr Ser Tyr Gln Glu Leu Gln Asp Met Thr Gly Glu Gln Ser
        115                 120                 125

Ala Gln Met Ala Val Tyr Phe Ile Lys Glu Ala Ala Lys Gln Ala Ala
    130                 135                 140

Pro Gly Ser Glu Leu Ser Ala Glu Leu Ile Met Leu Asp Lys Phe Gly
145                 150                 155                 160

Asp Arg Arg Tyr Leu Gly Glu Leu Glu Ser Arg Arg Ile Ala Gln Ile
                165                 170                 175

Glu Asn Ile Tyr His Ser Ser Lys Gln Thr
            180                 185


<210> SEQ ID NO 17
<211> LENGTH: 561
<212> TYPE: PRT
<213> ORGANISM: Photorhabdus temperate

<400> SEQUENCE: 17

Met Glu Tyr Glu Tyr Asp Lys Thr Asp Asp Arg Lys Arg Lys His Ser
1               5                   10                  15

Thr Gln Trp Ala Asp Tyr Glu Glu Lys Ser Phe Val Pro Thr Leu Asp
            20                  25                  30

Leu Ser Gln Ser Arg Gln His Asn Pro Ser His Asp Ala Leu Asn Arg
        35                  40                  45

Ala Asp Asn His Glu Thr Ser Pro Leu Leu His Asn Leu Ile Thr Ser
    50                  55                  60

Asp Asn Leu Arg Lys Glu Ala Ala Val Phe Ala Lys Arg Ile Gly Ser
65                  70                  75                  80

Ser Tyr Gln Gly Ile Leu Asp Gly Leu His Arg Ile His Thr Leu Ser
                85                  90                  95

Gly Asn Glu Gln Leu Thr Ala Gly Phe Glu Leu His Gln Arg Ile Thr
            100                 105                 110

Arg Tyr Leu Lys Thr His Pro Asp Ser Lys Arg Asn Thr Ser Leu Arg
        115                 120                 125

Arg Met Gln Thr Gln Leu Glu Asp Leu Met Phe Thr Gly Thr Leu Gln
    130                 135                 140

Met Val Arg Ser Pro Leu Leu Glu Met Ala Glu Thr Arg Pro Asp Met
145                 150                 155                 160

Ala Ser Arg Ile Tyr Gln Ile Ala Cys Asn Glu Thr Arg Gly Asn Thr
                165                 170                 175

Pro Gly Leu Thr Asp Leu Met Val Arg Trp Val Lys Glu Asp Pro Tyr
            180                 185                 190

Leu Ala Thr Lys Thr Gly Tyr Gln Gly Glu Ile Pro Asn Asp Leu Pro
        195                 200                 205
```

-continued

```
Phe Asp Pro Lys Phe His Val Glu Leu Gly Ala Gln Phe Asp Asp Phe
    210                 215                 220

Lys Lys Trp Leu Asn Ile Ala Gln Ser Gln Gly Leu Leu Thr His Ala
225                 230                 235                 240

Arg Leu Asp Glu Pro Ser Lys Arg Val His Leu Gly Tyr Ser Tyr Asn
                245                 250                 255

Glu Leu Leu Asp Met Thr Gly Val Glu Ser Val Gln Met Ala Val Tyr
            260                 265                 270

Phe Leu Lys Glu Ala Ala Lys Gln Ala Asp Pro Gly Phe Ala Gly Ser
        275                 280                 285

Gln Glu Ala Ile Leu Leu Asn Arg Phe Ala Asn Pro Ala Tyr Leu Ala
    290                 295                 300

Gln Leu Glu Gln Gly Arg Leu Ser Gln Ile Glu Ala Ile Tyr His Ser
305                 310                 315                 320

Ser His Asn Thr Asp Val Ala Ala Trp Asp Lys Gln Phe Asp Ala Asp
                325                 330                 335

Ala Leu Val Gln Leu Asn His Gln Leu Asn Gly Ser Thr Asp Leu Asp
            340                 345                 350

Ser Gln Leu Ser Leu Leu Leu Lys Asn Arg Gln Gly Leu Leu Ile Gly
        355                 360                 365

Glu Ser His Gly Ser Asp Leu Asn Gly Leu Arg Phe Val Asn Glu Gln
    370                 375                 380

Met Asn Ala Leu Lys Ala His Gly Val Ser Val Ile Gly Leu Glu His
385                 390                 395                 400

Leu Arg Ser Asp Leu Ala Gln Pro Leu Ile Asp Asn Phe Leu Ala Ser
                405                 410                 415

Gly Asp Met Ser Ala Glu Leu Ala Ala Met Ile Lys Thr Lys His Leu
            420                 425                 430

Asp Pro Ala Leu Phe Glu Gln Ala Arg Ile Lys Ser Met Lys Ile Ile
        435                 440                 445

Ala Leu Asp Asp Asn Ser Thr Thr Arg Pro Val Val Ala Gly Thr Gln
    450                 455                 460

His Gly Leu Met Tyr Arg Ala Gly Ala Ala Asn Asn Val Ala Val Glu
465                 470                 475                 480

Arg Leu Gln Gln Leu Pro Val Gly Glu Lys Phe Val Ala Ile Tyr Gly
                485                 490                 495

Asn Ala His Leu Gln Ser His Glu Gly Ile Asp His Phe Ile Pro Gly
            500                 505                 510

Met Thr His Arg Leu Gly Leu Pro Ala Leu Lys Val Asp Ala Asn Asn
        515                 520                 525

His Phe Val Ala Gln Ala Asp Asp Thr Ser Gln Arg Lys Arg Tyr Asp
    530                 535                 540

Asp Val Ala Asn Val Pro Arg Ile Gln Leu Ile Pro Gln Ala Lys Leu
545                 550                 555                 560

Leu


<210> SEQ ID NO 18
<211> LENGTH: 220
<212> TYPE: PRT
<213> ORGANISM: Photorhabdus temperate

<400> SEQUENCE: 18

Phe Glu Leu His Gln Arg Ile Thr Arg Tyr Leu Lys Thr His Pro Asp
1               5                   10                  15
```

-continued

Ser Lys Arg Asn Thr Ser Leu Arg Arg Met Gln Thr Gln Leu Glu Asp
20 25 30

Leu Met Phe Thr Gly Thr Leu Gln Met Val Arg Ser Pro Leu Leu Glu
35 40 45

Met Ala Glu Thr Arg Pro Asp Met Ala Ser Arg Ile Tyr Gln Ile Ala
50 55 60

Cys Asn Glu Thr Arg Gly Asn Thr Pro Gly Leu Thr Asp Leu Met Val
65 70 75 80

Arg Trp Val Lys Glu Asp Pro Tyr Leu Ala Thr Lys Thr Gly Tyr Gln
85 90 95

Gly Glu Ile Pro Asn Asp Leu Pro Phe Asp Pro Lys Phe His Val Glu
100 105 110

Leu Gly Ala Gln Phe Asp Asp Phe Lys Lys Trp Leu Asn Ile Ala Gln
115 120 125

Ser Gln Gly Leu Leu Thr His Ala Arg Leu Asp Glu Pro Ser Lys Arg
130 135 140

Val His Leu Gly Tyr Ser Tyr Asn Glu Leu Leu Asp Met Thr Gly Val
145 150 155 160

Glu Ser Val Gln Met Ala Val Tyr Phe Leu Lys Glu Ala Ala Lys Gln
165 170 175

Ala Asp Pro Gly Phe Ala Gly Ser Gln Glu Ala Ile Leu Leu Asn Arg
180 185 190

Phe Ala Asn Pro Ala Tyr Leu Ala Gln Leu Glu Gln Gly Arg Leu Ser
195 200 205

Gln Ile Glu Ala Ile Tyr His Ser Ser His Asn Thr
210 215 220

<210> SEQ ID NO 19
<211> LENGTH: 531
<212> TYPE: PRT
<213> ORGANISM: Xenorhabdus nematophila

<400> SEQUENCE: 19

Ala Leu Ser Gly Lys Asn Lys Thr Leu Glu Thr Val Ile Ala Glu Asn
1 5 10 15

Asp Gly Thr Pro Ser Leu Asn Glu Leu Ile Thr Lys Asp Gly Leu Arg
20 25 30

Lys Lys Ala Ser Val Phe Ala Lys Pro Ile Gly Pro Ala Tyr Gln Ala
35 40 45

Ile Leu Asp Lys Leu Asp His Ile His Asn Leu Thr Gly Asn Glu Gln
50 55 60

Leu Ser Ala Gly Phe Glu Leu Tyr Gln Arg Ile Thr Arg Tyr Leu Asn
65 70 75 80

Glu His Pro Asp Ser Lys Arg Asn Thr Ala Leu Ser Gly Val Gln Thr
85 90 95

Gln Leu Gly Asp Ile Met Phe Arg Gly Ala Leu Gln Glu Val Arg Ser
100 105 110

Pro Leu Leu Glu Ile Ala Gln Thr Arg Pro Glu Met Ala Ser Arg Ile
115 120 125

Tyr Gln Ile Ala Arg Asn Glu Ala Arg Gly Asp Thr Pro Gly Leu Thr
130 135 140

Asp Leu Met Val Arg Trp Val Lys Glu Asp Pro Tyr Leu Ala Ala Lys
145 150 155 160

Leu Gly Tyr Gln Gly Glu Ile Pro Ala Asp Leu Ala Phe Asn Pro Lys
165 170 175

```
Phe His Val Asp Leu Gly Asp Gln Phe Asp Asp Phe Lys Gln Cys Leu
            180                 185                 190

Ser Lys Ala Gln Asp Lys Gly Leu Leu Ile Asn Ala Arg Ile Asp Glu
        195                 200                 205

Gln Asn Lys Arg Val His Leu Gly Tyr Ser Tyr Asn Glu Leu Leu Asp
    210                 215                 220

Met Thr Gly Ser Glu Asp Val Lys Met Ala Val Tyr Phe Leu Lys Glu
225                 230                 235                 240

Val Ala Lys Gln Ala Asp Pro Asn Phe Ala Gly Ser His Glu Ala Ile
                245                 250                 255

Leu Leu Asn Arg Phe Ala Asn Pro Ala Tyr Leu Val Gln Leu Glu Gln
            260                 265                 270

Gly Arg Leu Ala Gln Ile Glu Ala Ile Tyr His Ser Ser His Gln Thr
        275                 280                 285

Asp Ile Ala Ala Trp Asp Lys Gln Tyr Ser Ser Asp Ala Leu Thr Gln
    290                 295                 300

Leu Asn Arg Gln Leu Ser Asp Gly Thr Asp Leu Asn Ser Gln Leu Ser
305                 310                 315                 320

Leu Leu Leu Lys Asp Arg Gln Gly Leu Leu Ile Gly Glu Ser His Gly
                325                 330                 335

Ser Asp Leu Asn Gly Leu Arg Phe Val Asn Glu Gln Met Asp Ala Leu
            340                 345                 350

Lys Val His Gly Val Thr Val Ile Gly Leu Glu His Leu Arg Ser Asp
        355                 360                 365

Leu Ala Gln Pro Leu Ile Asp Lys Phe Leu Ala Gly Gly Asp Met Pro
    370                 375                 380

Ala Glu Leu Thr Ala Met Ile Glu Thr Lys His Leu Pro Val Asp Leu
385                 390                 395                 400

Phe Glu Gln Ala Lys Ser Lys Gly Ile Lys Ile Ile Ala Leu Asp Asp
                405                 410                 415

Asn Ser Thr Thr Arg Pro Ala Ile Glu Gly Ser Gln His Gly Leu Met
            420                 425                 430

Tyr Arg Ala Gly Ala Ala Asn Asn Val Ala Val Lys Arg Leu Gly Leu
        435                 440                 445

Leu Ala Glu Gly Glu Lys Phe Val Ala Ile Tyr Gly Asp Ala His Leu
    450                 455                 460

Gln Ser His Glu Gly Ile Asp His Phe Val Pro Gly Met Thr His Arg
465                 470                 475                 480

Leu Gly Leu Pro Ala Leu Lys Val Asp Ala Asn Asn Arg Phe Thr Ala
                485                 490                 495

Gln Ala Asp Asp Ile Ser Leu Arg Lys His Tyr Asp Asp Val Pro Gln
            500                 505                 510

Leu Glu Lys Asn Leu Tyr Lys Pro Asn Arg Val Val Gly Gly Asp Leu
        515                 520                 525

Glu Val Leu
    530


<210> SEQ ID NO 20
<211> LENGTH: 186
<212> TYPE: PRT
<213> ORGANISM: Xenorhabdus nematophila

<400> SEQUENCE: 20

Phe Arg Gly Ala Leu Gln Glu Val Arg Ser Pro Leu Leu Glu Ile Ala
```

-continued

```
1               5                   10                  15

Gln Thr Arg Pro Glu Met Ala Ser Arg Ile Tyr Gln Ile Ala Arg Asn
            20                  25                  30

Glu Ala Arg Gly Asp Thr Pro Gly Leu Thr Asp Leu Met Val Arg Trp
        35                  40                  45

Val Lys Glu Asp Pro Tyr Leu Ala Ala Lys Leu Gly Tyr Gln Gly Glu
    50                  55                  60

Ile Pro Ala Asp Leu Ala Phe Asn Pro Lys Phe His Val Asp Leu Gly
65                  70                  75                  80

Asp Gln Phe Asp Asp Phe Lys Gln Cys Leu Ser Lys Ala Gln Asp Lys
                85                  90                  95

Gly Leu Leu Ile Asn Ala Arg Ile Asp Glu Gln Asn Lys Arg Val His
            100                 105                 110

Leu Gly Tyr Ser Tyr Asn Glu Leu Leu Asp Met Thr Gly Ser Glu Asp
        115                 120                 125

Val Lys Met Ala Val Tyr Phe Leu Lys Glu Val Ala Lys Gln Ala Asp
    130                 135                 140

Pro Asn Phe Ala Gly Ser His Glu Ala Ile Leu Leu Asn Arg Phe Ala
145                 150                 155                 160

Asn Pro Ala Tyr Leu Val Gln Leu Glu Gln Gly Arg Leu Ala Gln Ile
                165                 170                 175

Glu Ala Ile Tyr His Ser Ser His Gln Thr
            180                 185


<210> SEQ ID NO 21
<211> LENGTH: 568
<212> TYPE: PRT
<213> ORGANISM: Photorhabdus luminescens

<400> SEQUENCE: 21

Met Thr Gly Val Ser Glu Cys Ser Gln Gln Arg Ser Asn Leu Lys Asp
1               5                   10                  15

Asp Gly Tyr Ile Ser Ser Arg Lys Leu Thr Gly Asp Asn Met Val Tyr
            20                  25                  30

Glu Tyr Asp Lys Thr Ile Glu Arg Arg Arg Asn Pro Ser Ile Gln Leu
        35                  40                  45

Asn Asn Asn Glu Lys Ser Ser Glu Gln Ala Leu Glu Leu Ser Gln Asn
    50                  55                  60

Asn Pro Leu Leu His Asp Leu Ile Thr Ser Asn Asn Leu Arg Lys Glu
65                  70                  75                  80

Ala Ala Val Phe Ala Lys Arg Ile Gly Pro Ser Tyr Gln Glu Ile Leu
                85                  90                  95

Asp Glu Leu Glu His Leu His His Leu Ser Gly Asn Glu Gln Leu Ala
            100                 105                 110

Ala Gly Phe Glu Leu His Arg Arg Ile Thr His Tyr Leu Glu Glu His
        115                 120                 125

Pro Asp Ser Lys Arg Asn Thr Ala Leu Arg Arg Thr Gln Thr Gln Phe
    130                 135                 140

Gly Asp Leu Met Phe Thr Gly Thr Leu Gln Lys Ile Arg His Ser Leu
145                 150                 155                 160

Leu Glu Met Ala Glu Thr Arg Pro Glu Met Ala Ser His Ile Tyr Gln
                165                 170                 175

Ile Ala Arg Glu Glu Val Lys Gly Asn Thr Pro Gly Leu Thr Asp Leu
            180                 185                 190
```

-continued

```
Met Val Arg Trp Val Lys Glu Asp Pro Tyr Leu Ala Ala Lys Thr Gly
        195                 200                 205

Tyr Gln Gly Lys Ile Pro Asn Asp Leu Pro Phe Glu Pro Lys Phe His
    210                 215                 220

Val Glu Leu Gly Ala Gln Phe Asp Asp Phe Lys Lys Trp Leu Asp Thr
225                 230                 235                 240

Ala Gln Ser Lys Glu Leu Leu Thr His Thr Arg Leu Asp Glu Gln Asn
                245                 250                 255

Lys Gln Val His Leu Gly Tyr Ser Tyr Asn Glu Leu Leu Asp Met Thr
            260                 265                 270

Gly Val Glu Ser Val Gln Met Ala Val Tyr Phe Leu Lys Glu Ala Ala
        275                 280                 285

Lys Gln Ala Glu Pro Gly Ser Thr Lys Ser Gln Glu Asp Ile Leu Leu
    290                 295                 300

His Arg Phe Ala Asn Pro Thr Tyr Leu Ala Gln Leu Glu His Ser Arg
305                 310                 315                 320

Leu Ala Gln Ile Glu Ala Ile Tyr His Ser Ser His Asp Thr Asp Val
                325                 330                 335

Thr Ala Trp Asp Gln Gln Phe Ala Ser Asp Ala Leu Thr Gln Phe Asn
            340                 345                 350

His Gln Leu Asn Asn Thr Val Asp Leu Asn Ser Gln Leu Ser Leu Leu
        355                 360                 365

Leu Lys Asp Arg Gln Gly Leu Leu Ile Gly Glu Ser His Gly Ser Asp
    370                 375                 380

Leu Asn Gly Leu Arg Phe Val Glu Glu Gln Met Glu Val Leu Lys Ala
385                 390                 395                 400

His Gly Val Thr Val Ile Gly Leu Glu His Leu Arg Ser Asp Leu Ala
                405                 410                 415

Gln Pro Leu Ile Asp Lys Phe Leu Ala Ser Gly Asn Glu Pro Met Pro
            420                 425                 430

Ala Glu Leu Ala Ala Leu Leu Lys Thr Lys His Leu Ser Ala Asn Leu
        435                 440                 445

Phe Glu Gln Ala Arg Ser Lys Gln Met Lys Ile Ile Ala Leu Asp Asn
    450                 455                 460

Asn Ser Thr Thr Arg Pro Thr Val Glu Gly Thr Gln His Gly Leu Met
465                 470                 475                 480

Tyr Arg Ala Gly Ala Ala Asn Asn Val Ala Val Glu Arg Leu Arg Gln
                485                 490                 495

Leu Pro Ala Gly Glu Lys Phe Val Ala Ile Tyr Gly Asn Ala His Leu
            500                 505                 510

Gln Ser His Glu Gly Ile Asp His Phe Leu Pro Gly Ile Thr His Arg
        515                 520                 525

Leu Gly Leu Pro Ala Leu Lys Val Asp Glu Asn Asn Arg Phe Thr Ala
    530                 535                 540

Gln Val Asp Asn Ile Asn Gln Arg Lys Arg Tyr Asp Asp Val Val Glu
545                 550                 555                 560

Leu Pro Arg Ile Gln Leu Thr Ser
                565
```

<210> SEQ ID NO 22
<211> LENGTH: 220
<212> TYPE: PRT
<213> ORGANISM: Photorhabdus luminescens

<400> SEQUENCE: 22

```
Phe Glu Leu His Arg Arg Ile Thr His Tyr Leu Glu Glu His Pro Asp
1               5                   10                  15

Ser Lys Arg Asn Thr Ala Leu Arg Arg Thr Gln Thr Gln Phe Gly Asp
            20                  25                  30

Leu Met Phe Thr Gly Thr Leu Gln Lys Ile Arg His Ser Leu Leu Glu
        35                  40                  45

Met Ala Glu Thr Arg Pro Glu Met Ala Ser His Ile Tyr Gln Ile Ala
    50                  55                  60

Arg Glu Glu Val Lys Gly Asn Thr Pro Gly Leu Thr Asp Leu Met Val
65                  70                  75                  80

Arg Trp Val Lys Glu Asp Pro Tyr Leu Ala Ala Lys Thr Gly Tyr Gln
                85                  90                  95

Gly Lys Ile Pro Asn Asp Leu Pro Phe Glu Pro Lys Phe His Val Glu
            100                 105                 110

Leu Gly Ala Gln Phe Asp Asp Phe Lys Lys Trp Leu Asp Thr Ala Gln
        115                 120                 125

Ser Lys Glu Leu Leu Thr His Thr Arg Leu Asp Glu Gln Asn Lys Gln
    130                 135                 140

Val His Leu Gly Tyr Ser Tyr Asn Glu Leu Leu Asp Met Thr Gly Val
145                 150                 155                 160

Glu Ser Val Gln Met Ala Val Tyr Phe Leu Lys Glu Ala Ala Lys Gln
                165                 170                 175

Ala Glu Pro Gly Ser Thr Lys Ser Gln Glu Asp Ile Leu Leu His Arg
            180                 185                 190

Phe Ala Asn Pro Thr Tyr Leu Ala Gln Leu Glu His Ser Arg Leu Ala
        195                 200                 205

Gln Ile Glu Ala Ile Tyr His Ser Ser His Asp Thr
    210                 215                 220


<210> SEQ ID NO 23
<211> LENGTH: 542
<212> TYPE: PRT
<213> ORGANISM: Photorhabdus asymbiotica

<400> SEQUENCE: 23

Met Val Phe Glu His Asp Lys Thr Val Glu Arg Lys Arg Lys Pro Ser
1               5                   10                  15

Ile Gln Leu Gly Asn Asp Lys Glu Lys Ser Ser Glu Gln Ala Leu Glu
            20                  25                  30

Leu Pro Gln Ser Lys Gln Asn Asn Pro Leu Leu His Asp Leu Ile Thr
        35                  40                  45

Ser Asn Asn Leu Arg Lys Glu Ala Ala Val Phe Ala Lys Gln Ile Gly
    50                  55                  60

Pro Ser Tyr Gln Gly Ile Leu Asp Gly Leu Glu His Leu His Asn Leu
65                  70                  75                  80

Ser Gly Asn Glu Gln Leu Thr Ala Gly Phe Glu Leu His Arg Arg Ile
                85                  90                  95

Thr Arg Tyr Leu Glu Glu His Pro Asp Ser Lys Arg Asn Ala Ala Leu
            100                 105                 110

Arg Arg Thr Gln Thr Gln Leu Gly Asp Leu Met Phe Thr Gly Thr Leu
        115                 120                 125

Gln Glu Val Arg His Pro Leu Leu Glu Met Ala Glu Thr Arg Pro Ala
    130                 135                 140

Met Ala Ser Gln Ile Tyr Gln Ile Ala Arg Asp Glu Ala Lys Gly Asn
```

-continued

```
145                 150                 155                 160

Thr Pro Gly Leu Thr Asp Leu Met Val Arg Trp Val Lys Glu Asp Pro
                165                 170                 175

Tyr Leu Ala Ala Lys Ser Gly Tyr Gln Gly Lys Ile Pro Asn Asp Leu
            180                 185                 190

Pro Phe Glu Pro Lys Phe His Val Glu Leu Gly Asp Gln Phe Gly Glu
        195                 200                 205

Phe Lys Thr Trp Leu Asp Thr Ala Gln Asn Gln Gly Leu Leu Thr His
    210                 215                 220

Thr Arg Leu Asp Glu Gln Asn Lys Gln Val His Leu Gly Tyr Ser Tyr
225                 230                 235                 240

Asn Glu Leu Leu Asp Met Thr Gly Gly Val Glu Ser Val Lys Met Ala
                245                 250                 255

Val Tyr Phe Leu Lys Glu Ala Ala Lys Gln Ala Glu Pro Gly Ser Ala
            260                 265                 270

Lys Ser Gln Glu Ala Ile Leu Leu Asn Arg Phe Ala Asn Pro Ala Tyr
        275                 280                 285

Leu Thr Gln Leu Glu Gln Gly Arg Leu Ala Gln Met Glu Ala Ile Tyr
    290                 295                 300

His Ser Ser His Asn Thr Asp Val Ala Ala Trp Asp Gln Gln Phe Ser
305                 310                 315                 320

Pro Asp Ala Leu Thr Gln Phe Asn His Gln Leu Asp Asn Ser Val Asp
                325                 330                 335

Leu Asn Ser Gln Leu Ser Phe Leu Leu Lys Asp Arg Gln Gly Leu Leu
            340                 345                 350

Ile Gly Glu Ser His Gly Ser Asp Leu Asn Gly Leu Arg Phe Val Glu
        355                 360                 365

Glu Gln Met Asp Ala Leu Lys Ala His Gly Val Thr Val Ile Gly Leu
    370                 375                 380

Glu His Leu Arg Ser Asp Leu Ala Gln Pro Leu Ile Asp Lys Phe Leu
385                 390                 395                 400

Thr Ser Glu Asn Glu Pro Met Pro Ala Glu Leu Ala Ala Met Leu Lys
                405                 410                 415

Thr Lys His Leu Ser Val Asn Leu Phe Glu Gln Ala Arg Ser Lys Gln
            420                 425                 430

Met Lys Ile Ile Ala Leu Asp Asn Asn Ser Thr Thr Arg Pro Ala Glu
        435                 440                 445

Gly Glu His Ser Leu Met Tyr Arg Ala Gly Ala Ala Asn Asn Val Ala
    450                 455                 460

Val Glu Arg Leu Gln Gln Leu Pro Ala Glu Glu Lys Phe Val Ala Ile
465                 470                 475                 480

Tyr Gly Asn Ala His Leu Gln Ser His Glu Gly Ile Asp His Phe Leu
                485                 490                 495

Pro Gly Ile Thr His Arg Leu Gly Leu Pro Ala Leu Lys Val Asp Glu
            500                 505                 510

Asn Asn Arg Phe Thr Ala Gln Ala Asp Asn Ile Asn Gln Arg Lys Cys
        515                 520                 525

Tyr Asp Asp Val Val Glu Val Ser Arg Ile Gln Leu Thr Ser
    530                 535                 540
```

<210> SEQ ID NO 24
<211> LENGTH: 221
<212> TYPE: PRT
<213> ORGANISM: Photorhabdus asymbiotica

<400> SEQUENCE: 24

Phe Glu Leu His Arg Arg Ile Thr Arg Tyr Leu Glu Glu His Pro Asp
1               5                   10                  15

Ser Lys Arg Asn Ala Ala Leu Arg Arg Thr Gln Thr Gln Leu Gly Asp
            20                  25                  30

Leu Met Phe Thr Gly Thr Leu Gln Glu Val Arg His Pro Leu Leu Glu
        35                  40                  45

Met Ala Glu Thr Arg Pro Ala Met Ala Ser Gln Ile Tyr Gln Ile Ala
    50                  55                  60

Arg Asp Glu Ala Lys Gly Asn Thr Pro Gly Leu Thr Asp Leu Met Val
65                  70                  75                  80

Arg Trp Val Lys Glu Asp Pro Tyr Leu Ala Ala Lys Ser Gly Tyr Gln
                85                  90                  95

Gly Lys Ile Pro Asn Asp Leu Pro Phe Glu Pro Lys Phe His Val Glu
            100                 105                 110

Leu Gly Asp Gln Phe Gly Glu Phe Lys Thr Trp Leu Asp Thr Ala Gln
        115                 120                 125

Asn Gln Gly Leu Leu Thr His Thr Arg Leu Asp Glu Gln Asn Lys Gln
    130                 135                 140

Val His Leu Gly Tyr Ser Tyr Asn Glu Leu Leu Asp Met Thr Gly Gly
145                 150                 155                 160

Val Glu Ser Val Lys Met Ala Val Tyr Phe Leu Lys Glu Ala Ala Lys
                165                 170                 175

Gln Ala Glu Pro Gly Ser Ala Lys Ser Gln Glu Ala Ile Leu Leu Asn
            180                 185                 190

Arg Phe Ala Asn Pro Ala Tyr Leu Thr Gln Leu Glu Gln Gly Arg Leu
        195                 200                 205

Ala Gln Met Glu Ala Ile Tyr His Ser Ser His Asn Thr
    210                 215                 220

<210> SEQ ID NO 25
<211> LENGTH: 504
<212> TYPE: PRT
<213> ORGANISM: Yersinia kristensenii

<400> SEQUENCE: 25

Ile Glu Ser Asn Val Ile Ile Ser Lys Asp Glu Leu Lys Lys Gln Ala
1               5                   10                  15

Ser Val Met Gly Lys Pro Ile Gly Tyr Ser Tyr Lys Lys Ile Leu Asn
            20                  25                  30

Ile Ile Asp Leu Ile Asn Ser Thr Ser Asn Ser Glu Arg Ile Lys Asn
        35                  40                  45

Ile Phe Ile Leu Lys Ser Glu Ile Glu Arg Tyr Ile Asn Glu His Pro
    50                  55                  60

Ser Ser Gly Arg Asn Lys Ala Phe Leu Thr Leu Gly Glu Lys Ile Asp
65                  70                  75                  80

Lys Ser Leu Phe Asn Ser Lys Met Gln Pro Ala Lys Asn Ala Ile Leu
                85                  90                  95

Arg Leu Ser Lys Thr Gln Pro Glu Met Ala Ala Arg Leu Tyr Glu Val
            100                 105                 110

Ala Ala Arg Glu Ser Gln Gly Ser His Val Gly Leu Thr Asn Met Met
        115                 120                 125

His Val Trp Ile Ser Glu Asp Gly Tyr Leu Thr Leu Leu Lys Gly Phe
    130                 135                 140

Glu Gly Lys Ile Pro Asp Arg Asn Leu Leu Asn Phe Asp Pro Thr Tyr
145 150 155 160

His Ile Ala Thr Gly Asp Gln Phe Asp Glu Cys Lys Thr Lys Leu Leu
165 170 175

Gln Ala Gln Ser Asn Gly Glu Leu Arg Gln Val Tyr Ile Asn Glu Ser
180 185 190

Thr Arg Ser Phe Thr Ile Gly Tyr Thr Tyr Glu Glu Met Ala Ser Phe
195 200 205

Arg Ala Arg Gly Ser Glu Asn Ser Gln Phe Phe Ser Tyr Ile Leu Asn
210 215 220

Glu Val Ala Gly Arg Asn Asn Ser Thr Asp Arg Ser Lys Glu Leu Asn
225 230 235 240

Trp Leu Asp Asn Cys Ala Asp Lys Lys Phe Leu Lys Gln Leu Gln Leu
245 250 255

Ser Arg Leu Asp Gln Ile Glu Ser Ile Tyr Gln Arg Asn Asn Lys Ile
260 265 270

Asp Phe Ala Ser Trp Asp Ser Lys Tyr Ser Gly Ile Ser Arg Asp Arg
275 280 285

Ile Asn Arg Glu Leu Asn Gln Tyr Gly Asp Val Asp Gly Gln Leu Ser
290 295 300

Val Leu Leu Arg Gly Asn Gln Gly Leu Leu Ile Gly Glu Thr His Gly
305 310 315 320

Ser Gln Glu Glu Gly Arg Arg Phe Ile Ile Glu Gln Ile Ser Glu Leu
325 330 335

Lys Arg His Gly Val Thr Thr Ile Gly Leu Glu His Leu Arg Arg Asp
340 345 350

His Ile Gln Pro Leu Ile Asp Asp Tyr Tyr Arg Thr Gly Val Ile Ser
355 360 365

Pro Asp Leu Asn Thr Phe Leu Thr Ala Lys Gly Val Lys Asn Ile Val
370 375 380

Thr Thr Ala Phe Glu Asn Lys Val Lys Ile Ile Phe Leu Asp Asp Asn
385 390 395 400

Ser Thr Ser Lys Gly Ser Gly Asn His Ser Leu Met Tyr Arg Ala Gly
405 410 415

Ser Ala Asn Asn Ile Ala Val Asp Ile Leu Lys Gln Ile Pro Ala Asn
420 425 430

Glu Lys Phe Val Val Ile Tyr Gly Glu Ala His Leu Lys Ser His Ile
435 440 445

Gly Ile Glu Ser Pro Val Ser Gly Ile Ser His Gln Met Lys Leu Pro
450 455 460

Ile Leu Gln Val Asp Ala Asn Asn Arg Leu Thr Val Ser Ala Asp Asp
465 470 475 480

Pro Thr Gln Arg Thr Ile Tyr Pro Arg Asn Asn Thr Thr Gly Ser Pro
485 490 495

Arg Ile Ile Phe Pro Ala Thr Leu
500

<210> SEQ ID NO 26
<211> LENGTH: 189
<212> TYPE: PRT
<213> ORGANISM: Yersinia kristensenii

<400> SEQUENCE: 26

Phe Asn Ser Lys Met Gln Pro Ala Lys Asn Ala Ile Leu Arg Leu Ser

-continued

```
1               5                   10                  15

Lys Thr Gln Pro Glu Met Ala Ala Arg Leu Tyr Glu Val Ala Ala Arg
            20                  25                  30

Glu Ser Gln Gly Ser His Val Gly Leu Thr Asn Met Met His Val Trp
        35                  40                  45

Ile Ser Glu Asp Gly Tyr Leu Thr Leu Leu Lys Gly Phe Glu Gly Lys
    50                  55                  60

Ile Pro Asp Arg Asn Leu Leu Asn Phe Asp Pro Thr Tyr His Ile Ala
65                  70                  75                  80

Thr Gly Asp Gln Phe Asp Glu Cys Lys Thr Lys Leu Leu Gln Ala Gln
                85                  90                  95

Ser Asn Gly Glu Leu Arg Gln Val Tyr Ile Asn Glu Ser Thr Arg Ser
            100                 105                 110

Phe Thr Ile Gly Tyr Thr Tyr Glu Glu Met Ala Ser Phe Arg Ala Arg
        115                 120                 125

Gly Ser Glu Asn Ser Gln Phe Phe Ser Tyr Ile Leu Asn Glu Val Ala
    130                 135                 140

Gly Arg Asn Asn Ser Thr Asp Arg Ser Lys Glu Leu Asn Trp Leu Asp
145                 150                 155                 160

Asn Cys Ala Asp Lys Lys Phe Leu Lys Gln Leu Gln Leu Ser Arg Leu
                165                 170                 175

Asp Gln Ile Glu Ser Ile Tyr Gln Arg Asn Asn Lys Ile
            180                 185
```

<210> SEQ ID NO 27
<211> LENGTH: 510
<212> TYPE: PRT
<213> ORGANISM: Pasteurella multocida

<400> SEQUENCE: 27

```
Ile Gly Leu Glu Gly Val Trp Thr Pro Glu Val Leu Lys Ala Arg Ala
1               5                   10                  15

Ser Val Ile Gly Lys Pro Ile Gly Glu Ser Tyr Lys Arg Ile Leu Ala
            20                  25                  30

Lys Leu Gln Arg Ile His Asn Ser Asn Ile Leu Asp Glu Arg Gln Gly
        35                  40                  45

Leu Met His Glu Leu Met Glu Leu Ile Asp Leu Tyr Glu Glu Ser Gln
    50                  55                  60

Pro Ser Ser Glu Arg Leu Asn Ala Phe Arg Glu Leu Arg Thr Gln Leu
65                  70                  75                  80

Glu Lys Ala Leu Tyr Leu Pro Glu Met Glu Ala Leu Lys Lys Gln Ile
                85                  90                  95

Leu Gln Ile Pro Asn Lys Gly Ser Gly Ala Ala Arg Phe Leu Leu Arg
            100                 105                 110

Thr Ala Met Asn Glu Met Ala Gly Lys Thr Ser Glu Ser Thr Ala Asp
        115                 120                 125

Leu Ile Arg Phe Ala Leu Gln Asp Thr Val Ile Ser Ala Pro Phe Arg
    130                 135                 140

Gly Tyr Ala Gly Ala Ile Pro Glu Ala Ile Asp Phe Pro Val Lys Tyr
145                 150                 155                 160

Val Ile Glu Asp Ile Ser Val Phe Asp Lys Ile Gln Thr Asn Tyr Trp
                165                 170                 175

Glu Leu Pro Ala Tyr Glu Ser Trp Asn Glu Gly Ser Asn Ser Ala Leu
            180                 185                 190
```

-continued

```
Leu Pro Gly Leu Leu Arg Glu Ser Gln Ser Lys Gly Met Leu Ser Lys
        195                 200                 205

Cys Arg Ile Ile Glu Asn Ser Leu Tyr Ile Gly His Ser Tyr Glu Glu
    210                 215                 220

Met Phe Tyr Ser Ile Ser Pro Tyr Ser Asn Gln Val Gly Gly Pro Tyr
225                 230                 235                 240

Glu Leu Tyr Pro Phe Thr Phe Phe Ser Met Leu Gln Glu Val Gln Gly
                245                 250                 255

Asp Leu Gly Phe Glu Gln Ala Phe Ala Thr Arg Asn Tyr Phe Asn Thr
            260                 265                 270

Leu Val Ser Asp Arg Leu Ser Leu Met Glu Asn Thr Met Leu Leu Thr
        275                 280                 285

Glu Ser Phe Asp Tyr Thr Pro Trp Asp Ala Ile Tyr Gly Asp Ile Asn
    290                 295                 300

Tyr Asp Glu Gln Phe Ala Ala Met Ser Ile Asn Glu Arg Ile Glu Lys
305                 310                 315                 320

Cys Met Asn Thr Tyr Arg Gly Val Ala Phe Gln Asn Ser Ser Lys Ser
                325                 330                 335

Ile Asp Phe Phe Leu Asn Asn Leu Thr Thr Phe Ile Asp Asn Gly Leu
            340                 345                 350

Thr Glu Ile Ala Ile Ser Asp Leu Pro Tyr Asp Ile Val Gln Gln Glu
        355                 360                 365

Ile Ser Gln Phe Leu Gln Gly Ser Asn Glu Trp Lys Thr Leu Asp Ala
    370                 375                 380

Met Leu Phe Asn Leu Asp Lys Gly Asp Ile Asn Gly Ala Phe Arg Lys
385                 390                 395                 400

Leu Leu Gln Ser Ala Lys Asp Asn Asn Ile Lys Phe Arg Ala Ile Gly
                405                 410                 415

His Ser Asp Asn Ser Val Pro Pro Phe Asn Asn Pro Tyr Lys Ser Leu
            420                 425                 430

Tyr Tyr Lys Gly Asn Ile Ile Ala Glu Ala Ile Glu Lys Leu Asp Arg
        435                 440                 445

Glu Gly Gln Lys Phe Val Val Phe Ala Asp Ser Ser Leu Leu Asn Ser
    450                 455                 460

Thr Pro Gly Thr Gly Arg Pro Met Pro Gly Leu Val Gln Tyr Leu Lys
465                 470                 475                 480

Ile Pro Ala Thr Val Val Asp Ser Asp Gly Ala Trp Gln Phe Leu Pro
                485                 490                 495

Asp Val Ala Ser Ser Arg Val Pro Ile Glu Val Thr Glu Leu
            500                 505                 510


<210> SEQ ID NO 28
<211> LENGTH: 207
<212> TYPE: PRT
<213> ORGANISM: Pasteurella multocida

<400> SEQUENCE: 28

Tyr Leu Pro Glu Met Glu Ala Leu Lys Lys Gln Ile Leu Gln Ile Pro
1               5                   10                  15

Asn Lys Gly Ser Gly Ala Ala Arg Phe Leu Leu Arg Thr Ala Met Asn
            20                  25                  30

Glu Met Ala Gly Lys Thr Ser Glu Ser Thr Ala Asp Leu Ile Arg Phe
        35                  40                  45

Ala Leu Gln Asp Thr Val Ile Ser Ala Pro Phe Arg Gly Tyr Ala Gly
    50                  55                  60
```

```
Ala Ile Pro Glu Ala Ile Asp Phe Pro Val Lys Tyr Val Ile Glu Asp
65                  70                  75                  80

Ile Ser Val Phe Asp Lys Ile Gln Thr Asn Tyr Trp Glu Leu Pro Ala
                85                  90                  95

Tyr Glu Ser Trp Asn Glu Gly Ser Asn Ser Ala Leu Leu Pro Gly Leu
            100                 105                 110

Leu Arg Glu Ser Gln Ser Lys Gly Met Leu Ser Lys Cys Arg Ile Ile
        115                 120                 125

Glu Asn Ser Leu Tyr Ile Gly His Ser Tyr Glu Glu Met Phe Tyr Ser
    130                 135                 140

Ile Ser Pro Tyr Ser Asn Gln Val Gly Gly Pro Tyr Glu Leu Tyr Pro
145                 150                 155                 160

Phe Thr Phe Phe Ser Met Leu Gln Glu Val Gln Gly Asp Leu Gly Phe
                165                 170                 175

Glu Gln Ala Phe Ala Thr Arg Asn Tyr Phe Asn Thr Leu Val Ser Asp
            180                 185                 190

Arg Leu Ser Leu Met Glu Asn Thr Met Leu Leu Thr Glu Ser Phe
        195                 200                 205


<210> SEQ ID NO 29
<211> LENGTH: 9
<212> TYPE: PRT
<213> ORGANISM: Influenza virus

<400> SEQUENCE: 29

Tyr Pro Tyr Asp Val Pro Asp Tyr Ala
1               5


<210> SEQ ID NO 30
<211> LENGTH: 33
<212> TYPE: DNA
<213> ORGANISM: Artificial
<220> FEATURE:
<223> OTHER INFORMATION: Forward primer for amplying rtxA1 gene of
      Vibrio vulnificus

<400> SEQUENCE: 30

aaggtaccgt ttatcggtaa gatgcaagtt gcc                                33


<210> SEQ ID NO 31
<211> LENGTH: 32
<212> TYPE: DNA
<213> ORGANISM: Artificial
<220> FEATURE:
<223> OTHER INFORMATION: Reverse primer for amplying rtxA1 gene of
      Vibrio vulnificus

<400> SEQUENCE: 31

agaattctca caaactgccc ttgaacgtga tc                                 32


<210> SEQ ID NO 32
<211> LENGTH: 30
<212> TYPE: DNA
<213> ORGANISM: Artificial
<220> FEATURE:
<223> OTHER INFORMATION: Forward primer for amplying rtxA1 gene of
      Vibrio vulnificus

<400> SEQUENCE: 32

aaggtaccgg gtgataaaac caaggtcgtg                                     30
```

<210> SEQ ID NO 33
<211> LENGTH: 30
<212> TYPE: DNA
<213> ORGANISM: Artificial
<220> FEATURE:
<223> OTHER INFORMATION: Reverse primer for amplying rtxA1 gene of
Vibrio vulnificus

<400> SEQUENCE: 33
aaggtaccgg atattgacgc ttgggatcgt 30

<210> SEQ ID NO 34
<211> LENGTH: 169
<212> TYPE: DNA
<213> ORGANISM: Artificial
<220> FEATURE:
<223> OTHER INFORMATION: Coding sequence for mutant form of Vibrio
vulnificus DUF5 polypeptide having D3721R/R3841D mutations

<400> SEQUENCE: 34
atctttatgg tcgcgattga agaagccaac ggtaaacacg taggtttgac ggacatgatg 60
gttcgttggg ccaatgaaga accatacttg gcaccgaagc atggttacaa aggcgaaacg 120
ccaagtgacc ttggttttga tgcgaagtac cacgtagatc taggtgagc 169

<210> SEQ ID NO 35
<211> LENGTH: 43
<212> TYPE: DNA
<213> ORGANISM: Artificial
<220> FEATURE:
<223> OTHER INFORMATION: Forward primer for amplifying coding sequence
of Vibrio vulnificus DUF5

<400> SEQUENCE: 35
tacttccaat ccaatgctca agagctgaaa gaaagagcaa aag 43

<210> SEQ ID NO 36
<211> LENGTH: 43
<212> TYPE: DNA
<213> ORGANISM: Artificial
<220> FEATURE:
<223> OTHER INFORMATION: Reverse primer for amplifying coding sequence
of Vibrio vulnificus DUF5

<400> SEQUENCE: 36
tacttccaat ccaatgctca agagctgaaa gaaagagcaa aag 43

<210> SEQ ID NO 37
<211> LENGTH: 43
<212> TYPE: DNA
<213> ORGANISM: Artificial
<220> FEATURE:
<223> OTHER INFORMATION: Forward primer for amplifying coding sequence
for DUF5 polypeptide of Vibrio vulnificus

<400> SEQUENCE: 37
tacttccaat ccaatgctca agagctgaaa gaaagagcaa aag 43

<210> SEQ ID NO 38
<211> LENGTH: 38
<212> TYPE: DNA
<213> ORGANISM: Artificial
<220> FEATURE:
<223> OTHER INFORMATION: Reverse primer for amplifying coding sequence
for DUF5 polypeptide of Vibrio vulnificus

<400> SEQUENCE: 38

-continued ttatccactt ccaatgctac aaactgccct tgaacgtg 38

<210> SEQ ID NO 39
<211> LENGTH: 39
<212> TYPE: DNA
<213> ORGANISM: Artificial
<220> FEATURE:
<223> OTHER INFORMATION: Forward primer for amplifying coding sequence for DUF5 polypeptide of Aeromonas hydrophila

<400> SEQUENCE: 39
tacttccaat ccaatgctcc gggcaaaacg gtggtgacg 39

<210> SEQ ID NO 40
<211> LENGTH: 41
<212> TYPE: DNA
<213> ORGANISM: Artificial
<220> FEATURE:
<223> OTHER INFORMATION: Reverse primer for amplifying coding sequence for DUF5 polypeptide of Aeromonas hydrophila

<400> SEQUENCE: 40
ttatccactt ccaatgctag acatcggcgt actcgacccg c 41

<210> SEQ ID NO 41
<211> LENGTH: 42
<212> TYPE: DNA
<213> ORGANISM: Artificial
<220> FEATURE:
<223> OTHER INFORMATION: Forward primer for amplifying coding sequence for DUF5 polypeptide of Photorabdus asymbiotica

<400> SEQUENCE: 41
tacttccaat ccaatgctcc attactccat gacctcatca cc 42

<210> SEQ ID NO 42
<211> LENGTH: 40
<212> TYPE: DNA
<213> ORGANISM: Artificial
<220> FEATURE:
<223> OTHER INFORMATION: Reverse primer for amplifying coding sequence for DUF5 polypeptide of Photorabdus asymbiotica

<400> SEQUENCE: 42
ttatccactt ccaatgctac acatcatcat aacacttgcg 40

<210> SEQ ID NO 43
<211> LENGTH: 53
<212> TYPE: DNA
<213> ORGANISM: Artificial
<220> FEATURE:
<223> OTHER INFORMATION: Forward primer for amplifying coding sequence of human KRAS

<400> SEQUENCE: 43
tacttccaat ccaatgctat gactgaatat aaacttgtgg tagttggagc tgg 53

<210> SEQ ID NO 44
<211> LENGTH: 56
<212> TYPE: DNA
<213> ORGANISM: Artificial
<220> FEATURE:
<223> OTHER INFORMATION: Reverse primer for amplifying coding sequence of human KRAS

<400> SEQUENCE: 44
ttatccactt ccaatgctac ataattacac actttgtctt tgacttcttt ttcttc 56

<210> SEQ ID NO 45
<211> LENGTH: 45
<212> TYPE: DNA
<213> ORGANISM: Artificial
<220> FEATURE:
<223> OTHER INFORMATION: Forward primer for amplifying coding sequence of human HRAS

<400> SEQUENCE: 45
tacttccaat ccaatgctat gacggaatat aagctggtgg tggtg 45

<210> SEQ ID NO 46
<211> LENGTH: 41
<212> TYPE: DNA
<213> ORGANISM: Artificial
<220> FEATURE:
<223> OTHER INFORMATION: Reverse primer for amplifying coding sequence of human HRAS

<400> SEQUENCE: 46
ttatccactt ccaatgctag gagagcacac acttgcagct c 41

<210> SEQ ID NO 47
<211> LENGTH: 43
<212> TYPE: DNA
<213> ORGANISM: Artificial
<220> FEATURE:
<223> OTHER INFORMATION: Forward primer for amplifying coding sequence of human NRAS

<400> SEQUENCE: 47
tacttccaat ccaatgctat gactgagtac aaactggtgg tgg 43

<210> SEQ ID NO 48
<211> LENGTH: 41
<212> TYPE: DNA
<213> ORGANISM: Artificial
<220> FEATURE:
<223> OTHER INFORMATION: Reverse primer for amplifying coding sequence of human NRAS

<400> SEQUENCE: 48
ttatccactt ccaatgctac atcaccacac atggcaatcc c 41

<210> SEQ ID NO 49
<211> LENGTH: 40
<212> TYPE: DNA
<213> ORGANISM: Artificial
<220> FEATURE:
<223> OTHER INFORMATION: Forward primer for amplifying human EGF

<400> SEQUENCE: 49
gcttcgaatt ctgcacccgg gtggtctggt tccgcgtgga 40

<210> SEQ ID NO 50
<211> LENGTH: 41
<212> TYPE: DNA
<213> ORGANISM: Artificial
<220> FEATURE:
<223> OTHER INFORMATION: Reverse primer for amplifying human EGF

<400> SEQUENCE: 50
ctagatccgg tggatcccct cagtggtggt ggtggtggtg c 41

<210> SEQ ID NO 51

<211> LENGTH: 31
<212> TYPE: DNA
<213> ORGANISM: Artificial
<220> FEATURE:
<223> OTHER INFORMATION: Forward primer for amplifying mutant human KRAS
having the G13D mutation

<400> SEQUENCE: 51
tagttggagc tggtgacgta ggcaagagtg c 31

<210> SEQ ID NO 52
<211> LENGTH: 31
<212> TYPE: DNA
<213> ORGANISM: Artificial
<220> FEATURE:
<223> OTHER INFORMATION: Reverse primer for amplifying mutant human KRAS
having the G13D mutation

<400> SEQUENCE: 52
gcactcttgc ctacgtcacc agctccaact a 31

<210> SEQ ID NO 53
<211> LENGTH: 42
<212> TYPE: DNA
<213> ORGANISM: Artificial
<220> FEATURE:
<223> OTHER INFORMATION: Forward primer for amplifying mutant human KRAS
having the Q61R mutation

<400> SEQUENCE: 53
gatattctcg acacagcagg tagagaggag tacagtgcaa tg 42

<210> SEQ ID NO 54
<211> LENGTH: 42
<212> TYPE: DNA
<213> ORGANISM: Artificial
<220> FEATURE:
<223> OTHER INFORMATION: Reverse primer for amplifying mutant human KRAS
having the Q61R mutation

<400> SEQUENCE: 54
cattgcactg tactcctctc tacctgctgt gtcgagaata tc 42

<210> SEQ ID NO 55
<211> LENGTH: 38
<212> TYPE: DNA
<213> ORGANISM: Artificial
<220> FEATURE:
<223> OTHER INFORMATION: Forward primer for applying rtxA1 gene of
Vibrio vulnificus

<400> SEQUENCE: 55
gagctagcat gggtgataaa accaaggtcg tggattta 38

<210> SEQ ID NO 56
<211> LENGTH: 39
<212> TYPE: DNA
<213> ORGANISM: Artificial
<220> FEATURE:
<223> OTHER INFORMATION: Reverse primer for amplifying rtxA1 gene of
Vibrio vulnificus

<400> SEQUENCE: 56
gccgtcgacc aaactgccct tgaacgtgat cttcggttt 39

<210> SEQ ID NO 57
<211> LENGTH: 190

<212> TYPE: PRT
<213> ORGANISM: Homo sapiens

<400> SEQUENCE: 57

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser Asn
            180                 185                 190

<210> SEQ ID NO 58
<211> LENGTH: 45
<212> TYPE: DNA
<213> ORGANISM: Vibrio vulnificus

<400> SEQUENCE: 58
tacttccaat ccaatgctga taaaaccaag gtcgtggtcg attta                      45

<210> SEQ ID NO 59
<211> LENGTH: 37
<212> TYPE: DNA
<213> ORGANISM: Vibrio vulnificus

<400> SEQUENCE: 59
ttatccaatg tgaaagagcg gtatttgcgc cactcaa                               37

<210> SEQ ID NO 60
<211> LENGTH: 11
<212> TYPE: PRT
<213> ORGANISM: Homo sapiens

<400> SEQUENCE: 60

Glu Lys Tyr Asp Pro Thr Ile Glu Asp Ser Tyr
1               5                   10

<210> SEQ ID NO 61
<211> LENGTH: 11
<212> TYPE: PRT
<213> ORGANISM: Homo sapiens

<400> SEQUENCE: 61

-continued

Glu Lys Tyr Asp Pro Thr Ile Glu Asp Phe Tyr
1 5 10

<210> SEQ ID NO 62
<211> LENGTH: 11
<212> TYPE: PRT
<213> ORGANISM: Homo sapiens

<400> SEQUENCE: 62

Asp Tyr His Asp Pro Thr Ile Glu Asp Ala Tyr
1 5 10

<210> SEQ ID NO 63
<211> LENGTH: 11
<212> TYPE: PRT
<213> ORGANISM: Homo sapiens

<400> SEQUENCE: 63

Glu Asp His Asp Pro Thr Ile Glu Asp Ala Tyr
1 5 10

<210> SEQ ID NO 64
<211> LENGTH: 11
<212> TYPE: PRT
<213> ORGANISM: Homo sapiens

<400> SEQUENCE: 64

Asp Ser Tyr Asp Pro Thr Ile Glu Asn Thr Phe
1 5 10

<210> SEQ ID NO 65
<211> LENGTH: 11
<212> TYPE: PRT
<213> ORGANISM: Homo sapiens

<400> SEQUENCE: 65

Glu Gly Tyr Asp Pro Thr Val Glu Asn Thr Tyr
1 5 10

<210> SEQ ID NO 66
<211> LENGTH: 11
<212> TYPE: PRT
<213> ORGANISM: Homo sapiens

<400> SEQUENCE: 66

Glu Asp Tyr Glu Pro Thr Lys Ala Asp Ser Tyr
1 5 10

<210> SEQ ID NO 67
<211> LENGTH: 11
<212> TYPE: PRT
<213> ORGANISM: Homo sapiens

<400> SEQUENCE: 67

Ser Glu Tyr Val Pro Thr Val Phe Asp Asn Tyr
1 5 10

<210> SEQ ID NO 68
<211> LENGTH: 11
<212> TYPE: PRT
<213> ORGANISM: Homo sapiens

<400> SEQUENCE: 68

Gly Glu Tyr Ile Pro Thr Val Phe Asp Asn Tyr

-continued

```
1               5                   10


<210> SEQ ID NO 69
<211> LENGTH: 11
<212> TYPE: PRT
<213> ORGANISM: Homo sapiens

<400> SEQUENCE: 69

Glu Val Tyr Val Pro Thr Val Phe Glu Asn Tyr
1               5                   10


<210> SEQ ID NO 70
<211> LENGTH: 11
<212> TYPE: PRT
<213> ORGANISM: Homo sapiens

<400> SEQUENCE: 70

Asp Asp Ser Asn His Thr Ile Gly Val Glu Phe
1               5                   10


<210> SEQ ID NO 71
<211> LENGTH: 11
<212> TYPE: PRT
<213> ORGANISM: Homo sapiens

<400> SEQUENCE: 71

Leu Glu Ser Lys Ser Thr Ile Gly Val Glu Phe
1               5                   10


<210> SEQ ID NO 72
<211> LENGTH: 10
<212> TYPE: PRT
<213> ORGANISM: Homo sapiens

<400> SEQUENCE: 72

Thr Thr Ile Pro Thr Ile Gly Phe Asn Val
1               5                   10


<210> SEQ ID NO 73
<211> LENGTH: 11
<212> TYPE: PRT
<213> ORGANISM: Homo sapiens

<400> SEQUENCE: 73

Lys Lys Tyr Val Ala Thr Leu Gly Val Glu Val
1               5                   10
```

BACTERIAL TOXINS AND USES THEREOF AS Ras SPECIFIC PROTEASES FOR TREATING CELL PROLIFERATION DISEASES AND DISORDERS

CROSS-REFERENCE TO RELATED PATENT APPLICATIONS

This application is a continuation-in-part of U.S. application Ser. No. 17/093,628 filed Nov. 9, 2020, which is a continuation of U.S. application Ser. No. 15/957,396 filed Apr. 19, 2018, granted as U.S. Pat. No. 10,829,752 on Nov. 10, 2020, which claims the benefit of priority to U.S. Provisional Application 62/487,217, filed Apr. 19, 2017. U.S. application Ser. No. 15/957,396 is also a continuation-in-part of U.S. application Ser. No. 14/816,724, filed Aug. 3, 2015, which claims the benefit of priority to U.S. Provisional Applications 62/032,330, filed Aug. 1, 2014, and 62/172,432, filed Jun. 8, 2015. This application also claims the benefit of priority to U.S. Provisional Application 63/190,779, filed May 19, 2021. The contents of each application are incorporated herein by reference in their entireties.

STATEMENT REGARDING FEDERALLY SPONSORED RESEARCH OR DEVELOPMENT

This invention was made with government support under grant numbers RO1 AI092825 and RO1 AI098369 awarded by the National Institutes of Health. The government has certain rights in the invention.

REFERENCE TO AN ELECTRONIC SEQUENCE LISTING

This application is being filed electronically via EFS-Web and includes an electronically submitted Sequence Listing in .txt format. The contents of the electronic sequence listing (70258102152 ST25.txt; Size 99,201 bytes and Date of Creation: Apr. 30, 2025) is herein incorporated by reference in its entirety.

BACKGROUND

The field of the invention relates to bacterial toxins. In particular, the field of the invention relates to bacterial toxins that are specific proteases for Ras sarcoma oncoproteins (Ras) and uses therefor for treating Ras-dependent diseases and disorders.

Rat sarcoma (Ras) oncoproteins (e.g., KRas, HRas, and NRas) regulate cell growth, differentiation, and survival by mediating specific signal transduction within cells. Mutational activation of Ras genes is associated with 33% of human cancers, making it one of the most frequent oncogenic mutations. Cancer research has focused on developing several strategies to block mutant Ras and to inhibit the over-activation of the downstream signaling. However, three decades after the discovery of Ras, no drugs or therapeutics that target Ras proteins directly or act on Ras-driven human cancers have been developed successfully.

Here, we discovered a novel protease that cleaves Ras. This protein, known as domain of unknown function in the fifth position (DUF5) otherwise known as Rasaap1-specific endopeptidase (RRSP), is an effector domain of the Multifunctional-Autoprocessing Repeats-in-Toxins (MARTX) family of bacterial toxins. The domain is present in the toxin secreted by some strains of the bacterial pathogen *Vibrio vulnificus*. This domain is also found in the MARTX toxin of other bacterial species and as a toxic domain unlinked to a MARTX toxin in other bacteria, revealing that cleavage of Ras is a conserved toxic function among various bacterial species.

When RRSP (DUF5) from *V. vulnificus* ($DUF5_{Vv}$) is released into the cytosol of eukaryotic cells by natural toxin delivery from the bacterium, by transient expression following DNA transfection, or by the anthrax lethal factor N-terminal domain-protective antigen ($LF_N$-PA) delivery system, it is able to block the Ras pathway, resulting in loss of cell proliferation. Here, we demonstrate, both in vitro and in vivo, that this block occurs because RRSP ($DUF5_{Vv}$) is an endopeptidase that cleaves Ras within Switch I, an essential loop for exchange of guanosine nucleotide diphosphate (GDP) with guanosine nucleotide triphosphate (GTP) to activate Ras and for the interaction with several Ras-binding partners. The binding of guanosine nucleosides and binding partners then regulate the Ras downstream pathways that control cell growth, motility, differentiation and response to cell stress.

Because in many cancers Ras is constitutively activated by specific mutations, developing treatments against tumors harboring Ras mutations remains one of the most challenging goals in modern medicine. The use of protein toxin-based therapeutic approaches is a consolidated and alternative way of treating cancer disease compared to conventional radiation or chemical therapy. Because $DUF5_{Vv}$ specifically cleaves Ras, including Ras mutant isoforms found in cancer cells, resulting in loss of proliferation, we have found that Ras/Rap1-specific endopeptidase (RSP, $DUF5_{Vv}$) and proteins similar to $DUF5_{Vv}$ can be used as the toxic component to create new conjugated toxin-based therapies for cancer treatment. In addition, $DUF5_{Vv}$ can be used as a cell biological reagent to rapidly eliminate Ras from cells for research or industrial purposes.

SUMMARY

Disclosed are bacterial toxins and uses thereof as specific proteases for Ras sarcoma oncoproteins (Ras proteins). The bacterial toxins may be modified for use as therapeutic polypeptides pharmaceutical agents for treating Ras-dependent diseases and disorders including cell proliferation diseases and disorders such as cancer. Such modification may include, for example, fusion proteins that are capable of translocating into a cell.

The disclosed bacterial toxins include Ras/Rapt-specific endopeptidase (RRSP, also known as DUF5 proteases) and portions thereof comprising active subdomains thereof such as C2A and/or C2B that exhibit protease activity for Ras proteins, and preferably which exhibit specific protease activity for Ras proteins. Active subdomains of RRSP (DUF5) that exhibit protease activity for Ras proteins may include the C2A subdomain and/or the C2B subdomain.

In some embodiments, the RRSP or portions thereof are fused to a bacteria toxin or bacterial toxin element that facilitates the transport of RRSP into a cell.

The disclosed bacterial toxins may be utilized in methods for treating a cell proliferative disease or disorder in a subject. Contemplated treatment methods may include administering a therapeutic polypeptide comprising a RRSP (DUF5) protease or an active portion thereof comprising the C2A subdomain and the C2B subdomain to the subject. Typically, the cell proliferative disease or disorder is associated with an activating mutation in a Ras protein and is a Ras-dependent cell proliferative disease or disorder such as a Ras-dependent cancer.

The disclosed bacterial toxins include the RRSP (DUF5), a homolog thereof, or an active portion thereof comprising the C2A subdomain and/or the C2B subdomain from a number of microorganisms. These include, but are not limited to *Vibrio vulnificus, Vibrio ordalii, Vibrio cholerae, Vibrio splendidus, Moritella dasanensis, Aeromonas salmonicida, Aeromonas hydrophila, Photorhabdus temperata, Xenorhabdus nematophila, Photorhabdus luminescens, Photorhabdus asymbiotica, Yersinia kristensenii*, and *Pasteurella multocida.*

The disclosed bacterial toxins may be formulated as therapeutic polypeptides for delivery to the cytosol of proliferating cells. In some embodiments of the therapeutic polypeptides, the RRSP (DUF5), a homolog thereof, or a portion thereof comprising the C2A subdomain and/or the C2B subdomain may be fused or complexed with a carrier that facilitates transport of the RRSP (DUF5), the homolog thereof, or the C2A subdomain and/or the C2B sub domain thereof into the cytosol of proliferating cells.

Pharmaceutical compositions and kits comprising the disclosed bacterial toxins for treating cell proliferative diseases or disorders also are contemplated herein. The compositions may include a therapeutic polypeptide comprising a DUF5 protease, a homolog thereof, or a portion thereof comprising the C2A subdomain and/or the C2B subdomain, and a carrier that facilitates transport of the DUF5 protease, the homolog thereof, or the portion thereof comprising the C2A subdomain and/or the C2B subdomain into the cytosol of proliferating cells. In the therapeutic polypeptides of the compositions and kits, the DUF5 protease, the homolog thereof, or the portion thereof comprising the C2A subdomain and/or the C2B subdomain may be fused or conjugated to the carrier or complexed with the carrier. Specifically contemplated are fusion proteins comprising the amino acid sequence of the disclosed bacterial toxins fused to the amino acid sequence of a carrier polypeptide that facilitates transport of the bacterial toxins into proliferating cells. Suitable protein carriers include bacterial toxin elements, including bacterial toxins and region or element that allow for translocation of the fusion polypeptide into a cell, for example, anthrax toxin lethal factor (LF), described more herein.

BRIEF DESCRIPTION OF THE FIGURES

FIG. 1A. Linear schematic shows the overall domain structure of the toxin with the pore forming conserved regions and the autoprocessing cysteine protease (CPD). The cytotoxic and cytopathic “effector domains” are DUF1, RID, ABH, MCF, and DUF5 are described in text. FIG. 1B. The current model for toxin assembly on the eukaryotic cell membrane to form a pore for translocation of the central domains. After being translocated, the CPD binds inositol hexakisphosphate (InsP6) to initiate autoprocessing between effector domains for release to the cytosol. The five domains are then free to access targets in the cell.

FIG. 3A. Western blot to detect total ERK1/2 (upper panels) or phosphor-ERK1/2 (lower panels). Cellular actin in whole cell lysate was used as the loading control. Prior to collection, HeLa cell were incubated for 24 hr with protective antigen (PA), the N-terminus of Lethal factor (LFn), DUF5$_{Vv}$ fused to anthrax toxin lethal factor (LF$_N$DUF5), or mixture of proteins as shown. FIG. 3B. GLISA activation assay (Cytoskeleton Inc) to quantify total active Ras in the GTP bound form (% active Ras) from Hela cell lysates intoxicated as in panel A. FIG. 3C. Detection of total Ras in cell lysates by western blot using Ras10 monoclonal antibody (upper panels). Detection with anti-actin antibody was used as the loading control.

FIG. 6A, FIG. 6B, and FIG. 6C illustrate that intoxication of cells with DUF5$_{Vv}$ results in truncation of H-Ras. FIG. 6A. HeLa cells were transfected to overexpress HA-tagged HRas and then intoxicated with LF$_N$DUF5$_{Vv}$/PA for 24 hr. HA-HRas was immunoprecipitated with anti-HA peptide agarose beads and bound protein was eluted from the bead, separated by SDS-PAGE and visualized using Coomassie Brilliant blue. FIG. 6B. The 18 kDa band was excised and subjected to peptide mapping by mass spectrometry. Peptides matched to H-Ras region shown in underline. FIG. 6C Western blot analysis on IP elution fractions using both anti-HA antibody to detect full length expression product and an antibody specific to C-terminus of H-Ras to verify this protein is H-Ras from which the N-terminus comprised of the HA and Ras10 epitopes is absent.

FIG. 15A. Scale drawing of *V. vulnificus* MARTX and *P. multocida* PMT protein toxins with enlarged region showing C1, C2A, and C2B domains that are shared between the two toxins. FIG. 15B, FIG. 15C, FIG. 15D, FIG. 15E, FIG. 15F illustrate epifluorescent and DIC images (200×) of HeLa epithelial cells transfected with pEGFP-N3 plasmid clones expressing EGFP (FIG. 15B), $DUF5_{Vv}$-EGFP (FIG. 15C, FIG. 15D, and FIG. 15E), or C1C2Pm-EGFP (FIG. 15F). Panels in FIG. 15D and FIG. 15E are enlarged 200% to show detail of localization of $DUF5_{Vv}$-EGFP and cell blebbing, respectively. Arrows in FIG. 15E indicate EGFP-positive cells in DIC only image. Percent of rounded cells in each cell type is quantified from three independent experiments (FIG. 15G) and expression of protein in transfected cells is shown by western blot detection using an anti-GFP antibody (FIG. 15H).

(FIG. 16A) Structural model of $DUF5_{Vv}$ generated in HHPRED and Modeller based on published structure of PMT. C1, C2A, and C2B subdomains are indicated. FIG. 16B, FIG. 16C, and FIG. 16D illustrate epifluorescent and DIC images (200×) of HeLa epithelial cells transfected with pEGFP-N3 plasmid clones expressing EGFP (FIG. 16B), $DUF5_{Vv}$-EGFP (FIG. 16C), or C2-EGFP (FIG. 16D). FIG. 16E is a Western blot confirming expression of EGFP (FIG. 16B), $DUF5_{Vv}$-EGFP (FIG. 16C), or C2-EGFP (FIG. 16D). FIG. 16F illustrates the percentage (%) of EGFP-positive cells exhibiting rounding.

(FIG. 17A). Schematic of proteins expressed in the panel. FIG. 17B, FIG. 17C, FIG. 17D, FIG. 17E, FIG. 17F, FIG. 17G, and FIG. 17H illustrate epifluorescent and DIC images (200×) of HeLa epithelial cells transfected with pEGFP-N3 plasmid clones expressing EGFP (B), $DUF5_{Vv}$-EGFP (FIG. 17C), C2-EGFP (FIG. 17D), C2A-EGFP (FIG. 17E) and C2B-EGFP (FIG. 17F). Average of percent rounded cells in each cell type is quantified from three independent experiments (FIG. 17G) and expression of protein in transfected cells is shown by western blot detection using and anti-GFP antibody (FIG. 17H). Note that C2A-EGFP could not be detected due to consistent poor sample recovery from plates due to toxicity of this domain. FIG. 17I, FIG. 17J, and FIG. 17K illustrate DIC images of HeLa cells intoxicated with 7 nM PA in combination with 3 nM purified unmodified LFN (I), LFN fused to $DUF5_{Vv}$ (FIG. 17J) and LFN fused to only the C1-C2A subdomains of $DUF5_{Vv}$ (FIG. 17K).

(FIG. 20A (EV, ACD, $DUF5_{VV}$, C2, C1/GFP), FIG. 20B (C2, C2A, and C2B), and FIG. 20C (C2, V3906*, and G3948*)).

FIG. 21C and FIG. 21D illustrate a structural model of $DUF5_{Vv}$ showing polar contacts of D3721 and R3841 and potential cross association of R3841 with S3986 in C2B. Panel E shows the purified 6×His-tagged DUF5 and DUF5 D3721A proteins that were used in FTS experiments to determine melting temperature in panel F.

FIG. 22A, FIG. 22B, FIG. 22C, FIG. 22D, and FIG. 22E illustrate DIC images of HeLa cells intoxicated for 24 h (upper) or 48 h (lower) with 7 nM PA in combination with 3 nM purified unmodified LFN (FIG. 22A), LFN fused to $DUF5_{Vv}$ (FIG. 22B) and LFN fused to only the C1-C2A subdomains of $DUF5_{Vv}$ (FIG. 22C), or LFN fused to only the C1-C2A subdomains of $DUF5_{Vv}$ with D3721 (FIG. 22D) or R3841 (FIG. 22E) point mutations. Protein purity was assessed by SDS-PAGE in FIG. 22F. Three independent experiments were performed and cells were manually counted (FIG. 22G).

FIG. 24A illustrates major categories of yeast mutants enabling growth in the presence of $DUF5_{Vv}$-C2. FIG. 24B and FIG. 24D provide representative immunoblots (n=3) of lysates prepared from cells treated for 24 h (FIG. 24B) or time indicated (FIG. 24D) with $LFNDUF5_{Vv}$ in the absence (−) or the presence (+) of PA. Trimmed ERK1/2 blots are shown unedited in FIG. 29. FIG. 24C and FIG. 24E illustrate clonogenic colony-formation assay (n=2) of cells treated for 24 (FIG. 24C) or 1 h (FIG. 24E). Error bars represent the range of the data.

FIG. 25A illustrates a coomassie-stained 18% SDS-polyacrylamide gel of anti-HA immunoprecipitated proteins from cells expressing HA-HRas treated for 24 h as indicated. Lower band (HRas*) was excised for peptide sequencing with HRas peptide coverage highlighted in yellow. FIG. 25B illustrates the same fractions probed by immunoblotting to detect the N terminus (anti-HA) and C terminus (isotype-specific antibody). FIG. 25C illustrates lysates from cells expressing HA-tagged KRas, NRas or HRas probed by immunoblotting as indicated. FIG. 25D illustrates in-vitro cleavage of 10 mM rKRas to KRas* with 10 mM $rDUF5_{Vv}$ (inset) or concentration indicated. Error bars indicate mean±s.d. (n=3). FIG. 25E illustrates in-vitro cleavage of 10 mM rKRas, rHRas and rNRas with 10 mM $rDUF5_{Vv}$. Identical results of Edman degradation were obtained for all three proteins. In FIG. 25F, black arrow indicates the cleavage site in the Switch I region of HRas69.

FIG. 26A illustrates a schematic diagram of DUF5 within the mosaic architecture of effector domains in MARTX toxins from *V. vulnificus* (w), *A. hydrophila* (Ah), *Vibrio splendidus* (Vs), *Xenorhabdus nematophila* ($_{Xn}$) and *Yersinia kristensii* ($_{Yk}$) or as stand-alone proteins in *Photorhabdus luminescens* ($_{Pl}$) and *P. asymbiotica* ($_{Pa}$) as previously described[17,20]. FIG. 26B illustrates in-vitro cleavage of 10 mM KRas with 10 mM rDUF5 from various species. FIG. 26C illustrates $LFNDUF5_{Ah}$ tested for in-vivo loss of all Ras isoforms after 24 h under the same conditions as in b. FIG. 26D illustrates amino acid identity in Switch I regions of representative GTPases (left) from five major Ras families (right). (FIG. 26E illustrates a bar graph of percent GFP-fusion protein cleaved after delivery of $LFNDUF5_{Vv}$+PA, quantified from immunoblots (FIG. 34). Error bars indicate mean±s.d. (n=3). FIG. 26F illustrates a representative in-vitro cleavage (n=3) of GST-fusion proteins to release GST*. Negative cleavage reactions for nine other substrates are shown in FIG. 35.

FIG. 27A illustrates MARTX toxin effector domain configuration in *V. vulnificus* isolates CMCP6 ($DUF5_{Vv}$+) and M06-24/O ($DUF5_{Vv}$−). FIG. 27B illustrates representative immunoblots (n=2) of lysates from cells incubated with *V. vulnificus* as indicated and probed for Ras cleavage and ERK1/2 dephosphorylation. FIG. 27C illustrates phase-contrast images and immunoblot detection of Ras from HCT116 and MDAMB-231 cells treated as indicated for 24 h. FIG. 27D illustrates in-vitro processing of 10 mM rKRas with mutations as indicated.

FIG. 28A illustrates a diagram of pYC-C2 plasmid expressing DUF5Vv-C2 under control of the GAL1 galactose-inducible promoter. FIG. 28B illustrates plating efficiency of *S. cerevisiae* InvSc2 expressing DUF5Vv-C2 (C2Vv) compared to yeast transformed with empty vector (EV) and the more toxic full-length DUF5Vv and actin crosslinking domain from *V. cholerae* (ACDVc), which eliminates the actin cytoskeleton (Geissler B, et al. *Mol Microbiol* 73, 858-868 (2009)). FIG. 28C illustrates schematic showing the arrayed library of non-essential deletion strains transformed with pYC-C2, followed by selection on glucose to repress expression of DUF5Vv-C2. The resulting yeast colonies were patched onto galactose and raffinose to induce expression. FIG. 28D illustrates plate 24 of the library, showing the initial screen yeast transformed with empty vector (C) and strains selected for secondary screening by quantitative plating (circled).

FIG. 29A and FIG. 29B illustrate that DUF5Vv inhibits ERK1/2 phosphorylation, but not p38. FIG. 29A and FIG. 29B illustrate representative immunoblots (n=2) of lysates from cells treated as indicated for 24 h. Red boxes highlight differences in phospho-p38 (pp38) and phospho-ERK1/2 (pERK1/2) levels. Note that Panel b is the same figure from which lanes were removed to align with other western blots in FIG. 24.

FIG. 34C illustrates cell lysis over time after addition of bacteria. Note that after 3 h, even bacteria without rtxA1 induce cell lysis due to the vvhA-encoded cytolysin/hemolysin (Fan et al. *Infect Immun* 69, 5943-5948 (2001)). Error bars represent mean±standard deviation.

FIG. 37A illustrates SDS-Page analysis of cleavage of recombinant KRas, recombinant HRas, and recombinant NRas in vitro by recombinant $DUF5_{Vv}$. FIG. 37B illustrates SDS-Page analysis of cleavage of wild-type (WT), recombinant KRas G12V, recombinant KRas G13D, and recombinant KRas Q61R by recombinant $DUF5_{Vv}$.

FIG. 39A illustrates SDS-Page analysis. RRSP with alanine substitution for E321, H323, and E351 and recombinant KRas were purified and mixed at equimolar concentration (10 μM) for 30 minutes at 37° C. No cleavage was observed in the E351A variant. FIG. 39B illustrates SDS-Page analysis. RRSP with alanine substitution for H352 and H451 and recombinant KRas were purified and mixed at equimolar concentration (10 μM) for 30 minutes at 37° C. No cleavage was observed in the H451A variant.

FIG. 41A and FIG. 41B. Fluorescent Thermal Shift shows RRSP variants are structurally stable. FIG. 41A illustrates a denaturation profile of each RRSP variant. FIG. 41B illustrates melting temperature of each RRSP variant.

FIG. 42A illustrates SDS-Page analysis. RRSP and recombinant KRas were purified and mixed at equimolar concentration (10 μM) with varying concentrations of phenanthroline in DMSO for 30 minutes at 37° C. Cleavage was still observed. FIG. 42B illustrates SDS-Page analysis. RRSP and recombinant KRas were purified and mixed at equimolar concentration (10 μM) with varying concentrations of EDTA for 30 minutes at 37° C. Cleavage was still observed.

FIG. 68A-68 D. Effect of RRSP-$DT_B$ on the TNBC Hs578T $HRAS^{G12D}$ cell line. (A). Representative western blot and densitometric analysis of uncleaved RAS and phosphorylated ERK in Hs578T $HRAS^{G12D}$ cells treated with increasing doses of RRSP-$DT_B$ for 1 and 24 h. The catalytically-inactive RRSP*-$DT_B$ mutant was used as negative control at 10 nM and vinculin as gel loading control. Results are expressed as means±SD of three independent experiments (*p<0.05, ***p<0.001 versus corresponding control 0 nM; one-way ANOVA followed by Dunnett's multiple comparison test, n=3). (B and C) Fitted dose-response curve of RRSP-$DT_B$ in Hs578T cells following 24 (B) and (C) 72 h of treatment. Slopes of the dose-response curves for both RRSP-$DT_B$ and mutant RRSP*-$DT_B$ were not steep enough to retrieve an $IC_{50}$. Results are expressed as means±SEM (n=3). (D). Images of crystal violet-stained plates in triplicate of Hs578T cells treated with RRSP-$DT_B$ and RRSP*-$DT_B$ as indicated for 72 h.

DETAILED DESCRIPTION

Figure 1A:
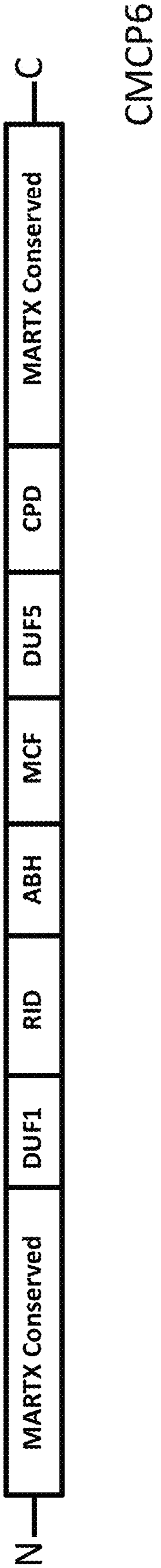
FIG. 1A and FIG. 1B illustrate the *Vibrio vulnificus* CMCP6 MARTX toxin CMCP6.

The present invention is described herein using several definitions, as set forth below and throughout the application.

As used in this specification and the claims, the singular forms "a," "an," and "the" include plural forms unless the context clearly dictates otherwise. For example, the term "a protease" should be interpreted to mean "one or more proteases" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

As used herein, the term "biological sample" should be interpreted to include bodily fluids (e.g., blood, serum, plasma, saliva, urine samples) and body tissue samples. Suitable tissue samples may include tissue samples from cancerous tissues and tumors.

The disclosed methods, compositions, and kits may be utilized to treat a subject in need thereof. A "subject in need thereof" is intended to include a subject having or at risk for developing diseases and disorders such as cell proliferative diseases and disorders which may include cancer and hyperproliferative disorders. A subject in need thereof may include a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus).

The bacterial toxins disclosed herein may include a Ras/Rap1-specific endopeptidase (RRSP or DUF5 protease), a homolog thereof, or a portion thereof comprising a subdomain thereof such as the C2A subdomain and/or the C2B subdomain of the RRSP (DUF5 protease). The terms Ras/Rap1-specific endopeptidase, RRSP and DUF5 protease are used herein interchangeable and refer to the protease of the present disclosure. The disclosed bacterial toxins may include polypeptides derived from a number of microorganisms, including, but not limited to, *Vibrio vulnificus, Vibrio harveyi, Vibrio ordalii, Vibrio cholerae, Vibrio splendidus, Moritella dasanensis, Aeromonas salmonicida, Aeromonas hydrophila, Photorhabdus temperata, Xenorhabdus nematophila, Photorhabdus luminescens, Photorhabdus asymbiotica, Yersinia kristensenii*, and *Pasteurella multocida.*

As utilized herein, a protein, polypeptide, and peptide refer to a molecule comprising a chain of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The amino acid sequence of the RRSP (DUF5 protease) of *Vibrio vulnificus* is provided as SEQ ID NO:1, and the amino acid sequence of the C2A subdomain is provided as SEQ ID NO:2 and the amino acid sequence of the C2B subdomain is provided in SEQ ID NO:1 which is C-terminal to the C2A subdomain. The amino acid sequence of the DUF5 protease of *Vibrio harveyi* is provided as SEQ ID NO:3, and the amino acid sequence of the C2A subdomain is provided as SEQ ID NO:4 and the amino acid sequence of the C2B subdomain is provided in SEQ ID NO:3 which is C-terminal to the C2A subdomain. The amino acid sequence of the DUF5 protease of *Vibrio ordalii* is provided as SEQ ID NO:5, and the amino acid sequence of the C2A subdomain is provided as SEQ ID NO:6 and the amino acid sequence of the C2B subdomain is provided in SEQ ID NO:5 which is C-terminal to the C2A subdomain. The amino acid sequence of the DUF5 protease of *Vibrio cholerae* is provided as SEQ ID NO:7, and the amino acid sequence of the C2A subdomain is provided as SEQ ID NO:8 and the amino acid sequence of the C2B subdomain is provided in SEQ ID NO:7 which is C-terminal to the C2A subdomain. The amino acid sequence of the DUF5 protease of *Vibrio splendidus* is provided as SEQ ID NO:9, and the amino acid sequence of the C2A subdomain is provided as SEQ ID NO:10 and the amino acid sequence of the C2B subdomain is provided in SEQ ID NO:9 which is C-terminal to the C2A subdomain. The amino acid sequence of the DUF5 protease of *Moritella dasanensis* is provided as SEQ ID NO:11, and the amino acid sequence of the C2A subdomain is provided as SEQ ID NO:12 and the amino acid sequence of the C2B subdomain is provided in SEQ ID NO:11 which is C-terminal to the C2A subdomain. The amino acid sequence of the DUF5 protease of *Aeromonas salmonicida* is provided as SEQ ID NO:13, and the amino acid sequence of the C2A subdomain is provided as SEQ ID NO:14 and the amino acid sequence of the C2B subdomain is provided in SEQ ID NO:13 which is C-terminal to the C2A subdomain. The amino acid sequence of the DUF5 protease of *Aeromonas hydrophila* is provided as SEQ ID NO:15, and the amino acid sequence of the C2A subdomain is provided as SEQ ID NO:16 and the amino acid sequence of the C2B subdomain is provided in SEQ ID NO:15 which is C-terminal to the C2A subdomain. The amino acid sequence of the DUF5 protease of *Photorhabdus temperata* is provided as SEQ ID NO:17, and the amino acid sequence of the C2A subdomain is provided as SEQ ID NO:18 and the amino acid sequence of the C2B subdomain is provided in SEQ ID NO:17 which is C-terminal to the C2A subdomain. The amino acid sequence of the DUF5 protease of *Xenorhabdus nematophila* is provided as SEQ ID NO:19, and the amino acid sequence of the C2A subdomain is provided as SEQ ID NO:20 and the amino acid sequence of the C2B subdomain is provided in SEQ ID NO:19 which is C-terminal to the C2A subdomain. The amino acid sequence of the DUF5 protease of *Photorhabdus luminescens* is provided as SEQ ID NO:21, and the amino acid sequence of the C2A subdomain is provided as SEQ ID NO:22 and the amino acid sequence of the C2B subdomain is provided in SEQ ID NO:21 which is C-terminal to the C2A subdomain. The amino acid sequence of the DUF5 protease of *Photorhabdus asymbiotica* is provided as SEQ ID NO:23, and the amino acid sequence of the C2A subdomain is provided as SEQ ID NO:24 and the amino acid sequence of the C2B subdomain is provided in SEQ ID NO:23 which is C-terminal to the C2A subdomain. The amino acid sequence of the DUF5 protease of *Yersinia kristensenii* is provided as SEQ ID NO:25, and the amino acid sequence of the C2A subdomain is provided as SEQ ID NO:26 and the amino acid sequence of the C2B subdomain is provided in SEQ ID NO:25 which is C-terminal to the C2A subdomain. The amino acid sequence of the DUF5 protease homolog of *Pasteurella multocida* is provided as SEQ ID NO:27, and the amino acid sequence of the C2A subdomain is provided as SEQ ID NO:28 and the amino acid sequence of the C2B subdomain is provided in SEQ ID NO:27 which is C-terminal to the C2A subdomain.

The terms “amino acid” and “amino acid sequence” refer to an oligopeptide, peptide, polypeptide, or protein sequence (which terms may be used interchangeably), or a fragment of any of these, and to naturally occurring or synthetic molecules. Where “amino acid sequence” is recited to refer to a sequence of a naturally occurring protein molecule, “amino acid sequence” and like terms are not meant to limit the amino acid sequence to the complete native amino acid sequence associated with the recited protein molecule.

The amino acid sequences contemplated herein may include one or more amino acid substitutions relative to a reference amino acid sequence. For example, a variant polypeptide may include non-conservative and/or conservative amino acid substitutions relative to a reference polypeptide. “Conservative amino acid substitutions” are those substitutions that are predicted to interfere least with the properties of the reference polypeptide. In other words, conservative amino acid substitutions substantially conserve the structure and the function of the reference protein. The following Table provides a list of exemplary conservative amino acid substitutions.

| Original Residue | Conservative Substitution |
|---|---|
| Ala | Gly, Ser |
| Arg | His, Lys |
| Asn | Asp, Gin, His |
| Asp | Asn, Glu |
| Cys | Ala, Ser |
| Gin | Asn, Glu, His |
| Glu | Asp, Gin, His |
| Gly | Ala |
| His | Asn, Arg, Gin, Glu |
| Ile | Leu, Val |
| Leu | Ile, Val |
| Lys | Arg, Gin, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain one or more of: (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally do not maintain one or more of: (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A “deletion” refers to a change in the amino acid sequence that results in the absence of one or more amino acid residues. A deletion removes at least 1, 2, 3, 4, 5, 10, 20, 50, 100, or 200 amino acids residues. A deletion may include an internal deletion or a terminal deletion (e.g., an N-terminal truncation or a C-terminal truncation of a reference polypeptide). A “variant,” “mutant,” or “derivative” of a reference polypeptide sequence may include a deletion relative to the reference polypeptide sequence.

The words “insertion” and “addition” refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues or a range of amino acid residues bounded by any of these values (e.g., an insertion or addition of 5-10 amino acids). A “variant” of a reference polypeptide sequence may include an insertion or addition relative to the reference polypeptide sequence.

A “fusion polypeptide” refers to a polypeptide, such as the bacterial toxins contemplated herein, comprising at the N-terminus, the C-terminus, or at both termini of its amino acid sequence a heterologous amino acid sequence, for example, an amino acid sequence that facilitates transport of the polypeptide into the cytosol of proliferating cells. Suitable polypeptides that allow translport into proliferating cells include bacterial toxins and elements known in the art. A “variant,” “mutant,” or “derivative” of a reference polypeptide sequence may include an fusion polypeptide comprising the reference polypeptide fused to a heterologous polypeptide.

A “fragment” is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide; or a fragment may comprise no more than 5, 10, 15, 20, 25, 30, 40, 50, 60, 70, 80, 90, 100, 150, 250, or 500 contiguous amino acid residues of a reference polypeptide; or a fragment may comprise a range of contiguous amino acid residues of a reference polypeptide bounded by any of these values (e.g., 40-80 contiguous amino acid residues). Fragments may be preferentially selected from certain regions of a molecule. The term “at least a fragment” encompasses the full length polypeptide. A “variant,” “mutant,” or “derivative” of a reference polypeptide sequence may include a fragment of the reference polypeptide sequence.

“Homology” refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant," "mutant," or "derivative" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

A "variant," "mutant" or a "derivative" may have substantially the same functional activity as a reference polypeptide. For example, a variant, mutant, or derivative of a DUF5 protease or the C2A subdomain or the C2B subdomain thereof may function as a protease of a Ras protein, for example, and specifically cleave the Ras protein between a tyrosine at amino acid position 32 and an aspartic acid at amino acid position 33 of the amino acid sequence of the Ras protein.

A protein, polypeptide, or peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

Also contemplated herein are peptidomimetics of the disclosed proteins, polypeptides, and peptides. As disclosed herein, a peptidomimetic is an equivalent of a protein, polypeptide, or peptide characterized as retaining the polarity, three dimensional size and functionality (bioactivity) of the protein, polypeptide, or peptide equivalent but where the protein, polypeptide, or peptide bonds have been replaced (e.g., by more stable linkages which are more resistant to enzymatic degradation by hydrolytic enzymes). Generally, the bond which replaces the amide bond conserves many of the properties of the amide bond (e.g., conformation, steric bulk, electrostatic character, and possibility for hydrogen bonding). A general discussion of prior art techniques for the design and synthesis of peptidomimetics is provided in "Drug Design and Development", Chapter 14, Krogsgaard, Larsen, Liljefors and Madsen (Eds) 1996, Horwood Acad. Pub, the contents of which are incorporated herein by reference in their entirety. Suitable amide bond substitutes include the following groups: N-alkylation (Schmidt, R. et. al., Int. J. Peptide Protein Res., 1995, 46,47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391), which all are incorporated herein by reference in their entireties. Contemplated herein are peptidomimetic equivalents of the disclosed therapeutic polypeptides comprising the amino acid sequence of a DUF5 protease C2A subdomain or the amino acid sequence of a DUF5 protease C2B subdomain.

Also disclosed herein are polynucleotides, for example polynucleotide sequences that encode the polypeptides and proteins disclosed herein (e.g., DNA that encodes a polypeptide having the amino acid sequence of any of SEQ ID NOs:1-28 or DNA that encodes a polypeptide variant having an amino acid sequence with at least about 20%, 30%, 40%, 50%, 60%, 70%, 80%, 90%, 95%, 96%, 97%, 98%, or 99% sequence identity to any of SEQ ID NOs: 1-28.

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

"Transformation" or "transfected" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. For example, a heterologous promoter for a LAMP may include a eukaryotic promoter or a prokaryotic promoter that is not the native, endogenous promoter for the LAMP As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refer to a recombinant nucleic acid that has been engineered to express a heterologous polypeptide (e.g., the fusion proteins disclosed herein). The recombinant nucleic acid typically includes cis-acting elements for expression of the heterologous polypeptide.

Any of the conventional vectors used for expression in eukaryotic cells may be used for directly introducing DNA into a subject. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Expression vectors as contemplated herein may include eukaryotic or prokaryotic control sequences that modulate expression of a heterologous protein (e.g. the fusion protein disclosed herein). Prokaryotic expression control sequences may include constitutive or inducible promoters (e.g., T3, T7, Lac, trp, or phoA), ribosome binding sites, or transcription terminators.

The vectors contemplated herein may be introduced and propagated in a prokaryote, which may be used to amplify copies of a vector to be introduced into a eukaryotic cell or as an intermediate vector in the production of a vector to be introduced into a eukaryotic cell (e.g. amplifying a plasmid as part of a viral vector packaging system). A prokaryote may be used to amplify copies of a vector and express one or more nucleic acids, such as to provide a source of one or more proteins for delivery to a host cell or host organism. Expression of proteins in prokaryotes may be performed using *Escherichia coli* with vectors containing constitutive or inducible promoters directing the expression of either a protein or a fusion protein comprising a protein or a fragment thereof. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; (iii) to aid in the purification of the recombinant protein by acting as a ligand in affinity purification (e.g., a His tag); (iv) to tag the recombinant protein for identification (e.g., such as Green fluorescence protein (GFP) or an antigen (e.g., HA) that can be recognized by a labelled antibody); (v) to promote localization of the recombinant protein to a specific area of the cell (e.g., where the protein is fused (e.g., at its N-terminus or C-terminus) to a nuclear localization signal (NLS) which may include the NLS of SV40, nucleoplasmin, C-myc, M9 domain of hnRNP A1, or a synthetic NLS). The importance of neutral and acidic amino acids in NLS have been studied. (See Makkerh et al. (1996) *Curr Biol* 6(8):1025-1027). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

The presently disclosed methods may include delivering one or more polynucleotides, such as or one or more vectors as described herein, one or more transcripts thereof, and/or one or proteins transcribed therefrom, to a host cell. Further contemplated are host cells produced by such methods, and organisms (such as animals, plants, or fungi) comprising or produced from such cells. The disclosed exosomes may be prepared by introducing vectors that express mRNA encoding a fusion protein and a cargo RNA as disclosed herein. Conventional viral and non-viral based gene transfer methods can be used to introduce nucleic acids in mammalian cells or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell.

In the methods contemplated herein, a host cell may be transiently or non-transiently transfected (i.e., stably transfected) with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. Suitable cells may include stem cells (e.g., embryonic stem cells and pluripotent stem cells). A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors, or transfection with RNA), and modified through the activity of a complex, in order to establish a new cell line comprising cells containing the modification but lacking any other exogenous sequence.

DUF5 Domain of Multifunctional, Autoprocessing RTX (MARTX) Toxin

Bacterial toxins can inactive host cellular processes. Ras is a cellular protein for the host response to stress that is modified in many human cancers to promote cell survival. We discovered that the DUF5 domain of the *Vibrio vulnificus* multifunctional, autoprocessing RTX (MARTX) toxin is an endopeptidase that specifically cleaves Ras between residues Y32 and D33. We determined the crystal structure, the minimally active portion, and the specificity for Ras among the small GTPases. Ras proteins with mutations common in cancer are also cleaved. We also have utilized a system and carriers to deliver the domain to cells independent of the holotoxin by fusion to a bacterial toxin element, Anthrax toxin Lethal Factor N-terminus, which allowa for delivery to cells by Protective antigen. Homology sequence analysis demonstrates that at least 12 bacteria produce a protein with at least 24% percent identity and the proteins from *Aeromonas hydrophila* and *Photorhabdus asymbiotica* are shown also to cleave Ras. We propose this family of proteins could be engineered for delivery to cancer cells as potential therapeutic agents for carcinoma, targeting both tumors with normal Ras and those with modified Ras proteins. We propose this family of proteins also for use in biological research to specifically and rapidly knock down or remove Ras.

Ras-Dependent Cancers

Ras-activating mutations are frequently observed in cancer. (See Fernandez-Medarde et al., "Ras in Cancer and Developmental Diseases," March 2011, vol. 2, no. 3: 344-358; Johannes L. Bos. "Ras Oncogenes in Human Cancer: A Review," Cancer Research 49, 4682-4689, Sep. 1, 1989; Julian Downward "Targeting RAS signalling pathways in cancer therapy," Nature Reviews Cancer 3, 11-22 (January 2003); Schubbert et al., "Hyperactive Ras in developmental disorders and cancer," Nature Reviews Cancer 7, 295-308 (January 2007); and Baines et al., "Inhibition of Ras for cancer treatment: the search continues," Future Med. Chem. 2011 October; 3(14): 1787-1808; the contents of which are incorporated herein by reference in their entireties). Ras-activating mutations are observed in 95% of pancreatic cancers, 45% of colorectal cancers, and 35% of lung adenocarcinoma. The RAS oncogenes (HRAS, NRAS and KRAS comprising activating mutations present in codon 12, 13, or 61) comprise the most frequently mutated class of oncogenes in human cancers (33%), stimulating intensive effort in developing anti-Ras inhibitors for cancer treatment. (See Prior et al., "A comprehensive survey of Ras mutations in cancer," Cancer Research. 2012 May 15; 72(10): 2457-2467, the content of which is incorporated herein by reference in its entirety). Unfortunately, there are no drugs that target Ras directly or indirectly, and there are currently no effective therapies for Ras-dependent cancers.

Targeted Delivery or Expression of Bacterial Toxins into the Cytosol of Proliferating Cells The bacterial toxins disclosed herein may be administered in order to treat cell proliferative diseases and disorders such as cancer. The bacterial toxins may be administered by transfecting cancer cells with a polynucleotide or a polynucleotide vector that expresses the bacterial toxins in the cancer cells. Alternatively, the bacterial toxins may be formulated for intracellular protein delivery using methods known in the art including the use of carriers, for example, bacterial toxin elements as carriers, more specifically for example, anthrax lethal toxin for targeted delivery of protein into cells. (See WO 2014031861 A1; WO2008/076939; and WO 2001/21656, the contents of which are incorporated herein by reference in their entireties). Other bacterial toxins and bacterial toxin elements are contemplated and known in the art to be able to target and deliver proteins into cells. Alternative approaches for targeted delivery of protein into cells are known in the art. (See, e.g., Weill et al., "A practical approach for intracellular protein delivery," Cytotechnology. 20089 January; 56(1) 41-48; Walev et al., "Delivery of proteins into living cells by reversible membrane permeabilization with steptolysin-O," PNAS, Mar. 13, 2001, vol. 98, no. 6, 3185-3190; Cronican et al., "Naturally supercharged human proteins (NSHPs)," Chemistry & Biology 18, 833-838, Jul. 29, 2011; Torchilin, "Intracellular deliver of protein and peptide therapeutics," Drug Discovery Today: Technologies, Protein Therapeutics, 2009; M. Grdisa "The Delivery of Biologically Active (Therapeutic) Peptides and Proteins into Cells," Cell-penetrating peptides (CPPS), Current Medicinal Chemistry, 2011. Vol. 18; Morris et al., "A Peptide Carrier for the Delivery of Biologically Active Proteins into Mammalian Cells: Application to the Delivery of Antibodies and Therapeutic Proteins," Cell Biology, Volume 204, Part 20A, Chapter 2, 2006; Futami et al. "Intracellular delivery of proteins into mammalian living cells by polyethylenimine-cationization," J Bioscience and Bioengineering, Vol. 99, Iss 2, Febr 2005 95-103; and Kurzawa et al., "PEP and CADY-mediated delivery of fluorescent peptides and proteins into living cells," Biochimica et a Biophysica Acta (BBA)—Biomembranes Vol. 1798, Issue 12, December 2010 2274-2285).

Applications and Advantages of Disclosed Bacterial Toxins

Uses of the bacterial proteases disclosed herein include, but are not limited to: (a) uses as toxin components in bacterial toxin-based therapeutics for cancer and other diseases requiring killing of cells, including but not limited to immunotoxins, tetramer-toxins, bacterial delivery of toxins, and nanoparticles and others; (b) uses as reagents to treat cells to knock down Ras during biological research by direct delivery to cell cytosol by any method including chemical, mechanical, or biological strategies; (c) specific delivery by Protective antigen of this family of proteins to cells when fused to Lethal Factor N terminus as therapeutics; (d) specific delivery by Protective antigen of this family of proteins to cells when fused to Lethal Factor N terminus as a reagent during biological research; (e) treatment of biochemical reactions involving Ras to rapidly remove Ras from an in vitro reaction; (f) linkage of this family of proteins to an antibody or tetramer to create an immunotoxin specifically developed to delivery to cancerous cells or other conditions requiring killing of cells; and (g) delivery of this family of proteins to tumors or malignant cells by any strategy that delivers protein to cell for use a cancer therapeutic.

Some advantages of using the disclosed DUF5 protease or related proteases for inactivated Ras include, but are not limited to: (a) the DUF5 protease permanently modifies Ras by nicking Ras at a site essential for function, a modification which is not reversible as are other modifications; (b) the DUF5 protease exhibits specificity for isoforms of Ras including isoforms found in cancerous cells; (c) the DUF5 protease has a natural lack of structure in vitro and is thus amenable to easy transfer into cells by processes that require folding and unfolding; and (d) the DUF5 protease can be delivered to cells via fusion to anthrax toxin lethal factor (LF) in the presence of protective antigen (PA).

Pharmaceutical Compositions

The compositions disclosed herein may include pharmaceutical compositions comprising the presently disclosed bacterial toxins (RRSP) and formulated for administration to a subject in need thereof. Such compositions can be formulated and/or administered in dosages and by techniques well known to those skilled in the medical arts taking into consideration such factors as the age, sex, weight, and condition of the particular subject, and the route of administration.

The compositions may include pharmaceutical solutions comprising carriers, diluents, excipients, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The pharmaceutical compositions may be administered therapeutically. In therapeutic applications, the compositions are administered to a subject in an amount sufficient to elicit a therapeutic effect (e.g., a response which cures or at least partially arrests or slows symptoms and/or complications of disease (i.e., a "therapeutically effective dose")).

EXAMPLES

The following examples are illustrative and are not intended to limit the scope of the claimed subject matter.

Example 1—A Bacterial Toxin that is a Ras-Specific Protease

Background

*Vibrio vulnificus* is a motile, Gram-negative, opportunistic human pathogen capable of causing severe gastrointestinal and wound infections, both of which can be fatal. Two major virulence factors have been identified associated with increased death during intestinal infection: the secreted cytolytic/hemolysin pore-forming toxin encoded by vvhA [3] and the multifunctional autoprocessing RTX ($MARTX_{Vv}$) toxin encoded by gene rbcA1 [4-6]. However, results among different studies suggest that $MARTX_{Vv}$ is the most significant virulence factor of *V. vulnificus* [7].

Figure 1B:
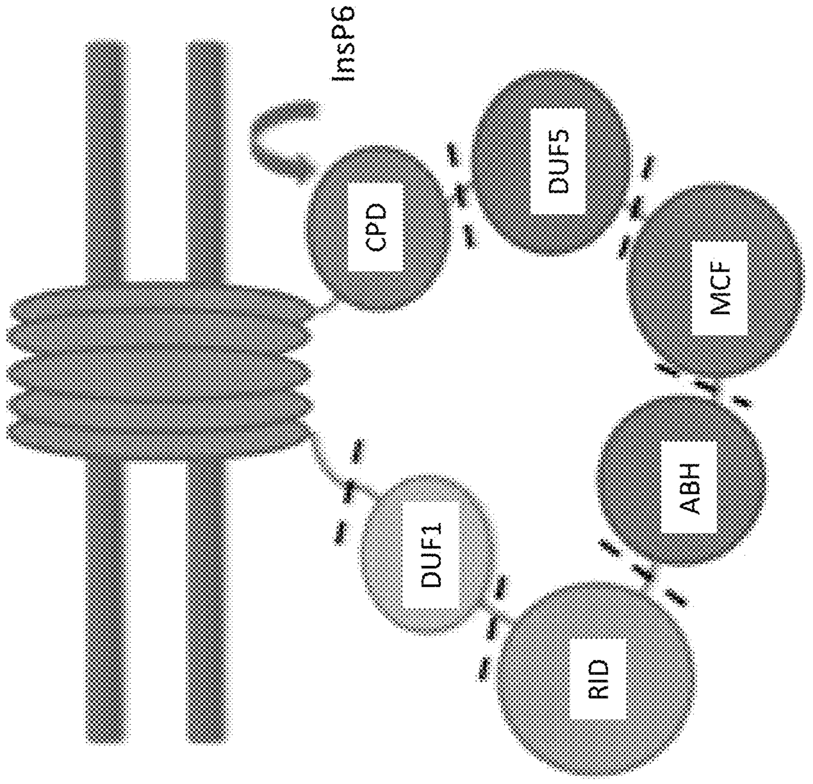

MARTX toxins are a recently described family of bacterial protein toxins originally characterized in *Vibrio cholerae*, but subsequently identified in many bacterial species [8][9, 10][6, 11][12]. These are large composite bacterial toxins that carry multiple effector domains that confer cellular toxicity after delivery by autoprocessing [9]. MARTX N- and C-termini repeats region are proposed to form a pore at the eukaryotic cell membrane for translocation of central "effector-domains" to the cytosol. Within the cytosol, the cysteine protease domain (CPD, covered by U.S. Pat. No. 8,257,946,B2) binds inositol hexakisphosphate and other inositol phosphate compounds, to initiate autoprocessing at leucine residues located in unstructured regions that link the "effector domains" [13-15]. The net result is release of the internal effector domains from the large protein toxin to the cytosol, where they are free to move throughout the cell to access cellular targets and to exert their toxic effects (FIG. 1).

Despite the sequence conservation of the repeats regions and the CPD in proteins produces by different bacteria, each bacterial MARTX toxin carries a distinct set of effector domains and thus a distinct array of potential cytotoxic activities [8, 9]. Further, different isolates of the same species can produce MARTX toxins that deliver distinct repertoire of effectors [6, 10, 12].

The first *V. vulnificus* MARTX toxin that was annotated was identified in the clinical isolates CMCP6 [8]. The central region of $MARTX_{Vv}$ CMCP6 (NP_759056.1) has five effector domains (FIG. 1A). Domain of unknown function in the first position (DUF1) has no functional homologs in the database, but is found also in MARTX toxins from *Xenorhabdus bovienii* and *Xenorhabdus nematophila* [8, 9] The second effector domain is Rho-inactivation domain (RID). This domain has been demonstrated to stimulate cell rounding by inactivating cellular Rho GTPases dependent upon a catalytic cysteine residue [16, 17] The third effector domain has homology to the αβ-hydrolase (ABH) family of enzymes [8, 9] and has recently been shown to have phospholipase activity (Agarwal SN and Satchell, manuscript in preparation). The fourth effector domain is 30% identical to a domain found within the *Photorhabdus luminescens* Makes Caterpillar Floppy (MCF) toxins [8, 9]. This domain is associated with induction of apoptosis (Agarwal S G and Satchell, manuscript in preparation).

DUF5 is the fifth effector domain in the toxin produced by *V. vulnificus* CMCP6 ($DUF5_{Vv}$), but absent in other isolates. Our group demonstrated that an in-frame genetic mutation on the chromosome of CMCP6 to remove $DUF5_{Vv}$ from expressed $MARTX_{Vv}$ toxin results in a 54-fold reduced virulence, compared with the isogenic strain CMCP6 that expresses the full-length toxin. In addition, a strain that naturally lacks this domain was at least 10-fold less virulent than CMCP6 [6]. Our interest in this domain was rooted in this identification that the presence of $DUF5_{Vv}$ in the MARTX toxin of *V. vulnificus* is associated with the more highly virulent nature of *V. vulnificus* CMCP6 so we ventured to understand the molecular mechanism of action of this domain.

Details on the Discovery of the Catalytic Activity of $DUF5_{Vv}$ and Related Proteins as Specific Endopeptidases for the Small GTPase Ras.

$DUF5_{Vv}$ Represents a Family of DUF5-Like Proteins.

The DUF5 domain of the *V. vulnificus* CMCP6 MARTX toxin ($DUF5_{Vv}$) is found at amino acids G3579-L4089 based on Genbank sequence NP_759056.1. Domains with similarity to $DUF5_{Vv}$ are also found in MARTX toxins of at least 8 other bacterial species with amino acid identity varying from 43-98% identity.

$DUF5_{Vv}$ Homologs in Other Bacteria (% Amino Acid Identity)

| Organisms with DUF5 homolog sequences | % Identity |
|---|---|
| *Vibrio ordalii* | 97.8 |
| *Vibrio choleras* | 97.2 |
| *Vibrio splendidus* | 81.2 |
| *Moritella dasanensis* | 71.6 |
| *Aeromonas salmonicida* | 61.9 |
| *Aeromonas hydrophila* | 61.8 |
| *Photorhabdus temperata* | 58.8 |
| *Xenorhabdus nematophila* | 58.2 |
| *Photorhabdus luminescences* | 56.9 |
| *Photorhabdus asymbiotica* | 56.0 |
| *Yersinia kristensenii* | 42.5 |
| *Pasteurella multocida* | 24.4 |

The domain is found also in *Photorhabdus* sp. as a single domain hypothetical protein with 56-59% amino acid sequence identity to $DUF5_{Vv}$ ([9] and search conducted for this document). $DUF5_{Vv}$ also has 24% amino acid sequence identity to a portion of the *Pasteurella multocida* toxin (PMT) [9].

The solved structure of the C-terminus of PMT (PDB 2EBF) revealed three independent domains termed C1, C2, and C3 [18, 19]. The C3 domain is the catalytically active domain of PMT [20] and is not conserved in $DUF5_{Vv}$. The C1 domain in $DUF5_{Vv}$, PMT, and other bacterial toxins that have a homologous domain, has been shown to be a four helical bundled structure necessary for targeting toxin proteins to the cytosolic side of eukaryotic membranes [18, 21-24]. No function has been identified for the C2 domain of PMT. Transfection studies reveal this domain is not toxic when ectopically expressed in cells and bioinformatics comparing $DUF5_{Vv}$ homologs suggest accumulated mutations in C2 may have rendered this domain inactive [39,40]. Thus, at the start of the project, there was no functional information regarding the activity of the C2 domain of $DUF5_{Vv}$ or any of its protein homologues.

Structure of $DUF5_{Vv}$.

Recombinant $DUF5_{Vv}$ ($rDUF5_{Vv}$; $MARTX_{Vv}$ Q3596-L4089 based on sequence NP_759056.1) was amplified from CMCP6 DNA and cloned into the expression vector pMCSG7 [25] to generate a fusion with a 6×HIS tag at its N-terminus for binding to a nickel column for affinity purification. The protein was expressed in *E. coli* and lysate prepared by sonication and centrifugation to recover the soluble fraction. $rDUF5_{Vv}$ was purified from the lysate by affinity chromatography using pre-packed GE Biosciences HisTrap FF resin and then by size exclusion chromatography using a pre-packed GE Biosciences Superdex S200 resin.

Figure 2:
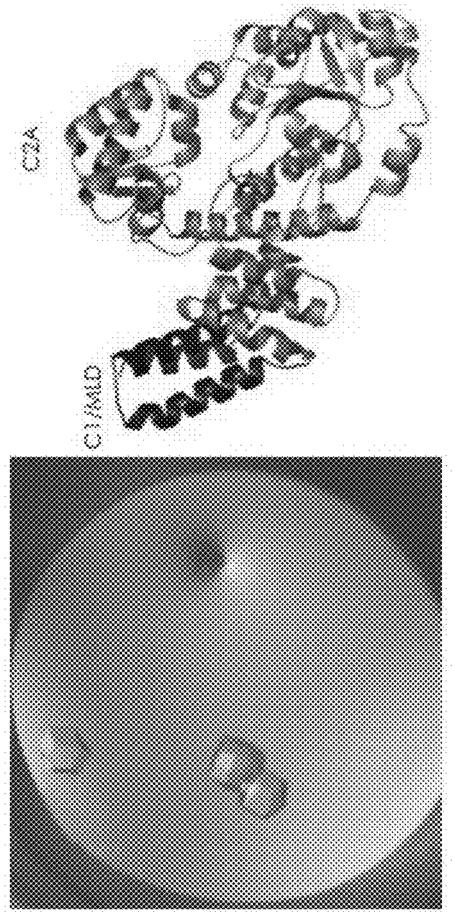
FIG. 2. Left: DUF5$_{Vv}$ crystals. Right: Domain structure of DUF5$_{Vv}$ based on crystal structure. C1/MLD: membrane localization domain; C2A: Smallest active domain; C2B: Putative stabilization or specificity domain.

This $rDUF5_{Vv}$ protein preparation was used for X-ray crystallography studies (FIG. 2). $rDUF5_{Vv}$ structure was solved with an overall resolution of 3.4 Å. The overall structure of the protein aligns with the previously determined structure of PMT C1/C2 domains (RMSD=2.75) despite the fact that the two proteins share only 24% amino acid identity. The solved structure revealed that $rDUF5_{Vv}$ as predicted by secondary structure alignment is composed also of C1 (aa 3579-3669) and C2 domains (amino acids 3670-4089). The C2 domain could likewise be bisected into two subdomains: C2A (amino acids 3669-3855) and C2B (amino acids 3856-4089). Bioinformatics studies had also predicted two subdomains for C2 but predicted the active catalytic activity would be focused on C2B[39,40].

The C2A Subdomain is the Cytotoxic Portion of $DUF5_{Vv}$.

To probe whether $DUF5_{Vv}$ has cytotoxic or cytopathic activity, the DNA sequence from *V. vulnificus* CMCP6 corresponding to $DUF5_{Vv}$ (amino acids 3579-4089) was amplified by PCR, cloned in the pEGFP-N3 (Clontech Laboratories Inc.) to generate a fusion with green fluorescent protein gene (egffi) and the resulting plasmid chemically transfected into HeLa cells. These studies showed rounding of cells that were expressing the EGFP fusion protein, but not control cells that were expressing EGFP alone. C2 also induced cell rounding when expressed in the eukaryotic yeast *Saccharomyces cerevisiae*. The minimal portion of $DUF5_{Vv}$ that demonstrated the cytopathic activity in HeLa cells was linked to the C2A domain by deletion analysis.

To further demonstrate that $DUF5_{Vv}$ is toxic to cells, the DNA sequence from *V. vulnificus* CMCP6 corresponding to $DUF5_{Vv}$ (amino acids 3579-4089) was amplified by PCR, cloned into pRT24 (a modified version of pABII [42]) to generate a fusion with 6×His-tagged anthrax toxin lethal factor N-terminus ($LF_N$) at the N-terminus. This protein $LF_NDUF5_{Vv}$ can be delivered to the cytosol of cells by adding the purified protein to the cell culture media along with anthrax toxin protective antigen (PA), which is purified separately as a 6×His-tagged protein. The PA portion of the bipartitite anthrax toxin associates with the $LF_N$ portion of the fusion protein and $LF_NDUF5_{Vv}$ is then translocated into the cell cytosol by PA, allowing for delivery of $DUF5_{Vv}$ to the cell cytosol independent of the remainder of the MARTX toxin. This intoxication system has been used for the study of many bacterial toxins and other proteins [16,41-44]. Several embodiments of the Lethal Factor/Protective antigen translocation system have been described (WO 2014031861 A1, WO 2001/21656 and WO2008/076939).

Cells intoxicated with $LF_NDUF5_{Vv}$ in combination with PA exhibited cell rounding, including HeLa cervical carcionoma cells, J774 macrophages, 293T fibroblasts, etc. Cells were not rounded by $LF_NDUF5_{Vv}$ in the absence of PA or by PA in combination with purified $LF_N$ alone (without the $DUF5_{Vv}$) The minimal portion of $DUF5_{Vv}$ essential for cytoxicity when delivered by $LF_N$ was mapped to $MARTX_{Vv}$ G3579-T3855 corresponding to the C1 domain plus C2A, as C1 is essential for toxin to reach the membrane after delivery though the PA pore.

Similarly, it was found that cells treated with $LF_N$ fused to the DUF5 domain from the *Aeromonas hydrophila* MARTX toxin (aa 3041-3575 based on sequence strain 7966, from ATCC, GI: 117618727) also demonstrated cell rounding when delivered to cells and only when in combination with PA. Thus, despite having only 62% amino acid identity, these proteins seem to share a toxic mechanism.

Discovery of $DUF5_{Vv}$ Targeting Ras.

Figure 3A:
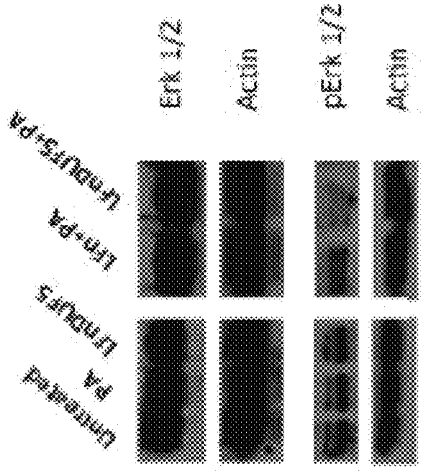
FIG. 3A, FIG. 3B, and FIG. 3C illustrate that cells intoxicated with DUF5$_{Vv}$ or C1/C2A show loss of all cellular Ras.

To further investigate the cytopathic function of $DUF5_{Vv}$, a screen was conducted for suppressors in yeast that would permit growth of yeast when $DUF5_{Vv}$ C2 subdomain was ectopically expressed. This screen revealed>100 suppressor mutations that mapped to a plethora of cellular signaling pathways, enriched in pathways linked to cellular stress responses. Based on this finding, we investigated if the major transcription factor activated under conditions of cell stress in human epithelial cells—ERK1/2—would be affected by $DUF5_{Vv}$ accounting for the observed wide variety of downstream effects in yeast. Cells intoxicated with $LF_NDUF5_{Vv}$ in the presence of PA were found to have reduced levels of phosphorylated ERK1/2 (pERK1/2) (FIG. 3A, lower panels), despite having no difference in total levels of ERK1/2 (FIG. 3A, upper panels). This result demonstrated that $DUF5_{Vv}$ does suppress the stress response pathways in cells controlled by ERK1/2.

Figure 3B:
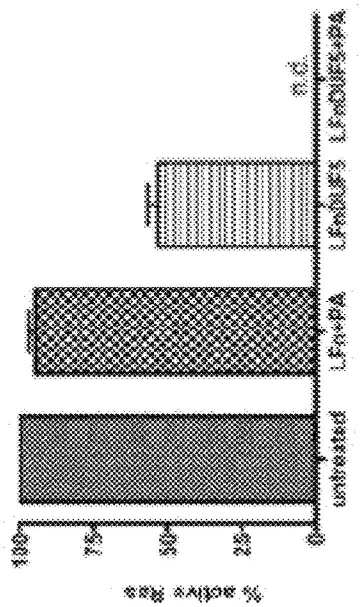
Figure 3C:
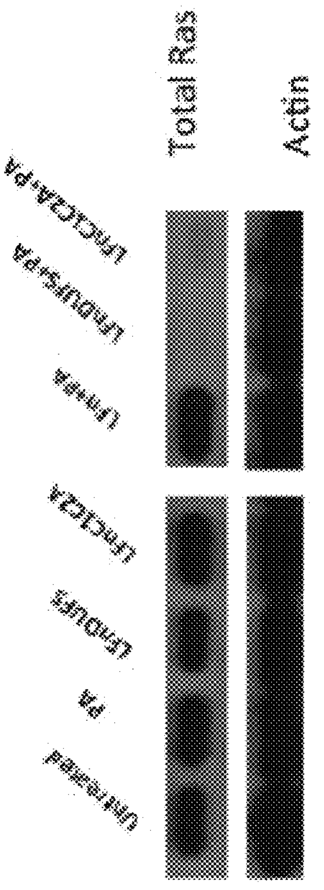
Figure 4:
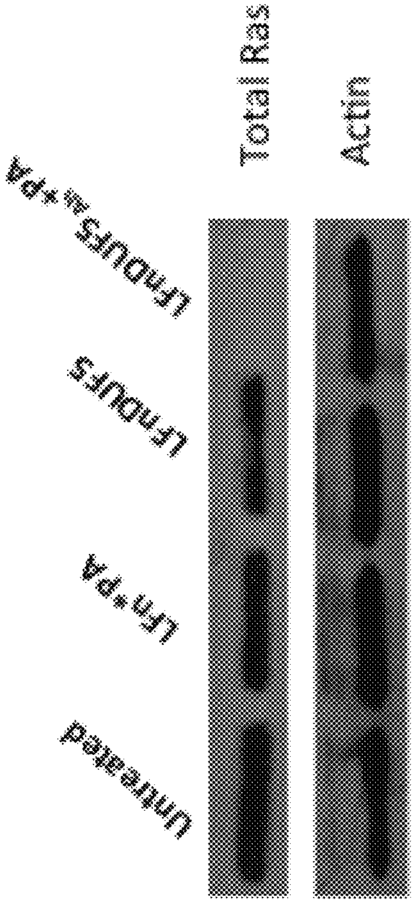
FIG. 4. HeLa cells intoxicated with DUF5$_{Vv}$ (LF$_N$DUF5$_{Vv}$+PA) show loss of all cellular Ras. Detection of total Ras in cell lysates by western blot using Ras10 monoclonal antibody (upper panels). Detection with anti-actin antibody was used as the loading control.

The relative concentration of active pERK1/2 in the cell is normally regulated by the Ras-Raf-MEK-ERK signaling cascade. At the top of the cascade, Ras is activated by conversion from an inactive, GDP-bound state to an active, GTP-bound state [26, 27]. As pERK1/2 levels were reduced, this led us to test if the activation state of Ras in $LF_NDUF5_{Vv}$ intoxicated HeLa cells was affected. The G-LISA activation assay, commercially available from Cytoskeleton, Inc., specifically detects the GTP-bound activated form of all Ras isoforms dependent upon the final detection of Ras by the monoclonal antibody Ras10. This assay detected no active Ras-GTP in intoxicated cells (FIG. 3B). Western blotting, using the Ras10 monoclonal antibody to detect the total amount of Ras within the HeLa whole cell lysate, showed that Ras was absent from lysates prepared from cells intoxicated with $LF_NDUF5_{Vv}$ or $LF_NC1C2A$ exclusively when incubated in the presence of PA (FIG. 3C). HeLa cells intoxicated for shorter time points than 24 hours revealed that loss of Ras detectable by the Ras10 monoclonal antibody occurred as early as 20 minutes from the time of exposure of cells to $LF_NDUF5_{Vv}$ in the presence of PA (FIG. 4).

Figure 5:
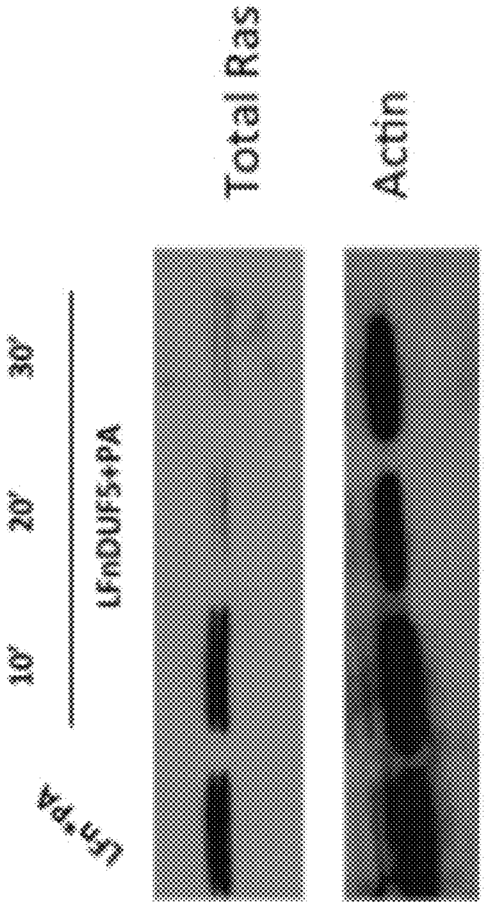
FIG. 5. Cells intoxicated with DUF5$_{Ah}$ show rapid loss of detectable Ras. Western blot detection of total Ras using Ras10 antibody (Upper panel). Prior to collection, HeLa cell were incubated for time shown with DUF5$_{Ah}$ fused to anthrax toxin lethal factor (LF$_N$DUF5) in the absence (first lane) or presence of PA.

Following a strategy similar to $DUF5_{Vv}$, we demonstrated that the HeLa cells intoxication with an $LF_N$ fusion of DUF5 from MARTX ($LF_NDUF_{Ah}$) (amino acid 3069-3570) also causes cell rounding after 24 hours. Western blot analysis was used to detect the total amount of Ras into the HeLa cell lysates demonstrated that Ras was undetectable into the HeLa cell lysate after intoxication with $DUF5_{Ah}$ (FIG. 5), similar to $DUF5_{Vv}$ intoxicated cells. This demonstrates that $DUF_{Ah}$ has potentially a similar mechanism as $DUF5_{Vv}$.

Ras is Truncated in $DUF5_{Vv}$ Intoxicated Cells.

The failure to detect all forms of Ras by the Ras10 antibody due to intoxication of cells by $DUF5_{Vv}$ and $DUF5_{Ah}$ was initially thought to be due to a covalent modification of Ras that disturbed the detection of Ras by the antibody. Other bacterial toxins are known to target Ras in this way. These include *Pseudomonas aeruginosa* ExoS that can ADP-ribosylate Ras (U.S. Pat. No. 5,599,665 A), but also modifies up to 20 other cellular proteins [28-30]. *Clostridium sordelli* TcsL or *Clostridium perfringens* TpeL are monoglucosyltransferases that can UDP-glucosylates Ras (Patent EP 0877622 B1), but also modifies many other small GTPase proteins like Rac [31-33][45]. Similarly, *C. difficile* TcdA and TcdB show UDP-glucosylation modification of many small GTPases including Ras [45]. The recently revealed lack of specificity of these proteins has made them poor candidates for toxins that would attack Ras when developed as toxin therapeutics.

Figure 6A:
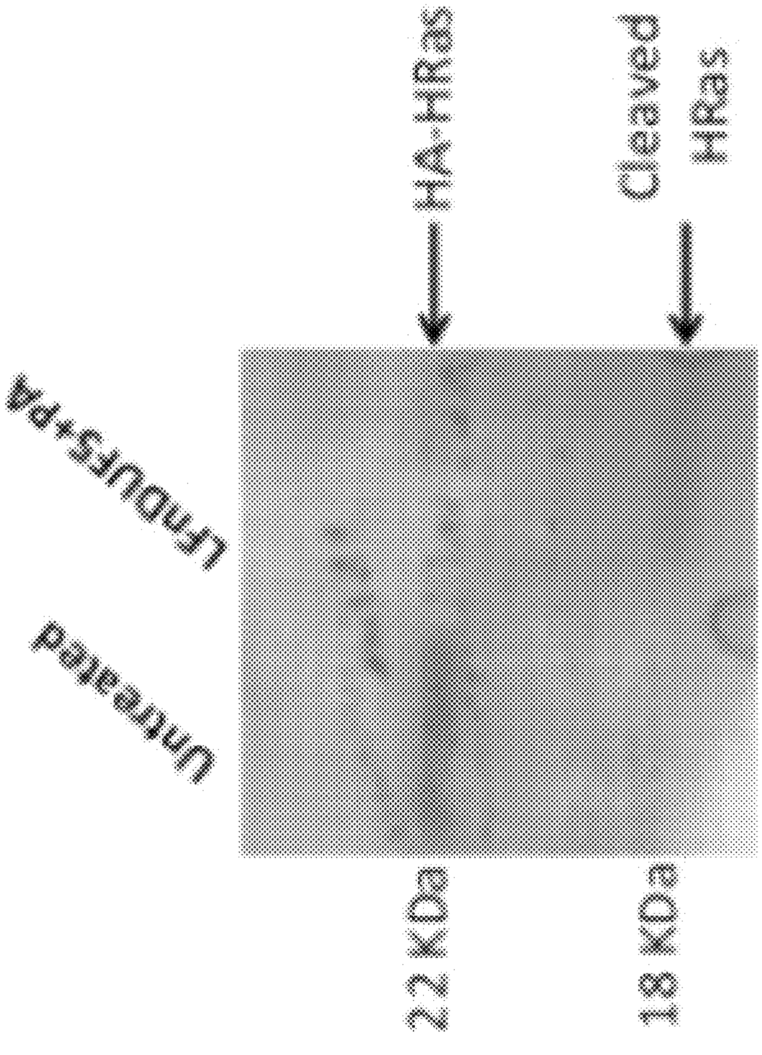
Figure 6C:
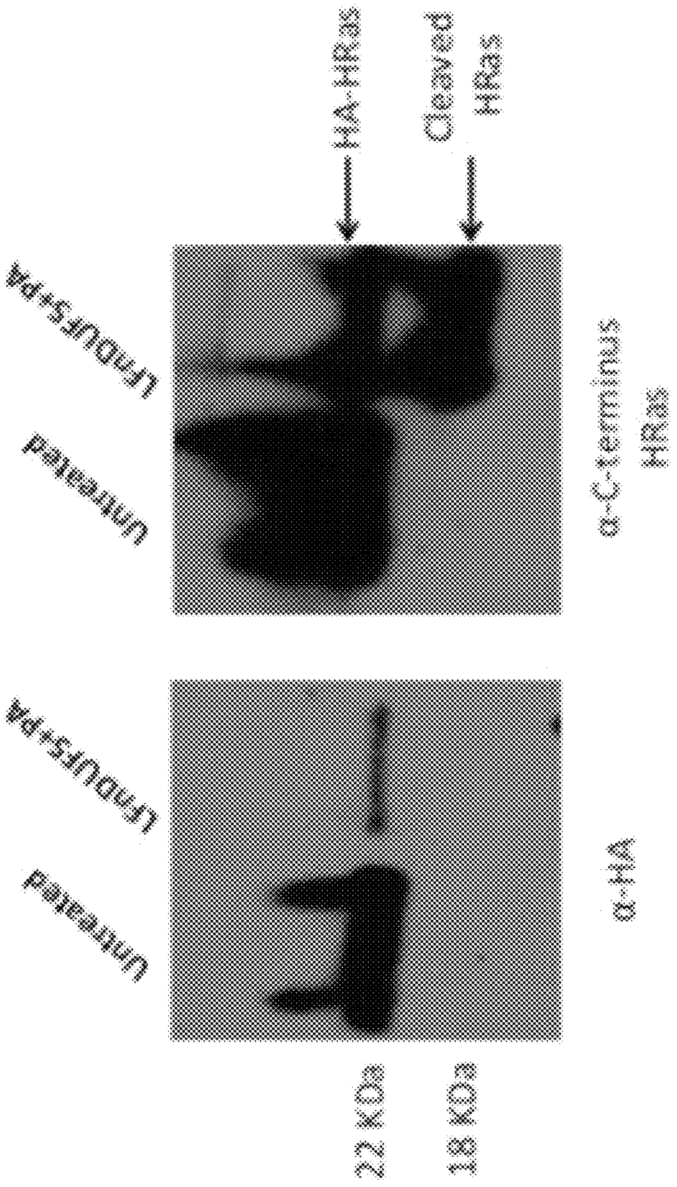

As a first step to identify the modification in Ras that prevented detection with the Ras10 monoclonal antibody in cells intoxicated with $DUF5_{Vv}$, HeLa cells were transiently transfected to express the H-Ras isoform with a hemagglutinin (HA) tag (sequence YPYDVPDYA, SEQ ID NO:29) fused at the N-terminus for detection by the HA peptide monoclonal antibody. These cells were intoxicated for 24 hr $LF_N DUF5_{Vv}$ in the presence of PA after which the HA-HRas protein was immunoprecipitated from cell lysate with using agarose beads conjugated with to the anti-HA peptide monoclonal antibody. The proteins specifically bound to the beads were eluted 3 M sodium thiocyanate solution and separated on an SDS-polyacrylamide gel. Coomassie brilliant blue staining of the gel revealed a 22 kDa protein band corresponding to HA-HRas for the unintoxicated Hela cells sample. However, for the intoxicated cells, an 18 kDa protein band was evident (FIG. 6A). Subsequent analysis of the trypsin-digested excised protein band by mass spectrometry revealed that the 18 kDa band was HRas, but absent the N-terminus (FIG. 6B). Western blot analysis, using anti-HA peptide monoclonal antibody and an anti-HRas polyclonal antibody specific for the C-terminus, confirmed that the 18 kDa band is HRas but truncated to remove the HA tag and the N-terminus of HRas (FIG. 6C). This result indicated that $DUF5_{Vv}$ is either an endopeptidase or activates a previously unknown host cell endopeptidase that targets the N-terminus of H-Ras.

Figure 7A:
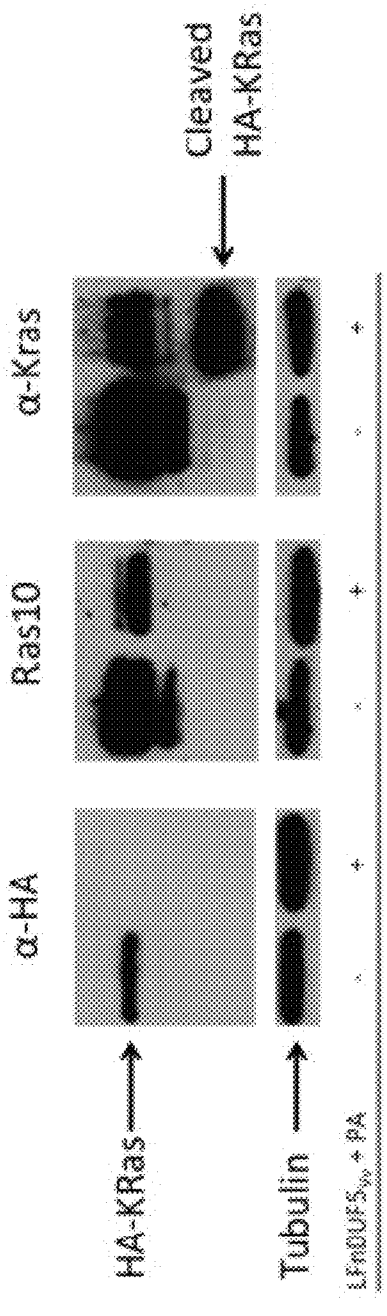
FIG. 7A, FIG. 7B and FIG. 7C illustrate that intoxication of cells with DUF5$_{Vv}$ (LF$_N$DUF5$_{Vv}$+PA) results in truncation of all Ras isoforms. HeLa cells were transfected to overexpress HA-tagged Ras isoforms as indicated and then intoxicated with LF$_N$DUF5$_{Vv}$/PA for 24 hr. Western blot analysis on HeLa whole cell lysates transfected with HA-KRas (FIG. 7A), HA-NRas (FIG. 7B) and HA-HRas (FIG. 7C). Cells were either untreated (−) or intoxicated with LF$_N$DUF5$_{Vv}$ in combination with PA (+).
Figure 7B:
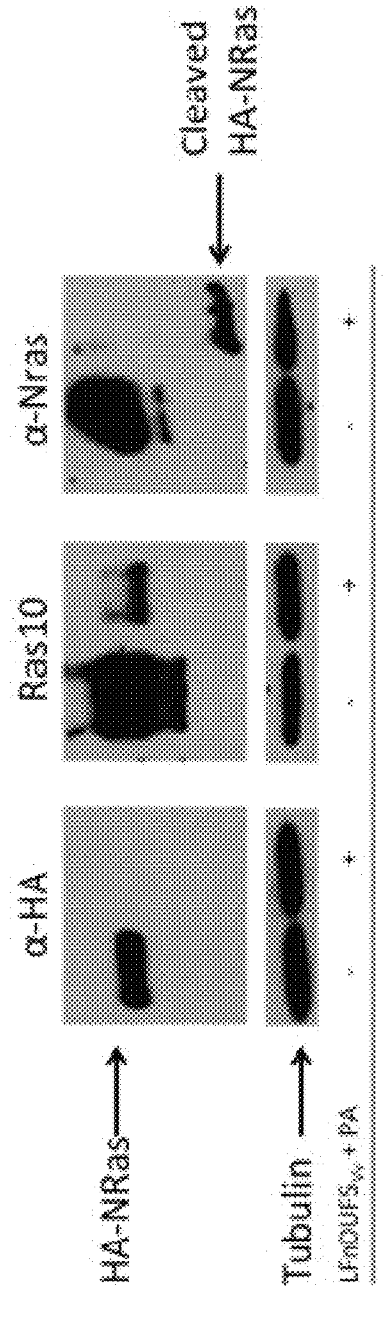
Figure 7C:
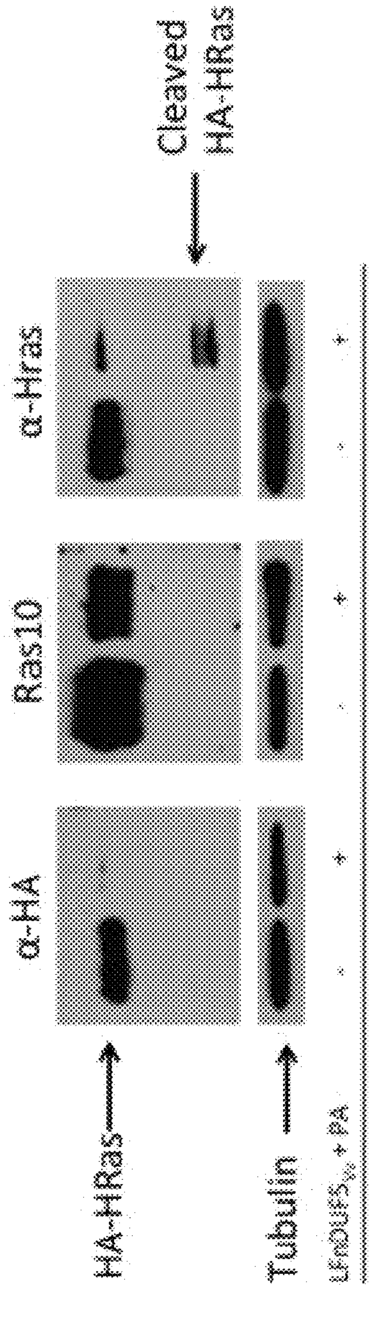

In addition, cells were transfected with plasmids to express HA-tagged versions of KRas, NRas, and HRas. All 3 isoforms of Ras were susceptible to cleavage in vivo resulting in truncated proteins that are not detected by the anti-HA antibody, but are detectable by isoform specific antibodies that recognize the unique C-terminus of each of the isoforms (FIG. 7).

$DUF5_{Vv}$ is Itself an Endopeptidase that Targets Ras.

Figure 8:
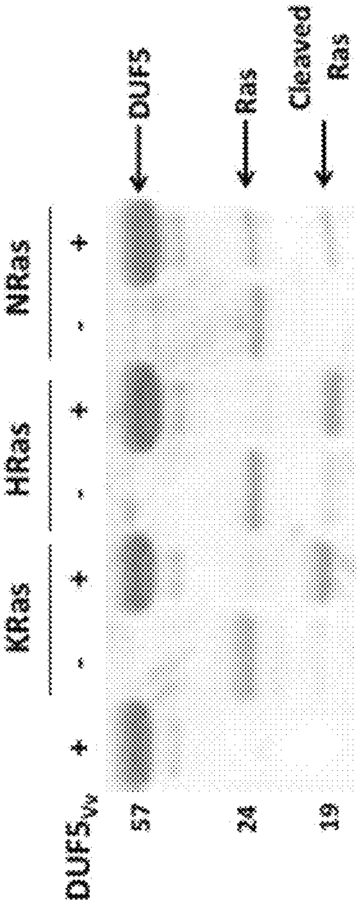
FIG. 8. DUF5$_{Vv}$ directly cleaves Ras isoforms in vitro. Reactions of rDUF5$_{Vv}$ recombinant Ras isoforms as indicated (1:1 molar ratio) was performed in 50 mM TRIS, 10 mM $MgCL_2$, 500 mM NaCl pH 7.5 at 37° C. Nucleotides were added as shown. After 10 minutes of incubation, each sample reaction was stopped by addition of 6×SDS-PAGE Loading buffer and boiling for 5 min. Samples were separated on 15% SDS-PAGE gel and bands were visualized with Coomassie brilliant blue.
Figure 9:
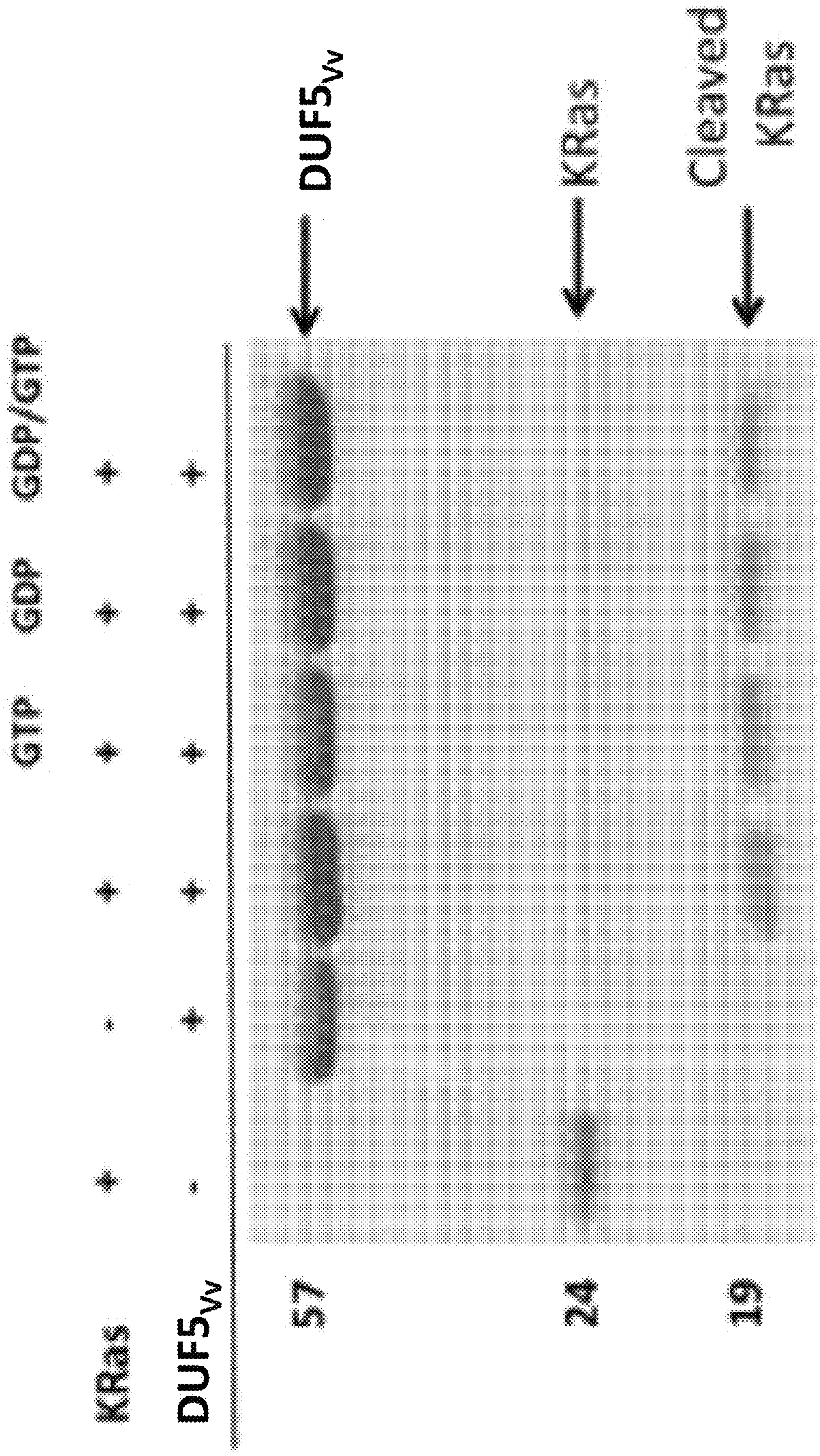
FIG. 9. DUF5$_{Vv}$ directly cleaves K-Ras in vitro. A reaction of rDUF5$_{Vv}$ with KRas performed in FIG. 8 in the presence of guanosine nucleotides as indicated show no dependence on nucleotide for proper conformation of rKRas in this reaction.
Figure 10:
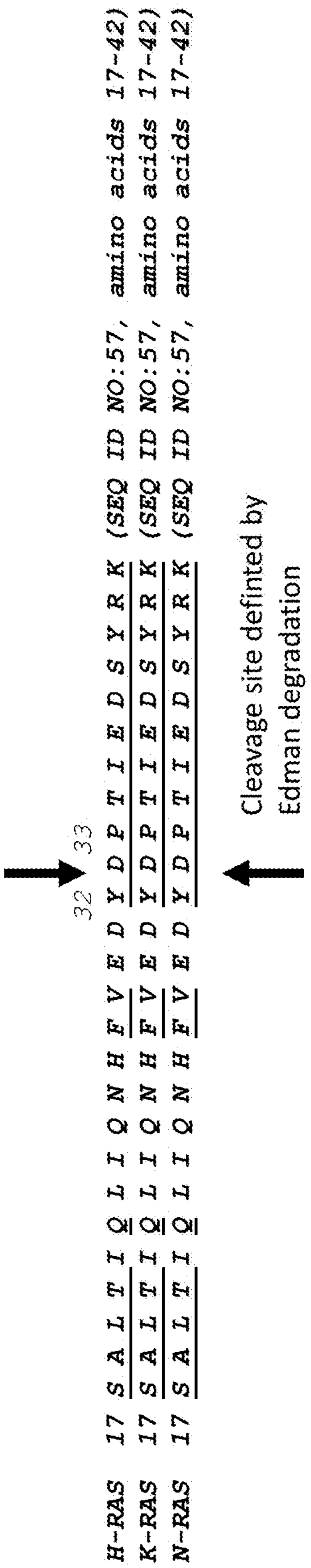
FIG. 10. DUF5$_{Vv}$ cleaves Ras isoforms between Y32 and D33. Bands in FIG. 8 were excised and N-terminal sequence determined by Edman degradation. All isoforms cleaved the same site shown by arrows.

To test if $DUF5_{Vv}$ is itself an endopeptidase that targets Ras isoforms rather than an activator of a host protease, gene sequences for KRas (KRas4B NP_004976.2), HRas (NP_001123914.1) and NRas (NP_002515.1) were cloned into pMCSG7 vector for *E. coli* expression with a 6×His tag at the N-terminus for nickel affinity purification. Recombinant rKRas and rHRas were purified from *E. coli* cell lysates using a pre-packed GE Biosciences His Trap FF column for single step NiNTA affinity chromatography. Recombinant NRas (rNRas) was expressed in inclusion bodies. The protein was therefore recovered from the insoluble fraction by suspension in buffer containing urea, purified by single step purification with NiNTA, and then rNRas refolded in the presence of excess GDP. rKRas, rHRas and rNRas were tested in vitro as substrate for $rDUF5_{Vv}$ (previously purified for crystallography studies described above) for an endopeptidase assay. The reaction products were analyzed by SDS-PAGE showed the cleavage of rKRas, rHRas, and rNRas by $rDUF5_{Vv}$. (FIG. 8). The cleavage of KRas was shown to occur regardless of the presence of guanosine nucleosides (FIG. 9). The cleavage of rNRas was less efficient compared to rKRas and rHRas, but this was likely due to the requirement to refold the protein resulting in a mixed pool of proper and improper folded substrate rather than a preference for substrate as there was no difference in substrate specificity in vivo (FIG. 7). Cleavage products for each reaction were analyzed by Edman degradation for N-terminal sequencing. The results revealed that DUF5 protein specifically cleaves KRas, HRas and NRas between residues Y32 and D33. (FIG. 10). These two residues are in the middle of Switch I region of KRas. Overall, these results confirm that $rDUF5_{Vv}$ is itself an endopeptidase able to cleave all common isoforms of Ras in vitro without host cell cofactors.

DUF5 Endopeptidase Activity in *Aeromonas hydrophila* and *Photorabdus asymbiotica.*

Figure 11:
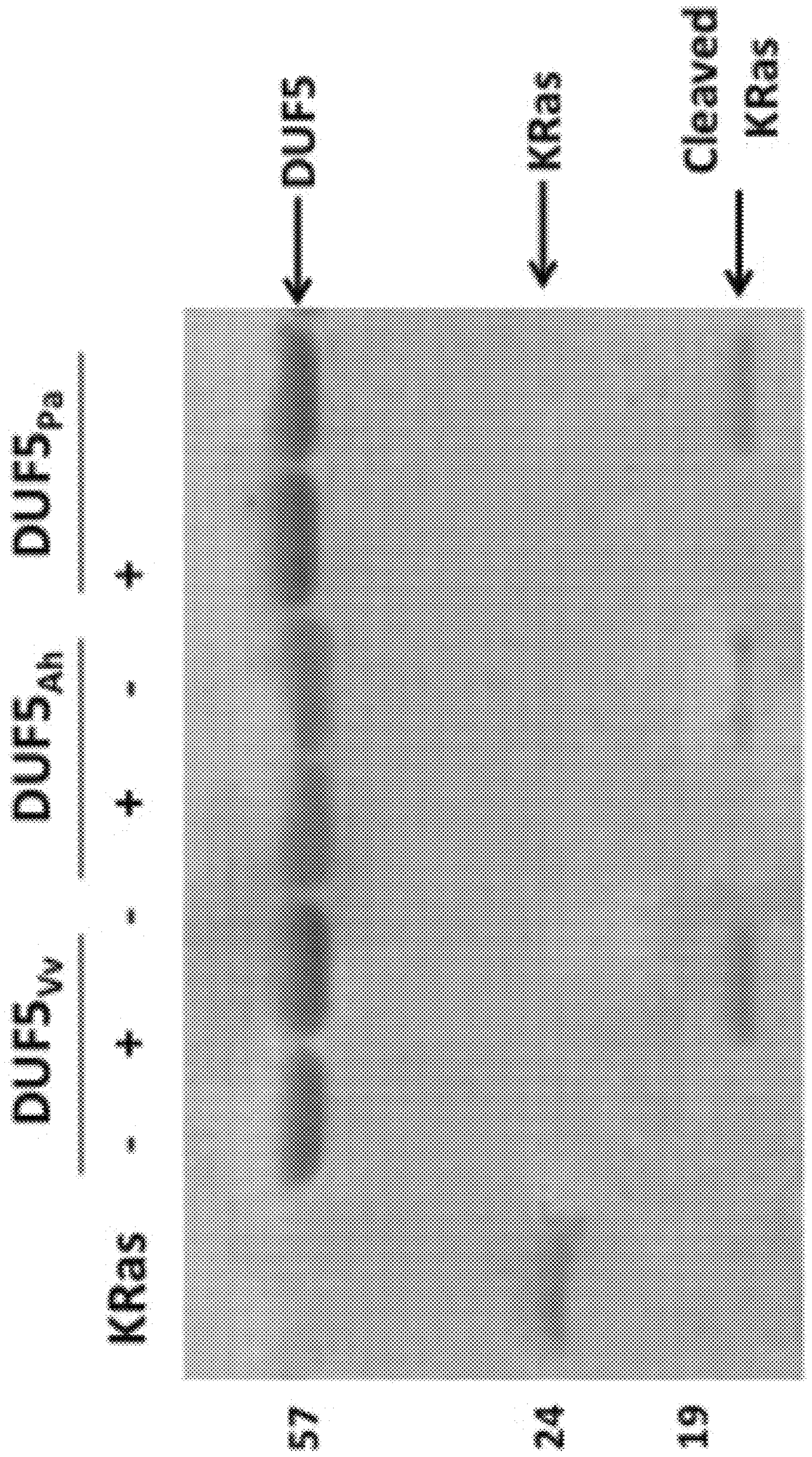
FIG. 11. rKRas is cleaved by DUF5 from *A. hydrophila* (DUF5$_{Ah}$) and by *P. asymbiotica* hypothetical protein PAT3833 (DUF5$_{Pa}$). A reaction of rDUF5$_{Vv}$ with KRas performed in FIG. 8 show that other proteins with homology to DUF5$_{Vv}$ can also cleave rKRas in vitro.

As detailed above, $DUF5_{Ah}$ from the *A. hydrophila* MARTX toxin effector domain is 62% identical to $DUF5_{Vv}$ and induced similar phenotypes as $DUF5_{Vv}$ when delivered to cells in vivo. Gene sequences for $DUF5_{Ah}$ were cloned into pMCSG7 vector for *E. coli* expression and purified similarly to $rDUF5_{Vv}$. The recombinant protein $rDUF5_{Ah}$ was able to cleave rKRas in the in vitro reaction (FIG. 11) demonstrating that the same domain from a different MARTX toxin is also an endopeptidase for Ras. This result indicates these are representative members of the larger family of MARTX effectors from at least 8 MARTX toxin and that all DUF5 domains from MARTX toxins will have this activity.

In addition to its presence in MARTX toxins, a hypothetical protein of *Photorhabdus* spp. (i.e. *P. asymbiotica* PAT3383 and *P. luminescens* Plu2400) has 56-59% similarity to $DUF5_{Vv}$. In *Photorhabdus* spp., this hypothetical proteins is not linked to a MARTX toxin but instead is found as a stand-alone gene that encodes a 542-568 aa hypothetical protein. Recombinant PAT3383 (here known as $DUF5_{Pa}$) was also successfully purified and shown to also cleave rKRas. N-terminal sequencing by Edman degradation of products excised from gel showed that all three DUF5 ($DUF5_{Vv}$, $DUF5_{Ah}$ and $DUF5_{Pa}$) cleave KRas between Y32 and D33. To our knowledge, none of the several DUF5 homologs identified has ever been characterized for its intrinsic function. $DUF5_{Ah}$ has been recently studied for its thermodynamic properties in the context on MARTX toxin unfolding and translocation [34].

$DUF5_{Vv}$ Endopeptidase is Specific for Ras and does not Process Representative Members of Other Small GTPases.

Figure 12:
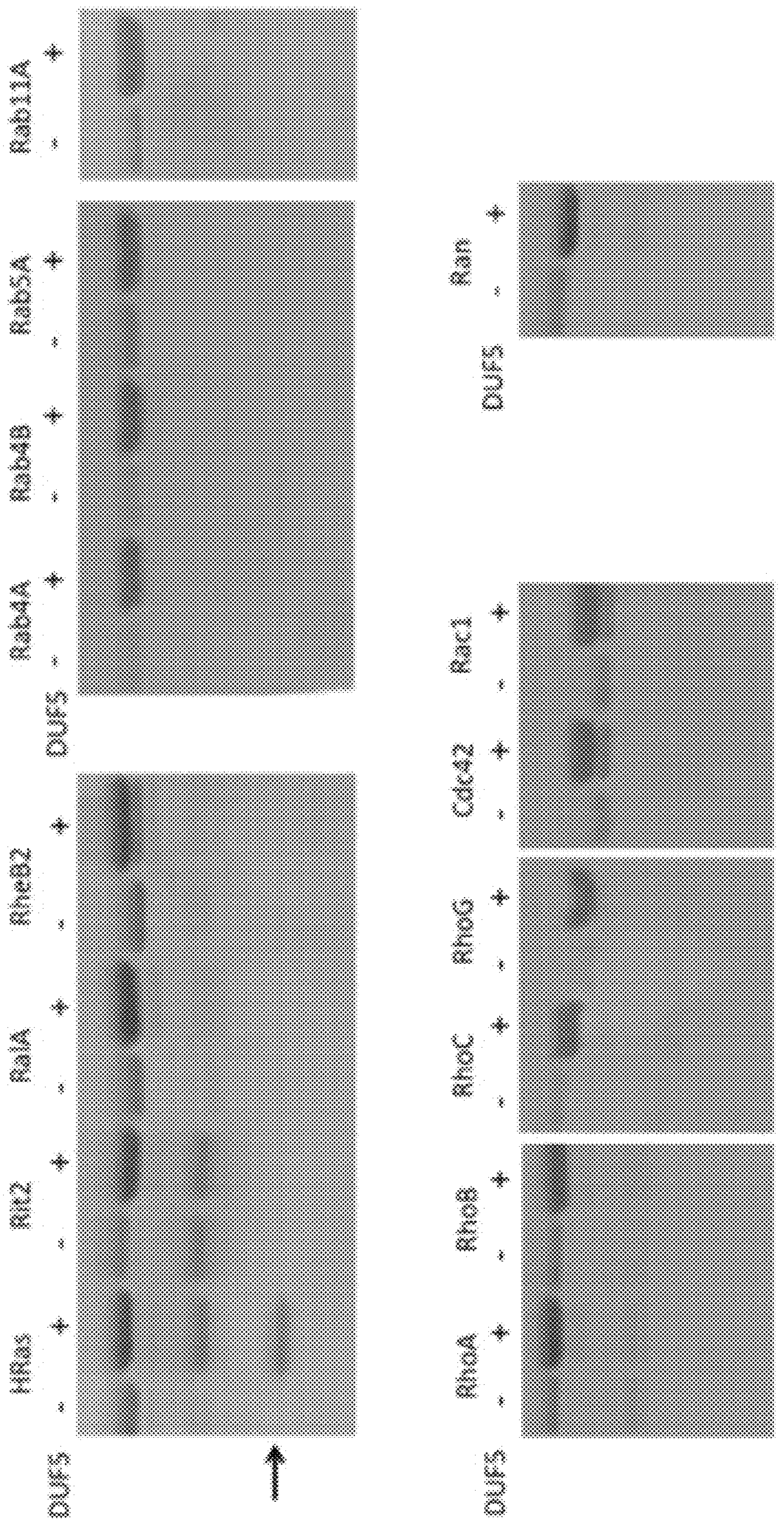
FIG. 12. Other small GTPase proteins are not cleaved by $DUF5_{Vv}$ A reaction performed as in FIG. 8 with $rDUF5_{Vv}$ with small GTPases proteins purified as fusions to glutathione-S-transfer as indicated. No other small GTPases were cleaved by $DUF5_{Vv}$.

$DUF5_{Vv}$ specificity was further tested by examining cleavage of representative members of small GTPase family. Recombinant proteins for other fused Ras family members (Rit2, RalA and RheB2) and small GTPase from other Ras superfamily groups: Rab (Rab4A, Rab4B, Rab5A and Rab11A), Rho (RhoA, RhoB, RhoC, RhoG, Cdc42 and Rac1) and Ran. Each protein was individually expressed in *E. coli* fused to glutathione-S-transferase for purification on glutathione agarose. Cloning, expression and purification condition of this rGTPase library was previously reported [35]. The in vitro cleavage assay was performed incubating each purified rGST-GTPase with $rDUF5_{Vv}$, rGST-HRas was used as positive control to demonstrate that the presence of GST does not interfere with the cleavage assay. The reaction products, analyzed by SDS-PAGE, showed that $DUF5_{Vv}$ could cleave only HRas. None of the other GTPase was cleaved by $DUF5_{Vv}$ (FIG. 12). The overall results demonstrate that $DUF5_{Vv}$ is a novel Ras endopetidase for, which cleaves specifically KRas, HRas and NRas.

DUF5 Endopeptidase Activity and Mutant KRas.

In this application, we propose that the Ras-directed endopeptidase activity of $DUF5_{Vv}$ and homologous proteins with similar activity can be directed toward treatment of cancers. As $DUF5_{Vv}$ targets normal Ras to compromise the cell, it can be utilized in a vast array of cancers. However, a particular focus of this work could be to target cancers that result from mutation of Ras itself. To achieve this, cells that have Ras with amino acid substitutions must be shown to be susceptible to $DUF5_{Vv}$.

Figure 13A:
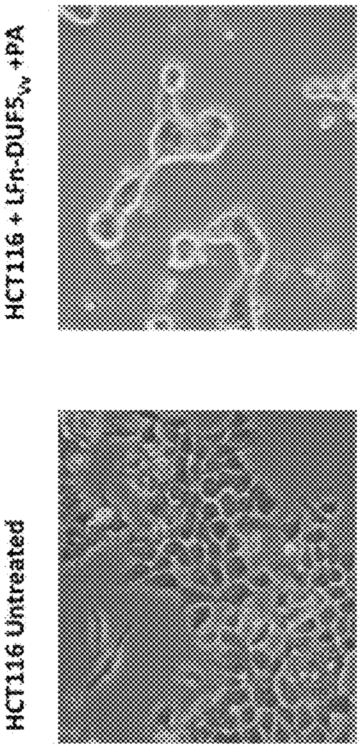
FIG. 13A and FIG. 13B illustrate that $LF_N DUF5_{Vv}$ is toxic to colorectal (HCT116, FIG. 13A) and breast cancer cell lines (MDA-MB-231, FIG. 13B). Cells were treated with $LFNDUF5_{Vv}$ in the presence of PA and cytotoxicity was observed.
Figure 13B:
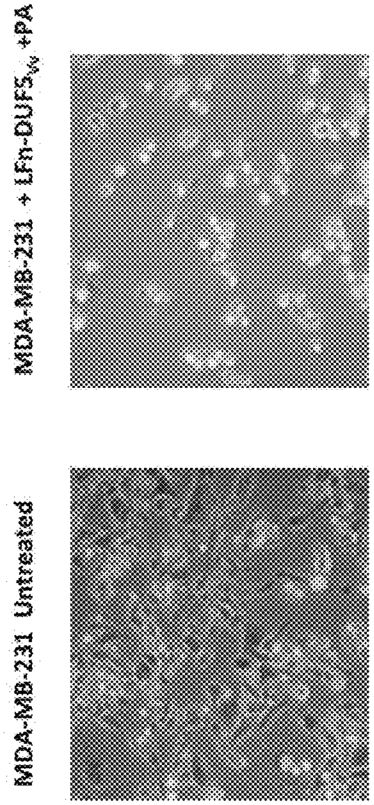

The cytotoxicity of $DUF5_{Vv}$ was tested in colorectal cancer cells (HCT116) and in breast cancer cells (MDA-MB-231). These two cells lines express, respectively, mutant KRas G12V and G13D. A dramatically morphology change was observed for HCT116 after 24 hours of intoxication with $LF_NDUF5_{Vv}$ in the presence of PA (FIG. 13A). The intoxicated cells showed a reduction in the number of cells and cell enlargement, suggesting swelling. In addition, the cells were observed to detach from the dish surface. MDA-MB-231 cells intoxicated with $LF_NDUF5_{Vv}$ for 24 hours showed a more "typical" cell rounding phenotype, similar to that previously observed in HeLa cells (FIG. 13B). With these experiments, we demonstrated the toxicity of $DUF5_{Vv}$ for cancer cells that are expressing mutant forms of KRas.

Figure 14:
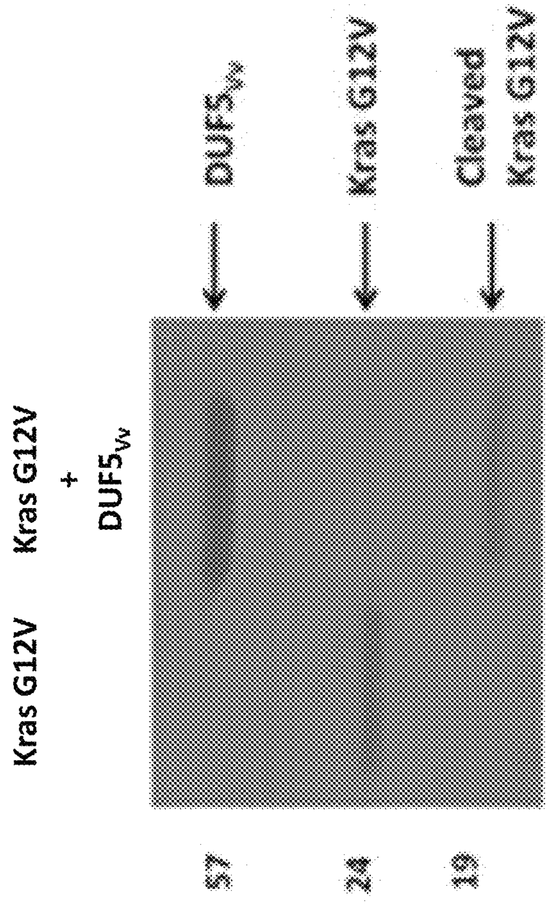
FIG. 14. rKRas G12V is cleaved by $DUF5_{Vv}$ A reaction of $rDUF5_{Vv}$ with rKRas bearing the common G12V mutation was performed as in FIG. 8. These data show that $DUF5_{Vv}$ can also mutant forms of rKRas that are common in cancer.

As further evidence of its applicability to treatment of Ras cancers, recombinant mutant KRas G12V was cloned into pMCSG7 and expressed in *E. coli*. The purified rKRas G12V was incubated with $rDUF5_{Vv}$ to check its cleavability in vitro. The reaction products, analyzed on SDS-PAGE, showed that $DUF5_{Vv}$ is still able to cleave mutant KRas (G12V) (FIG. 14).

Benefits Over Other Technologies.

Many bacterial toxins have been proposed for use in chemotherapy. Toxins that destroy the membrane, such as pore forming toxins have the potential to induce inflammation resulting in severe side effects. The advantage of this toxin over others is that it works from inside the cell to block normal cell survival pathways, thereby inducing loss of proliferation and normal non-inflammatory cell death.

Unlike toxins that target such processes as protein translation, this toxin directly targets a central regulatory pathway that is normal altered in cancer cells to promote cell survival and is thus key to the survival of the cancer itself. Ras cancers are among the most difficult to treat cancers due to the mutations in Ras. By directly targeting Ras in these cells, we can remove the protein that is driving the survival of the cancer.

A tripping point for some toxins (except those that form pores from the outside) is the ability to deliver to the cell cytosol where they can access target. We demonstrate that the DUF5 protein can be easily delivered to cells in an active form by the $LF_N$-PA delivery system. This system has already been modified to directly target cancer cells. A problem with the $LF_N$-PA delivery system, is that it is selective to translocate proteins that can rapidly unfold and spontaneously refold. We showed that this protein is able to cleave all molecules of Ras in cells at less then 30 minute after exposure indicating rapid translocation and delivery of active protein via the PA pore. Other delivery strategies will also require self-folding. We were able to purify this protein to homogeneity for the purpose of crystallography indicating that despite its plasticity, it is a stable protein for storage in vitro.

The specificity for Ras is also a benefit. Unlike other toxins that target Ras, this protein does not as yet show any specificity outside of HRas, NRas, and KRas. It does not target other small GTPases, which is the case for the Clostridial toxins TcsL, Tpel, TcdA, and TcdB. It does not show evidence of having cellular substrates in a wide range of protein families such as *Pseudomonas* Exotoxin A. Finally, these other proteins covalently modify the substrate, which there is some evidence is reversible. By contrast, DUF5 irreversibly cleaves the Ras proteins and thus cannot be reversed by the cell. For diversity of immunogenicity and increasing efficacy and activity are at least three different family members that share this activity and these are representative of the families across a wide range of bacteria species.

REFERENCES

1. Antignani A, Fitzgerald D: Immunotoxins: the role of the toxin. *Toxins* 2013, 5(8):1486-1502.
2. Shapira A, Benhar I: Toxin-based therapeutic approaches. *Toxins* 2010, 2(11):2519-2583.
3. Fan J J, Shao C P, Ho Y C, Yu C K, Hor L I: Isolation and characterization of a *Vibrio vulnificus* mutant deficient in both extracellular metalloprotease and cytolysin. *Infection and immunity* 2001, 69(9):5943-5948.
4. Chung K J, Cho E J, Kim M K, Kim Y R, Kim S H, Yang H Y, Chung K C, Lee S E, Rhee J H, Choy H E et al: RtxA1-induced expression of the small GTPase Rac2 plays a key role in the pathogenicity of *Vibrio vulnificus*. *The Journal of infectious diseases* 2010, 201(1):97-105.
5. Kim Y R, Lee S E, Kook H, Yeom J A, Na H S, Kim S Y, Chung S S, Choy H E, Rhee J H: *Vibrio vulnificus* RTX toxin kills host cells only after contact of the bacteria with host cells. *Cellular microbiology* 2008, 10(4):848-862.
6. Kwak J S, Jeong H G, Satchell K J: *Vibrio vulnificus* rtxA1 gene recombination generates toxin variants with altered potency during intestinal infection. *Proceedings of the National Academy of Sciences of the United States of America* 2011, 108(4): 1645-1650.
7. Jeong H G, Satchell K J: Additive function of *Vibrio vulnificus* MARTX($_{Vv}$) and $_{Vv}$hA cytolysins promotes rapid growth and epithelial tissue necrosis during intestinal infection. *PLoS pathogens* 2012, 8(3):e1002581.
8. Satchell K J: MARTX, multifunctional autoprocessing repeats-in-toxin toxins. *Infection and immunity* 2007, 75(11):5079-5084.
9. Satchell K J: Structure and function of MARTX toxins and other large repetitive RTX proteins. *Annual review of microbiology* 2011, 65:71-90.
10. Roig F. J. G-C, F. and Amaro C.: Domain organization and evolution of multifunctional autoprocessing repeats-in-toxin (MARTX) toxin in *Vibrio vulnificus*. *Appl Environ Microbiol* 2011, 77:657-668.
11. J. DJaSK: Analysis of *Vibrio cholerae* genome sequences reveals unique rtxA variants in environmental strains and an rtxA-null mutation in recent altered El Tor isolates. *mBio* 2013, 4:e00624-00612.
12. Ziolo K J, Jeong H G, Kwak J S, Yang S, Lavker R M, Satchell K J: *Vibrio vulnificus* biotype 3 multifunctional autoprocessing RTX toxin is an adenylate cyclase toxin essential for virulence in mice. *Infection and immunity* 2014, 82(5):2148-2157.
13. Egerer M, Satchell K J: Inositol hexakisphosphate-induced autoprocessing of large bacterial protein toxins. *PLoS pathogens* 2010, 6(7):e1000942.
14. Prochazkova K, Satchell K J: Structure-function analysis of inositol hexakisphosphate-induced autoprocessing of the *Vibrio cholerae* multifunctional autoprocessing RTX toxin. *The Journal of biological chemistry* 2008, 283 (35): 23656-23664.

15. Prochazkova K, Shuvalova L A, Minasov G, Voburka Z, Anderson W F, Satchell K J: Structural and molecular mechanism for autoprocessing of MARTX toxin of *Vibrio cholerae* at multiple sites. *The Journal of biological chemistry* 2009, 284(39):26557-26568.
16. Sheahan K L, Satchell K J: Inactivation of small Rho GTPases by the multifunctional RTX toxin from *Vibrio cholerae. Cellular microbiology* 2007, 9(5):1324-1335.
17. Ahrens S. GBaSKJ: Identification of small Rho GTPases by the multifunctional RTX toxin from *Vibrio cholerae. The Journal of biological chemistry* 2013, 288:1397-1408.
18. Kamitani S, Kitadokoro K, Miyazawa M, Toshima H, Fukui A, Abe H, Miyake M, Horiguchi Y: Characterization of the membrane-targeting C1 domain in *Pasteurella multocida* toxin. *The Journal of biological chemistry* 2010, 285(33):25467-25475.
19. Kitadokoro K, Kamitani S, Miyazawa M, Hanajima-Ozawa M, Fukui A, Miyake M, Horiguchi Y: Crystal structures reveal a thiol protease-like catalytic triad in the C-terminal region of *Pasteurella multocida* toxin. *Proceedings of the National Academy of Sciences of the U.S. Pat. No.* 2,007,104(12):5139-5144.
20. Orth J H, Preuss I, Fester I, Schlosser A, Wilson B A, Aktories K: *Pasteurella multocida* toxin activation of heterotrimeric G proteins by deamidation. *Proceedings of the National Academy of Sciences of the United States of America* 2009, 106(17):7179-7184.
21. Geissler B, Tungekar R, Satchell K J: Identification of a conserved membrane localization domain within numerous large bacterial protein toxins. *Proceedings of the National Academy of Sciences of the U.S. Pat. No.* 2,010, 107(12): 5581-5586. \
22. Geissler B, Ahrens S, Satchell K J: Plasma membrane association of three classes of bacterial toxins is mediated by a basic-hydrophobic motif. *Cellular microbiology* 2012, 14(2):286-298.
23. Brothers M C, Geissler B., Hisao G. S., Satchell K. J., Wilson B. A. and Rienstra C. M.: Backbone and side-chain resonance assignments of the membrane localization domain from *Pasteurella multocida* toxin. *Biomolecular NMR assignments* 2013.
24. Brothers M C, Geissler B, Hisao G S, Wilson B A, Satchell K J, Rienstra C M: Backbone and side-chain assignments of an effector membrane localization domain from *Vibrio vulnificus* MARTX toxin. *Biomolecular NMR assignments* 2013.
25. Stols L, Gu M, Dieckman L, Raffen R, Collart F R, Donnelly M I: A new vector for high-throughput, ligation-independent cloning encoding a tobacco etch virus protease cleavage site. *Protein expression and purification* 2002, 25(1):8-15.
26. Chang F, Steelman L S, Lee J T, Shelton J G, Navolanic P M, Blalock W L, Franklin R A, McCubrey J A: Signal transduction mediated by the Ras/Raf/MEK/ERK pathway from cytokine receptors to transcription factors: potential targeting for therapeutic intervention. *Leukemia* 2003, 17(7):1263-1293.
27. Steelman L S, Franklin R A, Abrams S L, Chappell W, Kempf C R, Basecke J, Stivala F, Donia M, Fagone P, Nicoletti F et al: Roles of the Ras/Raf/MEK/ERK pathway in leukemia therapy. *Leukemia* 2011, 25(7):1080-1094.
28. Ganesan A K, Vincent T S, Olson J C, Barbieri J T: *Pseudomonas aeruginosa* exoenzyme S disrupts Ras-mediated signal transduction by inhibiting guanine nucleotide exchange factor-catalyzed nucleotide exchange. *The Journal of biological chemistry* 1999, 274(31):21823-21829.
29. Maresso A W, Baldwin M R, Barbieri J T: Ezrin/radixin/moesin proteins are high affinity targets for ADP-ribosylation by *Pseudomonas aeruginosa* ExoS. *The Journal of biological chemistry* 2004, 279(37):38402-38408.
30. Simon N C, Barbieri J T: Exoenzyme S ADP-ribosylates Rab5 effector sites to uncouple intracellular trafficking. *Infection and immunity* 2014, 82(1):21-28.
31. Just I, Selzer J, Hofmann F, Green G A, Aktories K: Inactivation of Ras by *Clostridium sordellii* lethal toxin-catalyzed glucosylation. *The Journal of biological chemistry* 1996, 271(17):10149-10153.
32. Guttenberg G, Hornei S, Jank T, Schwan C, Lu W, Einsle O, Papatheodorou P, Aktories K: Molecular characteristics of *Clostridium perfringens* TpeL toxin and consequences of mono-O-G1cNAcylation of Ras in living cells. *The Journal of biological chemistry* 2012, 287(30): 24929-24940.
33. Nagahama M, Ohkubo A, Oda M, Kobayashi K, Amimoto K, Miyamoto K, Sakurai J: *Clostridium perfringens* TpeL glycosylates the Rac and Ras subfamily proteins. *Infection and immunity* 2011, 79(2):905-910.
34. Kudryashova E, Heisler D, Zywiec A, Kudryashov D S: Thermodynamic properties of the effector domains of MARTX toxins suggest their unfolding for translocation across the host membrane. *Molecular microbiology* 2014.
35. Mattoo S, Durrant E, Chen M J, Xiao J, Lazar C S, Manning G, Dixon J E, Worby C A: Comparative analysis of Histophilus somni immunoglobulin-binding protein A (IbpA) with other fic domain-containing enzymes reveals differences in substrate and nucleotide specificities. *The Journal of biological chemistry* 2011, 286(37):32834-32842.
36. Malumbres M, Barbacid M: RAS oncogenes: the first 30 years. *Nature reviews Cancer* 2003, 3(6):459-465.
37. Shimizu K, Goldfarb M, Perucho M, Wigler M: Isolation and preliminary characterization of the transforming gene of a human neuroblastoma cell line. *Proceedings of the National Academy of Sciences of the United States of America* 1983, 80(2):383-387.
38. Downward J: Targeting RAS signalling pathways in cancer therapy. *Nature reviews Cancer* 2003, 3 (1): 11-22.
39. Bazan J, Macdonald B, He X: The TIKI/TraB/PrgY family: a common protease fold for cell signaling from bacteria to metazoa? *Developmental Cell* 2013; 25(3): 225-227.
40. Sanchez-Pulido L, Ponting C: Tiki, at the head of a new superfamily of enzymes. *Bioinformatics* 2013; 29(19): 2371-2374.
41. Cordero C, Kudryahov D, Reisler E, Satchell K: The actin crosslinking domain of the *Vibrio cholerae* RTX toxin directly catalyzes the covalent cross-linking of actin. *The Journal of Biological Chemistry* 2006; 283(43) 32366-32374.
42. Spyres L, Qa'Dan M, Meader A, Tomasek J, Howeard E, Ballard J: Cytosolic delivery and characterization of the TcdB glycosylating domain by using a heterologous fusion protein. *Infection and Immunity* 2001; 69(1)599-601.
43. Ballard J, Doling A, Beauregard K, Collier R, Starnbach M: Anthrax toxin-mediated delivery in vivo and in vitro of a cytotoxic T-lymphocyte epitope from ovalbumin. *Infection and Immunity* 1998 66(2)615-619.

44. von Moltke J, Trinidad N J, Moayeri M, Kintzer A F, Wang S B, van Rooijen N, Brown C R, Krantz B A, Leppla S H, Gronert K, Vance R E: Rapid induction of inflammatory lipid mediators by the inflammasome in vivo. *Nature* 2012; 490(7418)107-11.

45. Zeiser J, Gerhard R, Just I, Pich A: Substrate specificity of clostridial glucosylating toxins and their function on colonocytes analyzed by proteomics techniques. *Journal of Proteomics Research* 2013, 12(4)1604-1608.

Example 2—Cytotoxicity of the *Vibrio vulnificus* MARTX Toxin Effector DUF5 is Linked to the C2A Subdomain Reference is made to Antic et al., *Proteins.* 2014 October; 82(10):2643-56, the content of which is incorporated herein by reference in its entirety.

Abstract

The multifunctional-autoprocessing repeats-in-toxin (MARTX) toxins are bacterial protein toxins that serve as delivery platforms for cytotoxic effector domains. The domain of unknown function in position 5 (DUF5) effector domain is present in at least six different species' MARTX toxins and as a hypothetical protein in *Photorhabdus* spp. Its presence in *Vibrio vulnificus* MARTX toxin increases potency of the toxin in mouse virulence studies, indicating DUF5 contributes to pathogenesis. In this work, DUF5 is shown to be cytotoxic when transiently expressed in HeLa cells. DUF5 localized to the plasma membrane dependent upon its C1 domain and the cells become rounded dependent upon its C2 domain. Both full-length DUF5 and the C2 domain caused growth inhibition when expressed in *Saccharomyces cerevisiae*. A structural model of DUF5 was generated based on the structure of *Pasteurella multocida* toxin facilitating localization of the cytotoxic activity to a 186 amino acid subdomain termed C2A. Within this subdomain, alanine scanning mutagenesis revealed aspartate-3721 and arginine-3841 as residues critical for cytotoxicity. These residues were also essential for HeLa cell intoxication when purified DUF5 fused to anthrax toxin lethal factor was delivered cytosolically. Thermal shift experiments indicated that these conserved residues are important to maintain protein structure, rather than for catalysis. The *Aeromonas hydrophila* MARTX toxin $DUF5_{Ah}$ domain was also cytotoxic, while the weakly conserved C1-C2 domains from *P. multocida* toxin were not. Overall, this study is the first demonstration that DUF5 as found in MARTX toxins has cytotoxic activity that depends on conserved residues in the C2A subdomain.

Introduction

Multifunctional-autoprocessing repeats-in-toxins (MARTX) toxins are large protein toxins (3500-5300 aa) secreted by Gram-negative bacteria[1]. These toxins carry from 1 to 5 protein effector domains, but also function as a delivery platform for transfer of these effector domains across the eukaryotic cell plasma membrane. These domains are then excised from the holotoxin by autoprocessing and released to the eukaryotic cell cytosol[2-4] where they function as "effectors" freed from the translocation system of the toxin[2-4]. Among the various MARTX toxins of different mammalian, aquatic, and insect pathogens, a total of 10 different effector domains are carried by MARTX toxins, although the number and positional organization of the arrayed effectors vary across strains and species[1]. The effector domain repertoire of the toxins can be exchanged by uptake of exogenous DNA and incorporation of the new sequences and/or loss of old sequences by homologous recombination resulting in novel toxins in different strains of the same species[5,6].

Within the target cell, the effector domains are thought to each have cytopathic or cytotoxic activity such that the overall role of the toxin in the eukaryotic cell is the sum of the activities of the effectors it delivers. Thus, it is important to individually characterize the function of each effector using genetics, biochemistry, and cell biology approaches to understand how an effector exchange will affect bacterial pathogenesis.

Among the 10 MARTX effector domains identified by sequence comparisons, only three have been functionally characterized[1]. The actin crosslinking domain (ACD) covalently links actin monomers via an isopeptide bond leading to actin cytoskeletal destruction[7-10]. The Rho GTPase inactivation domain (RID) disables the Rho regulatory pathway resulting in loss of active Rho and thereby to cytoskeleton depolymerization[11,12]. The ExoY domain is an adenylate cyclase[13]. The remaining seven MARTX toxin effector domains are uncharacterized but are often similar to domains of other large protein toxins[1].

Figures 15A, 15B, 15C, 15D, 15E, 15F, 15G, 15H:
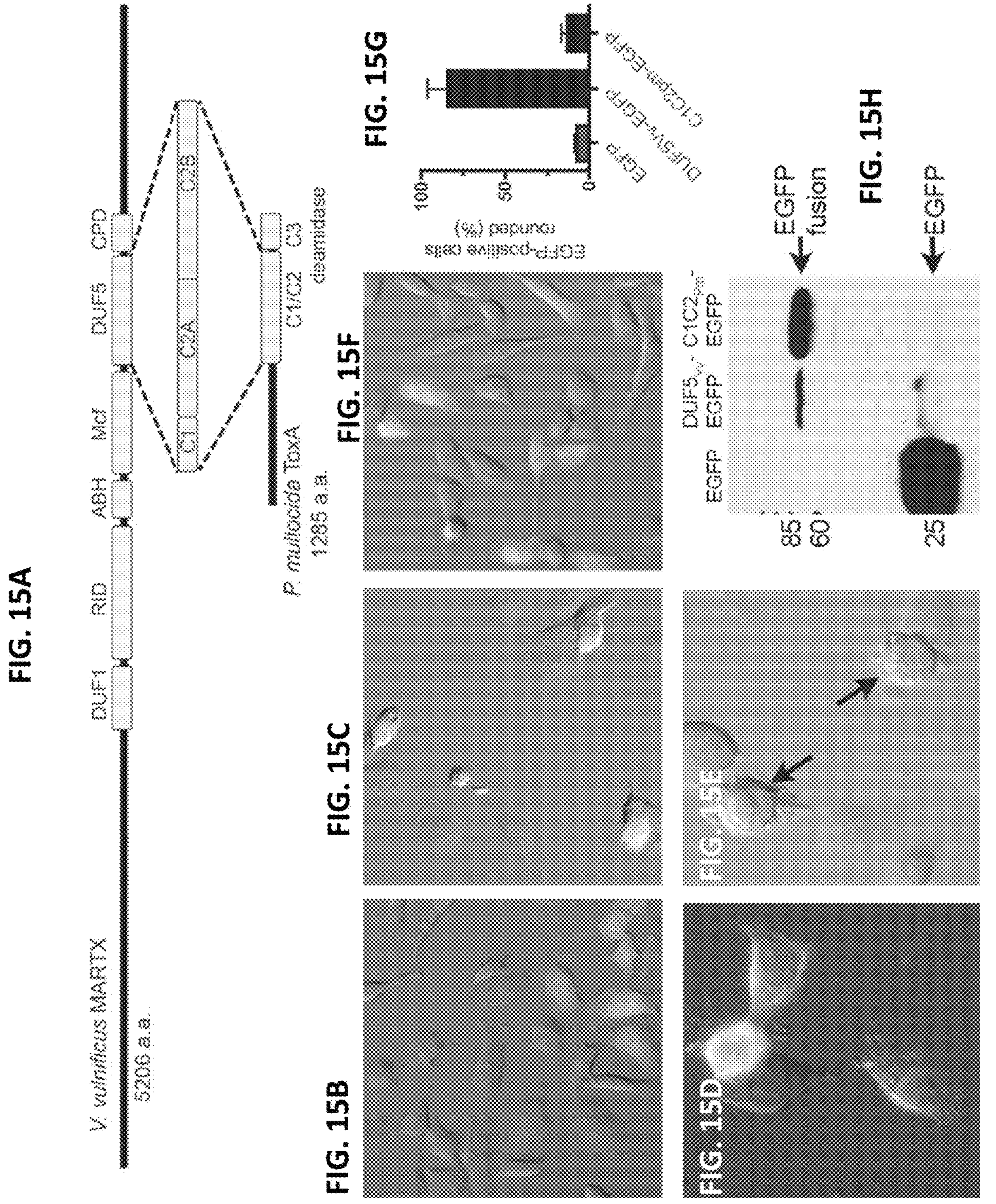
FIG. 15A, and FIG. 15B-H illustrate that DUF5 from *V. vulnificus* MARTX toxin is cytotoxic to HeLa cells.

One of the domains of unknown function is known as DUF5, indicating its presence in the 5th effector domain position of the *Vibrio vulnificus* strain CMCP6 MARTX toxin where it was first recognized[14] (holotoxin diagrammed in FIG. 15A). Within *V. vulnificus*, the presence of $DUF5_{Vv}$ increases the potency of the toxin during mouse infection resulting in a lower $LD_{50}$ compared to an isogenic strain from which the effector domain was deleted or a naturally occurring strain that lost $DUF5_{Vv}$ via a homologous recombination events. Thus, $DUF5_{Vv}$ is a virulence factor that increases the pathogenicity of the strains that carry it as a domain within the MARTX toxin.

$DUF5_{Vv}$ was initially recognized to have sequence similarity to *Pasteurella multocida* toxin (PMT), whose carboxyl-terminus is composed of three domains: C1, C2, and C315. The C1Pm subdomain from PMT is known to be a four helical bundled membrane localization domain (4HBM)[16]. The conserved $C1_{Vv}$ subdomain from $DUF5_{Vv}$ has also been demonstrated to localize to the eukaryotic plasma cell membrane, where it binds anionic lipids via a basic-hydrophobicmotif[12,17]. Structural determination by nuclear magnetic resonance of the isolated C1Pm and $C1_{Vv}$ subdomains confirm both of these domains form a four helical bundle in solution[18,19].

However, none of the extensive characterization of PMT has revealed the function of its C2 domain. The PMT C3 domain is a deamidase enzyme with a catalytic cysteine residue that acts on the Gα subunits of trimeric G proteins[20-23]. It is notable that the sequence similarity of $DUF5_{Vv}$ with PMT is limited to the C1 and C2 domains and $DUF5_{Vv}$ does not share the C3 deamidase domain and thus $DUF5_{Vv}$ is not expected to have a similar activity (FIG. 15A). DUF5 is present also within MARTX toxins of *Aeromonas hydrophila, Yersinia kristensenii, Vibrio splendidus*, and *Xenorhabdus nemotophila*1 and as the stand-alone hypothetical protein plu2400 in *Photorhabdus* sp.,[24] where it might be an effector with a distinct delivery mechanism such as Type III secretion or the Tc complex[25].

In this study, we initiated a de novo investigation on this protein of unknown function. We generated a structural model of $DUF5_{Vv}$ based on the structure of the PMT C-terminus[15]. We then show that ectopic expression of the domain in HeLa cells is cytotoxic. In *Saccharomyces cerevisiae*, expression of the $DUF5_{Vv}$ causes growth inhibition. The toxic effect in HeLa cells is mapped to a 186 amino acid C2A subdomain and shown to require an Asp and Arg residue. Overall, these studies mark our initial efforts to establish that DUF5 is a bona fide MARTX toxin effector.

Materials and Methods

Cell Lines, Media, Reagents and Plasmids

HeLa epithelial cells were grown at 37° C. with 5% $CO_2$ in Dulbecco's Modified Eagle Medium (DMEM, Life Technologies Gibco) with 10% fetal calf serum (Gemini Bio-Products, West Sacramento, CA), 100 U/ml penicillin, and 1 μg/ml streptomycin. J774 macrophages, COS7 fibroblasts, and HEp-2 epithelial cells were grown in identical conditions. *E. coli* DH5a, TOP10 (Life Technologies Invitrogen) and BL21(DE3) were grown at 37° C. in Luria-Bertani (LB) liquid or agar medium containing either 100 μg/ml ampicillin or 50 μg/ml kanamycin as needed. *S. cerevisiae* strain InvSc1 (Invitrogen) was grown on YPD liquid or agar medium at 30° C. or commercial synthetic complete (SC-ura) supplemented with yeast nitrogen base (MP Biomedicals) as detailed below. Media components and common reagents were obtained from Sigma-Aldrich, Fisher, or VWR and common restriction enzymes and polymerases from New England Biolabs or Invitrogen. Custom DNA oligonucleotides and gBlocks were purchased from Integrated DNA Technologies (Coralville, IA). Plasmids were prepared either by alkaline lysis with precipitation in ethanol or purified using Epoch spin columns according to manufacturer's recommended protocol.

Alignments and Structural Modeling

Proteins with homology to $DUF5_{Vv}$ from strain CMCP6 were identified using BLASTP26 at the National Center for Biotechnology Information website. Amino acid sequences were trimmed to $DUF5_{Vv}$ homology region and aligned with CLUSTALW using MacVector 12.6.0. The $DUF5_{Vv}$ and $DUF5_{Vv}$ D3721A protein sequences were also aligned to the pdb database using HHpred27 and a pdb structural model built based on published PMT structure (pdb 2EBF15) using Modeller 28. Figures were generated from the structural model using MacPyMol.

Construction of Plasmids for Ectopic Expression in HeLa Cells and Yeast

DNA corresponding to coding sequence for amino acids 3579-4089 of the *V. vulnificus* rtxA1 gene (GI: 27366913; vv2_0479) was amplified from purified *V. vulnificus* CMCP6 chromosomal DNA using Pfx50 DNA polymerase (Invitrogen) and primers 1 and 2 (5'-gagctagcatgggtgataaaaccaaggtcgtggattta (SEQ ID NO:55), and 5-gccgtcgaccaaactgcccttgaacgtgatcttcggttt (SEQ ID NO:56)). The insert was digested with enzymes NheI and SalI and ligated into the similarly digested vector. For expression of the *P. multocida* toxA gene sequence corresponding to aa 573-1113 of PMT from strain 4533 (GI:149228008), a synthetic codon optimized double stranded DNA sequence was obtained from GenScript (Piscataway, NJ) in pUC57 and subcloned into pEGFP-N3 via the HindIII and BamHI sites.

DNA sequences above were similarly amplified except with novel EcoRI and KpnI restriction sites incorporated into the oligonucleotides for transfer into yeast expression vector pYC2 NT/A (Invitrogen) using primers 6,7,8 and 11 (5'-aaggtaccgtttatcggtaagatgcaagttgcc (SEQ ID NO:30), 5'-agaattctcacaaactgcccttgaacgtgatc (SEQ ID NO:31), 5'-aaggtaccgggtgataaaaccaaggtcgtg (SEQ ID NO:32), and 5'-aaggtaccggatattgacgcttgggatcgt, SEQ ID NO:33).

Ectopic Expression of EGFP Fusion Proteins in HeLa Cells

Plasmids for transfection were prepared using the Qiagen Midi Prep kit. HeLa cells grown to approximately 80% confluency were transfected using Fugene HD (Promega) and 2 μg plasmid DNA at a 4:1 ratio for 5 h after which fresh media was exchanged. For western blotting, cells were collected 24 h after transfection in 2×SDS-PAGE buffer, boiled for 5 min, and the proteins were separated by SDS-PAGE and transferred to nitrocellulose by the tank blot method. Western blotting was done as previously described17 using anti-GFP antibody conjugated to horseradish peroxidase (Milteny Biotec 130-091-833) at a 1:1000 dilution. SuperSignal West Pico Chemiluminescent Substrate and autoradiography was used for detection.

For microscopy, HeLa cells were grown in 35 mm Mat-Tek glass bottom microwell dishes to approximately 60% confluency and transfected as described above. Live cells were imaged 24 h after transfection by epifluorescence and differential interference contrast (DIC) microscopy at 200× using the Andor Spinning Disk confocal microscope. Images were overlayed using NIH ImageJ64 and assembled into figures using Adobe Photoshop CS6. Rounded cells were manually counted from at least 3 different transfections. Histograms of representative cells were plotted using Graph-Pad Prism 4.0 or 6.0.

Purification of Proteins Fused to Anthrax Toxin Lethal Factor N-Terminus

Plasmid vector pRT24 is a variant of pABII29 in which the coding sequence for amino acids 1-254 of anthrax toxin lethal factor ($LF_N$) are expressed with an N-terminal His-tag under control of the T7 promoter. The plasmid was modified to replace the single BamH1 cloning site with an oligonucleotide that introduces the TEV cleavage site and ligation independent cloning site from pMCSG730. $DUF5_{Vv}$ DNA sequences were amplified with primers 3 and 4 (5'-tacttccaatccaatgctgataaaaccaaggtcgtggtcgattta (SEQ ID NO:58) and 5'-ttatccaatgtgaaagagcggtatttgcgccactcaa (SEQ ID NO:59)) and integrated into pRT24 by ligation-independent cloning[30]. A stop codon after the codon for Thr3765 was introduced to generate a sequence that would be truncated after C2A. Site-directed mutagenesis was then used to alter codons D3721 and R3841 to Ala as described above. DUF5 from *A. hydrophila* fused to LFN (LFN-$DUF5_{Ah}$) was generated in the same manner as LFN$DUF5_{Vv}$ except using primers 14 and (5'-tacttccaatccaatgctccgggcaaaacggtggtgacg (SEQ ID NO:39), and 5'-ttatccacttccaatgctagacatcggcgtactcgacccgc (SEQ ID NO:40)) to amplify the sequence corresponding to the MARTX toxin aa 3069-3570 (GI: 117618727) from chromosomal DNA prepared from *A. hydrophila* 7966 obtained from the American Type Culture Collection.

LFN and LFN fusion proteins were expressed in *E. coli* BL21 (DE3). Briefly, overnight cultures were diluted 1:100 in fresh LB containing the 100 μg/ml ampicillin and grown to OD600=1.0 at 37° C. before inducing the cultures with 1 mM isopropyl β-D-1-thiogalactopyranoside (IPTG) for 4 h at 32° C., except for $LF_N DUF5_{Vv}$ expression which was induced with 0.5 mM IPTG and cells were grown at 30° C. *E. coli* cells were harvested by centrifugation at 10,100×g and resuspended in 100 ml Urea Buffer A (500 mM NaCl, 20 mM Tris pH 7.4, 5 mM imidazole and 8 M urea with addition of protease inhibitor tablets (cOmplete, EDTA-free purchased Roche Applied Sciences). Resuspended cells were sonicated using a Branson Sonifier model 102C for 7 min at 50% amplitude with the standard disruptor. Crude lysates were centrifuged at 17,600×g for 30 min to remove particulates and the remainder of the lysate was filtered across a PALL Acrodisc 0.45μ syringe filter. Lysate was loaded onto a 1 ml GE Healthcare HisTrap column using the AKTA purifier protein purification system (GE Healthcare). Column was washed with 5 ml Urea Buffer A with 10 mM imidazole, followed by 5 ml 50 mM imidazole buffer to remove contaminating proteins. His-tagged LFN proteins were eluted using an imidazole gradient from 50 to 250 mM. Peak fractions corresponding to the protein of interest were collected, pooled, and dialyzed to remove imidazole into a buffer containing 500 mM NaCl, 20 mM Tris, and 2 M urea, pH 7.4. Proteins were further purified by gel exclusion chromatography in the same buffer using a 16×100 Superdex 200 column (GE Healthcare). Purified proteins were concentrated using Millipore Amicon Ultra 30K spin concentrators and glycerol was added so that the final buffer was 300 mM NaCl 12 mM Tris pH 7.4, 1.2M urea, 20% glycerol. Protein concentration was determined using the NanoDrop ND1000, and purity was estimated using SDS-PAGE. Proteins were stored at −80° C. until used.

Protective antigen (PA) was purified from the soluble fraction of *E. coli* BL21(DE3). Cells were grown at 37° C. to OD600=0.8, then the culture was induced with 1 mM IPTG for 4 h at 30° C. Bacterial culture was harvested by centrifugation, then resuspended in 500 mM NaCl, 20 mM Tris, 5 mM imidazole, pH 8.0. Lysate was prepared as for $LF_N$ fusion proteins above except buffers did not contain urea. Sizing was performed as described above in 500 mM NaCl, 20 mM Tris pH 8.0 buffer.

Intoxication of Mammalian Cells with $LF_N$ Fusion Proteins and PA

All cell types were grown in 24 well tissue culture treated dishes (Falcon). 7 nM PA and 3 nM $LF_N$-fusion proteins were added to 1 ml culture media overlaying the cells. Cells were incubated for 24 or 48 h at 37° C. in 5% $CO_2$, after which cells were imaged at 100× by phase microscopy using a Nikon CoolPix 995 digital camera affixed to a Nikon TS Eclipse 100 microscope. For quantification, rounded cells were manually counted representing at least 3 independent experiments and results were graphed as histograms using GraphPad Prism 4.0 or 6.0.

Assay for Cell Lysis

Lactate dehydrogenase (LDH) release from intoxicated cells was determined using the Cytotox 96 Non-Radioactive Cytoxicity Assay (Promega). After intoxication, 50 μl of culture media was removed from each well, mixed with 50 μl of reaction reagent, and incubated at room temperature protected from light for 30 min. Upon addition of stop solution, absorbance was measured at 490 nm. For determination of total LDH, cells from the same wells were lysed by addition of Triton X-100 to the residual media to a final concentration of 0.1% and then sampled and assayed as described above to determine the maximum lysis value for each well. Percent cell lysis was calculated using the formula $$\left(\frac{A490media}{(A490media+\text{cells})}\right)\text{exp}-\left(\frac{A490media}{(A490media+\text{cells})}\right)\text{untreated}*100.$$

Assessment of Yeast Growth Inhibition

*S. cerevisiae* strain InvSc1 was grown in YPD broth prior to transformation. Yeast cells were transformed using a PLATE solution method and transformants selected using SC agar medium without uracil, supplemented with glucose as previously described[31]. Transformed yeast cells were inoculated into liquid glucose synthetic complete medium (without uracil) and grown overnight at 30° C. The next day, cultures were centrifuged and washed three times with sterile water. Each sample was resuspended in water and $OD_{600}$ was measured for each using Beckman Coulter DU530 Spectrophotometer. All samples were normalized to $OD_{600}$=0.5 and then were 10-fold serially diluted. 5 μl of each dilution was spotted on solid agar selective medium (−uracil) with either 20 mg/ml glucose or 20 mg/ml galactose and 10 mg/ml raffinose. The plates were incubated at 30° C. for 3 days before growth was assessed and plates photographed using a digital camera. For growth cures, $OD_{600}$ of overnight cultures was measured and inoculi were normalized to each other and then diluted into 50 ml of SC medium containing 20 mg/ml galactose and 10 mg/ml raffinose (-uracil) to induce expression from the plasmid. $OD_{600}$ was measured every 2 h for 12 h to document growth patterns.

Alanine Scanning Mutagenesis

Site-directed mutagenesis to introduce an alanine or stop codon at locations noted in text was carried out using PfuTurbo DNA polymerase (Invitrogen) and custom oligonucleotides designed via Agilent PrimerDesign software. After amplification, DNA was treated with DpnI and transformed to *E. coli* TOP10. Isolated plasmids were sequenced to confirm gain of the desired mutation and to check for absence of unintended mutations during DNA amplification. Double mutant D3721R/R3841D in pYC-DUF5 plasmid was generated by cohesive end cloning of a synthetic DNA gBlock containing the R3841D mutation in exchange for the wild type sequence via flanking BamHI and AatII restriction enzyme sites (5'-atctttatggtcgcgattgaagaagccaacggtaaacacgtaggtttgacggacatgatggttcgttgggccaatgaagaaccatacttg gcaccgaagcatggttacaaaggcgaaacgccaagtgaccttggttttgatgcgaagtaccacgtagatctaggtgagc, SEQ ID NO:34). Purification of recombinant 6×HIS-tagged proteins for fluorescence thermal shift assays DNA corresponding to $DUF5_{Vv}$ was inserted into the overexpression vector pMSCG7 by ligation independent cloning using primers 12 and 13, (5'-tacttccaatccaatgctcaagagctgaaagaaagagcaaaag, SEQ ID NO:35 and 5'-tacttccaatccaatgctcaagagctgaaagaaagagcaaaag, SEQ ID NO:36). Additional mutations were generated by site directed mutagenesis. Plasmids were transformed into *E. coli* BL21 (DE3) for purification. Cells were grown to $OD_{600}$=0.8 at 37° C. The temperature was reduced to 18° C. and protein expression induced by the addition of IPTG to a final concentration of 1 mM. Cells were grown overnight with shaking and then harvested by centrifugation. Bacteria were resuspended in a buffer containing 50 mM Tris (pH 8.3), 500 mM NaCl, 0.1% Triton X-100, and 5 mM β-mercaptoethanol and lysed by sonication. After centrifugation at 30,000×g for 30 min, the soluble lysate was filtered through a 0.22 μm membrane and loaded onto a 1 ml HisTrap column using the ÄKTA purifier protein purification system (GE Healthcare). After washes with 50 mM Tris, 500 mM NaCl, 50 mM Imidazole pH 8.3, the proteins were eluted in the same buffer with 500 mM imidazole. Proteins were further purified by gel filtration chromatography (Superdex 75 (16/60), GE Healthcare) in buffer containing 10 mM Tris-HCl, 500 mM NaCl, 5 mM β-mercaptoethanol, pH 8.3.

Fluorescence Thermal Shift Assay

The experiment was performed using a 96-well thin-wall PCR plate (Axigen). 20 μl reactions consisted of 2 μM protein in a solution of 5×SYPRO orange dye (Life Technologies), 0.1 mM HEPES, 150 mM NaCl, pH 7.5. Fluorescence intensity was monitored using the StepOnePlus™ Real-Time PCR Systems (Life Technologies) instrument.

Samples were heated from 25° C. to 95° C. at a scan rate of 1° C./min. Tm values were extrapolated using Protein Thermal Shift™ Assay software (Life Technologies).

Results $DUF5_{Vv}$, but not C1C2Pm, is Cytotoxic when Ectopically Expressed in HeLa Cells To determine if DUF5 is a bona fide effector with cytotoxic effects on cells, the DNA sequence corresponding to *V. vulnificus* aa 3579-4089 ($DUF5_{Vv}$) was amplified and cloned into ectopic expression vector pEGFP-N3 for expression of $DUF5_{Vv}$ as a fusion to EGFP under control of the CMV promoter. The plasmid was transformed into cultured HeLa cervical carcinoma epithelial cells and EGFP-positive cells were imaged after 24 hr. Cells expressing EGFP had a normal, cuboidal shape with less than 8% of cells rounded (FIG. 15B). By contrast, 82% of cells ectopically expressing the $DUF5_{Vv}$-EGFP fusion were small and rounded and many of the cells showed signs of blebbing indicating necrosis (FIG. 15B,D). Some cells that had not yet fully rounded or necrosed showed $DUF5_{Vv}$-EGFP localized to the cell periphery, consistent with the presence of the C1 plasma membrane localization domain (FIG. 15C). Western blot detection of the $DUF5_{Vv}$-EGFP fusion showed less total protein than detected for the EGFP-expressing control cells (FIG. 15H), indicating that expression of this fusion protein was toxic to cells and many cells expressing the $DUF5_{Vv}$-EGFP may have detached.

$DUF5_{Vv}$ has 24% sequence identity with the C1-C2 domains of PMT (C1C2Pm) (FIG. 15A). Since the toxA gene is carried on a bacteriophage with a low GC content (35% GC), a eukaryotic codon-optimized, synthetic copy of toxA sequences corresponding to C1C2Pm was obtained and expressed in cells generating a protein similar in size to $DUF5_{Vv}$-EGFP (FIG. 15H). Cells expressing C1C2Pm-EGFP appeared similar to EGFP-control expressing cells (FIG. 15F). These results support previous data[20,21,32,33] that all toxic activities of PMT are due to the C3 deamidase domain that is absent in $DUF5_{Vv}$. Further, these data show that the cytotoxic activity of $DUF5_{Vv}$ may not be conserved in C1C2Pm, at least in HeLa cells.

Cytotoxicity of $DUF5_{Vv}$ in HeLa Cells is Linked to the C2A Domain

Despite the absence of functional conservation, C1C2Pm and $DUF5_{Vv}$ may share structural conservation, although the function of the domains diverged. A structural model of $DUF5_{Vv}$ was generated based on the PMT structures[15]. Based on this model, the amino acids of $DUF5_{Vv}$ responding to the $C1_{Vv}$ and $C2_{Vv}$ domain were identified. Upon deletion of gene sequences for the $C1_{Vv}$ subdomain, the $C2_{Vv}$-EGFP fusion is no longer localized to the cell periphery. Those cells highly expressing $C2_{Vv}$-EGFP appear rounded, while low expressing cells remained normal (FIG. 16D). These data are consistent with $C2_{Vv}$ being required for cytotoxicity and $C1_{Vv}$ being required for efficient delivery to the plasma membrane.

Figure 16A:
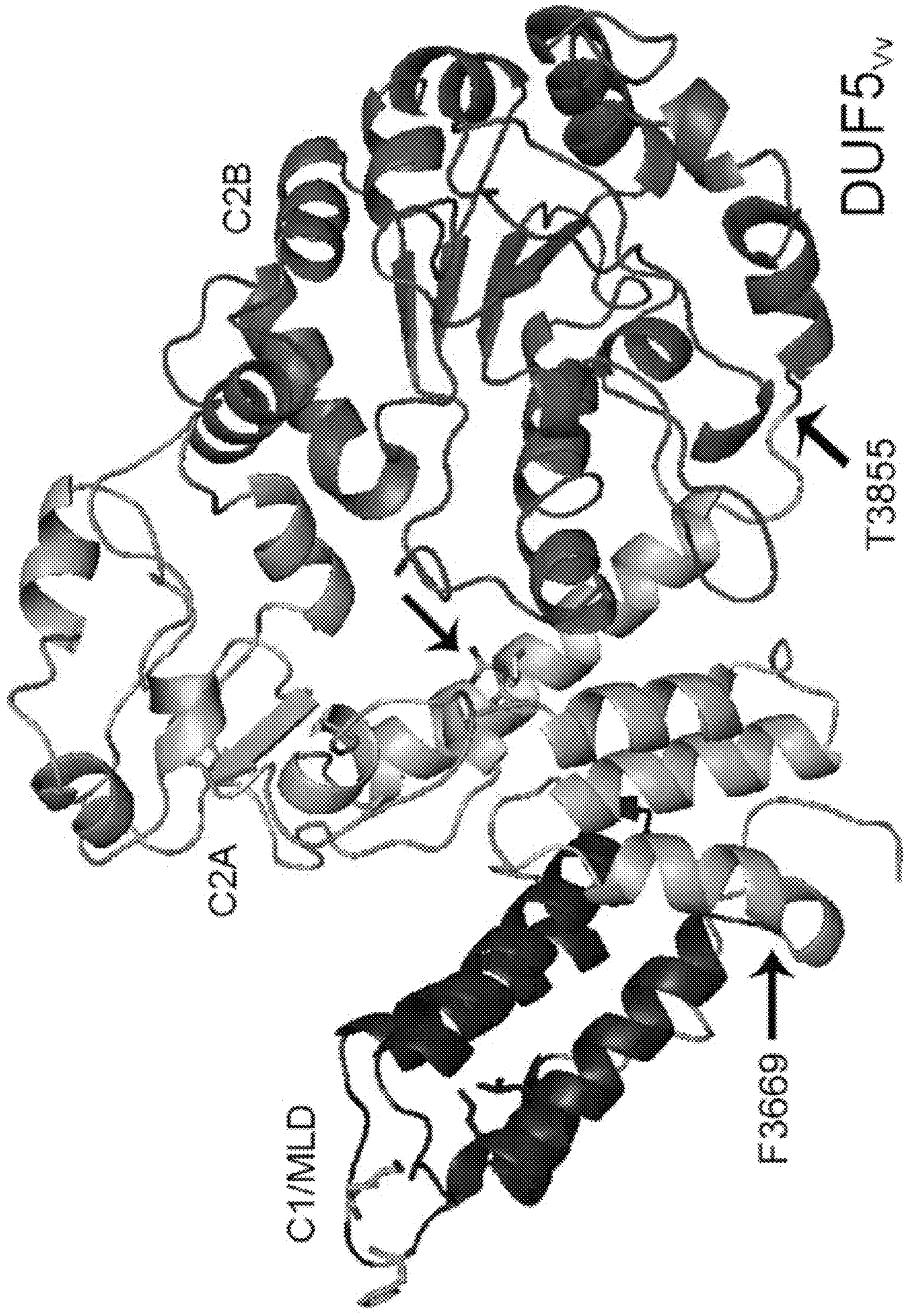
FIG. 16A, FIG. 16B, FIG. 16C, FIG. 16D, FIG. 16E and FIG. 16F illustrate that the C1 MLD of $DUF5_{Vv}$ is necessary only for efficient cell rounding.
Figures 16B, 16C, 16D:
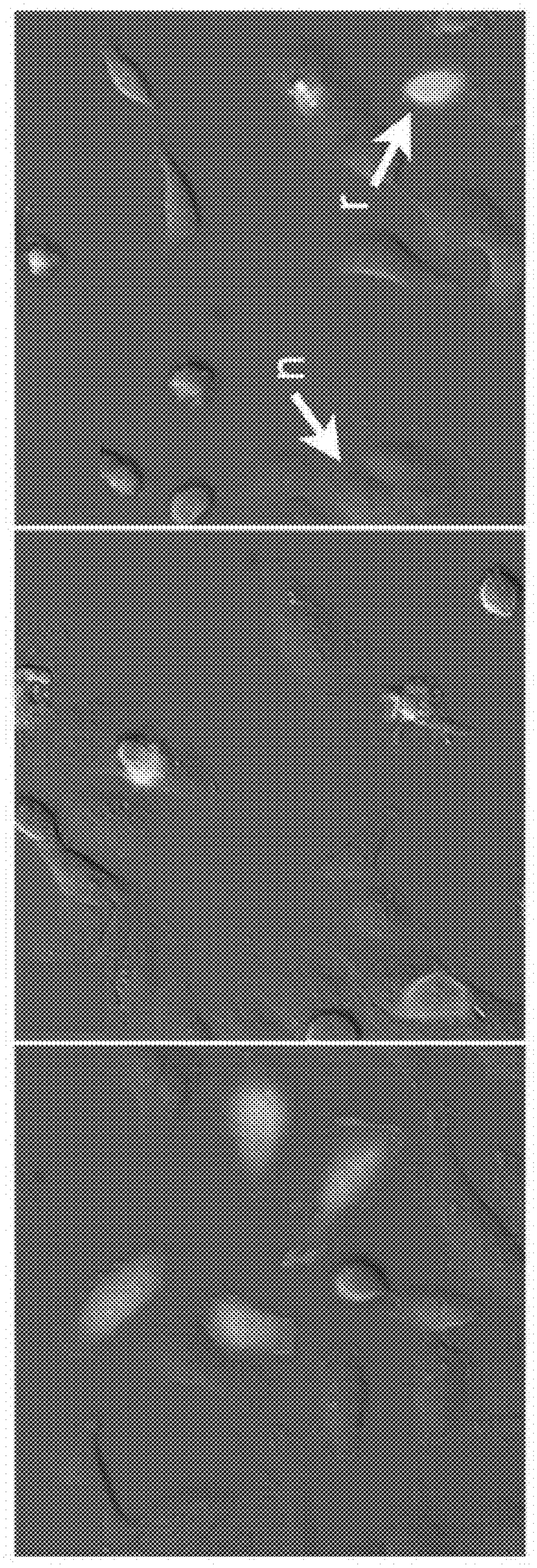
Figure 16F:
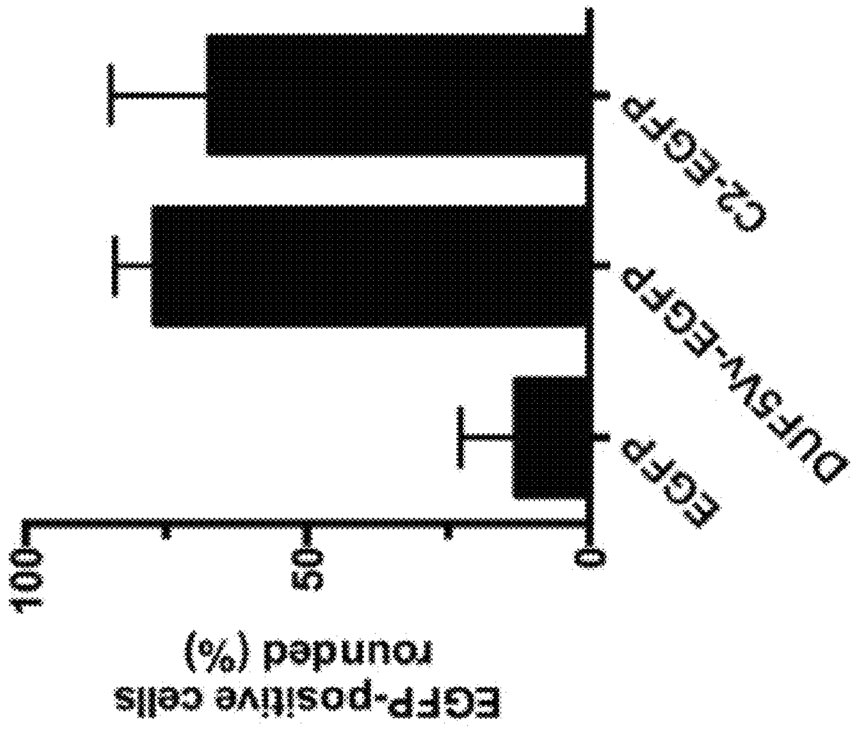
Figure 16E:
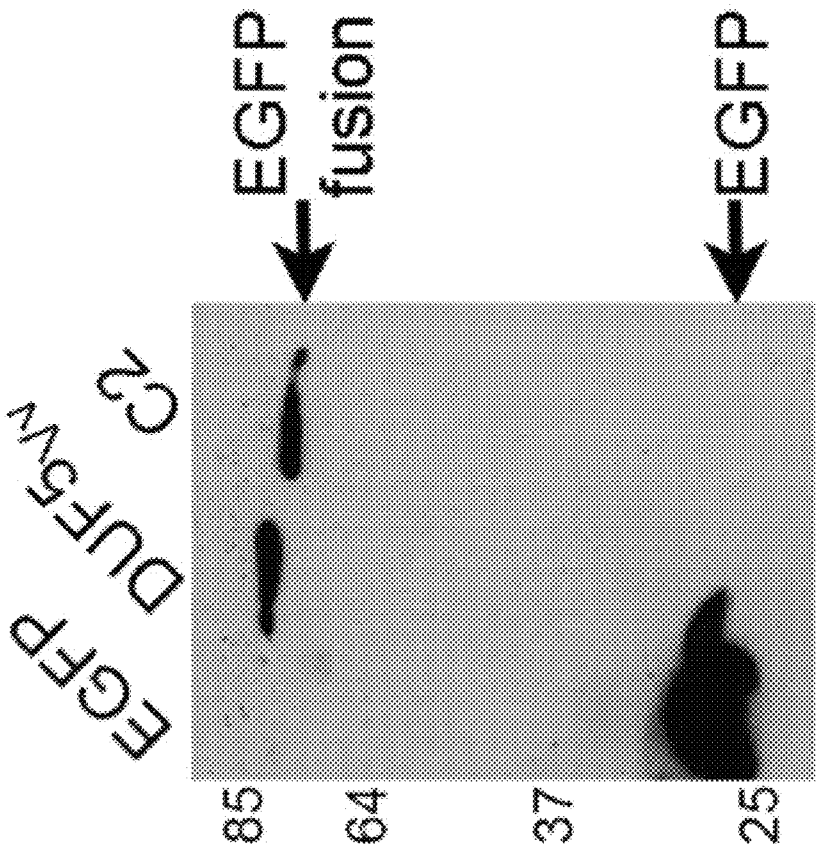
Figure 17A:
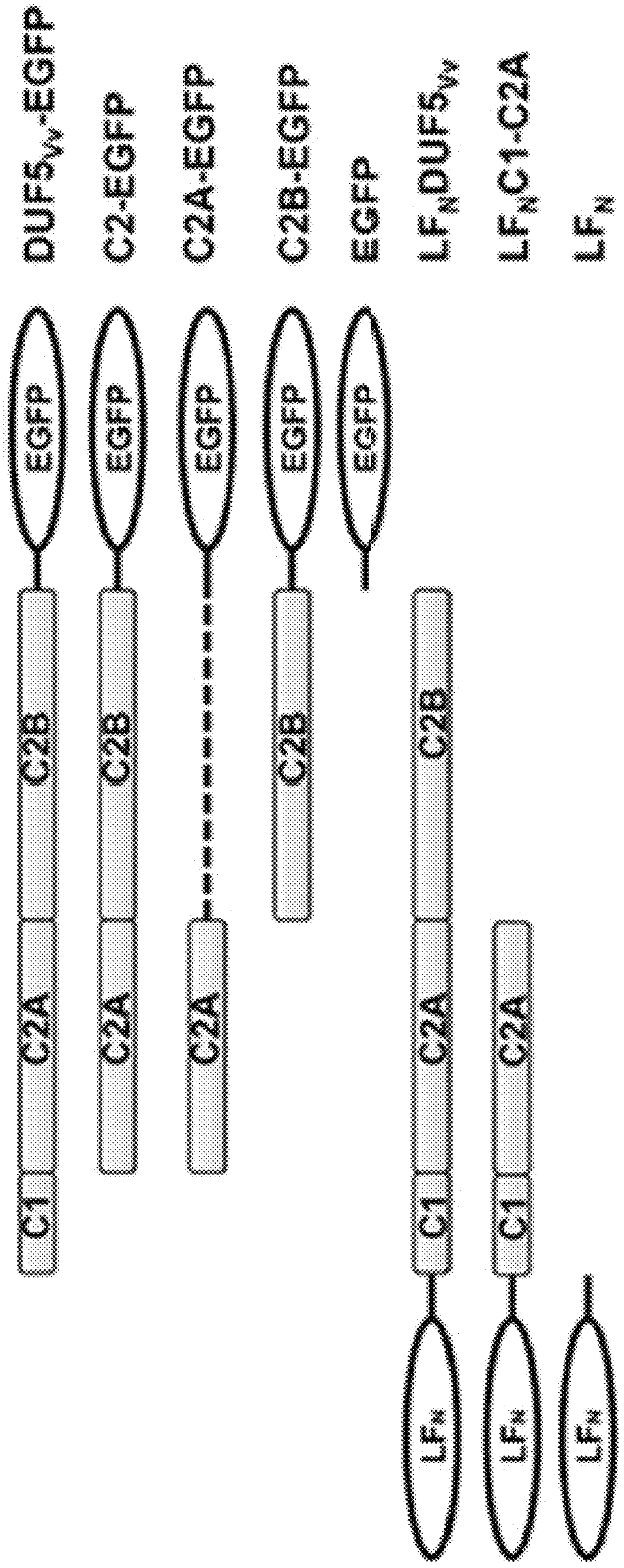
FIG. 17A, FIG. 17B, FIG. 17C, FIG. 17D, FIG. 17E, FIG. 17F, FIG. 17G, FIG. 17H, FIG. 17I, FIG. 17J and FIG. 17K illustrate that C2A is the cytotoxic subdomain of $DUF5_{Vv}$.
Figure 17B:
Figure 17C:
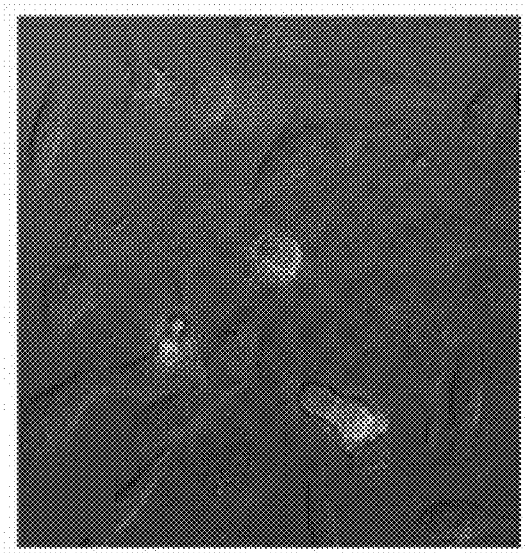
Figure 17D:
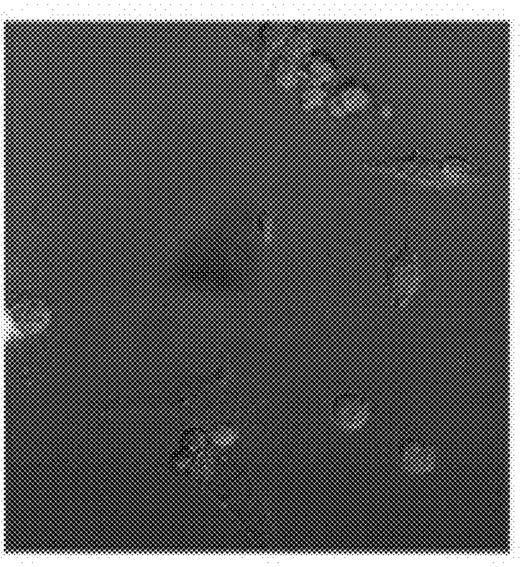
Figure 17E:
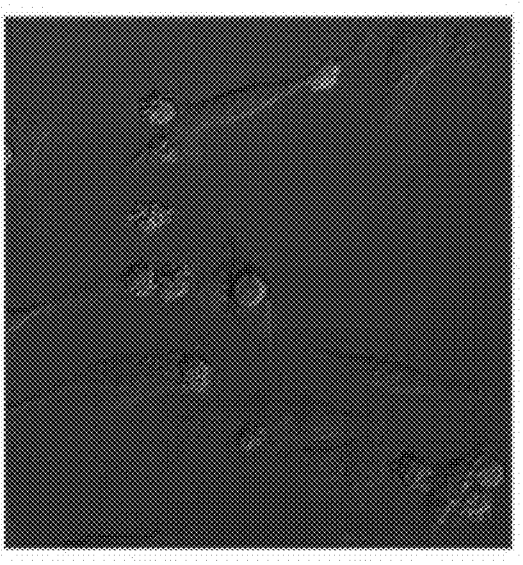
Figure 17F:
Figure 17H:
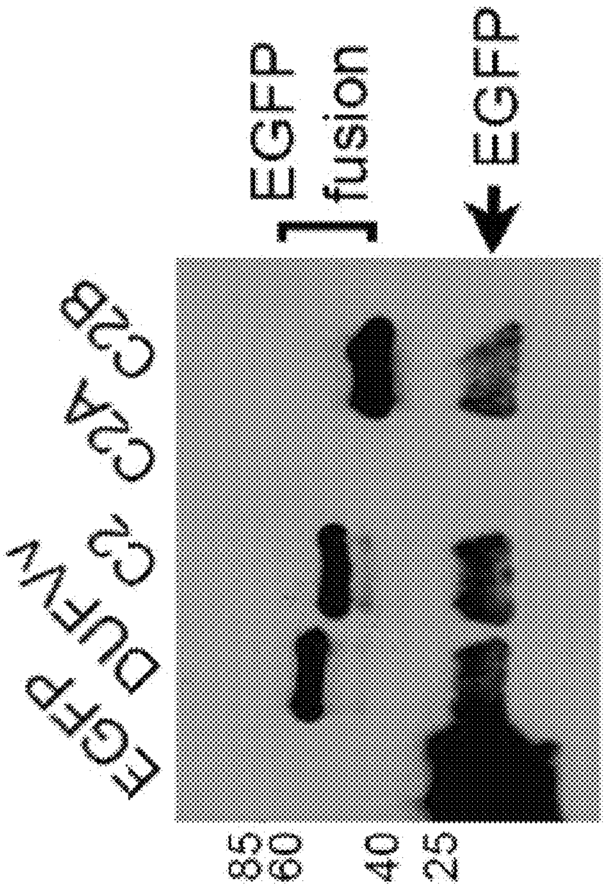
Figure 17G:
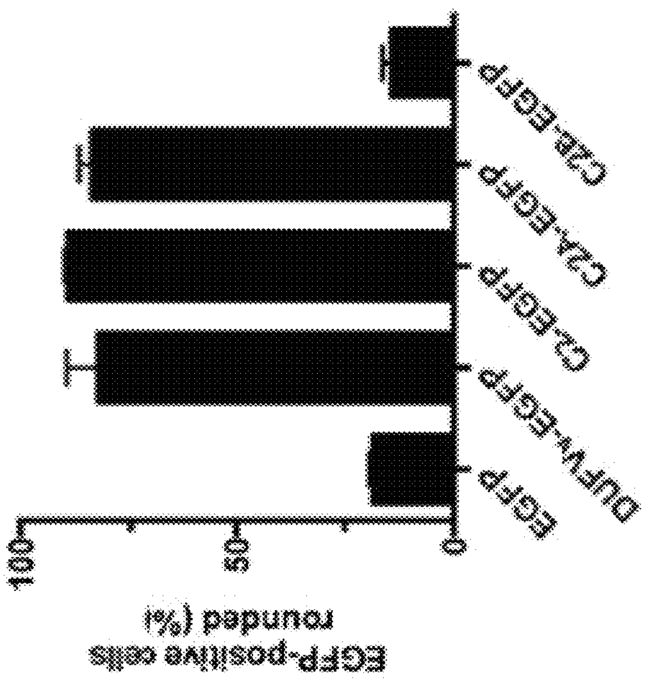

In addition, as shown also by two recent bioinformatics studies[34,35], the structural model showed that $C2_{Vv}$ could be split into two subdomains, $C2A_{Vv}$ and $C2B_{Vv}$ (FIG. 16A). To determine if the cytotoxic activity of $C2_{Vv}$ is linked its C2A or C2B subdomain, DNA corresponding to the individual subdomains was cloned fused to egfp and expressed in HeLa cells. Cells ectopically expressing only $C2A_{Vv}$-EGFP were highly necrotic, while cells expressing C2B alone appeared normal (FIG. 17B-G) and produced EGFP-fusion protein detectable by western blotting (FIG. 17H). However, due to the severe toxicity of C2A alone resulting in poor sample recovery, a corresponding fusion protein could not be detected by western blotting to confirm expression (FIG. 17H).

Figure 17K:
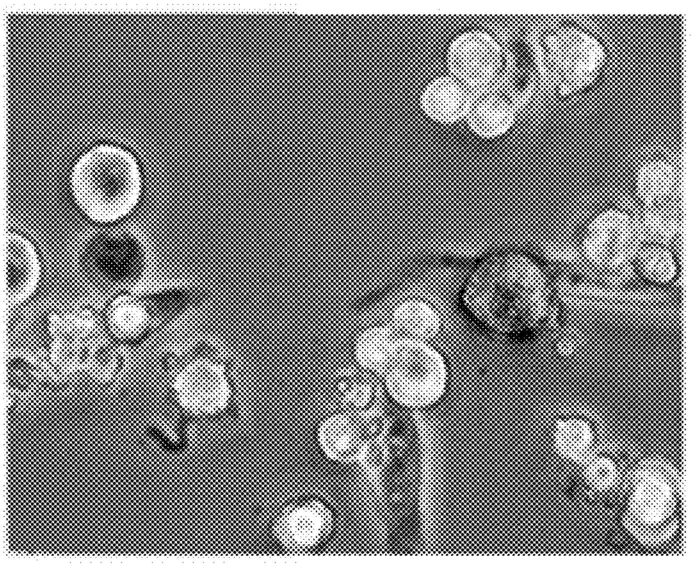
Figure 17J:
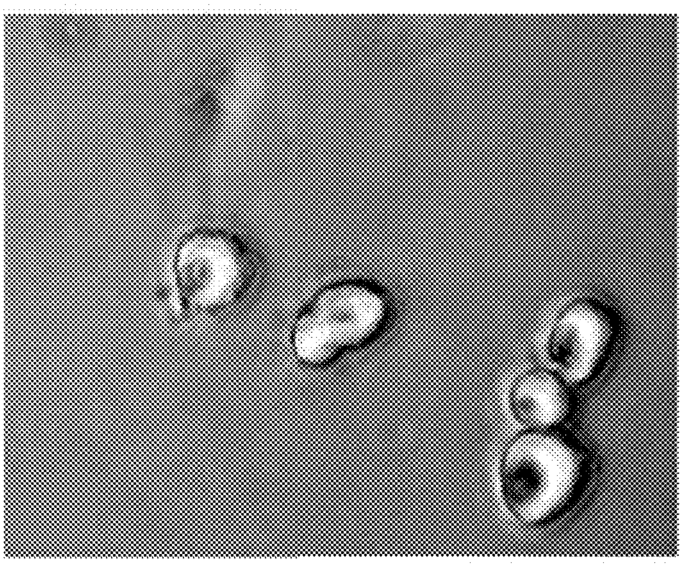
Figure 17I:
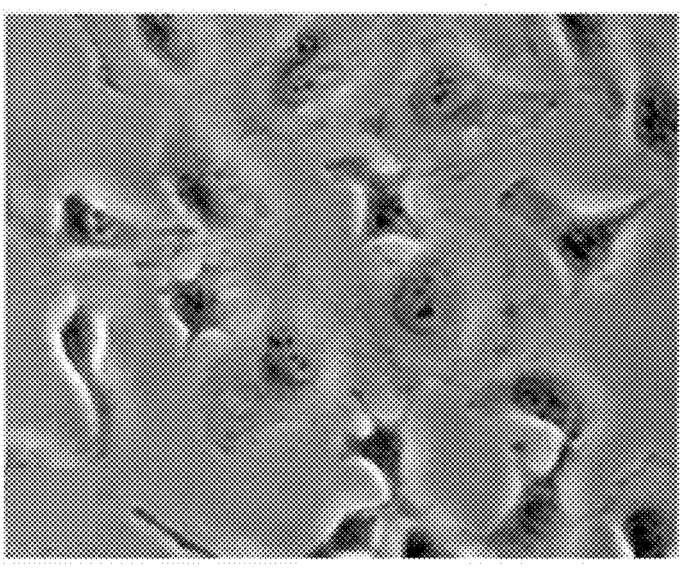
Figure 18C:
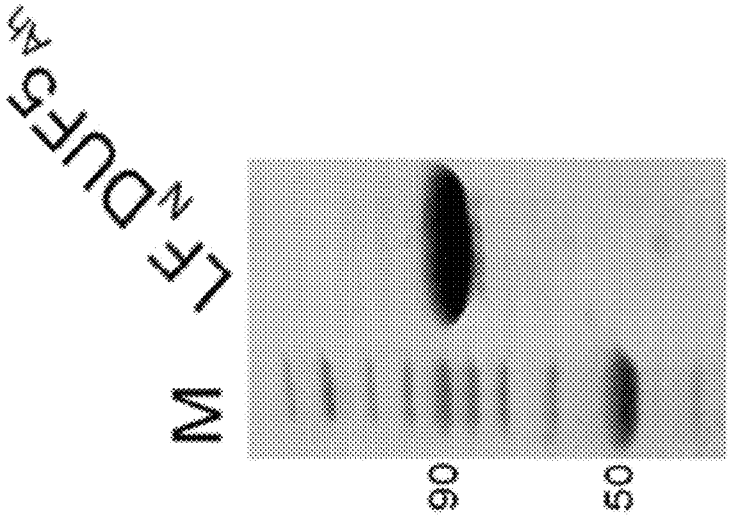
FIG. 18A, FIG. 18B, FIG. 18C, FIG. 18D, FIG. 18E, FIG. 18F and FIG. 18G illustrate that DUF5 from *A. hydrophila* is cytotoxic and causes cell rounding. LFN-$DUF5_{Ah}$ caused cell rounding when delivered to HeLa cells (FIG. 18A compared to FIG. 18B). Protein purity was assessed with SDS-PAGE (FIG. 18C). Rounding efficiency was comparable to $DUF5_{Vv}$, at all concentrations tested (FIG. 18D and repeated in FIG. 18E). Finally, release of LDH from intoxicated cells was measured (FIG. 18F and repeated in FIG. 18G), showing that there is no appreciable lysis when cells are intoxicated with either DUF5 protein.
Figure 18B:
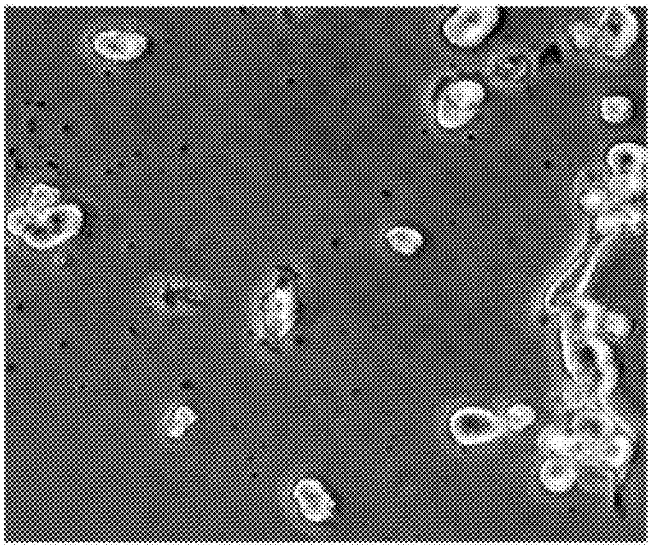
Figure 18A:
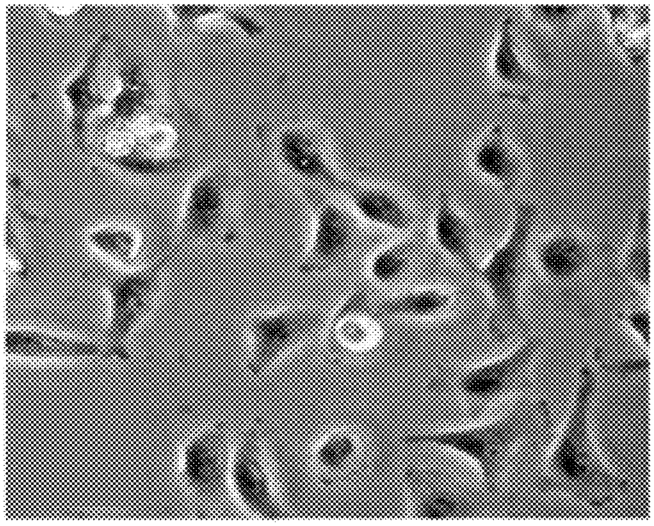
Figure 18E:
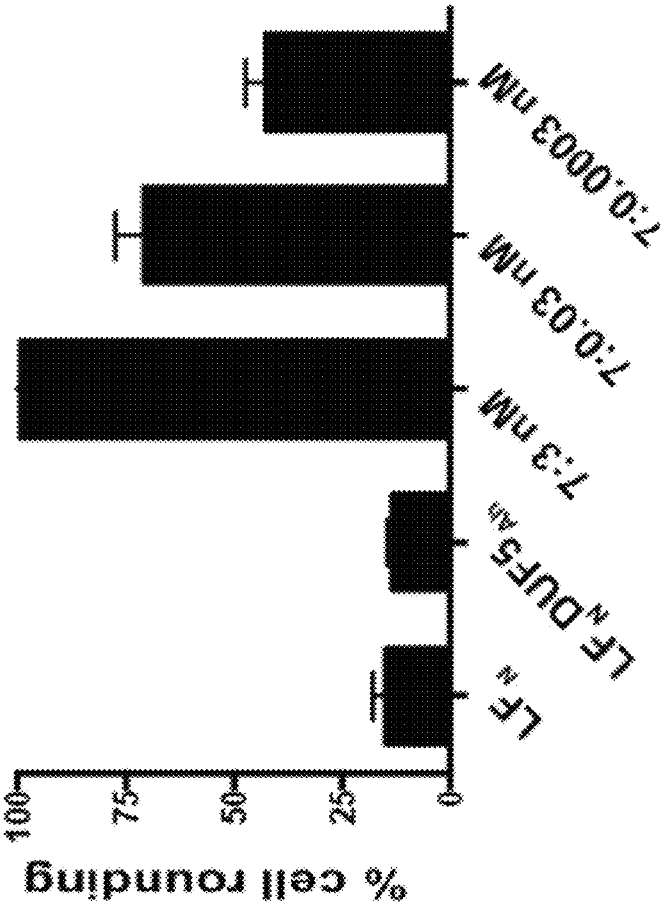
Figure 18D:
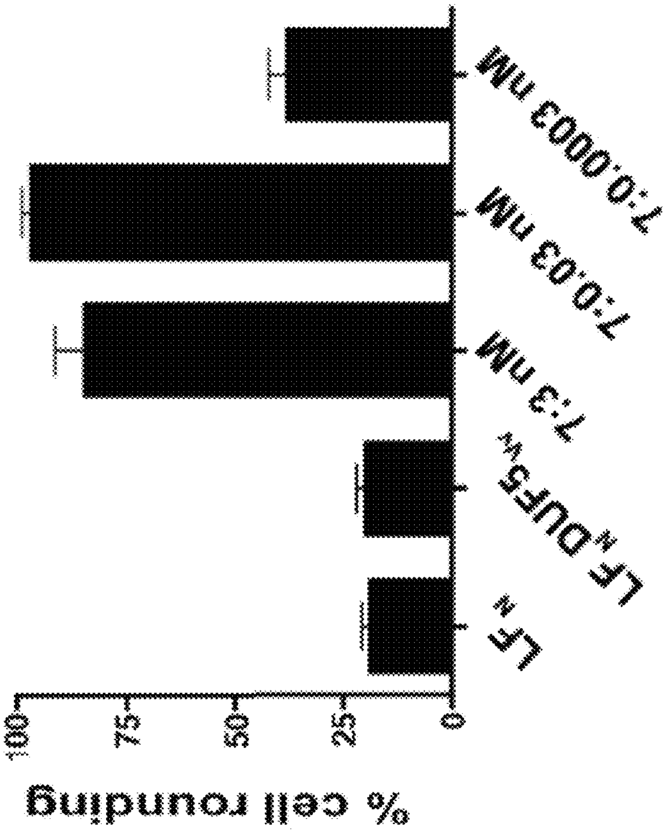
Figure 18G:
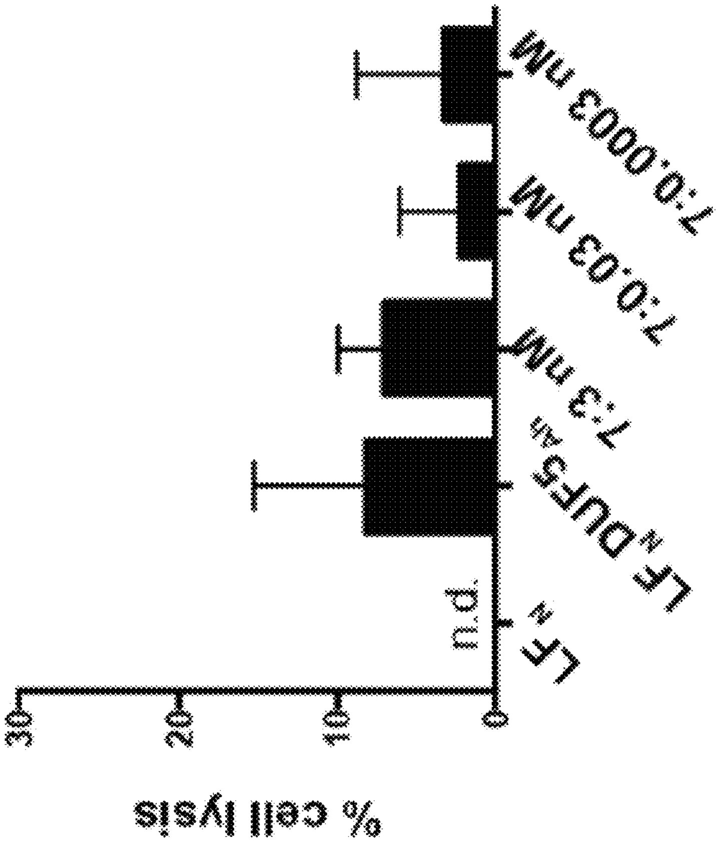
Figure 18F:
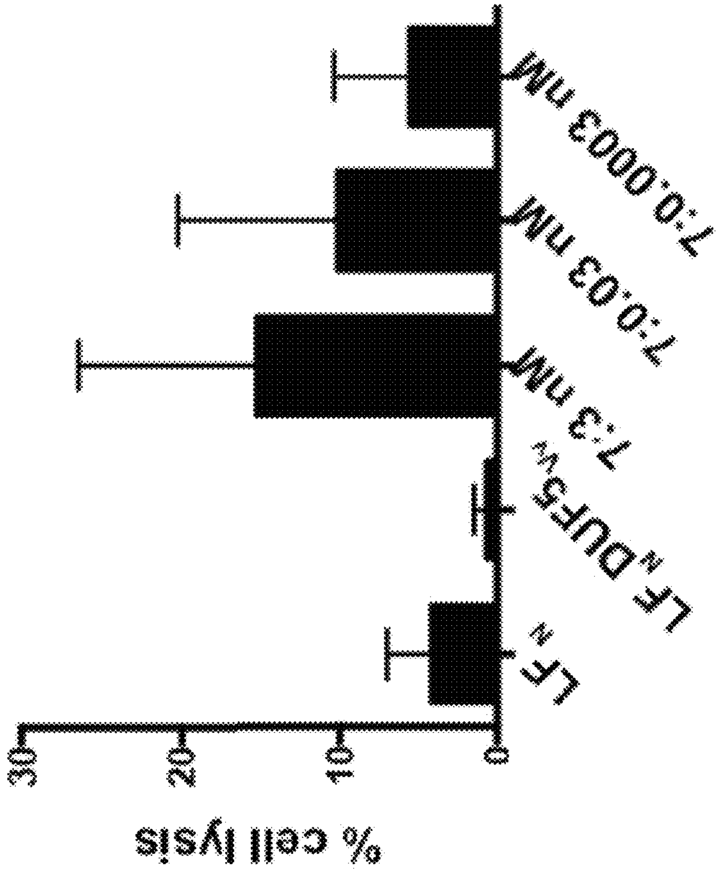

As an alternative verification of the cytotoxicity associated with $C2A_{Vv}$, both full-length $DUF5_{Vv}$ and C1-C2A from *V. vulnificus* were purified fused to His-tagged *B. anthracis* LFN that is often used as a bioporter for toxin effectors in the absence of the holotoxin[7,11,29,36]. The purified proteins were insoluble in less than 2M urea, but nevertheless retained toxicity after delivery to cells by PA. The snap dilution out of urea in the tissue culture media likely allowed folding of the LFN domain and the protein then associated with PA for translocation and successful refolding of the $DUF5_{Vv}$ domain within the cytosol. Notably, both the full-length protein (FIG. 17J) and the C1-C2A fragment (FIG. 17K) resulted in rounding of cells confirming transfection studies that C2A is sufficient for cytotoxicity of $DUF5_{Vv}$ in HeLa cells. Furthermore, LFN$DUF5_{Vv}$ was cytotoxic to other mammalian cell types as well, including J774 macrophages, COST fibroblasts, and HEp-2 epithelial cells (Table 1).

TABLE 1

Cell lines susceptible to DUF5V cytotoxicity[a]

| | Rounding induced by $LF_N DUF5_{Vv}$? | |
|---|---|---|
| Cell Line | +PA | −PA |
| HeLa human cervical carcinoma | + | − |
| COS7 African green monkey fibroblast | + | − |
| J774 murine macrophage | + | − |
| Hep-2 human laryngeal epithelial | + | − |

[a]Cells were intoxicated with LFNDUF5V in the presence (+) or absence (−) of PA. After 24 hr, rounding was observed by phase microscopy. Intoxication conditions were the same as reported in FIG. 17.

$DUF5_{Ah}$ from *A. hydrophila* is Also Cytotoxic

Figure 19:
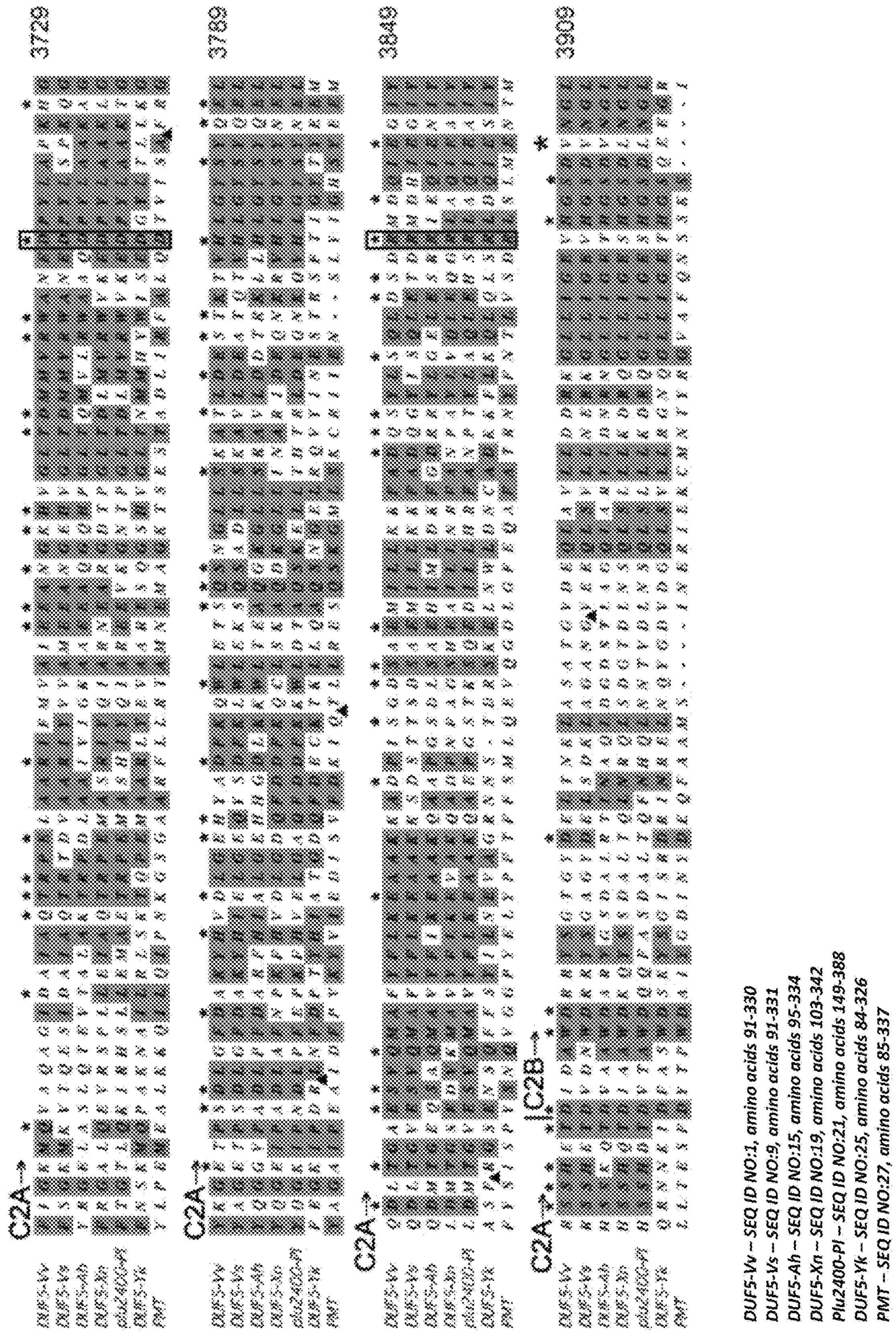
FIG. 19. Amino acid alignment generated in MacVector 12.6.0 of only the C2A and C2B subdomains. Grey shading indicates 100% identical residues. Triangles indicate that sections of sequence were removed during alignment calculations. Asterisk indicated residues changed to alanine via site directed mutagenesis and boxes indicate two aa identified as important for growth inhibition in yeast. Larger asterisks indicate residues G3948 and V3906 which were mutated to stop codons, while the last large asterisk indicates S3986, which was not targeted in the initial mutagenesis but was later found by structural modeling to potentially interact with R3841.
Figure 19:
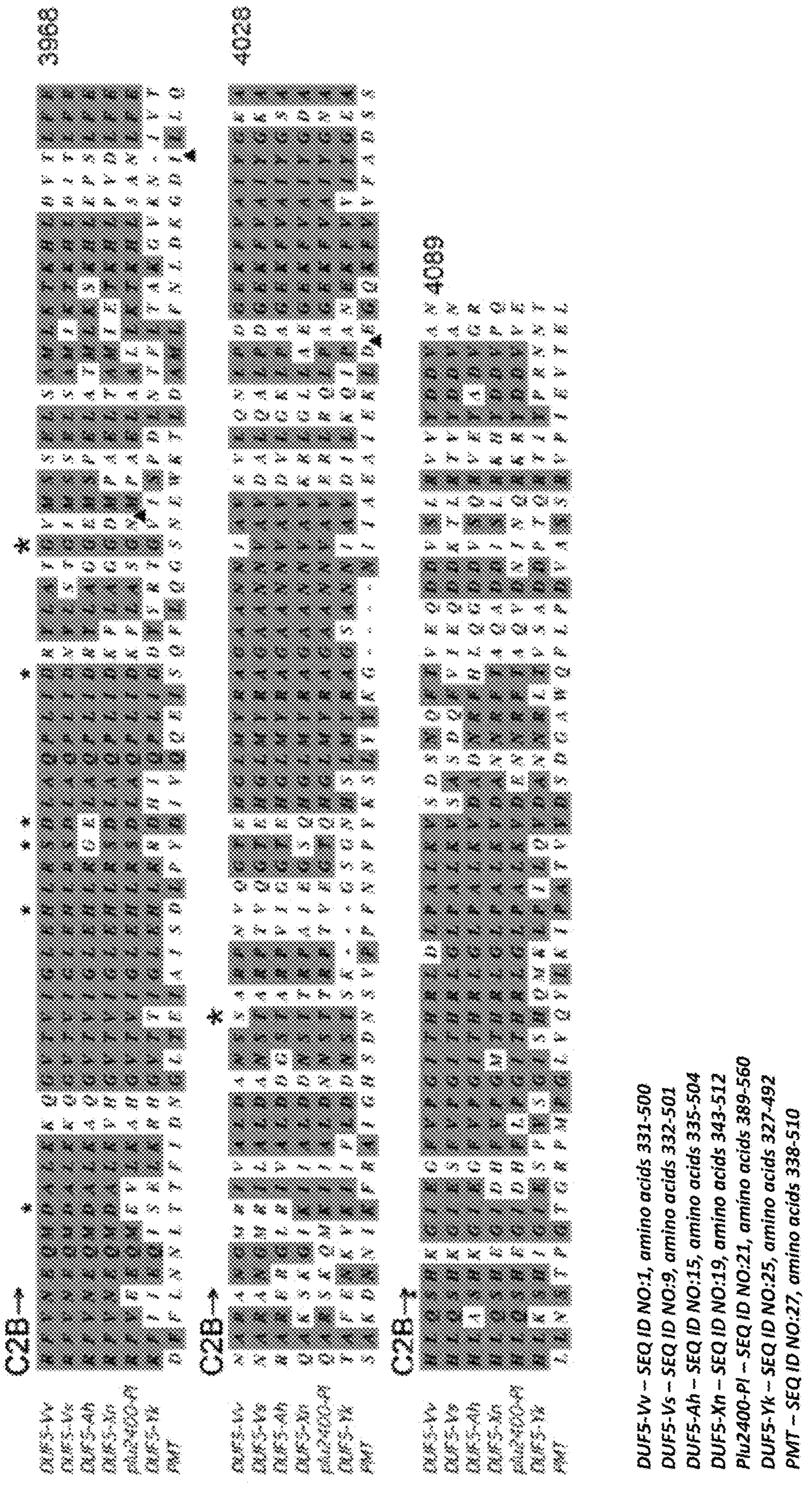

As shown in FIG. 19, proteins similar to $DUF5_{Vv}$ and PMT C1-C2 subdomains are found as uncharacterized proteins from other bacterial species. To further explore the possibility that these proteins comprise a novel functional family of cytotoxins, the DUF5-like effector domain from the *A. hydrophila* MARTX toxin was cloned in fusion with LFN and delivered to HeLa cells via PA. Protein purity was assessed by SDS-PAGE in panel 4C. After intoxication it was observed that HeLa cells were rounded similarly to what is seen with LFN-DUF5 (FIG. 18A,B) indicating that this effector domain also has cytotoxic function. Furthermore, the rounding efficiency is similar between the two toxins (FIG. 18 D, E). Finally, neither toxin induced cell lysis when delivered to HeLa cells, at any of the concentrations tested (FIG. 18 F, G).

Figure 20A:
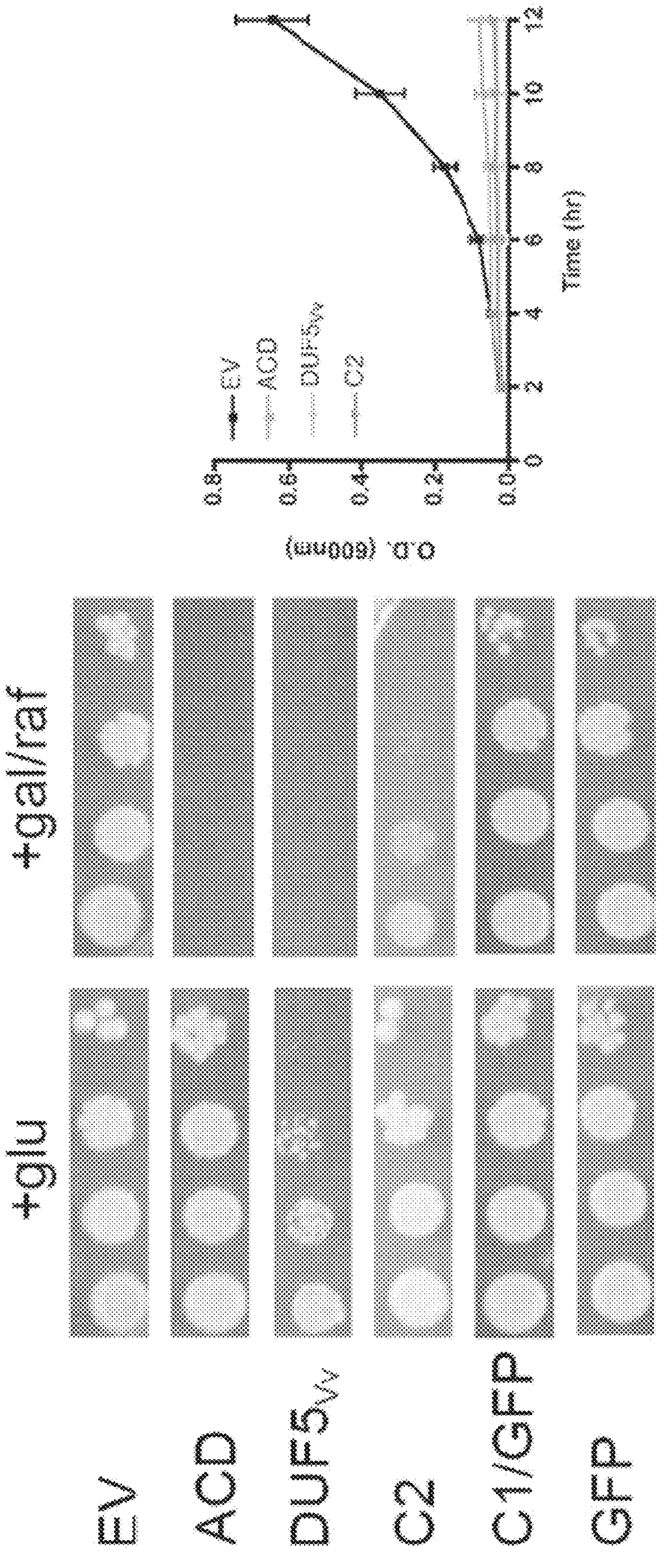
FIG. 20A, FIG. 20B and FIG. 20C illustrate that $DUF5_{Vv}$ and the C2 domain cause growth inhibition when expressed in yeast. *S. cerevisiae* strain InvSc1 was transformed with pYC2 NT/A plasmid expressing proteins indicated at left or with empty vector (EV), actin crosslinking domain from *V. cholerae* MARTX (ACD), or the C2 domain with stop codons introduced at V3906 or G3048. Panels show 5 µl of 10-fold serial dilutions spotted to SC agar without uracil supplemented with either glucose (non-inducing) or galactose and raffinose (inducing). Panels at right show 12 h growth curves of cultures in SC broth with galactose.

Both Full-Length $DUF5_{Vv}$ and C2 Alone Cause Growth Inhibition when Expressed in Yeast To further explore the function of $DUF5_{Vv}$, we tested if it would be toxic if expressed in *S. cerevisiae*. The gene sequence for $DUF5_{Vv}$ was cloned into the yeast expression vector pYC2/NTA placing the gene under the control of a galactose-inducible promoter. When transformed into yeast, the $DUF5_{Vv}$-expressing yeast strain grew poorly under non-inducing conditions and showed no growth under inducing conditions on either plates or broth culture (FIG. 20A). Indeed, expression of $DUF5_{Vv}$ was more toxic than the MARTX ACD effector domain that has been previously studied in yeast (FIG. 20A)[31]. Toxicity was reduced by removal of the C1 MLD such that cells expressing C2 alone were viable under non-inducing conditions with 100- to 1000-fold reduced plating efficiency on galactose and no growth in broth culture (FIG. 20A). The C1 MLD alone is not toxic when expressed in yeast (FIG. 20A), as previously shown[31,37].

Figure 20B:
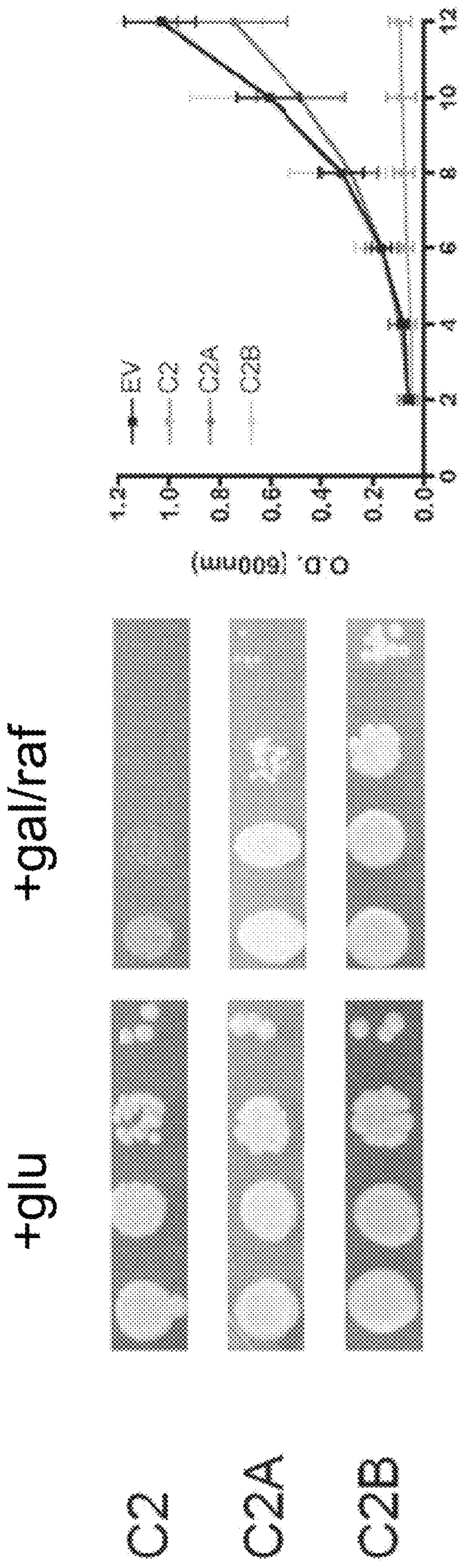
Figure 20C:
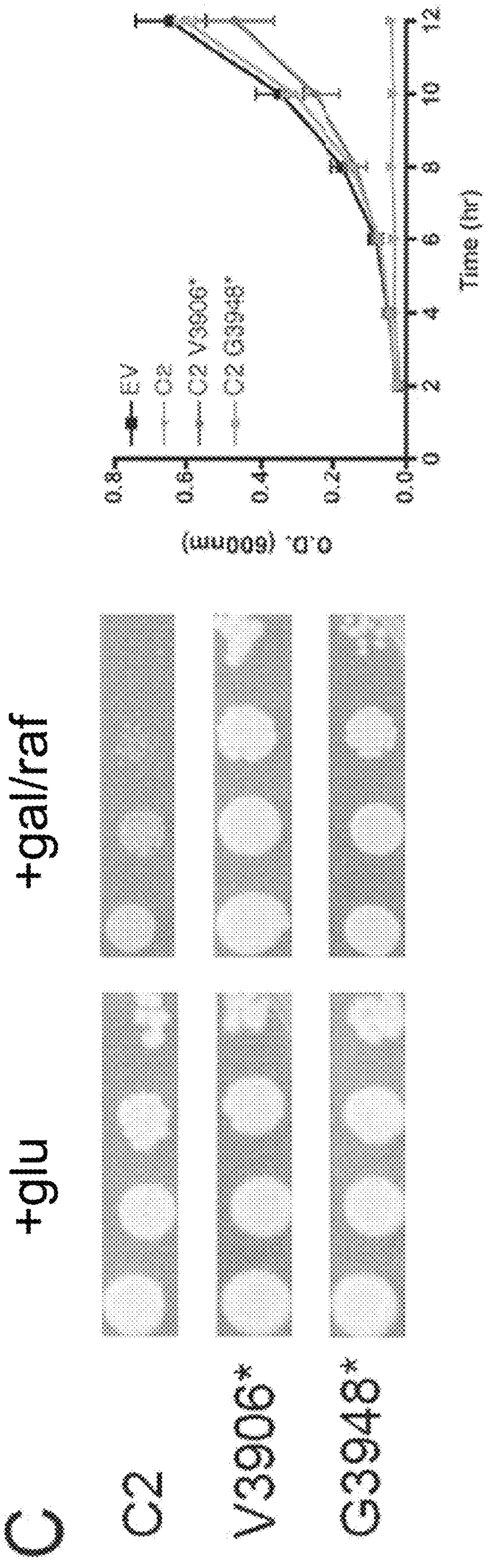

Distinct from studies in HeLa cells, yeast cells expressing C2A alone were viable when plated on galactose (FIG. 20B). As an alternative verification for the essentiality of C2B in yeast, stop codons were introduced in the yeast expression plasmid at the codons for V3906 and G3948. Similar to expression of C2A alone, cells expressing proteins truncated within C2B also grew under inducing conditions on both plates and in broth (FIG. 20C). Close examination of the plating efficiency of C2A compared to C2B indicates that expression of C2A alone may show a slight growth inhibition on plates or in broth but the effect is modest (FIG. 20B).

Overall, in yeast, distinct from HeLa cells, both C2A and C2B are required for full toxicity although some toxicity is exhibited by C2A alone. The additional requirement for C2B in yeast may reflect a modest difference in the stability of the protein in yeast.

Identification of a C2A Inactivating Mutation by Alanine Scanning Mutagenesis in *S. Cerevisiae*

Alanine scanning mutagenesis has proven to be a useful tool to identify critical residues for other of MARTX effector domains[12,31,38]. Alignment of DUF5 amino acid sequences from 5 MARTX toxins, Plu2400, and PMT showed that there are only 16 residues (8.5%) that are 100% identical across all proteins. If the potentially inactive PMT is excluded, 38 residues (20%) are identical across the remaining 6 effectors (FIG. 21).

To avoid severe toxicity associated with expression of full-length $DUF5_{Vv}$ in yeast, the plasmid for expression of C2 without the MLD was modified by site-directed mutagenesis targeting 65 total residues in C2A (FIG. 21, indicated by asterisks), focusing predominantly on polar residues known to be important for catalysis of other bacterial toxins. Both conserved and non-conserved residues were changed to alanine codons. In addition, nine highly conserved residues in C2B were changed for alanine.

*S. cerevisiae* transformed with mutagenized plasmids were recovered by growth on glucose and then tested for the ability to grown on galactose. Surprisingly, 73/74 of the mutations did not alter the growth inhibition exhibited by strains expression unaltered C2. The high frequency of mutations showing no relief of toxicity suggests that modest changes to overall structure are not sufficient to overcome the severe toxicity of this protein for yeast, even when the C1 MLD is absent.

Figure 21A:
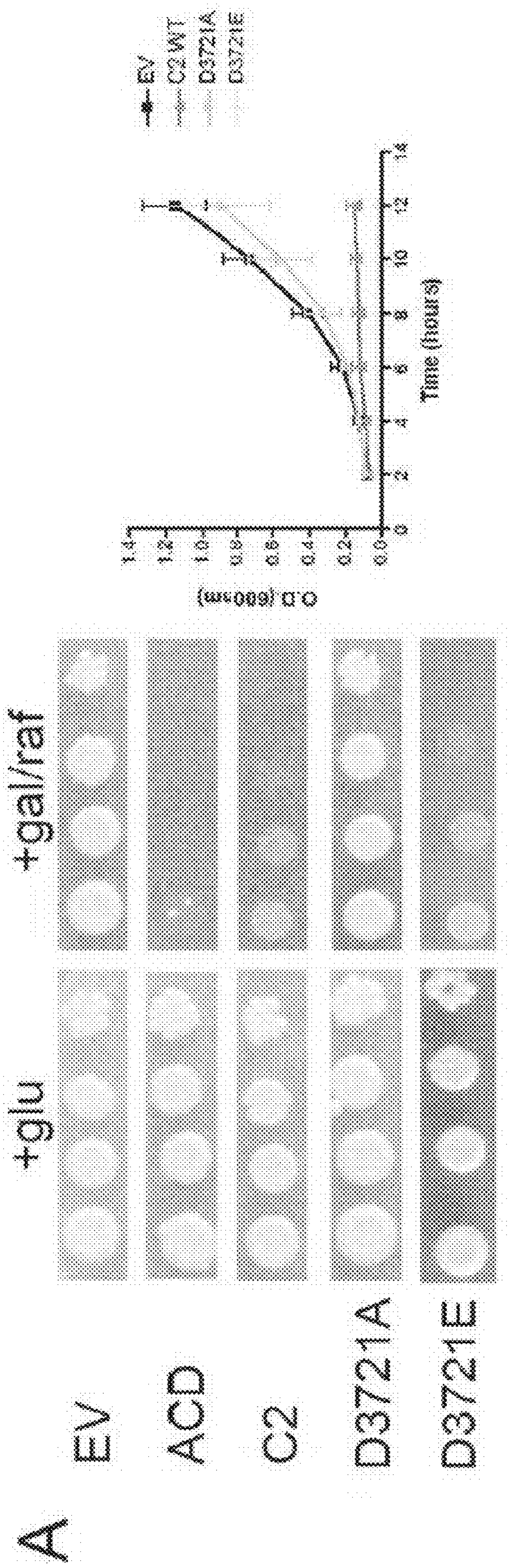
FIG. 21A, FIG. 21B, FIG. 21C, FIG. 21D, FIG. 21E and FIG. 21F illustrate that D3721 and R3841 are important residues for growth inhibition of yeast. Growth inhibition in yeast for C2-D3721A and C2-D3721E (FIG. 21A) and $DUF5_{Vv}$-D3721A, $DUF5_{Vv}$-R3841A, DUF5 with both residues mutated to alanine (DARA) and DUF5 with swapped residues (DRRD) in panel B. See FIG. 17A-17K for details.

Only one mutant, D3721A found within the C2A domain was identified that facilitated growth of yeast expressing C2. By contrast, a more conservative substitution to glutamic acid did not restore growth to yeast (FIG. 21A). D3721 is one of the 16 residues within C2A that is highly conserved in all the DUF5-like proteins, including PMT (FIG. 19).

Figure 21B:
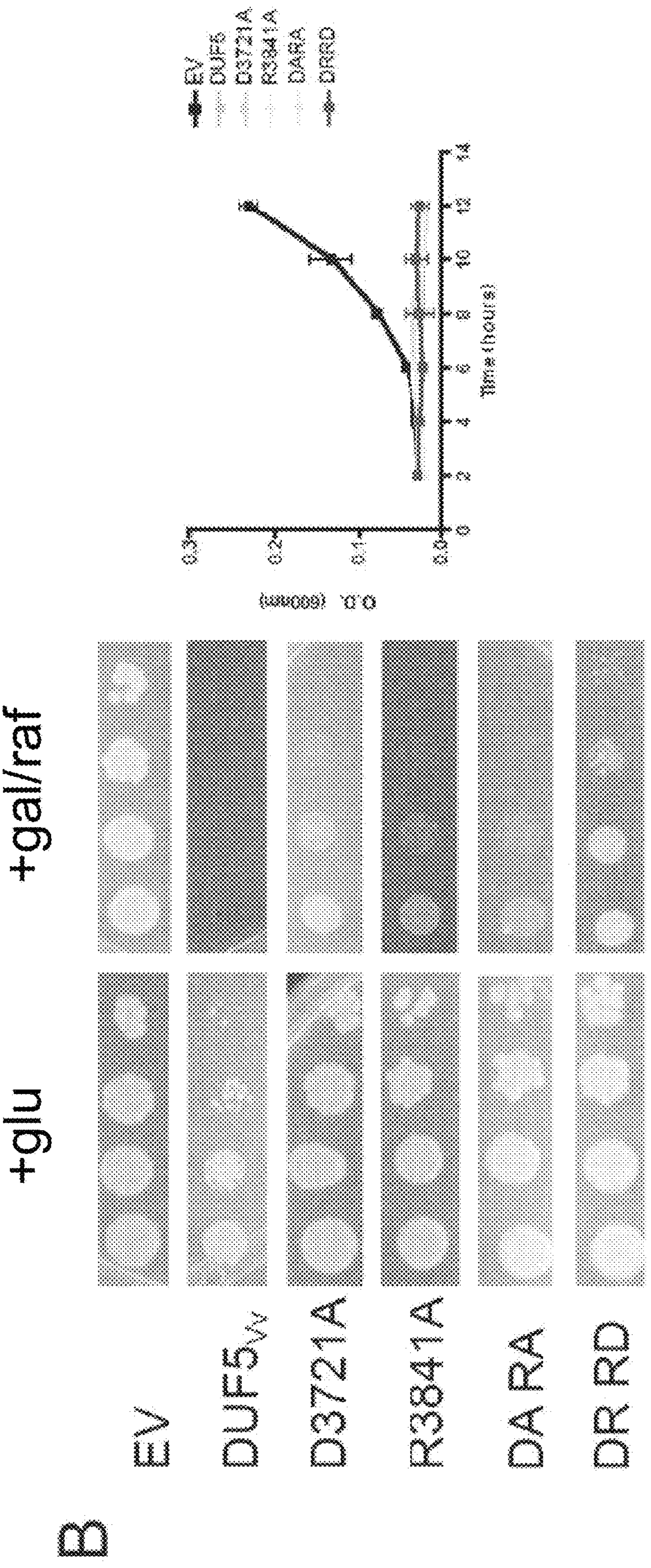

As an independent verification of the importance of this residue to the function $DUF5_{Vv}$, the mutation was transferred onto the full-length clone of $DUF5_{Vv}$ for expression in yeast. In this background, the mutation improved growth of yeast under non-inducing conditions to levels near vector control. Under inducing conditions, the plating efficiency was improved 100- to 1000-fold compared to expression of full-length $DUF5_{Vv}$, although the growth inhibition was not alleviated as shown in liquid culture experiments (FIG. 21B).

Figure 21D:
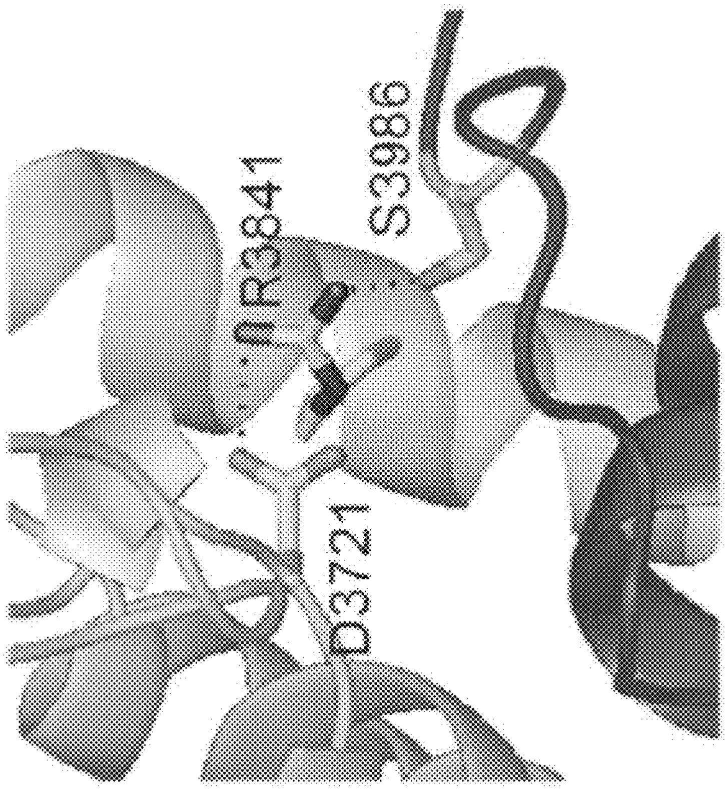
Figure 21C:
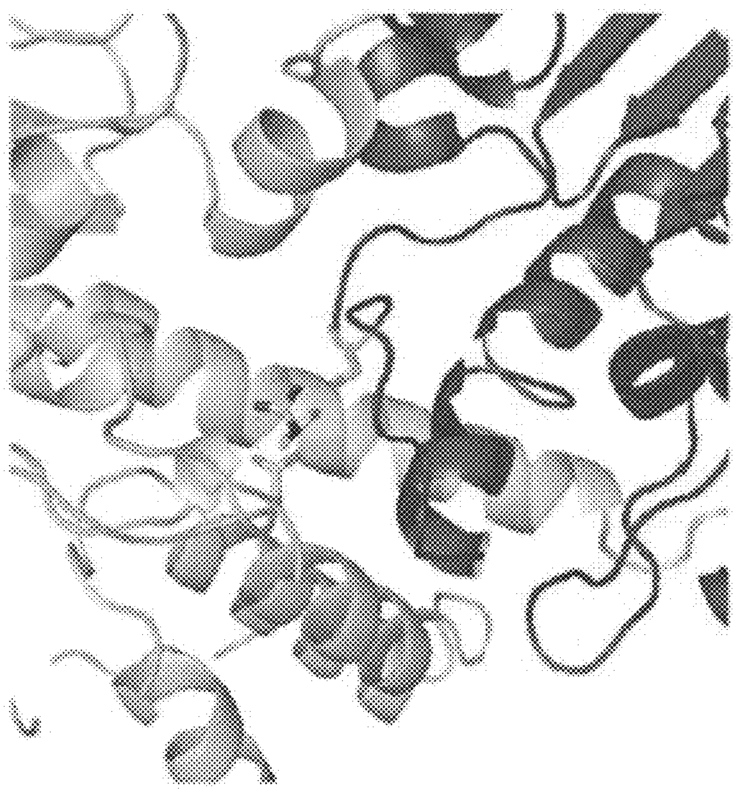

Examination of the structural model of $DUF5_{Vv}$ (FIG. 16A) showed that D3721 is present on helix 3 of C2A and makes polar contacts with R3841 on the final helix of C2A just before the start of C2B (FIG. 21C,D). Previous change of R3841 to Ala as part of the screen indicated this residue was not essential in the context of C2. However, in the context of the full-length $DUF5_{Vv}$ that includes the MLD, the phenotype of $DUF5_{Vv}$ R3841A is nearly identical to the phenotype of the D3721A resulting in an improved plating efficiency but poor growth in broth culture (FIG. 21B). This residue is also among the 16 100% identical residues found within C2A (FIG. 19). Combining the D3721A and R3841A resulted in a phenotype identical to that observed for either D3721A or R3841A substitutions alone and did not demonstrate an additive effect. Swapping the aspartate and arginine (D3721R/R3841D) did not improve growth either by plating or broth culture indicating that the potential bridge created by these residues is positional specific.

D3721 and R3841 are Essential for Cytotoxicity

Figure 21E:
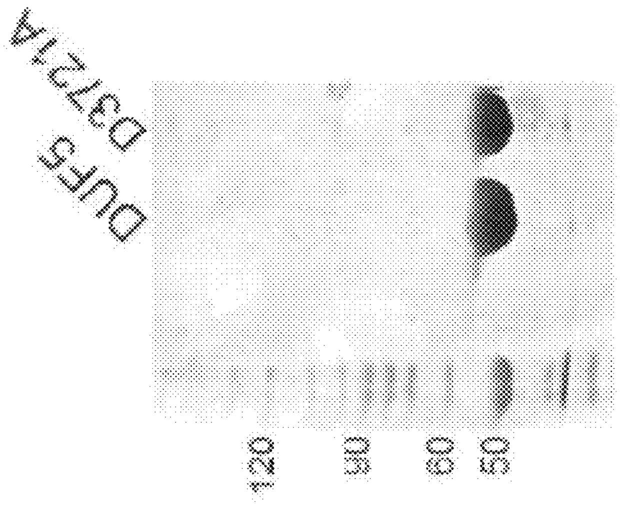
Figure 21F:
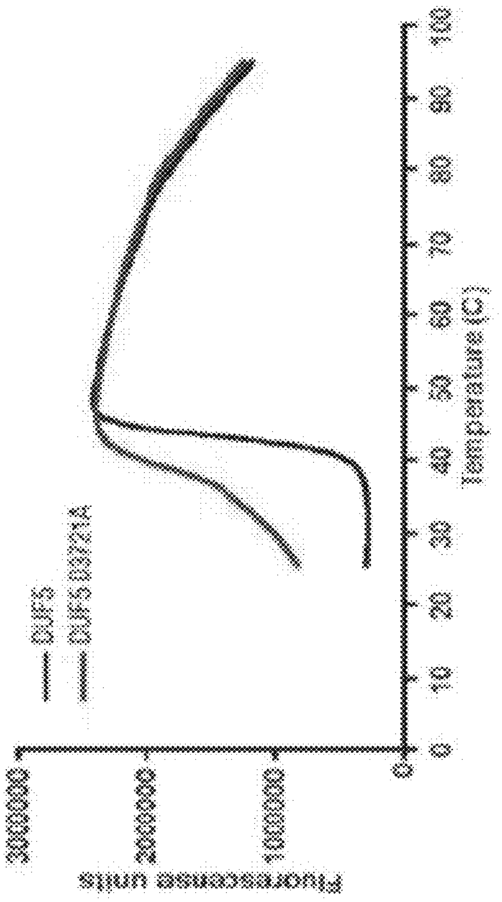
Figures 22A, 22B, 22C, 22D, 22E:
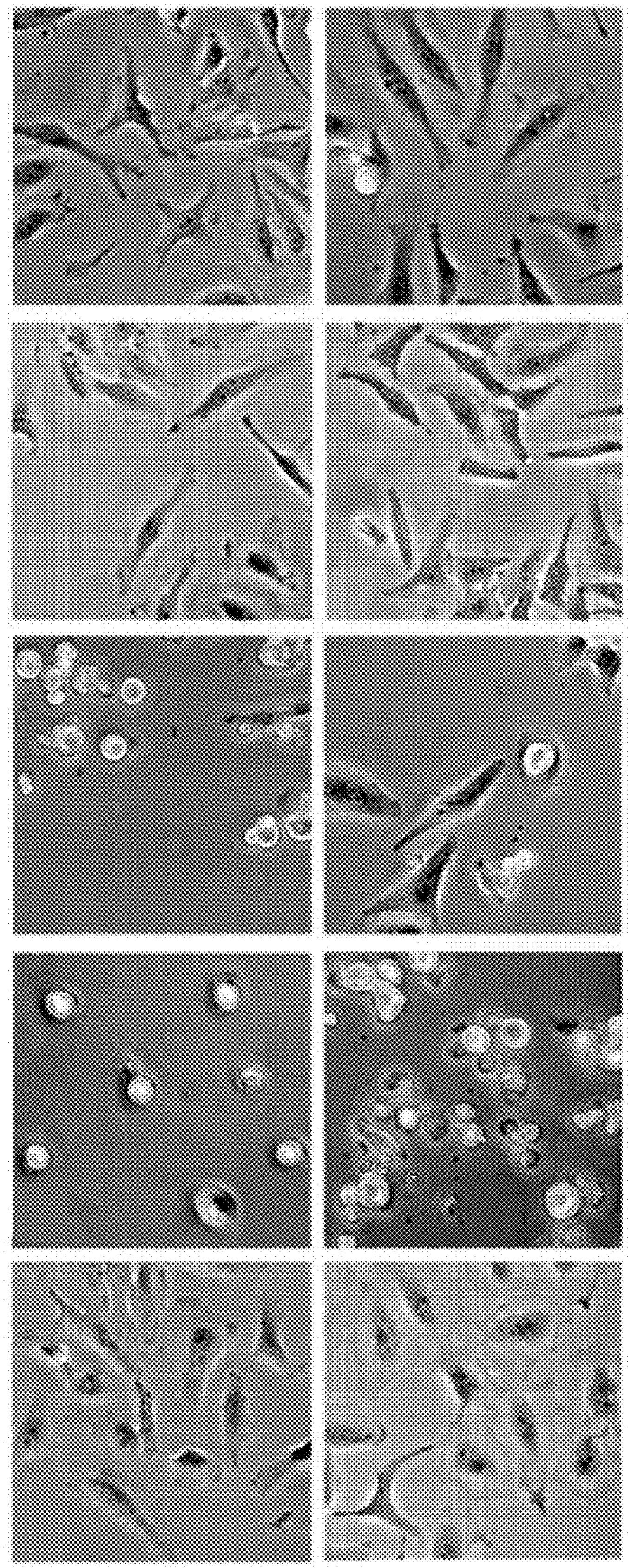
FIG. 22A, FIG. 22B, FIG. 22C, FIG. 22D, FIG. 22E, FIG. 22F and FIG. 22G illustrate that D3721 and R3841 are important residues for intoxication of HeLa cells.
Figure 22G:
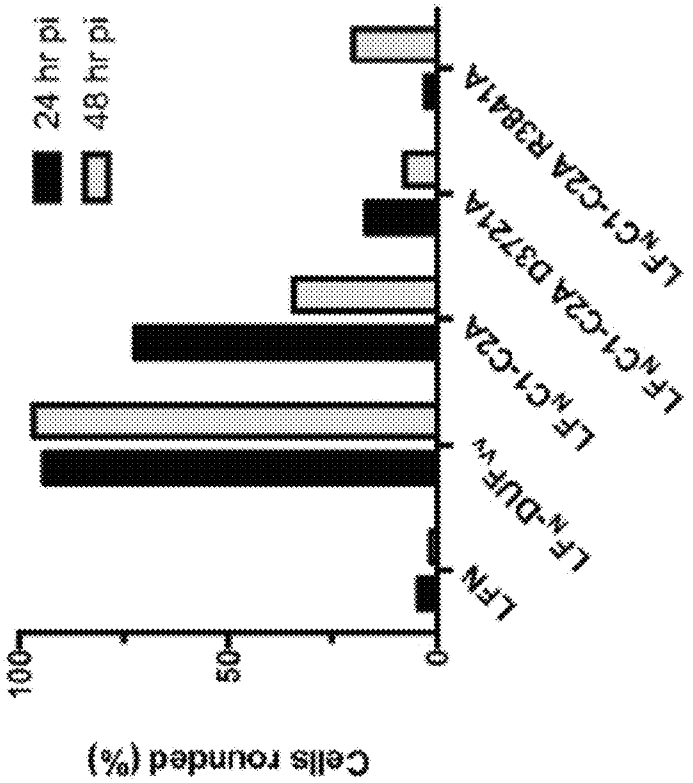
Figure 22F:
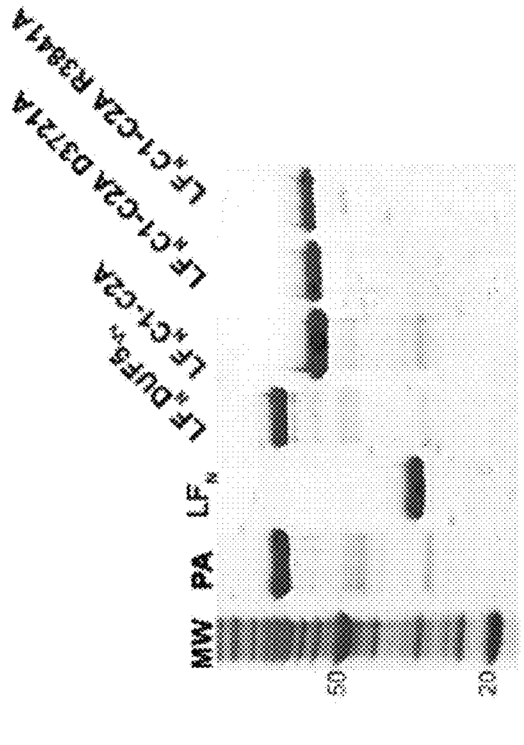

As a final demonstration of the structural requirements for cytoxicity, the D3271A and R3841A mutations were introduced onto the recombinant overexpression plasmid for production of C1-C2A fused to LFN. Proteins were prepared for each mutant from insoluble pellets, urea was reduced to 1.2 M, and the unfolded proteins were delivered to cells by PA. Both mutants lost function in cytotoxicity compared to the similarly prepared unmodified LFNC1-$C2A_{Vv}$ protein (FIG. 22A-E). Assessment of intoxication over time showed that cells treated with PA plus full length $LFNDUF5_{Vv}$ did not recover after 24 h intoxication and nearly 100% of cells remained rounded out to 48 hr. By contrast, ~50% of cells initially intoxicated with PA plus LFNC1-$C2A_{Vv}$ recovered between 24 and 48 h and returned to normal shape. These data suggest either that C2B carries an additional cytopathic function that prevents recovery of the rounded cells or, more likely, that C2B stabilizes C2A such that the toxin avoids turnover in the cells after successfully inducing cell intoxication. In support of this possibility, fluorescence thermal shift experiments were conducted with full-length recombinant 6×His-$DUF5_{Vv}$ without fusion to $LF_N$ (FIG. 21E). This recombinant 6×His-$DUF5_{Vv}$ has a half-maximal melting temperature (Tm) of 43.8° C., while the D3271A substitution lowers Tm by 6.0° C. to 37.8° C. The lower Tm indicates that D3271A causes a structural disturbance that can explain the reduced toxicity seen in yeast and HeLa cells indicating its interaction with R3841 may function to stabilize the protein structure rather than serve as a catalytic residue (FIG. 21F). This is also consistent with the structural model of DUF5 where D3721 is located within the core of the protein, such that a mutation to alanine would cause a disturbance consistent with a drop in Tm and would also account for the higher initial fluorescence seen with DUF5 D3721A than wild type protein.

Discussion

In this study, we undertook a structure-function approach to discover if the *V. vulnificus* MARTX toxin effector domain $DUF5_{Vv}$ is a cytotoxin accounting for its dramatic effect on virulence in mouse infection studies[5]. The $C1_{Vv}$ subdomain of this protein has been previously shown to localize to anionic membranes, but the function of the $C2_{Vv}$ subdomain at the membrane had not been previously investigated. Here, we demonstrate that $DUF5_{Vv}$ effector domain is cytotoxic to HeLa cells and to yeast resulting in growth inhibition. Further, the cytotoxic activity is localized to its C2A subdomain. In retrospect, mapping the cytotoxicity to the C2A subdomain is surprising because recent computer-based modeling studies of $DUF5_{Vv}$ and related proteins linked the C2B domain to the TIKI/TraB family of proteases leading to the proposal that C2B is a peptidase that functions in signaling[34,35]. However, we found that any putative protease activity associated with C2B would not contribute to cytotoxicity as complete removal of the subdomain from $DUF5_{Vv}$-EGFP did not affect cytotoxicity after ectopic expression studies in HeLa cells and expression of C2B-EGFP did not cause any observable effect in HeLa cells. Further the computer-based analysis indicated that C2B residue H3902 would be essential for peptidase activity, but this residue was among those modified during expression in yeast that did not restore the ability of yeast to grow (FIG. 19). These findings convincingly link the cytotoxic effect of $DUF5_{Vv}$ to its C2A subdomain; however, we cannot exclude that the C2B in addition to C2A could modify cell biological processes in manner that does not affect cell viability or morphology during MARTX intoxication and that $DUF5_{Vv}$ itself is a multifunctional effector domain.

The remainder of the study focused on identification of residues within $C2A_{Vv}$ that are essential for its cytotoxicity. Growth of yeast expressing $C2_{Vv}$ was used as a method to screen point mutations to identify those that would overcome the severe toxicity in yeast, a highly stringent phenotype generally indicative of an essential residue. The screen revealed a single essential Asp that initially was considered as a possible catalytic residue. However, the absence of additional residues in $C2A_{Vv}$ that would be predicted to form a catalytic site along with the finding that other highly conserved Gly, Pro, Tyr, Phe, Leu, and Ala are not essential suggests this subdomain functions by binding to a target protein rather than by covalent modification. The ability of the residue to tolerate substitution to the more structurally conservative glutamic acid also indicates this is not likely an aspartyl protease. We further found that the D3721A substitution reduced the Tm of the $DUF5_{Vv}$ indicating structural destabilization as opposed to loss of catalytic function.

Figure 23:
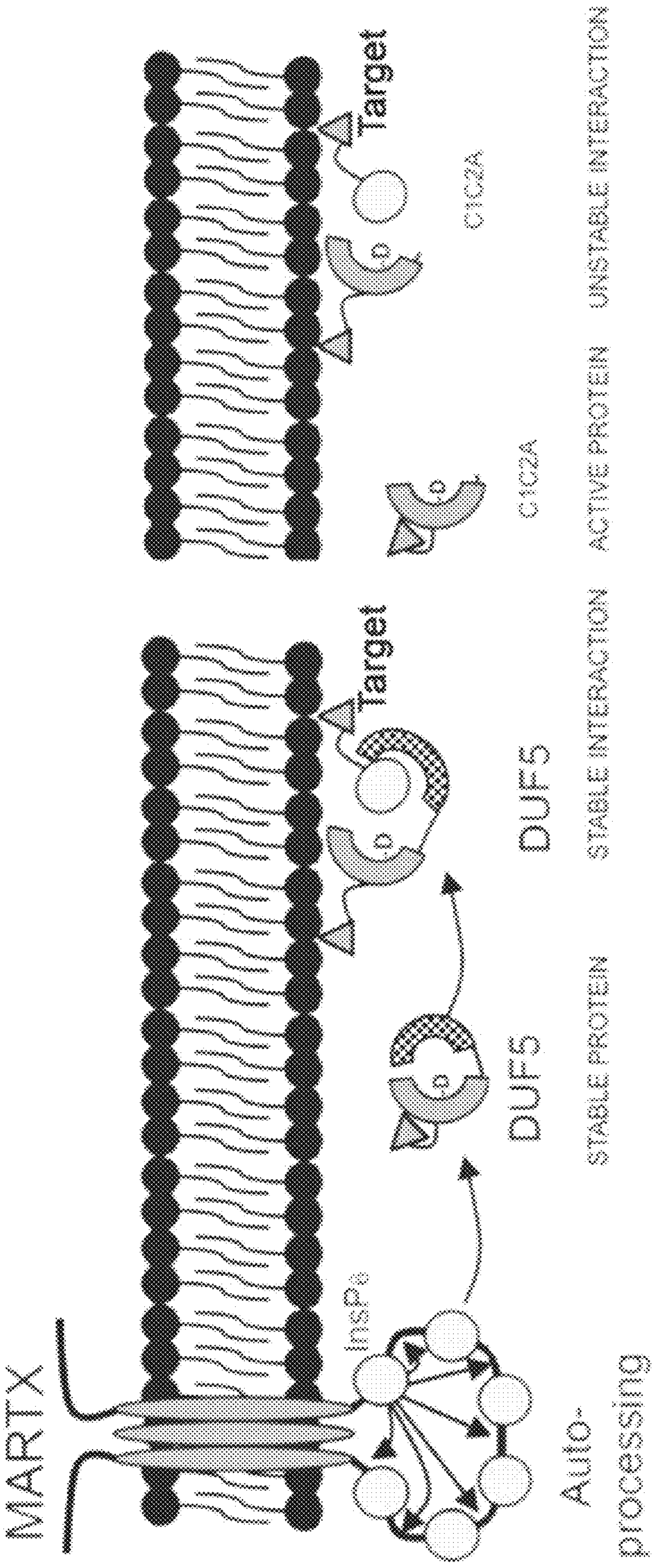
FIG. 23. MARTX toxin undergoes autoprocessing upon entry into the host cell. Autoprocessing by the inositol hexakisphosphate bound cysteine protease domain releases other effector domains and allows them to perform their functions. DUF5 has been shown to be a stable protein when all the subdomains are present, and is able to efficiently round cells when the C2 domain is intact. When C2B subdomain in removed from the protein, leaving only C1-C2A, cell rounding is less efficient, presumably due to protein turnover. Therefore, C2B is hypothesized to be involved in stabilizing the interaction between DUF5 and the cellular target. C2A and C2B are required for a stable interaction with the target protein, but C2A alone is sufficient for cytotoxic activity.

This stabilization may be due to its association with R3841 to retain optimal folding of the face that binds to the target protein or to serve as a switch to facilitate a change in the $DUF5_{Vv}$ structural conformation upon binding of $C1_{Vv}$ to the membrane (FIG. 21D). The role as a switch in the context of membrane binding is particularly interesting since reduced toxicity due to R3841A was observed only in the context of the $C1_{Vv}$ membrane localization domain in both yeast and HeLa cells. The contact between D3721 and R3841 could affect the conformation at the interface between $C2A_{Vv}$ and $C2B_{Vv}$ since R3 841 that makes polar contacts with D3721 also contacts a S3986 in an unstructured loop of C2B. In other DUF5 homologues, the Ser is replaced by a Thr. Further, this Ser is absent from PMT, although Ser residues are localized nearby in this otherwise poorly conserved regions between PMT and $DUF5_{Vv}$. Thus, it is intriguing to speculate that $C2B_{Vv}$ could function as a stabilization subdomain for $C2A_{Vv}$ with D3721 and R3841 functioning as part of the conformational switch to open up a binding site for the cellular target of C2A (FIG. 23).

A final component not addressed in this study is the biochemical mechanism or activity of $DUF5_{Vv}$ and $DUF5_{Ah}$. While two residues, D3721 and R3841 were found to be essential for rounding of mammalian cells by $DUF5_{Vv}$, this discovery does not as yet inform the biochemical or cell biological activity that results in cell rounding. This is particularly true since residues shown to be essential for $DUF5_{Vv}$ (D3721 and R3841) and conserved in $DUF5_{Ah}$ (D3215 and R33e5) are also conserved in PMT (as D720 and R861). Given that PMT is not able to round cells similar to $DUF5_{Vv}$ and DUF5Ah, we can only speculate that surrounding residues not conserved in PMT also contribute to the appropriate structure for $DUF5_{Vv}$ and $DUF5_{Ah}$ allowing these proteins but not PMT to properly interact with cellular components. Despite not yet directly demonstrating the biochemical or cell biological activity of the MARTX DUF5 effector domains, this study has provided numerous useful tools and reagents for these on-going studies but likewise reveals how identification of the cellular target could potentially be problematic. We found that the cytotoxicity is associated with C2A. However, this subdomain is highly toxic when ectopically overexpressed, which presents difficulties in identifying the target protein by common affinity precipitation techniques. A catalytically inactive variant is often highly useful to trap targets by affinity precipitation methods, but we found that the only inactive substitution also affects structural integrity and likely no longer binds its target in vivo. Our findings here that yeast is also affected by $DUF5_{Vv}$ does open the possibility that yeast-based genetic approaches could be very helpful to identify the target and these studies are currently ongoing.

REFERENCES

1. Satchell K J. Structure and function of MARTX toxins and other large repetitive RTX proteins. Annual review of microbiology 2011; 65:71-90.
2. Egerer M, Satchell K J. Inositol hexakisphosphate-induced autoprocessing of large bacterial protein toxins. PLoS Pathog 2010; 6(7):e1000942.
3. Prochazkova K, Shuvalova L A, Minasov G, Voburka Z, Anderson W F, Satchell K J. Structural and molecular mechanism for autoprocessing of MARTX Toxin of *Vibrio cholerae* at multiple sites. J Biol Chem 2009; 284:26557-26568.

4. Shen A, Lupardus P J, Albrow V E, Guzzetta A, Powers J C, Garcia K C, Bogyo M. Mechanistic and structural insights into the proteolytic activation of *Vibrio cholera* MARTX toxin. Nat Chem Biol 2009; 5(7):469-478.
5. Kwak J S, Jeong H G, Satchell K J. *Vibrio vulnificus* rtxA1 gene recombination generates toxin variants with altered potency during intestinal infection. Proceedings of the National Academy of Sciences of the United States of America 2011; 108(4):1645-1650.
6. Roig F J, Gonzalez-Candelas F, Amaro C. Domain organization and evolution of multifunctional autoprocessing repeats-in-toxin (MARTX) toxin in *Vibrio vulnificus*. Appl Environ Microbiol 2011; 77(2):657-668.
7. Cordero C L, Kudryashov D S, Reisler E, Satchell K J. The actin cross-linking domain of the *Vibrio cholerae* RTX toxin directly catalyzes the covalent cross-linking of actin. J Biol Chem 2006; 281(43):32366-32374.
8. Kudryashov D S, Durer Z A, Ytterberg A J, Sawaya M R, Pashkov I, Prochazkova K, Yeates T O, Loo R R, Loo J A, Satchell K J, Reisler E. Connecting actin monomers by isopeptide bond is a toxicity mechanism of the *Vibrio cholerae* MARTX toxin. Proceedings of the National Academy of Sciences of the United States of America 2008; 105(47): 18537-18542.
9. Fullner K J, Mekalanos J J. In vivo covalent crosslinking of actin by the RTX toxin of *Vibrio cholerae*. EMBO J 2000; 19:5315-5323.
10. Sheahan K L, Cordero C L, Satchell K J. Identification of a domain within the multifunctional *Vibrio cholerae* RTX toxin that covalently cross-links actin. Proc Natl Acad Sci USA 2004; 101(26):9798-9803.
11. Sheahan K L, Satchell K J. Inactivation of small Rho GTPases by the multifunctional RTX toxin from *Vibrio cholerae*. Cell Microbiol 2007; 9(5):1324-1335.

12. Ahrens S, Geissler B, Satchell K J. Identification of a His-Asp-Cys catalytic triad essential for function of the Rho inactivation domain (RID) of *Vibrio cholerae* MARTX toxin. The Journal of biological chemistry 2013; 288(2): 1397-1408.
13. Ziolo K. J. J H, Kwak J. S., Yang S., Lavker R. M. and Satchell K. J. F. *Vibrio vulnificus* biotype 3 MARTX toxin is an adenylate cyclase toxin essential for virulence in mice. Infection and Immunity 2014.
14. Satchell K J. MARTX: Multifunctional-Autoprocessing RTX Toxins. Infect Immun 2007; 75:5079-5084.
15. Kitadokoro K, Kamitani S, Miyazawa M, Hanajima-Ozawa M, Fukui A, Miyake M, Horiguchi Y. Crystal structures reveal a thiol protease-like catalytic triad in the Cterminal region of *Pasteurella multocida* toxin. Proceedings of the National Academy of Sciences of the United States of America 2007; 104(12):5139-5144.
16. Kamitani S, Kitadokoro K, Miyazawa M, Toshima H, Fukui A, Abe H, Miyake M, Horiguchi Y. Characterization of the membrane-targeting C1 domain in *Pasteurella multocida* toxin. The Journal of biological chemistry 2010; 285(33):25467-25475.
17. Geissler B, Tungekar R, Satchell K J. Identification of a conserved membrane localization domain within numerous large bacterial protein toxins. Proceedings of the National Academy of Sciences of the United States of America 2010; 107(12):5581-5586.
18. Brothers M C, Geissler B, Hisao G S, Satchell K J, Wilson B A, Rienstra C M. Backbone and side-chain resonance assignments of the membrane localization domain from *Pasteurella multocida* toxin. Biomolecular NMR assignments 2014; 8(1):221-224.
19. Brothers M C, Geissler B, Hisao G S, Wilson B A, Satchell K J, Rienstra C M. Backbone and side-chain assignments of an effector membrane localization domain from *Vibrio vulnificus* MARTX toxin. Biomolecular NMR assignments 2013.
20. Pullinger G D, Sowdhamini R, Lax A J. Localization of functional domains of the mitogenic toxin of *Pasteurella multocida*. Infect Immun 2001; 69(12):7839-7850.
21. Aminova L R, Luo S, Bannai Y, Ho M, Wilson B A. The C3 domain of *Pasteurella multocida* toxin is the minimal domain responsible for activation of Gq-dependent calcium and mitogenic signaling. Protein Sci 2008; 17(5): 945-949.
22. Orth J H, Preuss I, Fester I, Schlosser A, Wilson B A, Aktories K. *Pasteurella multocida* toxin activation of heterotrimeric G proteins by deamidation. Proc Natl Acad Sci USA 2009.
23. Orth J H, Fester I, Siegert P, Weise M, Lanner U, Kamitani S, Tachibana T, Wilson B A, Schlosser A, Horiguchi Y, Aktories K. Substrate specificity of *Pasteurella multocida* toxin for alpha subunits of heterotrimeric G proteins. FASEB J 2013; 27(2):832-842.
24. ffrench-Constant R, Waterfield N, Daborn P, Joyce S, Bennett H, Au C, Dowling A, Boundy S, Reynolds S, Clarke D. *Photorhabdus*: towards a functional genomic analysis of a symbiont and pathogen. FEMS Microbiol Rev 2003; 26(5):433-456.
25. Wilkinson P, Waterfield N R, Crossman L, Corton C, Sanchez-Contreras M, Vlisidou I, Barron A, Bignell A, Clark L, Ormond D, Mayho M, Bason N, Smith F, Simmonds M, Churcher C, Harris D, Thompson N R, Quail M, Parkhill J, Ffrench-Constant R H. Comparative genomics of the emerging human pathogen *Photorhabdus asymbiotica* with the insect pathogen *Photorhabdus luminescens*. BMC Genomics 2009; 10:302.
26. Altschul S F, Gish W, Miller W, Myers E W, Lipman D J. Basic local alignment search tool. J Mol Biol 1990; 215(3):403-410.
27. Soding J, Biegert A, Lupas A N. The HHpred interactive server for protein homology detection and structure prediction. Nucleic acids research 2005; 33 (Web Server issue):W244-248.
28. Sali A, Potterton L, Yuan F, van Vlijmen H, Karplus M. Evaluation of comparative protein modeling by MODELLER. Proteins 1995; 23(3):318-326.
29. Spyres L M, Qa'Dan M, Meader A, Tomasek J J, Howard E W, Ballard J D. Cytosolic delivery and characterization of the TcdB glucosylating domain by using a heterologous protein fusion. Infect Immun 2001; 69(1):599-601.
30. Stols L, Gu M, Dieckman L, Raffen R, Collart F R, Donnelly M I. A new vector for highthroughput, ligation-independent cloning encoding a tobacco etch virus protease cleavage site. Protein Expr Purif 2002; 25(1):8-15.
31. Geissler B, Bonebrake A, Sheahan K L, Walker M E, Satchell K J. Genetic determination of essential residues of the *Vibrio cholerae* actin cross-linking domain reveals functional similarity with glutamine synthetases. Molecular microbiology 2009; 73(5):858-868.
32. Busch C, Orth J, Djouder N, Aktories K. Biological activity of a C-terminal fragment of *Pasteurella multocida* toxin. Infect Immun 2001; 69(6):3628-3634.
33. Baldwin M R, Lakey J H, Lax A J. Identification and characterization of the *Pasteurella multocida* toxin translocation domain. Molecular microbiology 2004; 54(1): 239-250.
34. Bazan J F, Macdonald B T, He X. The TIKI/TraB/PrgY family: a common protease fold for cell signaling from bacteria to metazoa? Dev Cell 2013; 25(3):225-227.
35. Sanchez-Pulido L, Ponting C P. Tiki, at the head of a new superfamily of enzymes. Bioinformatics 2013; 29(19): 2371-2374.
36. Wesche J, Elliott J L, Falnes P O, Olsnes S, Collier R J. Characterization of membrane translocation by anthrax protective antigen. Biochemistry 1998; 37(45):15737-15746.
37. Geissler B, Ahrens S, Satchell K J. Plasma membrane association of three classes of bacterial toxins is mediated by a basic-hydrophobic motif. Cellular microbiology 2012; 14(2):286-298.
38. Prochazkova K, Satchell K J. Structure-function analysis of inositol hexakisphosphateinduced autoprocessing of the *Vibrio cholerae* multifunctional autoprocessing RTX toxin. J Biol Chem 2008; 283(35):23656-23664.

Example 3—Site-Specific Processing of Ras and Rap1 Switch I by a MARTX Toxin Effector Domain Reference is made Antic, I., et al., Site-specific processing of Ras and Rap1 Switch I by a MARTX toxin effector domain. Nat Commun, 2015. 6: p. 7396, the content of which is incorporate herein by reference in its entirety.

Abstract

Ras (Rat sarcoma) protein is a central regulator of cell growth and proliferation. Mutations in the RAS gene are known to occur in human cancers and have been shown to contribute to carcinogenesis. In this study, we show that the multifunctional-autoprocessing repeats-intoxin (MARTX) toxin-effector domain DUF5$_{Vv}$ from *Vibrio vulnificus* to be a site-specific endopeptidase that cleaves within the Switch 1 region of Ras and Rap1. DUF5$_{Vv}$ processing of Ras, which occurs both biochemically and in mammalian cell culture, inactivates ERK1/2, thereby inhibiting cell proliferation. The ability to cleave Ras and Rap1 is shared by $DUF5_{Vv}$ homologues found in other bacteria. In addition, $DUF5_{Vv}$ can cleave all Ras isoforms and KRas with mutations commonly implicated in malignancies. Therefore, we speculate that this new family of Ras/Rap1A-specific endopeptidases (RRSPs) has potential to inactivate both wild-type and mutant Ras proteins expressed in malignancies.

Introduction

Rat sarcoma (Ras) oncoprotein is a small GTPase ubiquitous in eukaryotic cells and is a critical node that coordinates incoming signals and subsequently activates downstream target proteins. These targets include rapidly accelerated fibrosarcoma kinase (Raf), phosphatidylinositol-4,5-bisphosphate 3-kinase and mitogen-activated protein kinase (MAPK), which ultimately induces expression of genes directing cell proliferation, differentiation and survival. Regulation of Ras enzymatic activity is achieved by cycling between an inactive (GDP-bound) state and an active (GTP-bound) state. On activation, conformational changes in the Ras protein structure trigger Ras downstream signalling cascades by binding specific protein effectors[1-4]. Mutations in Ras proto-oncogenes are found in 9-30% of all human malignancies. In addition, Ras point mutations, which are observed at residues G12 and G13 in the P-loop and at Q61 in the Switch II region, are the most common mutations in human malignancies and are present in 98% of pancreatic ductal adenocarcinomas, 53% of colorectal adenocarcinomas and 32% of lung adenocarcinomas[5-7]. However, effective targeting of Ras has been very difficult and is considered a critical roadblock on the path towards generating new therapeutics against intractable human cancers[8-12]. Despite the potential of Ras proteins as therapeutic targets, there are no inhibitors for any of the three main human isoforms—HRas, KRas and NRas—or their constitutively activated mutant forms[8-11].

From a microbial pathogenesis perspective, activation of Ras is central to cellular detection of bacterial lipopolysaccharide and other pathogen-associated molecular patterns resulting in activation of innate immune defenses[13]. Although several bacterial toxins are known to target Ras by posttranslational modification to circumvent this important host response to infection, to date none have been shown to be highly specific for Ras[14-16].

Multifunctional-autoprocessing repeats-in-toxin (MARTX) toxins proteins are large composite-secreted bacterial protein toxins that translocate across the eukaryotic cell plasma membrane and deliver multiple cytopathic and cytotoxic effector proteins from a single holotoxin by autoprocessing[17,18]. In our previous work, we showed that the most highly virulent strains of the sepsis-causing pathogen *V. vulnificus* produce a 5,206-amino acid (aa) MARTX toxin with an extra effector domain termed $DUF5_{Vv}$, for the domain of unknown function in the 5$^{th}$ position[19]. In fact, bacterial strains that produce a MARTX toxin with $DUF5_{Vv}$ are found to be 10- to 50-fold more virulent in mice than strains that produce a MARTX toxin without $DUF5_{Vv}$ (ref. 19). These data directly connect $DUF5_{Vv}$ with increased virulence during infection.

The 509-aa $DUF5_{Vv}$ effector domain of the MARTX toxin was highly cytotoxic when ectopically expressed as a fusion to green fluorescent protein (GFP), resulting in rounding and shrinkage of cells[20]. Structural and functional bioinformatics studies have demonstrated that $DUF5_{Vv}$ is comprises two subdomains[20,21]. The amino-terminal C1 subdomain is a four-helix bundle that mediates localization to the plasma membrane by binding anionic phospholipids[21,22]. The carboxy-terminal C2 subdomain confers the cell rounding activity[20]. Moreover, $DUF5_{Vv}$-C2 was found to inhibit growth when conditionally overexpressed in *Saccharomyces cerevisiae*[20].

In this study, we used a combination of genetic, cell biological and biochemical strategies to probe the mechanism of action of the C2 subdomain, to understand the connection of $DUF5_{Vv}$ to both cytotoxicity and increased virulence of the pathogen. We find that $DUF5_{Vv}$ site-specifically processes both Ras and the closely related small GTPase Rap1. Both proteins are critical for activation of the innate immune response during infection, which explains the crucial role of this effector domain in the increased virulence of *V. vulnificus* strains that have $DUF5_{Vv}$ As Ras is also important for cell proliferation in carcinogenesis, this enzyme could potentially be developed as a treatment for various types of tumours.

Results $DUF5_{Vv}$ Causes ERK1/2 Dephosphorylation.

Figure 24A:
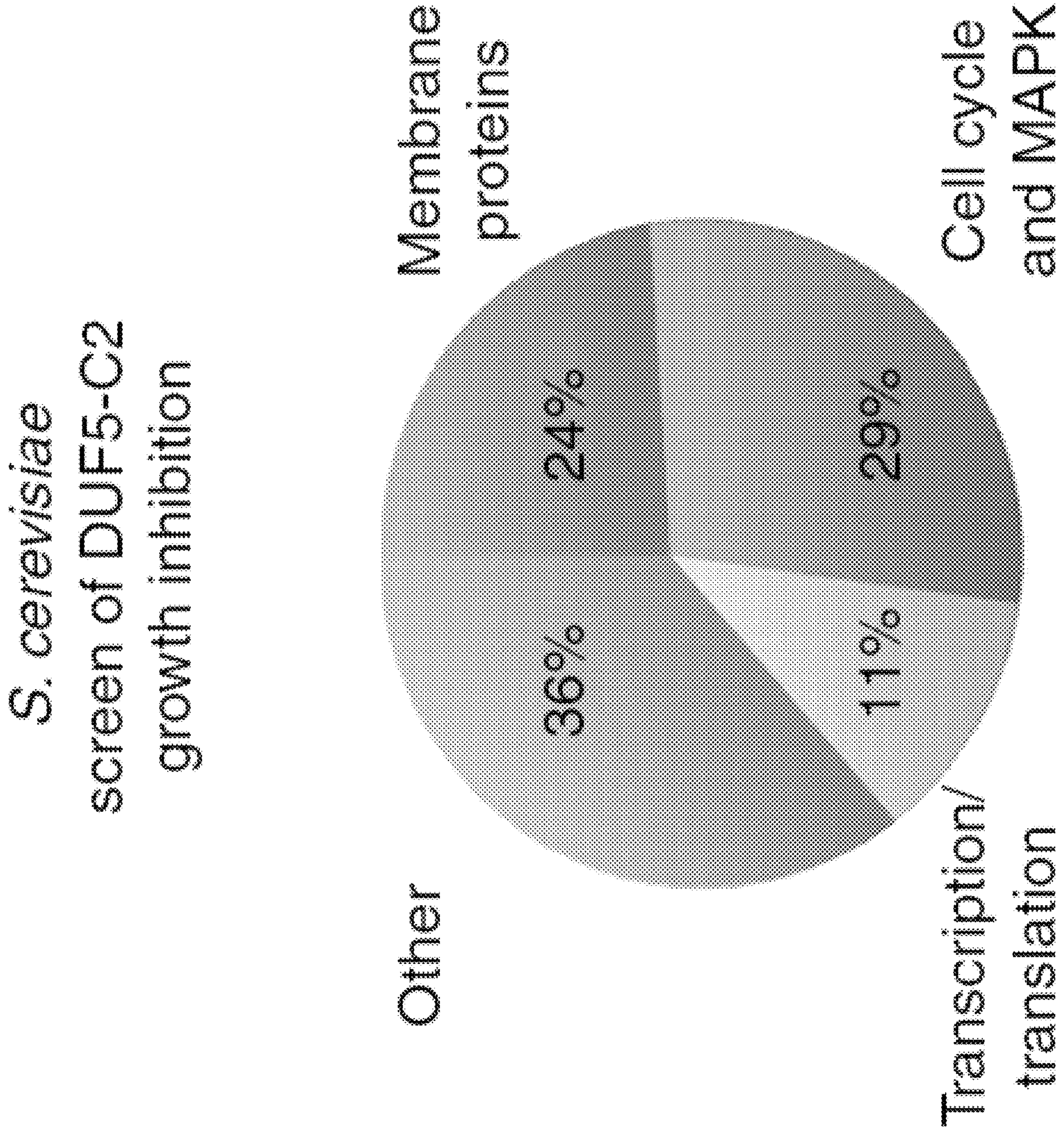
FIG. 24A, FIG. 24B, FIG. 24C, FIG. 24D and FIG. 24E illustrate $DUF5_{Vv}$-dependent disruption of Ras-ERK-dependent cell proliferation.

Previously we showed that $DUF5_{Vv}$-C2 is cytotoxic when ectopically expressed in cells[20]. As a strategy to identify molecular targets accounting for this cytotoxicity[20], a genome-wide, arrayed, non-essential gene deletion library was screened for yeast strains that survived enforced expression of C2 (FIG. 28). Of 4,709 yeast strains screened, 3.6% formed colonies on plates containing the inducer galactose, indicating that the yeast gene disruption suppressed C2-dependent growth inhibition. The hits were categorized based on information in the *Saccharomyces* Genome Database23. Eleven percent of the mutant yeast strains that overcame growth inhibition due to $DUF5_{Vv}$-C2 expression harboured deletions in genes for transcription and/or translation. These mutations probably reduce $DUF5_{Vv}$-C2 expression, accounting for suppression of growth inhibition. Twenty-four percent of the recovered yeast strains had defects affecting membrane or membrane proteins, possibly causing suppression of cytotoxicity due to the absence of the cellular target at the membrane (FIG. 24A).

Among the remaining hits, nearly half were connected to MAPKs or processes they regulate. Therefore, it was postulated that mammalian MAPK p38 and ERK1/2 could have altered activity during exposure of cells to $DUF5_{Vv}$. We have previously demonstrated that the cytotoxic activity of $DUF5_{Vv}$ can be isolated away from the large MARTX by fusing $DUF5_{Vv}$ to the N terminus of anthrax toxin lethal factor ($LFNDUF5_{Vv}$) and subsequently delivering the fusion protein to cells in culture using anthrax toxin protective antigen (PA20). Therefore, we used this system to test for changes in MAPK signalling dependent on exposure of cells to $DUF5_{Vv}$.

Figure 24B:
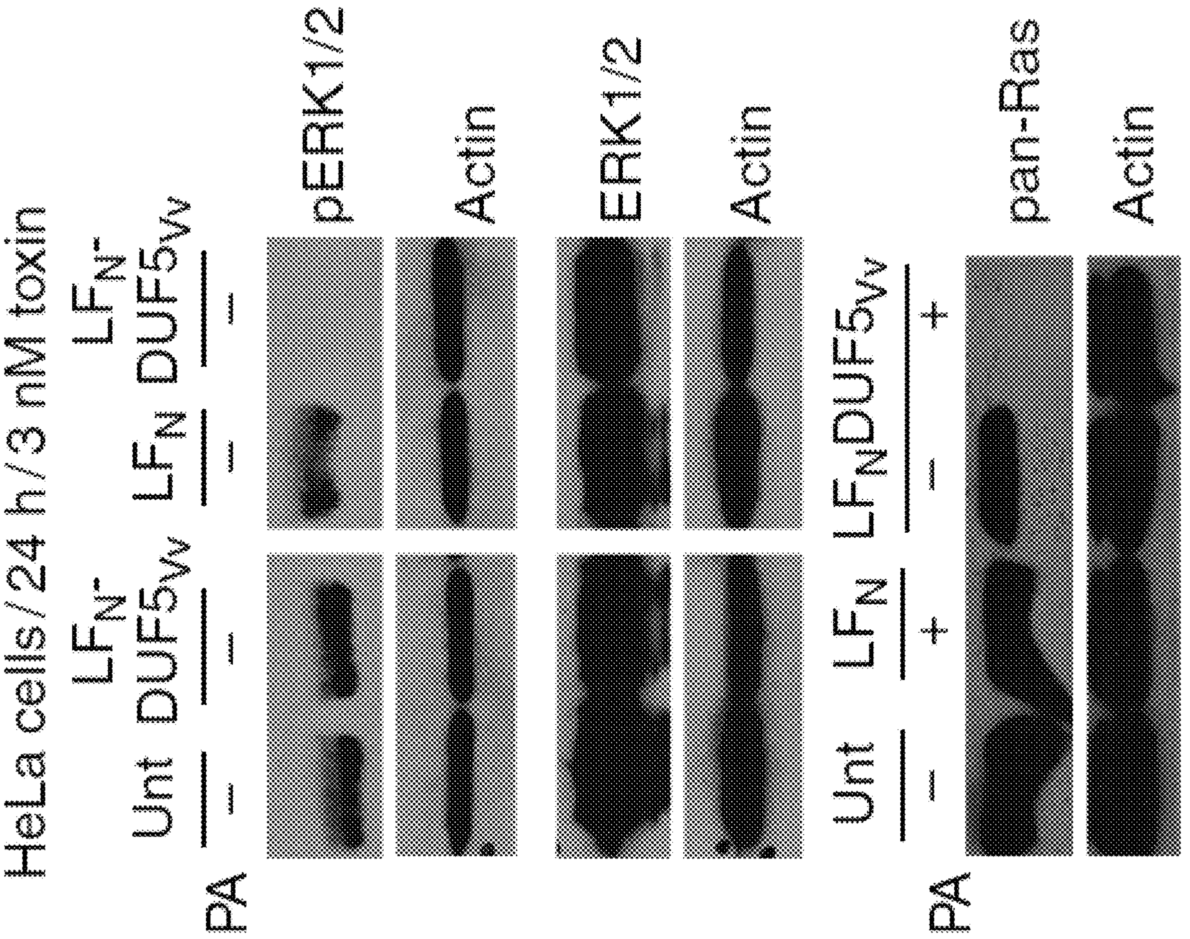

HeLa cervical carcinoma cells constitutively produce high levels of phospho-p38 and phospho-ERK1/2 (pERK1/2), making these cells an ideal model system to determine the underlying mechanism by which $DUF5_{Vv}$ interferes with MAPK signaling (FIG. 29). For cells intoxicated with $LF_NDUF5_{Vv}$ in combination with PA for 24 h, no change in levels of phosphop[38] was observed (FIG. 29*a*). However, there was a marked absence of pERK1/2 in HeLa cells treated with $LF_NDUF5_{Vv}$+PA (FIG. 24B and FIG. 29*a*). In addition, the first 276 aa of $DUF5_{Vv}$, corresponding to the C1 membrane-targeting subdomain and the first 186 of C2 ($C1C2A_{Vv}$), were sufficient to reduce pERK1/2 levels (FIG. 29*b*), consistent with previous results showing that $C1C2A_{Vv}$ is sufficient for cell rounding activity[20]. Thus, the yeast screen and subsequent studies in HeLa cells revealed that $DUF5_{Vv}$ modulates the activation state of ERK1/2 without affecting p38.

Ras Depletion by $DUF5_{Vv}$ Inhibits Cell Division.

Figure 30:
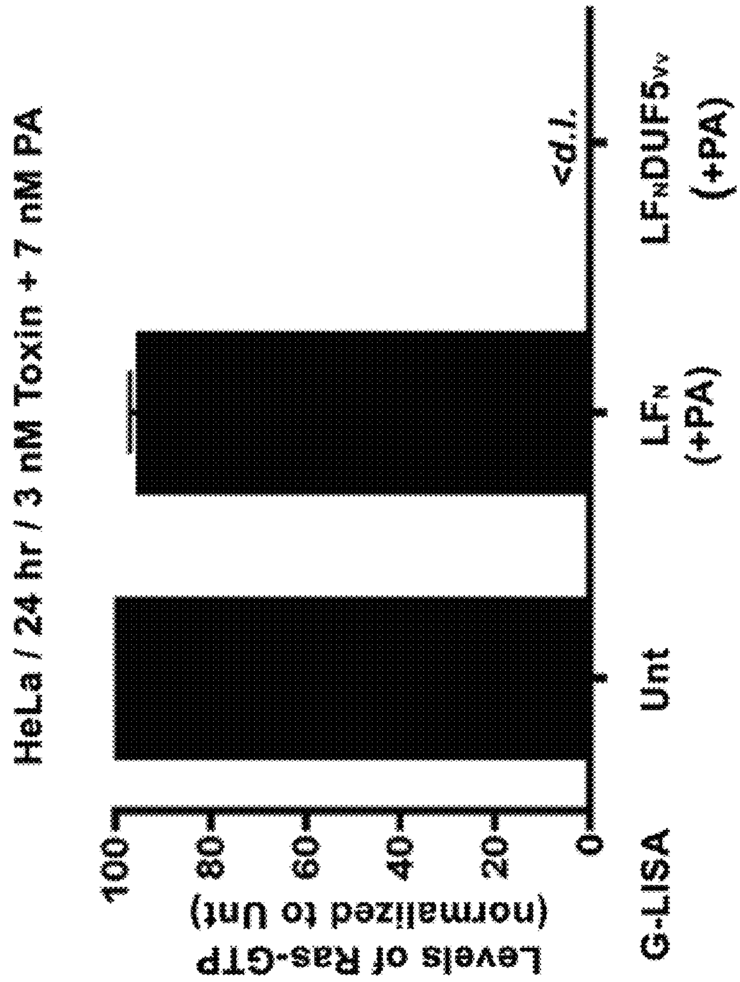
FIG. 30. HeLa cells treated with DUF5Vv lack active (GTP-bound) Ras. Bar graph of relative detection of active GTP-bound Ras (all isoforms) by G-LISA. Failure to detect active Ras was ultimately explained by the complete absence of Ras detectable by the monoclonal RAS10 antibody provided with the assay kit.

Owing to its C1 membrane-targeting subdomain, $DUF5_{Vv}$ is exclusively present at the plasma membrane[21]; hence, inactivation of membrane localized Ras GTPases that control activation of ERK1/2 (refs 24,25) seemed a plausible mechanism for $DUF5_{Vv}$ dependent ERK1/2 dephosphorylation. Active Ras (GTP-bound) was probed using a G-LISA assay, where wells are coated with a Ras GTP-binding protein domain. Surprisingly, active Ras was undetectable in cell lysates intoxicated with $LF_N DUF5_{Vv}$+PA, suggesting that Ras was exclusively in the inactive, GDP-bound state (FIG. 30). This result initially suggested that $DUF5_{Vv}$ affects levels of active Ras-GTP. However, additional control experiments revealed that Ras protein itself was undetectable in cell lysates, as measured by immunoblotting with a monoclonal anti-RAS10 antibody that detects all isoforms of Ras26, including KRas, HRas and NRas (FIG. 24*b*). This experiment shows that $DUF5_{Vv}$ directly targets the Ras protein rather than indirectly affecting its regulation.

Figure 24C:
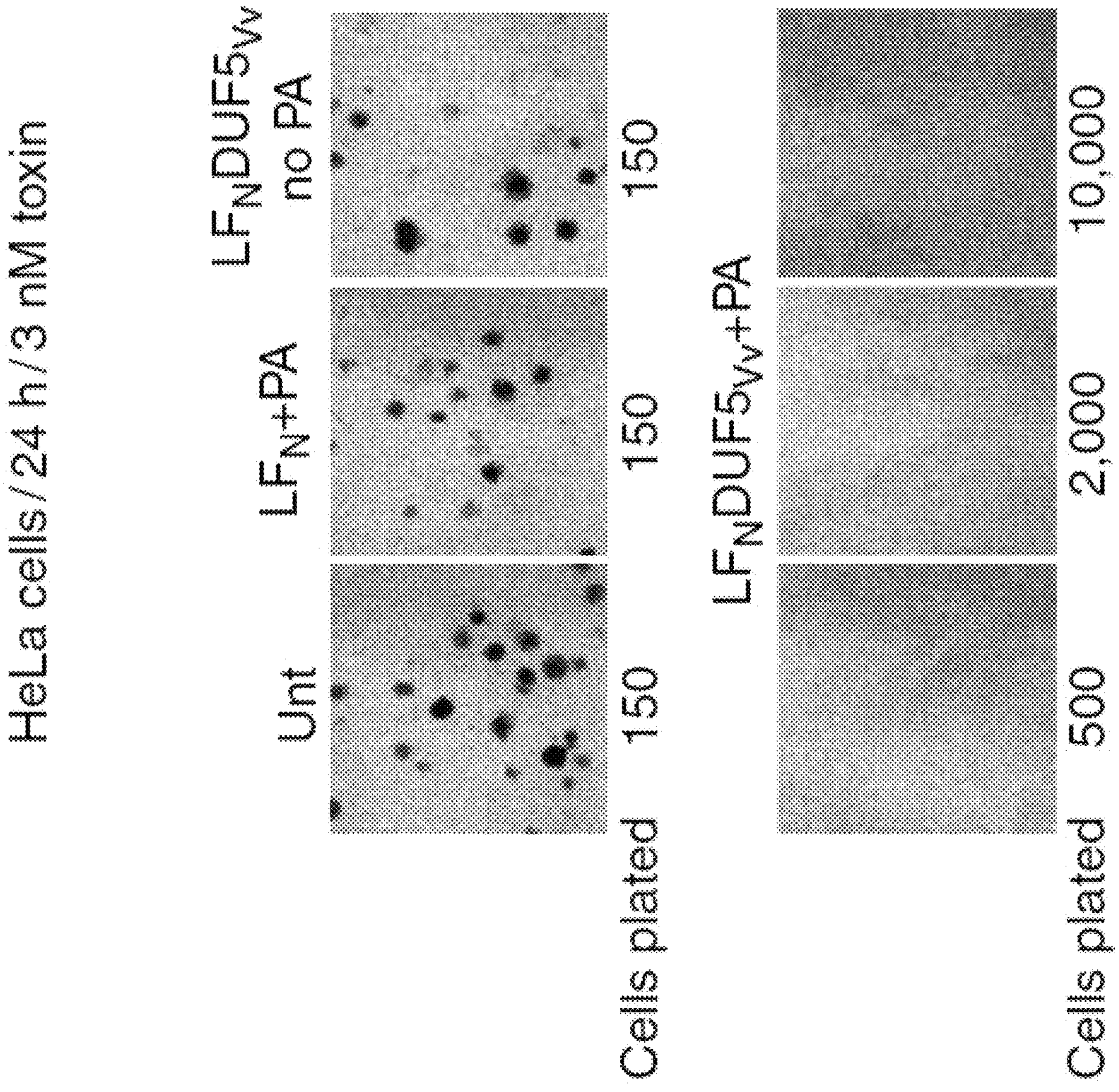
Figure 24D:
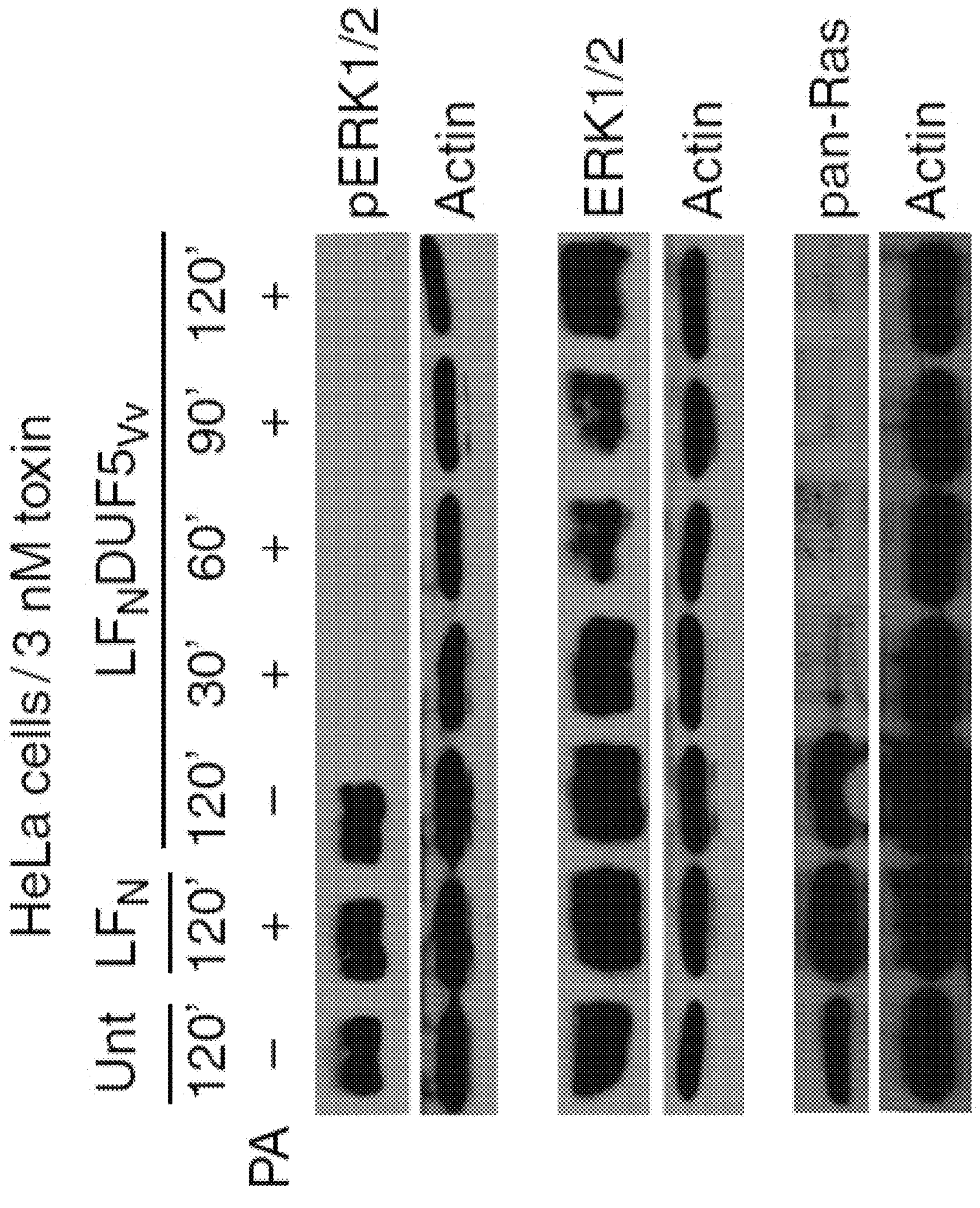
Figure 24E:
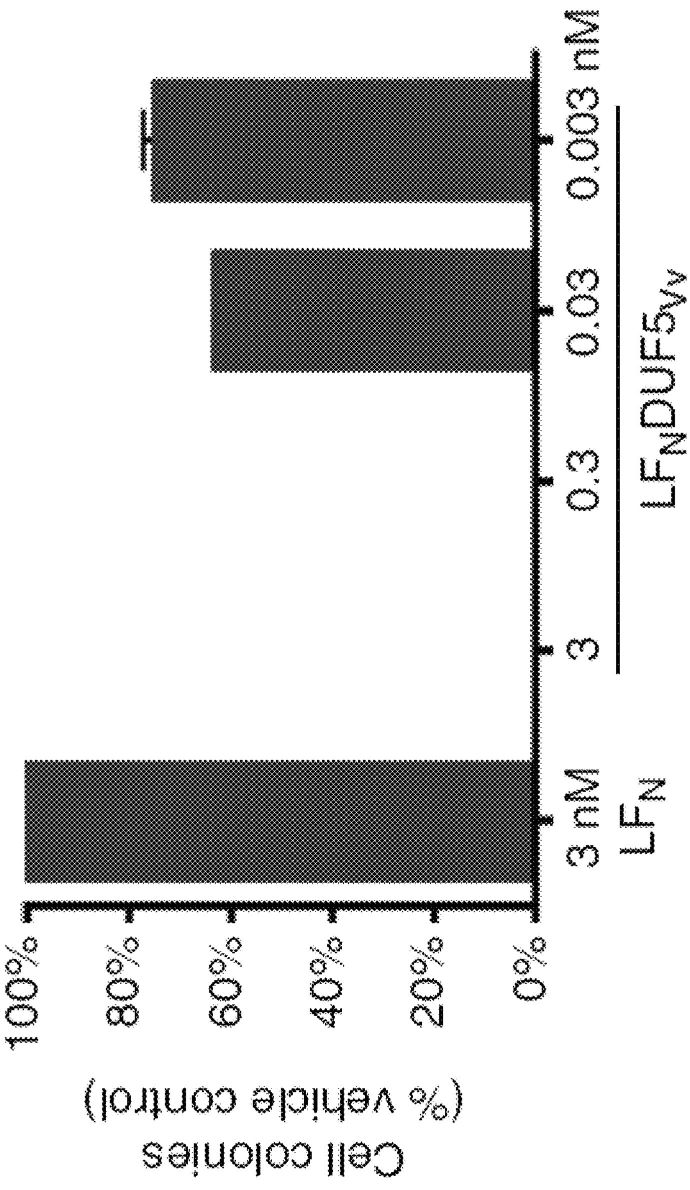
Figure 31:
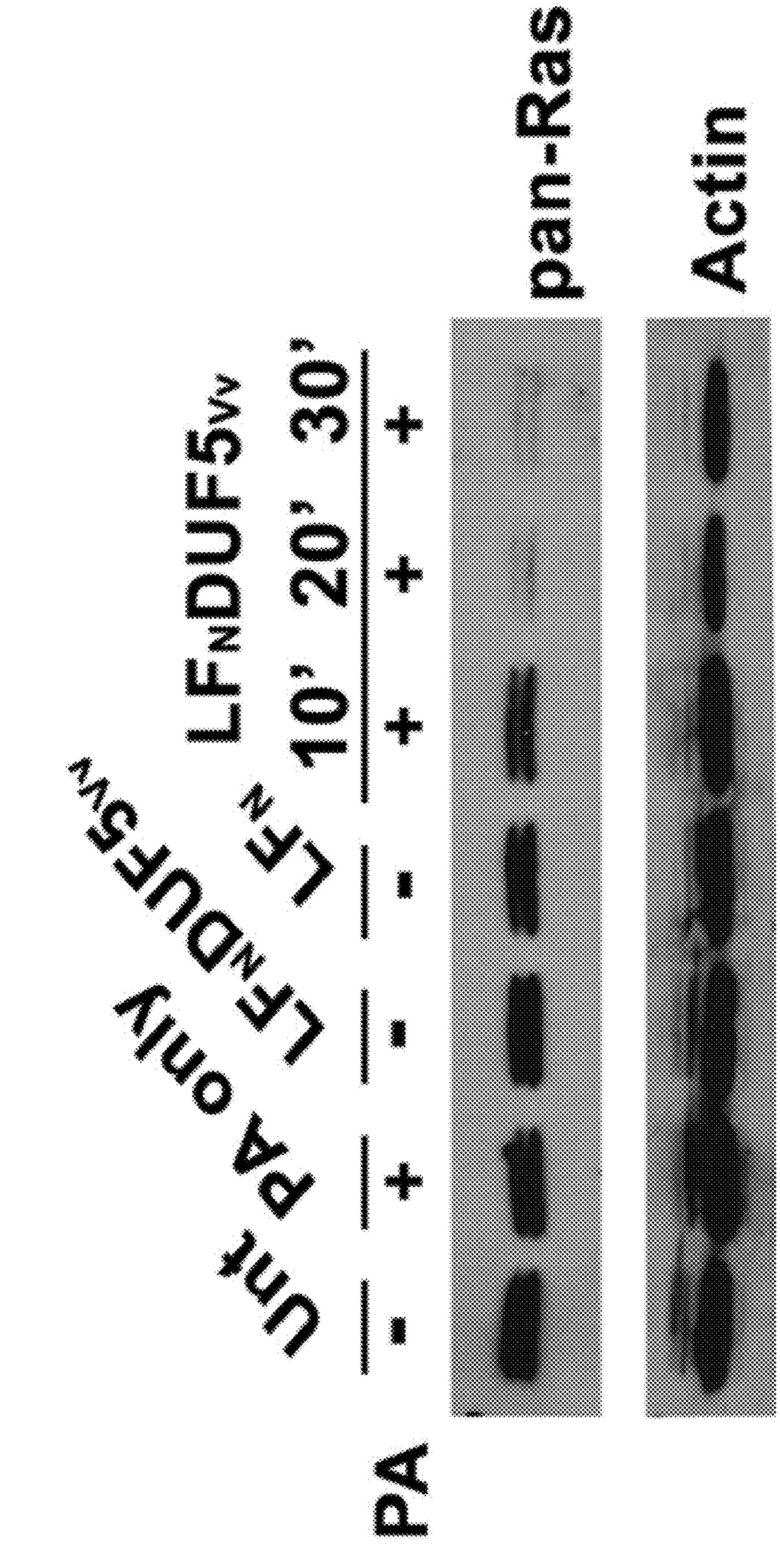
FIG. 31. Ras inactivation by $DUF5_{Vv}$ occurs rapidly. Immunoblot of lysates from cells treated for time indicated. Control samples (first four lanes) were collected 30 minutes after intoxication.

If Ras and pERK1/2 are truly absent from $DUF5_{Vv}$-treated cells, proliferation should be inhibited in intoxicated samples. To measure disruption in cell proliferation due to the inhibition of the Ras-ERK pathway, the toxin was removed by washing, and treated cells were plated and resulting colonies counted after a 14-day incubation period. HeLa cells intoxicated for 24 h did not produce colonies even when plated at almost 70-fold higher seeding densities than control-treated cells (FIG. 24C). Examination of ERK1/2 and Ras inactivation over time revealed that exposure of cells to 3 nM $LFNDUF5_{Vv}$ for only 30 min was sufficient for nearly 100% inactivation (FIG. 24D and FIG. 31). In addition, exposure of cells to $LFNDUF5_{Vv}$ concentrations as low as 30 pM for 1 h was sufficient to significantly decrease cell proliferation (FIG. 24E). Overall, these studies reveal that $DUF5_{Vv}$ directly targets Ras, resulting in loss of ERK1/2 phosphorylation and cell proliferation.

Ras is Cleaved at the N Terminus in $DUF5_{Vv}$-Treated Cells.

Figure 25A:
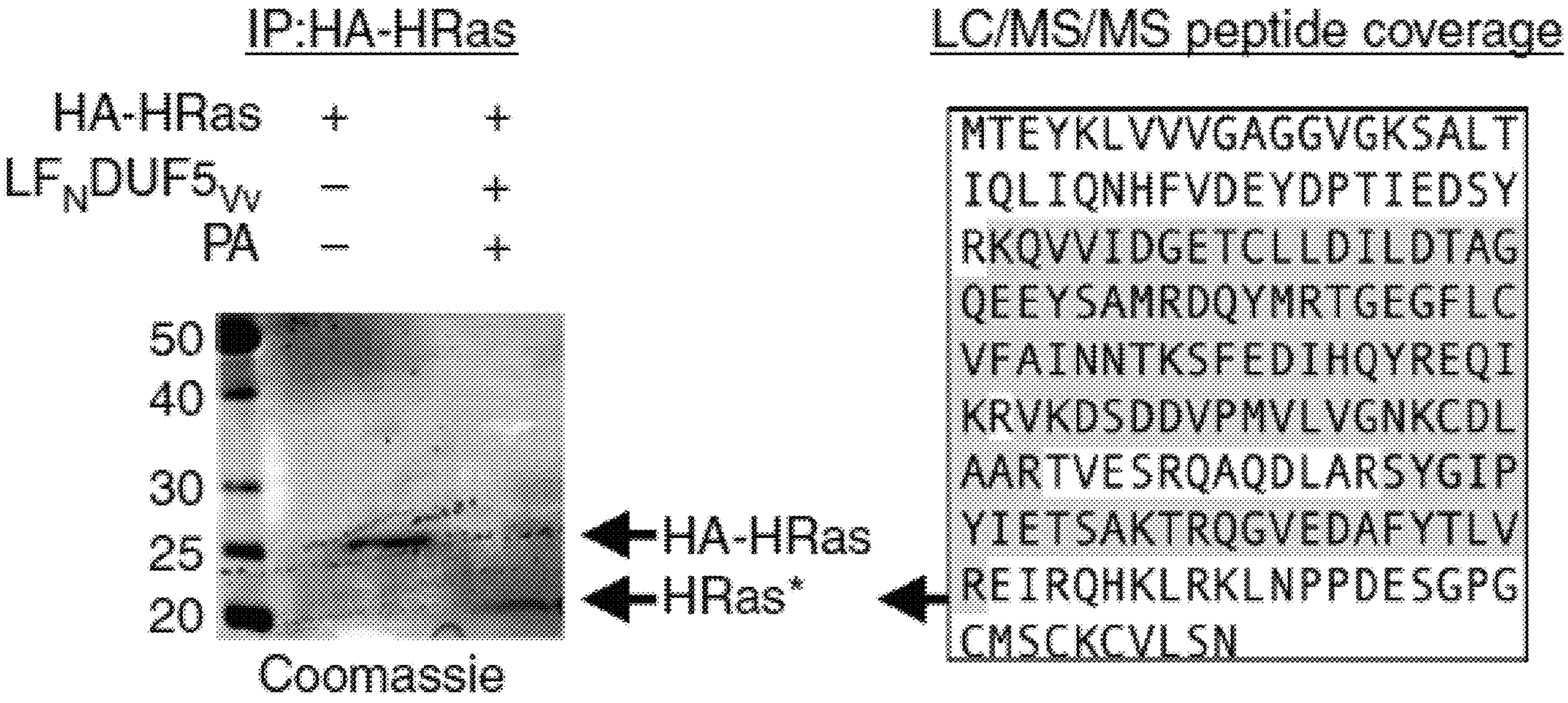
FIG. 25A, FIG. 25B, FIG. 25C, FIG. 25D, FIG. 25E and FIG. 25F illustrate that $DUF5_{Vv}$ is a Ras site-specific endopeptidase.

Only a few bacteria are known to specifically target Ras as a strategy to circumvent the host response and all do so by covalent attachment of nucleotide-sugar moieties to critical residues[14-16]. To investigate whether the loss of detectable Ras protein levels was due to proteolysis and/or a posttranslational modification that would mask the antibody epitope, HeLa cells were transfected to ectopically express HRas with a haemagglutinin (HA)-tag on the N terminus (HA-HRas), so as to facilitate immunoprecipitation with anti-HA antibody-coupled beads. Analysis of proteins immunoprecipitated from $LFNDUF5_{Vv}$+PA intoxicated cells revealed a Coomassie-stained band with a molecular weight B5 kDa smaller than the band observed in the untreated cells. Liquid chromatography—tandem mass spectrometry sequencing Q2 of tryptic peptides identified this protein as HRas, with no detection of the first three expected N-terminal peptides (FIG. 25A).

Figure 25B:
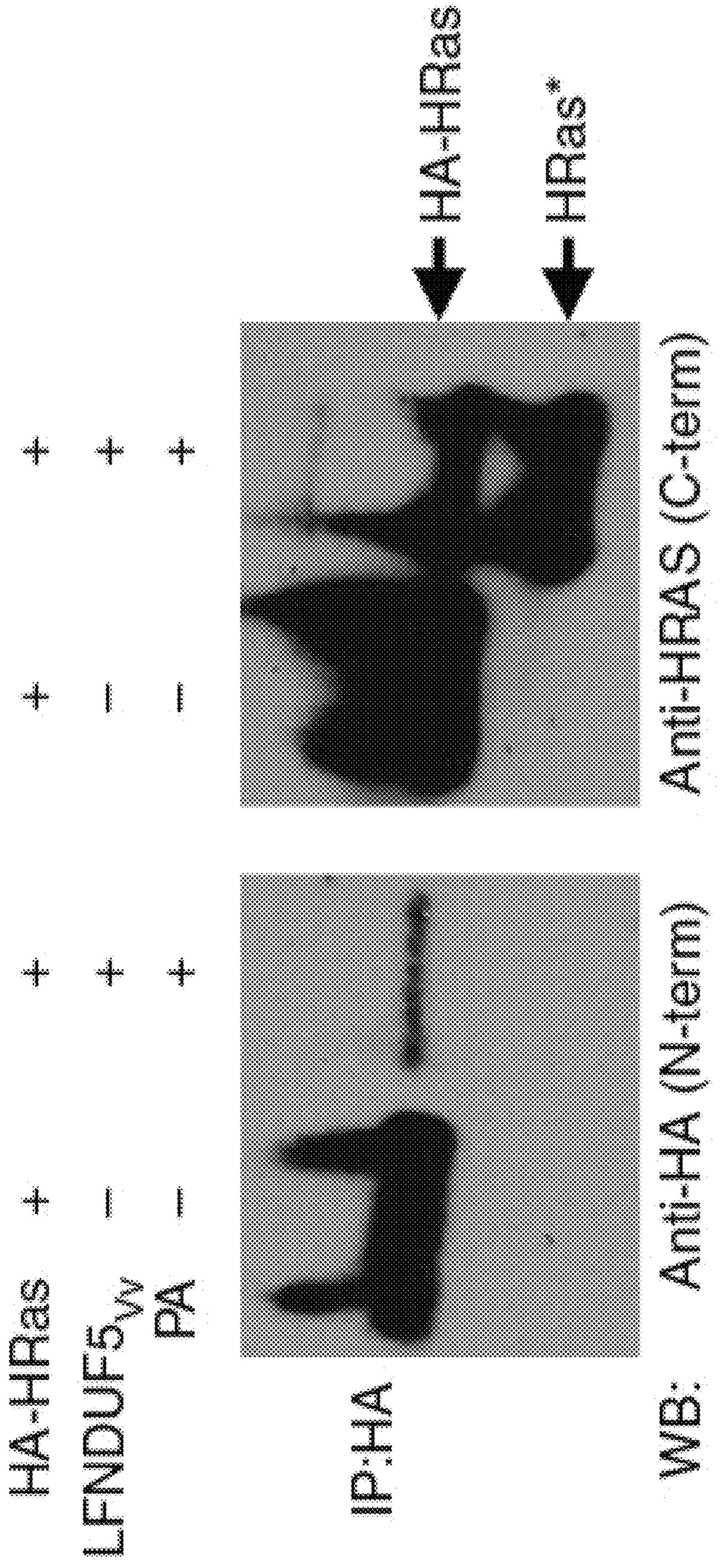

When the elution fraction was probed with anti-HA or anti-RAS10 monoclonal antibodies that detect the N terminus, a quantitative loss of the full-length protein from intoxicated cells was observed (FIG. 25B, left panel). By contrast, an isoform-specific polyclonal antibody that detects the C terminus of HRas identified two bands of HRas: one representing the full-length HA-HRas and one B5 kDa smaller. We speculate this cleaved form of HRas was present in the immunoprecipation despite lacking the HA tag, because the HA-tagged fragment remained associated with the larger C-terminal fragment in the folded protein. This experiment suggested that $DUF5_{Vv}$ induces cleavage of Ras within the N terminus of the protein.

Figure 25C:
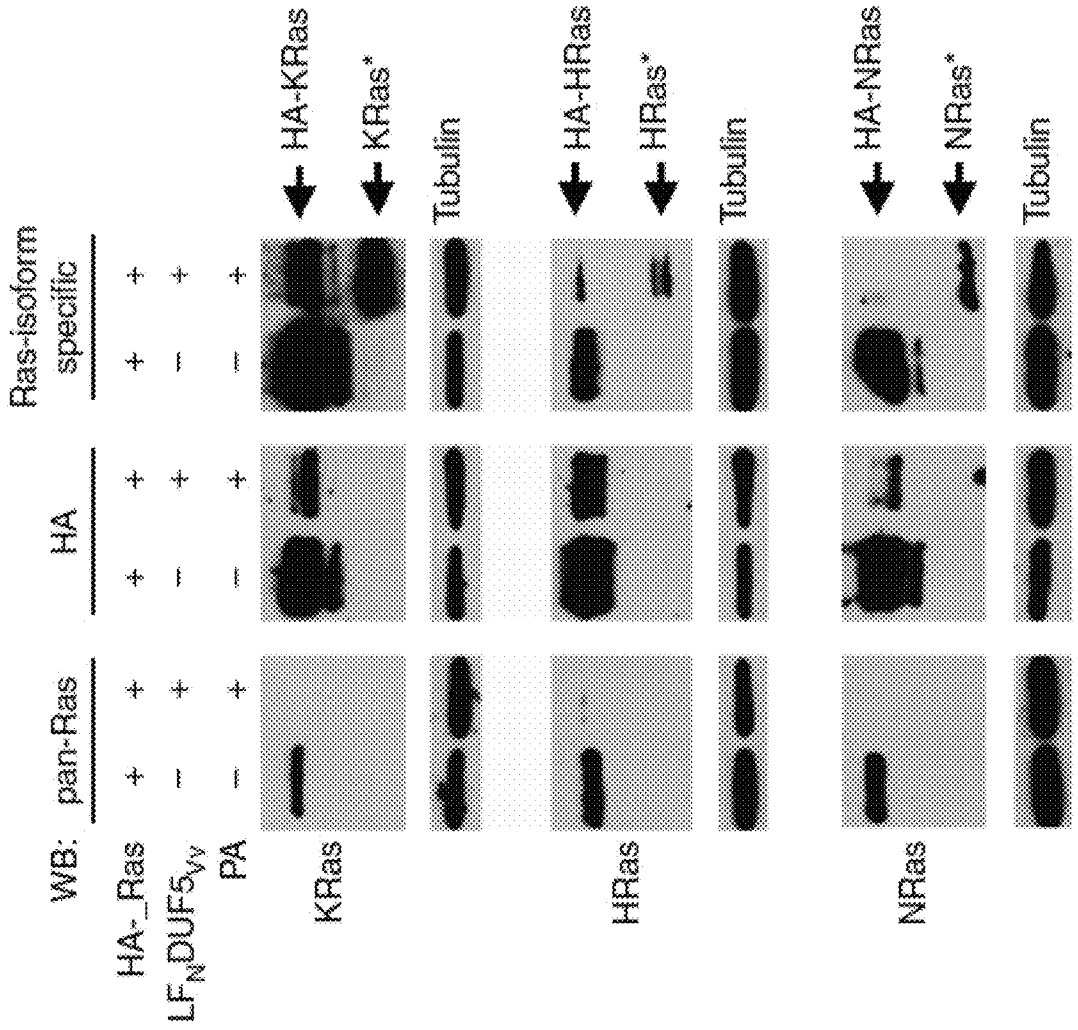

To verify that Ras is processed and to determine which isoforms of Ras are affected, cells were transfected to express HA-tagged KRas, NRas or HRas. In cells treated with $LFNDUF5_{Vv}$+PA, western blot analysis of whole-cell lysates showed that all three isoforms were cleaved at the N terminus. The anti-HA and RAS10 monoclonal antibodies directed against the N terminus did not detect KRas, NRas or HRas in treated cells, whereas isotype-specific antibodies directed against the C terminus detected the smaller processed forms (FIG. 25C). A reduction in the total protein detected by the isoform-specific antibodies was also observed. This suggests that subsequent to processing, the cleaved forms are degraded, especially for HA-NRas and HA-HRas. These data show that Ras isoforms are not modified by addition of moieties but are instead severed near the N terminus, which is a novel mechanism for Ras inactivation.

Recombinant $DUF5_{Vv}$ can Process all Ras Isoforms In Vitro.

Figure 25D:
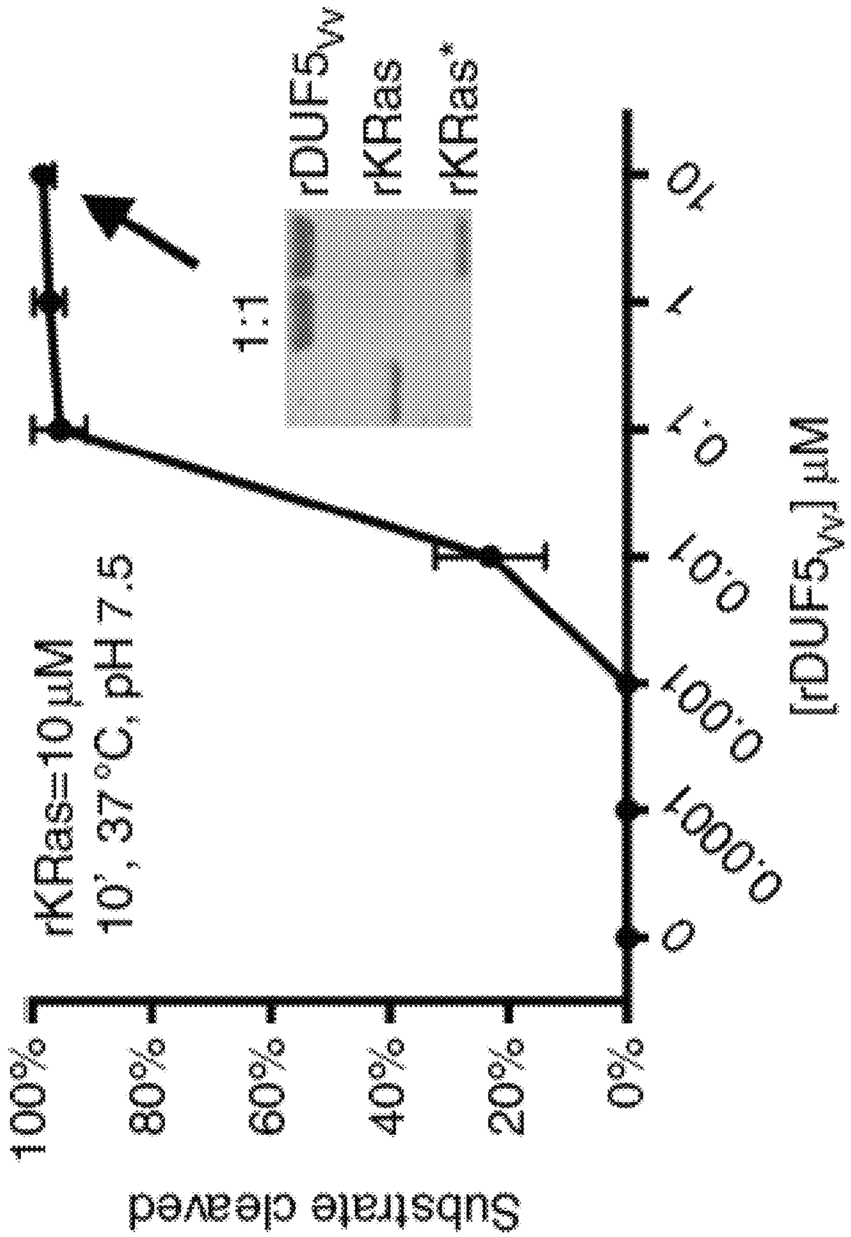
Figure 25E:
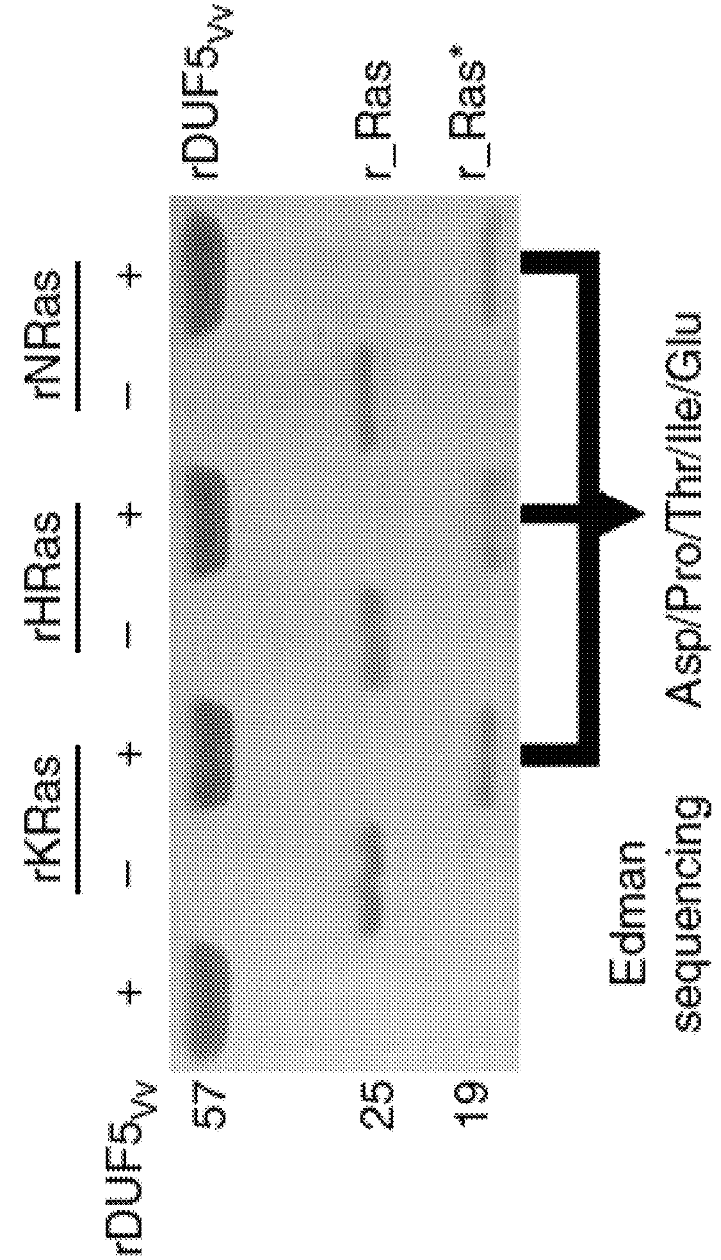

Two possible explanations of our results are that $DUF5_{Vv}$ activates a previously unknown cellular peptidase or functions as a Ras peptidase itself. To distinguish whether $DUF5_{Vv}$ directly catalyses proteolytic processing of Ras, recombinant 6×His-tagged $DUF5_{Vv}$ ($rDUF5_{Vv}$) and Ras isoforms (r_Ras) were expressed in *Escherichia coli* and purified. When mixed together for an in-vitro reaction, rKRas was efficiently cleaved within 10 min in a concentration-dependent manner (FIG. 25D). This reaction did not require addition of any other proteins or co-factors. rHRas and rNRas were likewise efficiently processed by purified $rDUF5_{Vv}$ (FIG. 25E).

Figure 25F:
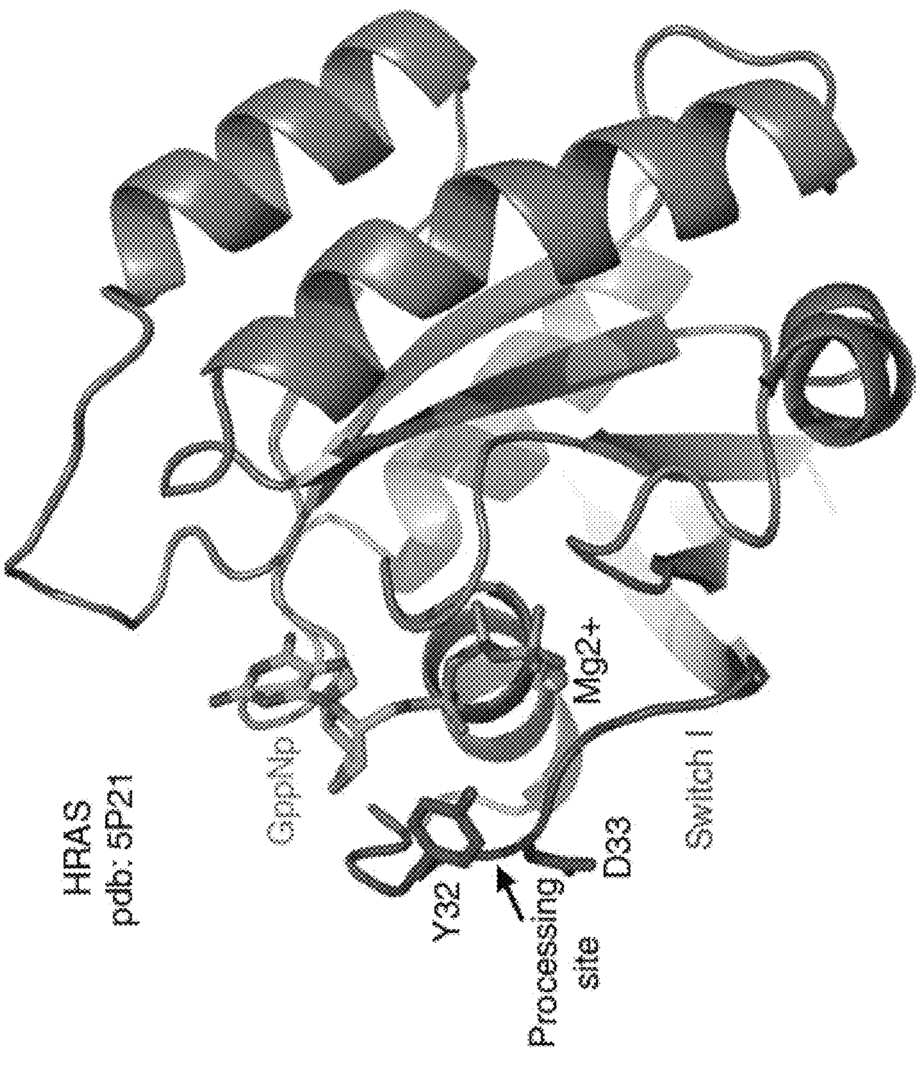

N-terminal sequencing of KRas, HRas and NRas cleaved products revealed that all Ras isoforms were identically cleaved between Y32 and D33 (FIG. 25F). These amino acids are found within the Ras Switch I region. Processing at this site would be expected to entirely abolish Ras signalling, as Y32 is required to orient and stabilize Switch I in the active (GTP-bound) state27. Cleavage within the Switch I region would further prevent the activation of downstream signalling cascades by disrupting the Ras effector protein interactions, thereby inhibiting activation of the ERK1/2 transcriptional regulator and decreasing cell proliferation[28-30].

Other DUF5 Homologues Cleave Ras.

Figure 26A:
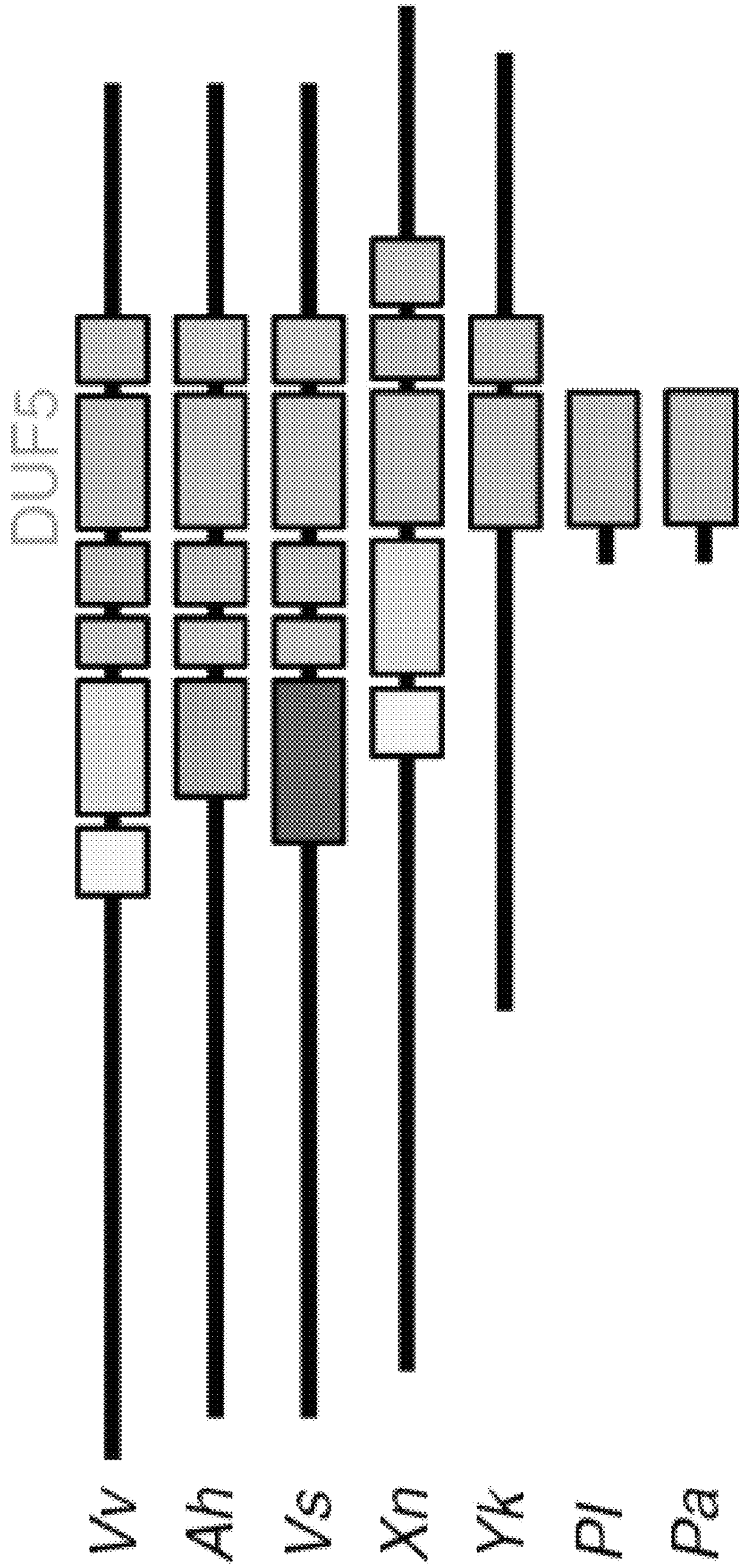
FIG. 26A, FIG. 26B, FIG. 26C, FIG. 26D, FIG. 26E and FIG. 26F illustrate DUF5 homologues and other GTPase substrates.
Figure 26B:
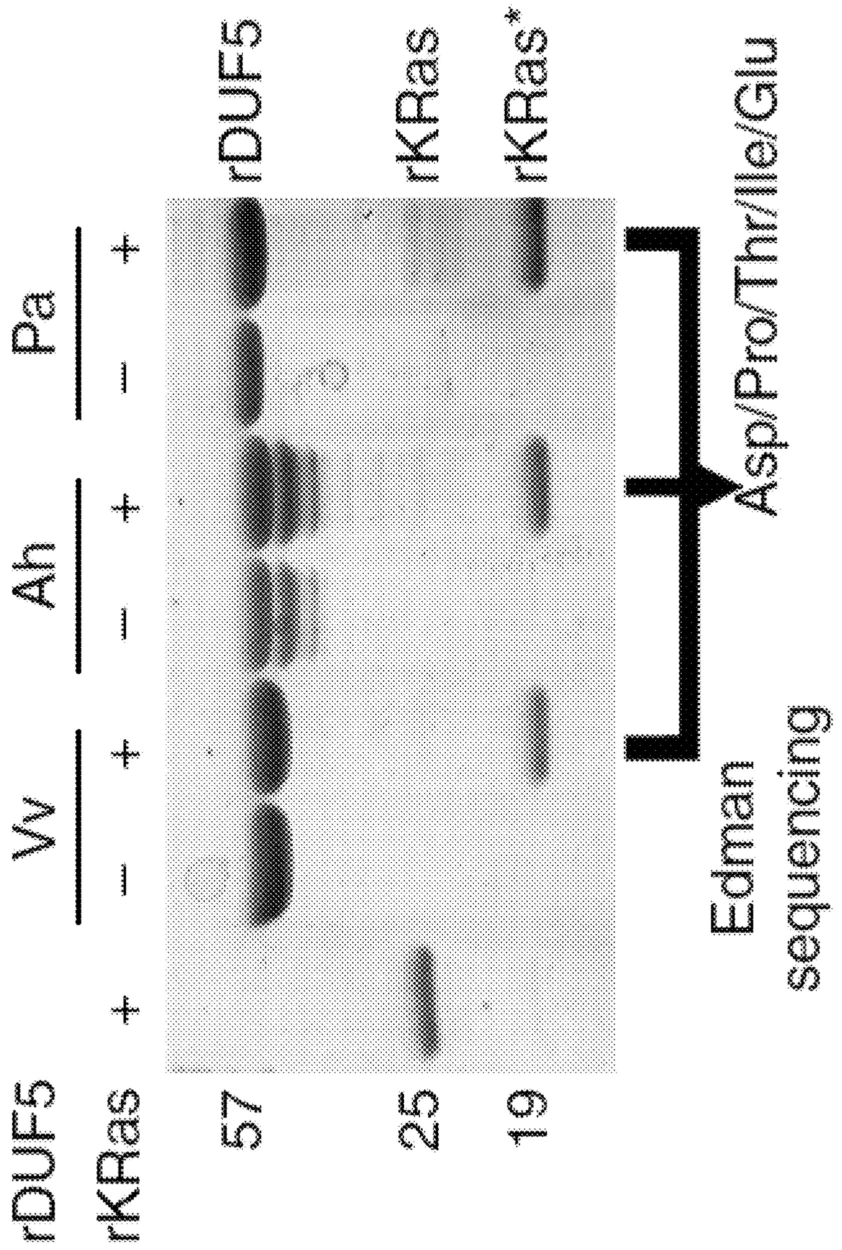
Figure 26C:
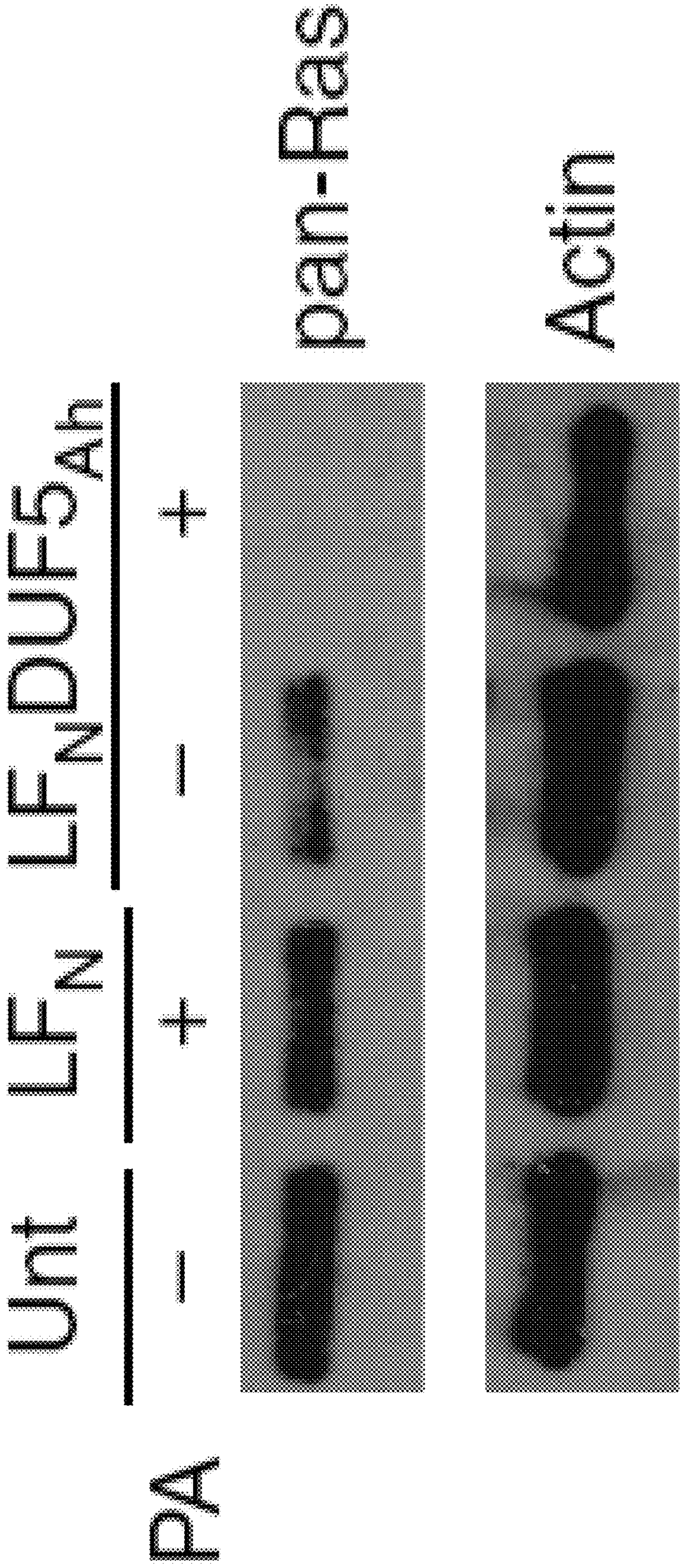

Domains similar to $DUF5_{Vv}$ have been identified in other bacterial species (FIG. 26A). To determine whether Ras processing is a conserved function among bacteria, the effector domain from the *Aeromonas hydrophila* MARTX toxin ($rDUF5_{Ah}$) and a hypothetical effector protein from insect pathogen *Photorhabdus asymbiotica* ($rDUF5_{Pa}$) were also purified and tested for proteolytic activity. Both proteins were found to cleave rKRas in vitro with cleavage occurring between Y32 and D33 (FIG. 26B). As further validation, $DUF5_{Ah}$ was fused to LFN ($LFNDUF5_{Ah}$). This protein induced both cytotoxicity and Ras cleavage in intoxicated cells when delivered to cells by PA (FIG. 26C). Thus, DUF5 represents a new family of bacterial toxin effectors that catalyses site-specific processing of the Switch I region of all three major isoforms of Ras independently of any other cellular proteins.

Rap1 is Also a Substrate for $DUF5_{Vv}$.

Figure 26D:
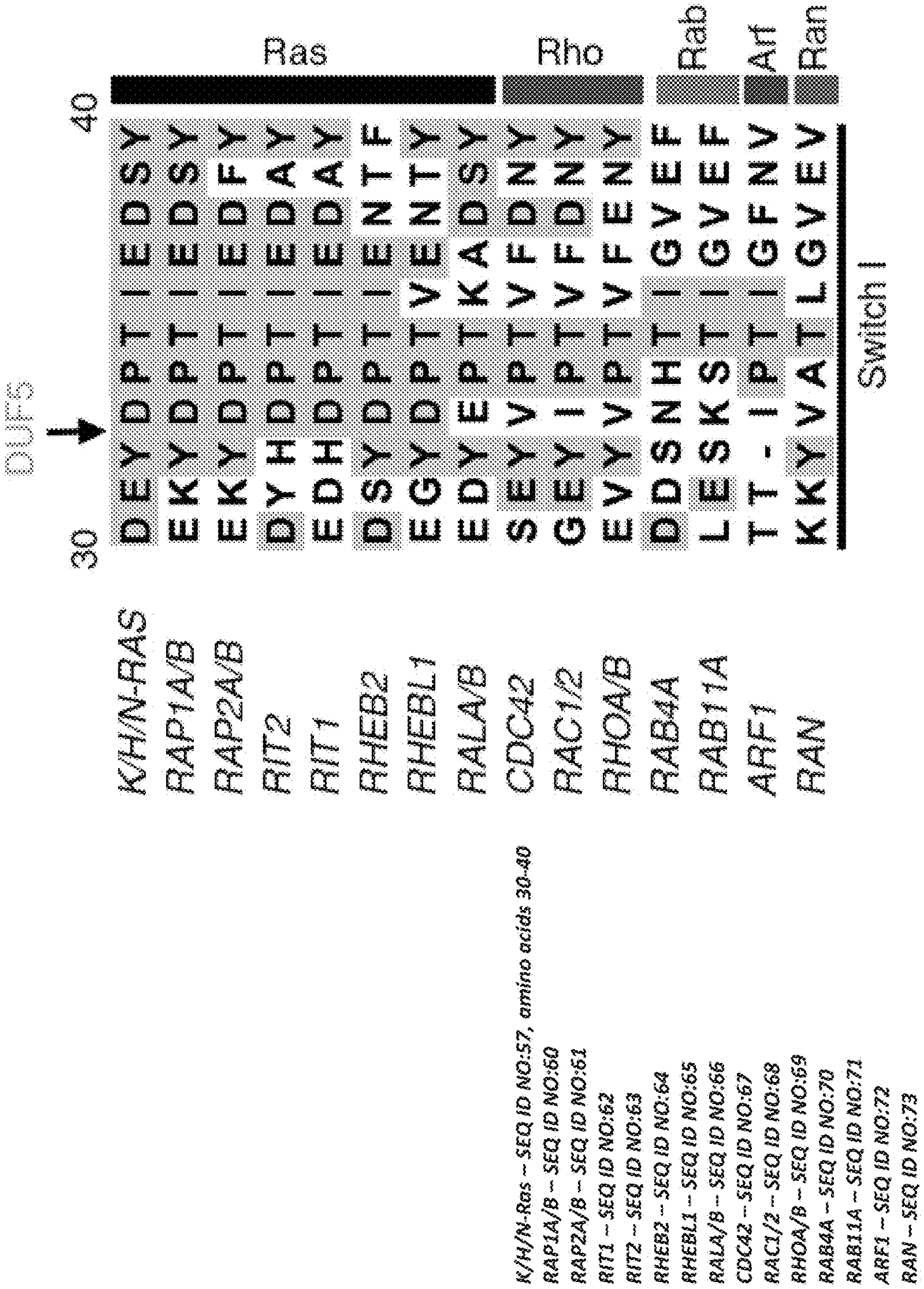
Figure 26E:
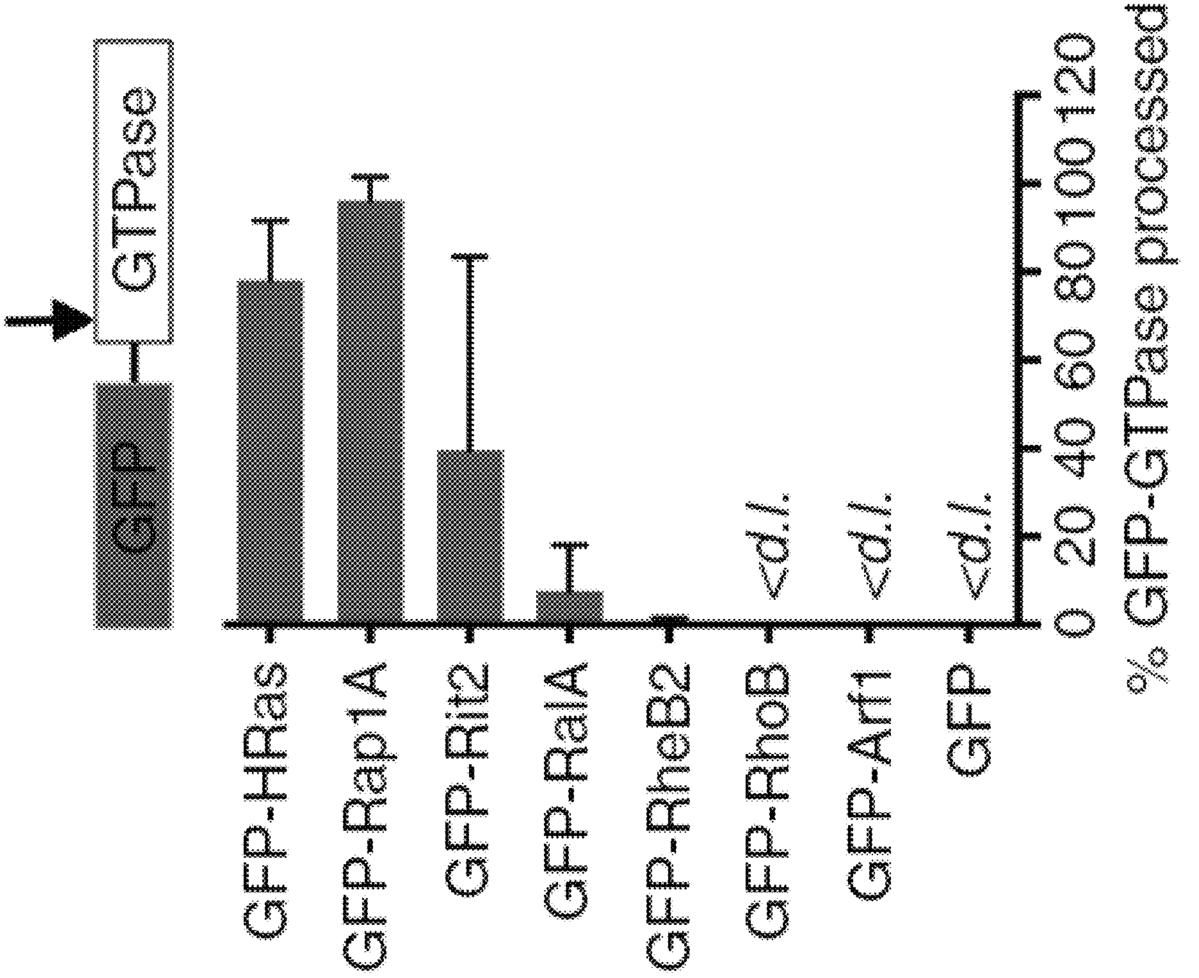
Figure 32:
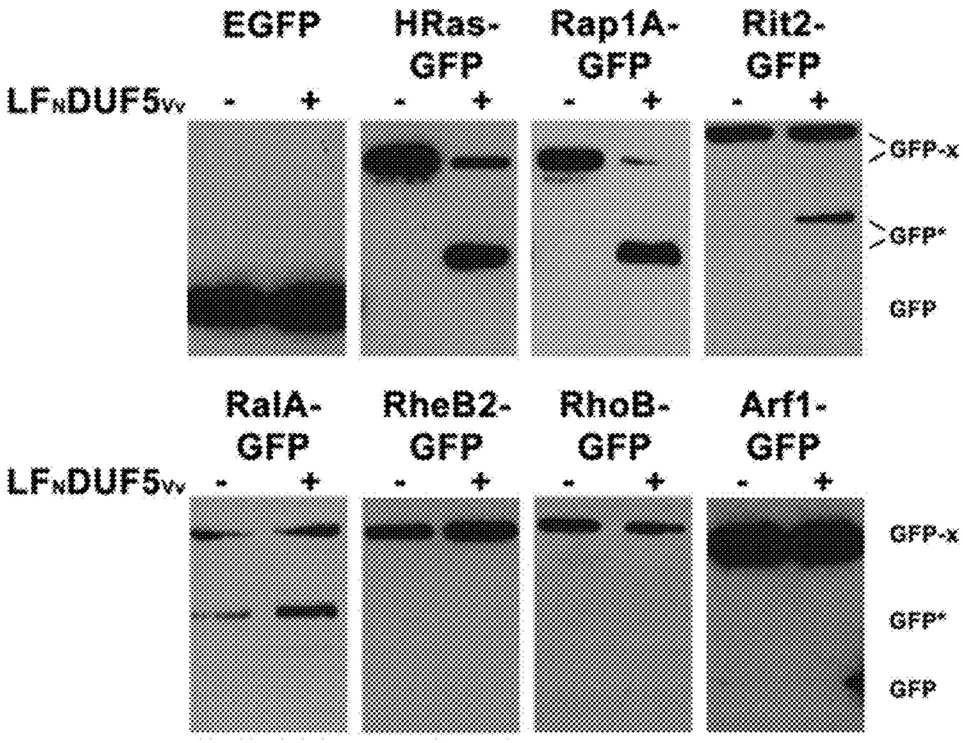
FIG. 32. DUF5Vv specificity against GFP-tagged small GTPases. HEK 293T cells transfected to express small GTPases with N-terminal EGFP-fusion as indicated were either untreated (−) or intoxicated with LFNDUF5Vv in combination with PA (+) for 24 h, at which time cell lysates were probed with anti-EGFP antibody. For triplicate blots, GFP* and GFP-x bands were quantified by Image J 1.64 and percent cleavage determined as GFP*/(GFP*+GFP-x). For FIG. 26, samples were normalized to untreated cells to account for closely sized non-specific bands or natural breakdown. Raw pixel data is shown in table.

Other bacterial protein toxins are known to promiscuously target a wide range of small GTPases and other cellular proteins[15]. As the amino acid sequence of the Switch I region of Ras is well conserved across Ras subfamily members (FIG. 26D), it was considered that DUF5$_{Vv}$ might also cleave other small GTPases. To test this, representative Ras subfamily small GTPases fused via their N termini to enhanced GFP (EGFP) were ectopically expressed in HEK 293T cells and anti-GFP antibody was used to detect the released N-terminal fragment. In cells treated with LF$_N$DUF5$_{Vv}$+PA, EGFP-HRas and EGFP-Rap1 were both cleaved with 480% efficiency. Processing of another Ras subfamily member, Rit2, was also detected in this assay, but with inconsistent efficiency, resulting in a large s.d. across multiple experiments (FIG. 26E). This indicates that Rit2 may be a low-affinity substrate resulting in experimental variation dependent on the ratio of toxin to GFP-Rit2 in each cell or sample (FIG. 26E). Other small EGFP-GTPases (RalA, RheB2, RhoB and Arf1) showed no cleavage, indicating they are not in-vivo substrates (FIG. 26E and FIG. 32).

Figure 26F:
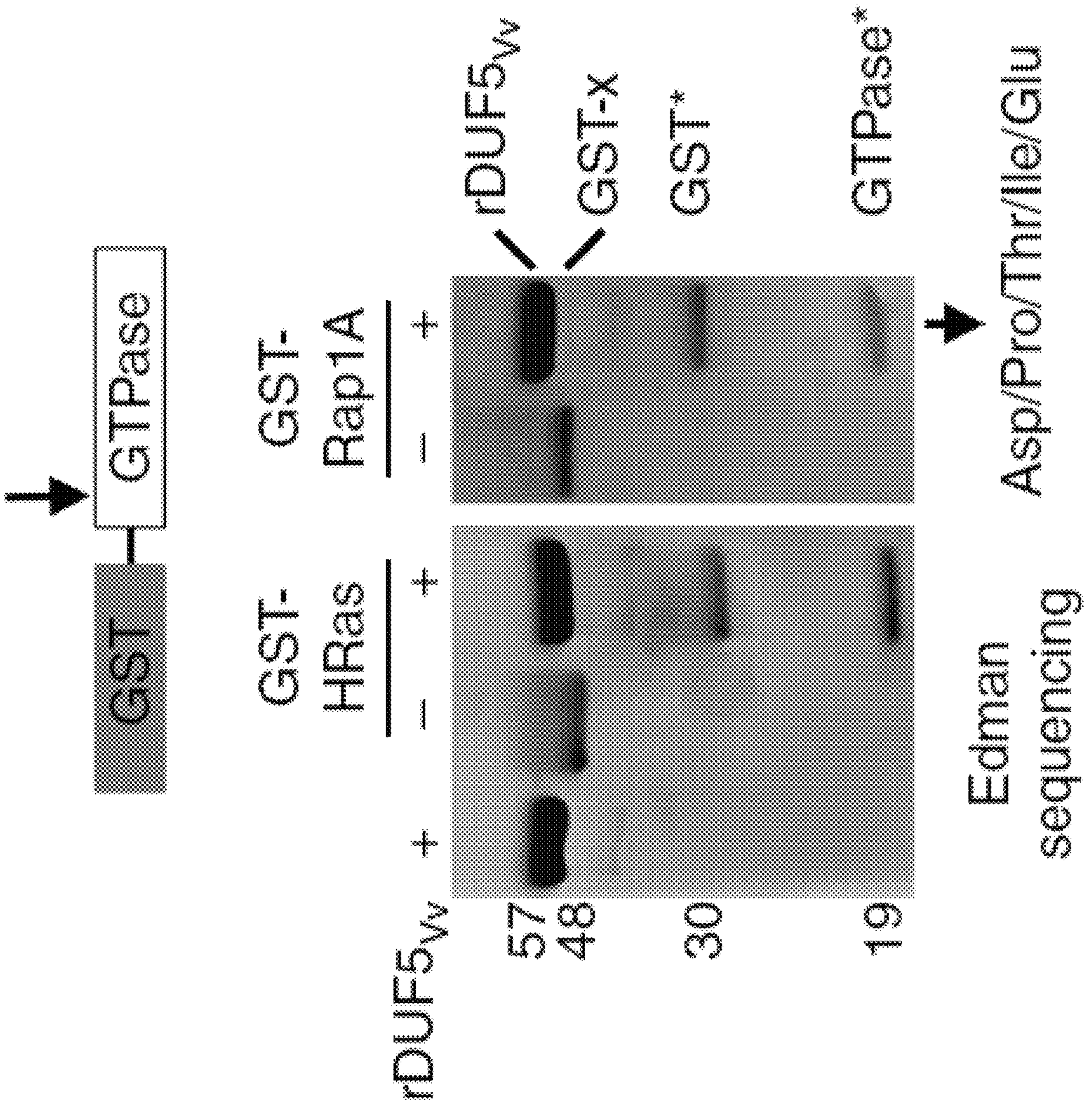
Figure 33:
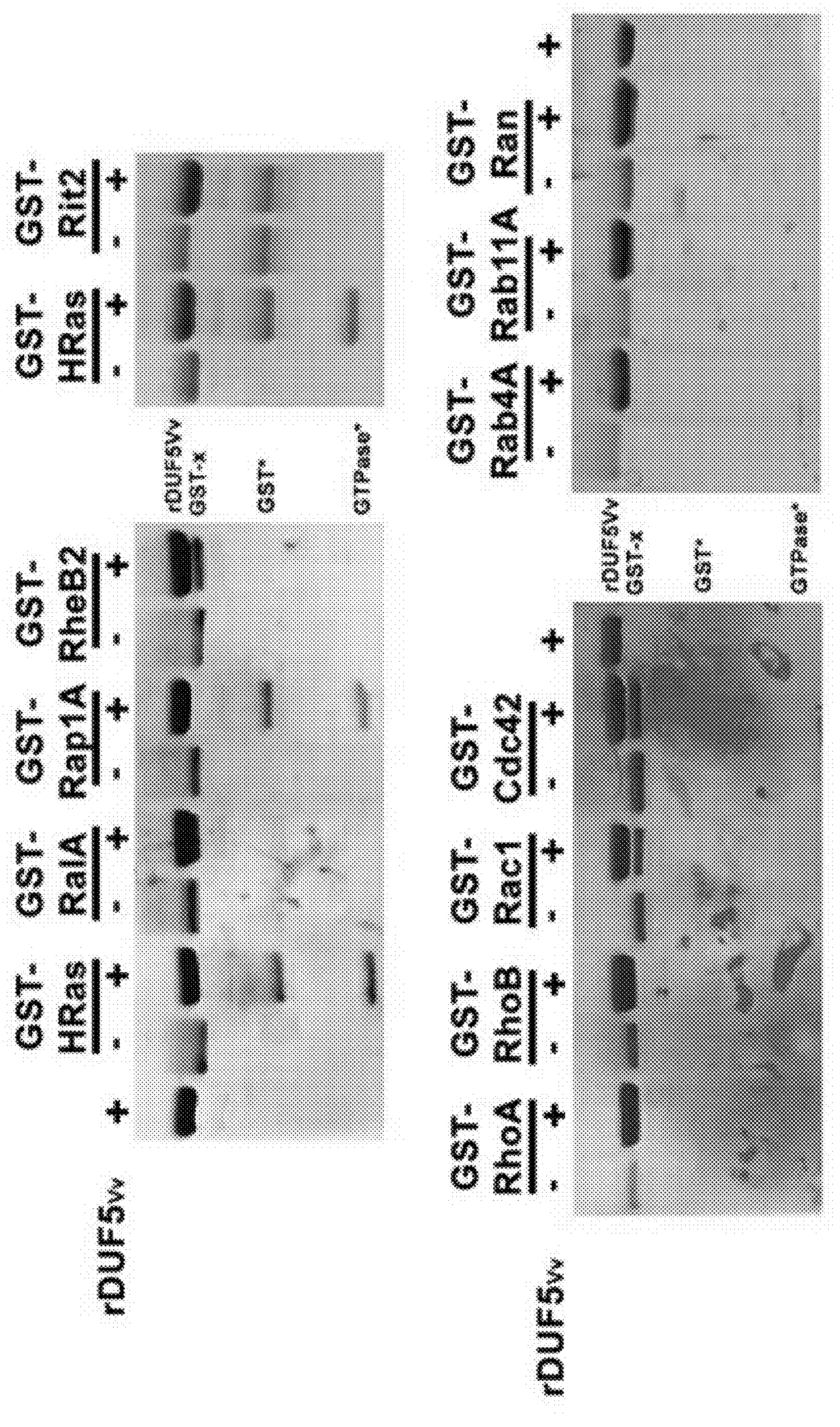
FIG. 33. DUF5Vv specificity against GST-tagged small GTPases. In vitro processing of 10 μM purified small GTPases with N-terminal fusion of GST (GST-x) to two fragments (GST* and GTPase*) by 10 μM rDUF5Vv for 10 min. This extended FIG. shows representative data (n=3). Only the positive samples, HRas and Rap1A, are duplicated in FIG. 26F.

DUF5$_{Vv}$ specificity for Ras and Rap1 was further verified biochemically. Small Ras GTPases covering the diversity of Ras subfamilies were purified as substrates for in-vitro assay to assess whether rDUF5$_{Vv}$ could catalyse their cleavage. Among the 11 GTPases tested (FIG. 33), only Rap1 was confirmed as a DUF5$_{Vv}$ substrate, with cleavage occurring after Y32 (FIG. 26F), whereas Rit2 was not cleaved at all, confirming that in cells this is a low-affinity substrate (FIG. 33). Other GTPases belonging to the Ras, Rho, Rab and Ran subfamilies were not processed (FIG. 33). Thus, DUF5$_{Vv}$ is a specific protease that preferably cleaves Ras and Rap1 without cellular cofactors. The detection of Rap1 as an additional substrate is especially interesting for bacterial pathogenesis, as Rap1 activates ERK in response to bacterial components other than lipopolysaccharide and is critical for macrophage phagocytosis31,32.

DUF5$_{Vv}$ Targets Ras During Bacterial Infection.

Figure 27A:
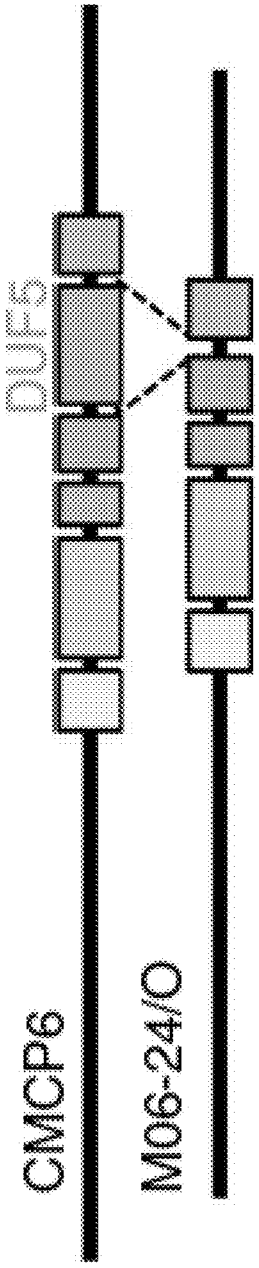
FIG. 27A, FIG. 27B, FIG. 27C and FIG. 27D illustrate $DUF5_{Vv}$ during bacterial infection and as a potential treatment of malignancies.
Figure 34:
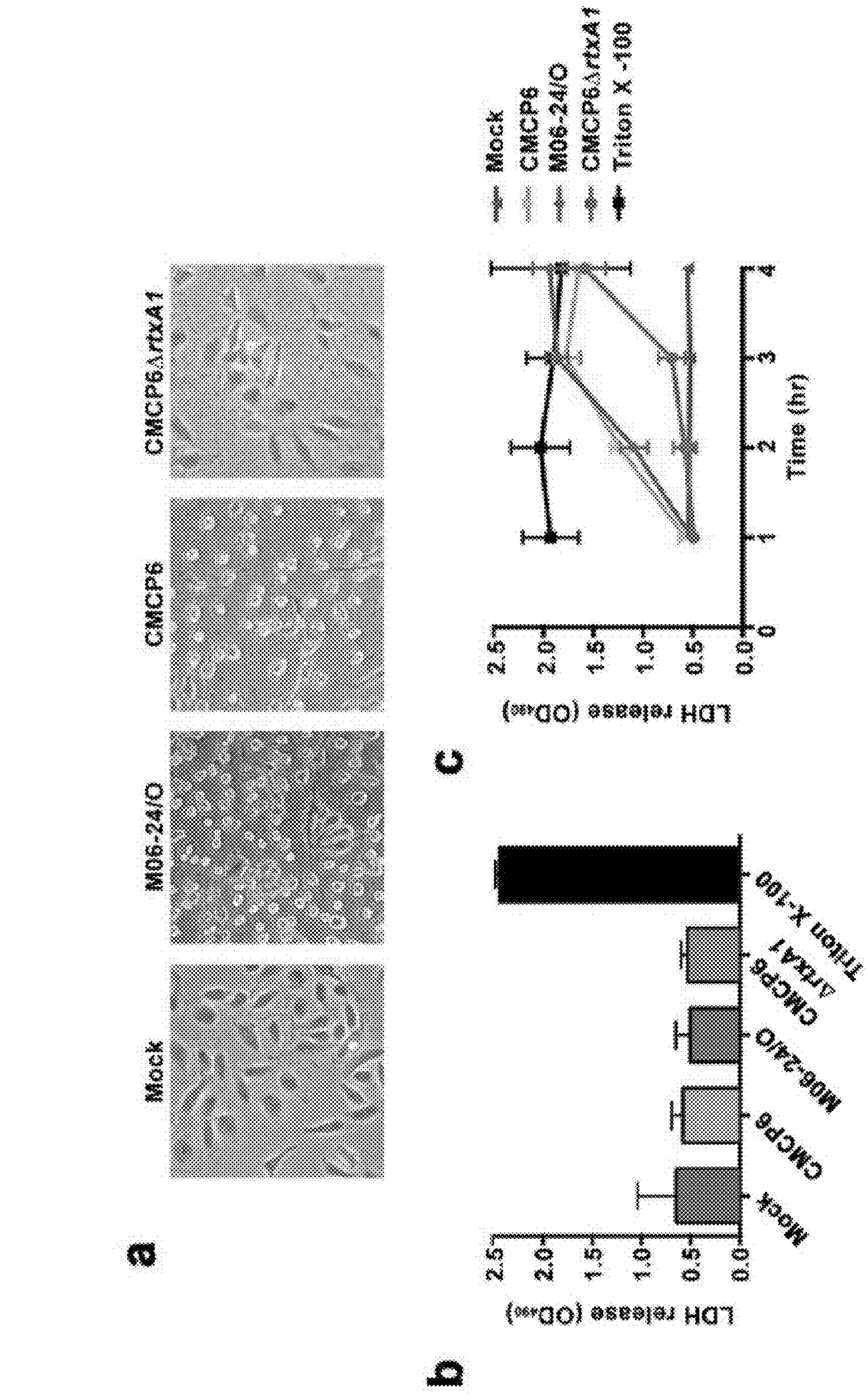
FIG. 34A, FIG. 34B, and FIG. 34C illustrate HeLa cell rounding and lysis due to *V. vulnificus*. *V. vulnificus* MARTX toxins have distinct compositions dependent upon the strain isolate, as shown in FIG. 27. Representative (n=3) phase images of cell rounding (FIG. 34A) and LDH release (FIG. 34B) induced after 60 min co-incubation of bacteria as indicated with HeLa cells, at which point cells were collected for detection of Ras and pERK in FIG. 27.

Given the importance of Ras and Rap1 in the host response to bacterial infection, it is not surprising that DUF5$_{Vv}$ was previously shown to contribute to *V. vulnificus* virulence[19]. The strain CMCP6 produces a MARTX toxin that carries five effector domains, including DUF5$_{Vv}$ in the fifth position. By contrast, M06-24/O produces a toxin with only four effector domains (FIG. 27A), having undergone a genetic recombination that resulted in an in-frame deletion of the DNA sequence for the DUF5$_{Vv}$ domain[19,33]. As a result of the loss of DUF5$_{Vv}$, M06-24/O is tenfold less virulent than CMCP6 (ref. 19). The increased virulence of CMCP6 was found to be specifically due to DUF5$_{Vv}$ 19, even though both toxin forms induce cellular necrosis[34,35] (FIG. 34).

Figure 27B:
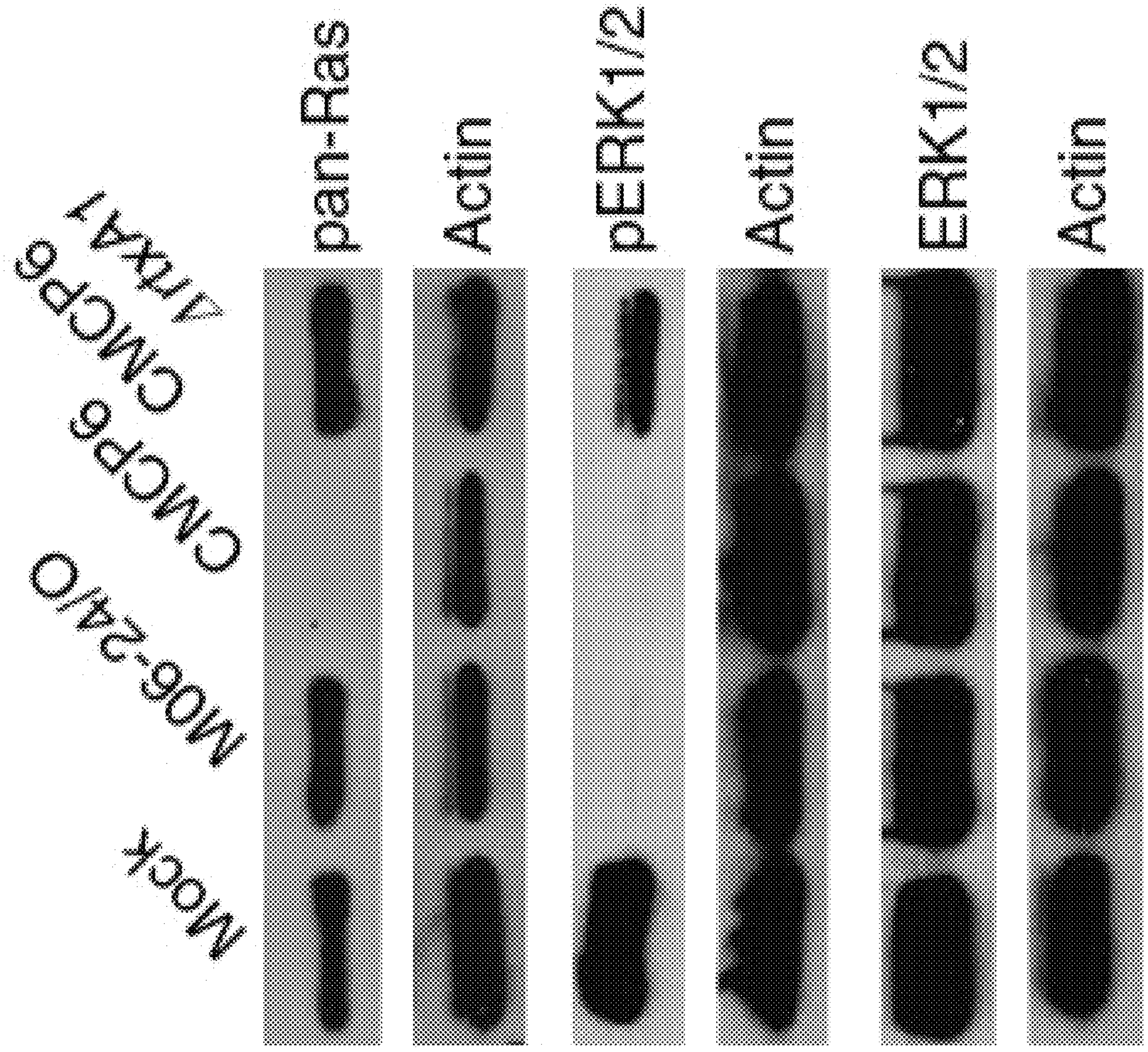

To link this defect in virulence to Ras activation and demonstrate that Ras can be processed during normal toxin delivery, HeLa cells were co-cultured for 1 h with *V. vulnificus* and proteins in cell lysates were analysed by western blotting. Cells treated with wild-type bacteria producing full-length active MARTX toxin no longer showed detectable Ras or pERK1/2. This inactivation was dependent on an intact rtxA1 toxin gene, as a null mutation in rtxA1 of *V. vulnificus* CMCP6 did not show loss of detectable Ras or pERK1/2. Further, co-culture of cells with *V. vulnificus* M06-24/O, which produces the MARTX toxin naturally missing DUF5$_{Vv}$, did not affect Ras, linking this MARTX-dependent activity specifically to the DUF5$_{Vv}$ effector domain. Interestingly, cells treated with M06-24/O unexpectedly still showed a reduction of pERK1/2, revealing that these multifunctional toxins probably have redundant strategies to inactivate ERK during infection (FIG. 27B).

Oncogenic KRas is Processed by DUF5$_{Vv}$.

Point mutations resulting in constitutive activation of Ras have long been associated with many different types of adenocarcinomas[5-7]. The discovery of a novel bacterial toxin mechanism to halt cell proliferation through processing of Ras is not only important for understanding the function of bacterial toxins during infection but also presents an opportunity to potentially target Ras during carcinogenesis through delivery of DUF5. This strategy would be most successful if mutant forms of Ras found in cancer cells are also DUF5 substrates.

Figure 27C:
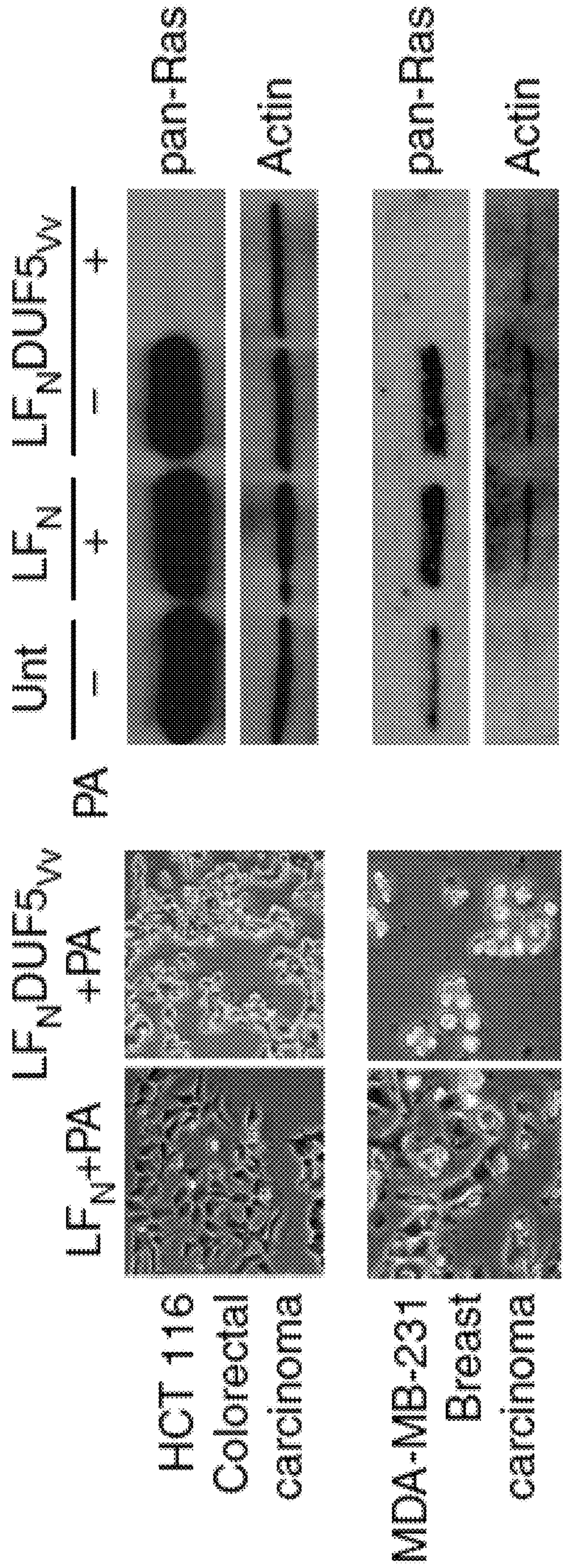
Figure 35:
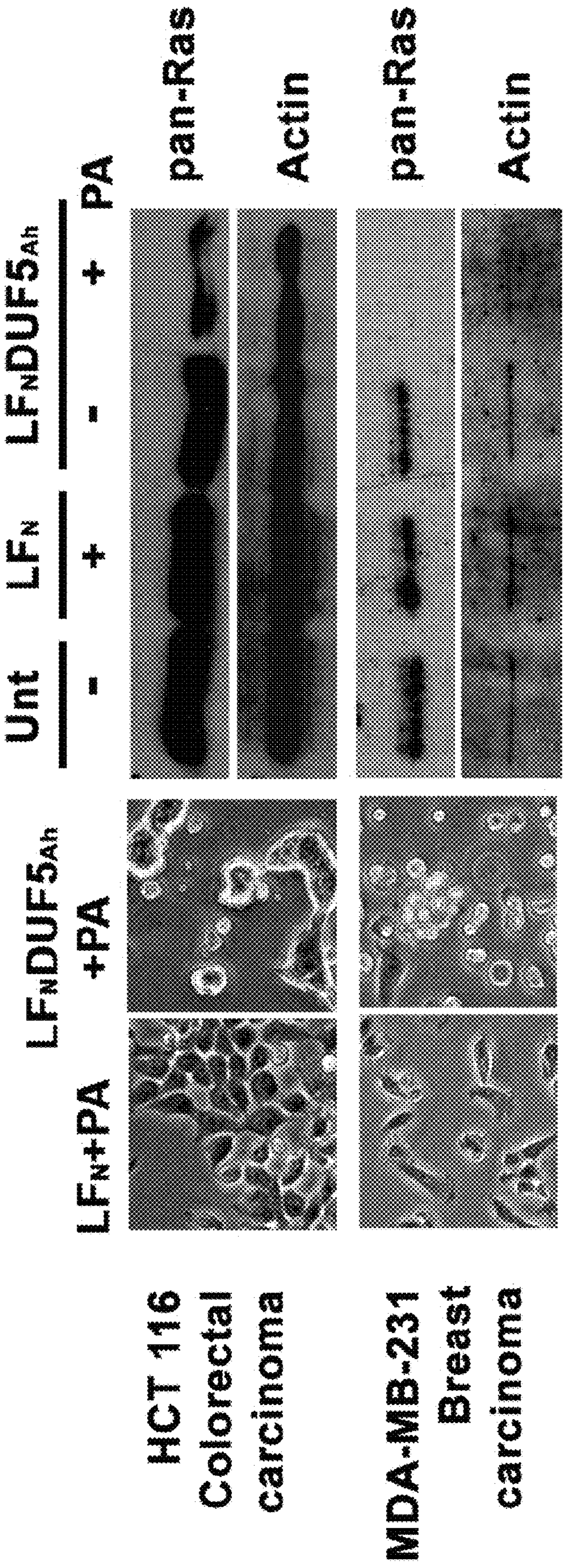
FIG. 35. Malignant cells are affected by DUF5Ah from *A. hydrophila*. Phase images and immunoblot detection of Ras from HCT116 and MDA-MB-231 treated as indicated for 24 h.

When HCT116 colorectal carcinoma cells, which express KRas with a G13D mutation, were intoxicated with PA in combination with LFNDUF5$_{Vv}$ (FIG. 27C) or LFNDUF5$_{Ah}$ (FIG. 35), significant cell morphological changes were observed and Ras was undetectable by western blotting. Similar results were obtained with the breast cancer cell line MDA-MB-231 that likewise carries the KRas G13D mutation. This cell line also contains a G464V mutation in B-Raf36, an effector of both Ras and Rapt (ref 37), demonstrating that DUF5$_{Vv}$ can effectively intoxicate cells even if they have additional activating mutations downstream of Ras and Rap1.

Figure 27D:
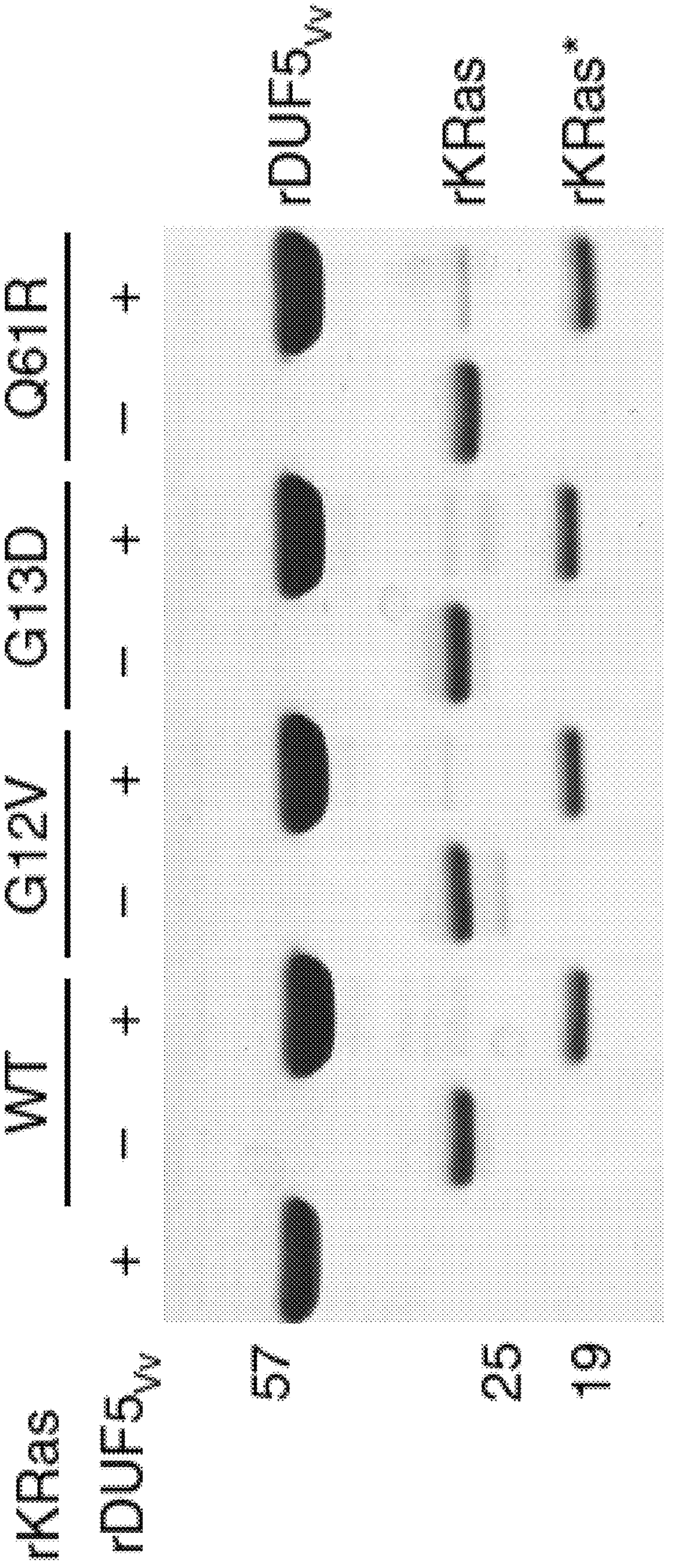
Figure 28A:
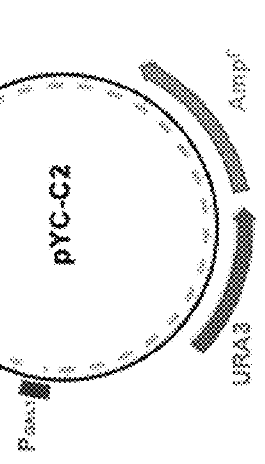
FIG. 28A, FIG. 28B, FIG. 28C, and FIG. 28D illustrate a schematic summary of yeast deletion screen.
Figure 28B:
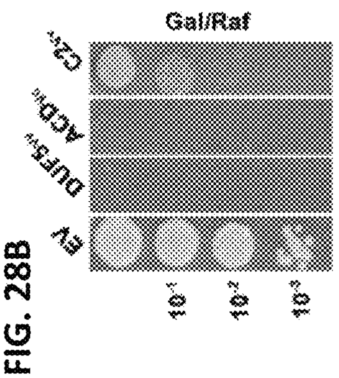
Figure 28C:
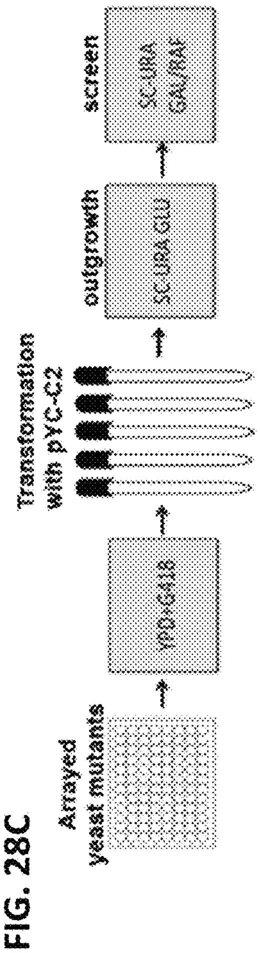
Figure 28D:
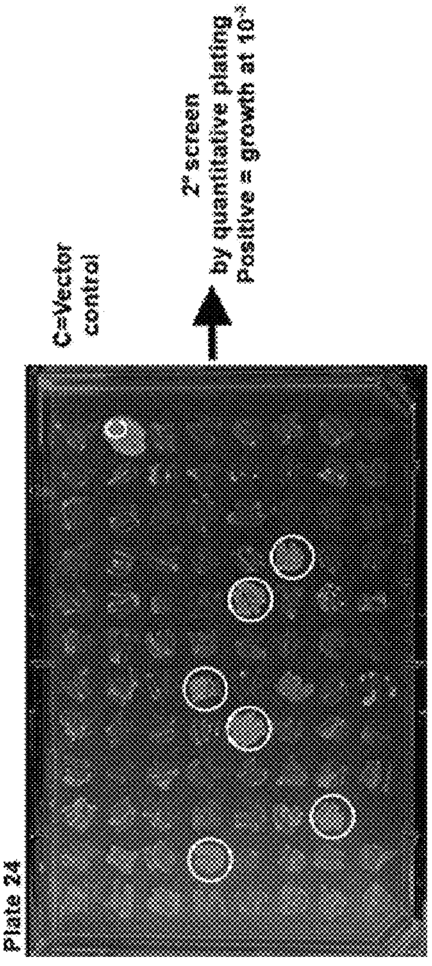

As further demonstration that DUF5$_{Vv}$ could be employed as a cancer treatment, rKRas was modified to carry three of the most common Ras mutations associated with tumorigenesis: G12V, G13D or Q61R7. All three mutant forms of KRas were confirmed as in vitro substrates for rDUF5$_{Vv}$-dependent site-specific processing (FIG. 27D). Thus, the ability of DUF5$_{Vv}$ to cleave KRas is unaffected by the most common RAS mutations. Overall, these data show that cells carrying constitutively active forms of Ras are not protected from DUF5$_{Vv}$ cytotoxicity and thus DUF5$_{Vv}$ is a valid candidate for use as an anti-tumour agent.

Discussion

MARTX toxins are large bacterial toxins that carry multiple effector domains, each with a specific enzymatic activity. DUF5$_{Vv}$, the extra effector domain of the MARTX toxin from the most virulent strains of the sepsis-causing pathogen *V. vulnificus*, was previously shown to be highly cytotoxic for mammalian cells, although the mechanism of this cytotoxicity was unknown[20]. In this work, we demonstrate that DUF5$_{Vv}$ is a representative member of a new family of bacterial toxin effectors that catalyse site-specific processing of the Switch I region of Ras and Rap1. Activated Ras or Rap1 would normally interact with downstream effectors such as c-Raf, to stimulate the phosphorylation of ERK1/2. In particular, Y32 in the Switch I region plays an important role in stabilizing the GTP-bound form of Ras and its interaction with the Raf kinases[27]. Thus, it is predicted that DUF5$_{Vv}$ cleavage between Y32 and D33 would destabilize the Switch I and presumably the interactions of Ras and Rap1 with their binding partners. As Ras and Rap1 form parallel pathways that relay signals from surface receptors and guanine nucleotide exchange factors to activate ERK1/2, disabling both small GTPases simultaneously nullifies all downstream signaling pathways[38], resulting in the complete loss of pERK1/2 in DUF5$_{Vv}$-treated cells. In the context of bacterial infection, this is important to inactivate innate immune responses, accounting for the direct linkage of this toxin effector domain to virulence of *V. vulnificus*. We propose that the DUF5 effector domain be renamed RRSP for Ras/Rap1-specific protease, acknowledging its site-specific processing of the Switch I region of Ras and Rap1.

As small GTPases are responsible for regulating essential cell functions, many other bacterial protein toxins and effectors target GTPases by posttranslational modification or by manipulating Q3 their function[15]. However, few of these toxins target Ras specifically, for example, *Pseudomonas aeruginosa* ExoS ADP ribosylates R41 of Ras and Rap[39-41], and thereby directly inhibits phagocytosis in mice[42]. However, ExoS also has broad substrate recognition including other GTPases[43] and other proteins such as moesin and vimentin[16,44,45]. Similarly, *Clostridium sordellii* lethal toxin TcsL (also known as LT) has been shown to glucosylate Ras at T35 in the Switch I[46,47] resulting is cellular apoptosis[48]. In addition, TcsL UDP-glucosylates other small Ras, Rap, Ral, Rho and Rac GTPases with some specificity differences depending on strain[49]. Through a similar process, *Clostridium perfringens* large toxin TpeL modifies T35 of Ras and, to a lesser extent, Rap1 and possibly Rac1, except it preferentially uses UDP-Nacetylglucosamine as a sugar donor[50,51].

The unique feature of RRSP demonstrated here is its irreversible mechanism of action by cleaving rather than modifying Ras and Rap1. The biochemical basis for the specificity of RRSP for Ras and Rap1 should be explored further in the future. Although it is possible that the specificity is dictated by the conservation of the amino acid sequence in the Ras and Rap1 Switch I regions, it is more likely to be that recognition of the target is multifactorial depending on a multifaceted protein-protein interaction between RRSP and Ras or Rap1. This possibility is supported by studies of *Clostridium difficile* toxin TcdB recognition of RhoA as a substrate for glucosylation, which is mediated in part by specificity for target residue T37 in the Switch I region[52], but also by Ser73 outside the Switch I[53]. In addition, amino acids of TcdB essential to discriminate substrate are found outside the catalytic site, further indicating that specificity of TcdB from Rho in not driven solely by the Switch I sequence[54].

In addition to protein-protein interactions, specificity of RRSP for Ras and Rap1 may include spatial localization to anionic membranes or specificity for the active or inactive state conformation when bound to GTP or GDP, respectively. However, in cells, we routinely observed 100% processing of all Ras isoforms in as little as 30 min and we also observed 100% cleavage of KRas G12V, G13D and Q61R in vitro, despite not controlling the GTP or GDP state using buffers. These data would seem to support the hypothesis that RRSP can target both active and inactive forms of Ras and thereby access both membrane and cytoplasmic pools of Ras. In addition, as the Switch I region undergoes structural changes with activation state, and both active and inactive forms of Ras seem to be substrates for RRSP, we suppose specificity is at least in part driven by protein-protein interaction outside the Switch I region and this will be explored in the future through detailed structural and binding studies.

A critical question for bacterial infection is how the processing of Ras and Rap1 contributes to increased virulence. The MARTX toxin of *V. vulnificus* is known to play a role during infection both in paralysing phagocytic cells[55] and in breaching the epithelial barrier to promote spread of the bacterium from the intestine to other organs[56-58]. Overall, small GTPases play a central role in the barrier function of epithelial layers such that loss of this control could contribute to bacterial spread across the intestinal barrier[15]. In particular, Ras and Rap1 are essential for sensing and signalling pathogen-associated molecular patterns and for regulating inflammatory responses of the host organism[15,59]. Ras and Rap1 function in response to bacterial components such as LPS and for macrophage phagocytosis, activating the ERK1/2 Q4 pathway cascade[31,32]; in the context of bacterial infection, inhibition of these cascades would slow down the host response to bacterial infection, such that *V. vulnificus* strains that carry this domain are more virulent[19].

A final impact of our discovery is the possibility that the RRSP effector domain could be deployed across the cell membrane to specifically target tumour cells using different delivery strategies. More than three decades after the discovery of Ras implication in cancer development, targeting Ras remains one of the hardest challenges of cancer research and drug discovery[7]. Here, we propose that proteins in this new RRSP effector family could be employed immediately as research tools, but in the future developed as new anti-cancer therapeutic agents. Of particular immediate interest, re-engineered PA selectively targeting cancer cells could be used to deliver LFNDUF5 into cells to destroy Ras and thereby deregulate tumour growth and proliferation. This approach has already been validated in cell systems in which PA was fused to the epidermal growth factor for delivery of LFN-tethered cargo into cancer cells with upregulated expression of the epidermal growth factor receptor[60]. This system has also been proven with PA modified to bind to the HER2 receptor, a protein strongly upregulated in tumour cells, in particular breast cancer[61]. As alternative future approaches, RRSP effector domains could be fused to specific antibodies for use as an immunotoxin[62], or expressed and delivered by *Salmonella* bacteria that home to solid tumours[63]. It could also be expressed by viruses engineered to specifically infect cancer cells[64]. The ability of RRSP to cleave both normal and mutant forms of Ras indicates that any developed reagent could be successful whether used for Ras cancers, non-Ras cancers, or other Ras-associated diseases.

Methods

General Molecular Biology Techniques.

*E. coli* DH5a and TOP10 cells (Life Technologies) were grown at 37° C. in Luria-Bertani liquid or on agar medium supplemented with either 100 μg $ml^{-}1$ ampicillin or 50 μg $ml^{-}1$ kanamycin, as needed. Common reagents were obtained from Sigma-Aldrich, Fisher or VWR, and common restriction enzymes and polymerases were obtained from New England Biolabs or Life Technologies. Custom DNA oligonucleotides were purchased from Integrated DNA Technologies (Coralville, IA). Plasmids were prepared by alkaline lysis followed by precipitation in ethanol or purified using Epoch spin columns according to the manufacturer's recommended protocol. A Qiagen Midi Prep kit was used for preparation of plasmids used in yeast transformations. Plasmids were introduced into *E. coli* by electroporation and into HeLa cells by transfection using polyethylenimine (PEI).

Yeast Non-Essential Gene Deletion Screen.

The Life Technologies YKO yeast deletion library covering all non-essential genes was replicated from stocks at the Northwestern University High Throughput Analysis Laboratory using a Genetix QPixII Automatic colony picker. Each strain from the library was subsequently grown in 1 ml yeast extract peptone dextrose with addition of 50 ug ml 1 G418. After overnight growth at 30° C. with agitation, each strain was transformed with plasmid pYC-C2 using a PLATE solution method and transformants were selected on synthetic complete agar without uracil and with 2% glucose to repress $DUF5_{Vv}$-C2 expression. Colonies were patched with toothpicks onto synthetic complete agar supplemented with 2% galactose and 1% raffinose to induce $DUF5_{Vv}$-C2 expression. Initial positive selection was defined as yeast that formed a patch when grown on galactose. These were subsequently rescreened in a dilution plating assay as previously described[20] and those with a plating efficiency comparable to a strain transformed with empty vector were considered validated hits. Identified strains were analysed and classified based on information in the Saccharomyces Genome Database website, last accessed on 25 Oct. 2014.

Intoxication of Cells with Proteins Fused to $LF_N$.

HeLa, HCT116 and HEK293 cells were grown at 37° C. with 5% $CO_2$ in DMEM medium (Life Technologies) with 10% fetal bovine serum (Gemini Bio-Products, West Sacramento, CA), 100 Uml 1 penicillin and 1 μg $ml^{-}1$ streptomycin. Purification of LFN, LFNDUF5$_{Vv}$ and LFNDUF5$_{Ah}$ has been previously described20. PA purified as previously described[65] was provided by Shivani Agarwal (Northwestern University). Cell lines were seeded overnight into tissue culture-treated dishes and flasks, except for HCT116 cells, which were seeded for 48 h. Before intoxication, the media was exchanged for fresh media and then 7 nM PA and 3 nM LFN-tagged toxins were added to the media and incubated for the times indicated in the legend at 37° C. with 5% $CO_2$. Cells were imaged at ×10 at times indicated in the legend using a Nikon TS Eclipse 100 microscope equipped with a Nikon CoolPix 995 digital camera or processed for western blotting or colony formation as detailed below.

Western Blotting.

A total of 2.5-5×$10^4$ treated cells were washed with PBS, then resuspended in 120 ml of 2× Laemmli sample buffer and boiled for 10 min. Ten microlitres of lysate were separated by SDS-PAGE and transferred to nitrocellulose (Amersham) using the Bio Rad Trans-Blot Turbo system. Nitrocellulose membranes were blocked overnight at 4° C. in 5% (w/v) powdered milk diluted in Trisbuffered saline containing 0.001% Tween-20 (TBS-T). Immunodetection of proteins was conducted as previously described[20], using primary antibodies purchased from Cell Signaling Technologies (p44/42 MAPK (ERK1/2) rabbit mAb 137F5 (1:1,000), phospho-p44/42 (ERK1/2) rabbit mAb 197G2 (1:1,000), p38 MAPK rabbit polyclonal 9212 (1:1,000) and phospho-p38 rabbit mAb 12F8 (1:1,000)), EMD Millipore (pan-Ras mouse mAb RAS10 (05-516, 1:1,000)), Thermo Scientific (HRas PAS-22392 (1:1,000), KRas PAS-27234 (1:1,000) and NRas PAS-28861 (1:1,000)) and Sigma-Aldrich (H6908 rabbit polyclonal (1:5,000), actin mouse mAb AC-40 (1:1, 000) and Tubulin T6074, (1:10,000)). Antibody binding to proteins was detected using anti-mouse (1:5,000) or anti-rabbit (1:5,000) secondary antibodies conjugated to horseradish peroxidase from Jackson Immuno Research and developed using SuperSignal WestPico chemiluminescent reagents (Thermo Scientific) and X-ray film. For serial detection of proteins and detection of the actin-loading controls from the same nitrocellulose membrane, membranes were washed in TBS-T for 10 min and then stripped of antibody by washing the membrane for 10 min with stripping buffer (1.5% glycine, 1% Tween-20, 0.1% SDS). After two more 10-min washes with TBS-T, the membrane was re-probed for other proteins. Tubulin-loading controls were performed by cutting the membrane horizontally to separate the upper loading control portion containing tubulin from the lower portion containing the small Ras family GTPases. Uncropped western blottings are not shown but are provided herein but are provided in the Supplementary Material for Antic, I., et al., Site-specific processing of Ras and Rap1 Switch I by a MARTX toxin effector domain. Nat Commun, 2015. 6: p. 7396, which is incorporated herein by reference in its entirety.

Ras G-LISA.

Active (GTP-bound) Ras in intoxicated cells was measured using the Ras G-LISA activation colorimetric assay kit from Cytoskeleton, Inc. (Denver, CO). HeLa cells were seeded into 10-$cm^2$ tissue culture-treated dishes and grown to ~80% confluency, at which time the cells were intoxicated with $LF_N$ proteins in combination with PA for 24 h as described above. Cells were collected in the lysis buffer and total protein content was determined by the Precision Red assay using reagents supplied with the kit. The lysate was frozen in a dry ice-ethanol bath and stored at 80° C. Active Ras in each lysate was then determined according the manufacturer's protocol. This kit used the pan-Ras RAS10 mAb for detection of active Ras and this antibody was subsequently obtained directly from Millipore for western blotting detection of Ras as described above.

Clonogenic Colony-Formation Assay.

A total of $10^5$ HeLa cells were seeded into six-well dishes overnight, intoxicated with LFN protein as described above and assessed by a clonogenic colony-formation assay as described previously[66]. Briefly, cells were released from wells with 0.25% trypsin/EDTA (Sigma), counted in a hemocytometer and then diluted. The number of cells indicated was replated in fresh media in duplicate. After 14 days, cells were fixed with 70% ethanol and stained with 0.5% crystal violet, and colonies of more than 50 cells were counted. The surviving fraction was compared with cells treated with LFN+PA.

Ectopic Expression of HA-Tagged Ras Isoforms.

Plasmids for ectopic expression of HA-HRas (pcDNA3-HA-HRas wt, 14723) and HA-NRas (pCGN NRas wt, 39503) were obtained from Addgene (Cambridge, MA). Plasmids for overexpression of HA-KRas and HA-KRas G12V were obtained from Athanasios Vassilopoulos (Northwestern University). Plasmid DNA (2 mg) was mixed with 90 ml PEI diluted in incomplete DMEM media, vortexed 15 times and then incubated for 15 min at room temperature. Seven hundred microlitres of complete DMEM were added into the plasmid-PEI mix and the whole volume was added to HeLa cells. After 24 h, cells were intoxicated as described above.

Immunoprecipitation of HA-HRas and mass spectrometry.

HeLa cells, either untreated or intoxicated with $LF_N$DUF5$_{Vv}$+PA as described above, were washed with cold PBS and then resuspended in RIPA buffer (50 mM Tris-HCl pH 7.5, 150 mM NaCl, 0.1% SDS, 0.5% sodium deoxycholate, 1% Triton and 'cOmplete' protease inhibitors). HeLa cell lysates were incubated with 50 ml of anti-HA agarose beads (Sigma) for 2 h at 4° C. under mild agitation. Beads were then washed five times with 500 ml of RIPA buffer and five times with 500 ml of washing buffer (50 mM Tris-HCl pH 7.5, 150 mM NaCl). Proteins bound to the beads were eluted with 3M sodium thiocyanate buffer (50 mM Tris-HCl pH 7.5, 150 mM NaCl). Elution fractions were analysed by SDS-PAGE followed by Coomassie staining or immunoblotting using anti-HA and isotype-specific anti-HRas antibody as described above. The smaller HRas band was excised from the gel, put in water and then frozen for shipping. Trypsin digestion followed by liquid chromatography—tandem mass spectrometry on the Thermo LTQ-FT Ultra spectrophotometer was conducted at the University of Illinois at Chicago Mass Spectrometry, Metabolomics and Proteomics Facility according to their standard protocols.

Preparation of 6×his- or GST-Tagged Small GTPases.

DNA sequences corresponding to KRas (KRas4B, NP_004976.2), HRas (NP_001123914.1) and Q5 NRas (NP_002515.1) genes were amplified from templates as described above, using primers designed for ligation-independent cloning, and the products were cloned into the pMCSG7 expression vector by ligation-independent cloning[67]. The G12V, G13D and Q61R mutations were introduced by site-directed mutagenesis using the pMCSG7-KRas vector as a template. Primers are listed in the Table 2 below:

TABLE 2

| Oligonucleotides Used in this Example | |
|---|---|
| DUF5 VV FWD | TACTTCCAATCCAATGCTCAAGAGCTGAAAGAAAG AGCAAAAG (SEQ ID NO: 37) |
| DUF5 VV REV | TTATCCACTTCCAATGCTACAAACTGCCCTTGAAC GTG (SEQ ID NO: 38) |
| DUF5 AH FWD | TACTTCCAATCCAATGCTCCGGGCAAAACGGTGGT GACG (SEQ ID NO: 39) |
| DUF5 AH REV | TTATCCACTTCCAATGCTAGACATCGGCGTACTCG ACCCGC (SEQ ID NO: 40) |
| DUF5 PA FWD | TACTTCCAATCCAATGCTCCATTACTCCATGACCT CATCACC (SEQ ID NO: 41) |
| DUF5 PA REV | TTATCCACTTCCAATGCTACACATCATCATAACAC TTGCG (SEQ ID NO: 42) |
| KRAS FWD | TACTTCCAATCCAATGCTATGACTGAATATAAACT TGTGGTAGTTGGAGCTGG (SEQ ID NO: 43) |
| KRAS REV | TTATCCACTTCCAATGCTACATAATTACACACTTT GTCTTTGACTTCTTTTTCTTC (SEQ ID NO:44) |
| HRAS FWD | TACTTCCAATCCAATGCTATGACGGAATATAAGCT GGTGGTGGTG (SEQ ID NO: 45) |
| HRAS REV | TTATCCACTTCCAATGCTAGGAGAGCACACACTTG CAGCTC (SEQ ID NO: 46) |
| NRAS FWD | TACTTCCAATCCAATGCTATGACTGAGTACAAACT GGTGGTGG (SEQ ID NO: 47) |
| NRAS REV | TTATCCACTTCCAATGCTACATCACCACACATGGC AATCCC (SEQ ID NO: 48) |
| EGFPC3-GST FWD | GCTTCGAATTCTGCACCCGGGTGGTCTGGTTCCGC GTGGA (SEQ ID NO: 49) |
| EGFPC3-GST REV | CTAGATCCGGTGGATCCCCTCAGTGGTGGTGGTGG TGGTGC (SEQ ID NO: 50) |
| KRAS_G13D FWD | TAGTTGGAGCTGGTGACGTAGGCAAGAGTGC (SEQ ID NO: 51) |
| KRAS_G13D REV | GCACTCTTGCCTACGTCACCAGCTCCAACTA (SEQ ID NO: 52) |
| KRAS_Q61R FWD | GATATTCTCGACACAGCAGGTAGAGAGGAGTACAG TGCAATG (SEQ ID NO: 53) |
| KRAS_Q61R REV | CATTGCACTGTACTCCTCTCTACCTGCTGTGTCGA GAATATC (SEQ ID NO: 54) |

Plasmids were confirmed to be accurate by DNA sequencing and then transformed into *E. coli* BL21(DE3). Cultures of *E. coli* were grown at 25° C. in Terrific Broth supplemented with 100 μg ml$^{-}$1 ampicillin to an OD600 of 0.6-0.7 and then induced with 1 mM isopropyl-β-D-thiogalactoside and growth was continued at 18° C. for ~18 h. Bacteria were harvested by centrifugation, re-suspended in buffer A1 (50 mM Tris pH 7.5, 500 mMNaCl, 10 mM MgCl2, 0.1% Triton X-100, 5 mM β-mercaptoethanol) and lysed by sonication. After centrifugation at 30,000 g for 30 min, the soluble lysate was loaded onto a 5-ml HisTrap column using the ÄKTA protein purification system (GE Healthcare). The column was washed with buffer B1 (10 mM Tris pH 7.5, 500 mM NaCl, 10 mM MgCl2, 50 mM imidazole) followed by elution in the same buffer with 500 mM imidazole (buffer C1). Proteins were further purified by size-exclusion chromatography (Superdex 200 (26/60), GE Healthcare) in buffer D1 (10 mM Tris-HCl pH 7.5, 500 mM NaCl, 10 mM MgCl2, 5 mMb-mercaptoethanol). GST-fusion GTPases were obtained from Seema Mattoo (Purdue University, IN), and expressed and purified as previously reported68.

Preparation of 6×His-Tagged DUF5 Proteins.

DNA sequences corresponding to DUF5$_{Vv}$ (*V. vulnificus* CMCP6—MARTX$_{Vv}$ Q3596-L4089, NP_759056.1), DUF5$_{Ah}$ (*A. hydrophila* ATCC7966—MARTXAh P3069-V3570—locus WP_011705266) and DUF5$_{Pa}$ (*P. asymbiotica* ATCC43949—P41-V532 locus WP_011705266) were amplified from their respective genomes using primers designed for ligation-independent cloning and the products were cloned into the pMCSG7 expression vector by ligation-independent cloning[67]. Primers are listed in Supplementary Table 1. Plasmids were confirmed to be accurate by DNA sequencing and then transformed into *E. coli* BL21(DE3). Cultures were grown in Terrific Broth supplemented with 100 μg ml$^{-1}$ ampicillin at 37° C. until $OD_{600}$=0.7-0.8 and then induced with 1 mM isopropyl-β-D-thiogalactoside at 18° C. for ~18 h. Proteins were purified as described above for Ras proteins, except all buffers were adjusted to pH 8.3 instead of 7.5.

In-Vitro Cleavage Assay and N-Terminal Sequencing.

rKRas, rHRas, rNRas and GST-fused small GTPases were incubated with rDUF5 proteins at equimolar concentrations (10 mM) in 10 mM Tris pH 7.5, 500 mM NaCl, 10 mM MgCl2 at 37° C. for 10 min, unless otherwise indicated. Reactions were stopped by adding 6× Laemmli sample buffer and incubating the sample at 90° C. for 5 min. Proteins were separated on 18% SDS-polyacrylamide gels and visualized using Coomassie stain. Cleavage of Ras isoforms and GTPases was quantified from scanned gels using NIH Image J 1.64. To identify the cleavage site, proteins separated by 18% SDS-polyacrylamide were transferred onto a polyvinylidene difluoride membrane. After Coomassie staining, processed bands were excised from the membrane and sequenced on an ABI 494 Procise Protein Sequencer (Applied Biosystem) using automated Edman degradation at the Tufts University Core Facility.

In-Vivo Cleavage Assay of Small GTPases.

DNA sequences coding for HRas, Rap1A, Rit2, RalA, Rheb2A, RhoB and Arf1 were amplified from plasmids for overexpression of GST-GTPases as described above68. Products were inserted into pEGFP-C3 (Clontech) using SmaI and the Gibson Assembly Cloning Kit (NEB). HEK 293T cells were transfected with the resulting plasmids as described above. After 24 h, cells were intoxicated with $LF_N$ proteins and cleavage detected using monoclonal GFP-HRP antibody (Miltenyi Biotec) as described above. The amount of cleaved protein as a percent of total GFP protein was quantified from scanned gels using NIH Image J 1.64 and data were normalized to the pixels detected in the absence of intoxication.

Bacterial Challenge of HeLa Cells.

*V. vulnificus* rifampicin-resistant isolates of strains CMCP6, M06-24/O and CMCP6DrtxA1 (ref. 19) were grown at 30° C. in Luria-Bertani medium with 50 μg ml$^{1}$ rifampicin. Overnight cultures were diluted 1:500 and grown at 30° C. with shaking until the $OD_{600}$ reached 0.55-0.6. Bacteria from 1 ml were pelleted at 1,800 g for 4 min, washed once in PBS and then resuspended in 1 ml PBS. Media were exchanged over 5×10$^{4}$ HeLa cells previously seeded in 12-well plates overnight for antibiotic-free media. *V. vulnificus* in PBS (multiplicity of infection=100) or an equal volume of buffer was added to media over cells and plates were centrifuged at 25° C. for 5 min at 500 g. After 60 min, cells were photographed as described above, to assess rounding before collection of lysate and western blotting of proteins in 15 ml of lysate as described above. In a separate set of experiments, cells in phenol red-free DMEM with 10% fetal bovine serum but no antibiotics were incubated up to 4 h. At 1-h intervals, 50 ml of supernatant were sampled and assayed for release of lactate dehydrogenase using the Cytotox 96 Non-Radioactive Cytotoxicity Assay (Promega), according to the manufacturer's protocol. Percent cell lysis was calculated as the lactate dehydrogenase release in the sample divided by a positive control lysed with 0.1% Triton X-100.

REFERENCES

1. Santos, E. et al. Malignant activation of a K-ras oncogene in lung carcinoma but not in normal tissue of the same patient. Science 223, 661-664 (1984).
2. Malumbres, M. & Barbacid, M. RAS oncogenes: the first 30 years. Nat. Rev. Cancer 3, 459-465 (2003).
3. Cox, A. D. & Der, C. J. Ras history: the saga continues. Small GTPases 1, 2-27 (2010).
4. Young, A., Lou, D. & McCormick, F. Oncogenic and wild-type Ras play divergent roles in the regulation of mitogen-activated protein kinase signaling. Cancer Discov. 3, 112-123 (2013).
5. Vogelstein, B. et al. Cancer genome landscapes. Science 339, 1546-1558 (2013).
6. Prior, I. A., Lewis, P. D. & Mattos, C. A comprehensive survey of Ras mutations in cancer. Cancer Res. 72, 2457-2467 (2012).
7. Cox, A. D., Fesik, S. W., Kimmelman, A. C., Luo, J. & Der, C. J. Drugging the undruggable RAS: Mission Possible? Nat. Rev. Drug Discov. 13, 828-851 (2014).
8. Burns, M. C. et al. Approach for targeting Ras with small molecules that activate SOS-mediated nucleotide exchange. Proc. Natl Acad. Sci. USA 111, 3401-3406 (2014).
9. Khvalevsky, E. Z. et al. Mutant KRAS is a druggable target for pancreatic cancer. Proc. Natl Acad. Sci. USA 110, 20723-20728 (2013).
10. Ostrem, J. M., Peters, U., Sos, M. L., Wells, J. A. & Shokat, K. M. K-Ras(G12C) inhibitors allosterically control GTP affinity and effector interactions. Nature 503, 548-551 (2013).
11. Russo, M., Di Nicolantonio, F. & Bardelli, A. Climbing RAS, the everest of oncogenes. Cancer Discov. 4, 19-21 (2014).
12. Shima, F. et al. In silico discovery of small-molecule Ras inhibitors that display antitumor activity by blocking the Ras-effector interaction. Proc. Natl Acad. Sci. USA 110, 8182-8187 (2013).
13. David, M. D., Cochrane, C. L., Duncan, S. K. & Schrader, J. W. Pure lipopolysaccharide or synthetic lipid a induces activation of p21Ras in primary macrophages through a pathway dependent on Src family kinases and PI3K. J. Immunol. 175, 8236-8241 (2005).
14. Zeiser, J., Gerhard, R., Just, I. & Pich, A. Substrate specificity of clostridia! glucosylating toxins and their function on colonocytes analyzed by proteomics techniques. J. Proteome Res. 12, 1604-1618 (2013).
15. Aktories, K. & Schmidt, G. in Ras Superfamily Small G Proteins: Biology and Mechanisms 1. (ed. Wittinghofer, A.) 65-97 (Springer-Verlag Wein, 2014).
16. Simon, N. C., Aktories, K. & Barbieri, J. T. Novel bacterial ADP-ribosylating toxins: structure and function. Nat. Rev. Microbiol. 12, 599-611 (2014).
17. Satchell, K. J. Structure and function of MARTX toxins and other large repetitive RTX proteins. Annu. Rev. Microbiol. 65, 71-90 (2011).
18. Egerer, M. & Satchell, K. J. Inositol hexakisphosphate-induced autoprocessing of large bacterial protein toxins. PLoS Pathog. 6, e1000942 (2010).
19. Kwak, J. S., Jeong, H. G. & Satchell, K. J. *Vibrio vulnificus* rtxA1 gene recombination generates toxin variants with altered potency during intestinal infection. Proc. Natl Acad. Sci. USA 108, 1645-1650 (2011).
20. Antic, I., Biancucci, M. & Satchell, K. J. Cytotoxicity of the *Vibrio vulnificus* MARTX toxin effector DUF5 is linked to the C2A subdomain. Proteins 82, 2643-2656 (2014).
21. Geissler, B., Tungekar, R. & Satchell, K. J. Identification of a conserved membrane localization domain within numerous large bacterial protein toxins. Proc. Natl Acad. Sci. USA 107, 5581-5586 (2010).
22. Brothers, M. C. et al. Backbone and side-chain assignments of an effector membrane localization domain from *Vibrio vulnificus* MARTX toxin. Biomol. NMR Assign. 8, 225-228 (2014).
23. Cherry, J. M. et al. *Saccharomyces* genome database: the genomics resource of budding yeast. Nucleic Acid Res. 40, D700-D705 (2012).
24. Mendoza, M. C., Er, E. E. & Blenis, J. The Ras-ERK and PI3K-mTOR pathways: cross-talk and compensation. Trends Biol. Sci. 36, 320-328 (2011).
25. Eisenberg, S. et al. The role of palmitoylation in regulating Ras localization and function. Biochem. Soc. Trans. 41, 79-83 (2013).
26. Hamer, P. J. et al. Production and characterization of anti-RAS p21 monoclonal antibodies. Hybridoma 9, 573-587 (1990).
27. Buhrman, G., Holzapfel, G., Fetics, S. & Mattos, C. Allosteric modulation of Ras positions Q61 for a direct role in catalysis. Proc. Natl Acad. Sci. USA 107, 4931-4936 (2010).
28. Rubinfeld, H. & Seger, R. The ERK cascade: a prototype of MAPK signaling. Mol. Biotechnol. 31, 151-174 (2005).
29. Seger, R. & Krebs, E. G. The MAPK signaling cascade. FASEB J. 9, 726-735 (1995).
30. Spoerner, M., Herrmann, C., Vetter, I. R., Kalbitzer, H. R. & Wittinghofer, A. Dynamic properties of the Ras switch I region and its importance for binding to effectors. Proc. Natl Acad. Sci. USA 98, 4944-4949 (2001).
31. Caron, E., Self, A. J. & Hall, A. The GTPase Rap1 controls functional activation of macrophage integrin alphaMbeta2 by LPS and other inflammatory mediators. Curr. Biol. 10, 974-978 (2000).
32. Moon, E. Y. & Pyo, S. Lipopolysaccharide stimulates Epacl-mediated Rap1/NFkappaB pathway in Raw 264.7 murine macrophages. Immunol. Lett. 110, 121-125 (2007).
33. Roig, F. J., Gonzalez-Candelas, F. & Amaro, C. Domain organization and evolution of multifunctional autoprocessing repeats-in-toxin (MARTX) toxin in *Vibrio vulnificus*. Appl. Environ. Microbiol. 77, 657-668 (2011).
34. Liu, M., Alice, A. F., Naka, H. & Crosa, J. H. The HlyU protein is a positive regulator of rtxA1, a gene responsible for cytotoxicity and virulence in the human pathogen *Vibrio vulnificus*. Infect. Immun. 75, 3282-3289 (2007).

35. Lee, J. H. et al. Identification and characterization of the *Vibrio vulnificus* rtxA essential for cytotoxicity in vitro and virulence in mice. J. Microbiol. 45, 146-152 (2007).
36. Davies, H. et al. Mutations of the BRAF gene in human cancer. Nature 417, 949-954 (2002).
37. Okada, T. et al. The strength of interaction at the Raf cysteine-rich domain is a critical determinant of response of Raf to Ras family small GTPases. Mol. Cell. Biol. 19, 6057-6064 (1999).
38. Raaijmakers, J. H. & Bos, J. L. Specificity in Ras and Rap signaling. J. Biol. Chem. 284, 10995-10999 (2009).
39. Coburn, J. & Gill, D. M. ADP-ribosylation of p21ras and related proteins by *Pseudomonas aeruginosa* exoenzyme S. Infect. Immun. 59, 4259-4262 (1991).
40. Ganesan, A. K. et al. *Pseudomonas aeruginosa* exoenzyme S, a double ADPribosyltransferase, resembles vertebrate mono-ADP-ribosyltransferases. J. Biol. Chem. 274, 9503-9508 (1999).
41. Riese, M. J., Wittinghofer, A. & Barbieri, J. T. ADP ribosylation of Arg41 of Rap by ExoS inhibits the ability of Rap to interact with its guanine nucleotide exchange factor, C3G. Biochemistry 40, 3289-3294 (2001).
42. Rangel, S. M., Logan, L. K. & Hauser, A. R. The ADP-ribosyltransferase domain of the effector protein ExoS inhibits phagocytosis of *Pseudomonas aeruginosa* during pneumonia. mBio 5, e01080-e01014 (2014).
43. Fraylick, J. E., Rucks, E. A., Greene, D. M., Vincent, T. S. & Olson, J. C. Eukaryotic cell determination of ExoS ADP-ribosyltransferase substrate specificity. Biochem. Biophys. Res. Commun. 291, 91-100 (2002).
44. Maresso, A. W., Deng, Q., Pereckas, M. S., Wakim, B. T. & Barbieri, J. T. *Pseudomonas aeruginosa* ExoS ADP-ribosyltransferase inhibits ERM phosphorylation. Cell Microbiol. 9, 97-105 (2007).
45. Coburn, J., Dillon, S. T., Iglewski, B. H. & Gill, D. M. Exoenzyme S of *Pseudomonas aeruginosa* ADP-ribosylates the intermediate filament protein vimentin. Infect. Immun. 57, 996-998 (1989).
46. Just, I., Selzer, J., Hofmann, F., Green, G. A. & Aktories, K. Inactivation of Ras by *Clostridium sordellii* lethal toxin-catalyzed glucosylation. J. Biol. Chem. 271, 10149-10153 (1996).
47. Popoff, M. R. et al. Ras, Rap, and Rac small GTP-binding proteins are targets for *Clostridium sordellii* lethal toxin glucosylation. J. Biol. Chem. 271, 10217-10224 (1996).
48. Dreger, S. C. et al. Killing of rat basophilic leukemia cells by lethal toxin from *Clostridium sordellii*: critical role of phosphatidylinositide 3'-OH kinase/Akt signaling. Biochemistry 48, 1785-1792 (2009).
49. Genth, H. & Just, I. Functional implications of lethal toxin-catalysed glucosylation of (H/K/N)Ras and Rac1 in *Clostridium sordellii*-associated disease. Eur. J. Cell Biol. 90, 959-965 (2011).
50. Guttenberg, G. et al. Molecular characteristics of *Clostridium perfringens* TpeL toxin and consequences of mono-O-G1cNAcylation of Ras in living cells. J. Biol. Chem. 287, 24929-24940 (2012).
51. Pauillac, S. et al. Characterization of the enzymatic activity of *Clostridium perfringens* TpeL. Toxicon 75, 136-143 (2013).
52. Just, I. et al. Glucosylation of Rho proteins by *Clostridium difficile* toxin B. Nature 375, 500-503 (1995).
53. Jank, T., Pack, U., Giesemann, T., Schmidt, G. & Aktories, K. Exchange of a single amino acid switches the substrate properties of RhoA and RhoD toward glucosylating and transglutaminating toxins. J. Biol. Chem. 281, 19527-19535 (2006).
54. Jank, T., Giesemann, T. & Aktories, K. *Clostridium difficile* glucosyltransferase toxin B-essential amino acids for substrate binding. J. Biol. Chem. 282, 35222-35231 (2007).
55. Lo, H. R. et al. RTX toxin enhances the survival of *Vibrio vulnificus* during infection by protecting the organism from phagocytosis. J. Infect. Dis. 203, 1866-1874 (2011).
56. Jeong, H. G. & Satchell, K. J. F. Additive function of *Vibrio vulnificus* $MARTX_{Vv}$ and vvhA cytolysins promotes rapid growth and epithelial tissue necrosis during intestinal infection. PLoS Pathog. 8, e1002581 (2012).
57. Kashimoto, T. et al. *Vibrio vulnificus* detected in the spleen leads to fatal outcome in a mouse oral infection model. FEMS Microbiol. Lett. 362, fnv005 (2015).
58. Thiaville, P. C. et al. Genotype is correlated with but does not predict virulence of *Vibrio vulnificus* biotype 1 in subcutaneously inoculated, iron dextrantreated mice. Infect. Immun. 79, 1194-1207 (2011).
59. Lemichez, E. & Aktories, K. Hijacking of Rho GTPases during bacterial infection. Exp. Cell. Res. 319, 2329-2336 (2013).
60. Mechaly, A., McCluskey, A. J. & Collier, R. J. Changing the receptor specificity of anthrax toxin. mBio 3, e00088-12 (2012).
61. McCluskey, A. J., Olive, A. J., Starnbach, M. N. & Collier, R. J. Targeting HER2-positive cancer cells with receptor-redirected anthrax protective antigen. Mol. Oncol. 7, 440-451 (2013).
62. Antignani, A. & Fitzgerald, D. Immunotoxins: the role of the toxin. Toxins 5, 1486-1502 (2013).
63. Van Dessel, N. et al. Potent and tumor specific: arming bacteria with therapeutic proteins. Ther. Deliv. 6, 385-399 (2015).
64. Bell, J. & McFadden, G. Viruses for tumor therapy. Cell. Host Microbe 15, 260-265 (2014).
65. Willhite, D. C. & Blanke, S. R. Soluble expression and one-step purification of recombinant *Bacillus anthracis* protective antigen. Protein Peptide Lett. 5, 273-278 (1998).
66. Puck, T. T. & Marcus, P. I. A rapid method for viable cell titration and clone production with HeLa cells in tissue culture—the use of X-irradiated cells to supply conditioning factors. Proc. Natl Acad. Sci. USA 41, 432-437 (1955).
67. Stols, L. et al. A new vector for high-throughput, ligation-independent cloning encoding a tobacco etch virus protease cleavage site. Protein Expr. Purif. 25, 8-15 (2002).
68. Mattoo, S. et al. Comparative analysis of Histophilus somni immunoglobulinbinding protein A (IbpA) with other Fic domain-containing enzymes reveals differences in substrate and nucleotide specificities. J. Biol. Chem. 286, 32834-32842 (2011).
69. Pai, E. F. et al. Refined crystal-structure of the triphosphate conformation of H-Ras P21 at 1.35 a resolution—implications for the mechanism of GTP hydrolysis. EMBO J. 9, 2351-2359 (1990).

Example 4—RRSP Exhibits Novel Proteolytic Activity

Reference is made to the poster presentation entitled "RRSP Exhibits Novel Proteolytic Activity," Matthew Lam, Marco Biancucci, and Karla J F Satchell, an Abstract of which was published on-line on Apr. 1, 2017. (See Lam et al., the FASEB Journal, Vol. 31, No. 1_supplement, April 2017, the content of which is incorporated herein by reference in its entirety).

Title—RRSP Exhibits Novel Proteolytic Activity

Abstract

Rat sarcoma protein (Ras) is a protein involved in the transduction of signals necessary for cell survival and proliferation. Mutations in Ras can inhibit its enzymatic function and leave it constitutively active, resulting in uncontrollable cell proliferation, culminating in tumor growth. In addition, many bacterial protein toxins and effector domains target Ras GTPases to destroy eukaryotic cells and reduce cellular response against bacterial infection. The Multifunctional-Autoprocessing-Repeats-in-Toxins (MARTX) toxin is the primary virulence factor of *Vibrio vulnificus*, a bacterium that causes sepsis and death from wound infections or contaminated seafood. The domain in the 5th position of MARTX toxins produced by *V. vulnificus* has been shown to cleave between Y32 and D33 residues within the Switch I region of all Ras isoforms, inhibiting the Ras-MAPK pathway and subsequently cell proliferation.

Identification of the catalytic site of this Ras/Rap1-specific endopeptidase (RRSP) was directed by bioinformatics suggesting that the C2B subdomain of RRSP is similar to the active sites of other enzymes such as bacterial erythromycin esterases EreA and EreB, and mammalian protein Tiki2. Despite these enzymes having different substrates, it was revealed that RRSP-C2B shares highly conserved residues that form the active sites of the otherwise distinct proteins. Consequently, a putative active site of RRSP composed of two conserved glutamate and three histidine residues could be modeled.

Point mutations targeting these suspected catalytic residues were generated to assess the enzymatic activity of RRSP mutants. The purified mutants were then incubated with recombinant KRas. Alanine substitutions in three of the five conserved residues prevented in vitro processing of KRas only partially, suggesting that these residues play a more supportive role, such as substrate binding. However, mutations in the other two residues inhibited in vitro KRas processing entirely, and they were deemed as catalytic residues. Fluorescence thermal shift (FTS) was conducted to confirm that the structure of the RRSP mutant variants did not differ significantly from that of the wild type, indicating that the amino acid substitutions impacted enzyme activity and not the overall structural fold of the protein. Thus, the active site of RRSP is shown to be comprised of a pair of Glu/His residues and is most similar to that of the erythromycin esterase EreB. Unlike the metalloproteins EreA and Tiki2, treating RRSP with metal ions chelators such as EDTA and phenanthroline had no effect on substrate processing. Overall, these findings suggest that RRSP conserves a specific set of catalytic residues representative of a proposed erythromycin esterase-Tiki family, within which it has novel protease activity divergent from the metalloproteases of this family.

Background

Figure 36:
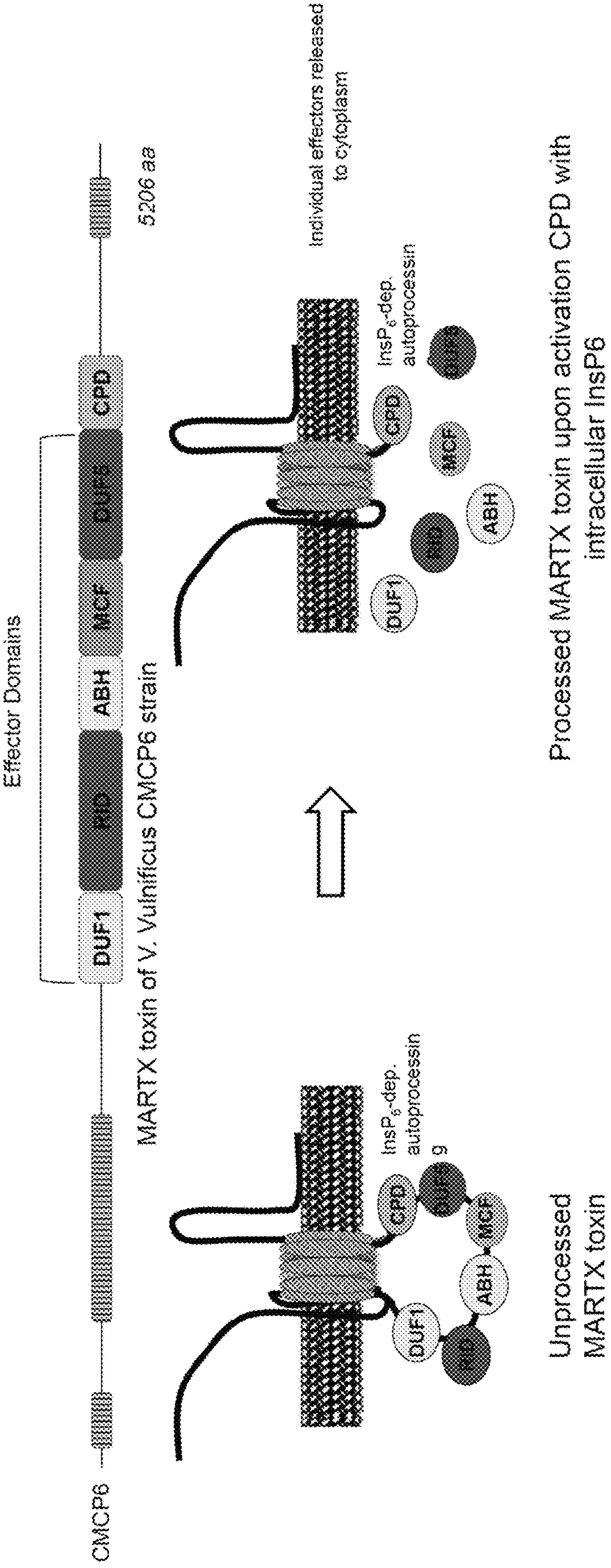
FIG. 36. Schematic illustration of MARTX toxin and processing steps.

*Vibrio vulnificus* is a gram-negative bacteria commonly found in marine environments and is found as a contaminant of oysters and other shellfish. As such, *V. vulnificus* is an observed foodborne pathogen that causes gastroenteritis, wound infections, necrotizing fasciitis, and fatal septicemia in humans. Two two of the major virulence factors of *V. vulnificus* are a bacteria hemolysin and so-called "multifunctional autoprocessing repeats-in-toxin or "MARTX" toxin. A schematic illustration of the MARTX toxin and its processing steps is provided in FIG. 36. Notably, deletions in rtxA1, which is the gene that encodes the MARTX toxin, or the DUF5 domain of MARTX specifically reduce the $LD_{50}$ of the wild-type CMCP6 strain in mice by 2600× and 54×, respectively. (See Kwak I., et al., 2011).

Figure 37B:
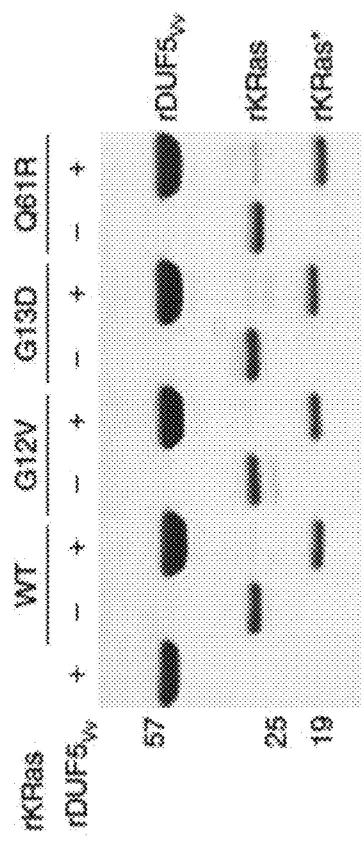
FIG. 37A and FIG. 37B illustrate that RRSP (DUF5) cleaves all Ras isoforms and oncogenic KRas.
Figure 37A:
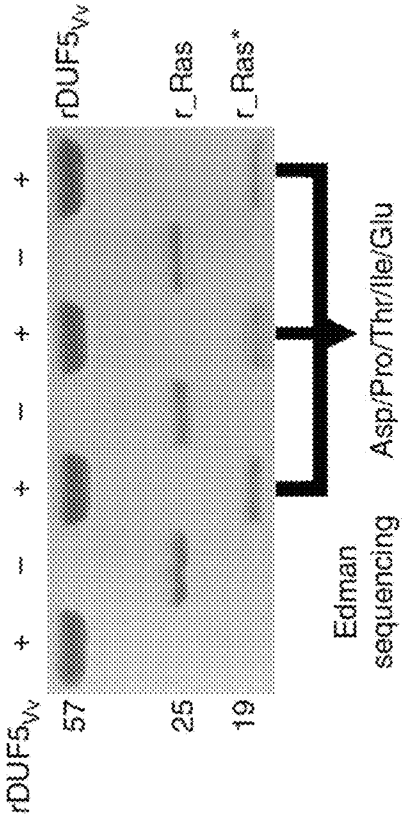

Using an in vitro cleavage assay, we observed that a recombinant $DUF5_{Vv}$ ($rDUF5_{Vv}$) could cleave recombinant KRas (rKRas), HRas (rHRas), and NRas (rNRas) between Y32 and D33. (See FIG. 37). In FIG. 37A, $rDUF5_{Vv}$ was incubated with rKRas, rHRas, or rNRas at equimolar ratios (10 μM) and incubated at 37° C. for 30 minutes. Reaction products were analyzed by SDS-Page. The band labeled as r_Ras is uncleaved Ras protein, whereas the band labeled as r_Ras* is cleaved Ras protein. In FIG. 37B, rKRas or or oncogenic variants thereof (i.e., G12V, G13D, and Q61R) were used as substrates for $rDUF5_{Vv}$. $rDUF5_{Vv}$ was observed to cleave not only WT KRas but also oncogenic forms G12V, G13D, and Q61R, which are the most commonly found oncogenic mutations in KRas-implicated cancers. (See also Antic, I., et al., Site-specific processing of Ras and Rap1 Switch I by a MARTX toxin effector domain. Nat Commun, 2015. 6: p. 7396).

We performed a bioinformatics analysis of $DUF5_{Vv}$ which suggested that catalytic residues for the Ras-protease activity lie in the C2B region (data not shown). The tertiary structures of members of the DUF399 and erythromycin esterase families had been solved, allowing a model of TIKI, which has a very similar primary structure, to be generated. (See Sanchez-Pulido, L. and C. P. Ponting, "Tiki, at the head of a new superfamily of enzymes," Bioinformatics, 2013. 29(19): p. 2371-4; the content of which is incorporated herein by reference in its entirety). Furthermore, the active site of TIKI had been determined and could be mapped onto the model. (See id.). The pocket of TIKI containing its catalytic residues shared structural similarities to a pocket on the C2B region of RRSP. We preformed an overlay of RRSP-C2B and BcR135 of the erythromycin esterase family which informed us of the putative catalytic residues of RRSP including E321, H323, E351, H352, and H451 (data not shown).

Figure 38:
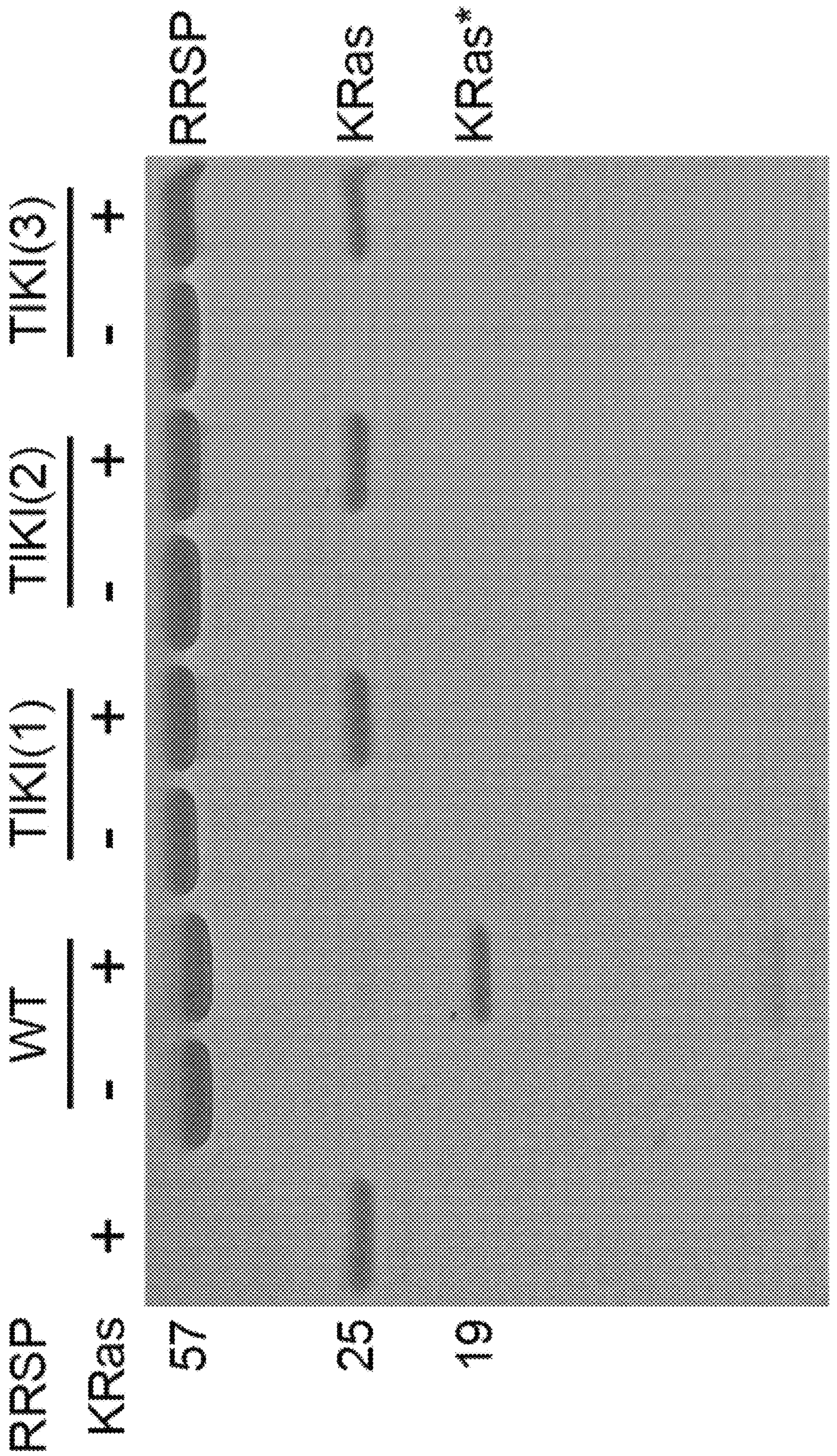
FIG. 38. Mutation of putative active site residues eliminates RRSP activity. Suspected catalytic residues E321, H323, E351, H352, and H451 (cumulatively referred to as "TIKI" residues) were mutated to alanines. RRSP TIKI with the five aforementioned substitutions and recombinant KRas were purified and mixed at equimolar concentration (10 μM) for 30 minutes at 37° C. Cleavage was analyzed by SDS-Page analysis. No cleavage was observed.

We then assessed whether mutation of putative active site residues E321, H323, E351, H352, and H451 eliminates RRSP activity. Suspected catalytic residues E321, H323, E351, H352, and H451 (cumulatively referred to as "TIKI" residues) were mutated to alanines. Cleavage of recombinant KRas by recombinant WT RRSP and TIKI mutant RRSP then was performed in vitro and analyzed by SDS-Page analysis. RRSP with the five aforementioned substitutions and recombinant KRas were purified and mixed at equimolar concentration (10 μM) for 30 minutes at 37° C. No cleavage was observed. (See FIG. 38).

Figure 39A:
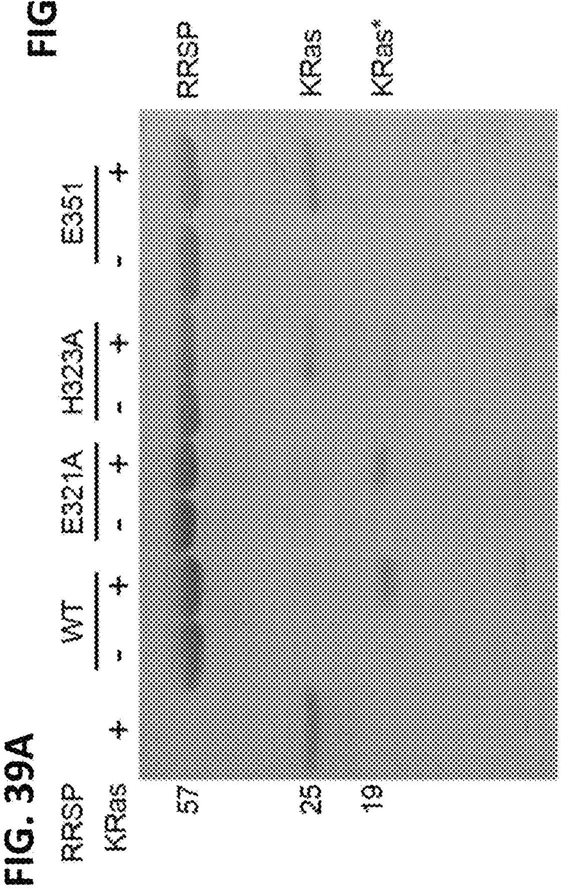
FIG. 39A and FIG. 39B illustrate that Glu/His Pair catalyzes RRSP activity.
Figure 39B:
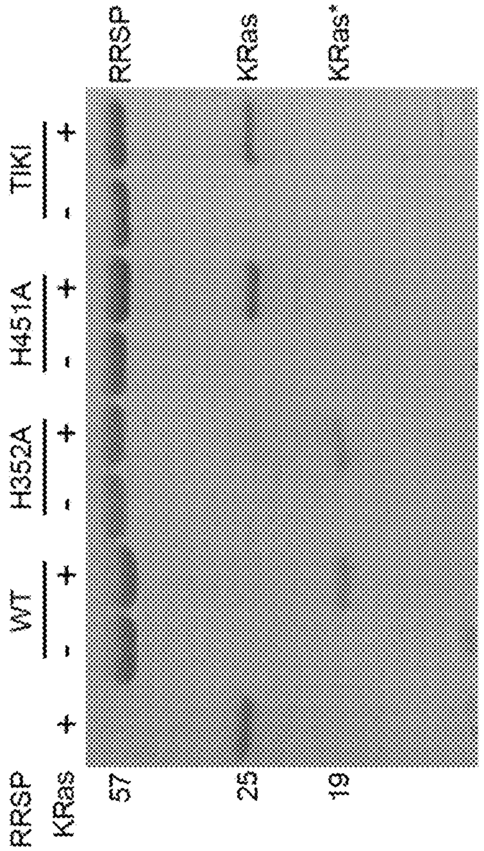

We next tested individual putative active site residues E321, H323, E351, H352, and H451 in RRSP. Each of E321, H323, E351, H352, and H451 were substituted with alanine in RRSP to create five variant forms of RRSP called E321A, H323A, E351A, H352A, and H451A. Recombinant forms of each of E321A, H323A, E351A, H352A, and H451A was synthesized and purified and mixed with recombinant KRas at equimolar concentration (10 μM) for 30 minutes at 37° C. Cleavage was assessed by SDS-Page analysis. No cleavage was observed in the E351A variant and the H451A variant. (See FIG. 39). This suggests that E351 and H451 are required for the cleavage activity of RRSP for KRas.

Figure 40:
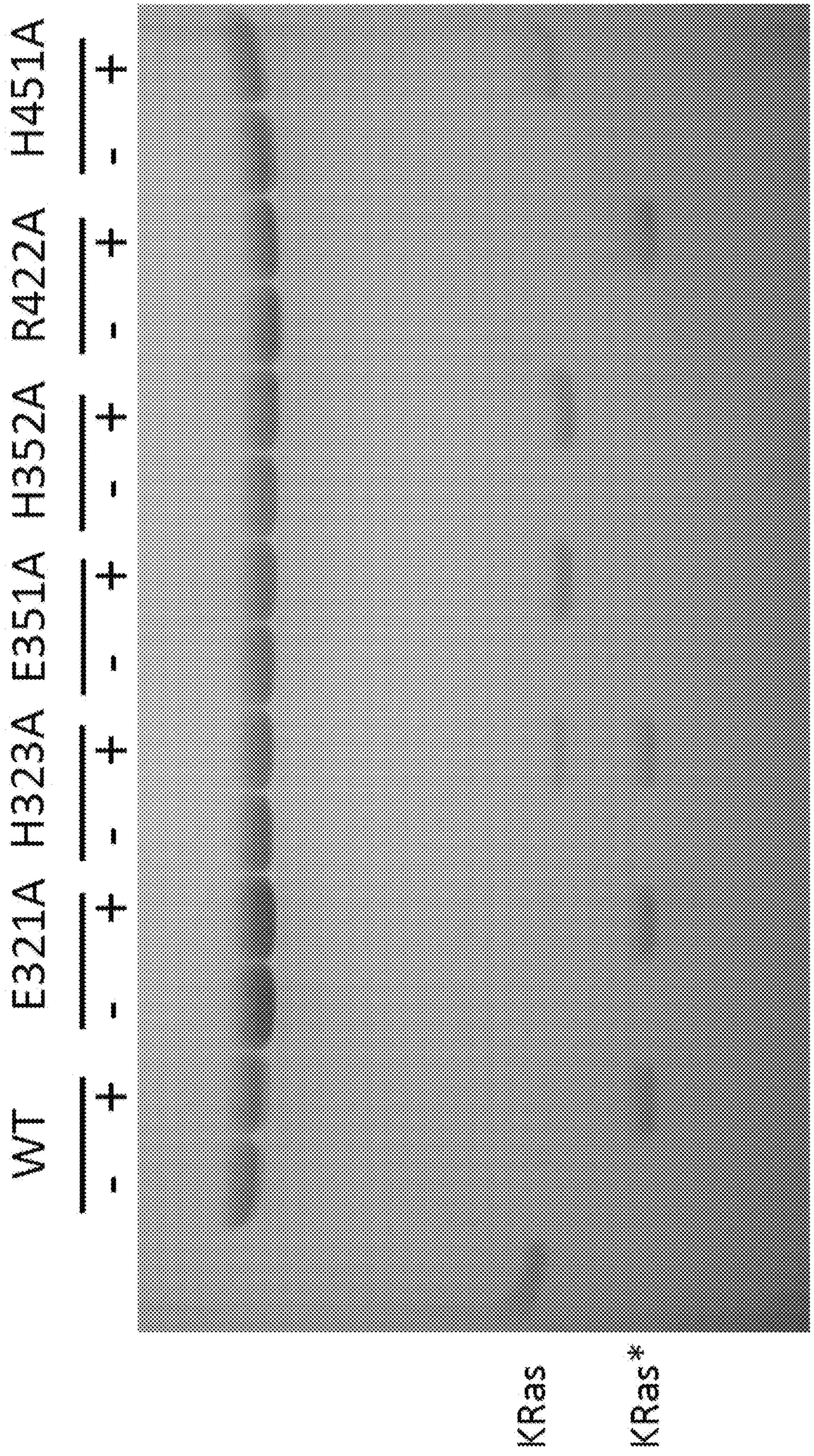
FIG. 40. KRas(1-169) was used as substrate for RRSP wild type and variant proteins. KRas and RRSP protein were mixed at equimolar ratio (10 μM) and incubated at 37° C. for 30 minutes. Reaction products were analyzed by SDS-Page.

Next, using DALI server, we identified significant structural homologs with RRSP C2B domain (residues 277-508). In particular, secondary structure folding comprised between residues 303-474 of RRSP C2B showed similar topology with the bacterial type III effector protein HopBA1 of *Pseudomonas syringae* (PDB:5TO9), the erythromycin esterase (EraA)-like Bcr136 from *Bacillus cereus* (PDB: 3BB5) and the ChaN heme-binding protein from *Campylobacter jejuni* (PDB:2G5G) (data not shown). Interestingly, we identified residues in RRSP C2B that were 100% conserved with the putative catalytic residues in HopBA1, Bcr136 and ChaN which included E321, H323, E351, and H451 (data not shown). Alanine substitution of E321 did not affected the catalytic activity of RRSP (see FIG. 40) while RRSP H323A showed 50% reduction of Ras cleavage (see FIG. 40). However, RRSP E351A and H451A did not process KRas (see FIG. 40), suggesting their major role in the catalytic mechanism. RRSP H352 and R422 residues are in structural proximity of E351 and H451, and they were substituted with alanines residues to test their possible involvement with RRSP activity. Although RRSP R422A was still able to cleave Ras, RRSP H352A barely cleaved Ras (see FIG. 40). Overall, these results demonstrate that RRSP E351 and H451 are putative catalytic residues, in accordance to HopBA1, Bcr136 and ChaN. However, H352 is present only in RRSP sequence suggesting an additional role of this residue, which could be involved in substrate recognition.

We next tested whether the RRSP variants were structurally stable. FIG. 41 illustrates the fluorescent thermal shift for wild-type RRSP and RRSP variants are structurally stable. The denaturation profile of each RRSP variant does not vary greatly from that of the wild type, demonstrating that their respective mutations did not significantly alter tertiary structure. In addition, the melting temperature of each RRSP variant as determined by denaturation curves does not vary greatly from that of the wild type, again demonstrating that their respective mutations did not significantly alter tertiary structure.

Figure 42B:
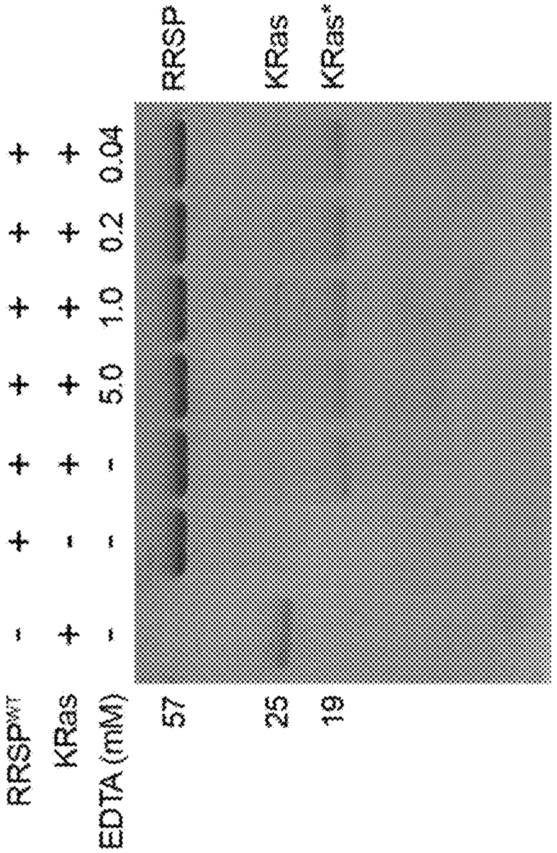
FIG. 42A and FIG. 42B illustrate that RRSP is not a metalloprotease.
Figure 42A:
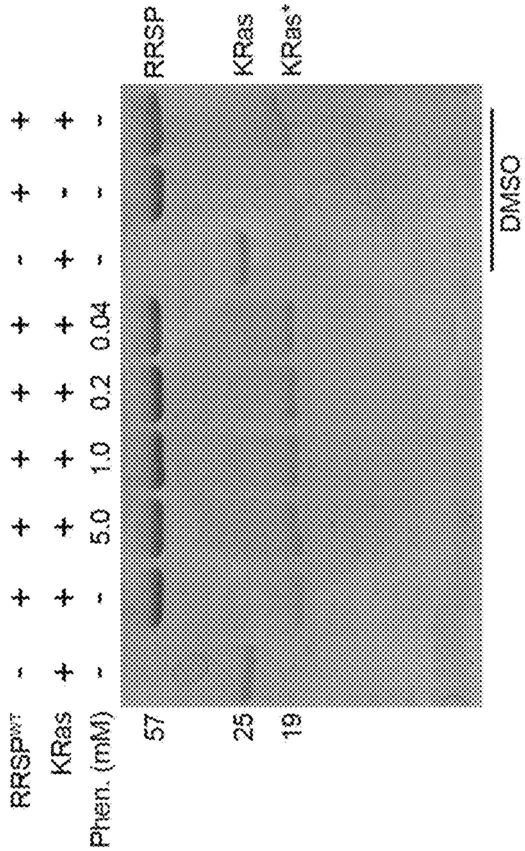

Finally, we tested whether RRSP is a metalloprotease. Recombinant RRSP and recombinant KRas were purified and mixed at equimolar concentration (10 μM) with varying concentrations of phenanthroline (which is a metal complexing reagent) in DMSO for 30 minutes at 37° C. Cleavage was still observed. (See FIG. 42A). In addition, recombinant RRSP and recombinant KRas were purified and mixed at equimolar concentration (10 μM) with varying concentrations of EDTA for 30 minutes at 37° C. Cleavage was still observed. (See FIG. 42A).

Conclusions

We conclude that RRSP processing of Ras is catalyzed by a Glu/His pair in the C2B region of DUF5. However, RRSP is not a metalloprotease, but rather utilizes a mechanism of cleavage novel to its family of proteases.

Example 5—Proteolytic Pan-RAS Cleavage Leads to Tumor Regression in Patient-Derived Pancreatic Cancer Xenografts Reference is made Vidimas V., et al, Proteolytic pan-RAS cleavage leads to tumor regression in patient-derived pancreatic cancer xenografts. Mol. Cancer Ther. 2022, 5 (21), the content of which is incorporate herein by reference in its entirety.

Abstract

The lack of effective RAS inhibition represents a major unmet medical need in the treatment of pancreatic ductal adenocarcinoma (PDAC). Here, we investigate the anticancer activity of RRSP-DTB, an engineered biologic that cleaves the Switch I of all RAS isoforms, in KRAS-mutant PDAC cell lines and patient-derived xenografts (PDXs). We first demonstrate that RRSP-DTB effectively engages RAS and impacts downstream ERK signaling in multiple KRAS-mutant PDAC cell lines inhibiting cell proliferation at picomolar concentrations. We next tested RRSP-DTB in immunodeficient mice bearing KRAS-mutant PDAC PDXs. Treatment with RRSP-DTB led to ≥95% tumor regression after 29 days. Residual tumors exhibited disrupted tissue architecture, increased fibrosis and fewer proliferating cells compared to controls. Intratumoral levels of phospho-ERK were also significantly lower, indicating in vivo target engagement. Importantly, tumors that started to regrow without RRSP-DTB shrank when treatment resumed, demonstrating resistance to RRSP-DTB had not developed. Tracking persistence of the toxin activity following intraperitoneal injection showed that RRSP-DTB is active in sera from immunocompetent mice for at least one hour, but absent after 16 hours, justifying use of daily dosing. Overall, we report that RRSP-DTB strongly regresses hard-to-treat KRAS-mutant PDX models of pancreatic cancer, warranting further development of this pan-RAS biologic for the management of RAS-addicted tumors.

Introduction

Pancreatic cancer is the 11th most commonly diagnosed cancer in the U.S. and the 3rd leading cause of cancer-related deaths, with an overall 5-year survival rate of 9%[1]. Poor prognosis is mainly attributed to late-stage clinical detection, early metastatic dissemination and lack of effective treatment options[2, 3]. Pancreatic ductal adenocarcinoma (PDAC) is the most common histologic subtype of pancreatic cancer, accounting for ~90% of cases[4, 5]. PDAC genetic profiling has found that KRAS is mutated in ~95% of patients, with NRAS and HRAS mutations accounting for <1% each and wild-type KRAS (KRASWT) for the remaining 5%[6-8]. Mutations in RAS genes (H-, N- and KRAS) result in RAS proteins being locked in the active GTP-bound state with consequent permanent activation of downstream RAS/MEK/ERK signaling, which controls cancer cell proliferation and survival[9-11]. Following decades of failures, inhibition of KRAS specific subtypes has had recent success[12-16]. Notably, sotorasib (LUMAKRAS™) was recently approved by the FDA as the first therapy for patients with KRASG12C-mutant non-small cell lung cancer[17, 18].

However, the usefulness of these KRASG12C inhibitors for PDAC is limited to ~2% of patients[19]. Therefore, there is an urgent need for effective therapeutic strategies that target KRAS directly in PDAC.

We recently demonstrated that the pan-RAS biologic RRSP-$DT_B$ inhibits tumor growth in xenograft models of triple-negative breast cancer (TNBC) and colorectal cancer (CRC) in mice via direct RAS cleavage[20]. RRSP-DTB is an engineered chimeric toxin comprised of the RAS/RAP1 specific endopeptidase (RRSP) from Gram-negative *Vibrio vulnificus* and the protein delivery machinery of diphtheria toxin (DTB). DTB delivers RRSP intracellularly via Heparin-binding EGF-like growth factor (HB-EGF)-mediated endocytosis in receptor-bearing cells only[20]. Human HB-EGF acts as the unique receptor of diphtheria toxin (DT) and is widely expressed in epithelial tumors, including PDAC[21]. where it has been shown to cooperate with KRAS to promote KRAS-driven tumorigenesis[22]. Once released into the cytoplasm, RRSP cleaves RAS and RAP1 with high specificity within the Switch I region, which enables RAS binding to effectors and downstream signal transduction[23, 24]. All three RAS isoforms (H-, N- and KRAS) are cleaved by RRSP whether they are bound to GDP or GTP, so that the entire RAS cellular pool is inactivated[25]. Importantly, RRSP processes the main oncogenic RAS proteins with activating point mutations at residues G12, G13 and Q61 23. Cleavage of all RAS isoforms, mutant and wild-type, is an inherent advantage of RRSP and represents a potent strategy to reduce or regress growth in a broader spectrum of tumor types. The processing of RAS by RRSP-DTB leads to a variety of cellular outcomes including cell cycle arrest via upregulation of p27, apoptosis, or senescence. The differential cell fates were not correlated with the KRAS mutation, but rather, the mechanisms for inhibition of cell growth upon loss of RAS depend on signaling networks downstream of RAS[26].

Here, we use human KRAS-mutant PDAC cell lines and clinically relevant PDAC patient-derived xenografts (PDXs) to demonstrate preclinical effectiveness of the pan-RAS inhibitor RRSP-$DT_B$ against hard-to-treat PDAC. We also provide data on the stability of the toxin in the bloodstream following intraperitoneal (i.p.) injection, useful to support advanced RRSP-$DT_B$ therapeutic development.

Materials and Methods

Protein Preparations, Chemicals and Cell Lines

Purification of RRSP-DTB and catalytically inactive RRSP*-DTB proteins and endotoxin removal were performed as previously described[20]. All chemicals were from Sigma-Aldrich unless otherwise specified. Validated cell lines were kindly provided from the Reference Reagent Resource of the National Cancer Institute RAS Initiative at Frederick National Laboratory for Cancer Research (FNLCR). Cell lines at this resource are obtained by the Ras Initiative from collaborators or commercial sources and confirmed free of *Mycoplasma* using VenorGeM *Mycoplasma* Classic Endpoint PCR assay and are also subjected to short tandem repeat analysis using the AmpFLSTR Identifier PCR Amplification Kit to authenticate the cell lines, comparing the results to information located at https://web.expasy.org/cellosaurus/. Cells were cultured at 37° C. and 5% CO2 atmosphere. YAPC and SUIT-2 were grown in RPMI-1640 (ATCC formulation) containing 10% fetal bovine serum (FBS; Gemini) and 1% penicillin/streptomycin (P/S; Invitrogen). KP-1N were grown in RPMI-1640 containing 5% FBS and 1% P/S. KP-4 were grown in DMEM-F12 with Glutamax (Gibco) containing 5% FBS and 1% P/S. PANC-1 were grown in DMEM (ATCC formulation) with 10% FBS and 1% P/S.

Cytotoxicity, Viability, Clonogenic and Apoptosis Assays

Cytotoxicity was assessed by staining cells with crystal violet. Briefly, 50,000 cells/well were cultured in 48-well plates and treated with RRSP-DTB and RRSP*-DTB for 72 hours. Cells were washed and crystal violet fixing/staining solution was added for 20 min at room temperature as previously described 20. Images of air-dried plates were acquired using a conventional desktop scanner.

Cell viability was measured using CellTiter-Glo (Promega). 10,000 cells/well were grown in 96-well clear bottom white plates and treated with RRSP-DTB and RRSP*-DTB for 72 hours. CellTiter-Glo was then added to each well following the manufacturer's instructions and luminescence was recorded using a Tecan Safire2 plate reader. IC50 were calculated using the log(inhibitor) vs. response—variable slope (four parameters) function in Graphpad Prism v8.

Cell proliferation was assessed by colony-formation assay. RRSP-DTB and RRSP*-DTB-treated cells for 72 hours were trypsinized, counted on a hemocytometer and replated in 48-well plates at 250 cells per well. Culture medium was replaced biweekly. On day 14, a crystal violet fixing/staining solution was added to the plates. Quantitative changes in cytotoxicity or clonogenicity were determined by solubilizing crystal violet-stained plates with 10% acetic acid and measuring the absorbance at 590 nm using a plate reader (Tecan Safire2).

Apoptosis was assessed by Caspase-Glo 3/7 assay (Promega). 10,000 cells/well were grown in 96-well clear bottom white plates and treated with 0.1 and 10 nM of RRSP-DTB and RRSP*-DTB as well as 1 μM of Staurosporine (positive control) for 24 and 48 hours. Caspase-Glo 3/7 was then added to each well following the manufacturer's instructions and luminescence was recorded using a Tecan Safire2 plate reader.

SDS-PAGE and Western Blotting

Protein extracts were prepared from cells by adding M-PER mammalian protein extraction reagent (Thermo Fisher Scientific) with protease and phosphatase inhibitors (Sigma-Aldrich). Protein content was measured using the Bio-Rad protein assay dye reagent concentrate (#5000006). Equal amounts of proteins were separated by SDS-PAGE followed by western blot analysis as previously described 24. Membranes were blotted using the following antibodies: anti-panRAS (Thermo Fisher Scientific Cat #MA1-012, RRID:AB 2536664), which recognizes RAS Switch I and thus detects only uncleaved RAS. Anti-mAb 4E8, a pan-RAS monoclonal antibody that recognizes both cleaved and uncleaved bands of all three RAS isoforms was prepared from a hybridoma cell line obtained from the National Cancer Institute RAS Initiative. The antibody preparation used in this study was previously validated 20. Anti-Phospho-p44/42 MAPK (pERK1/2; Cell Signaling Technology Cat #4377, RRID:AB_331775), anti-p44/42 MAPK (ERK1/2; Cell Signaling Technology Cat #4696, RRID:AB_390780), and anti-HB-EGF (Abcam, #ab185555). Anti-vinculin (Cell Signaling Technology Cat #13901, RRID:AB_2728768) was used for normalization. Secondary antibodies used were fluorescent-labeled IRDye 680RD goat anti-mouse (LI-COR Biosciences Cat #926-68070, RRID:AB_10956588) and IRDye 800CW goat anti-rabbit (LI-COR Biosciences Cat#926-32211, RRID:AB_621843). Blot images were acquired using the Odyssey Infrared Imaging System (LI COR Biosciences) and quantified by densitometry using NIH ImageJ software (ImageJ, RRID:SCR 003070). Percentage of uncleaved RAS was calculated as previously described[24].

Patient-Derived Xenograft (PDX) Studies

Human PDAC biospecimens were obtained from the Pathology Core Facility (PCF) Biobank at Northwestern University. Collection of human tissue specimens and the PDX mouse protocol were approved by the Institutional Review Board and Institutional Animal Care and Use Committee (IACUC) at Northwestern University. All PDAC tumor models used have been fully tested and validated across the entire spectrum of creating, propagating, and characterizing the PDX models. The established PDAC tumor models are defined as the surgical collected fresh tumor tissue are subcutaneously implanted into NSG mice. This process is repeated two more times to ensure that the tumors can be propagated through at least three passages. Cryopreserved fragments are thawed and re-implanted to make sure that frozen tissue will regrow. At each passage, tumor tissue is compared to the original patient tumor on the basis of histopathology, immunohistochemistry for expression of clinically relevant biomarkers. Only PDX tumors that retain the histological characteristics of the patient tumor and to exclude development of lymphoma are considered confirmed. All tissues are routinely tested for *Mycoplasma* using the Universal *Mycoplasma* Detection Kit (American Type Culture Collection, Cat #30-1012K) for our studies. Molecular profiling for tumor genomic and transcriptomic characteristics and response to a standard-of-care combination therapy for PDAC PDX tumor are also used to establish the baseline characteristics of the model. At the time of this study, multiple KRASG12V PDXs were available from the repository and we selected two of them from patients that did not receive any adjuvant or neo-adjuvant therapy highlighting the different sex (female vs male) as a valuable variable. Although our repository included one KRASG12D PDX, it was from a patient that received multiple neo-adjuvant therapies (gemcitabine, oxaliplatin), tumor pathology/staging report was not available at the time of the study and therefore was not considered representative for this study. PDXs were established by the Center for Developmental Therapeutics (CDT) at Northwestern University 27. Briefly, cryopreserved human PDAC biospecimens (passage 0, P0) were thawed, cut into small fragments, and two tissue fragments were xenografted into the dorsal region of two female NSG mice (P1). When tumor masses reached ~1500 mm3 in size, tumors were excised, divided into equally sized specimens (~2×2×2 mm) and implanted subcutaneously into the dorsal region of the appropriate number of female NSG mice (P2). Once tumors reached 150-200 mm3, mice underwent balanced randomization based on tumor size. Briefly, mice were grouped three per cage (two cages used for each treatment) so that differences in the median tumor size were minimized among groups prior to treatment administration. Next, mice were dosed i.p. with endotoxin-free 0.1 mg/kg of RRSP-DTB or RRSP*-DTB on a 5 days ON/2 days OFF schedule for four weeks. Control mice received endotoxin-free phosphate buffered saline (MilliporeSigma). After four weeks, all mice (except three mice from the RRSP-DTB-treatment group) were humanely euthanized, tumors excised, and fixed in 10% formalin overnight. The remaining three mice from the RRSP-DTB group were housed without treatment for three weeks and subsequently dosed with RRSP-DTB at the indicated treatment regimens. Tumor growth was monitored by digital caliper measurements of length (1) and width (w) of the tumors. Tumor volume was calculated using the following formula: volume (mm3)=(1×w2)/2. Mouse body weight was also measured regularly. Percentage change in tumor volume between day 1 and day 29 was calculated for each individual tumor as described in Patel et al.[28]

In Vivo Stability Study

Five female C57BL/6 mice per group were injected i.p. with 0.1 mg/kg or 0.5 mg/kg of RRSP-DTB. Saline was used as vehicle control. After 1 and 16 hours, blood was collected from anesthetized mice via orbital bleeding, transferred to serum separator collection tubes (BD Biosciences, #365967), allowed to clot for at least 30 minutes and then centrifuged for 10 minutes at 10,000×g. The serum supernatant was aliquoted and stored at −80° C. until use. To determine whether RRSP-DTB was active in the blood after a single injection, serum collected from mice was diluted 1:100 dilution with saline, added directly to YAPC or KP-4 cultured pancreatic cells, and total levels of intracellular RAS cleaved after 24 hours was assessed by western blot as described above.

Histology, Immunohistochemistry and Image Analysis

Paraffin-embedding, sectioning, hematoxylin and eosin (H&E) and Masson's trichrome stainings as well as immunohistochemical staining of PDX specimens were performed by the Robert H. Lurie Comprehensive Cancer Center Pathology Core Facility. Tumor sections were stained with anti-Cytokeratin 19 ((CK-19), #ab76539; Abcam), anti-Ki-67 (#GA626; Dako), anti-cleaved caspase 3 ((CC3, #9661; Cell Signaling Technology), anti-pan-RAS ((RAS), #PA5-85947; Thermo Fisher Scientific) and anti-Phospho-p44/42 MAPK ((ERK1/2) (Thr202/Tyr204, (D13.14.4E) XP, #4370; Cell Signaling Technology) antibodies as described previously 20. Primary antibodies were detected using the appropriate secondary antibodies and 3,3'-diaminobenzidine (DAB) revelation (Dako).

All slides were scanned using a Nanozoomer HT slide scanner (Hamamatsu). Quantification of positively immunostained cells was performed using customized Application Protocol Packages (APPs) within the VIS image analysis software (Visiopharm). Positive cells were counted in the whole tumor sections and expressed as the percentage ratio over the area of the whole section. Because the pattern of cytoplasmic RAS staining was diffuse, we quantified RAS signal intensity by color deconvolution using ImageJ (Fiji version) as previously described[29].

Statistical Analysis

Graphpad Prism v.8 software was used for statistical analysis. Bar plots represent the mean of at least three independent experiments±the standard deviation (SD). Statistical significance was assessed using one-way analysis of variance (ANOVA) assuming normal distribution. Dunnett's multiple comparison post-test was employed to compare the mean of the control group to the mean of treatment groups. Tukey's multiple comparison test was used to compare the mean of each group with the mean of every other group. Points in the fitted dose-response curve represent mean±standard error of the mean (SEM). Statistical analysis on fold-change data was performed after log transformation to obtain a more normalized distribution. For in vivo PDXs, data are reported as mean±SEM and one-way ANOVA was performed to assess differences among the treatment arms. Values of $p<0.05$ were considered statistically significant.

Results

RRSP-$DT_B$ Cleaves RAS in KRAS-Mutant PDAC Cell Lines

Figure 48A:
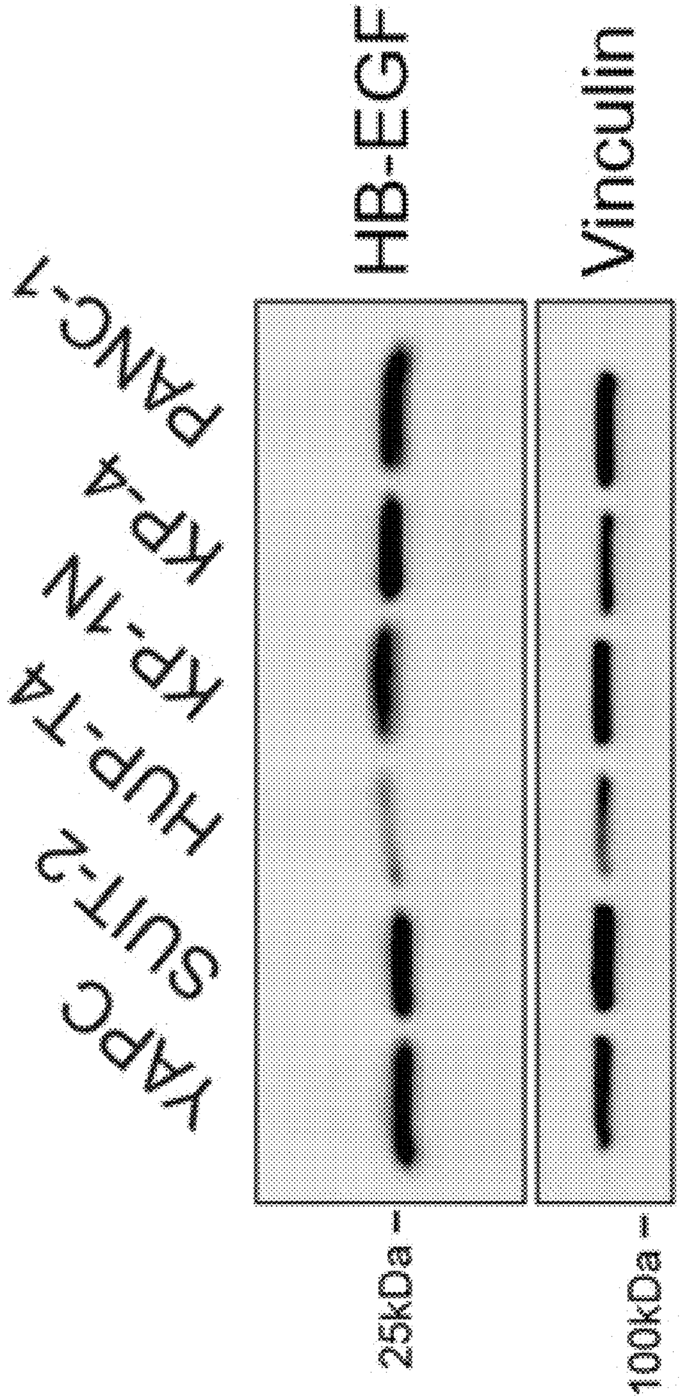
FIG. 48A-48B. Assessment of HB-EGF levels in PDAC cell lines and crystal violet cytotoxicity assay quantification. (A) Representative western blot image of HB-EGF expression in six different KRAS-mutant PDAC cell lines. (B) PDAC cells treated with increasing doses of RRSP-$DT_B$ and 10 nM of RRSP*-$DT_B$ for 72 hours were fixed and stained with crystal violet, which was subsequently dissolved in 10% acetic acid and measured by absorbance at 590 nm. Bar plots represent mean±SD of three independent experiments (*$p<0.05$, $p<0.01$, **$p<0.0001$ versus control 0 nM; one-way ANOVA followed by Dunnett's multiple comparison test; n=3).

For this study, we selected five different KRAS mutant PDAC cell lines, including YAPC (G12V), SUIT-2 (G12D), KP-1N (G12D), KP-4 (G12D) and PANC-1 (G12D). All five cell lines used expressed the DT receptor HB-EGF. However, an originally selected cell line HUP-T4 cells expressed low levels of HB-EGF, and subsequently was excluded from the study (FIG. 48A).

Figure 43A:
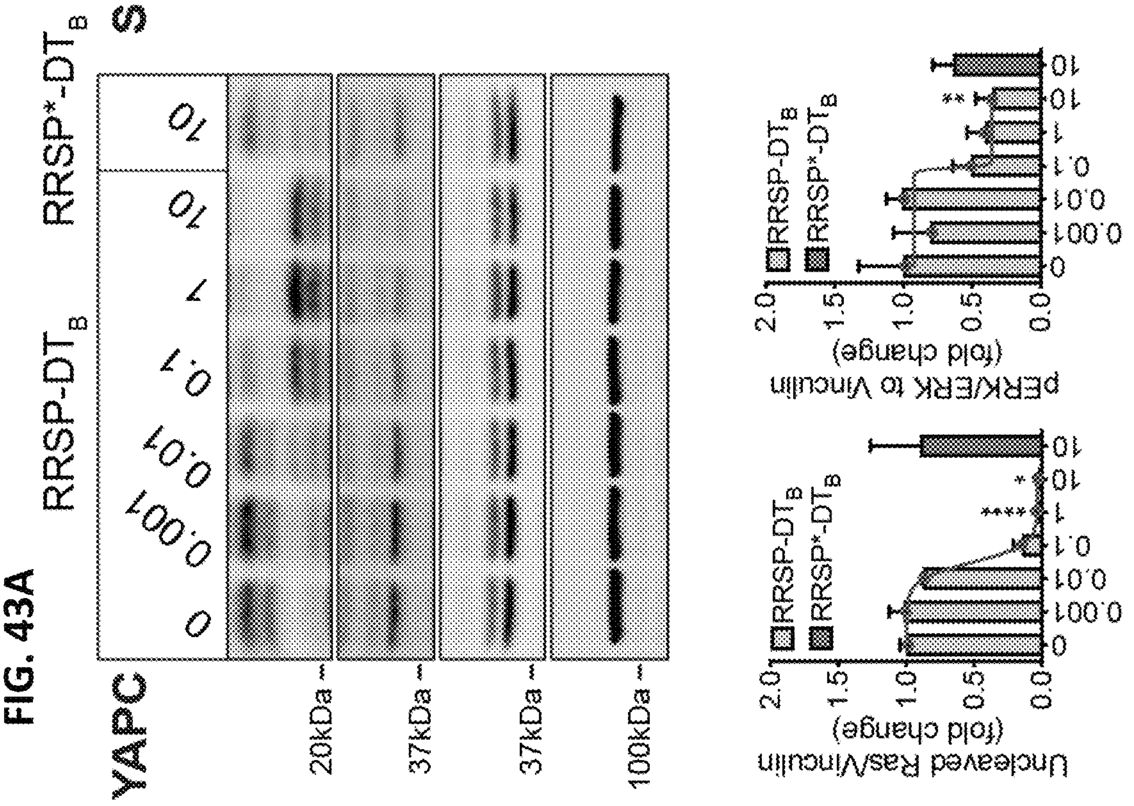
FIG. 43A-43F: Assessment of RAS cleavage by RRSP-$DT_B$ in KRAS-mutant PDAC cell lines. (A-E) Representative western blots and quantification of uncleaved/cleaved RAS and pERK levels in (A) YAPC, (B) SUIT-2, (C) KP-1N, (D) KP-4 and (E) PANC-1 PDAC cell lines following treatment with increasing doses of RRSP-DTB as indicated or 10 nM of catalytically inactive mutant RRSP*-$DT_B$ for 24 hours. Bar plots represent mean±SD of three independent experiments (*p<0.05, p<0.01, **p<0.0001 versus control 0 nM; one-way ANOVA followed by Dunnett's multiple comparison test; n=3). Superimposed solid red dose-response curves were used to extrapolate the concentration of RRSP-$DT_B$ required to cleave 50% of RAS in the corresponding cell line, as reported in (F).
Figure 43B:
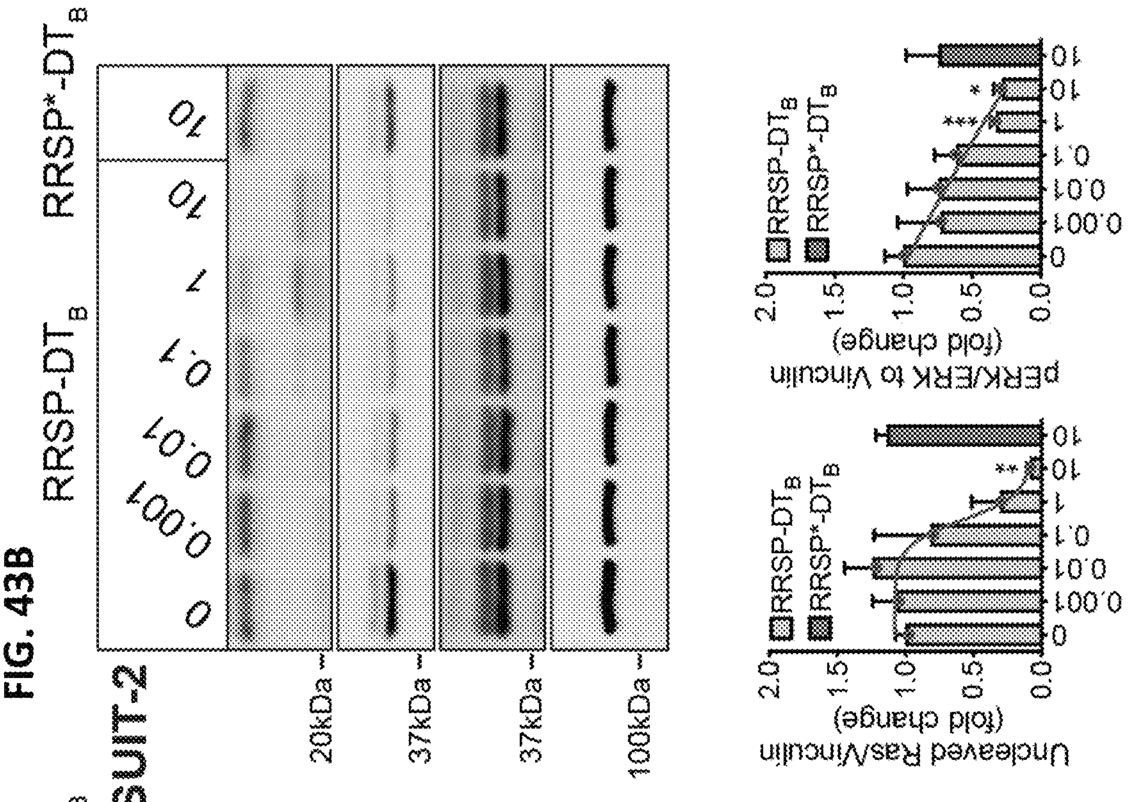
Figures 43C, 43D:
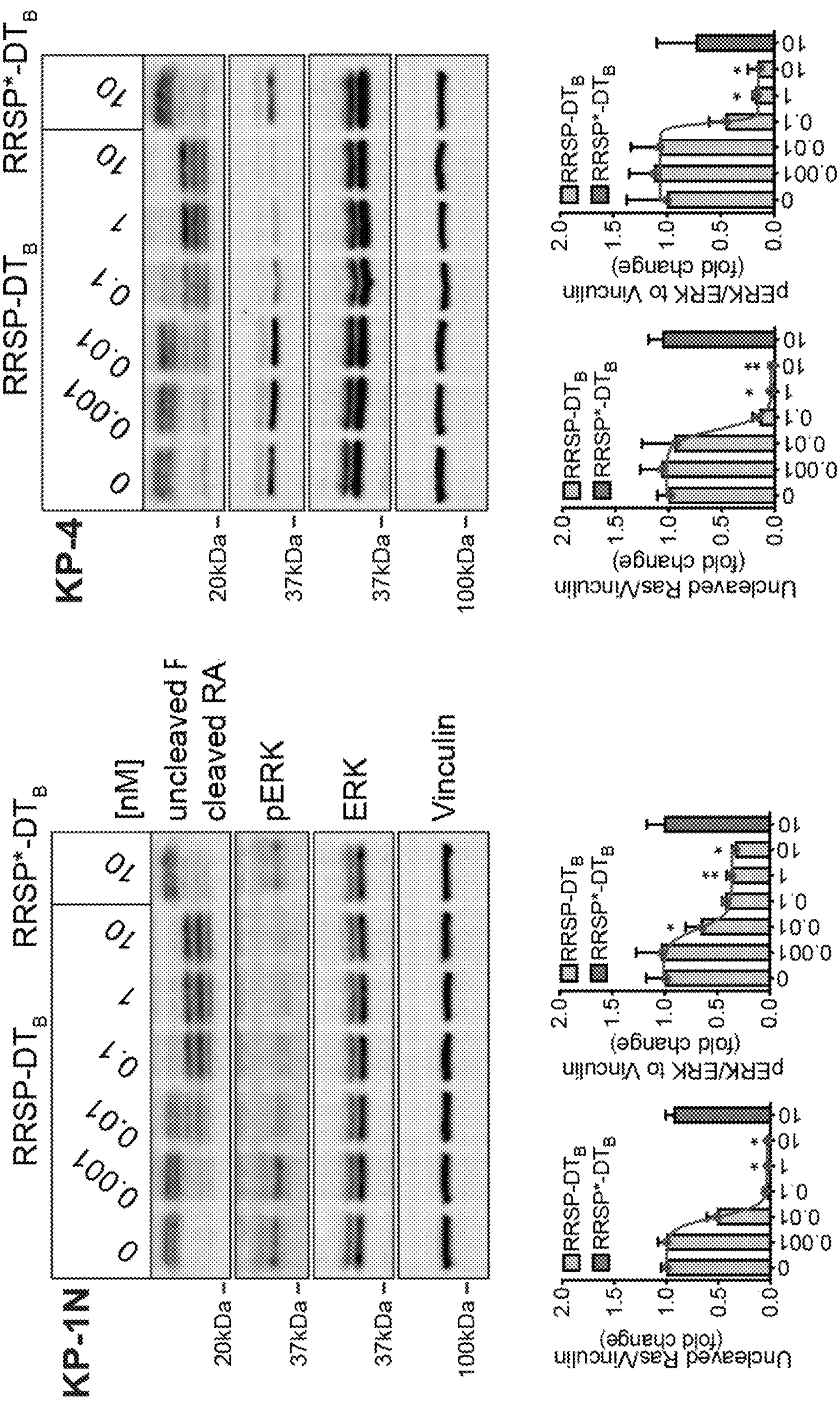
Figures 43E, 43F:
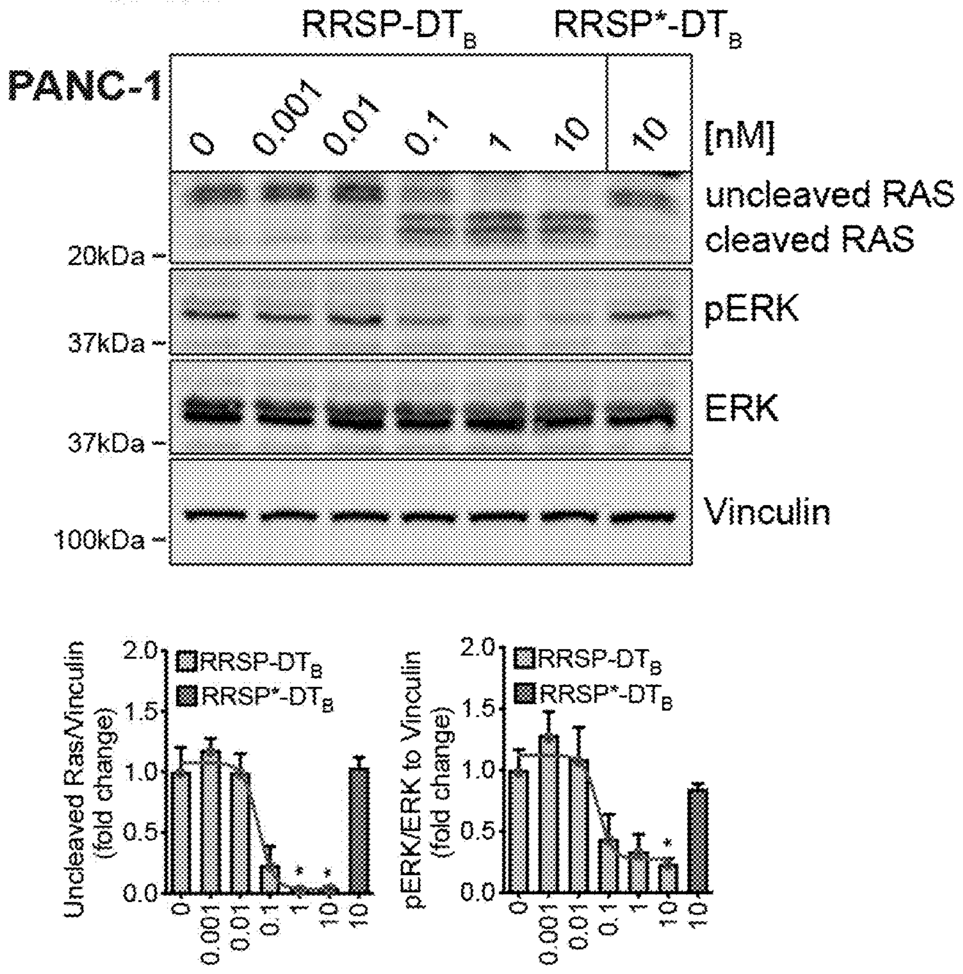

In order to assess intracellular delivery of RRSP via $DT_B$ and successful RAS target engagement, PDAC cells were treated with increasing concentrations of RRSP-$DT_B$ up to 10 nM and with 10 nM of catalytically inactive RRSP*-$DT_B$ for 24 hours. Western blotting of cell lysates showed that RRSP-$DT_B$ cleaved total RAS in all PDAC cell lines with similar picomolar potency (FIG. 43A-E). The half-maximal inhibition concentration ($IC_{50}$) values extrapolated from dose-response curves of uncleaved RAS normalized to vinculin showed that 50% of RAS cleavage was achieved with concentrations ranging between 10 and 280 pM (FIG. 43F). The appearance of cleaved RAS also tracked with a significant reduction in levels of phosphorylated ERK (pERK) in all five cell lines (FIG. 43A-F). Altogether, these data demonstrate successful $DT_B$-mediated delivery of RRSP in PDAC cells and effective target engagement as shown by RAS cleavage and reduced pERK.

RRSP-$DT_B$ Impacts Viability and Proliferation of KRAS-Mutant PDAC Cell Lines

Figure 44A:
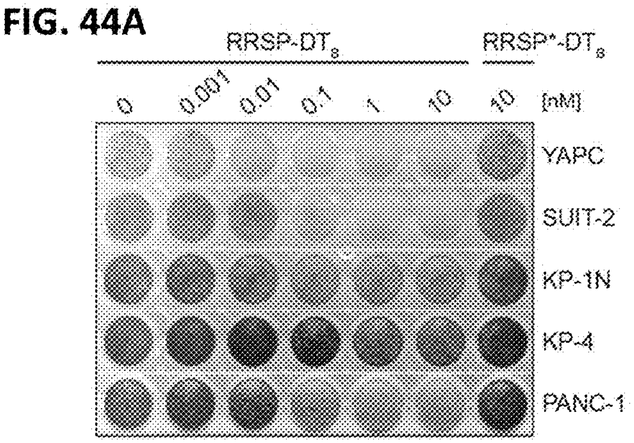
FIG. 44A-44E: Effect of RRSP-$DT_B$ on viability and proliferation of KRAS-mutant PDAC cell lines. (A) Representative image of crystal violet-stained YAPC, SUIT-2, KP-1N, KP-4 and PANC-1 cells following 72 hours of treatment with varying doses of RRSP-$DT_B$ as indicated and 10 nM of RRSP*-$DT_B$ for 72 hours. (B) Dose-response curves showing the effect of RRSP-$DT_B$ and RRSP*-$DT_B$ on viability of multiple PDAC cell lines following 72 hours of treatment and summary of extrapolated $IC_{50}$ values. Results are expressed as mean±SEM (n=3). (C) Dose-response curves of RRSP-$DT_B$ and RRSP*-$DT_B$ on 3D cultures of KP-4 cells and representative pictures of corresponding spheroids. (D) Representative image of crystal violet-stained colonies from YAPC, SUIT-2, KP-1N, KP-4 and PANC-1 cells pretreated with RRSP-$DT_B$ and RRSP*-$DT_B$ for 72 h and replated at low density to form colonies over 14 days. (E) Quantification of colonies shown in (D) from three independent experiments. Results are expressed as means±SD (p<0.01, **p<0.0001 versus corresponding control 0 nM; one-way ANOVA followed by Dunnett's multiple comparison test, n=3).
Figure 44B:
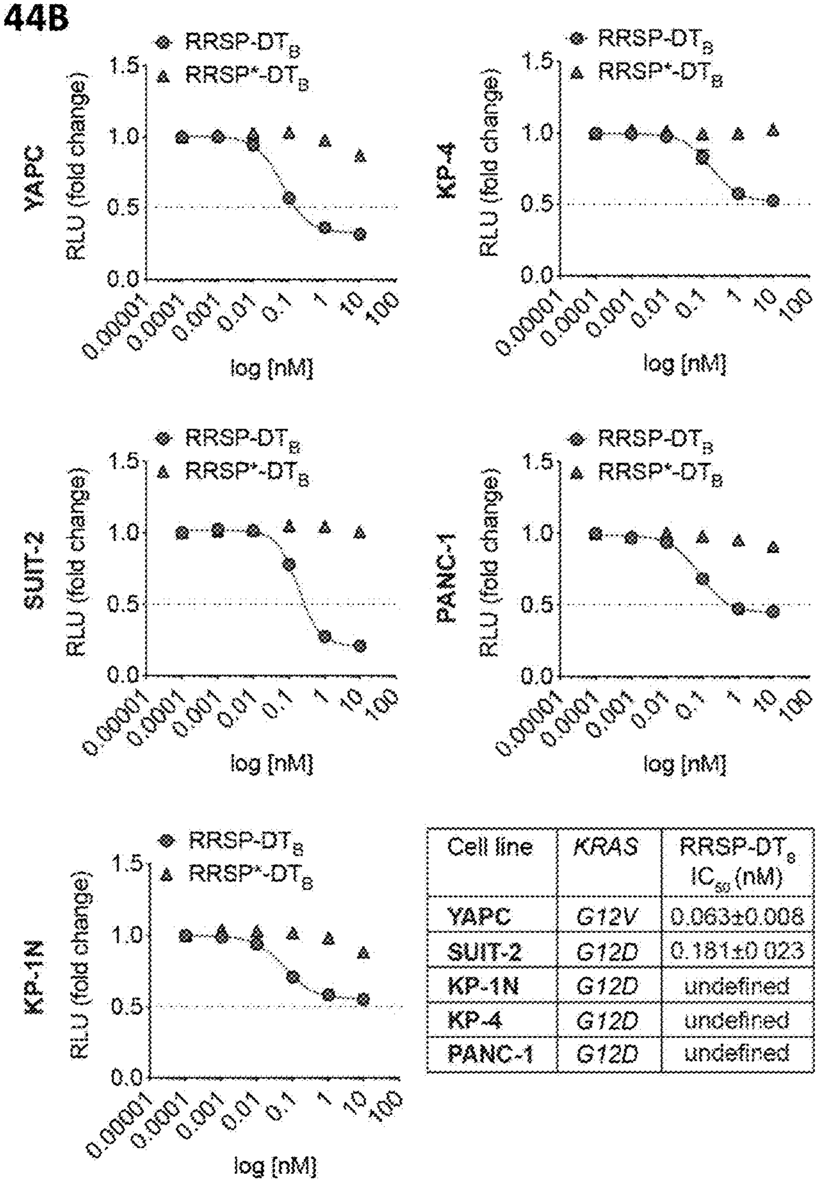
Figure 44D:
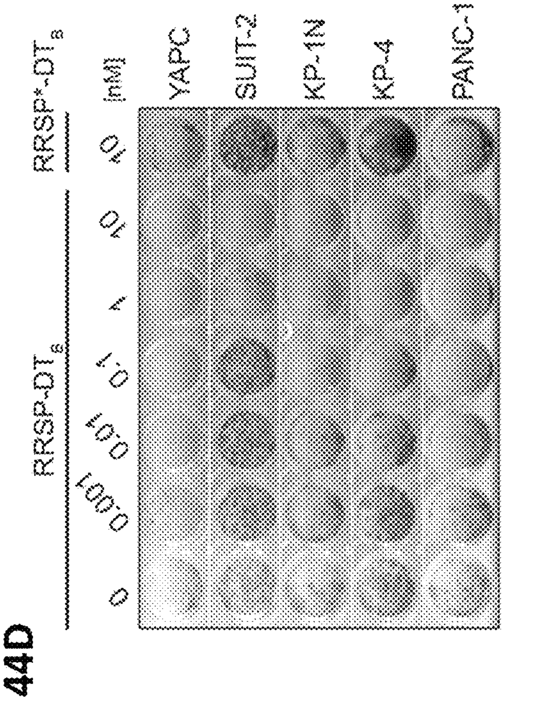
Figure 44C:
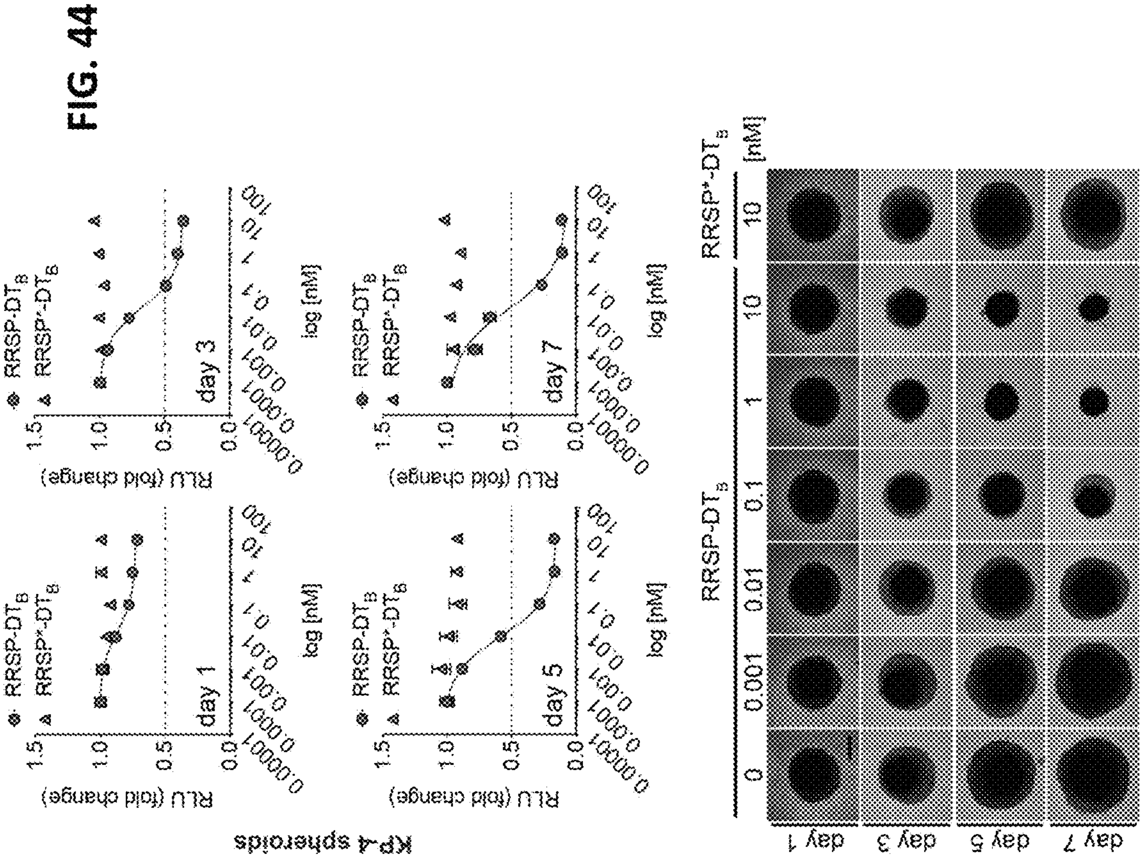
Figure 44E:
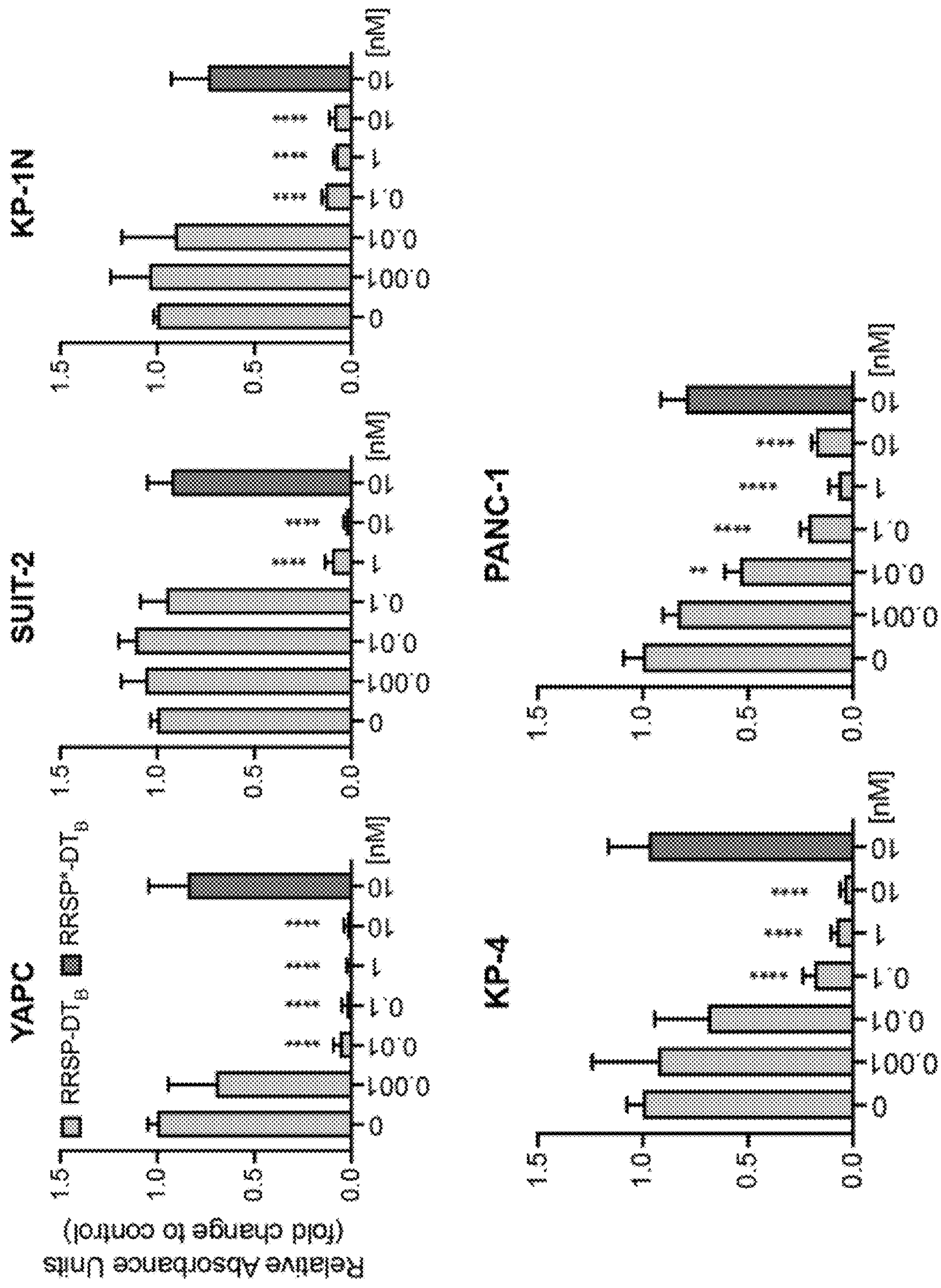
Figure 48B:
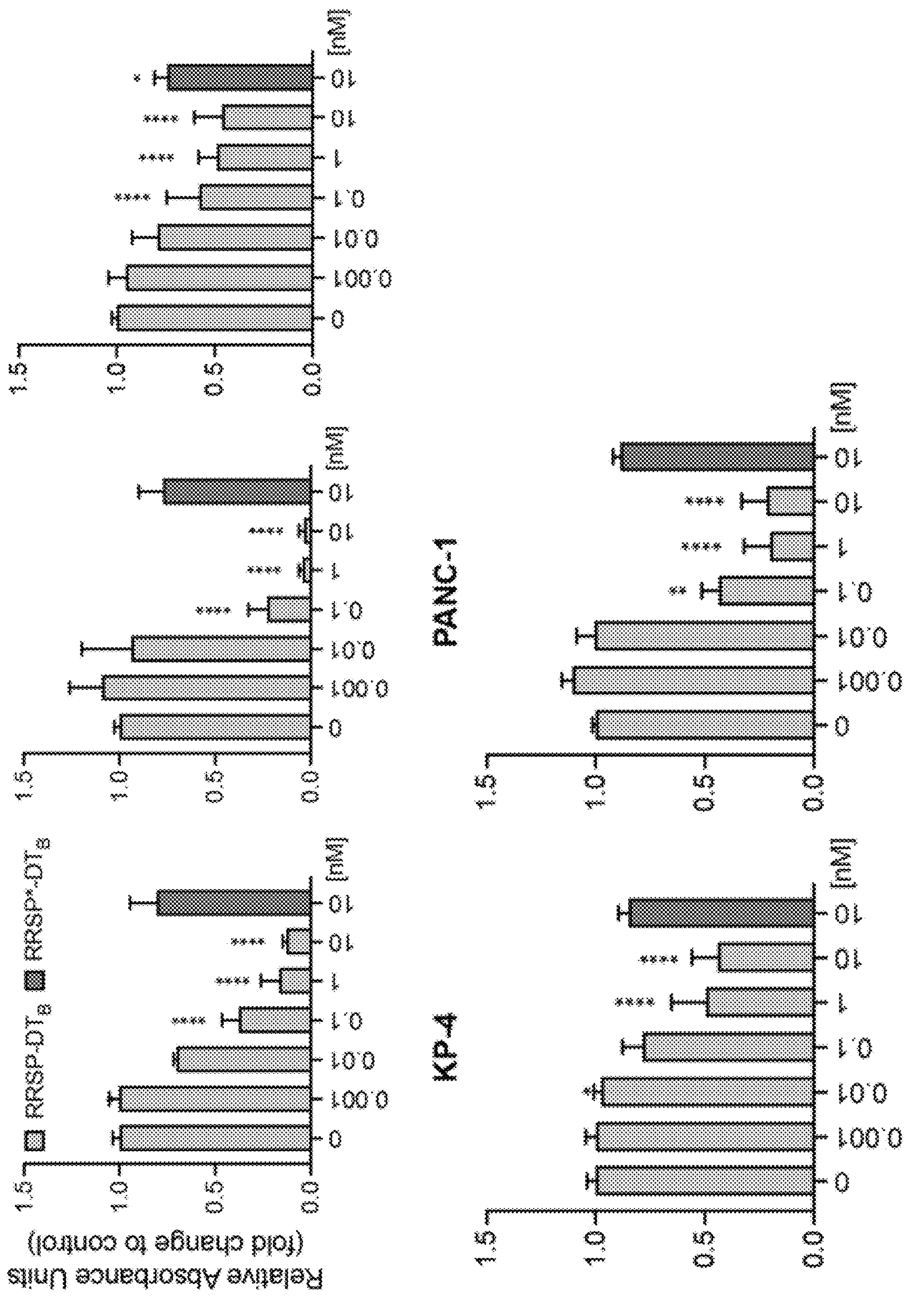

To examine the cytotoxic and/or growth inhibitory effects of RRSP-$DT_B$, the treatment of PDAC cell lines was extended to 72 hours. A crystal violet cytotoxicity assay showed reduced confluency for YAPC and SUIT-2 cells indicating cytotoxicity, and moderate cell loss in KP-1N, KP-4 and PANC-1 cells compared to the control treatments indicating growth inhibition (FIG. 44A and FIG. 48B). Quantitative assessment of cell viability using CellTiter-Glo, which detects metabolic activity, confirmed that YAPC and SUIT-2 cells lost viability with $IC_{50}$ in the picomolar range, while KP-1N, KP-4, and PANC-1 remained viable although with reduced proliferation (FIG. 44B).

Figure 45A:
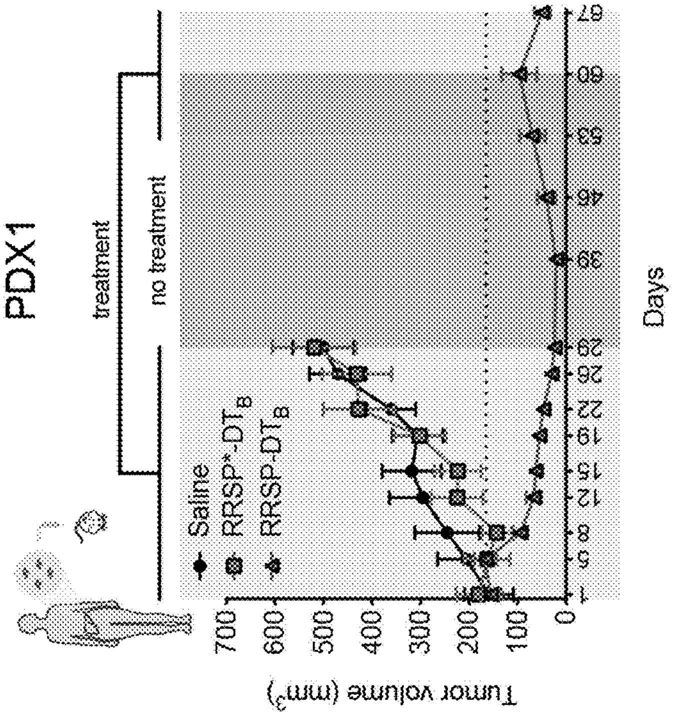
FIG. 45A-45F: Evaluation of the in vivo activity of RRSP-$DT_B$ in KRAS-mutant PDAC PDXs. (A, B) Average growth curves of $KRAS^{G12V}$PDAC PDX tumors from a female donor (A, PDX1) and a male donor (B, PDX2) in NSG mice treated with vehicle (saline), 0.1 mg/kg of RRSP-$DT_B$ and 0.1 mg/kg of RRSP*-$DT_B$. Mice were injected intraperitoneally every day (weekends excluded) for four weeks followed by a drug-washout phase of 24 days (no treatment). Drug treatment was resumed on day 24 in three mice from PDX1 that received 0.1 mg/kg of RRSP-$DT_B$ q.o.d during the first week and q.d. during the second week following washout (A). In PDX2, mice received 0.1 mg/kg of RRSP-$DT_B$ q.d. for four additional weeks after drug washout (B). Dotted lines indicate the average tumor volume on the first day of treatment. In PDX1, grey data point in FIG. 3B and grey bar in FIG. 3C are from a mouse that was euthanized earlier because of excessive tumor burden compare to its weight. (C, D) Representative images of PDX1 (C) and PDX2 (D) tumors at day 29 and corresponding column scatter plots showing individual tumor volumes. Data are means±SEM (n=6 mice per group; p<0.01, **p<0.0001; one-way ANOVA followed by Tukey's multiple comparison test, n=6). (E, F) Waterfall plots depicting tumor regression as percentage change in tumor size from baseline for individual mice.
Figure 45B:
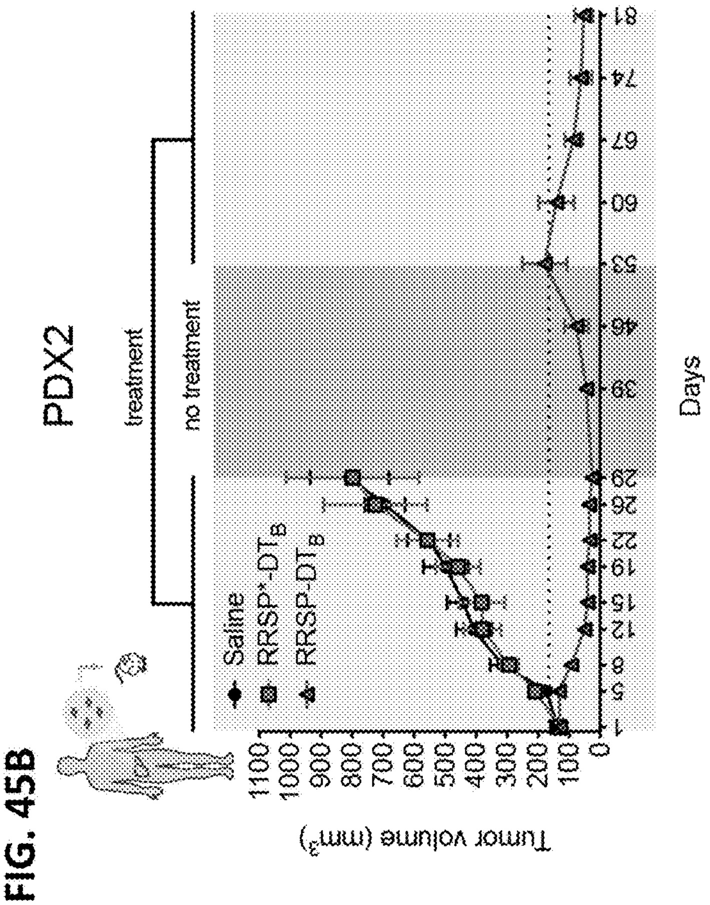
Figure 45C:
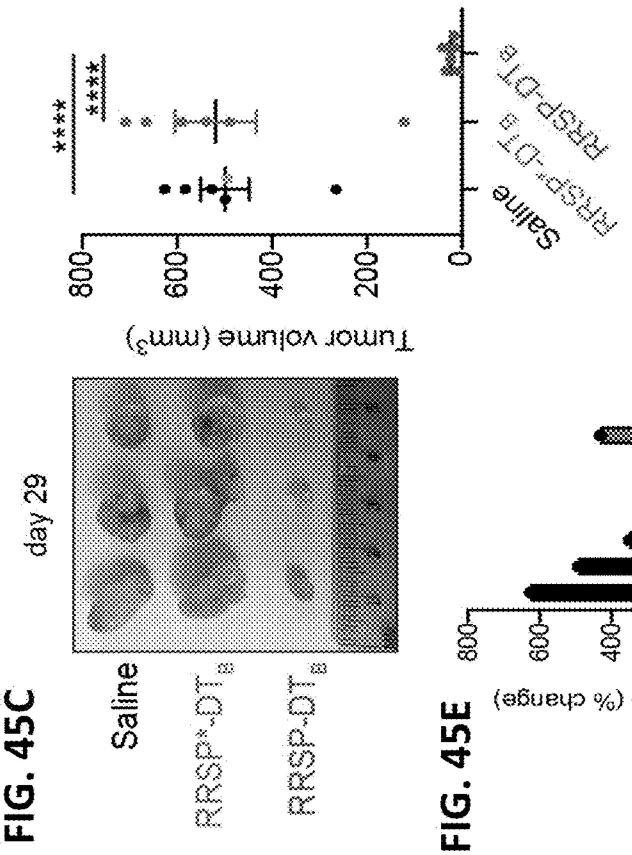

KP-4 cells were found to generate structurally well-defined three-dimensional (3D) spheroids. When treated with RRSP-$DT_B$, these spheroids not only showed a strong dose- and time-dependent reduction of size, but also of viability as measured by the 3D CellTiter-Glo assay (FIG. 45C). These data show that the KRAS-mutant KP-4 cell line became more sensitive to RAS inhibition in 3D spheroid culture conditions compared to monolayers, consistent with previous findings[30].

The sensitivity of all cells to RRSP-$DT_B$ resulting in either cytotoxicity or irreversible growth inhibition was confirmed using a clonogenic assay. Following RRSP-$DT_B$ treatment for 72 hours, cells were harvested, counted, and replated at low density. At day 14, all cell lines failed to form colonies equivalent to the control treatment groups demonstrating an inability of residual cells to proliferate. Overall, these data reveal that RRSP-$DT_B$ strongly affects viability and proliferation of KRAS-mutant PDAC cell lines. Importantly, cell lines previously classified as KRAS-dependent were confirmed to be highly susceptible, and those classified as KRAS-independent (KP-1N, KP-4 and PANC-1)[31] were also sensitive to RRSP-$DT_B$ treatment.

RRSP-$DT_B$ Leads to In Vivo Regression of KRAS-Mutant PDAC Xenografts

Figure 45D:
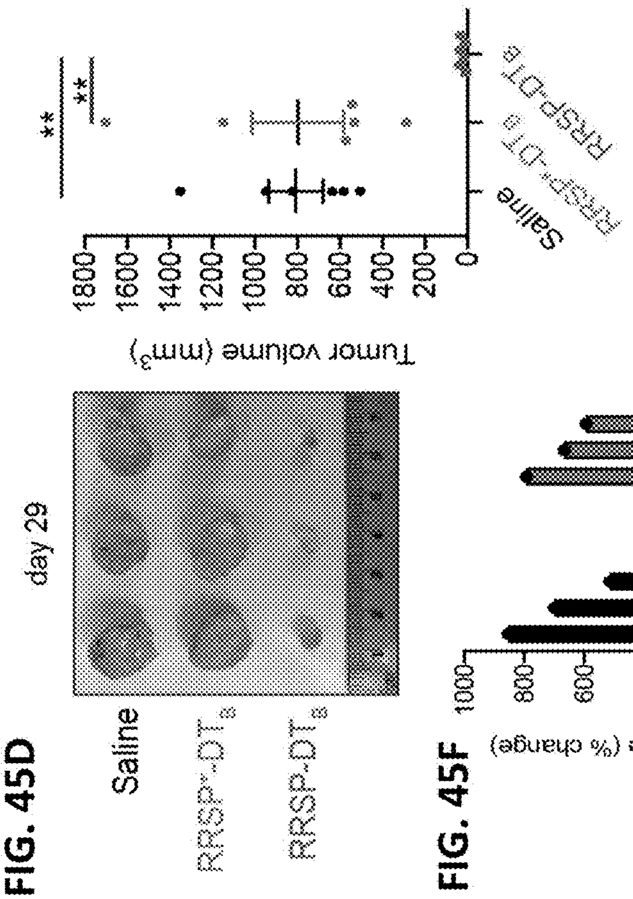
Figure 45E:
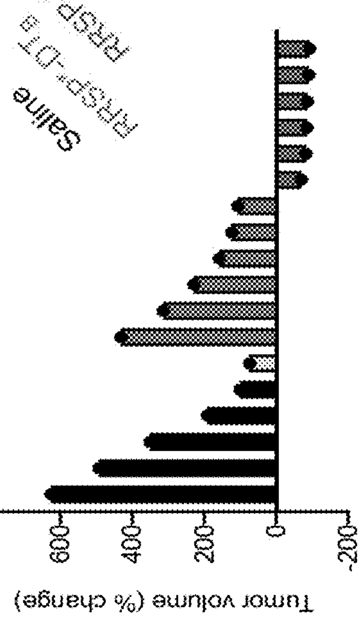
Figure 45F:
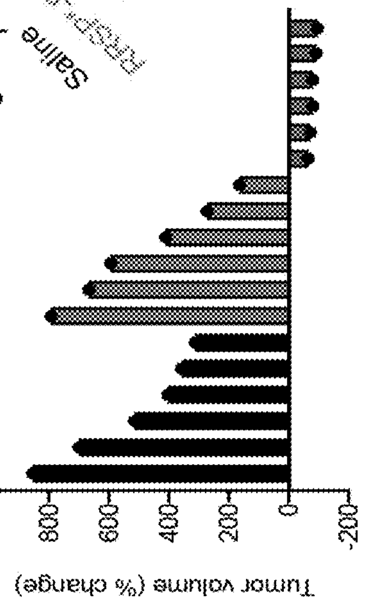

Patient-derived xenografts (PDXs) are a powerful tool in translational cancer research because they retain biological characteristics of the parental tumor specimens and can better predict a patient response to an investigational drug than classic cell line-based in vivo models of cancer[32]. We established two PDAC PDX models, one from a female donor (PDX1) and one from a male donor (PDX2), both harboring a KRAS G12V mutation, which accounts for 30% of KRAS mutations in PDAC[27]. NSG mice were engrafted with patient-derived PDAC tumors (eighteen mice per PDX group) and then six mice per group were treated i.p. with 0.1 mg/kg of RRSP-$DT_B$ or RRSP*-$DT_B$ once per day (q.d.) for 4 weeks (weekends excluded) or were mock-injected with saline. RAS inhibition by RRSP-$DT_B$ significantly reduced the growth of subcutaneously implanted KRAS-mutant PDX1 and PDX2 tumors, starting as soon as 8 days after treatment initiation (FIGS. 45A and 45B). After four weeks of treatment, on day 29, maximum growth inhibition was observed (FIGS. 45C and 45D). In both PDX1 and PDX2 studies, tumor regression, not just inhibition of tumor growth, was observed in all twelve mice treated with RRSP-$DT_B$ indicating successful treatment of pre-established tumors (FIGS. 45E and 45F). The reduction of tumor size was specifically due to the proteolytic action of RRSP, since the catalytically inactive RRSP*-$DT_B$ did not affect tumor growth.

In order to determine whether tumor growth occurred in residual tumors after stopping the treatment, three mice from the RRSP-$DT_B$ group were left untreated from day 29 for about three weeks and tumor growth was regularly monitored. In both PDX1 and PDX2, we did not observe an increase in tumor size during the first 10 days (day 29-39) following RRSP-$DT_B$ withdrawal. Between day 39 and day 53, a slight increase in tumor size occurred in mice from PDX1 (FIG. 45A) and PDX2 (FIG. 45B), where the average tumor size reached the initial baseline. On day 53, treatment with RRSP-$DT_B$ was reinitiated. The treatment of PDX1 mice was originally de-escalated to every other day (q.o.d). As there was no reduction in tumor size after one week, RRSP-$DT_B$ treatment frequency was increased to five days per week during the second week. Increase in the treatment frequency ultimately led to a reduction in tumor size (FIG. 45A).

Figure 49A:
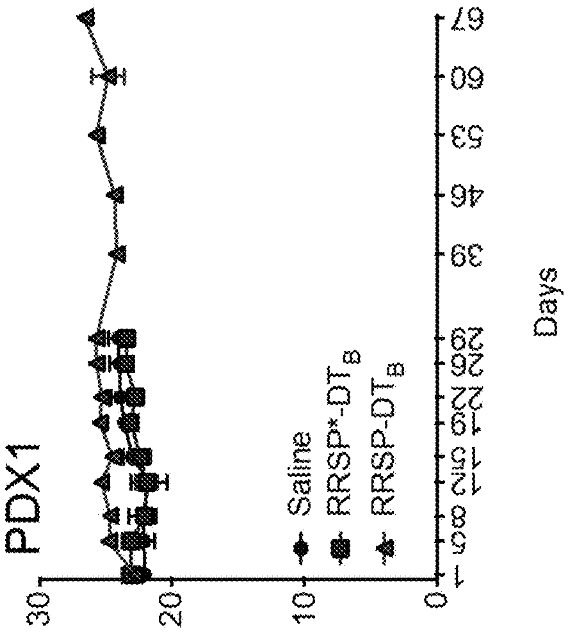
FIG. 49A-49B. Monitoring of mouse weight during PDX studies. (A) and (B) Mouse weight was recorded during PDX1 (A) and PDX2 (B) studies and plotted against time (days).
Figure 49B:
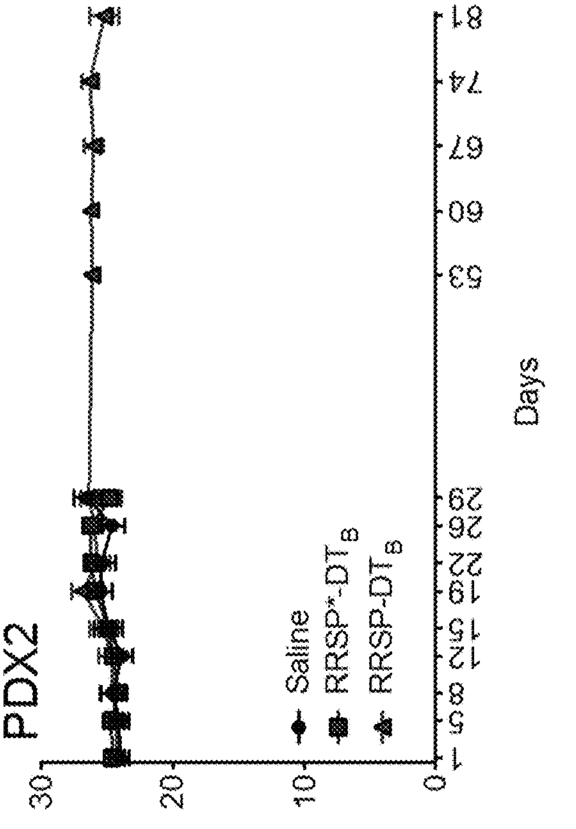

Since tumors from PDX2 had a higher growth rate compared to those from PDX1, mice were retreated with RRSP-$DT_B$ once per day (q.d.) for four weeks. At the end of this additional four-week treatment cycle, tumors reached a size comparable to that observed around day 39 (FIG. 45B). Of importance, RRSP-$DT_B$ treatment was well tolerated in mice, as demonstrated by the lack of weight loss (FIG. 49) across both treatment cycles.

Altogether, these data demonstrate that RRSP-$DT_B$ treatment resulted in rapid in vivo regression of PDAC PDXs. Most importantly, PDAC tumors retained sensitivity to RRSP-$DT_B$ over time, did not develop resistance and remained sensitive for a second round of treatment.

Figure 46A:
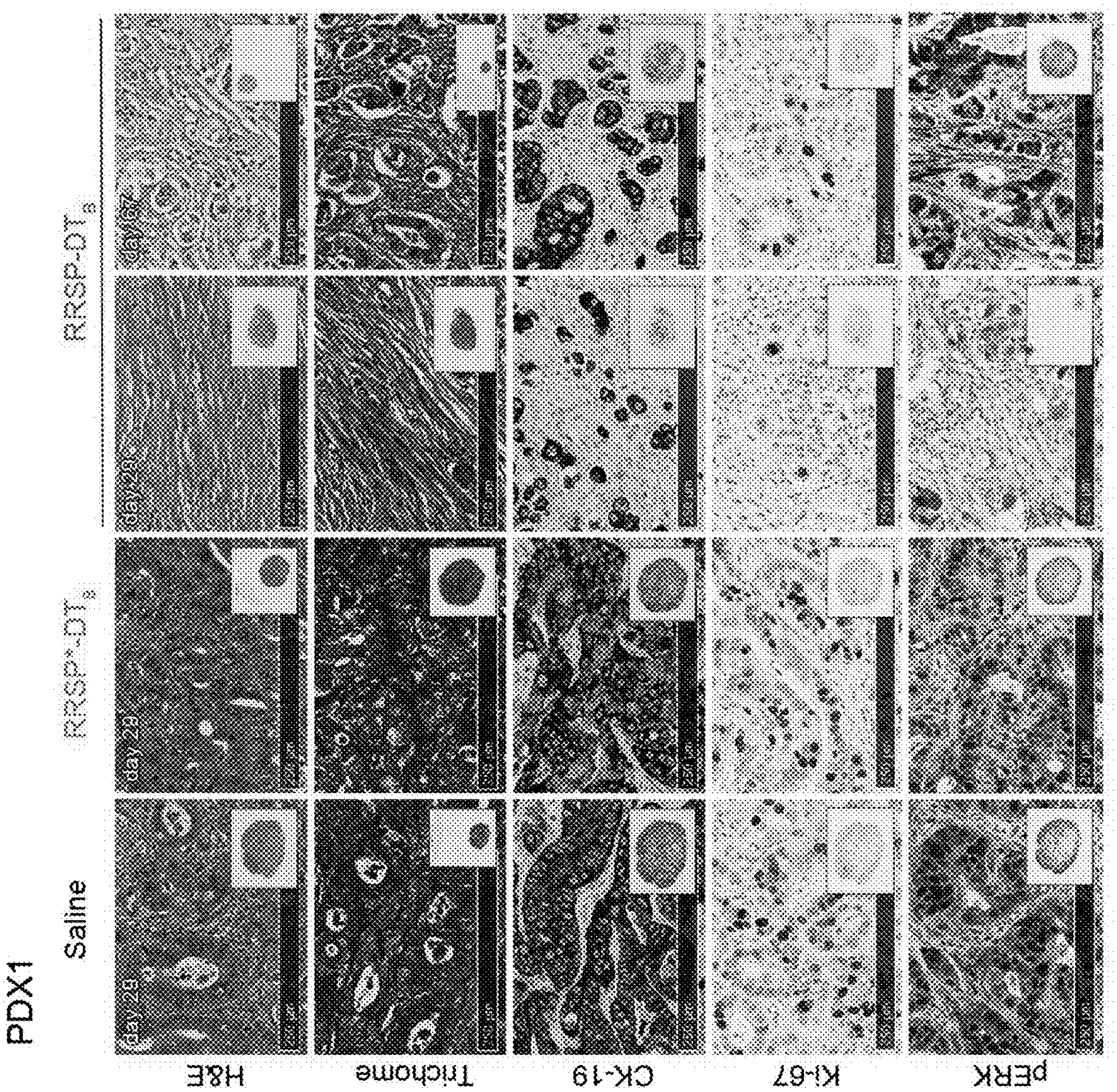
FIG. 46A-46H: Histological and immunohistochemical analysis of PDAC PDX tumors following treatment with RRSP-$DT_B$. (A, B) Representative images of saline, RRSP*-$DT_B$ and RRSP-$DT_B$-treated PDAC PDX1 (A) and PDX2 (B) tumors stained with H&E and Masson's trichrome stain as well as CK-19, Ki-67 and pERK antibodies (scale bar=250 μm). (C-E) Bar plots represent cell positivity to CK-19, Ki-67 and pERK antibodies expressed as the percentage of immunoreactive cells in the entire tumor sections in PDX1 and (F-H) PDX2. Data are means±SEM (*p<0.05, p<0.01, *p<0.001, ****p<0.0001 versus saline; #p<0.05, ##p<0.01, ###p<0.001 versus RRSP*-$DT_B$; one-way ANOVA followed by Tukey's multiple comparison test, n=3).
Figure 46B:
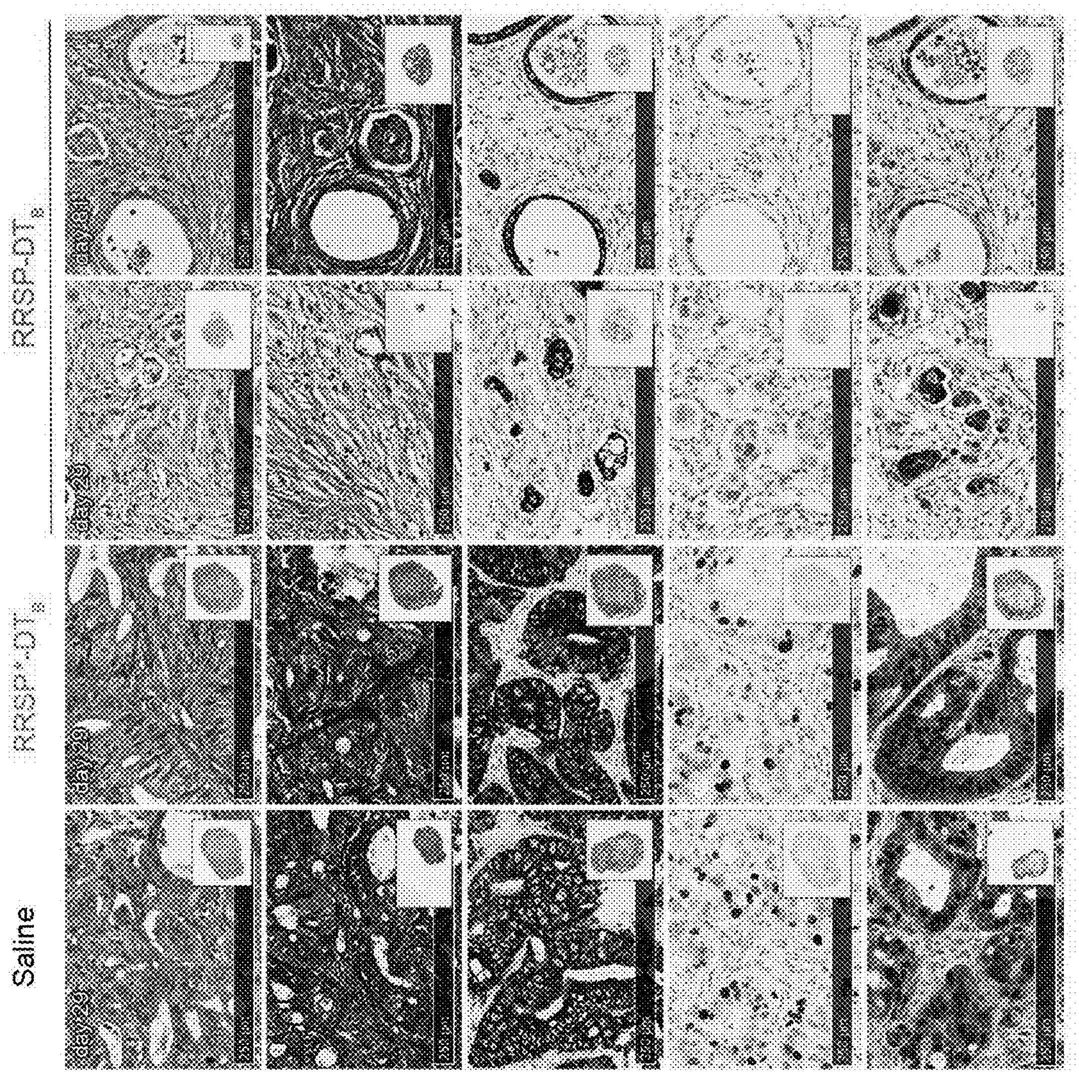
Figure 50A:
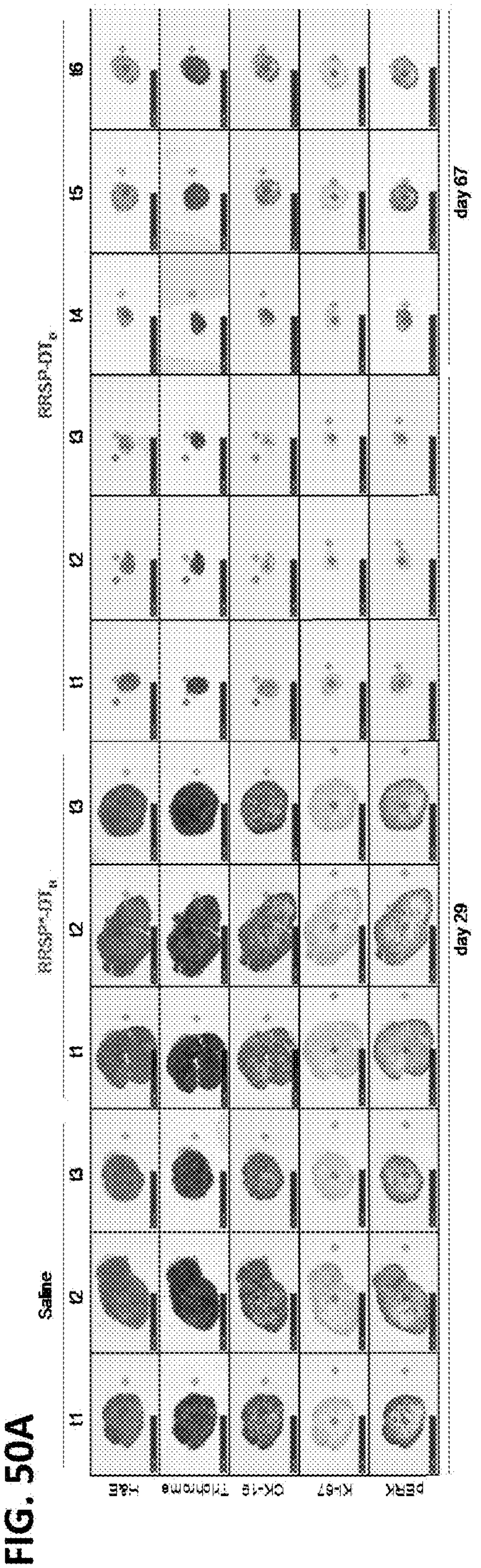
FIG. 50A-50B. Whole tumor sections from PDX1 and PDX2 studies. (A) and (B) Whole tumor sections from PDX1 (A) and PDX2 (B) studies stained with hematoxylin and eosin, Masson's trichrome staining, CK-19, Ki-67 and pERK antibodies from three mice per group (saline and RRSP*-$DT_B$) and all six mice in the RRSP*-$DT_B$ group. Scale bar=10 mm.
Figure 50B:
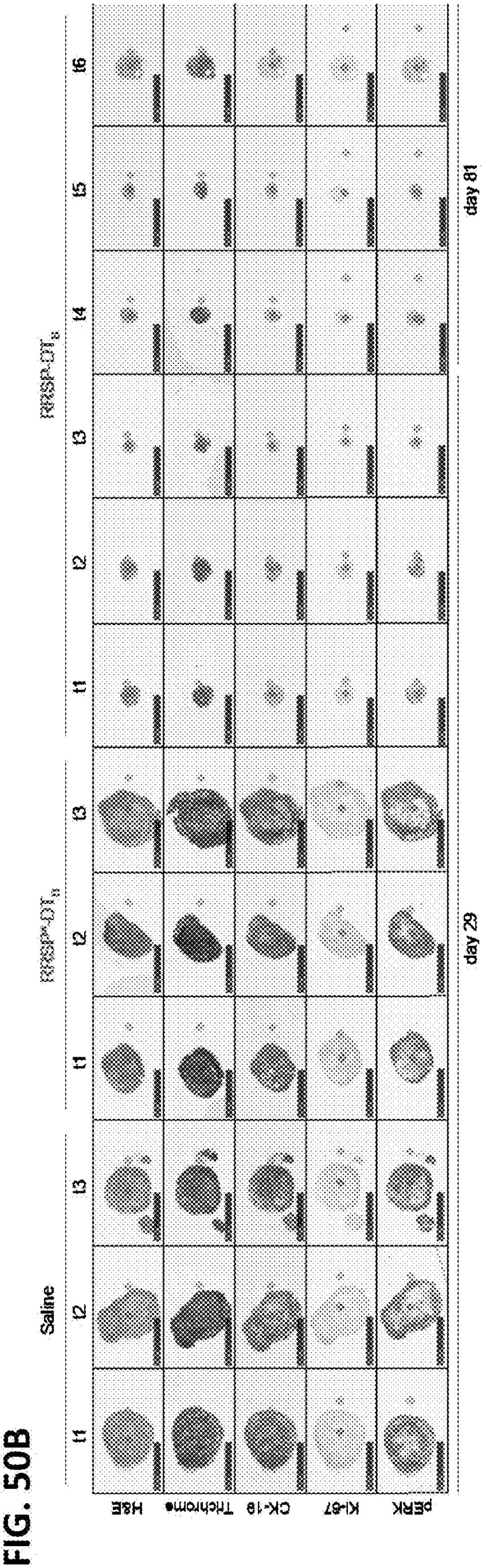

RRSP-$DT_B$ Treatment Results in Increased Fibrosis, Reduced Proliferation and Downregulation of pERK in In Vivo PDAC Tumors Histological and immunohistochemical analysis showed that the large PDX tumors resected from vehicle- and RRSP*-$DT_B$-treated mice were characterized by small glandular components and extensive necrosis in the inner tumor core typical of clinical PDAC. By contrast, tumors from mice treated with RRSP-$DT_B$ showed absence of necrosis, reduction in the cell number, larger residual tumor cells and appearance of vacuolar structures indicative of tissue degeneration (FIG. 50). In addition, RRSP-$DT_B$-treated tumors were highly fibrotic (FIGS. 46A and 46B).

Figures 46C, 46D, 46E, 46F, 46G, 46H:
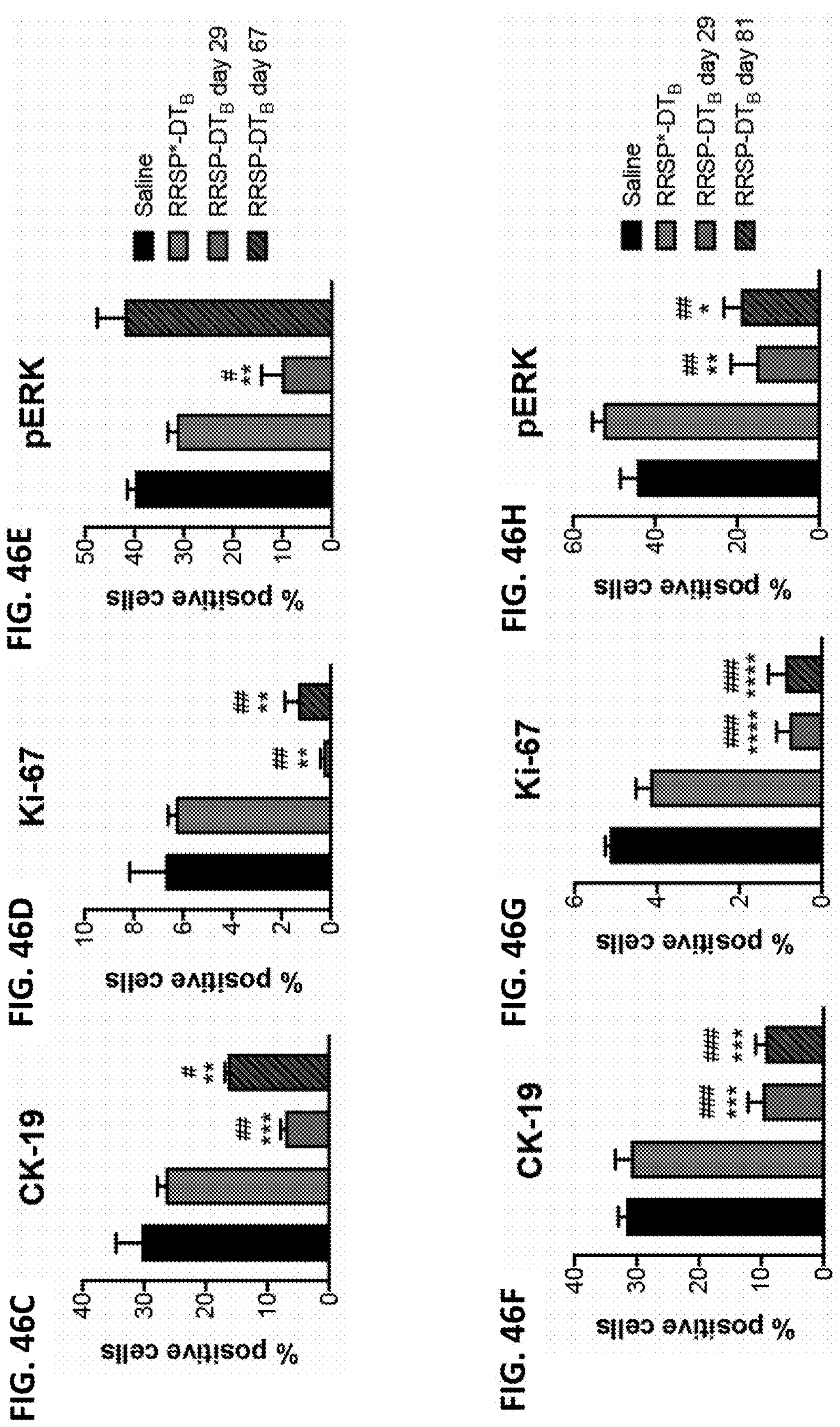

Cytokeratin 19 (CK-19) is a characteristic ductal epithelial marker and poor prognostic factor in PDAC 33, 34 The percentage of cells in the tumors that stained positive for CK-19 was significantly lower in all tumors treated with RRSP-$DT_B$ compared to saline and RRSP*-$DT_B$-treated mice (FIGS. 46C and 46F). This result indicated that fewer PDAC cells were present in the residual tumors. In addition, tumors from mice in the RRSP-$DT_B$ treatment group showed a marked reduction in proliferating Ki-67 positive cells, both after the first 4 weeks of treatment and also after the second treatment regimen that started at day 53 (FIGS. 46D and 46G).

Figure 51A:
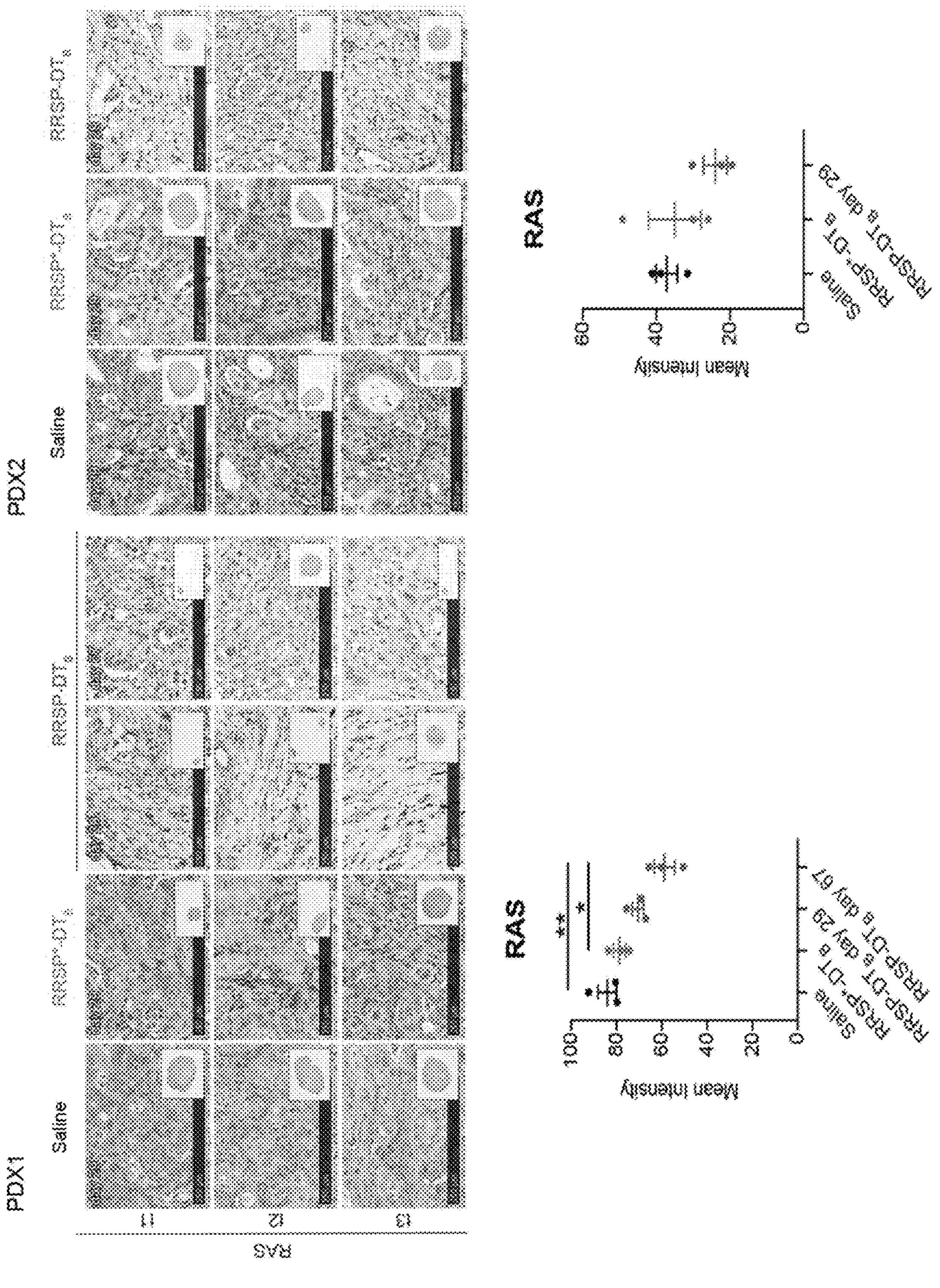
FIG. 51A. Immunohistochemical analysis of total RAS levels in PDAC PDX tumors following treatment with RRSP-$DT_B$. (A) Representative images of saline, RRSP*-$DT_B$ and RRSP-$DT_B$-treated PDAC PDX1 and PDX2 tumors stained with an anti-RAS antibody (scale bar=250 μm) and corresponding jitter plots representing the mean DAB intensity of RAS antibody in the entire tumor sections. Data are means±SEM (*$p<0.05$, **$p<0.01$; one-way ANOVA, n=3).

In addition, PDAC tumors from PDX1 and PDX2 excised at day 29 showed significantly lower detection of pERK compared to saline and RRSP*-$DT_B$-treated tumors (FIGS. 46E and 46H). In PDX1, we observed an increase in pERK levels on day 67 in tumors from mice that received RRSP-$DT_B$ every other day (q.o.d) during the first week and once per day (q.d.) during the second week following RRSP-$DT_B$ withdrawal. This tracked with a higher percentage of residual cancer cells positive to CK-19 and Ki-67 compared to day 29. By contrast, in mice from PDX2 that received the more aggressive second round of treatment, low levels of pERK were also observed in tumors resected on day 81. Analysis of total RAS levels showed significant reduction of RAS expression in sections from tumors treated with RRSP-$DT_B$ at day 67 in PDX1 and, although not significant, a similar trend was observed in PDX2 at day 29 (FIG. 51). RAS levels in histological sections from PDX2 tumors at day 81 are not shown because of staining-related technical issues.

Figure 52A:
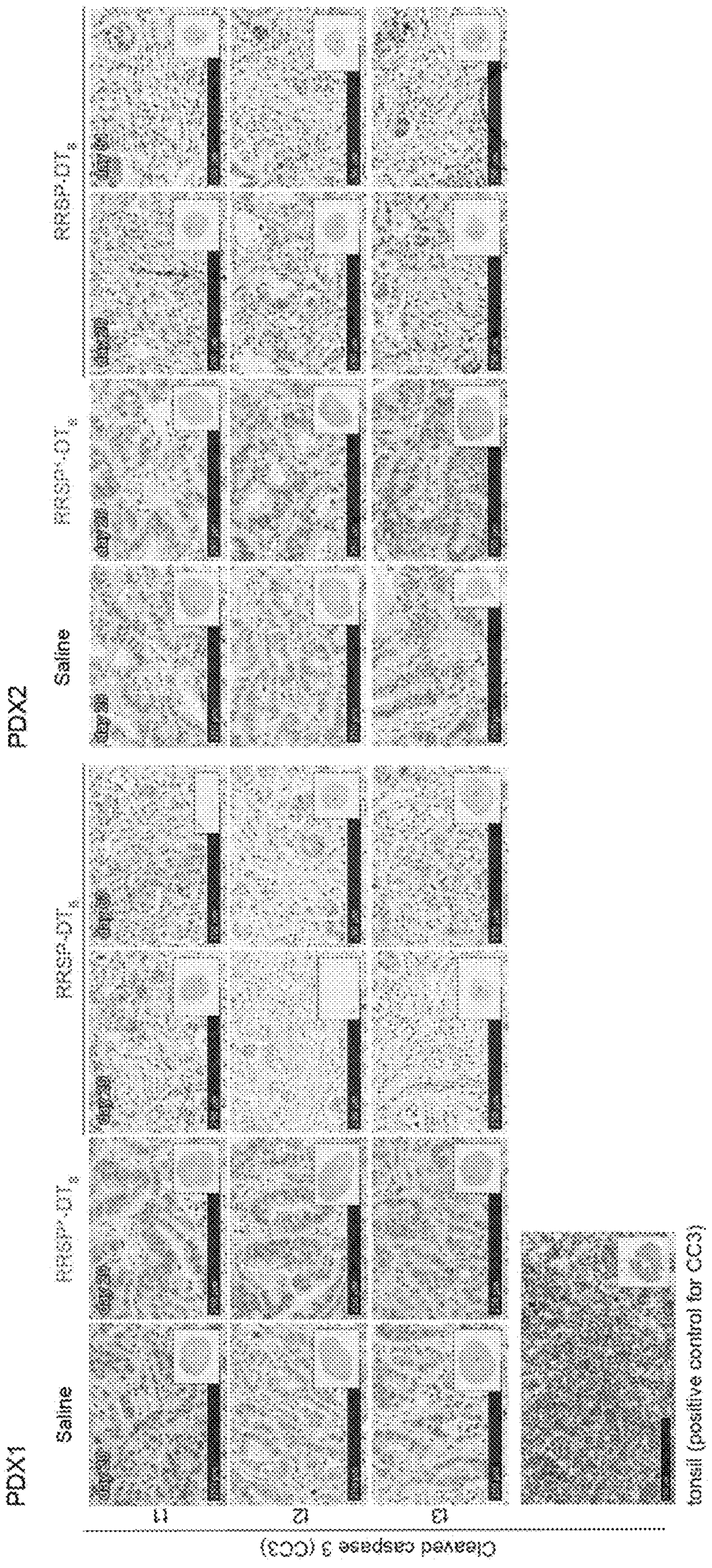
FIG. 52A-52B. Immunohistochemical analysis of cleaved caspase 3 in PDAC PDX tumors and caspase 3/7 activity in PDAC cell lines following treatment with RRSP-$DT_B$. (A) Representative images of saline, RRSP*-$DT_B$ and RRSP-$DT_B$-treated PDAC PDX1 and PDX2 tumors stained with an anti-cleaved caspase 3 (CC3) antibody (scale bar=250 μm). A section from human tonsils was used as positive control for CC3. (B) Activity of caspase 3/7 in PDAC cell lines after 24- and 48-hour treatment with RRSP*-$DT_B$ and RRSP-$DT_B$ at the indicated concentrations. Data are means±SEM (*$p<0.05$, $p<0.01$, *$p<0.001$ vs corresponding vehicle control; one-way ANOVA, n=3).
Figure 52B:
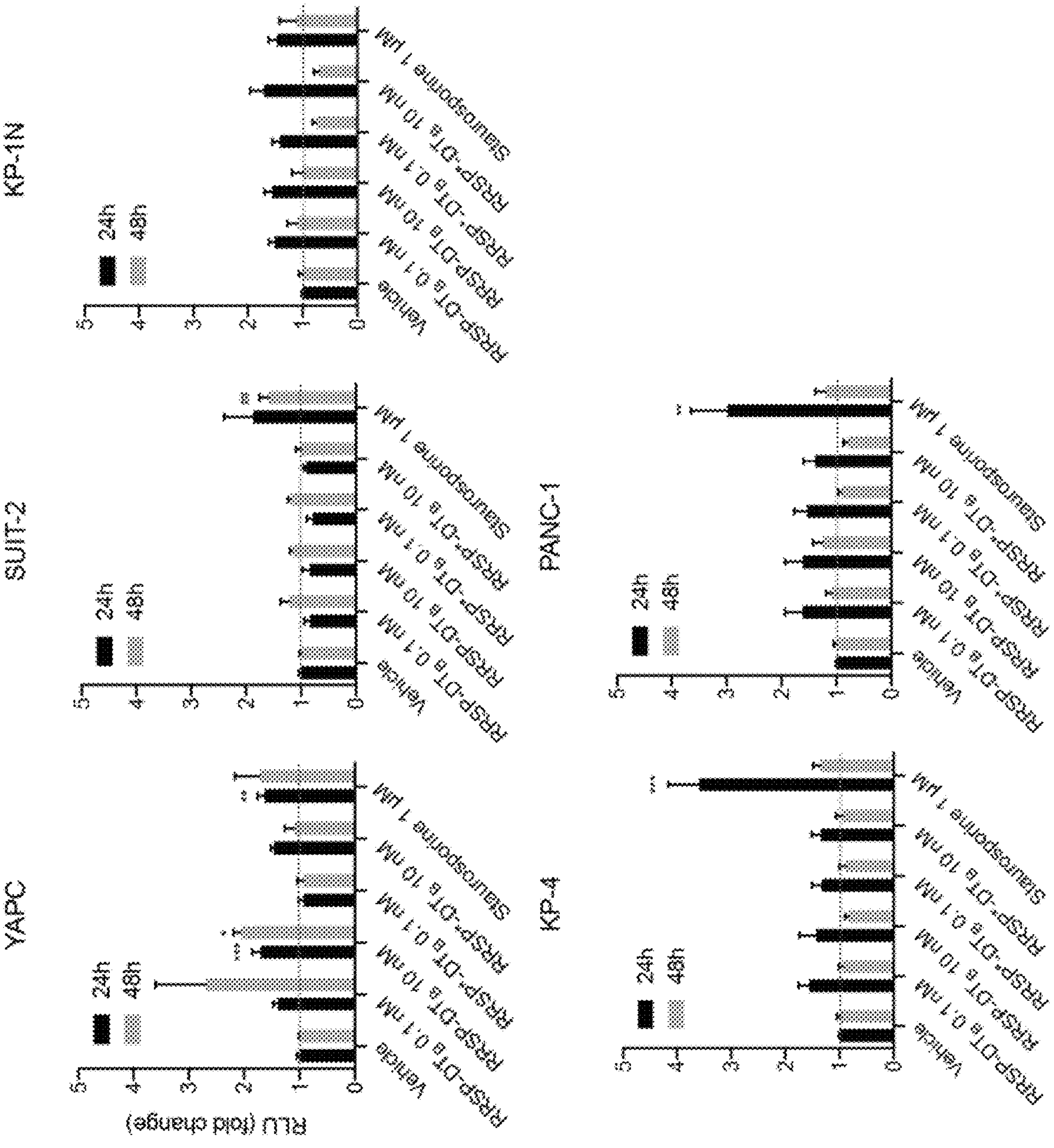

Next, to investigate whether apoptosis was involved in RRSP-$DT_B$-mediated anti-tumor activity, cleaved caspase 3 (CC3) expression was assessed in both PDX1 and PDX2. No changes in CC3 levels were detected in tumors treated with RRSP-$DT_B$ compared to controls. Similarly, activation of caspase 3/7 was not observed in four out of five PDAC cell lines tested. Only YAPC cells showed an increase of caspase 3/7 activity upon treatment with RRSP-$DT_B$ (FIG. 52).

Taken together, these results demonstrate that treatment of PDAC PDXs with RRSP-$DT_B$ leads to significant reduction in the percentage of cancer cells, increased fibrosis and decreased proliferation independently of apoptosis. Importantly, RRSP-$DT_B$ strongly reduces pERK levels, which is indicative of effective downstream RAS signaling downregulation.

Evaluation of the In Vivo Stability of RRSP-$DT_B$ in Immunocompetent Mice

An important aspect underlying the translatability of RRSP-$DT_B$ as an anticancer agent is to determine its in vivo stability. In order to do this, immunocompetent C57/BL6 mice were given a single i.p. injection of 0.1 or 0.5 mg/kg of RRSP-$DT_B$. Serum from mice collected one and 16 hours after injection was diluted 1:100 and then was added to YAPC and KP-4 cells to test for recovery of cellular active RRSP-$DT_B$ from the bloodstream.

Figure 47A:
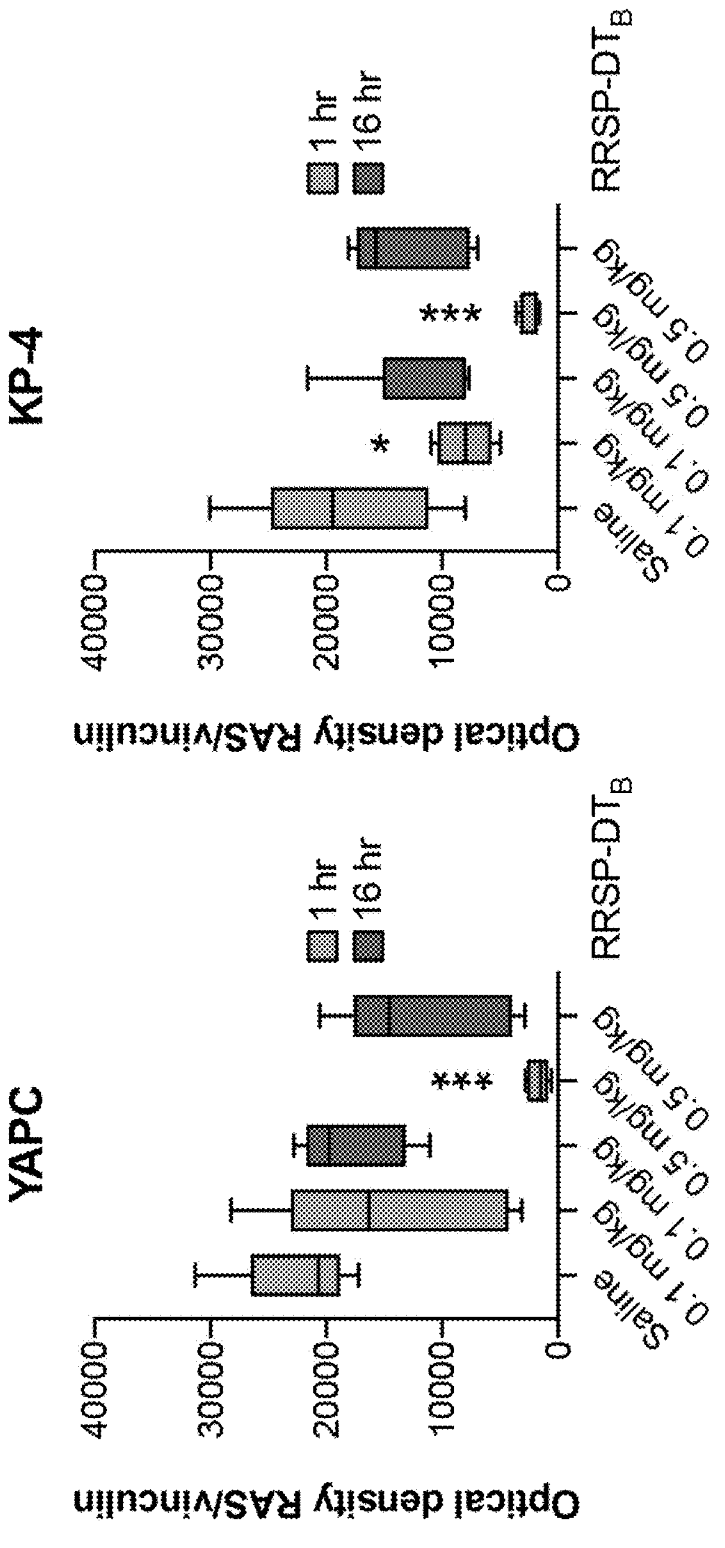
FIG. 47A: Stability of RRSP-$DT_B$ in sera from immunocompetent mice. (A) Densitometric quantification of total RAS levels in KRAS-mutant YAPC and KP-4 cells treated with serum from mice that were previously injected with 0.1 mg/kg or 0.5 mg/kg of RRSP-$DT_B$ for 1 hour and 16 hours. Each bar represents the mean±SEM of RAS levels from 5 different mice per group (*$p<0.05$, ***$p<0.001$ versus saline; one-way ANOVA followed by Dunnett's multiple comparison test, n=5).
Figure 53A:
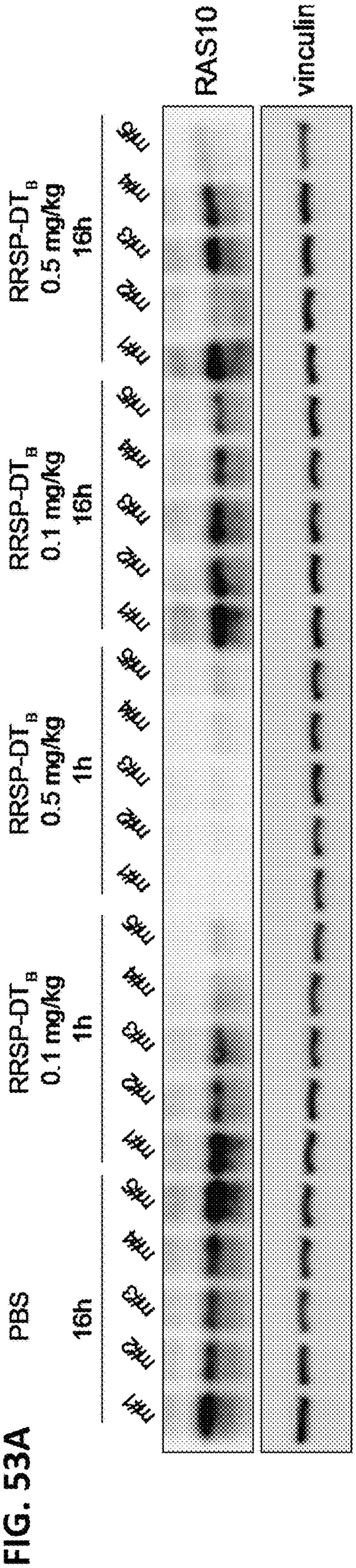
FIG. 53A-53B. Western blot images of RAS levels in YAPC and KP-4 cell lines treated with sera from mice previously exposed to RRSP-$DT_B$. (A) and (B) Western blots showing total RAS levels in YAPC (A) and KP-4 (B) cells treated for 24 hours with serum from immunocompetent mice treated with RRSP-$DT_B$ at 0.1 mg/kg or 0.5 mg/kg for 1 hour and 16 hours. Five mice for each treatment group were employed. Vinculin was used as loading control.
Figure 53B:
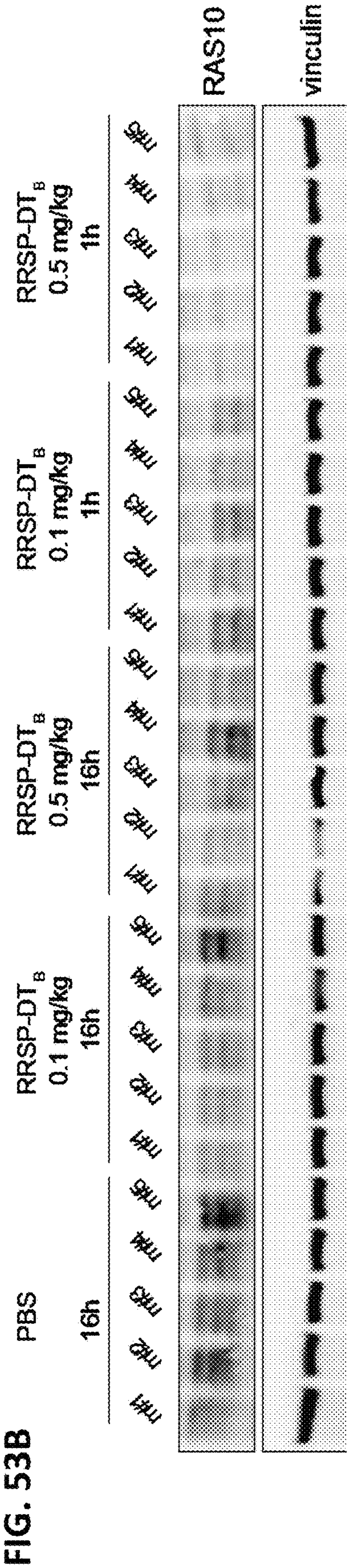

We found that in sera from mice that received 0.5 mg/kg of RRSP-$DT_B$ for one hour, RRSP-$DT_B$ was active. Indeed, a remarkable reduction in RAS levels was observed in both YAPC and KP-4 cells treated with mouse sera. In KP-4 cells, reduced RAS levels were also detected at 0.1 mg/kg of RRSP-$DT_B$. We did not observe a significant decrease of RAS levels in cells treated with sera from mice that received RRSP-$DT_B$ for 16 hours (FIG. 47A and FIG. 53), suggesting that RRSP-$DT_B$ that had been exposed to mouse serum for a longer time became less active and was not able to significantly reduce RAS levels as efficiently as at earlier times.

Discussion

Aberrant KRAS signaling is considered the core hallmark of pancreatic cancer onset and progression[35]. Although significant advances have been made over recent years in the treatment of pancreatic cancer[36], there are currently no KRAS inhibitors approved for PDAC, which still remains an urgent unmet medical need in oncology.

We recently reported the therapeutic potential of biologic RRSP-$DT_B$ as a potent pan-RAS inhibitor that halts tumor growth of multiple TNBC and CRC xenografts harboring either wild-type or mutant RAS[37]. The NCI-60 human tumor cell line screening revealed that RRSP-$DT_B$, in addition to its potency, has a broad spectrum of antitumor activity against several cancer types[20]. Because the NCI-60 screen does not include pancreatic cancer, we tested RRSP-$DT_B$ on a panel of five KRAS-mutant PDAC cell lines and demonstrated that picomolar concentrations of RRSP-$DT_B$ leads to growth inhibition and loss of cell proliferation, although only cells treated with the highest dose of 10 nM showed loss of metabolic activity. This was not completely unexpected since KP-1N, KP-4 and PANC-1 cells were previously classified as KRAS-independent by Singh and coauthors[31]. Interestingly, when KRAS-independent KP-4 cells were cultured as 3D spheroids, a stronger decrease in viability and spheroids' size was observed compared to monolayers. We believe the greater sensitivity of KP-4 spheroids to RRSP-$DT_B$ might be due to the 3D suspension culture environment, thus corroborating previous findings showing that different culture systems have an impact on KRAS dependency[30]. These data confirm that PDAC cell lines previously listed as KRAS-dependent were extremely susceptible to RRSP-$DT_B$. Most importantly, long-lasting growth inhibitory effects were seen in mutant KRAS-independent PDAC cell lines as well. Although the mechanisms underlying RRSP-$DT_B$-induced growth inhibition in PDAC cell lines are still unknown, we have recently demonstrated that RRSP-$DT_B$ can lead to irreversible G1 cell cycle growth arrest via p27, induce a senescence-like phenotype and trigger apoptosis in a subset of colorectal cancer cell lines[38]. Our data show that apoptosis is not overall activated in PDAC tumors or cell lines following RRSP-$DT_B$ treatment. Although this was surprising, it was not completely unexpected since, in a bacterial pathogenesis context, toxins such as RRSP have evolved to hijack cellular pathways in order to avoid host innate responses and promote systemic spread without killing of the host. Overall, our data suggest that the main mechanisms underlying RRSP's antitumor activity involve cell cycle arrest and/or senescence rather than apoptosis[26]. In support of our findings, an independent study has recently shown that RRSP from *Photorhabdus asymbiotica*, which is 73% similar in amino acid sequence to RRSP from *Vibrio vulnificus*, also cleaves RAS[24] and induces G1 cell cycle arrest via direct binding to CDK1[39].

Our data suggest that, unlike currently available KRAS inhibitors, RRSP-$DT_B$ has the potential to target undruggable KRAS in a wide spectrum of KRAS-mutant pancreatic cancers whether they rely or not on KRAS for survival. One of the inherent advantages of RRSP is that it cleaves all RAS isoforms, mutant and wild-type, thus representing a potent strategy to inhibit tumor growth. While one line of research has been focusing on targeting mutant KRAS only with molecules that enter all cells to ensure safety, our current efforts are directed to transporting RRSP preferentially into cancer cells while sparing normal cells, an approach previously found to be successful for other toxin-based targeting strategies[40, 41], including the therapeutic Lumoxiti®, which is an FDA-approved treatment for hairy cell leukemia[42].

RRSP-$DT_B$ has been shown to halt tumor growth in mouse xenografts derived from TNBC and CRC cell lines[37]. Here, we report that administration of RRSP-$DT_B$ to NSG mice bearing KRAS-mutant PDAC PDXs not only slowed tumor growth, but also led to tumor regression as early as one week after treatment initiation. Following a drug washout period, tumors from both PDX1 and PDX2 started to slowly regrow. Most importantly, upon re-administration of RRSP-$DT_B$, these tumors maintain sensitivity to the drug without becoming resistant, which is something rarely seen in monotherapy regimens and might be advantageous for future development of RRSP as an anticancer therapeutic. Lack of resistance could also be explained by the fact that at day 29 residual tumors are mainly composed by a dense network of collagen fibers with few interspersed CK-19-positive PDAC cancer cells that can be readily targeted by RRSP-$DT_B$. PDAC tumors have extensive fibrosis, which is believed to contribute to their resistance to most therapies.

We showed that RRSP-$DT_B$ increased intracellular fibrosis in vivo, which could be considered disadvantageous. However, contrary to expectations, experimental[43, 44] and clinical[45] studies have demonstrated that depletion of the stroma component of PDAC results in more aggressive tumors in mice and worse outcomes in patients. Therefore, rather that depleting the stroma, strategies that specifically target or modify the extracellular matrix (ECM) are preferred and currently being investigated in PDAC. Although we do not have a definitive answer to the question of whether RRSP-mediated increase in fibrosis is advantageous or disadvantageous following RRSP-$DT_B$ treatment, based on the available literature and our findings, we can speculate that it will be beneficial. In addition, we believe that because $DT_B$ has been shown to be extremely efficient at delivering RRSP in cells expressing the HB-EGF receptor, the non-cellular ECM component present in the tumor does not represent an obstacle for RRSP-$DT_B$ to reach the residual cancer cells interspersed within the ECM, effectively inhibiting their growth.

In PDX1, because mice were subjected to a shorter RRSP-$DT_B$ treatment regimen following the drug-washout phase, we observed a larger number of positive CK-19 cells and increase pERK levels despite no increased proliferation. These findings have helped us improve RRSP-$DT_B$ treatment schedule. Indeed, a more aggressive dosing regimen as in PDX2 resulted in fewer CK-19-positive cells and reduced pERK expression comparable to those seen before RRSP-$DT_B$ washout phase. Moreover, the in vivo stability study showed that RRSP-$DT_B$ injected i.p. is delivered to the bloodstream in immunocompetent mice although with minimal activity persisting until 16 hours, supporting the more aggressive daily dosing schedule. Notably, despite the extended and more frequent in vivo administration of RRSP-$DT_B$, no systemic toxicity was observed in mice.

Altogether, our study provides compelling evidence that engineered RAS endopeptidase RRSP-$DT_B$ is highly efficacious against PDAC. Another as yet untested potential advantage of RRSP-$DT_B$ is that in addition to RAS, RRSP cleaves the metastasis-associated GTPase RAP1. Future studies in metastatic cancer models could be done to probe RRSP efficacy against metastatization and local invasion as an added advantage of RRSP in the treatment of PDAC, In recent years, protein degradation has become a promising therapeutic modality to target RAS. Besides RRSP, the bacterial protease toxin subtilisin was recently re-engineered to degrade RAS in vitro and degraded RAS also when ectopically expressed in mammalian cells[46]. In addition, several studies showed that degradation of endogenous KRAS can be achieved following ectopic expression in cancer cells of chimeric proteins that tether RAS-targeting peptides[47-50] and monobodies[51] to a E3 ligase that ultimately drives KRAS ubiquitination and proteasomal degradation. RAS degradation, unlike inhibition of the protein activity, is a strategy that may lead to prolonged inactivation of downstream RAS signaling bypassing the problem of intrinsic resistance of RAS proteins that have been covalently inhibited with small molecules. We likewise showed in 2015 that RRSP can cleave RAS when ectopically expressed resulting in loss of activity and reduced RAS levels[23]. In contrast to all other studies on engineered RAS degraders that depend on stable transfection and ectopic expression, RRSP-$DT_B$ is the only RAS degrader shown to cleave RAS when added exogenously to cells and to reduce tumors following injection in mice. Further, we found that the active toxin moves from the peritoneum to the bloodstream. Thus, RRSP-$DT_B$ is a first-in-class RAS degrader now shown herein to have potential to treat PDAC resulting in tumor regression. In contrast to small molecule inhibitors that target only one form of RAS[52], treatment with RRSP-$DT_B$ showed no resistance in mice that received RRSP-$DT_B$ after a drug washout phase. Because of the unique way RRSP readily cleaves and degrades RAS proteins and the fact that, to our knowledge, RRSP-$DT_B$ is the most advanced and documented RAS biodegrader as for in vitro potency and in vivo activity, we believe that it is the leading player in the growing targeted RAS degradation space. Thus, further investigation of RRSP-$DT_B$ as a therapeutic tool for degrading RAS is warranted and optimization of the delivery modality is planned to achieve selective cancer cell receptor targeting.

REFERENCES

1. Siegel, R L, Miller, K D, and Jemal, A (2020). *Cancer statistics,* 2020. *CA Cancer J Clin* 70: 7-30.
2. Iovanna, J, Mallmann, M C, Goncalves, A, Turrini, O, and Dagorn, J C (2012). Current knowledge on pancreatic cancer. *Front Oncol* 2: 6.
3. Neoptolemos, J P, Kleeff, J, Michl, P, Costello, E, Greenhalf, W, and Palmer, D H (2018). Therapeutic developments in pancreatic cancer: current and future perspectives. *Nature reviews Gastroenterology & hepatology* 15: 333-348.
4. Pezzilli, R, Fabbri, D, and Imbrogno, A (2012). Pancreatic ductal adenocarcinoma screening: new perspectives. *World J Gastroenterol* 18: 4973-4977.
5. Hezel, A F, Kimmelman, A C, Stanger, B Z, Bardeesy, N, and Depinho, R A (2006). Genetics and biology of pancreatic ductal adenocarcinoma. *Genes & development* 20: 1218-1249.
6. Lanfredini, S, Thapa, A, and O'Neill, E (2019). RAS in pancreatic cancer. *Biochemical Society transactions* 47: 961-972.
7. Miglio, U, Oldani, A, Mezzapelle, R, Veggiani, C, Paganotti, A, Garavoglia, M, et al.
(2014). KRAS mutational analysis in ductal adenocarcinoma of the pancreas and its clinical significance. *Pathol Res Pract* 210: 307-311.
8. Waddell, N, Pajic, M, Patch, A M, Chang, D K, Kassahn, K S, Bailey, P, et al. (2015). Whole genomes redefine the mutational landscape of pancreatic cancer. *Nature* 518: 495-501.
9. Bos, J L, Rehmann, H, and Wittinghofer, A (2007). GEFs and GAPs: critical elements in the control of small G proteins. *Cell* 129: 865-877.
10. Downward, J (2003). Targeting RAS signalling pathways in cancer therapy. *Nature reviews Cancer* 3: 11-22.
11. Schubbert, S, Shannon, K, and Bollag, G (2007). Hyperactive Ras in developmental disorders and cancer. *Nature reviews Cancer* 7: 295-308.
12. Genentech, I (2020). A Study to Evaluate the Safety, Pharmacokinetics, and Activity of GDC-6036 Alone or in Combination in Participants With Advanced or Metastatic Solid Tumors With a KRAS G12C Mutation—Full Text View—ClinicalTrials.gov https://clinicaltrials.gov/ct2/show/NCT04449874.
13. Janssen Research & Development (2019). First-in-Human Study of JNJ-74699157 in Participants With Tumors Harboring the KRAS G12C Mutation—Full Text View—ClinicalTrials.gov https://clinicaltrials.gov/ct2/show/NCT04006301.
14. Mirati Therapeutics Inc. (2021). Phase 3 Study of MRTX849 vs Docetaxel in Patients With Advanced Non-Small Cell Lung Cancer With KRAS G12C Mutation (KRYSTAL-12)—Full Text—View ClinicalTrials.gov https://clinicaltrials.gov/ct2/show/NCT04685135.

15. *Mirati Therapeutics Inc.* (2021). Phase 3 Study of MRTX849 With Cetuximab vs Chemotherapy in Patients With Advanced Colorectal Cancer With KRAS G12C Mutation (KRYSTAL-10)—Full Text View—ClinicalTrials.gov https://clinicaltrials.gov/ct2/show/NCT04793958.
16. Novartis Pharmaceuticals (2021). Study of JDQ443 in Patients With Advanced Solid Tumors Harboring the KRAS G12C Mutation—Full Text View—ClinicalTrials-.gov https://clinicaltrials.gov/ct2/show/NCT04699188.
17. Skoulidis, F, Li, B T, Dy, G K, Price, T J, Falchook, G S, Wolf, J, et al. (2021). Sotorasib for Lung Cancers with KRAS p.G12C Mutation. *New England Journal of Medicine.*
18. U.S. Food and Drug Administration (2021). FDA grants accelerated approval to sotorasib for KRAS G12C mutated NSCLC fda.gov/drugs/drug-approvals-and-databases/fda-grants-accelerated-approval-sotorasib-kras-g12c-mutated/nscls.
19. Bryant, K L, Mancias, J D, Kimmelman, A C, and Der, C J (2014). KRAS: feeding pancreatic cancer proliferation. *Trends in biochemical sciences* 39: 91-100.
20. Vidimar, V, Beilhartz, G L, Park, M, Biancucci, M, Kieffer, M B, Gius, D R, et al. (2020). An engineered chimeric toxin that cleaves activated mutant and wild-type RAS inhibits tumor growth. *Proceedings of the National Academy of Sciences of the United States of America.*
21. Kobrin, M S, Funatomi, H, Friess, H, Buehler, M W, Stathis, P, and Korc, M (1994). Induction and expression of heparin-binding EGF-like growth factor in human pancreatic cancer. *Biochem Biophys Res Commun* 202: 1705-1709.
22. Ray, K C, Moss, M E, Franklin, J L, Weaver, C J, Higginbotham, J, Song, Y, et al. (2014). Heparin-binding epidermal growth factor-like growth factor eliminates constraints on activated Kras to promote rapid onset of pancreatic neoplasia. *Oncogene* 33: 823-831.
23. Antic, I, Biancucci, M, Zhu, Y, Gius, D R, and Satchell, K J (2015). Site-specific processing of Ras and Rap1 Switch I by a MARTX toxin effector domain. *Nat Commun* 6: 7396.
24. Biancucci, M, Minasov, G, Banerjee, A, Herrera, A, Woida, P J, Kieffer, M B, et al. (2018). The bacterial Ras/Rap1 site-specific endopeptidase RRSP cleaves Ras through an atypical mechanism to disrupt Ras-ERK signaling. *Sci Signal* 11.
25. Biancucci, M, Rabideau, A E, Lu, Z, Loftis, A R, Pentelute, B L, and Satchell, K J F (2017). Substrate Recognition of MARTX Ras/Rap1-Specific Endopeptidase. *Biochemistry* 56: 2747-2757.
26. Stubbs, C K, Biancucci, M, Vidimar, V, and Satchell, K J F (2021). RAS specific protease induces irreversible growth arrest via p27 in several KRAS mutant colorectal cancer cell lines. *Sci Rep* 11: 17925.
27. Romero-Calvo, I, Weber, C R, Ray, M, Brown, M, Kirby, K, Nandi, R K, et al. (2019). Human Organoids Share Structural and Genetic Features with Primary Pancreatic Adenocarcinoma Tumors. *Mol Cancer Res* 17: 70-83.
28. Patel, R A, Forinash, K D, Pireddu, R, Sun, Y, Sun, N, Martin, M P, et al. (2012). RKI-1447 is a potent inhibitor of the Rho-associated ROCK kinases with anti-invasive and antitumor activities in breast cancer. *Cancer research* 72: 5025-5034.
29. Crowe, A R, and Yue, W (2019). Semi-quantitative Determination of Protein Expression using Immunohistochemistry Staining and Analysis: An Integrated Protocol. *Bio Protoc* 9.
30. Janes, M R, Zhang, J, Li, L S, Hansen, R, Peters, U, Guo, X, et al. (2018). Targeting KRAS Mutant Cancers with a Covalent G12C-Specific Inhibitor. *Cell* 172: 578-589 e517.
31. Singh, A, Greninger, P, Rhodes, D, Koopman, L, Violette, S, Bardeesy, N, et al. (2009). A gene expression signature associated with "K-Ras addiction" reveals regulators of EMT and tumor cell survival. *Cancer cell* 15: 489-500.
32. Garcia, P L, Miller, A L, and Yoon, K J (2020). Patient-Derived Xenograft Models of Pancreatic Cancer: Overview and Comparison with Other Types of Models. *Cancers* (*Basel*) 12.
33. Jain, R, Fischer, S, Serra, S, and Chetty, R (2010). The use of Cytokeratin 19 (CK19) immunohistochemistry in lesions of the pancreas, gastrointestinal tract, and liver. *Appl Immunohistochem Mol Morphol* 18: 9-15.
34. Zapata, M, Cohen, C, and Siddiqui, M T (2007). Immunohistochemical expression of SMAD4, CK19, and CA19-9 in fine needle aspiration samples of pancreatic adenocarcinoma: Utility and potential role. *Cytojournal* 4: 13.
35. Bernard, V, Fleming, J, and Maitra, A (2016). Molecular and Genetic Basis of Pancreatic Carcinogenesis: Which Concepts May be Clinically Relevant? *Surg Oncol Clin N Am* 25: 227-238.
36. Nevala-Plagemann, C, Hidalgo, M, and Garrido-Laguna, I (2020). From state-of-the-art treatments to novel therapies for advanced-stage pancreatic cancer. *Nat Rev Clin Oncol* 17: 108-123.
37. Vidimar, V, Beilhartz, G L, Park, M, Biancucci, M, Kieffer, 1\4B, Gius, D R, et al. (2020). An engineered chimeric toxin that cleaves activated mutant and wild-type RAS inhibits tumor growth. *Proceedings of the National Academy of Sciences of the United States of America* 117: 16938-16948.
38. F., SCKBMVVSKJ (2021). RAS specific protease Induces Irreversible Growth Arrest via p27 in several KRAS Mutant Colorectal Cancer cell lines. bioRxiv.
39. Wang, X, Shen, J, Jiang, F, and Jin, Q (2020). The *Photorhabdus* Virulence Cassettes RRSP-Like Effector Interacts With Cyclin-Dependent Kinase 1 and Causes Mitotic Defects in Mammalian Cells. *Frontiers in microbiology* 11: 366.
40. Jen, E Y, Gao, X, Li, L, Zhuang, L, Simpson, N E, Aryal, B, et al. (2020). FDA Approval Summary: Tagraxofusp-erzs For Treatment of Blastic Plasmacytoid Dendritic Cell Neoplasm. *Clinical cancer research: an official journal of the American Association for Cancer Research* 26: 532-536.
41. Prince, H M, Duvic, M, Martin, A, Sterry, W, Assaf, C, Sun, Y, et al. (2010). Phase III placebo-controlled trial of denileukin diftitox for patients with cutaneous T-cell lymphoma. *J Clin Oncol* 28: 1870-1877.
42. Kreitman, R J, and Pastan, I (2020). Development of Recombinant Immunotoxins for Hairy Cell Leukemia. *Biomolecules* 10.
43. Ozdemir, B C, Pentcheva-Hoang, T, Carstens, J L, Zheng, X, Wu, C C, Simpson, T R, et al. (2014). Depletion of carcinoma-associated fibroblasts and fibrosis induces immunosuppression and accelerates pancreas cancer with reduced survival. *Cancer cell* 25: 719-734.

44. Rhim, A D, Oberstein, P E, Thomas, D H, Mirek, E T, Palermo, C F, Sastra, S A, et al. (2014). Stromal elements act to restrain, rather than support, pancreatic ductal adenocarcinoma. *Cancer cell* 25: 735-747.
45. Apte, M V, Pirola, R C, and Wilson, J S (2012). Pancreatic stellate cells: a starring role in normal and diseased pancreas. *Front Physiol* 3: 344.
46. Chen, Y, Toth, E A, Ruan, B, Choi, E J, Simmerman, R, Chen, Y, et al. (2021).
Engineering subtilisin proteases that specifically degrade active RAS. *Commun Biol* 4: 299.
47. Bery, N, Miller, A, and Rabbitts, T (2020). A potent KRAS macromolecule degrader specifically targeting tumours with mutant KRAS. *Nat Commun* 11: 3233.
48. Lim, S, Khoo, R, Juang, Y C, Gopal, P, Zhang, H, Yeo, C, et al. (2021). Exquisitely Specific anti-KRAS Biodegraders Inform on the Cellular Prevalence of Nucleotide-Loaded States. *ACS Cent Sci* 7: 274-291.
49. Roth, S, Macartney, T J, Konopacka, A, Chan, K H, Zhou, H, Queisser, M A, et al. (2020). Targeting Endogenous K-RAS for Degradation through the Affinity-Directed Protein Missile System. *Cell Chem Biol* 27: 1151-1163 e1156.
50. Simpson, L M, Macartney, T J, Nardin, A, Fulcher, L J, Roth, S, Testa, A, et al. (2020). Inducible Degradation of Target Proteins through a Tractable Affinity-Directed Protein Missile System. Cell *Chem Biol* 27: 1164-1180 e1165.
51. Teng, K W, Tsai, S T, Hattori, T, Fedele, C, Koide, A, Yang, C, et al. (2021). Selective and noncovalent targeting of RAS mutants for inhibition and degradation. *Nat Commun* 12: 2656.
52. Jiao, D, and Yang, S (2020). Overcoming Resistance to Drugs Targeting KRAS(G12C) Mutation. Innovation (N Y) 1.

Example 6—A Novel Engineered Chimeric Toxin that Cleaves Activated Mutant and Wild-Type RAS Inhibits Tumor Growth Reference is, Vidimar V. et al. An engineered chimeric toxin that cleaves activated mutant and wild-type RAS inhibits tumor growth. PNAS 2020, 117 (29)., which is incorporated in its entirety.

Despite nearly four decades of effort, broad inhibition of onco-genic RAS using small-molecule approaches has proven to be a major challenge. Here we describe the development of a pan-RAS biologic inhibitor composed of the RAS-RAP1-specific endo-peptidase fused to the protein delivery machinery of diphtheria toxin. We show that this engineered chimeric toxin irreversibly cleaves and inactivates intracellular RAS at low picomolar concen-trations terminating downstream signaling in receptor-bearing cells. Furthermore, we demonstrate in vivo target engagement and reduction of tumor burden in three mouse xenograft models driven by either wild-type or mutant RAS. Intracellular delivery of a potent anti-RAS biologic through a receptor-mediated mecha-nism represents a promising approach to developing RAS thera-peutics against a broad array of cancers.

Significance

RAS oncoproteins have long been considered among the most elusive drug targets in cancer research. At issue is the lack of accessible drug binding sites and the extreme affinity for its GTP substrate. Covalent inhibitors against the KRAS G12C mutant have shown early clinical promise, however, targeting the other oncogenic RAS mutants across three RAS isoforms has proven challenging. Inhibition of activated wild-type RAS in the absence of canonical RAS mutations is also highly desirable in certain tumors. Here, we demonstrate delivery of an extremely potent pan-RAS and RAP1 cleaving enzyme in therapeutic quantities to specific receptor-bearing cells in vitro and in vivo. We aim to advance this approach to engineer the first targeted pan-RAS inhibitor for cancer therapy.

Introduction

More than one-third of all human cancers harbor activating mutations in RAS oncogenes. Among the major isoforms, KRAS is the most frequently mutated oncogene, found in nearly 25% of malignancies and 85% of RAS-driven cancers (1-3). Notably, three of the four deadliest cancers (pancreatic, co-lorectal, and lung) exhibit a high frequency of KRAS mutations (2, 3). Moreover, NRAS and HRAS are also known oncogenic drivers in other neoplasms (2). Activating point mutations in RAS genes impair the intrinsic capacity of RAS proteins to hydrolyze OTP, thus locking them in a constitutively activated OTP-bound state. This leads to constitutive activation of downstream transduction-signaling networks, such as the RAF/MEK/ERK (MAPK) axis, which drives survival and uncontrolled proliferation (4-6). Even in the absence of gain-of-function mutations, RAS genes still play a major role in tumorigenesis due to hlper-activation of RAS-signaling pathways via overexpression of up-stream receptor tyrosine kinases (RTKs) and/or amplification of wild-type RAS, such as in head and neck squamous cell carcinoma (7), espphageal and gastic cancers (8), ovarian adenocarcinoma (9), and triple-negative breast cancer (TNBC) (10, 11).

Due to their major role in a wide spectrum of cancers, RAS proteins have become a primary target for drug discovery, and extensive effort has been directed to the development of selec-tive RAS inhibitors (12). However, the high affinity for OTP and the absence of drug-accessible binding pockets have complicated efforts for decades, earning RAS the moniker "undruggable" (12-14). Nevertheless, recent success has been achieved by se-lectively targeting KRAS G12C with small molecules that co-valently bind to Cys12 in the KRAS Switch-II pocket (15-17), and clinical trials are underway to validate their effectiveness (18-20). However, these pharmacophores are specific for KRAS G12C and cannot be expanded to other mutants. Furthermore, $KRAS^{G12c}$ mutations account for only ~11% of all KRAS mutations in cancer (21), detected mainly in lung (14%), colorectal (5%), and pancreatic (1 to 3%) cancer (13, 15). Therefore, there remains an urgent need for a broadly applicable pan-RASinhibitor for use against all RAS-driven tumors, either mutation-dependent or -independent.

Recently, we discovered a RAS/RAP1 specific endopeptidase (RRSP) from *Viblio vulnificus* that site-specifically cleaves RAS and its close homolog RAP1 between residues Y32 and D33 within the Switch I, a region crucial to RAS-mediated signal transduction (22). RRSP is highly specific for RAS and RAP1 and does not cleave other closely related GTPases (23). Importantly, RRSP cleaves all three major RAS isoforms, as well as oncogenic RAS with mutations at position 12, 13, and 61 (22). RRSP also targets both active (OTP-bound) and inactive (GDP-bound) RAS, resulting in destruction of the entire cellular RAS pool (23). By proteolytically cleaving the Switch I loop, RRSP prevents RAS from undergoing GDP-OTP exchange and binding the downstream effector kinase RAF, ultimately terminating ERK signaling in cells (24).

Assessing the therapeutic potential of RRSP, however, is precluded by the fact that RRSP is a 56-kDa domain of a larger protein toxin that alone does not readily diffuse across biological membranes. Recently, we demonstrated that the translocation machinery of diphtheria toxin (DT) can be engineered to deliver a broad diversity of passenger proteins into target cells (25, 26). In this study, we exploit the receptor-targeting and membrane translocation properties of DT to deliver RRSP into targeted cancer cells.

We created an engineered chimeric toxin that uses the DT translocation system and show that RRSP potently and irreversibly destroys RAS. We demonstrate the anticancer properties of this engineered chimeric toxin both in vitro and in vivo, providing proof-of-concept for the therapeutic development of RRSP as a pan-RAS inhibitor.

Results

Figures 54A, 54B, 54C, 54D, 54E:
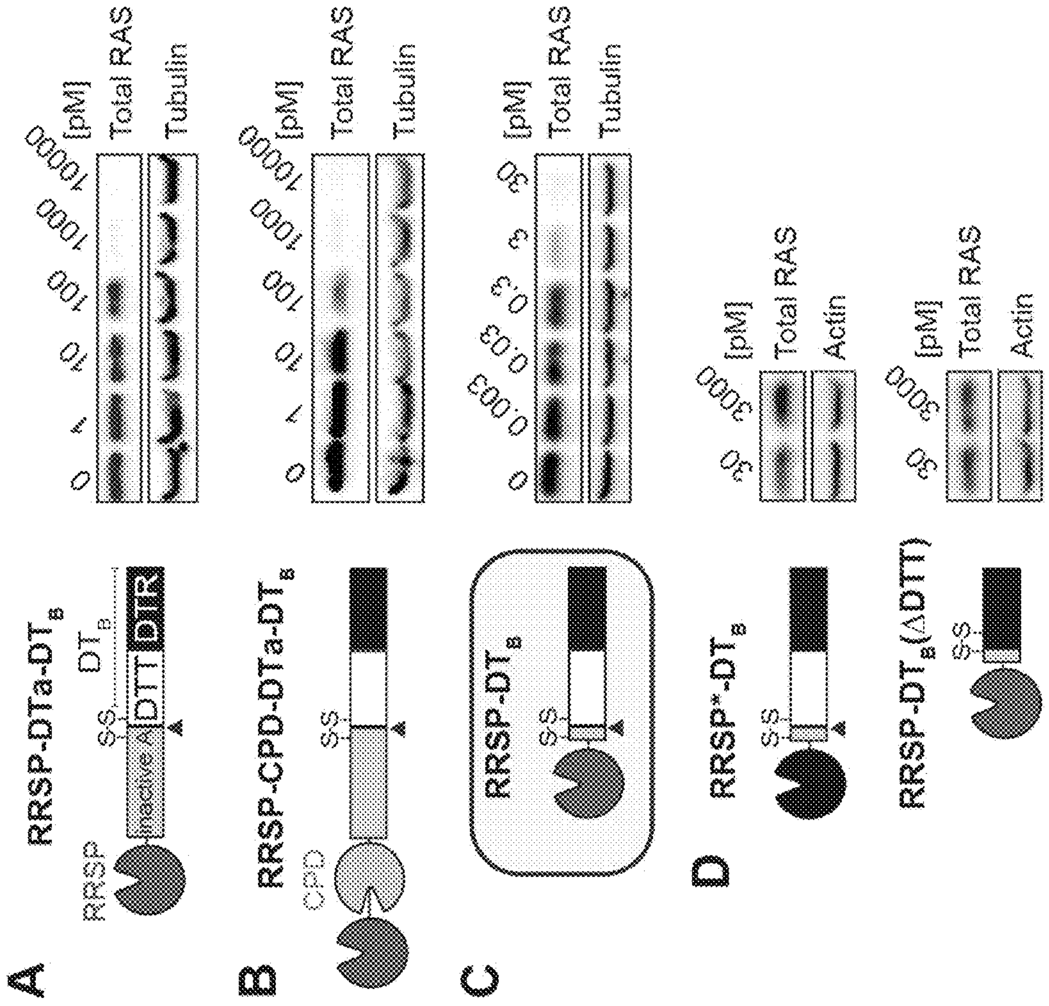
FIG. 54A-54E. Engineered diphtheria toxin delivery machinery enables intracellular delivery of RRSP. Schematic of chimeric fusions of RRSP to (A) the amino terminus of non-toxic, full-length diphtheria toxin (RRSP-DTa-DTT-DTR), (B) to autoprocessing cysteine protease domain (CPD) of MARTX toxin from *Vibrio vulnificus* (RRSP-CPD-DTa-DTT-DTR), and (C) to DTT-DTR without the DTa domain (RRSP-DTT-DTR or RRSP-$DT_B$) and corresponding immunoblots against total RAS of lysates prepared from HCT-116 cells treated with RRSP-DT variants for 24 hours. (D) Immunoblots showing that the catalytically-dead RRSP*-$DT_B$ mutant and the translocation-deficient control (RRSP-$DT_B$(ΔDTT)) do not affect RAS levels in HCT-116 cells. (E) Schematic diagram illustrating transport and intracellular trafficking of RRSP fused to the translocation T and receptor R binding domains of diphtheria toxin fragment B ($DT_B$) via a receptor-mediated endocytic mechanism. Once in the cytosol, RRSP cleaves RAS resulting in downregulation of the MAPK/ERK signaling cascade. Empty cell and vesicles were taken from Servier Medical Art database (smart.seriver.com). HB-EGF, human heparin-binding epidermal growth factor-like growth factor.
Figures 54A, 54B, 54C, 54D, 54E:
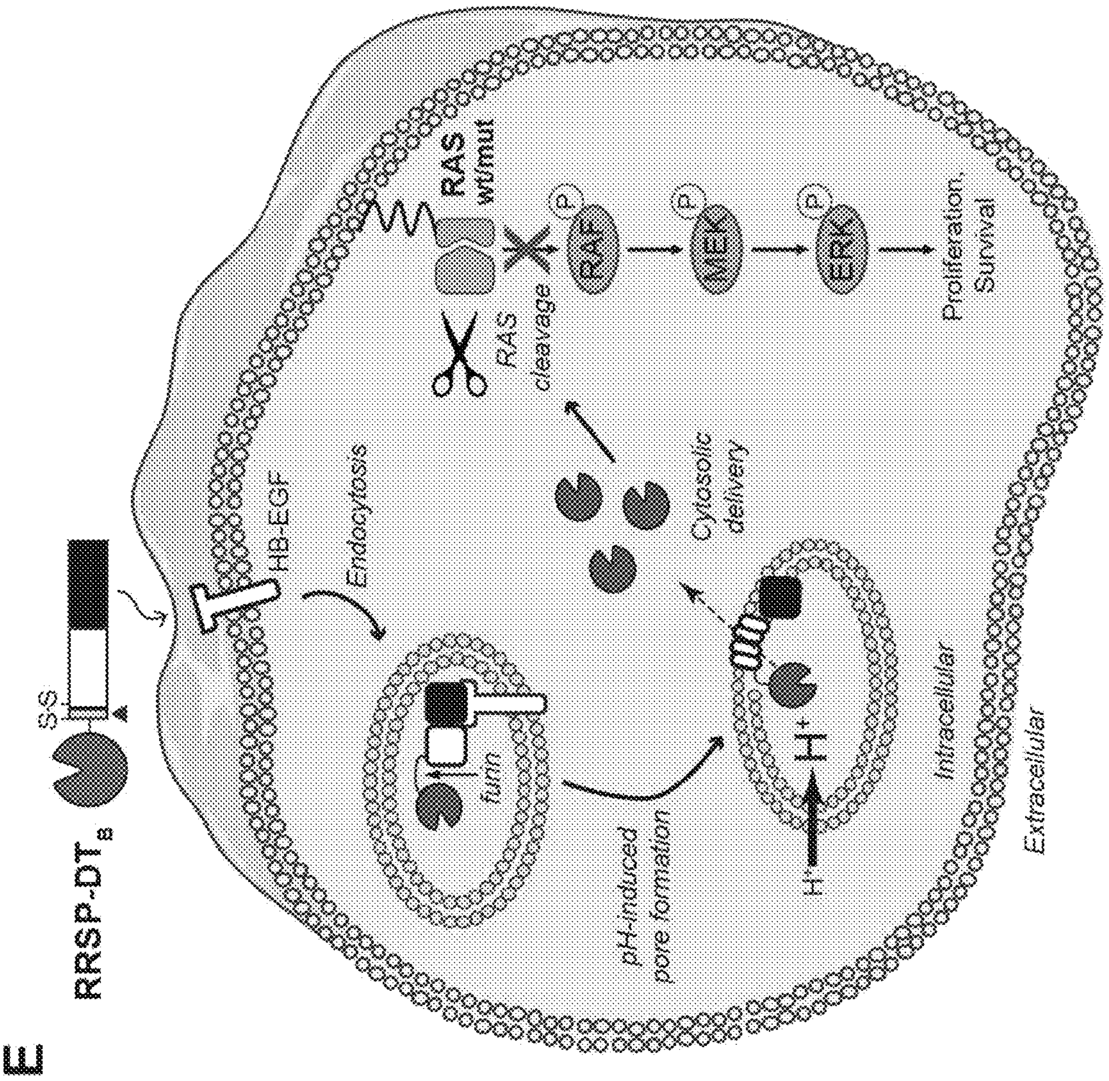
Figures 61A, 61B, 61C:
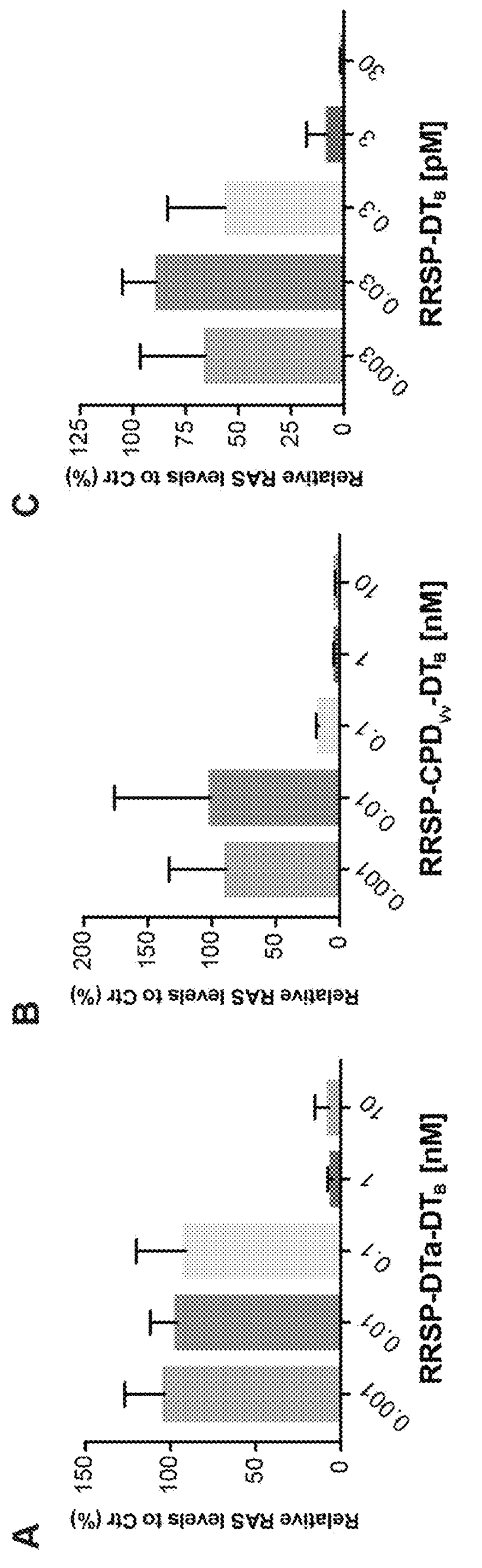
FIG. 61A-61C. Densitometric analysis showing the effect of various RRSP chimeras on total RAS levels in HCT-116 cells. Densitometric analysis of western blots from HCT-116 cells ($KRAS^{G13D}$) treated with the indicated amount of various RRSP chimeras. (A) RRSP-DTa-$DT_B$ is RRSP fused to a detoxified mutant DT (K51E/E148K) (DTa) via a (Gly-Gly-Gly-Gly-Ser)X2 ((G4S)2) linker. (B) RRSP-CPD-DTa-$DT_B$ is RRSP fused to the cysteine protease domain (CPD) of the *V. vulnificus* MARTX toxin as in (A). (C) RRSP-$DT_B$ is RRSP fused directly to DT residues 186-535 via a (G4S)2 linker.
Figures 62A, 62B, 62C, 62D, 62E, 62F, 62G, 62H, 62I:
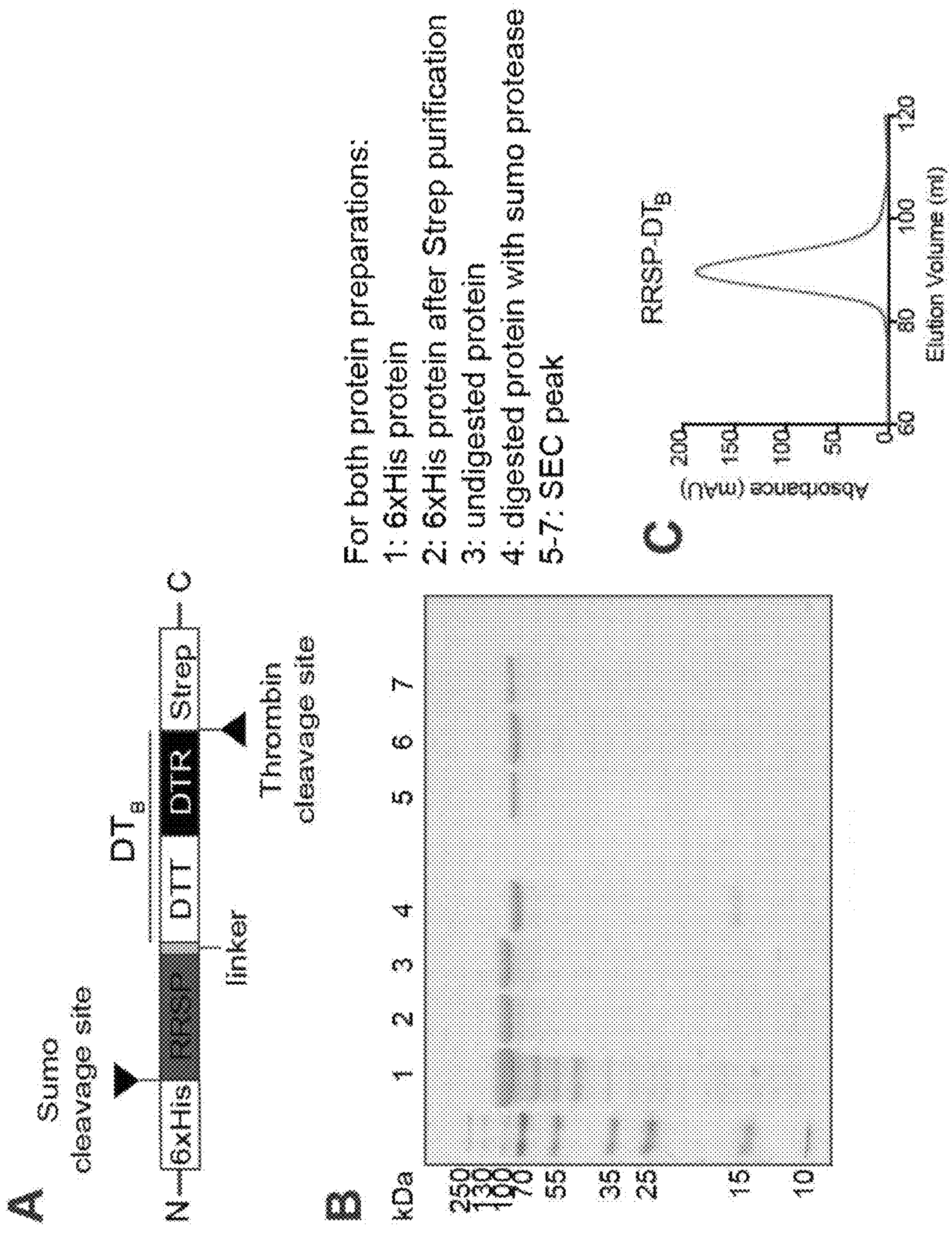
FIG. 62A-62I. Purification of RRSP-$DT_B$ and RRSP*-$DT_B$ proteins and validation of panRAS antibody for detection of uncleaved/cleaved RAS. (A, D) Schematic representation of RRSP-$DT_B$ (A) and RRSP*-$DT_B$ (D) plasmid constructs. (B, E). Coomassie gel images of RRSP-$DT_B$ (B) and RRSP*-$DT_B$ (E) proteins showing degree of protein purity after nickel affinity purification, Strep-purification, removal of the SUMO-tag and size exclusion chromatography (SEC). (C, F). SEC peaks of purified RRSP-$DT_B$ (C) and RRSP*-$DT_B$ (F). (G) Left, western blot indicating presence of the Strep-tag in the RRSP-$DT_B$ purified protein. Right, western blot showing the effect of Strep-tagged and untagged RRSP-$DT_B$ on RAS processing and phosphorylated ERK in HCT-116 cells. Cells were treated with 10 pM of RRSP-$DT_B$ for 1 and 24 hours. Strep-tagged RRSP*-$DT_B$ was also used as negative control. (H) Standard curve displaying efficiency in endotoxin removal from RRSP-$DT_B$ and RRSP*-$DT_B$ protein preparations for in vivo applications. Bar plots show residual endotoxin content (expressed in EU/ml) in both RRSP-$DT_B$ and RRSP*-$DT_B$ protein preparations. (I) Western blot image showing validation of the purified pan-RAS antibody used for detection of uncleaved/cleaved RAS. Recombinant HRAS, NRAS and KRAS were incubated with or without recombinant RRSP and samples were run on a SDS-PAGE gel followed by western blotting. The antibody recognized both cleaved and uncleaved bands of all RAS isoforms.
Figures 62A, 62B, 62C, 62D, 62E, 62F, 62G, 62H, 62I:
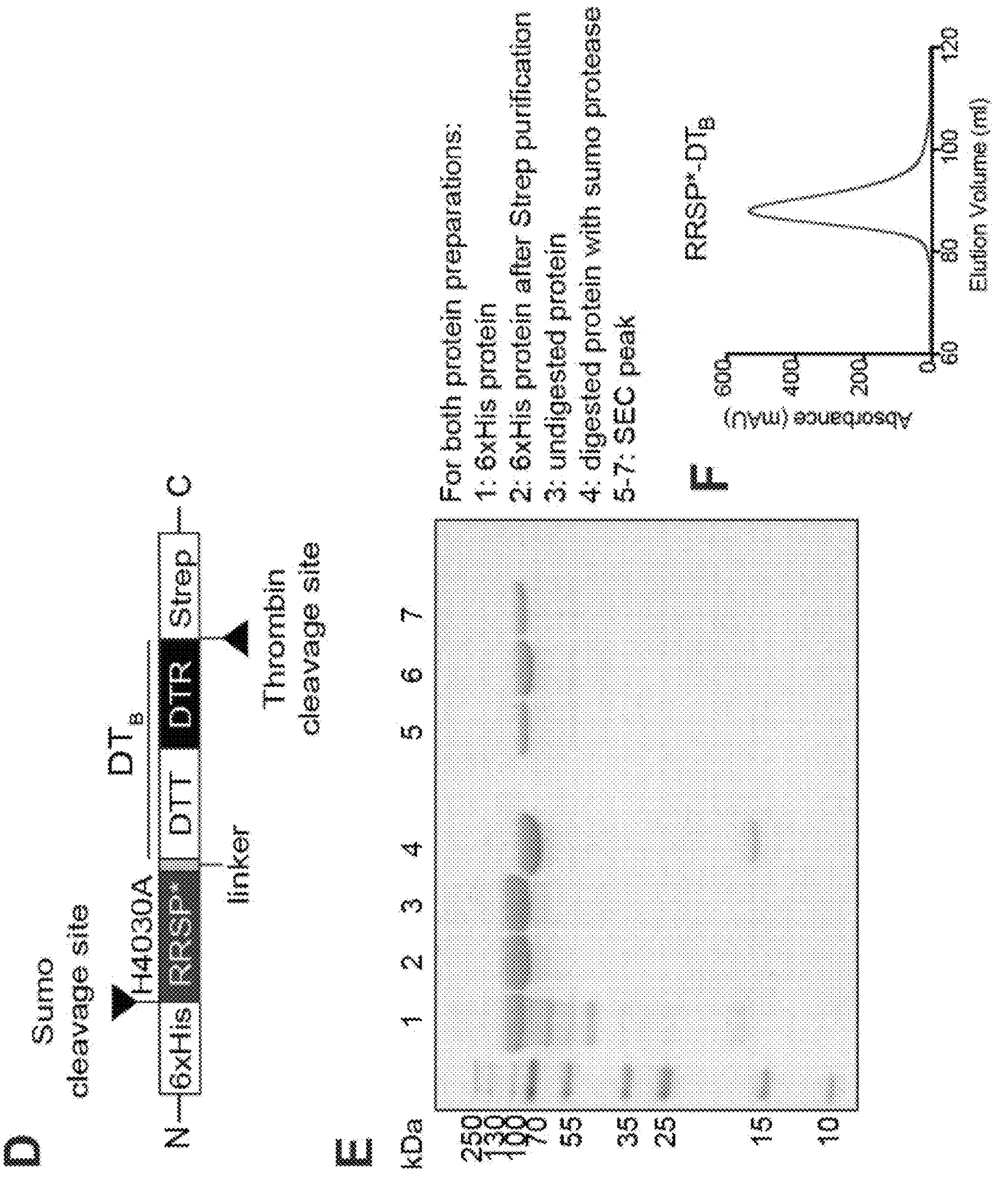
Figures 62A, 62B, 62C, 62D, 62E, 62F, 62G, 62H, 62I:
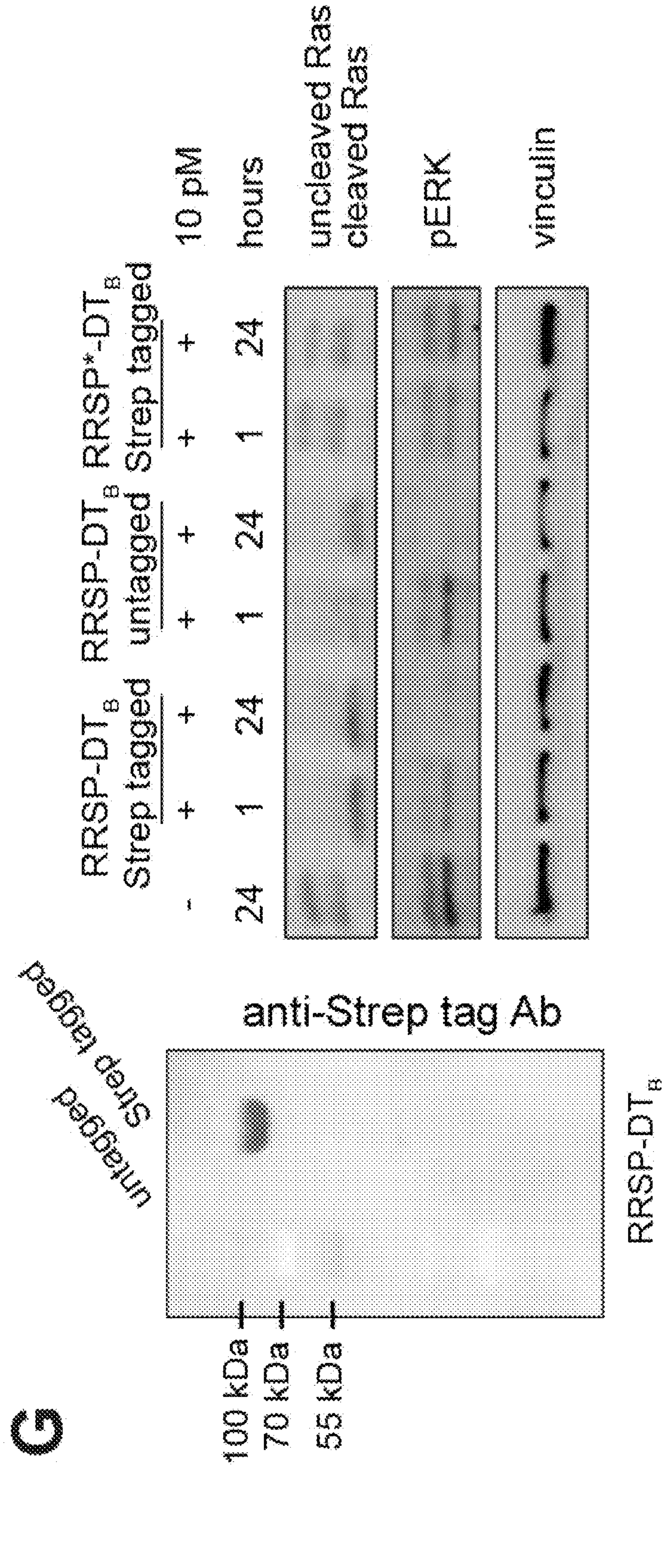
Figures 62A, 62B, 62C, 62D, 62E, 62F, 62G, 62H, 62I:
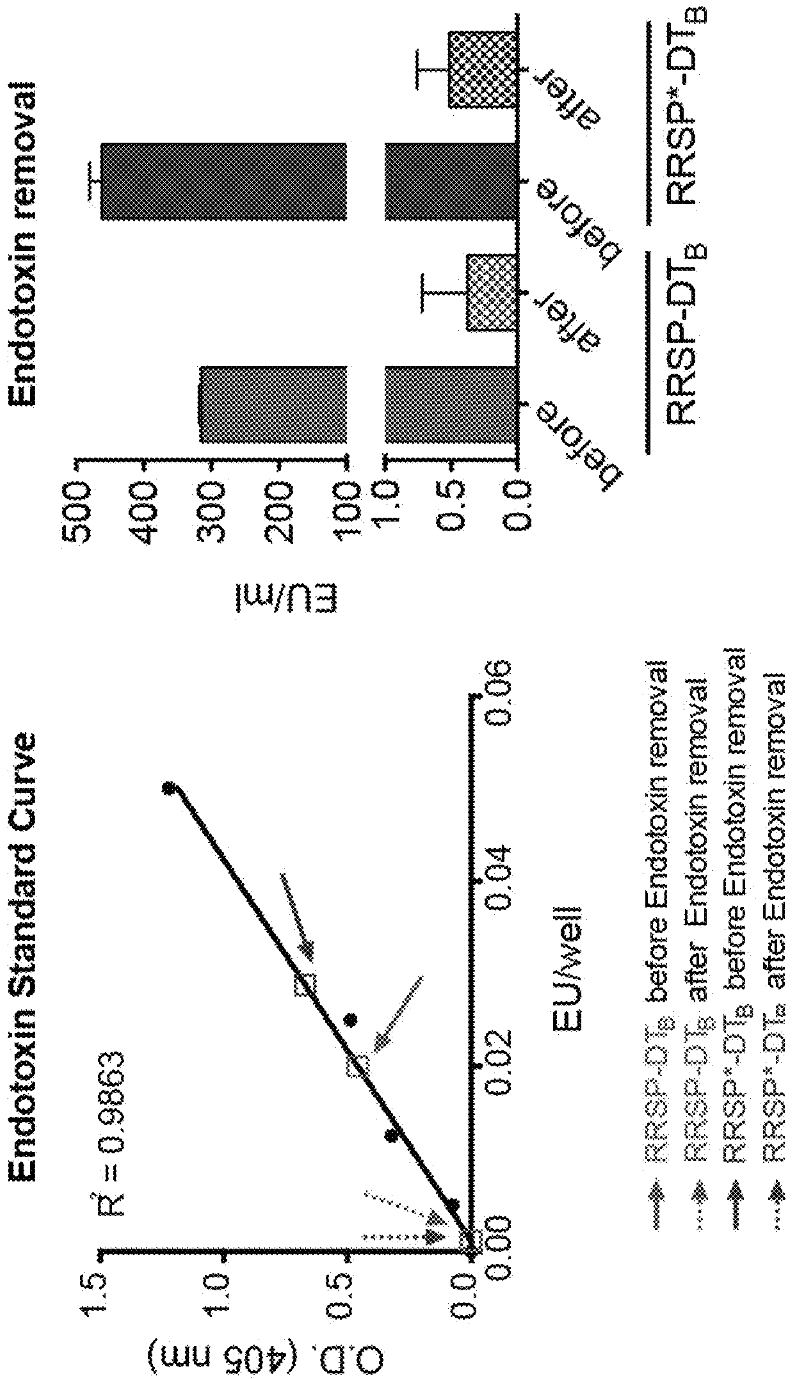
Figures 62A, 62B, 62C, 62D, 62E, 62F, 62G, 62H, 62I:
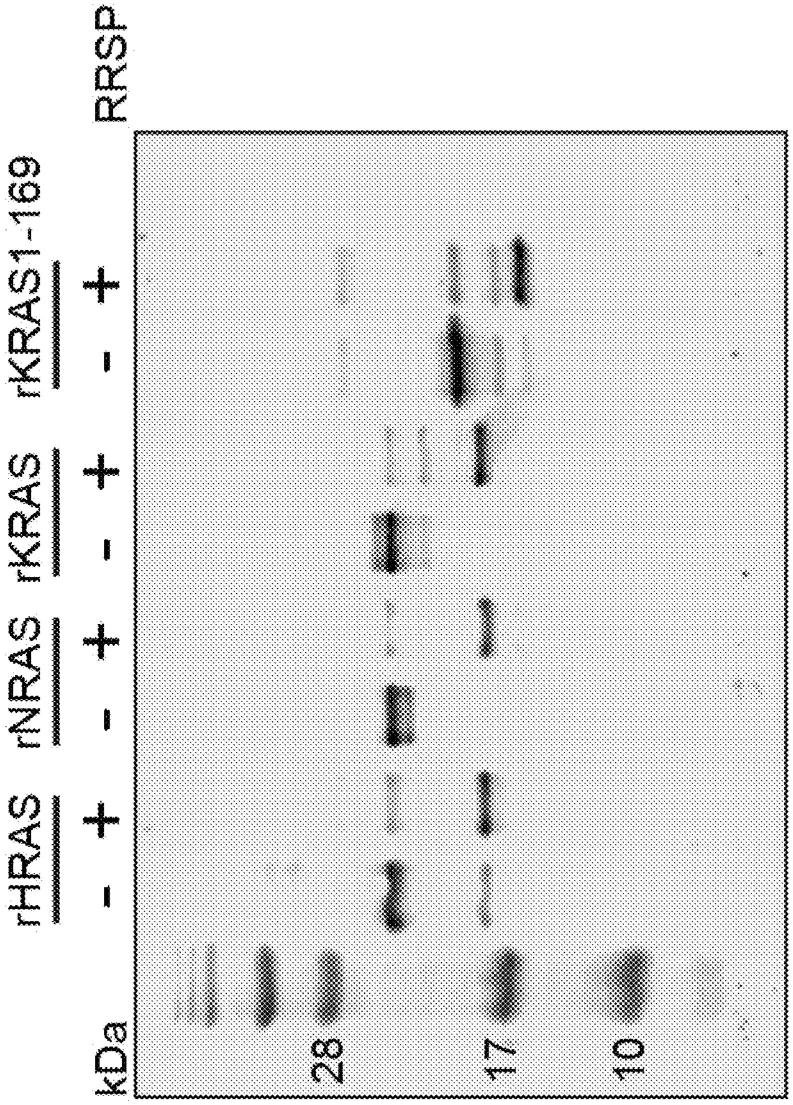

Engineered Diphtheria Toxin Binding and Translocation Domain DT 8 Efficiently Delivers RRSP into Cells. DT consists of a catalytically active A fragment (DTA) and a B fragment (DTB) that includes both a receptor-binding domain (DTR) and a translocation do-main (DTT). $DT_B$ alone can bind its surface receptor, the heparin-binding epidermal growth factor-like growth factor (HB-EGF), and transfer a wide range of protein cargos to the cell cytosol via a receptor-mediated endocytic mechanism (25). The introduction of two amino acid substitutions (K51E and E148K) into DTA resulted in a nontoxic, catalytically inactive A fragment, herein referred to as DTa. To examine RRSP in-tracellular delivery, we expressed RRSP fused at the amino terminus of DTa with an intervening $(G_4S)_2$ linker, a design previously used to deliver other protein cargos (25, 26). Western blotting with the RAS10 pan-RAS antibody showed that treatment with RRSP-$(G_4S)_2$-DTa-$DT_B$ resulted in depletion of RAS in HCT-116 ($KRAS^{G13D}$) cells at 1 nM (FIG. 54A, 61A).

An intrinsic feature of the first-generation design is that RRSP is codelivered with the DTa domain. To generate chimeras that would deliver RRSP alone into cells without DTa, we added the autoprocessing cysteine protease domain (CPD) from *V. vulnificus* MARTX toxin that autocleaves and thereby releases its toxin effectors (i.e., RRSP) upon binding inositol hexakisphosphate in the host cytosol (27). When added to cells, RRSP-CPD-DTa-$DT_B$ improved RAS cleavage (partial inactivation at 100 pM) (FIG. 54B and FIG. 61B). In the third iteration design, we removed DTa entirely and appended RRSP via a $(G4S)_2$ linker to the native release machinery of DT that includes DIT and DTR ($DT_B$) and named it RRSP-DTB. Indeed, cells treated with this much smaller protein showed complete loss of detectable RAS at concentrations as low as 3 pM (FIG. 54C and FIG. 61C). Control proteins with the catalytically inactive mutant $RRSP_{H4030A}$ (RRSP*-$DT_B$) or with the DTT domain removed (RRSP-$DT_B$[ΔDTT]) failed to deplete RAS from cells (FIG. 54D). The uptake of RRSP-$DT_B$, translocation to cytosol, and subsequent RAS cleavage are summarized in FIG. 54E. Altogether, these results demonstrate that $DT_B$ is highly effective for intracellular translocation of RRSP across membranes to target RAS within cells. This final chimeric recombinant toxin was purified on a large scale, enabling the experimental investigation of the anticancer potential of RRSP (FIG. 62A-H).

RAS Processing by RRSP Strongly Affects Viability and Proliferation of TNBC Cancer Cells with Activated Wild-Type RAS.

Figures 55A, 55B, 55C, 55D, 55E:
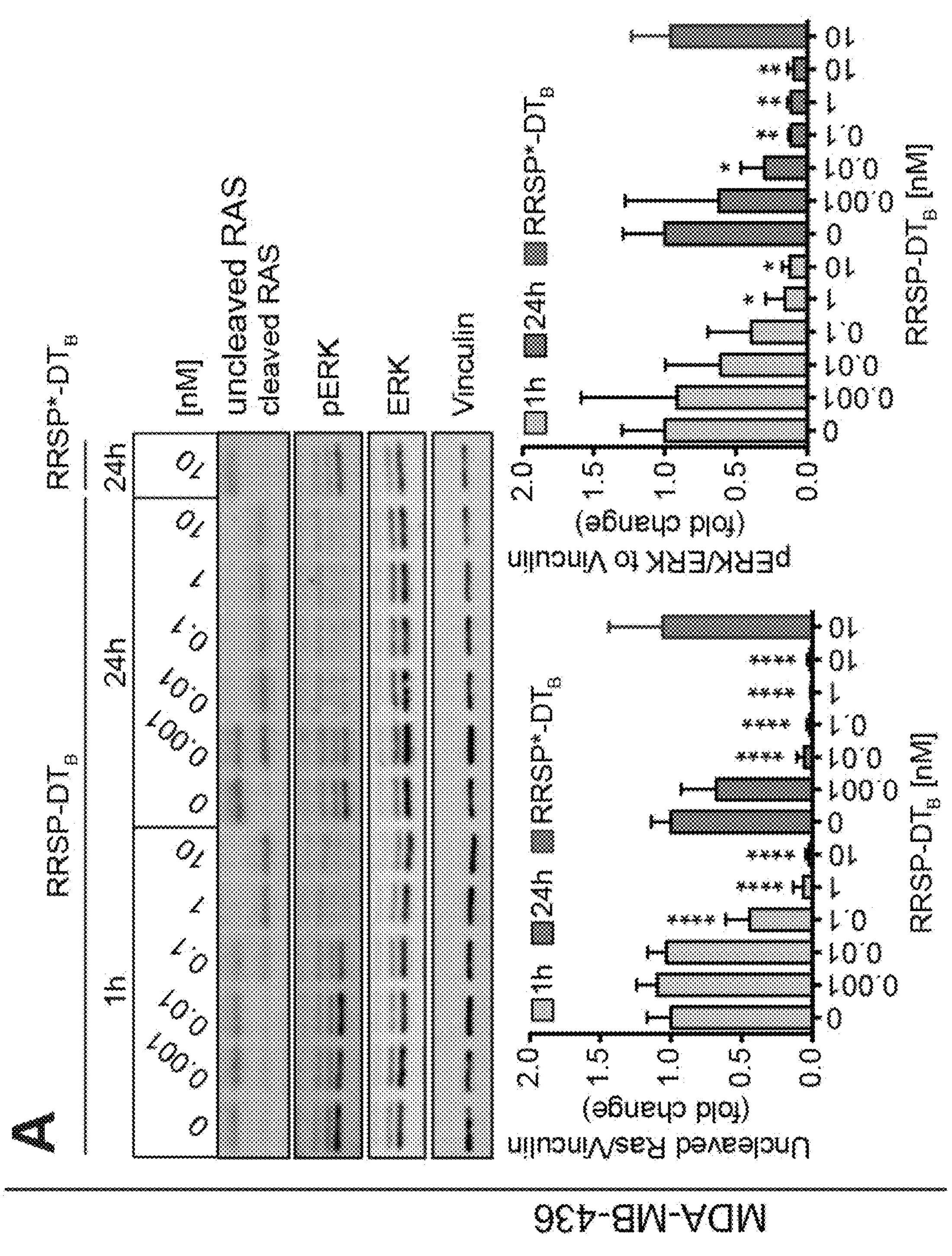
FIG. 55A-55E. RAS processing by RRSP leads to reduced viability and proliferation of a triple-negative $KRAS^{WT}$ breast cancer cell line. (A). Representative western blot and densitometric analysis of uncleaved RAS and phosphorylated ERK (hereafter pERK) levels in MDA-MB-436 $KRAS^{WT}$ cells treated with increasing doses of RRSP-$DT_B$ for 1 and 24 hours. The catalytically-inactive RRSP*-$DT_B$ mutant was used as negative control at 10 nM and vinculin as gel loading control. Results are expressed as means±SD of four independent experiments (*$p<0.05$, $p<0.01$, *$p<0.001$, ****$p<0.0001$ versus corresponding control 0 nM; one-way ANOVA followed by Dunnett's multiple comparison test, n=4). (B). Fitted dose-response curve of RRSP-$DT_B$ in MDA-MB-436 cells following 72 hours of treatment. Results are expressed as mean±SEM (n=3). (C). Representative images of crystal violet staining of MDA-MB-436 cells treated with RRSP-$DT_B$ or RRSP*-$DT_B$ as indicated for 72 hours. (D). Representative images and quantitative analysis of crystal violet-stained colonies from MDA-MB-436 cells pre-treated with RRSP-$DT_B$ and RRSP*-$DT_B$ at the indicated concentrations for 72 hours and replated at 2,500 cells/well to form colonies over 10 days. Results are expressed as means±SD of three independent experiments (*$p<0.05$, **$p<0.01$ versus corresponding control 0 nM; one-way ANOVA followed by Dunnett's multiple comparison test, n=3). (E) Bright field images of MDA-MB-436 cells treated with RRSP-$DT_B$ and RRSP*-$DT_B$ at the indicated doses for 48 hours (scale bar=50 μM) and corresponding cell rounding quantification (*$p<0.001$, **$p<0.0001$ versus corresponding control 0 nM; one-way ANOVA followed by Dunnett's multiple comparison test, n=3).
Figures 55A, 55B, 55C, 55D, 55E:
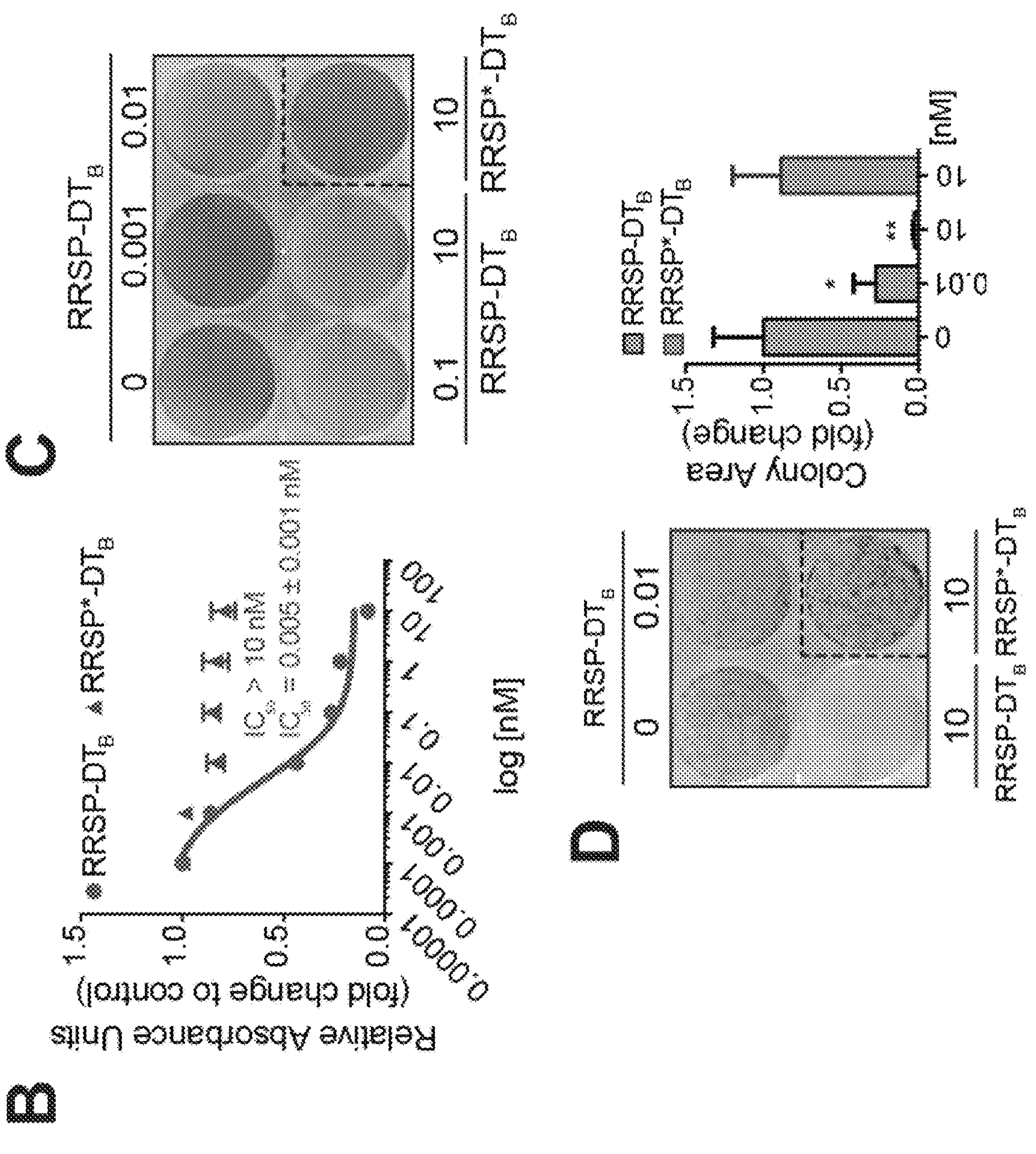
Figures 55A, 55B, 55C, 55D, 55E:
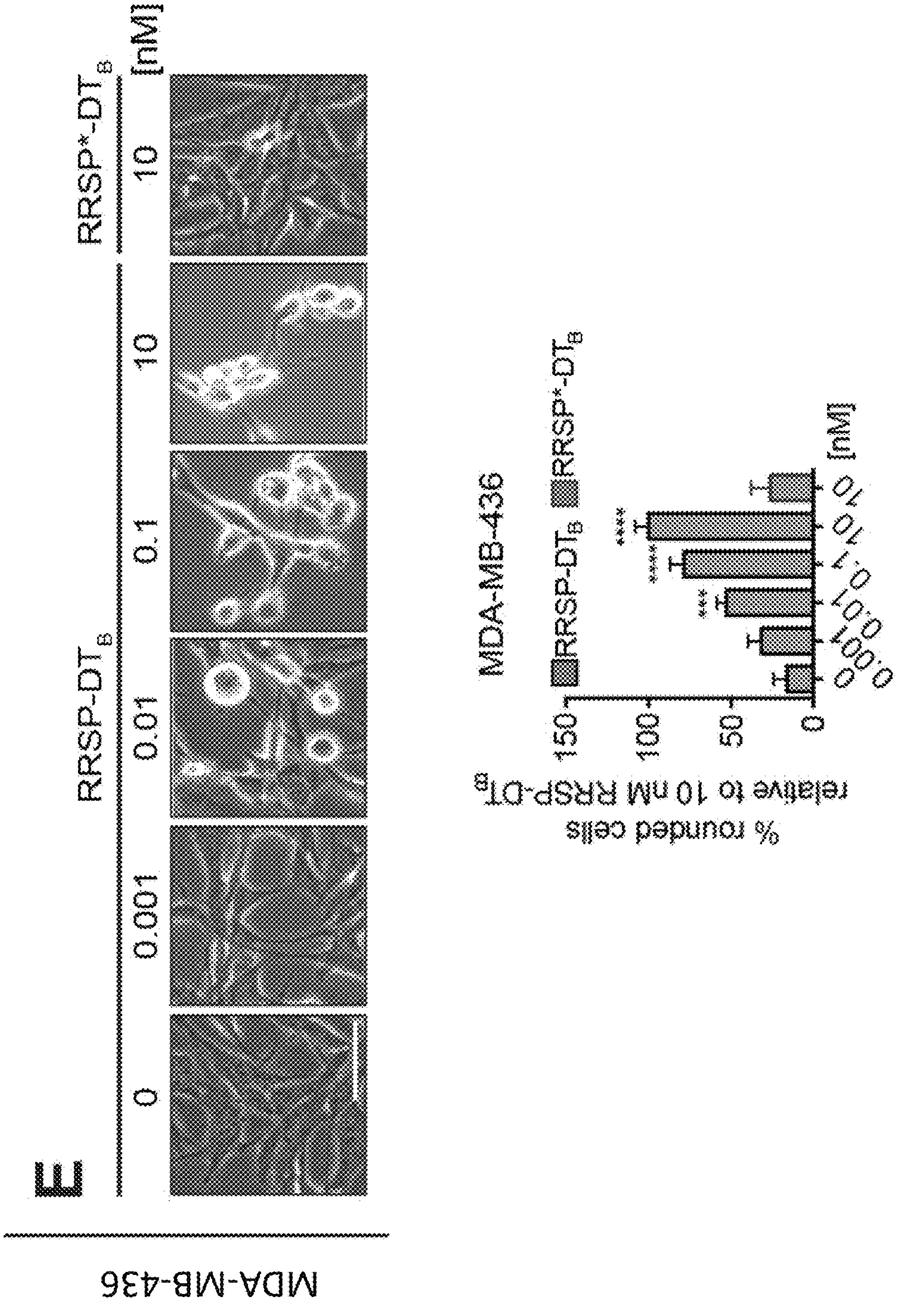
Figures 63A, 63B, 63C:
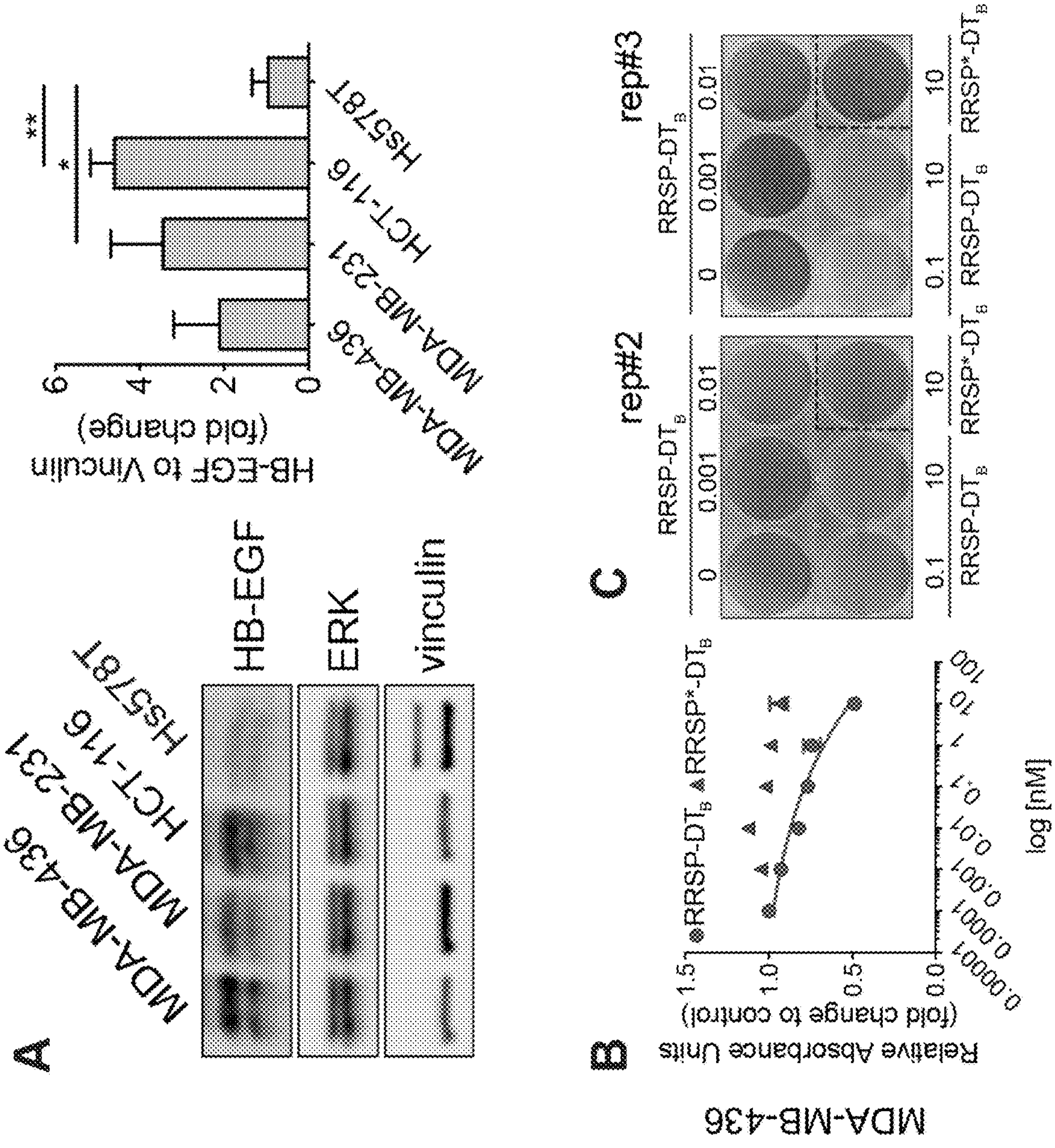
FIG. 63A-63C. HB-EFG protein levels and additional data on the effect of RRSP-$DT_B$ on viability of MDA-MB-436. (A) Western blot image and densitometry showing expression of the DT receptor HB-EGF across MDA-MB-436, MDA-MB-231, HCT-116 and Hs578T cell lines. (B) Dose-response curve of RRSP-$DT_B$ in MDA-MB-436 cells following 24 h of treatment. Slopes of the dose-response curves for both RRSP-$DT_B$ and mutant RRSP*-$DT_B$ were not steep enough to retrieve an $IC_{50}$. Results are expressed as means±SEM (n=3). (C) Additional two replicate images of crystal violet staining of MDA-MB-436 cells treated for 72 h with RRSP-$DT_B$ and RRSP*-$DT_B$ as indicated.

We first investigated the anticancer potential of RRSP-$DT_B$ in TNBC, a devastating disease and the last frontier in breast cancer research (28). Although only ~5% of breast cancers harbor RAS mutations (10), RAS proteins can be pathologically activated in TNBC via upregulation of RTKs and/or amplification of wild-type RAS (10, 29, 30). The basal-like MDA-MB-436 cell line features over-expression of $KRAS^{wt}$ and hyperactivation of ERK signaling (31). Protein levels of HB-EGF, the DT receptor, were assessed by Western blotting in MDA-MB-436 cells and additional cell lines used in this study as a correlation parameter between HB-EGF expression and cytotoxicity (FIG. 63A). HB-EGF-expressing MDA-MB-436 cells were treated with increasing concentrations of RRSP-$DT_B$ for 1 and 24 h, and levels of intracellular RAS and phosphorylated ERK1/2 (pERK) were measured by Western blot. Treatment with RRSP-$DT_B$ resulted in complete cleavage of RAS at 10 nM after 1 h, while 0.01 nM RRSP-$DT_B$ was sufficient to completely cleave RAS after 24 h. At all concentrations, levels of pERK were reduced in lockstep with RAS cleavage (FIG. 55). While pERK levels were markedly re-duced after 24 h, effects on cell viability reached a maximum at 72 h (IC50=0.005±0.001 nM) (FIG. 55B and FIG. 63B). In addition, crystal violet staining showed cell loss starting at 0.01 nM after a 72-h exposure to RRSP-$DT_B$ (FIG. 55C and FIG. 56C), while a colony formation assay showed that RRSP-$DT_B$ had a significant effect on cell proliferation at 0.01 nM and completely prevented colony fmmation at 10 nM over 10 d (FIG. 55D). Phenotypically, RRSP-$DT_B$ caused significant cell rounding in MDA-1\ffi-436 cells at 0.01 nM (FIG. 55E). Overall, RRSP-$DT_B$ causes highly potent cytotoxic effects via the efficient ablation of RAS signaling in a KRAS' cell line.

RRSP Halts Tumor Growth of a KRAS' TNBC Xenograft

Figures 56A, 56B, 56C, 56D, 56E:
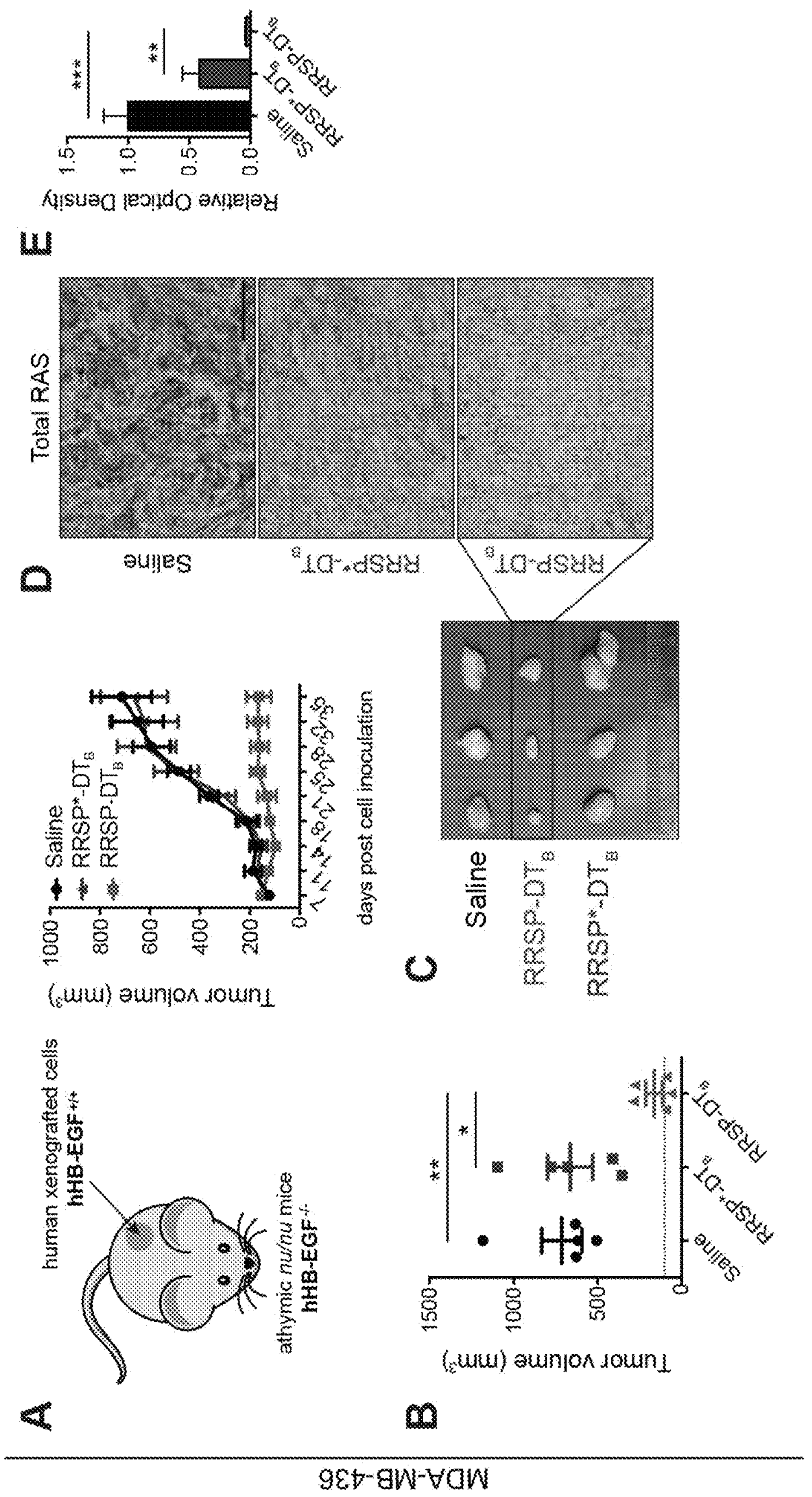
FIG. 56A-56E. RRSP halts tumor growth in a $KRAS^{WT}$ TNBC xenograft in vivo. (A). Tumor growth curve of vehicle, RRSP-$DT_B$ and RRSP*-$DT_B$-treated athymic nu/nu female mice bearing MDA-MB-436-derived tumors. Mice received 0.1 mg/kg of RRSP-$DT_B$ and 0.1 mg/kg of RRSP*-$DT_B$ every other day (weekends excluded) via IP injection. (B). Column scatter plots showing individual tumor volumes at the end of the treatment schedule for MDA-MB-436 xenografts. Horizontal dashed line indicates the average tumor volume (baseline) on the first day of treatment (140 $mm^3$). Data are means±SEM (n=5 mice per group; *$p<0.05$, $p<0.01$). (C). Representative images of MDA-MB-436 tumors at the experimental endpoint. (D). Representative images of immunoreactivity to total RAS in sections from MDA-MB-436 tumors and (E) corresponding quantification of DAB optical density ($p<0.01$, ***$p<0.001$, one-way ANOVA followed by Tukey's multiple comparison test, n=3; scale bar=100 μM).
Figures 64A, 64B, 64C, 64D:
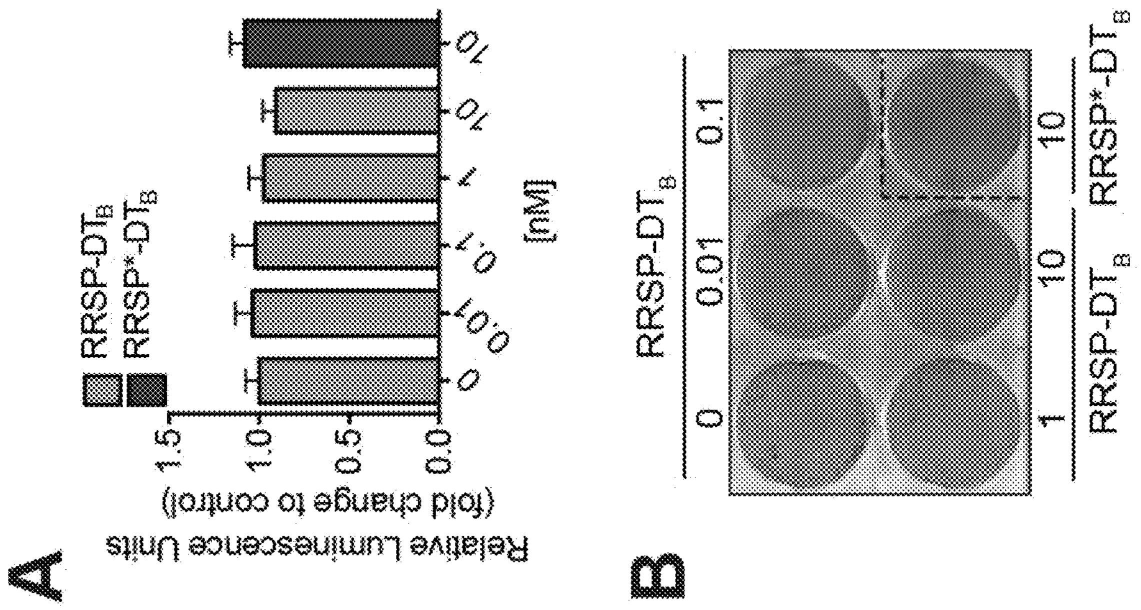
FIG. 64A-64D. Effect of RRSP-$DT_B$ on mouse embryonic fibroblasts (MEF) and in vivo Maximum Tolerated Dose (MTD) study. (A) Viability and (B) crystal violet staining of RAS-less $KRAS^{WT}$ MEF cells following 72 h of treatment with RRSP-$DT_B$ and RRSP*-$DT_B$ as indicated. (C) Body weight expressed as percentage of initial weight over time from the MTD study that was performed treating athymic female nu/nu nude mice at the indicated doses every day for two weeks (weekends excluded, F=female, M=male). (D) Kaplan-Meier plot showing overall survival of mice treated with RRSP-$DT_B$ and RRSP*-$DT_B$.
Figures 64A, 64B, 64C, 64D:
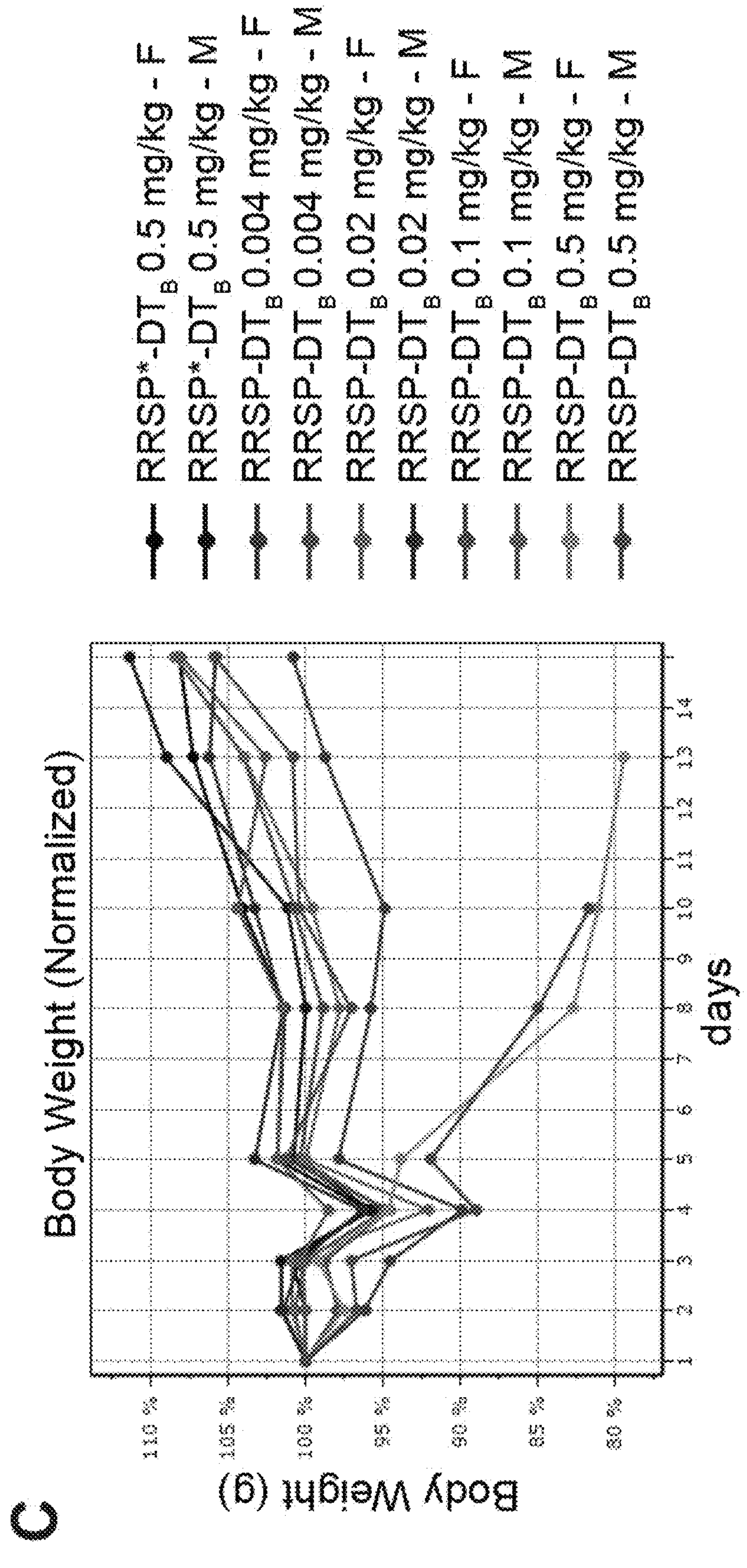
Figures 64A, 64B, 64C, 64D:
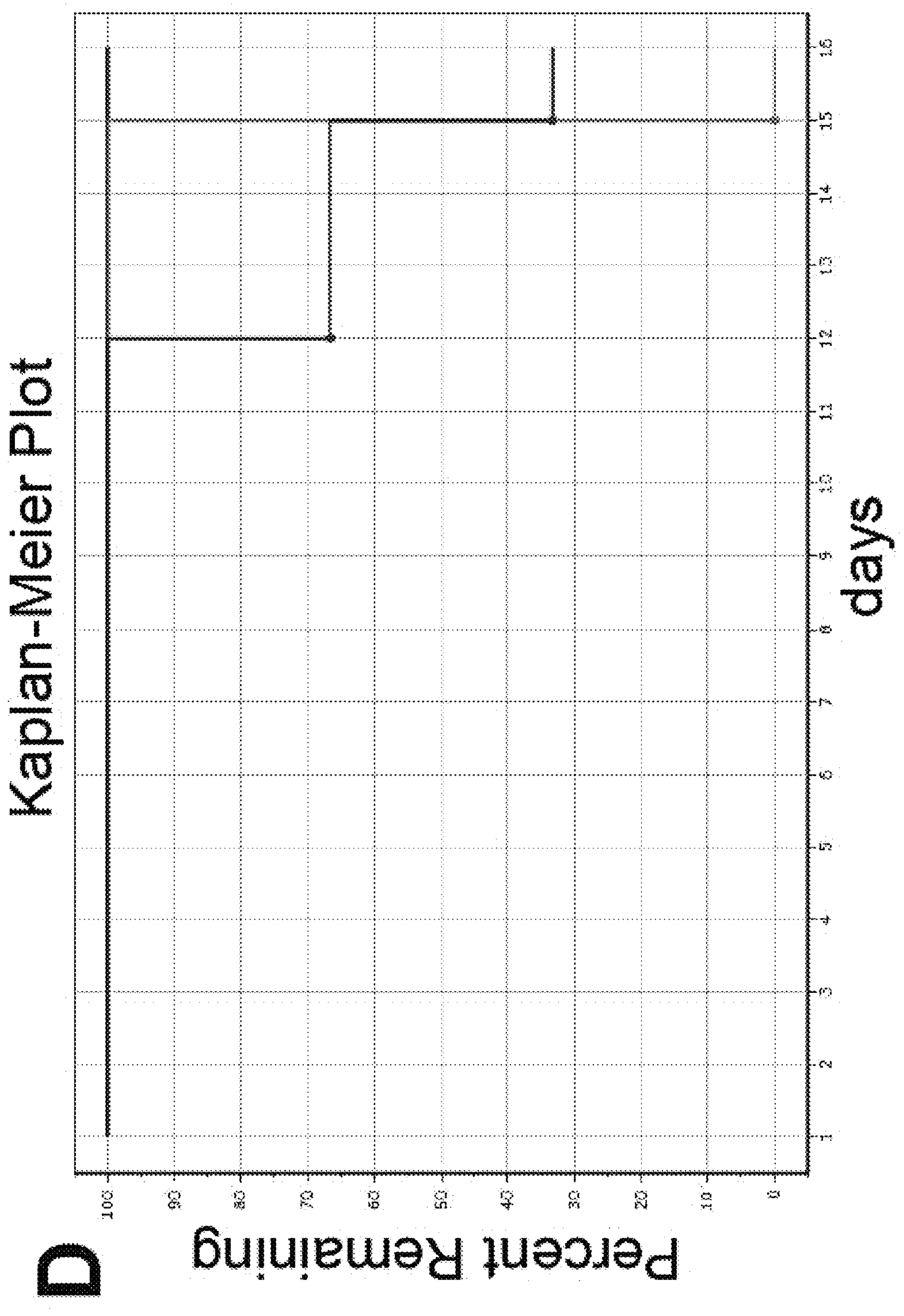
Figures 65A, 65B, 65C:
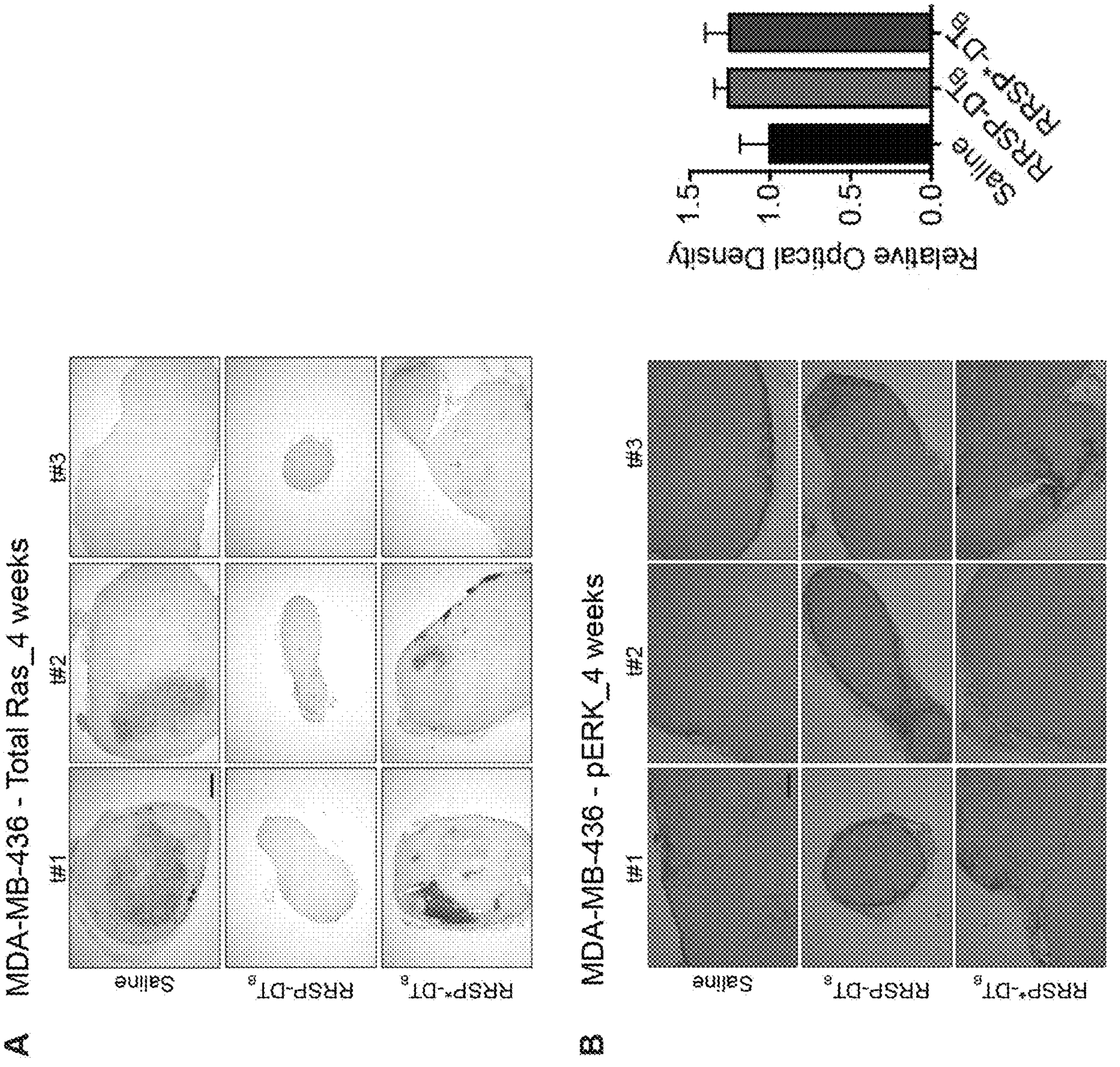
FIG. 65A-65C. Whole tumor IHC images and analysis of total RAS and pERK levels from the MDA-MB-436 xenograft. (A) Sections of whole tumors from the MDA-MB-436 xenograft immunostained with a total RAS antibody (n=3; scale bar=200 μm). Mice were treated every other day (weekends excluded) at the indicated treatment conditions for about 4 weeks. (B) Sections of whole tumors from the same MDA-MB-436 xenograft immunostained with a pERK antibody (scale bar=100 μm). Bar plot shows quantification of pERK DAB signal (n=3). (C). Sections of whole tumors from a shorter, 2-week long MDA-MB-436 xenograft immunostained with a pERK antibody and quantification of DAB signal (*p<0.05, one-way ANOVA followed by Tukey's multiple comparison test, n=3; scale bar=200 μM).
Figures 65A, 65B, 65C:
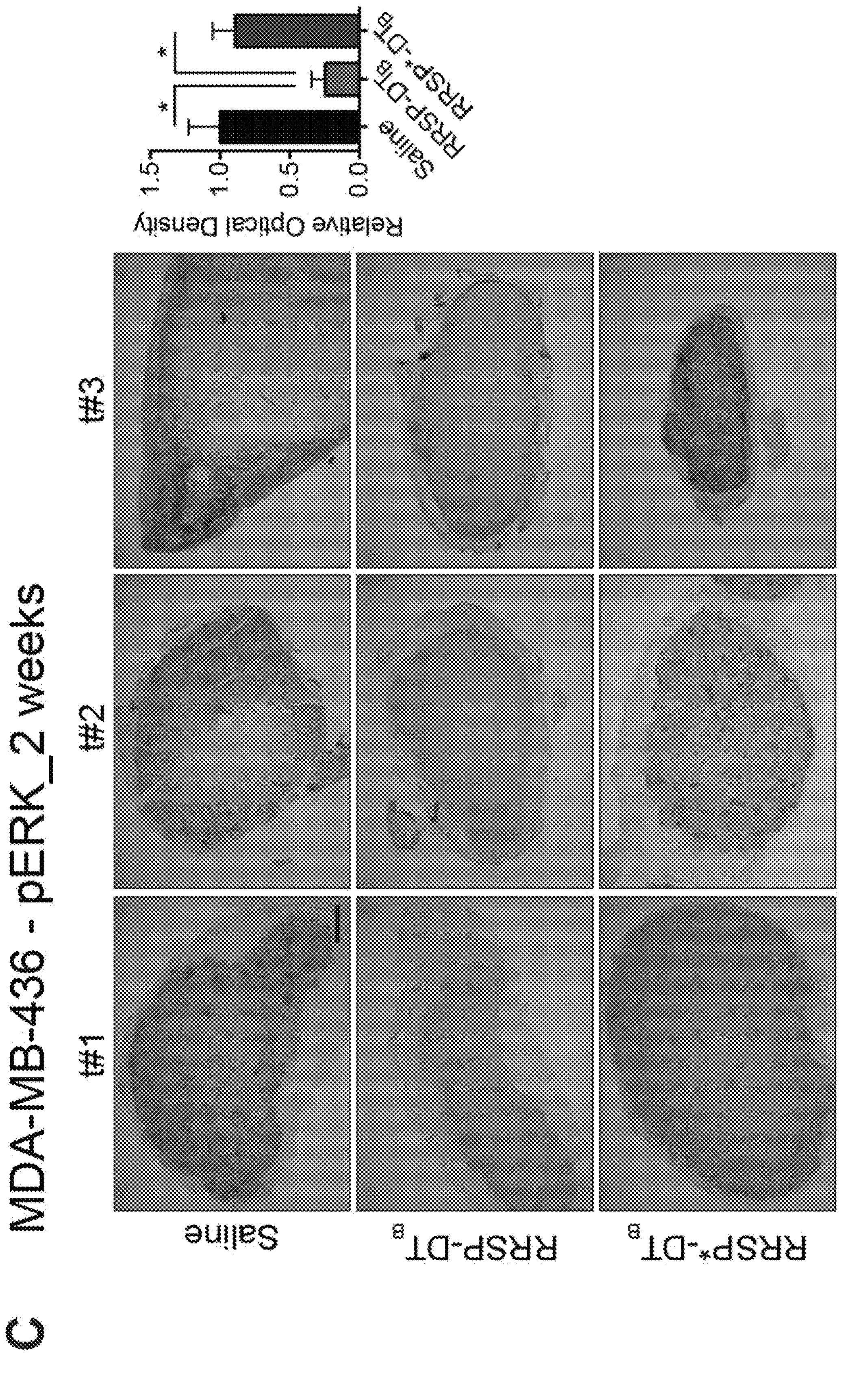
Figures 66A, 66B, 66C, 66D, 66E, 66F, 66G:
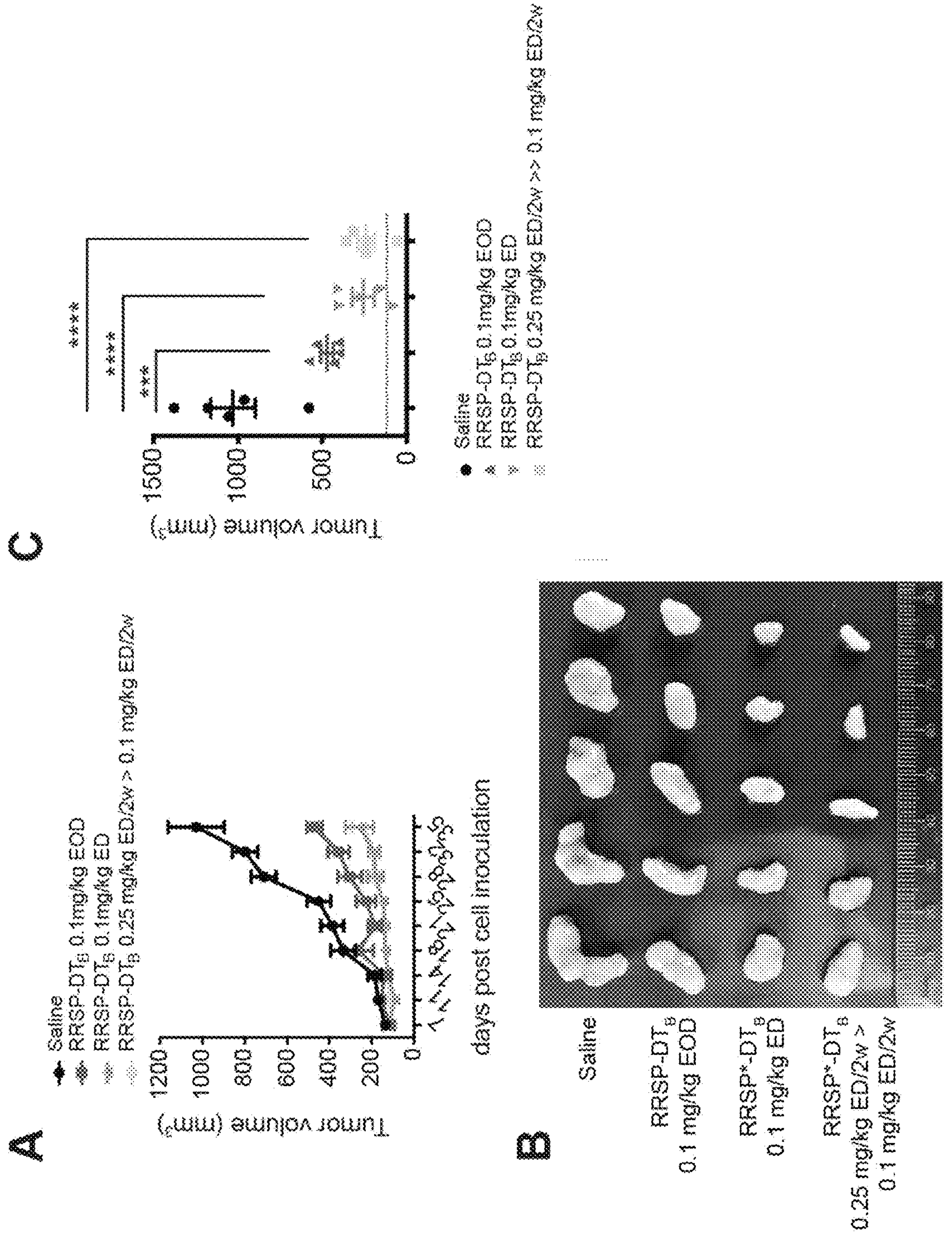
FIG. 66A-66G. Summary of the effect of RRSP-$DT_B$ on an additional MDA-MB-436 xenograft. (A) Tumor growth curve of vehicle and RRSP-$DT_B$-treated athymic nu/nu female mice bearing MDA-MB-436 tumors at the indicated doses and treatment schedule. EOD, every other day. ED, every day. (B) Representative images of MDA-MB-436 tumors at the experimental endpoint. (C) Column scatter plots showing individual tumor volumes at the end of the treatment schedule. Horizontal dashed lines indicate the baseline tumor volume on the first day of treatment, which corresponds to the average of tumor volumes at the indicated time (118 $mm^3$). Data are means±SEM and n=5 mice in every group. Statistical analysis between vehicle and treatment groups was performed using one-way ANOVA followed by Tukey's multiple comparison test (*p<0.001, p<0.0001). (D) Representative IHC images of immunoreactivity to total RAS in sections from MDA-MB-436 tumors and (E) corresponding quantification of DAB optical density (**p<0.0001, one-way ANOVA followed by Tukey's multiple comparison test, n=3; scale bar=100 μM). (F). Sections of whole tumors from the MDA-MB-436 xenograft immunostained with a total RAS antibody and (G) pERK antibody (n=3; scale bar=200 μm). Bar plot shows quantification of pERK DAB signal.
Figures 66A, 66B, 66C, 66D, 66E, 66F, 66G:
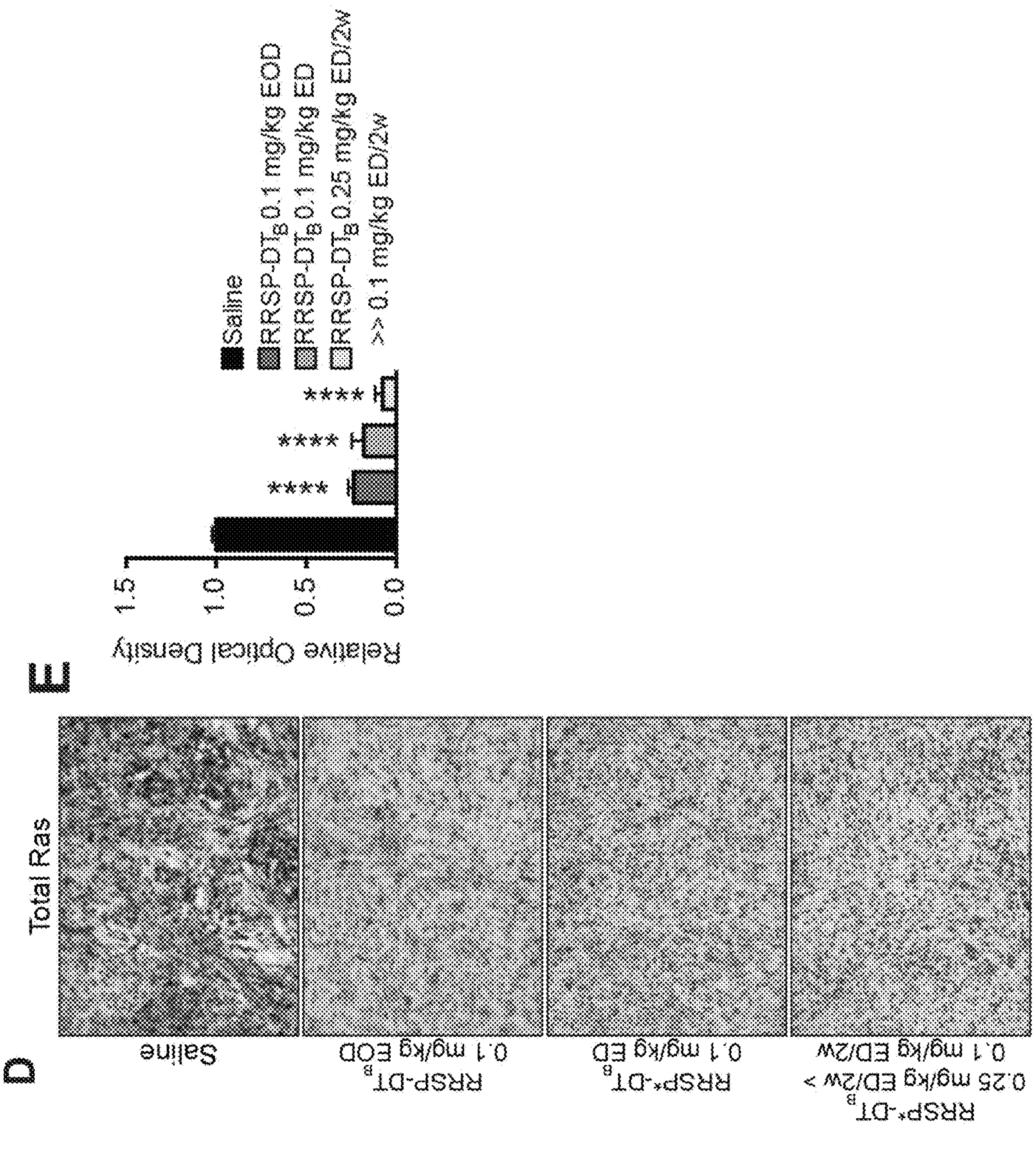
Figures 66A, 66B, 66C, 66D, 66E, 66F, 66G:
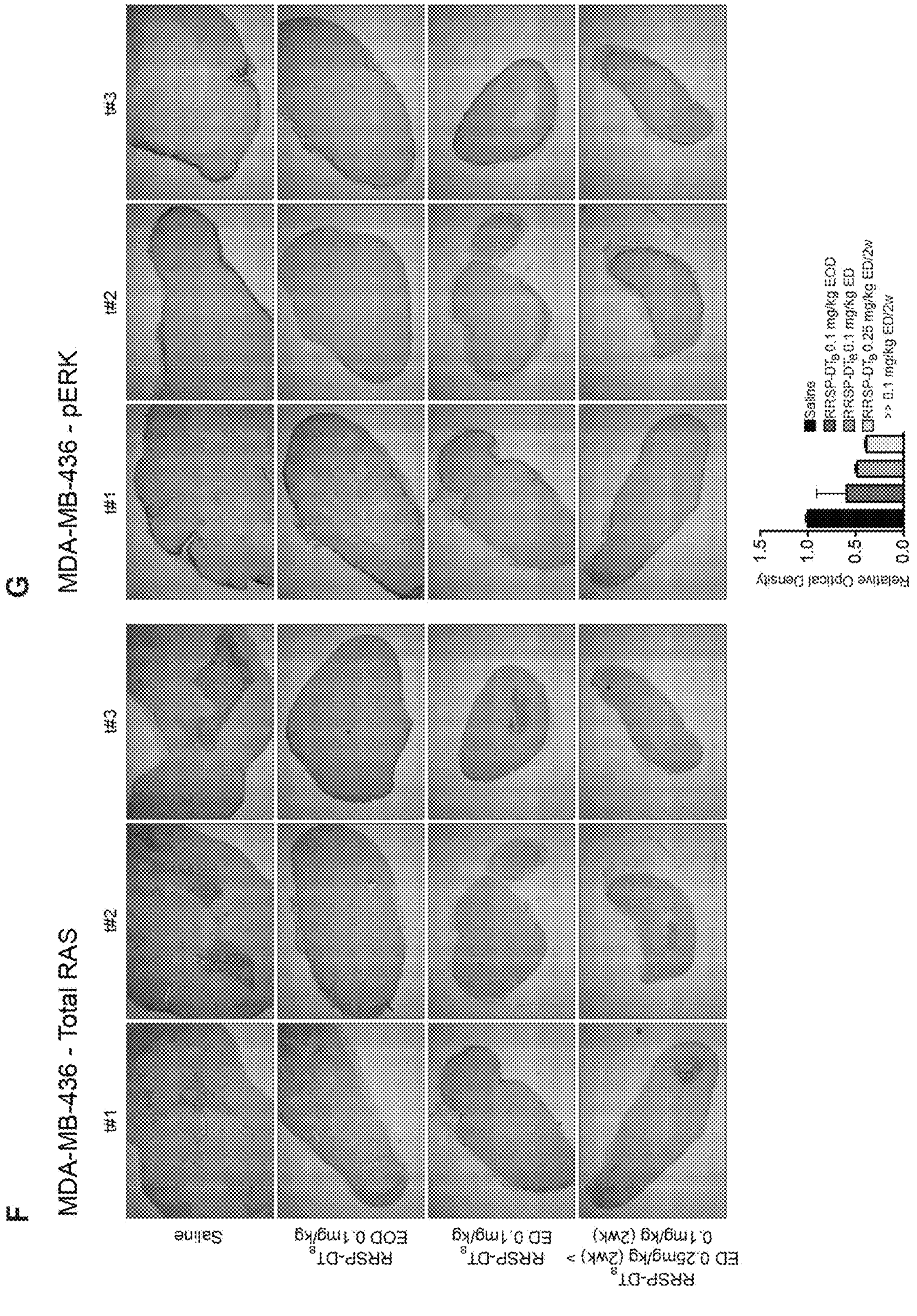

Retaining the native receptor targeting of $DT_B$ to translocate RRSP is advantageous as a test system for mouse xenografts since DT is at least 1000-fold less potent on cells expressing murine HB-EGF than cells expressing human HB-EGF (32-34). Indeed, RRSP-$DT_B$ treatment did not affect the viability of mouse embryonic fibroblasts (MEFs) (FIG. 64A-B). A maximum tolerated dose (MTD) study determined that 0.1 mg/kg administered intraperitoneally (IP) every day (q.d.) was well tolerated, while dosage at or above 0.5 mg/kg caused weight loss (FIG. 64C-D). In the MDA-MB-436 xenograft, IP administration of RRSP-$DT_B$ at 0.1 mg/kg every other day (weekends excluded) for 4 weeks halted tumor growth (FIG. 56A-B). Importantly, three of five mice treated with RRSP-$DT_B$ showed tumor regression by the end of the treatment schedule (FIG. 56B). Most importantly, catalytically-inactive RRSP*-$DT_B$ did not affect tumor growth compared to vehicle (saline) control, demonstrating that tumor regression was due specifically to RRSP-mediated RAS processing activity. Indeed, RRSP-$DT_B$ dramatically reduced total RAS immunoreactivity in residual tumors, confirming effective RAS cleavage in vivo (FIG. 56D-E and FIG. 65A). Additional experimental groups using slight variations of the dosing strategy corroborated these findings (FIG. 66A-F). Since ERK phosphorylation was limited to the outer rim of control MDA-MB-436 tumors excised from mice at 4 weeks (FIG. 65B and FIG. 66G), we assessed pERK levels at an earlier time point when the smaller size of large control tumors is more amenable to pERK detection. In tumors harvested at two weeks, we observed staining throughout the sections with high basal pERK levels in both saline and RRSP*-$DT_B$-treated tumors and with significant reduction in pERK in the RRSP-$DT_B$ treatment group (FIG. 65C). These results demonstrate that RRSP-$DT_B$ effectively engages and ablates RAS in vivo, resulting in decreased ERK activation and tumor regression.

Assessment of Relative Susceptibility to RRSP-$DT_B$ Using the NCI-60 Panel

We next screened RRSP-$DT_B$ against the National Cancer Institute NCI-60 human tumor cell line panel comprised of 60 cell lines representing nine different cancer types with various genetic backgrounds, including RAS mutations. Growth inhibition caused by RRSP-$DT_B$ was measured by sulforhodamine B assay after 48 hours and reported in FIG. 57A for the highest dose employed (13.5 nM). Fourteen cell lines were classified as “highly susceptible” to RRSP-$DT_B$ as they showed growth inhibition greater than or equal to 90%. Thirty-eight cell lines showed varying degrees of growth inhibition from 25 to 90% and were designated as “susceptible” to RRSP-$DT_B$ (FIG. 57A).

Figures 57A, 57B, 57C:
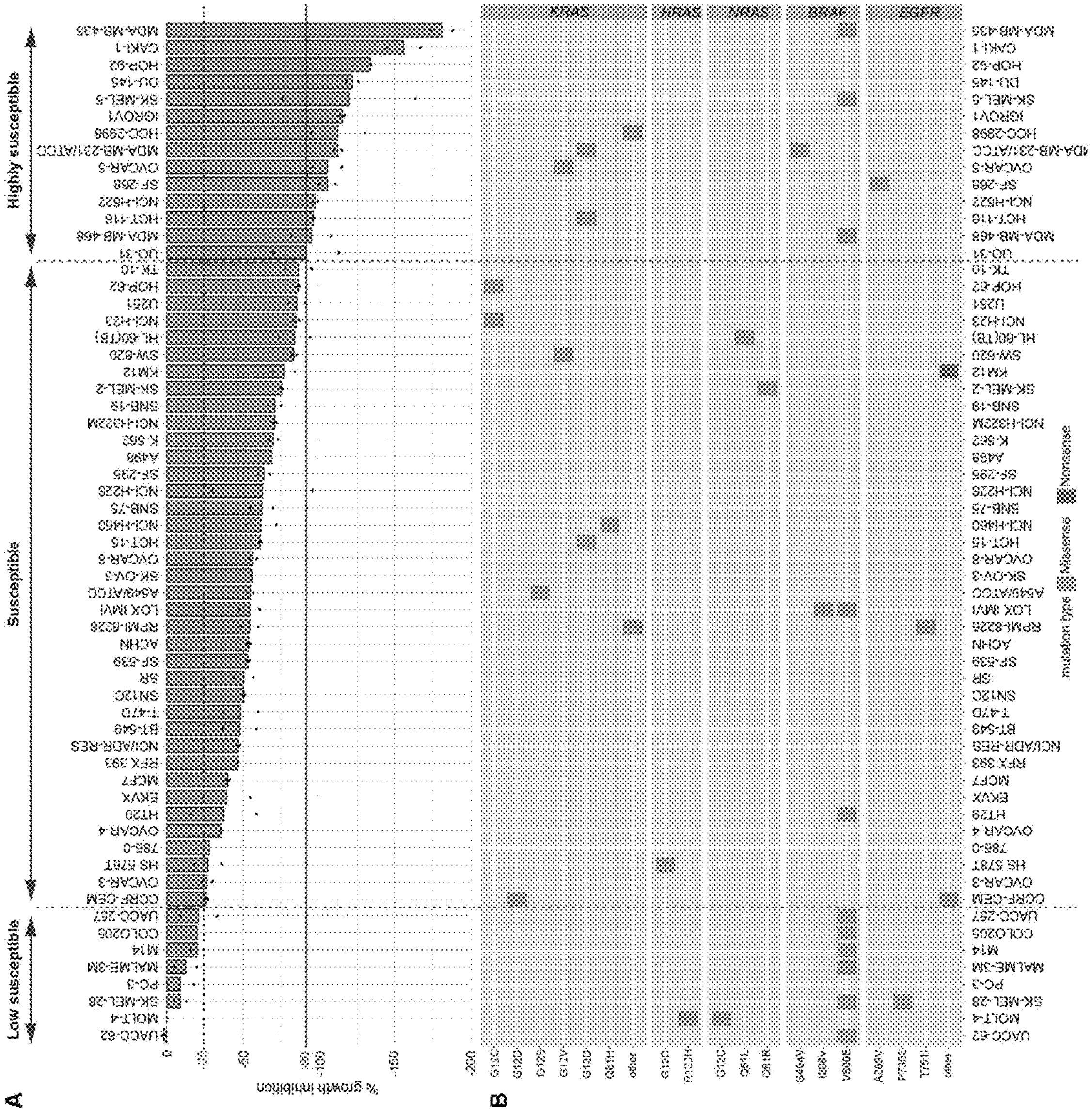
FIG. 57A-57C. Comprehensive analysis of the effect of RRSP on the NCI-60 cancer cell line panel. (A). Bar plot showing the percent growth inhibition of RRSP-$DT_B$ on the NCI-60 panel. Cancer cell lines were ranked in descending order based on their growth inhibition % value. The presence of two dots on the bars indicate that two replicates were performed per each cell line and bars represent means. No dots indicate that only one replicate was available. (B). Spectrum of missense and nonsense mutations in KRAS, HRAS, NRAS, BRAF and EGFR genes in the 60 cell lines of the panel. (C). Violin plot showing the median percent growth inhibition of cell lines treated with RRSP-$DT_B$ and grouped per tumor type in descending order. Only tumor types that had at least 5 cell lines per group were plotted in the graph.
Figures 57A, 57B, 57C:
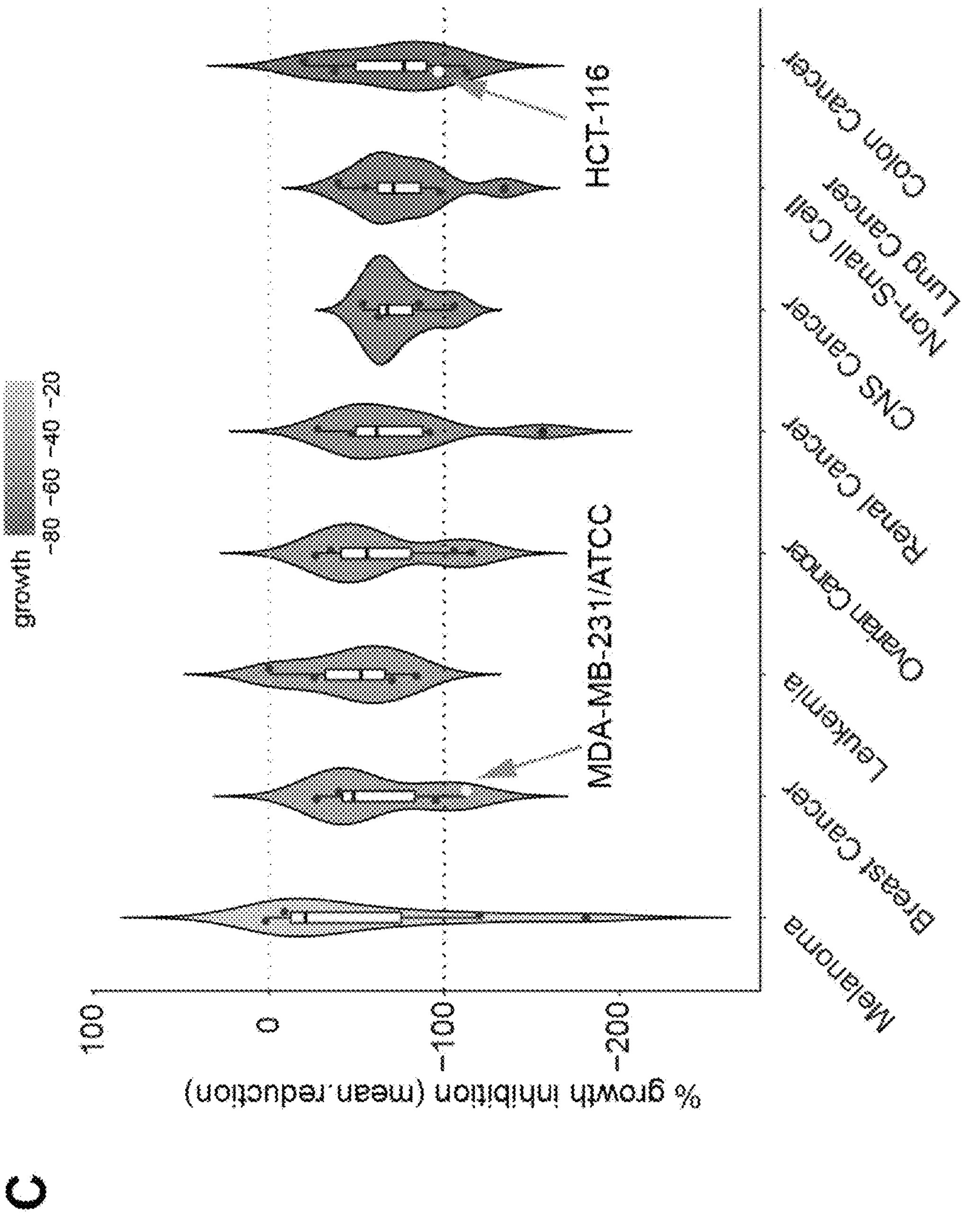
Figures 67A, 67B, 67C:
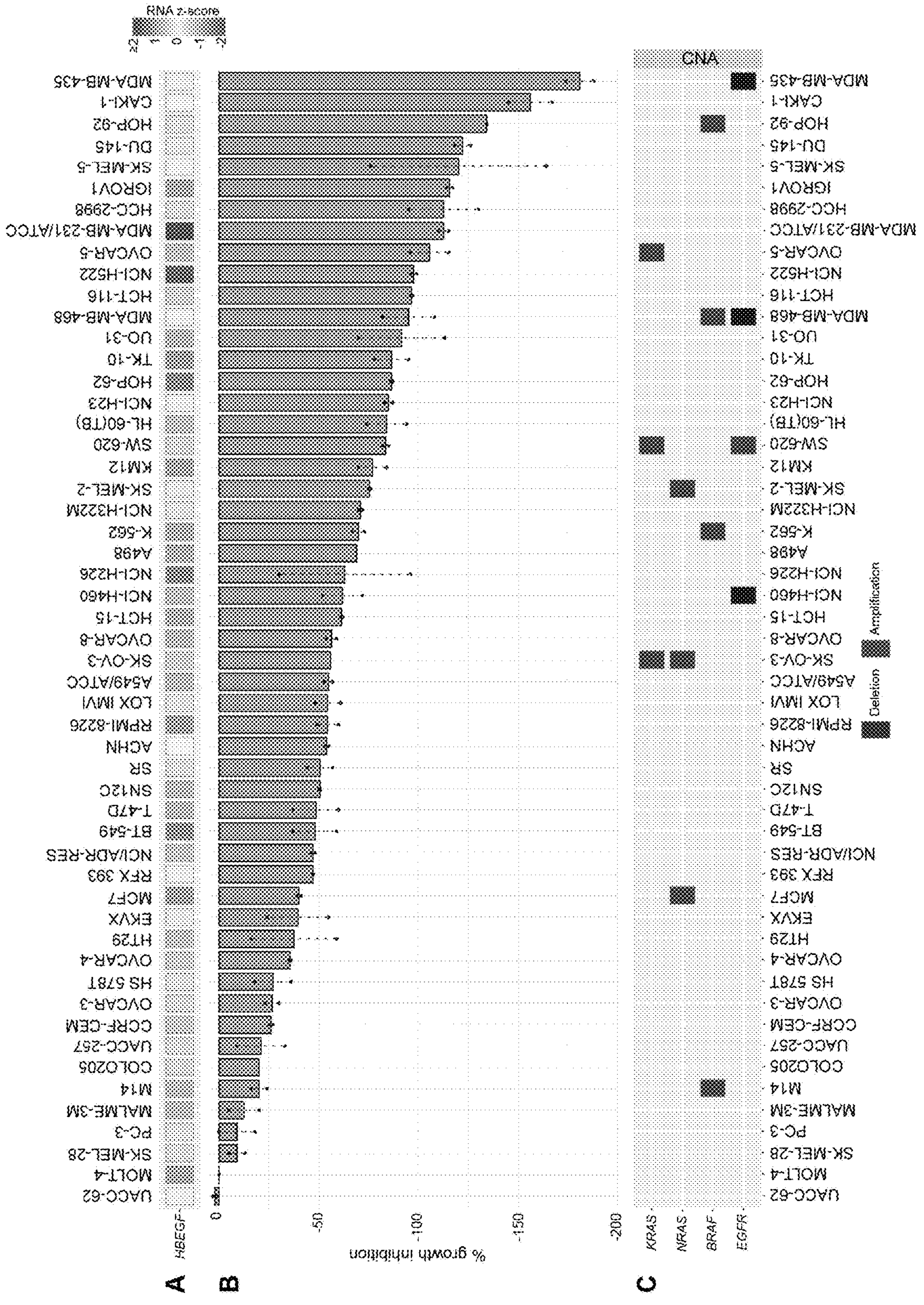
FIG. 67A-67C. Expression of HB-EGF and copy number alterations of KRAS, NRAS, BRAF and EGFR across several cell lines from the NCI-60 panel. (A). Heatmap of RNA-Seq expression z-scores for human HB-EGF in 53 out of 60 cell lines included in the NCI-60 panel. Data were retrieved from cBioPortal website for the study with id "cellline_nci60". The color key indicates gene expression value (pink for upregulated and green for downregulated). (B). Bar plot showing the percent growth inhibition of RRSP-DTB for the 56 cell lines included in the analysis. Cancer cell lines were ranked in descending order based on their growth inhibition % value. The presence of two dots on the bars indicate that two replicates were performed per each cell line and bars represent means. No dots indicate that only one replicate was available. (C). Map of copy number alterations in KRAS, NRAS, BRAF and EGFR genes across the 53 cell lines from the NCI-60 panel. Red indicates gene amplification and blue gene deletions.
Figures 68A, 68B, 68C, 68D:
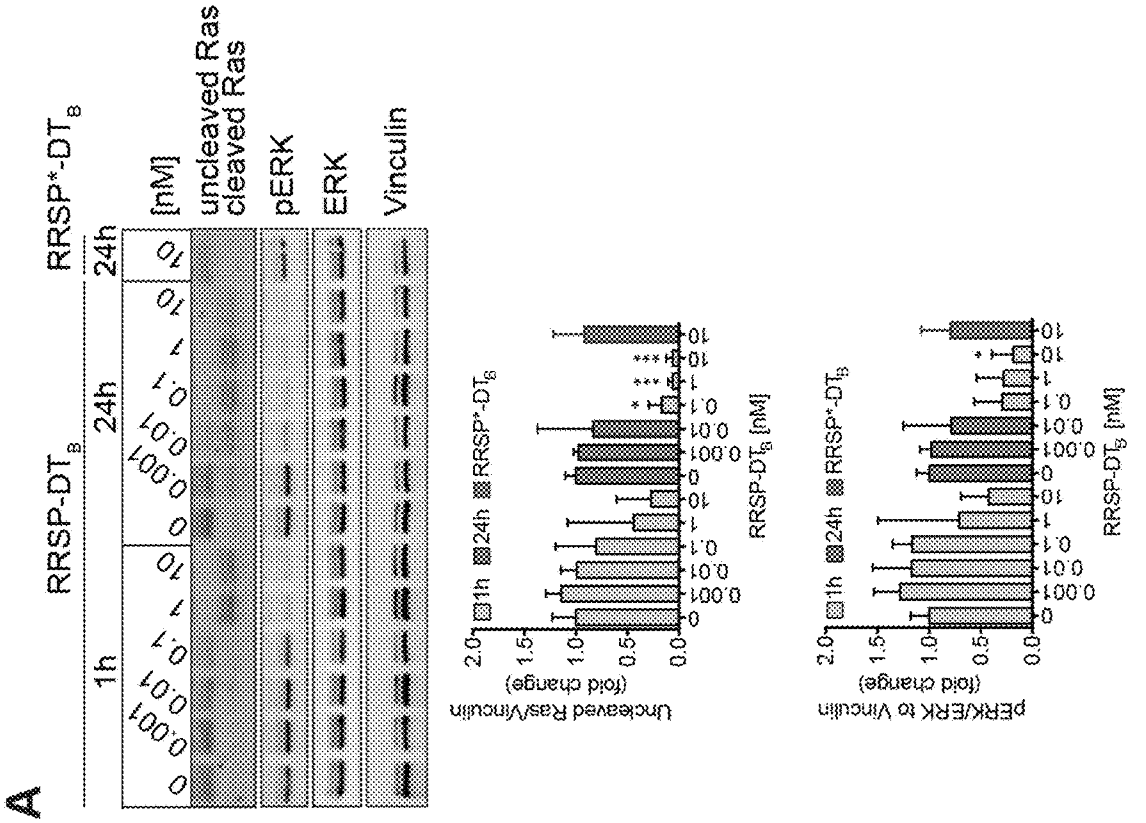
Figures 68A, 68B, 68C, 68D:
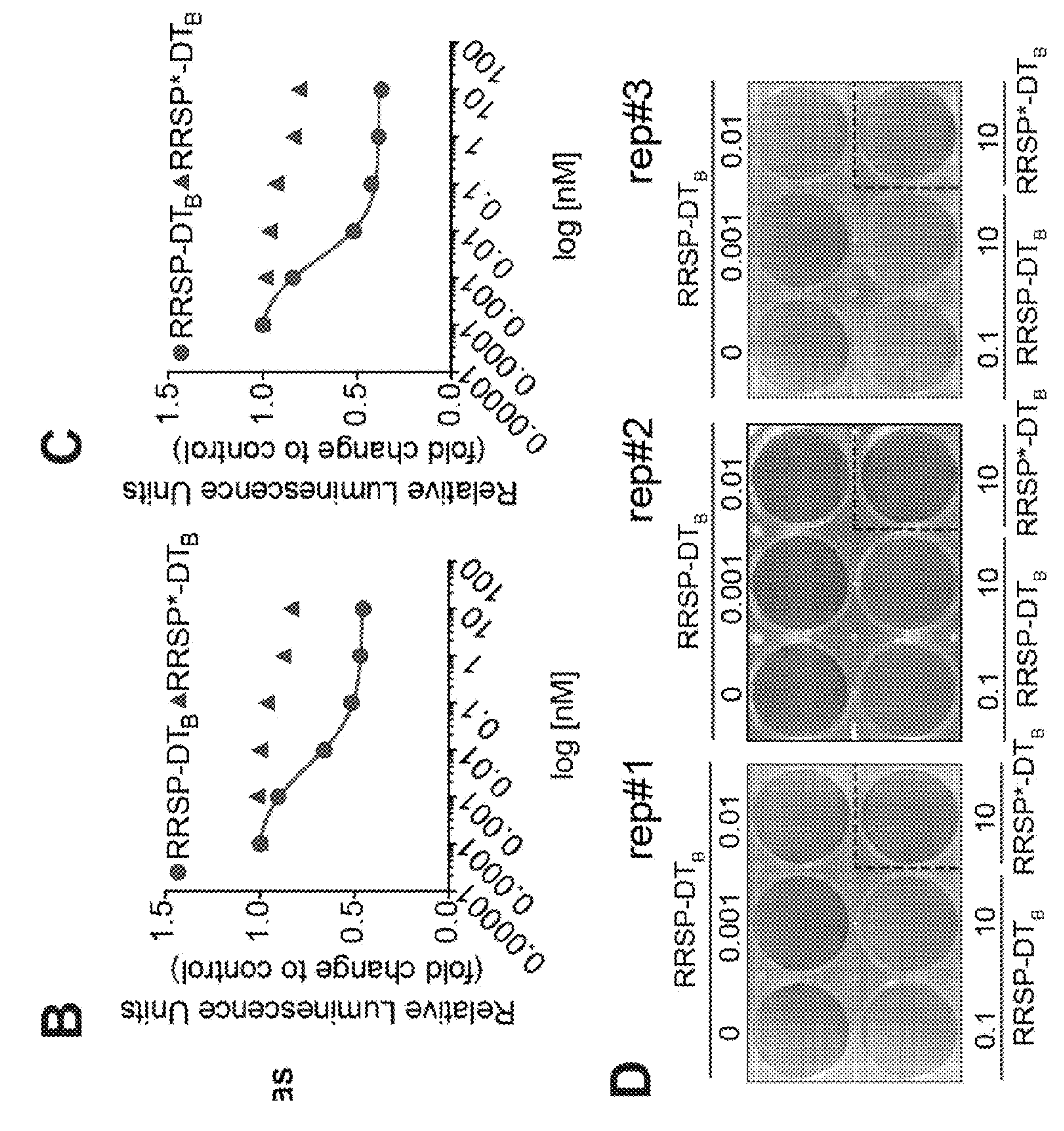

Generally, cell lines that carry KRAS missense mutations were among the most responsive to RRSP-$DT_B$, while cell lines with mutations in BRAF (especially $BRAF^{V600E}$) tended to be less responsive (FIG. 57B). Mutations in HRAS, NRAS, or EGFR were not associated with a response pattern to RRSP-$DT_B$ treatment (FIG. 57B). Notably, analysis of copy number alterations from exome data available for 53 out of 60 NCI cell lines showed amplification of KRAS and NRAS, as well as deletions in EGFR, in the cell lines most sensitive to RRSP-$DT_B$ (FIG. 67B-C). Further, colon cancer cell lines as a group were the most sensitive to RRSP-$DT_B$ overall, followed by non-small cell lung cancer lines (FIG. 57C).

Eight cell lines in the NCI-60 screen showed<25% growth inhibition compared to mock treated and were categorized as “less susceptible”. In this group, growth of UACC-62 and MOLT-4 cells was not affected by RRSP-$DT_B$. One requirement for RRSP-$DT_B$ cytotoxicity is expression of the DT receptor HB-EGF on the cell surface. Available HBEGF gene expression data (FIG. 67A) showed that, while the correlation between RRSP-$DT_B$ sensitivity and HBEGF expression is not linear, many of the cell lines that responded to RRSP-$DT_B$ had higher expression of HBEGF. In addition, the TNBC Hs578T cell line ($HRASG^{12}D$), categorized as less sensitive in the NCI-60 screen, was confirmed to have lower expression of HB-EGF protein and a moderate reduction in cell viability after 72 hours, although RAS cleavage and ERK dephosphorylation were detected at earlier time points (FIG. 63A and FIG. 68A-E). Overall, results from the NCI-60 screen indicate that most tumor types were sensitive to RRSP-$DT_B$ and cell lines with genomic abnormalities in RAS genes were markedly sensitive to RRSP-$DT_B$ treatment.

RRSP Reduces Tumor Burden in a Mutant KRAS TNBC Xenograft Model

Figures 58A, 58B, 58C, 58D, 58E, 58F, 58G, 58H:
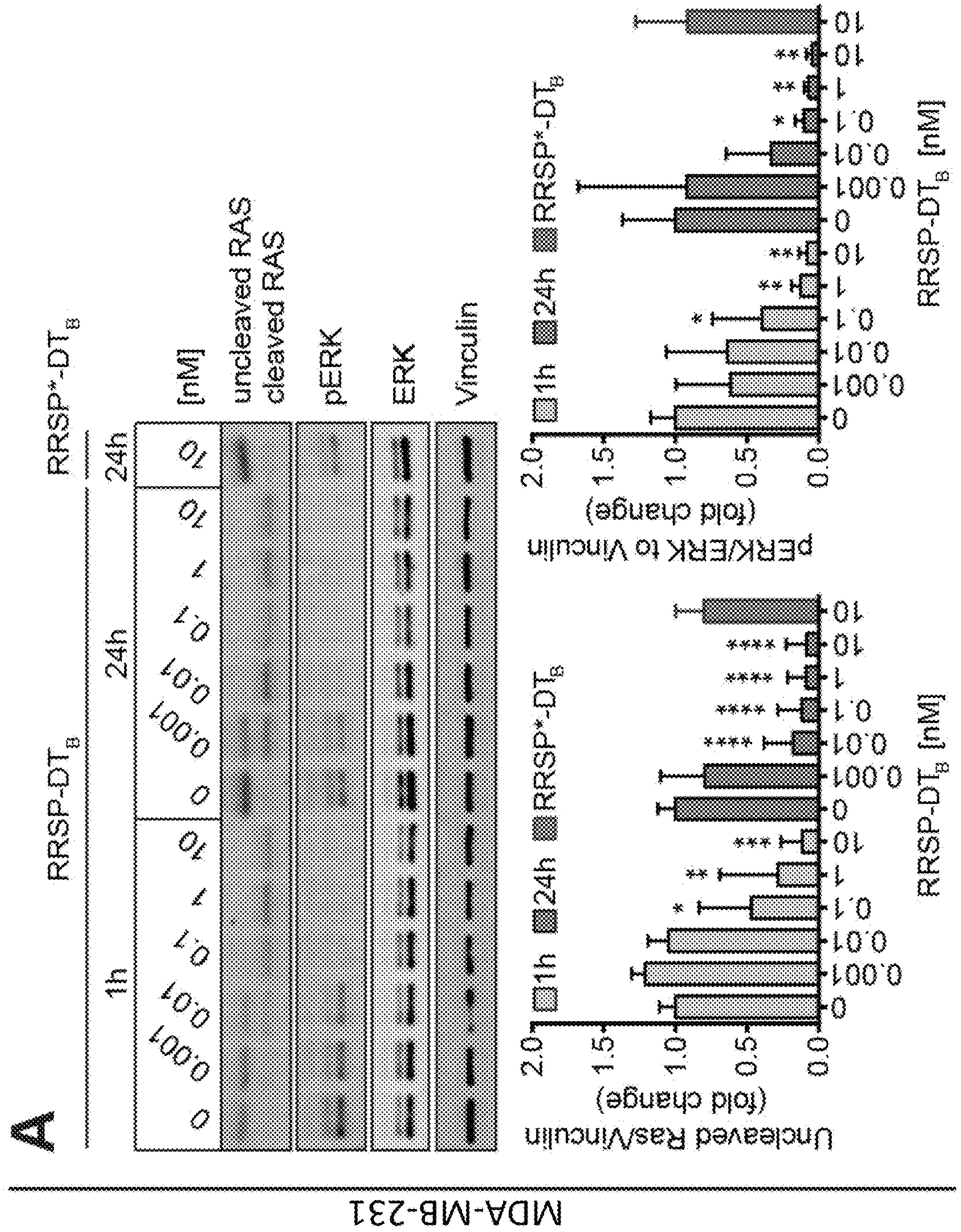
FIG. 58A-58H. RRSP inhibits cell viability, proliferation and tumor growth in a $KRAS^{G13D}$-dependent TNBC xenograft in vivo. (A). Representative western blot and densitometric analysis of uncleaved RAS and pERK levels in MDA-MB-231 $KRAS^{G13D}$ cells treated with increasing doses of RRSP-$DT_B$ and with 10 nM of RRSP*-$DT_B$. Results are expressed as means±SD of four independent experiments (*p<0.05, p<0.01, *p<0.001, ****p<0.0001 versus corresponding control 0 nM; one-way ANOVA followed by Dunnett's multiple comparison test, n=4). (B). Fitted dose-response curve of RRSP-$DT_B$ in MDA-MB-231 cells following 72 hours of treatment. Results are expressed as means±SEM (n=3). (C). Representative images of crystal violet staining of MDA-MB-231 cells treated with RRSP-$DT_B$ or RRSP*-$DT_B$ as indicated for 72 hours. (D). Representative images and quantitative analysis of crystal violet-stained colonies from MDA-MB-231 cells pre-treated with RRSP-$DT_B$ and RRSP*-$DT_B$ at the indicated concentrations for 72 hours and replated at 2,500 cells/well to form colonies over 10 days. Results are expressed as means±SD of three independent experiments (**p<0.01 versus corresponding control 0 nM; one-way ANOVA followed by Dunnett's multiple comparison test, n=3). (E) Bright field images of MDA-MB-231 cells treated with RRSP-$DT_B$ and RRSP*-$DT_B$ at the indicated concentrations for 48 hours (scale bar=50 μM) and corresponding cell rounding quantification (***p<0.001 versus corresponding control 0 nM; one-way ANOVA followed by Dunnett's multiple comparison test, n=3). (F). Tumor growth curve of vehicle, RRSP-$DT_B$ and RRSP*-$DT_B$-treated athymic nu/nu female mice bearing MDA-MB-231-derived tumors. Mice received 0.1 mg/kg of RRSP-$DT_B$ and 0.1 mg/kg of RRSP*-$DT_B$ every day (weekends excluded). (G). Representative images of tumors at the experimental endpoint. (H). Column scatter plots showing individual tumor volumes at the end of the treatment schedule. Horizontal dashed line indicates the average tumor volume (baseline) on the first day of treatment (194 $mm^3$). Empty points indicate tumors from mice that were sacrificed earlier because they exceeded the 1500 $mm^3$ threshold. Data are means±SEM (n=5 mice per group). Statistical analysis between vehicle and treatment groups was performed using one-way ANOVA followed by Tukey's multiple comparison test (p<0.01, *p<0.001).
Figures 58A, 58B, 58C, 58D, 58E, 58F, 58G, 58H:
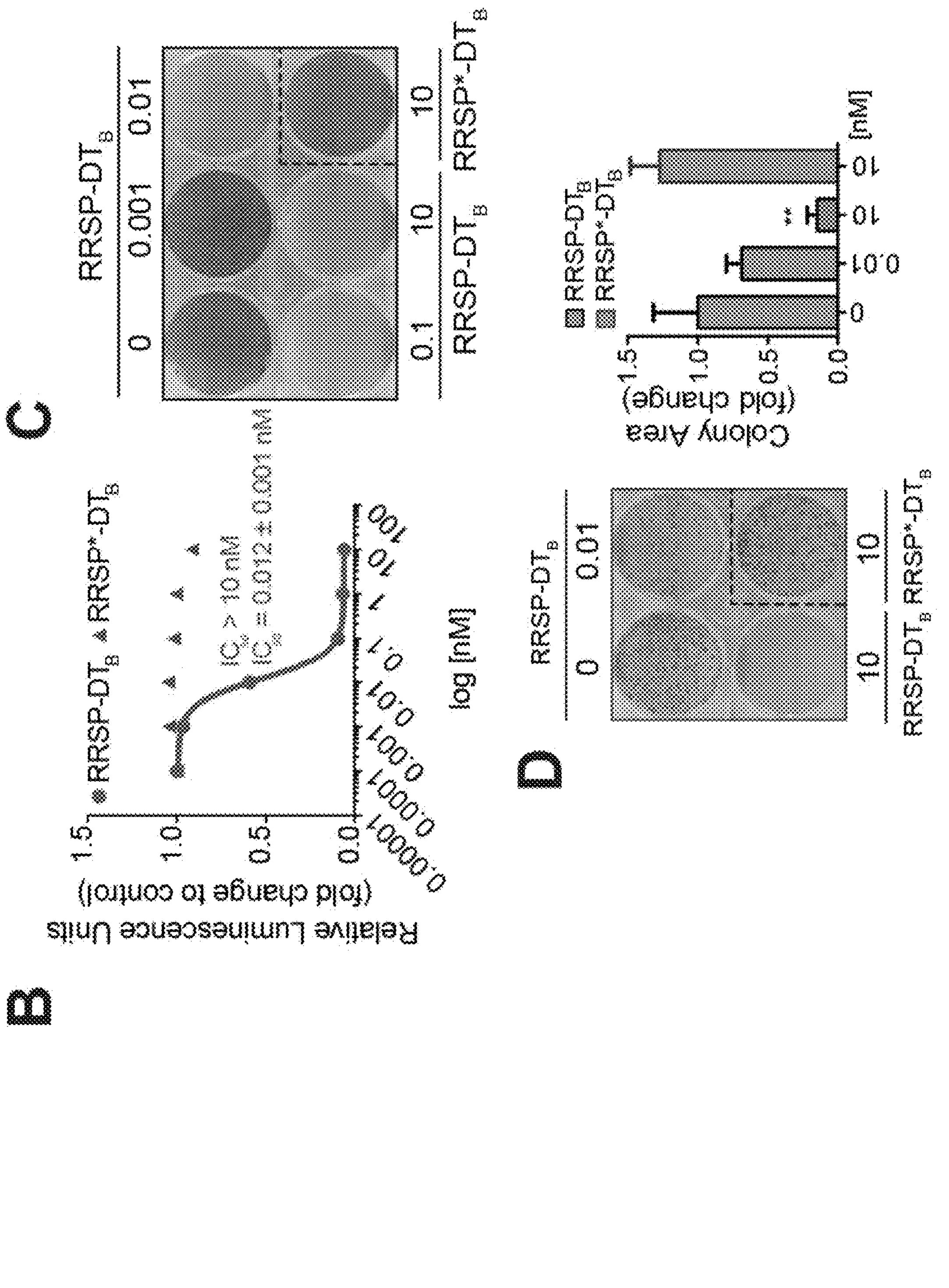
Figures 58A, 58B, 58C, 58D, 58E, 58F, 58G, 58H:
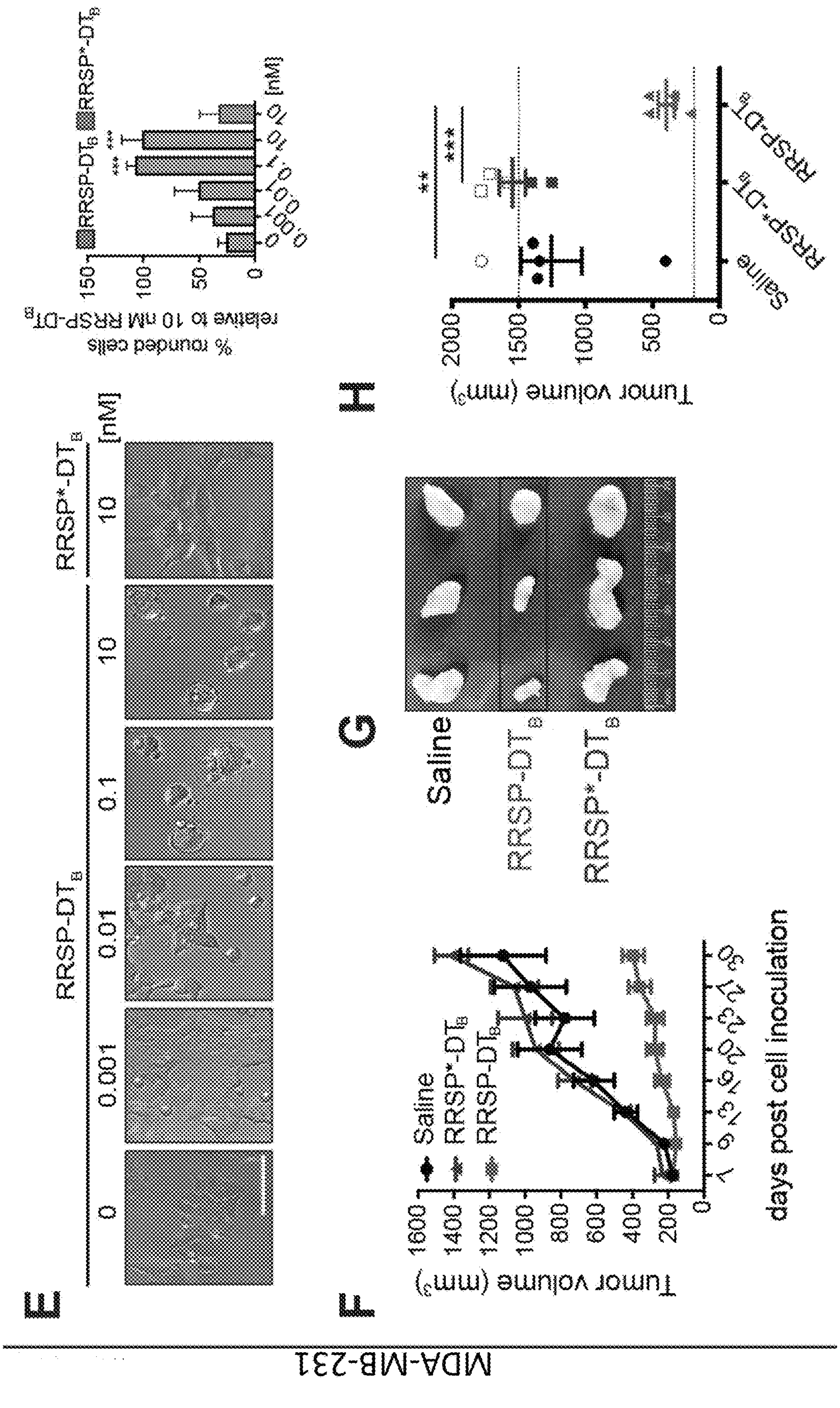
Figures 69A, 69B, 69C, 69D:
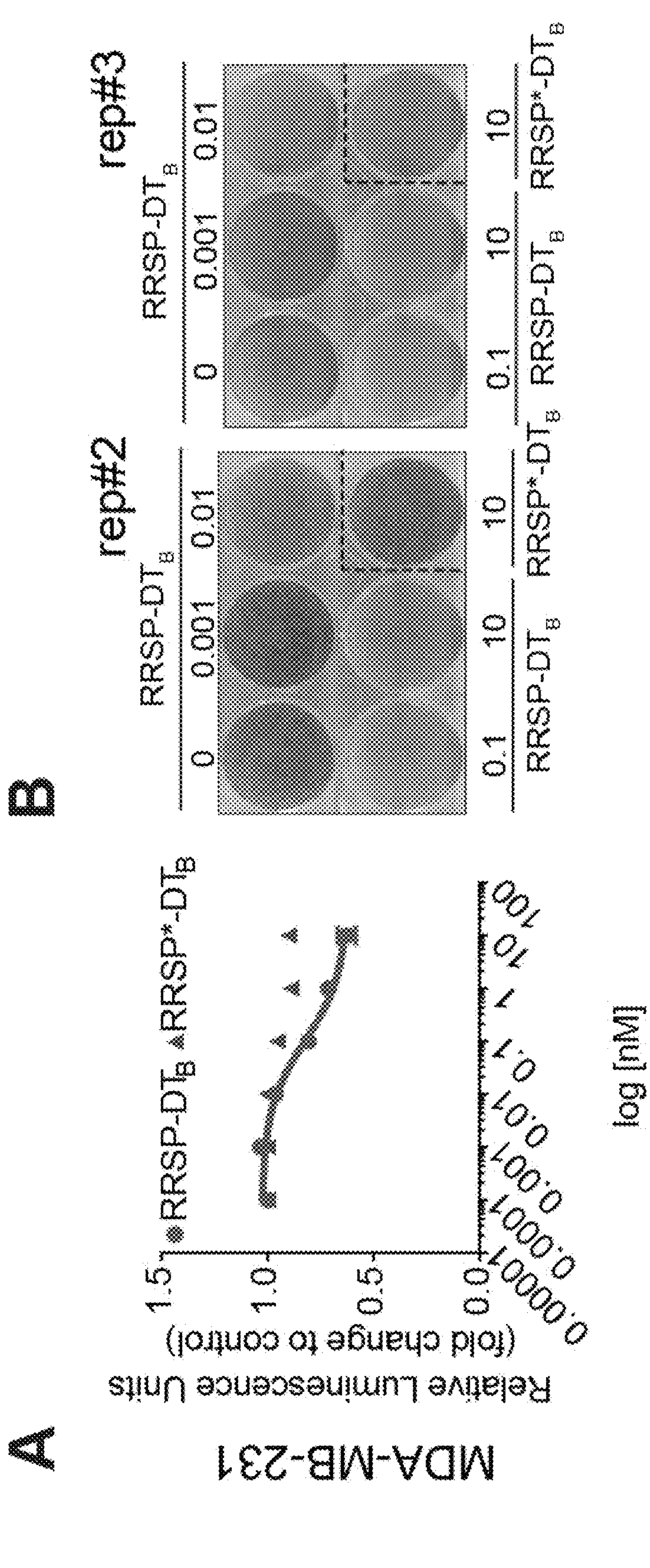
FIG. 69A-69D. Additional data on the effect of RRSP-$DT_B$ on viability of MDA-MB-231 cells and whole tumor IHC images and analysis of total RAS and phosphorylated ERK from the MDA-MB-231 xenograft. (A). Dose-response curve of RRSP-$DT_B$ in MDA-MB-231 cells following 24 h of treatment. Slopes of the dose-response curves for both RRSP-$DT_B$ and mutant RRSP*-$DT_B$ were not steep enough to retrieve an $IC_{50}$. Results are expressed as means±SEM (n=3). (B) Additional two replicate images of crystal violet staining of MDA-MB-231 cells treated with RRSP-$DT_B$ and RRSP*-$DT_B$ as indicated for 72 h. (C) Sections of whole tumors from the MDA-MB-231 xenograft immunostained with a total RAS antibody (n=3; scale bar=200 μm). Mice were treated every day (weekends excluded) at the indicated treatment conditions for about 4 weeks. (D) Sections of whole tumors from the same MDA-MB-231 xenograft immunostained with a pERK antibody (scale bar=200 μm).
Figures 69A, 69B, 69C, 69D:
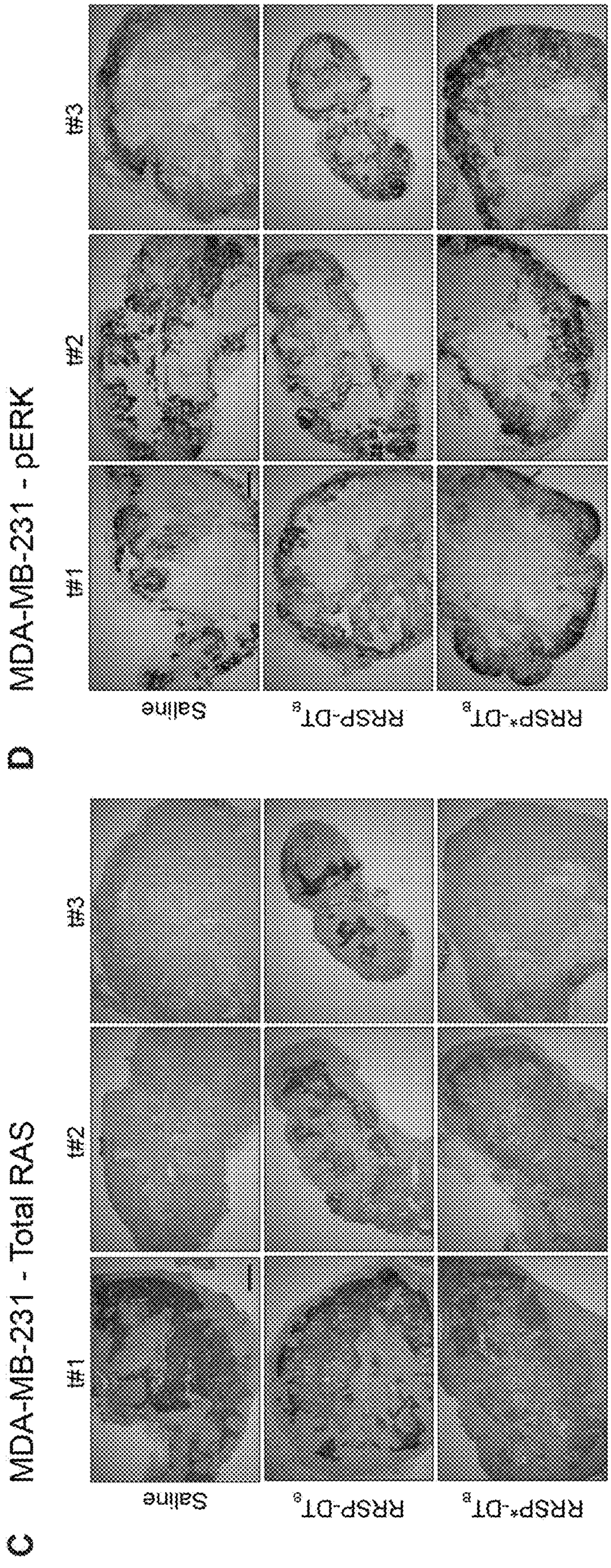

The highly sensitive basal-like MDA-MB-231 TNBC cell line in the NCI-60 screen (FIG. 57A) has a $KRAS^{G13D}$ mutation, is a KRAS-dependent cell line (31, 35), and was among the first cell lines characterized as sensitive to RRSP (22) (FIG. 57A). Consistent with these findings, treatment of MDA-MB-231 cells with the engineered chimeric toxin RRSP-$DT_B$ cleaved RAS and reduced pERK levels to a similar extent as in MDA-MB-436 cells (FIG. 58A). Also similar to MDA-MB-436 cells, cell viability ($IC_{50}$=0.012±0.001 nM; FIG. 58B-C and FIG. 69A-B) and cell proliferation (FIG. 58D) were strongly affected, and RRSP-$DT_B$ induced significant cell rounding in MDA-MB-231 cells starting at 0.1 nM (FIG. 58E). As this cell line has a more rapid doubling time than MDA-MB-436 cells (36), mice with MDA-MB-231 xenografts were treated daily (5 days ON/2 days OFF) (FIG. 58F). After 4 weeks, the RRSP-$DT_B$ treatment group had markedly smaller tumors than saline and RRSP*-$DT_B$ controls (FIG. 58G-H). Moreover, the RRSP-$DT_B$-treated tumors had a more focal/patchier staining pattern for RAS and pERK than tumors from saline and RRSP*-$DT_B$ treated mice, which instead exhibited a more diffuse staining pattern (FIG. 69C-D). Indeed, MDA-MB-231 tumors (FIG. 58G) were pale in color compared to the MDA-MB-436 tumors (FIG. 56C) consistent with reports that MDA-MB-231 tumors exhibit low vascularization (37). This supports that MDA-MB-231 tumors in our study may be poorly vascularized, and tumor size reduction may be predominantly due to RRSP-$DT_B$ diffusion from the tumor periphery, resulting in the partial cleavage of RAS in the center of residual tumors. Even still, RRSP-$DT_B$ was highly effective in targeting TNBC MDA-MB-231 tumors resulting in a significant inhibition of tumor growth, thus confirming RRSP-$DT_B$ is effective against TNBC.

Figures 59A, 59B, 59C, 59D, 59E, 59F, 59G, 59H:
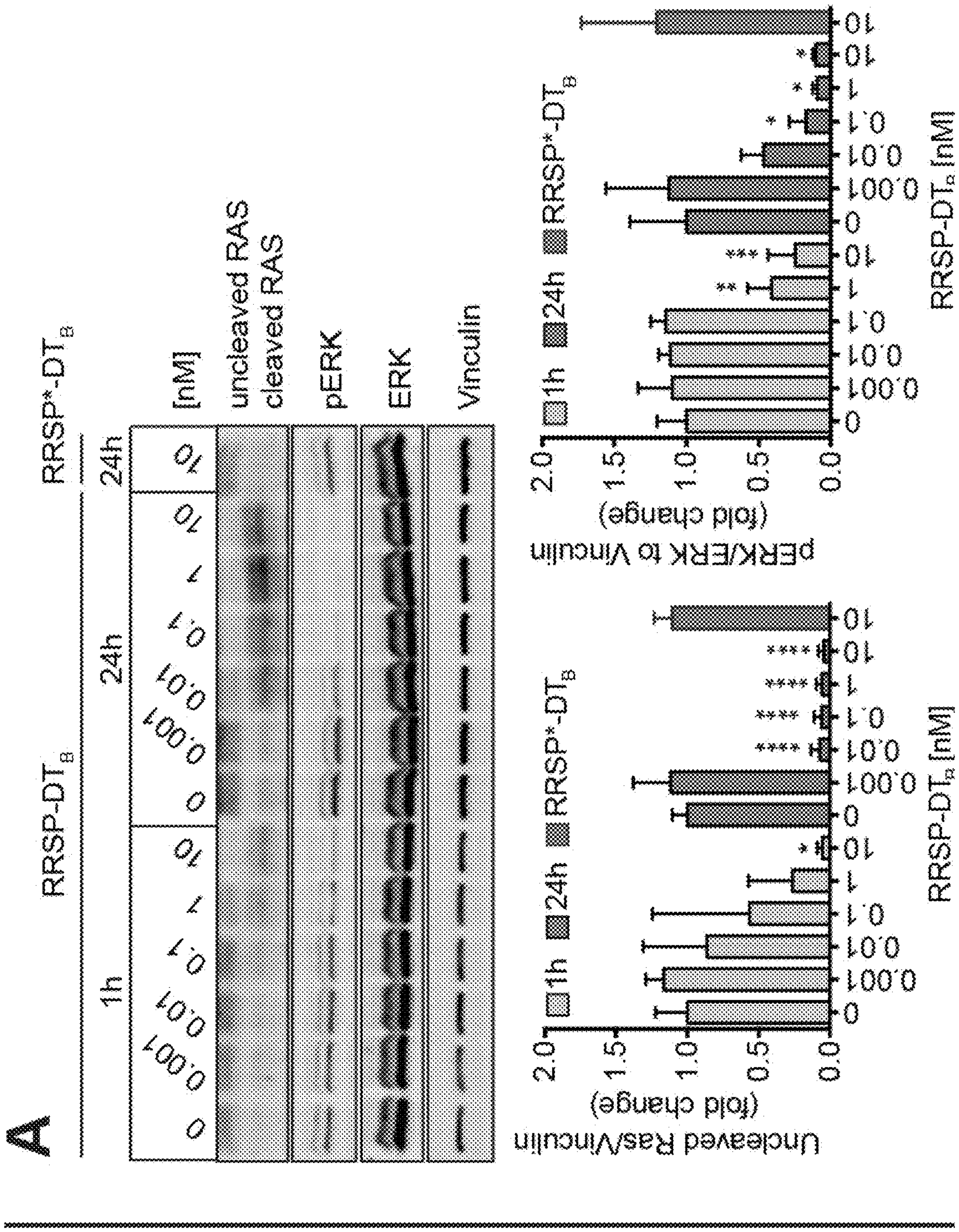
FIG. 59A-59H. Effect of RRSP on viability and proliferation of colorectal HCT-116 $KRAS^{G13D}$ cells in 2D and 3D cellular models. (A) Representative western blot and densitometric analysis of uncleaved RAS and phosphorylated ERK in HCT-116 cells treated with increasing doses of RRSP-$DT_B$ for 1 and 24 h. Catalytically-inactive RRSP*-$DT_B$ was used as negative control at 10 nM. Results are expressed as means±SD of three independent experiments (*p<0.05, p<0.01, *p<0.001, ****p<0.0001 versus corresponding control 0 nM; one-way ANOVA followed by Dunnett's multiple comparison test, n=3). (B) Fitted dose-response curve of RRSP-$DT_B$ in HCT-116 cells following 72 h of treatment. (C). Representative images of crystal violet staining of HCT-116 cells treated with RRSP-$DT_B$ or RRSP*-$DT_B$ as indicated for 72 h. (D) Representative images and quantitative analysis of crystal violet-stained colonies from HCT-116 cells pre-treated with RRSP-$DT_B$ or RRSP*-$DT_B$ at the indicated concentrations for 72 h and reseeded at 2,500 cells/well to form colonies over 10 days. Results are expressed as means±SD of three independent experiments (p<0.01, *p<0.001 versus corresponding control 0 nM; one-way ANOVA followed by Dunnett's multiple comparison test, n=3). (E). Bright field images of HCT-116 cells treated with RRSP-$DT_B$ and RRSP*-$DT_B$ at the indicated concentrations for 48 h and corresponding cell rounding quantification (*p<0.05, *p<0.001, **p<0.0001 versus corresponding control 0 nM; one-way ANOVA followed by Dunnett's multiple comparison test, n=3). (F). Fitted dose-response curves in HCT-116 spheroids following treatment with RRSP-$DT_B$ and RRSP*-$DT_B$ at the indicated time and concentration. Results are expressed as means±SEM (n=4). (G) Representative bright field images of HCT-116 spheroids treated at the indicated time and concentrations with RRSP-$DT_B$ and RRSP*-$DT_B$ and quantitative analysis of spheroids' volume (scale bar=200 μm). Results are expressed as means±SD of three independent experiments (p<0.01, **p<0.0001 versus corresponding control 0 nM; one-way ANOVA followed by Dunnett's multiple comparison test, n=3). (H). Representative images of immunoreactivity to total RAS and pERK in sections from HCT-116 spheroids and corresponding quantification of DAB optical density via color deconvolution (*p<0.05, *p<0.001, **p<0.0001; one-way ANOVA followed by Tukey's multiple comparison test, n=3; scale bar=400 μM).
Figures 59A, 59B, 59C, 59D, 59E, 59F, 59G, 59H:
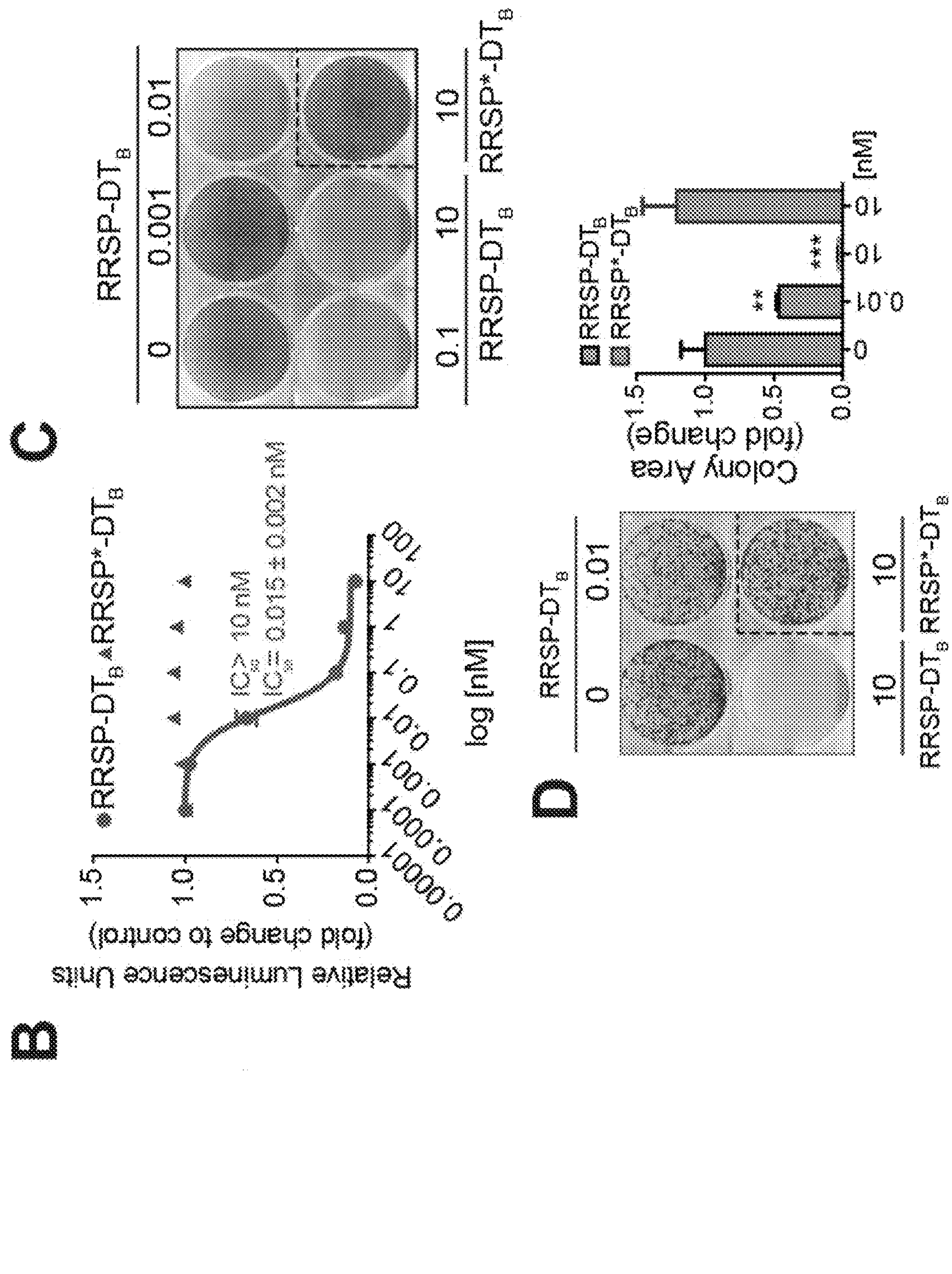
Figures 59A, 59B, 59C, 59D, 59E, 59F, 59G, 59H:
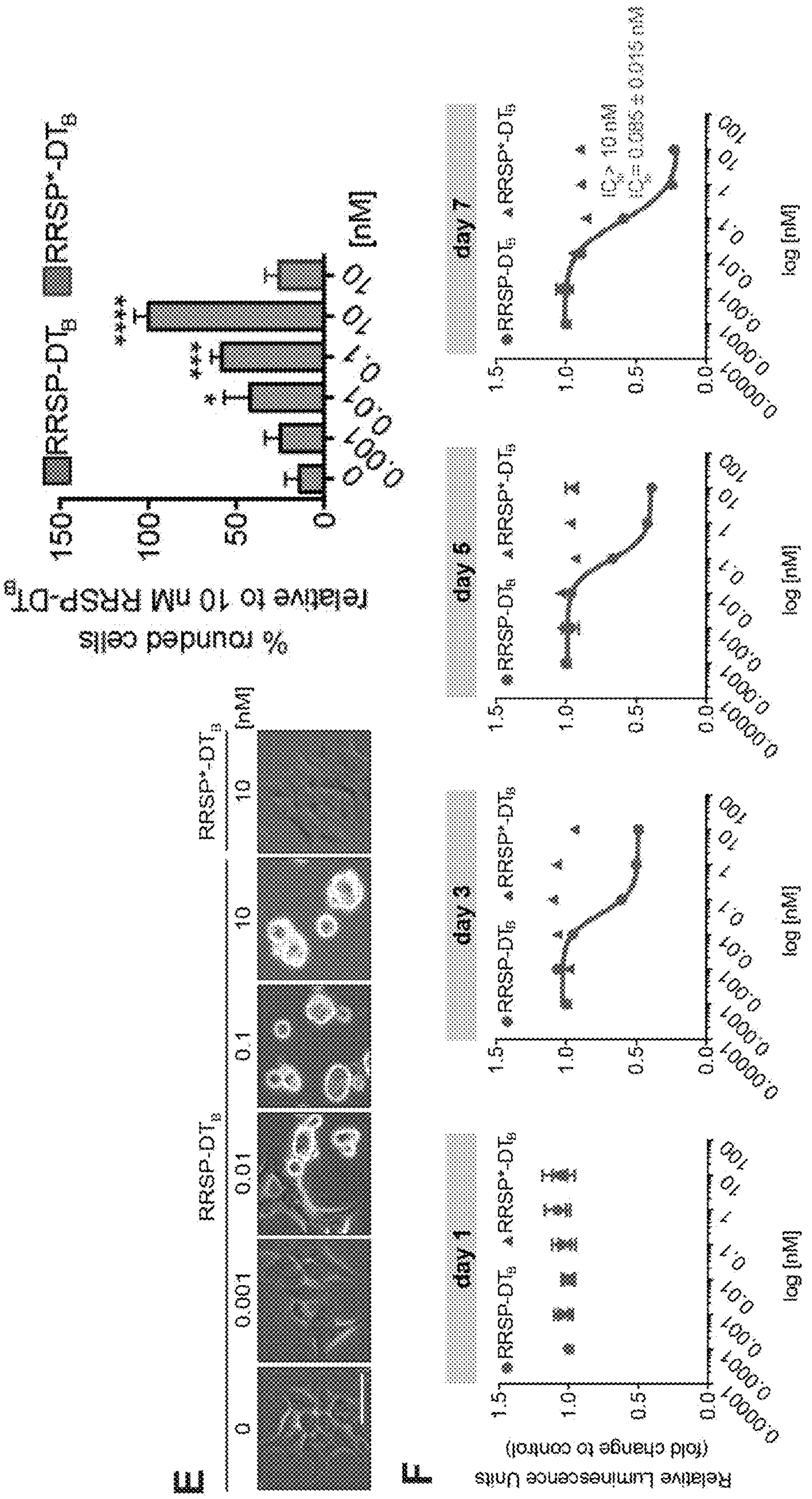
Figures 59A, 59B, 59C, 59D, 59E, 59F, 59G, 59H:
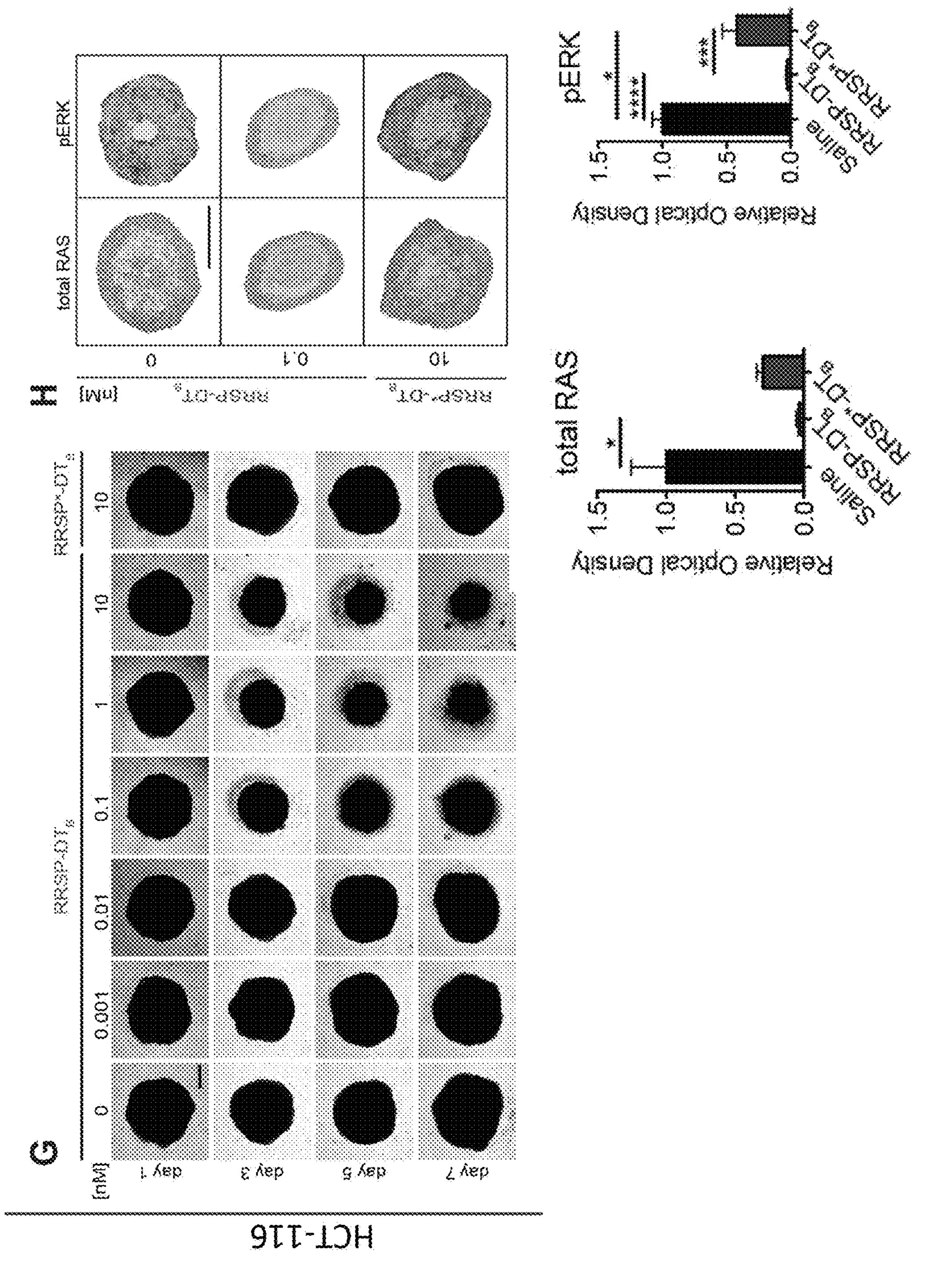
Figures 70A, 70B, 70C:
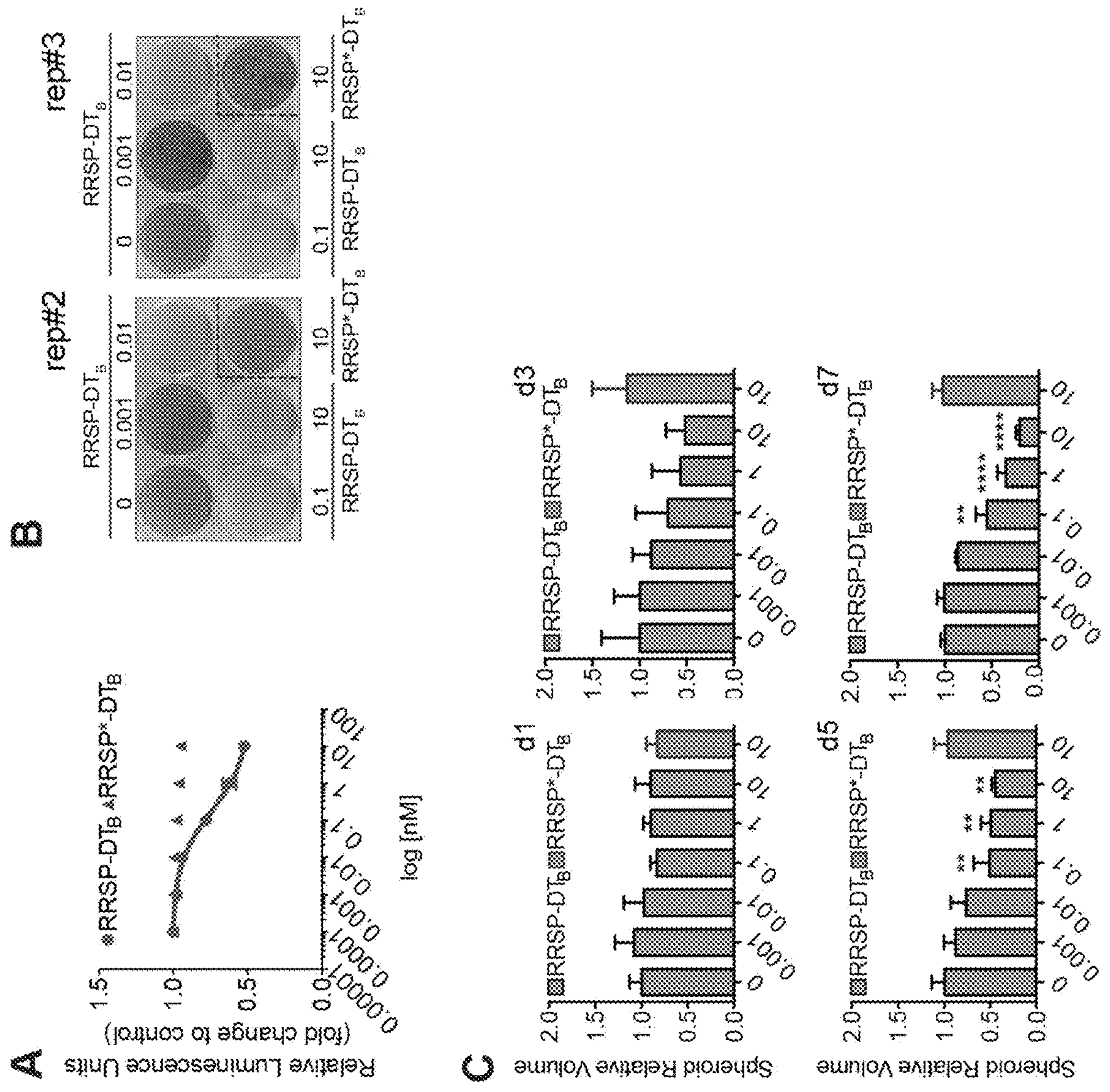
FIG. 70A-70C. Effect of RRSP-$DT_B$ on viability of CRC HCT-116 KRAS G13D cells after 24 hours of treatment and spheroid volume quantification. (A) Dose-response curve of RRSP-$DT_B$ in HCT-116 cells following 24 h of treatment. Slopes of the dose-response curves for both RRSP-$DT_B$ and mutant RRSP*-$DT_B$ were not steep enough to retrieve an $IC_{50}$. Results are expressed as means±SEM (n=3). (B) Additional two replicate images of crystal violet staining of HCT-116 cells treated with RRSP-$DT_B$ or RRSP*-$DT_B$ as indicated for 72 h. (C). Quantitative analysis of spheroids' volumes. Results are expressed as means±SD of three independent experiments (p<0.01, **p<0.0001 versus corresponding control 0 nM; one-way ANOVA followed by Dunnett's multiple comparison test, n=3; d=day).

RRSP-$DT_B$ Inhibits Cell Viability of Colorectal Cancer Cells in 2D Monolayers and 3D Spheroids KRAS mutations are found in ~50% of colorectal carcinomas (CRC), the third leading cause of cancer-related deaths, representing a major target population for anti-RAS therapy (38). Colon cancer cell lines were the most susceptible to RRSP-$DT_B$ in the NCI-60 screen. Here, we examined the anti-cancer potential of RRSP-$DT_B$ on the CRC cell line HCT-116 harboring a $KRAS^{G13D}$ mutation. Treatment of cells with RRSP-$DT_B$ at 10 pM led to RAS processing and reduced pERK levels at 10 pM after 24 hours (FIG. 59A) and strongly decreased the viability of HCT-116 cells after 72 hours ($IC_{50}$=0.0015±0.002 nM) (FIG. 59B and FIG. 70A). Crystal violet staining showed remarkable cell loss after treatment with RRSP-$DT_B$ as low as 10 pM (FIG. 59C and FIG. 70B). Clonogenic assays showed a significant reduction in HCT-116 colonies following treatment with 10 pM of RRSP-$DT_B$ and almost no colonies were found at 10 nM RRSP-$DT_B$ (FIG. 59D) demonstrating complete loss of cell proliferation. These data agree with the RRSP-$DT_B$-induced cell rounding phenotype observed with this and other sensitive cell lines (FIG. 59E).

Unlike two-dimensional cell monolayers, three-dimensional spheroids can recapitulate the architectural, microenvironmental and functional features of in vivo tumors, while retaining reproducibility and easy-to-use properties (39, 40). Effects on cell viability of spheroids from HCT-116 cells were observed after 3 days, with maximum effect observed after 7 days of treatment ($IC_{50}$=0.085±0.015 nM) (FIG. 59F). Bright field images and quantitative analysis showed a dose- and time-dependent reduction in spheroid size following RRSP-$DT_B$ treatment (FIG. 59G and FIG. 70C). Immunostaining of spheroid sections treated with 0.1 nM RRSP-$DT_B$ for 3 days showed that intracellular RAS was essentially absent and pERK undetectable (FIG. 5911). Collectively, these results demonstrate that RRSP-$DT_B$-dependent RAS ablation and subsequent loss of pERK is highly cytotoxic to CRC HCT-116 ($KRAS^{G13D}$) cells in 2D monolayers and 3D spheroids.

RRSP-$DT_B$ Exhibits Antitumor Activity in a Colorectal Cancer Xenograft Model

Figures 60A, 60B, 60C, 60D:
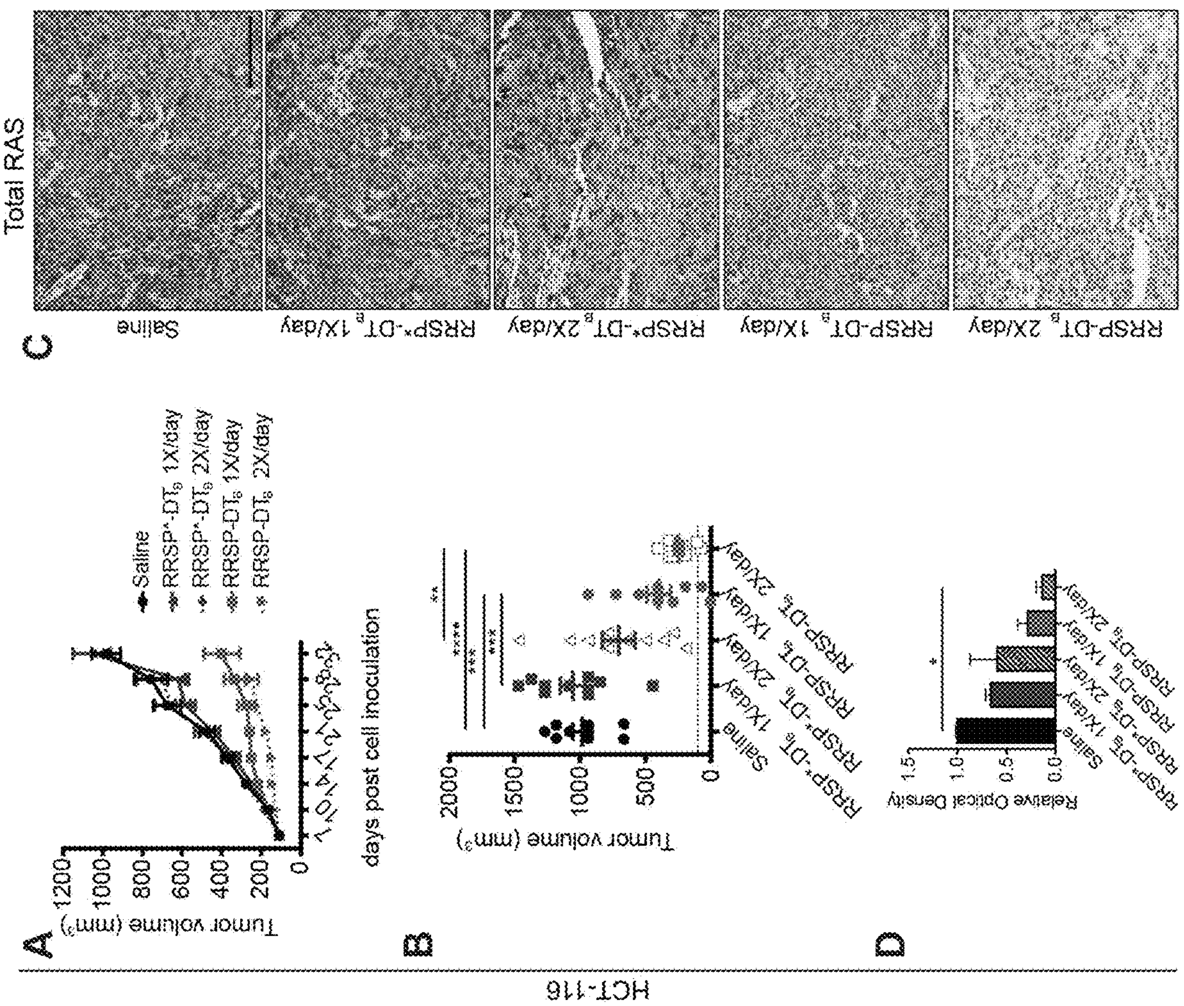
FIG. 60A-60D. RRSP slows tumor growth in a CRC xenograft in vivo. (A) Tumor growth curve of vehicle, RRSP-$DT_B$ and RRSP*-$DT_B$-treated athymic nu/nu female mice bearing HCT-116-derived tumors. Mice received 0.1 mg/kg of RRSP-$DT_B$ and 0.1 mg/kg of RRSP*-$DT_B$ every day (1×/day) or twice per day (2×/day) weekends excluded. (B) Column scatter plots showing HCT-116 individual tumor volumes at the end of the treatment schedule. Horizontal dashed lines indicate the average tumor volume (baseline) on the first day of treatment (100 $mm^3$). Data are means±SEM. In all groups, n=10 mice. In the saline group, one mouse was sacrificed on day 28 due to a too large tumor. Statistical analysis between vehicle and treatment groups was performed using one-way ANOVA followed by Tukey's multiple comparison test (p<0.01, *p<0.001, ****p<0.0001). (C). Representative IHC images of immunoreactivity to total RAS in sections from HCT-116 tumors and (D) corresponding quantification of DAB optical density (*p<0.05, one-way ANOVA followed by Tukey's multiple comparison test, n=3; scale bar=100 μM).

Since HCT-116 cells are fast-growing cells (doubling time≤20 hours) that generate fast-growing tumors in vivo (41), we administered 0.1 mg/kg of RRSP-$DT_B$ to mice on a q.d. (1×/day) or twice per day (2×/day, b.i.d.) schedule (weekends excluded) for 4 weeks. Both dosing schedules resulted in significant tumor size reduction and tumor regression was observed in 2/10 mice in both RRSP-$DT_B$ treatment groups (FIG. 60A-B). The residual tumors showed that RRSP-$DT_B$ effectively cleaved RAS, although only the b.i.d. dosing group achieved statistical significance (FIG.

Figures 71A, 71B:
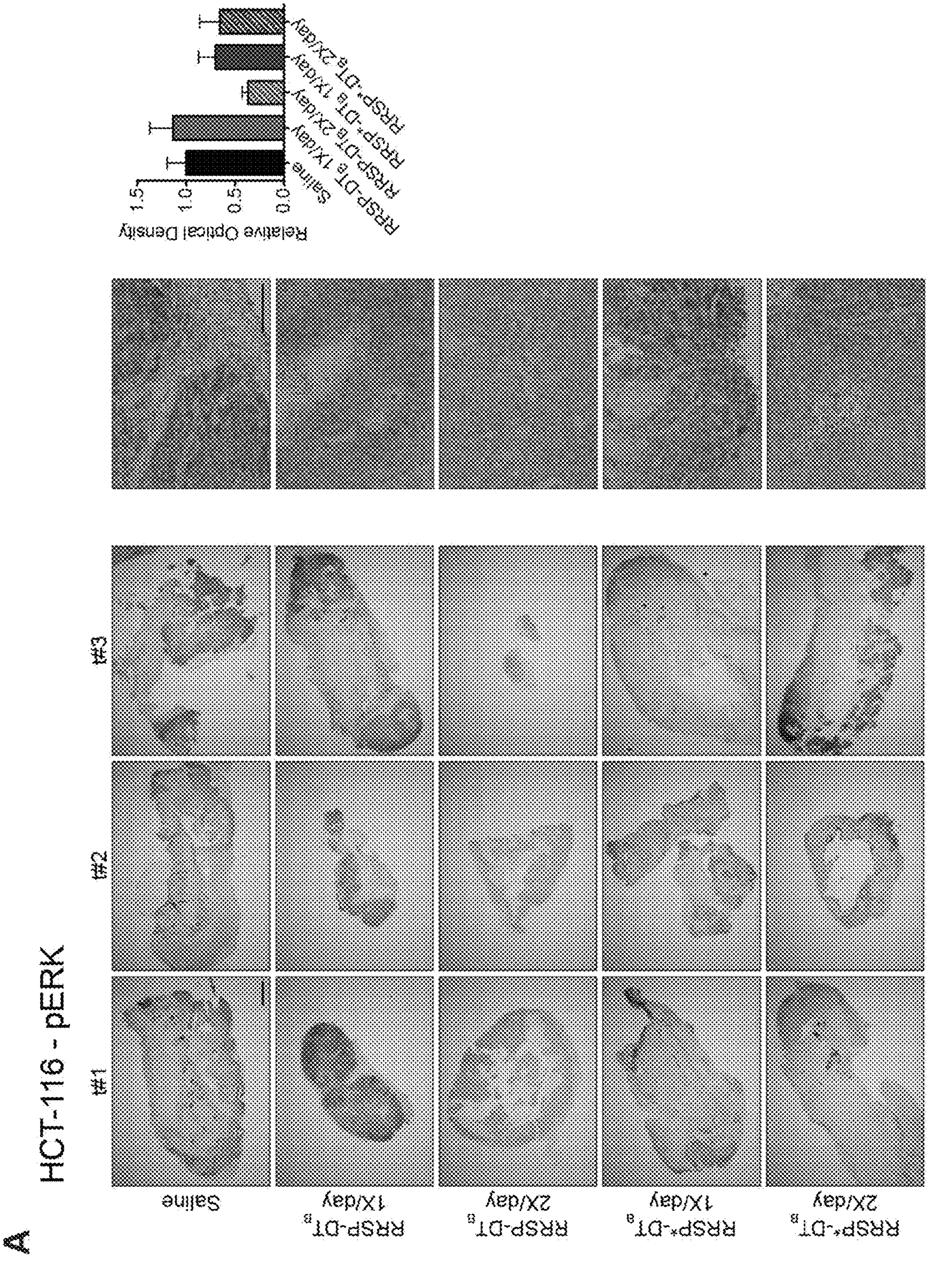
FIG. 71A-71B. Whole tumor IHC images and analysis of total RAS and phosphorylated ERK from the HCT-116 xenograft. (A) Sections of whole tumors from the same HCT-116 xenograft immunostained for phosphorylated ERK (scale bar=200 μm). Bar plot shows quantification of pERK DAB signal (n=3). (B) Sections of whole tumors from the HCT-116 xenograft immunostained with a total RAS antibody (n=3; scale bar=200 μm, left panel; scale bar=100 μm, right panel). Mice were treated every day (1×/day) and twice per day (2×/day) weekends excluded at the indicated treatment conditions for about 4 weeks.
Figures 71A, 71B:
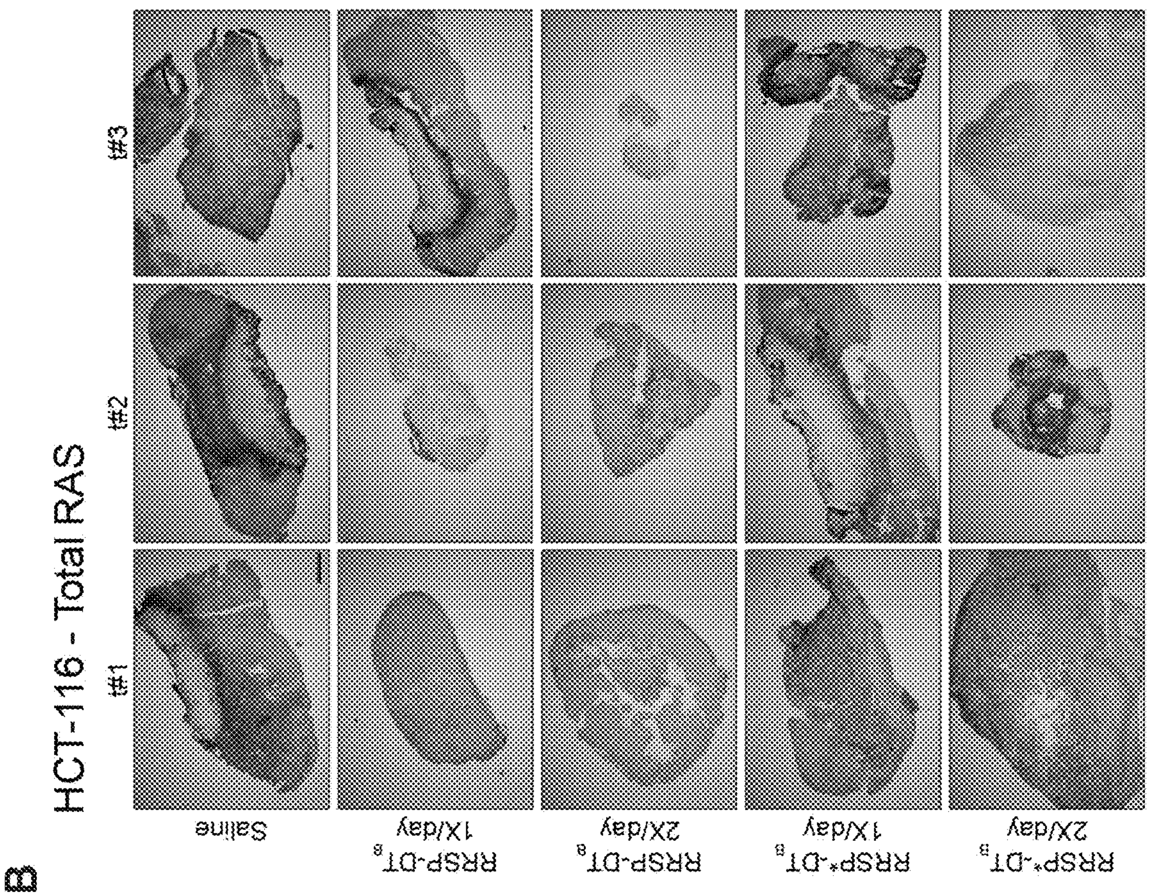

60C-D and FIG. 71A). Quantitative analysis of pERK showed that the b.i.d. dosing group had a 2.5-fold reduction in pERK levels relative to controls and some tumors displayed focal staining patterns (FIG. 71B). Overall, these data show that RRSP-$DT_B$ exhibited strong anti-tumor activity in a CRC xenograft model via irreversible inactivation of RAS.

Discussion

Almost four decades ago, the discovery of RAS as the first human oncogene changed our understanding of cancer. Despite tremendous effort, the three RAS isoforms (KRAS, NRAS and HRAS) have been called "undruggable" and no direct therapies are currently in clinical use (1, 12-14). Nevertheless, promising results for small molecules that irreversibly bind the G12C mutant form of KRAS have led to ongoing phase I clinical trials to evaluate the efficacy and safety profile of AMG510, MRTX849 and ARS3248 (18-20, 42, 43). However, the $KRAS^{G122C}$ mutation is found in only a subpopulation of cancers, limiting the applicability of these compounds. Further, while RAS oncoproteins remain the main oncogenic drivers in RAS-addicted tumors, several studies have pinpointed the tumorigenic role of wild-type RAS proteins (44). Indeed, amplification of wild-type RAS genes or activation of wild-type RAS proteins via acute growth factor stimulation have been shown to sustain growth of multiple tumor types (7-10). Moreover, it has been previously reported that depletion of mutant RAS in heterozygous RAS cells can lead to overactivation of EGFR/RAS signaling from the remaining wild-type RAS (45). Therefore, there is an urgent need for broadly applicable pan-RAS inhibitors that target not only the most common RAS mutants, but also wild-type RAS proteins aberrantly overactivated by mutation-independent mechanisms.

Here, we describe a novel engineered chimeric toxin comprised of an endopeptidase from *V. vulnificus* that is highly specific for RAS and RAP1 and the protein translocation machinery of DT. This fusion protein mediates the endocytosis and cytosolic delivery of RRSP exclusively into HB-EGF receptor-bearing cells. Of note, HB-EGF is highly expressed in several human cancers, including gastric, ovarian and TNBC, and the non-toxic diphtheria toxoid CRM197 showed anti-tumor effects on TNBC xenografts (46). As such, we predicted TNBC could be highly susceptible to RRSP-$DT_B$. We show that picomolar amounts of RRSP-$DT_B$ completely cleaved RAS proteins in these cells, eliminating RAS-dependent ERK phosphorylation. This resulted in a very potent effect on MDA-MB-436 cell viability ($IC_{50}$=5 pM). Similarly, RRSP-$DT_B$ treatment led to a large reduction in tumor burden in MDA-MB-436 xenografts, with all mice showing significantly smaller tumors than control groups and 60% of mice showing tumor regression. Target engagement was confirmed by immunohistochemistry analysis of tumor sections showing complete depletion of RAS in residual tumors. We also observed low pERK staining in small dissected RRSP-$DT_B$-treated tumors, although pERK levels in these specimens were not significantly different than control tumors that showed limited detection of pERK after four weeks. However, assessment of resected tumors from a shorter 14-day xenograft study revealed that RRSP-$DT_B$ significantly reduced levels of pERK. This effect was masked at four weeks likely due to technical factors. Specifically, a previous study reported that in large (>1 cm) glioma specimens, immunoreactivity of pERK was limited to the tumor periphery and was very low in the tumor core, as we also observed. This study suggested that due to time-dependent penetration of the formalin fixative, pERK state is lost in the deeper tissue cores by the time the fixative has permeated (47).

The study of TNBC was extended then to demonstrate susceptibility of another TNBC cell line, MDA-MB-231. This cell line, which harbors an oncogenic mutations $KRAS^{G13D}$ and $BRAF^{G464V}$, is characterized as KRAS-dependent (35) and is highly sensitive to RRSP (22). In xenograft studies using MDA-MB-231, RRSP-$DT_B$ induced a significant reduction in tumor size. Interestingly, the residual tumors did not show significant reduction in RAS or pERK, but instead revealed a patchy or focal distribution. Thus, the true reduction in RAS detection may be masked by the low vascularization of MDA-MB-231 tumors such that RRSP-$DT_B$ reduces overall tumor size by diffusion from the tumor periphery rather than infiltrating equally throughout the tumor center, as occurred with the MDA-MB-436 xenografts.

We finally investigated the effects of RRSP-$DT_B$ treatment on the CRC cell line HCT-116 ($KRAS^{G13D}$). As with the other cell lines tested, RRSP-$DT_B$ treatment resulted in complete RAS cleavage and pERK reduction in the low picomolar range, with a corresponding reduction in cell viability. Similar results were obtained in HCT-116 spheroids, including complete loss of RAS and pERK immunoreactivity. Notably, depletion of RAS and reduction in pERK were also observed in spheroids treated with the catalytically-inactive mutant RRSP*-$DT_B$, but at a 10-fold higher dose. Previous binding studies showed that RRSP* retains its ability to bind recombinant KRAS, especially at high KRAS:RRSP* molar ratios (24). Therefore, although RRSP*-$DT_B$ does not cleave RAS, it might impact its activity when used at high doses and after longer exposure both in vitro and in vivo.

As with the other tumor models, RRSP-$DT_B$ treatment resulted in significant reduction in tumor size in an HCT-116 xenograft study. Both q.d. and b.i.d. dosing strategies showed similar median reductions in tumor size, however the b.i.d. arm showed less variability represented by a small interquartile range. Effective target engagement was demonstrated by a reduction in total RAS levels in residual RRSP-$DT_B$-treated tumors. We did not observe statistically significant differences between controls and RRSP-$DT_B$-treated tumors when analyzing pERK immunoreactivity. However, as noted above, large control tumors also showed poor immunostaining for pERK, and thus low values for control may have caused the lack of statistical significance in the small sample size when data are normalized. Even still, we observed reduced tumor size in all treatment groups and a decrease in pERK in the b.i.d. treatment group.

In order to assess the broader applicability of RRSP-$DT_B$ and have a better understanding of its efficacy as an anticancer agent, RRSP-$DT_B$ was tested against the NCI-60 cell line panel. Results showed that RRSP-$DT_B$ inhibited cell growth in a wide variety of cell lines. Cell lines with missense mutations or amplifications in RAS genes were enriched in the highly responsive group. Moreover, although the expression levels of the DT receptor HB-EGF play an important role in determining RRSP-$DT_B$ susceptibility, some cancer cell lines that express less HB-EGF were still sensitive to RRSP-$DT_B$, suggesting differential susceptibility of tumor cells to RAS/RAP1 inhibition. Thus, RRSP-$DT_B$ has the potential to be broadly applicable against many types of cancers, including both wild-type and mutant RAS tumors. In addition, cancer cell lines from colon and lung are particularly sensitive to RRSP-$DT_B$. However, several tumor cell lines with no genetic defects in RAS or the MAPK pathway remain very sensitive to RRSP-$DT_B$.

Figure 72:
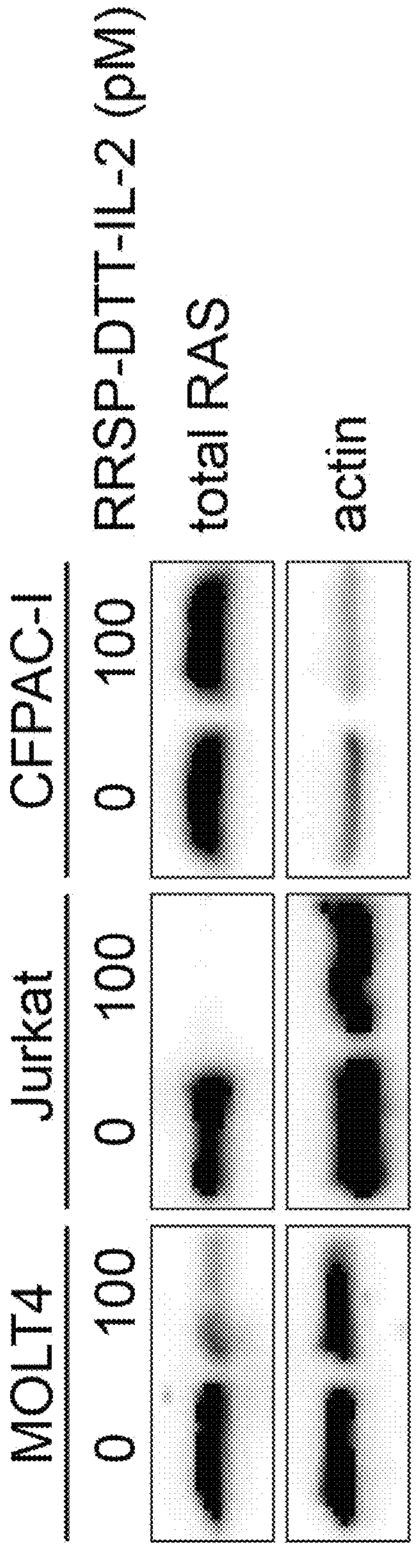
FIG. 72. Selective targeting of RRSP-$DT_B$ to IL-2 expressing cancer cells via replacement of the DTR domain. Western blot image showing total RAS levels following treatment with RRSP-DTT-IL-2 of lymphoblast MOLT4 and Jurkat cells expressing high levels of IL-2 receptor and pancreatic CFPAC-I cells expressing none to low levels of the IL-2 receptor.

In total, this study provides solid proof-of-concept that the effective, receptor-mediated, intracellular delivery of a potent anti-RAS biologic represents a promising new approach for the development of RAS-targeted therapeutics. We contend that the ability of RRSP to directly and irreversibly inactivate both wild-type and mutant RAS proteins represents an attractive mechanism compared to the current approach of targeting RAS mutants individually. However, a pan-RAS inhibitor is expected to induce dose-limiting toxicity due to the critical importance of RAS signaling in non-cancerous tissues. The ability of DT to deliver cargos exclusively to receptor-bearing cells provides a solution to this toxicity. While HB-EGF is upregulated on various tumor types, it is also widely expressed in humans, and may not represent the ideal receptor for tumor-targeting. In order to restrict the delivery of RRSP to tumor cells, the DT-based delivery platform described here can be re-targeted to various cell types by replacing the receptor-binding domain of DT with other binding moieties, such as antibody fragments or ligands. For instance, the recombinant immunotoxins Ontak and Tagraxofusp comprise wild-type DTA with DTR replaced by interleukin 2 (IL-2) or interleukin 3 (IL-3), respectively (48, 49). These drugs specifically target cells expressing the IL-2 receptor (IL-2R) or IL-3 receptor (IL-3R) and rely on the membrane translocating ability of DT to deliver the DTA domain into the cell cytosol, where it terminates protein synthesis leading to cell death. These immunotoxins are extremely potent and are indicated for treatment of cutaneous T-cell lymphoma (Ontak) and blastic plasmacytoid dendritic-cell neoplasm (Tagraxofusp) (48, 49). RRSP-$DT_B$ can be re-targeted in the same fashion, and RRSP-DTT-IL2 is able to efficiently cleave RAS in both MOLT-4 and Jurkat cell lines which express IL-2R, but not in CFPAC-I cells, which do not (FIG. 72). In fact, MOLT-4 was amongst the least responsive cell lines in the NCI-60 screen, suggesting that even cancers currently in the low sensitivity group would be much more sensitive to RRSP-$DT_B$ following advanced engineering to target the chimeric toxin to alternative receptors appropriated for that cell type. Further study into engineered chimeric toxins, such as RRSP-$DT_B$, could usher in the next-generation of anti-cancer biologics.

Materials and Methods

Plasmids Design, Protein Purification and Endotoxin Removal

DNA sequence corresponding to RRSP aa 3580-4089 was amplified from a plasmid containing the effector domain region cloned from *V. vulnificus* CMCP6 in vector pXL PCR-TOPO (1). The amplified gene was fused to different DT variants using the NEBuilder® HiFi DNA Assembly Cloning Kit (New England Biolabs Inc.). DNA sequence corresponding to CPD (nucleotides nt 12269-12894 of rtxA1) of MARTX toxin from *V. vulnificus* was codon-optimized and synthesized as a double-stranded DNA fragment (IDT) and inserted into the DT vector as above (2). A point mutation was made in RRSP using QuikChange Lightning Multi Site-Directed Mutagenesis Kit (Agilent Technologies) to change His4030 CAT codon to Ala (GCT) to generate the catalytically inactive $RRSP_{H4030A}$ mutant (RRSP*-$DT_B$). The final products were cloned into the Champion pET-SUMO expression system (Invitrogen). The different DT variants fused to RRSP were expressed as N-terminal His6-tagged and C-terminal StrepTagII-tagged proteins, transformed into either *E. coli* NiCo21(DE3) or BL21 (DE3) cells, and grown overnight in Luria-Bertani (LB) broth containing 50 μg/mL kanamycin. Next, overnight cultures were diluted 1:50 in fresh TB containing 35 μg/mL kanamycin and grown to $OD_{600}$=0.8-1.0 at 37° C. Cultures were then induced with 1 mM isopropyl β-d-1-thiogalactopyranoside (IPTG) for 5 h at 25° C. Bacteria were pelleted by centrifugation at 10,000 rpm for 15 min and resuspended in 150 mL of Lysis Buffer (20 mM Tris-HCl pH 8.0, 500 mM NaCl, 20 mM imidazole, 2 mg/ml lysozyme and one tablet of EDTA-free protease inhibitor cocktail). Resuspended cells were sonicated using a Branson Digital Sonifier for 30 min (parameters: pulse ON 10 sec, pulse OFF 20 sec, 10 min, Amplitude 50%), the lysate spun down at 12,000×g for 30 min and then loaded onto a 5 ml His-Trap Crude FF column (GE Healthcare) using a ÄKTA Purifier protein purification system (GE Healthcare). His-tagged proteins were eluted with a buffer containing 20 mM Tris-HCl pH 8.0, 500 mM NaCl and 500 mM imidazole. Fractions corresponding to the protein peaks were collected, pooled and loaded onto a gravity column containing Strep-Tactin Superflow high capacity resin (#2-1208-025, Iba Lifesciences). Strep-tagged proteins were eluted using 20 mM Tris-HCl pH 8.0, 150 mM NaCl and 10 mM d-Desthiobiotin. The His-Sumo tag was then removed by adding 0.01 μg of Sumo protease per 100 μg of purified protein in 20 mM Tris-HCl pH 8.0, 150 mM NaCl and 1 mM dithiothreitol at 30° C. for 1 h. Next, proteins were further purified by size exclusion chromatography (SEC) using the HiLoad Superdex 16/600 200 prep grade column (GE Healthcare) run in 20 mM Tris-HCl pH 8.0 and 150 mM NaCl. Proteins were then dialyzed overnight using a ThermoFisher Slide-A-lyzer cutoff 20K in 20 mM Tris-HCl pH 8.0 and 150 mM NaCl and concentrated with a Millipore Amicon Ultra 30K spin concentrator. Finally, glycerol was added to the final protein solution containing 20 mM Tris-HCl pH 8.0, 150 mM NaCl, 10 mM imidazole and 8% glycerol. Protein purity was assessed by SDS-PAGE/Coomassie blue staining and concentration determined using NanoDrop ND1000 Spectrophotometer. Protein aliquots were flash frozen and stored at −80° C. until use. For in vivo applications, endotoxin was removed from all protein preparations using Pierce High-Capacity Endotoxin Removal Resin (#88270) and residual endotoxin was quantified using Pierce LAL Chromogenic Endotoxin Quantitation Kit (#88282) following manufacturer's instructions (Thermo Scientific).

Cell Culture and Chemicals

All cell lines were purchased from the American Type Culture Collection, except for the $KRAS^{WT}$-expressing RAS-less MEF cells that were kindly provided by the RAS Initiative at Frederick National Laboratory for Cancer Research (FNLCR) (Designation RPZ26216, expressed transgene KRAS 4B WT) (3). Cells were cultured at 37° C. and 5% $CO_2$ atmosphere. MDA-MB-436, MDA-MB-231 and HCT-116 were grown in DMEM-F12 with Glutamax (Gibco) containing 10% fetal bovine serum (FBS; Gemini) and 1% penicillin/streptomycin (P/S; Invitrogen). Hs578T were grown in DMEM containing 10% FBS and 1% P/S (complete DMEM). MEF cells were cultured in complete DMEM with 4 μg/ml of blasticidin. All chemicals, unless otherwise specified, were purchased for Sigma-Aldrich.

Antibodies

The anti-RAS 4E8 hybridoma cell line was kindly provided by the Frederick National Laboratory for Cancer Research (FNLCR). The antibody was purified by affinity chromatography as described in (4). Antibody validation was performed as follows. 10 μM of recombinant K-, N- or H-RAS proteins were incubated alone or together with 1 μM of recombinant RRSP for 5 minutes at room temperature and then 1 μg of each sample was run on an SDS-PAGE gel followed by western blotting. The purified antibody used at 1:2000 dilution specifically recognized both cleaved and uncleaved bands of all three RAS isoforms (FIG. S2I). This antibody thus is a pan-RAS monoclonal, here designated as mAb 4E8.

Some western blots and immunohistochemistry were performed with the commercially available anti-panRAS (Ras10, MA1-012; Thermo Fisher Scientific) antibody, that recognizes RAS Switch I and thus detects only uncleaved RAS. Other primary antibodies used are anti-Phospho-p44/42 MAPK (phosphorylated ERK1/2, Thr202/Tyr204, 197G2, Cell Signaling Technology #4377), anti-p44/42 MAPK (ERK1/2, L34F12, Cell Signaling Technology #4696), anti-HB-EGF (R&D Systems, #AF-259-NA;), and precision protein StrepTactin-HRP Conjugate rabbit Bio-Rad (#1610381) The anti-vinculin (Cell Signaling Technology #13901) was used for normalization. Secondary antibodies used were fluorescent-labeled IRDye 680RD goat anti-mouse (926-68070), IRDye 800CW goat anti-rabbit (925-322211) and IRDye 800CW donkey anti-goat (925-32214) from LI-COR Biosciences. Blot images were acquired using an Odyssey Infrared Imaging System (LI-COR Biosciences) and quantified by densitometry using NIH ImageJ software. Percentage of uncleaved RAS was calculated as previously described (5).

SDS-PAGE and Western Blotting

At the experimental endpoint, cells were washed once with ice-cold PBS and protein lysates were extracted using M-PER mammalian protein extraction reagent (Thermo Fisher Scientific) with protease and phosphatase inhibitors (Sigma-Aldrich). Protein concentration was quantified using Bio-Rad protein assay dye reagent concentrate (#5000006). Equal amounts of proteins were separated by SDS-PAGE followed by western blot analysis as previously described (5).

Cell Viability, Proliferation and Growth Inhibition Assays

For quantitative viability assays, 10,000 cells per well were cultured in 96-well clear bottom white plates in the corresponding complete growth medium and treated the next day with RRSP-$DT_B$ and RRSP*-$DT_B$. At the end of treatments, CellTiter-Glo (Promega) was added to each well according to the manufacturer's manual and luminescence was acquired using a Tecan Safire2 plate reader. CellTiter-Glo was incompatible with assessment of MDA-MB-436 cell viability under the experimental conditions used. Indeed, despite the cells being very sensitive to RRSP-$DT_B$, no change in luminescence were detected between untreated and treated cells presumably due to release of ATP to the media that complicates the CellTiter-Glo reaction. Therefore, for this cell line, viability was determined via crystal violet assay. Briefly, MDA-MB-436 cells (10,000 cells/well) were plated in 96-well plates and treated with RRSP-$DT_B$ and RRSP*-$DT_B$. At the experimental endpoint, medium was carefully removed and cells gently washed with PBS. Crystal violet fixing/staining solution (0.05% (g/vol) crystal violet, 1% formaldehyde, 1% (v/v) methanol in phosphate buffered saline (PBS)) was then added to each well and the plate incubated at room temperature for 20 min. Next, wells were washed with tap water, air-dried, crystal violet solubilized using 10% acetic acid and absorbance recorded at 570 nm using a Tecan Safire2 plate reader. $IC_{50}$ were calculated using the log(inhibitor) vs. response—variable slope (four parameters) function in Graphpad Prism. Crystal violet assay was also performed to visually assess viability of adherent cells using the same procedure described above but instead of solubilizing the dye, images of 6-well air-dried plates were acquired using a conventional desktop scanner. Cell proliferation was measured by colony-formation assay. Cells were treated with RRSP-$DT_B$ and 10 nM RRSP*-DTB. After 72 hours, cells were harvested by trypsinization, counted on a hemocytometer and replated in 6-well plates at 2,500 cells per well. Colony formation was monitored over 10 days period, during which medium was replaced every two days. On day 10, crystal violet was applied to visualize the colonies. The open source ColonyArea ImageJ plug-in was used for quantitative analysis of the area % covered by the stained colonies (6). Quantification of cell rounding was carried out by manually counting up to 200 rounded cells (with sharp edges and no protrusions) per image and means±SD of three independent experiments were plotted. Because all cells treated with 10 nM of RRSP-$DT_B$ appeared round, this condition was set as 100% cell roundness.

An NCI-60 five dose growth inhibition screen was performed on a panel of 60 human tumor cell lines derived from nine different tumor types by the National Cancer Institute Developmental Therapeutics Program (NCI-DTP) and growth inhibition percentage was calculated in accordance with their standard protocol previously published (7). We normalized all data such that 0% growth inhibition corresponded to no change in the cell number relative to control after 48 hours of treatment with the high dose of RRSP-$DT_B$ (13.5 nM), while a drop of 100% corresponded to no cell growth relative to time zero (100% growth inhibition); values below 100% correspond to cell loss. Additional information about the screening methodology can be found on the NCI-DTP website (8).

Maximum Tolerated Dose (MTD) and Xenograft Studies

The MTD study was performed at Charles River Laboratories (Wilmington, MA). Both female and male athymic NU(NCr)-Foxn1$^{nu}$ mice were used (5 mice/group). Mice received increasing dosing of RRSP-$DT_B$ (0.004, 0.02, 0.1 and 0.5 mg/kg) and RRSP*-$DT_B$ (0.5 mg/kg) via IP injection on an everyday schedule—weekends excluded—for two weeks. Mouse weight was monitored on a regular basis until the end of the experiment. Mice were humanely euthanized after loss of 20% body weight and counted as non-survivors.

MDA-MB-436 and MDA-MB-231 mouse xenografts were performed following our animal protocol, which was approved by the Institutional Animal Care and Use Committee (IACUC) at Northwestern University. Mice were maintained in Allentown cages in a sterile housing facility under controlled environmental conditions. 5-week old athymic NU(NCr)-Foxn1$^{nu}$ female mice were injected subcutaneously with $2.5\times10^6$ cells in 100 μl/mouse of 50% 1× endotoxin-free PBS/50% Matrigel (Corning #356237) onto the right flank under anesthesia. On day 7, when tumors reached 100-200 $mm^3$ in size, mice were randomized into groups of 5 and treatment started. For the MDA-MB-436 xenograft, control mice were administered IP with saline (endotoxin-free PBS) and treatment groups with 0.1 mg/kg of RRSP-$DT_B$ and 0.1 mg/kg of RRSP*-$DT_B$ on an every-other-day schedule (weekends excluded) for about 4 weeks. In a second experiment with the same cell line, mice were treated with 0.1 mg/kg of RRSP-$DT_B$ every other day (EOD) and 0.1 mg/kg of RRSP-$DT_B$ every day (ED) for about 4 weeks as well as with 0.25 mg/kg of RRSP-$DT_B$ for two weeks followed by 0.1 mg/kg RRSP-$DT_B$ for additional two weeks (weekends excluded). For the MDA-MB-231 xenograft, mice were treated with 0.1 mg/kg of RRSP-$DT_B$ and 0.1 mg/kg of RRSP*-$DT_B$ on an ED schedule (weekends excluded) for 4 weeks. Tumor size was measured twice a week using a digital caliper and tumor volume was calculated using the following formula: volume ($mm^3$)=($1\times w^2$)/2, where 1 is the length and w the width of the tumor. Mouse body weight was also measured twice a week.

The HCT-116 xenograft study was performed at Charles River Laboratories (Wilmington, MA). $5\times10^6$ cells in 100 µl PBS (no Matrigel) were inoculated into the right flank of athymic NU(NCr)-Foxn1$^{nu}$ female mice. When tumors reached an average size of 80-120 $mm^3$, mice were randomized into 5 groups of 10 and treatment started. The first group received PBS (saline), the second 0.1 mg/kg of RRSP-$DT_B$ every day (1×/day), the third 0.1 mg/kg of RRSP-$DT_B$ twice per day (2×/day), the fourth 0.1 mg/kg of RRSP*-$DT_B$ 1×/day and the fifth 0.1 mg/kg of RRSP*-$DT_B$ 2×/day. Both tumor size and mouse body weight were measured biweekly. For all the in vivo experiments performed in this study, when tumors exceeded 1500 $mm^3$, mice were sacrificed as per protocol. At the end of the treatment schedule, mice were euthanized, tumors excised, and fixed in 10% formalin overnight.

Spheroid Formation, Viability and Image Analysis

For tumor spheroids generation, a single cell suspension of HCT-116 cells was seeded at a concentration of 10,000 cells/well into 96-well ultra-low attachment plates (Corning #4520) in complete medium. Two days after cell seeding, treatments were added and viability assessed after 1, 3, 5 and 7 days using the Promega CellTiter-Glo 3D Cell Viability Assay following the manufacturer's protocol. Spheroids were imaged at every time point with an EVOS XL Core imaging system and their volume analyzed using a freely available ImageJ plug-in as described in (9). Spheroids fixation and agarose-embedding prior to immunohistochemical analysis was performed as previously described (10).

Immunohistochemistry of Spheroids and In Vivo Tumors

Spheroids as well as in vivo tumors processing, paraffin-embedding, sectioning and immunohistochemical stainings were performed by the Robert H. Lurie Comprehensive Cancer Center's Pathology Core Facility. Anti-rabbit pan-Ras (#PA5-85947; Thermo Fisher Scientific) and anti-rabbit Phospho-p44/42 MAPK (Erk1/2) (Thr202/Tyr204, (D13.14.4E) XP Cell Signaling #4370) antibodies were used at 1:500 and 1:300 dilutions, respectively. Primary antibodies were detected using a standard anti-rabbit secondary antibody followed by 3,3'-diaminobenzidine (DAB) revelation (Dako). Quantification of immunohistochemical signal intensity was performed by color deconvolution using ImageJ (Fiji version) as previously described (10).

Bioinformatic Analysis

Bioinformatics analyses were performed using R version 3.5.2. NCI-60 mutation data were retrieved from Reinhold W C et al (11). For the A549/ATCC and MDA-MB-231/ATCC cell lines, mutations were obtained from the ATCC website. NCI-60 gene copy number alteration data and RNA expression z-scores were downloaded from cBioPortal website for the study with id "cellline_nci60" using the TCGA-retriever R package from the cran R-project website. Bar plots, tile plots, and violin plots were built using ggplot2.

Statistics

Statistical analysis was performed using Graphpad Prism software v.8. Bar plots represent mean of at least three independent experiments±the standard deviation (SD). Statistical significance was determined using one-way analysis of variance (one-way ANOVA) assuming normal distribution. Dunnett's multiple comparison post-test was used to compare the mean of treatment groups to the mean of the control group and Tukey's multiple comparison test was used to compare the mean of each group with the mean of every other group. Points in the fitted dose-response curve are mean±standard error of the mean (SEM). Statistical analysis on fold change data was carried out after log transformation of the data to obtain a more normalized distribution. For in vivo xenografts, data are reported as mean±SEM and one-way ANOVA was performed to test for differences among the groups. Values of $p<0.05$ were considered statistically significant.

REFERENCES

1. A. D. Cox, C. J. Der, Ras history: The saga continues. Small GTPases 1, 2-27 (2010).
2. G. A. Hobbs, C. J. Der, K. L. Rossman, RAS isoforms and mutations in cancer at a glance. J Cell Sci 129, 1287-1292 (2016).
3. I. A. Prior, P. D. Lewis, C. Mattos, A comprehensive survey of Ras mutations in cancer. Cancer research 72, 2457-2467 (2012).
4. J. L. Bos, H. Rehmann, A. Wittinghofer, GEFs and GAPs: critical elements in the control of small G proteins. Cell 129, 865-877 (2007).
5. S. Schubbert, K. Shannon, G. Bollag, Hyperactive Ras in developmental disorders and cancer. Nature reviews. Cancer 7, 295-308 (2007).
6. J. Downward, Targeting RAS signalling pathways in cancer therapy. Nature reviews. Cancer 3, 11-22 (2003).
7. M. Hoa, S. L. Davis, S. J. Ames, R. A. Spanjaard, Amplification of wild-type K-ras promotes growth of head and neck squamous cell carcinoma. Cancer research 62, 7154-7156 (2002).
8. A. M. Dulak et al., Gastrointestinal adenocarcinomas of the esophagus, stomach, and colon exhibit distinct patterns of genome instability and oncogenesis. Cancer research 72, 4383-4393 (2012).
9. J. S. Ross et al., Comprehensive genomic profiling of epithelial ovarian cancer by next generation sequencing-based diagnostic assay reveals new routes to targeted therapies. Gynecol Oncol 130, 554-559 (2013).
10. L. B. Eckert et al., Involvement of Ras activation in human breast cancer cell signaling, invasion, and anoikis. Cancer research 64, 4585-4592 (2004).
11. N. Cancer Genome Atlas, Comprehensive molecular portraits of human breast tumours. Nature 490, 61-70 (2012).
12. B. Papke, C. J. Der, Drugging RAS: Know the enemy. Science 355, 1158-1163 (2017).
13. A. D. Cox, S. W. Fesik, A. C. Kimmelman, J. Luo, C. J. Der, Drugging the undruggable RAS: Mission possible? Nature reviews. Drug discovery 13, 828-851 (2014).
14. F. McCormick, KRAS as a Therapeutic Target. Clinical cancer research: an official journal of the American Association for Cancer Research 21, 1797-1801 (2015).
15. M. R. Janes et al., Targeting KRAS Mutant Cancers with a Covalent G12C-Specific Inhibitor. Cell 172, 578-589 e517 (2018).
16. J. M. Ostrem, U. Peters, M. L. Sos, J. A. Wells, K. M. Shokat, K-Ras(G12C) inhibitors allosterically control GTP affinity and effector interactions. Nature 503, 548-551 (2013).
17. M. P. Patricelli et al., Selective Inhibition of Oncogenic KRAS Output with Small Molecules Targeting the Inactive State. Cancer discovery 6, 316-329 (2016).
18. Amgen (2019) A Phase 1/2, Study Evaluating the Safety, Tolerability, PK, and Efficacy of AMG 510 in Subjects With Solid Tumors With a Specific KRAS Mutation.—Full Text View—ClinicalTrials.gov.
19. Janssen Research & Development (2019) First-in-Human Study of JNJ-74699157 in Participants With Tumors Harboring the KRAS G12C Mutation—Full Text View—ClinicalTrials.gov.
20. Mirati Therapeutics Inc. (2019) Phase 1/2 Study of MRTX849 in Patients With Cancer Having a KRAS G12C Mutation—Full Text View—ClinicalTrials.gov.
21. J. P. O'Bryan, Pharmacological targeting of RAS: Recent success with direct inhibitors. Pharmacol Res 139, 503-511 (2019).
22. I. Antic, M. Biancucci, Y. Zhu, D. R. Gius, K. J. Satchell, Site-specific processing of Ras and Rap1 Switch I by a MARTX toxin effector domain. Nat Commun 6, 7396 (2015).
23. M. Biancucci et al., Substrate Recognition of MARTX Ras/Rap1-Specific Endopeptidase. Biochemistry 56, 2747-2757 (2017).
24. M. Biancucci et al., The bacterial Ras/Rap1 site-specific endopeptidase RRSP cleaves Ras through an atypical mechanism to disrupt Ras-ERK signaling. Sci Signal 11 (2018).
25. A. Auger et al., Efficient Delivery of Structurally Diverse Protein Cargo into Mammalian Cells by a Bacterial Toxin. Mol Pharm 12, 2962-2971 (2015).
26. M. Park et al., Intracellular Delivery of Human Purine Nucleoside Phosphorylase by Engineered Diphtheria Toxin Rescues Function in Target Cells. Mol Pharm 15, 5217-5226 (2018).
27. M. Egerer, K. J. Satchell, Inositol hexakisphosphate-induced autoprocessing of large bacterial protein toxins. PLoS pathogens 6, e1000942 (2010).
28. O. Metzger-Filho et al., Dissecting the Heterogeneity of Triple-Negative Breast Cancer. 30, 1879-1887 (2012).
29. A. Adeyinka et al., Activated mitogen-activated protein kinase expression during human breast tumorigenesis and breast cancer progression. Clinical cancer research: an official journal of the American Association for Cancer Research 8, 1747-1753 (2002).
30. J. M. Giltnane, J. M. Balko, Rationale for targeting the Ras/MAPK pathway in triple-negative breast cancer. Discov Med 17, 275-283 (2014).
31. H. A. Mokhlis et al., The Modulatory Role of MicroRNA-873 in the Progression of KRAS-Driven Cancers. Mol Ther Nucleic Acids 14, 301-317 (2019).
32. J. H. Cha, M. Y. Chang, J. A. Richardson, L. Eidels, Transgenic mice expressing the diphtheria toxin receptor are sensitive to the toxin. Mol Microbiol 49, 235-240 (2003).
33. T. Mitamura, S. Higashiyama, N. Taniguchi, M. Klagsbrun, E. Mekada, Diphtheria toxin binds to the epidermal growth factor (EGF)-like domain of human heparin-binding EGF-like growth factor/diphtheria toxin receptor and inhibits specifically its mitogenic activity. The Journal of biological chemistry 270, 1015-1019 (1995).
34. R. Palmiter, Interrogation by toxin. Nat Biotechnol 19, 731-732 (2001).
35. C. Scholl et al., Synthetic lethal interaction between oncogenic KRAS dependency and STK33 suppression in human cancer cells. Cell 137, 821-834 (2009).
36. S. Hassan, A. Esch, T. Liby, J. W. Gray, L. M. Heiser, Pathway-Enriched Gene Signature Associated with 53BP1 Response to PARP Inhibition in Triple-Negative Breast Cancer. Molecular cancer therapeutics 16, 2892-2901 (2017).
37. J. M. Fleming, T. C. Miller, M. J. Meyer, E. Ginsburg, B. K. Vonderhaar, Local regulation of human breast xenograft models. J Cell Physiol 224, 795-806 (2010).
38. J. Ferlay et al., Cancer incidence and mortality worldwide: sources, methods and major patterns in GLOBOCAN 2012. Int J Cancer 136, E359-386 (2015).
39. L. P. Ferreira, V. M. Gaspar, J. F. Mano, Design of spherically structured 3D in vitro tumor models—Advances and prospects. Acta Biomater 75, 11-34 (2018).
40. V. Vidimar et al., The AKT/BCL-2 Axis Mediates Survival of Uterine Leiomyoma in a Novel 3D Spheroid Model. Endocrinology 159, 1453-1462 (2018).
41. D. Ahmed et al., Epigenetic and genetic features of 24 colon cancer cell lines. Oncogenesis 2, e71 (2013).
42. J. Canon et al., The clinical KRAS(G12C) inhibitor AMG 510 drives anti-tumour immunity. Nature 575, 217-223 (2019).
43. J. Hallin et al., The KRASG12C Inhibitor, MRTX849, Provides Insight Toward Therapeutic Susceptibility of KRAS Mutant Cancers in Mouse Models and Patients. Cancer discovery 10.1158/2159-8290.CD-19-1167 (2019).
44. B. Zhou, C. J. Der, A. D. Cox, The role of wild type RAS isoforms in cancer. Semin Cell Dev Biol 58, 60-69 (2016).
45. A. Young, D. Lou, F. McCormick, Oncogenic and wild-type Ras play divergent roles in the regulation of mitogen-activated protein kinase signaling. Cancer discovery 3, 112-123 (2013).
46. S. O. Nam et al., Anti-tumor Effect of Intravenous Administration of CRM197 for Triple-negative Breast Cancer Therapy. Anticancer Res 36, 3651-3657 (2016).
47. J. W. Mandell, Phosphorylation state-specific antibodies: applications in investigative and diagnostic pathology. The American journal of pathology 163, 1687-1698 (2003).
48. E. Y. Jen et al., FDA Approval Summary: Tagraxofusp-erzs For Treatment of Blastic Plasmacytoid Dendritic Cell Neoplasm. Clinical cancer research: an official journal of the American Association for Cancer Research 26, 532-536 (2020).
49. H. M. Prince et al., Phase III placebo-controlled trial of denileukin diftitox for patients with cutaneous T-cell lymphoma. J Clin Oncol 28, 1870-1877 (2010).

Example 7—RAS/RAP1 Specific Protease (RRSP) Cleaves all Major Oncogenic Forms of KRAS and Inhibits Growth in KRAS/BRAF Mutant Colon Cancers

Introduction

Figure 73:
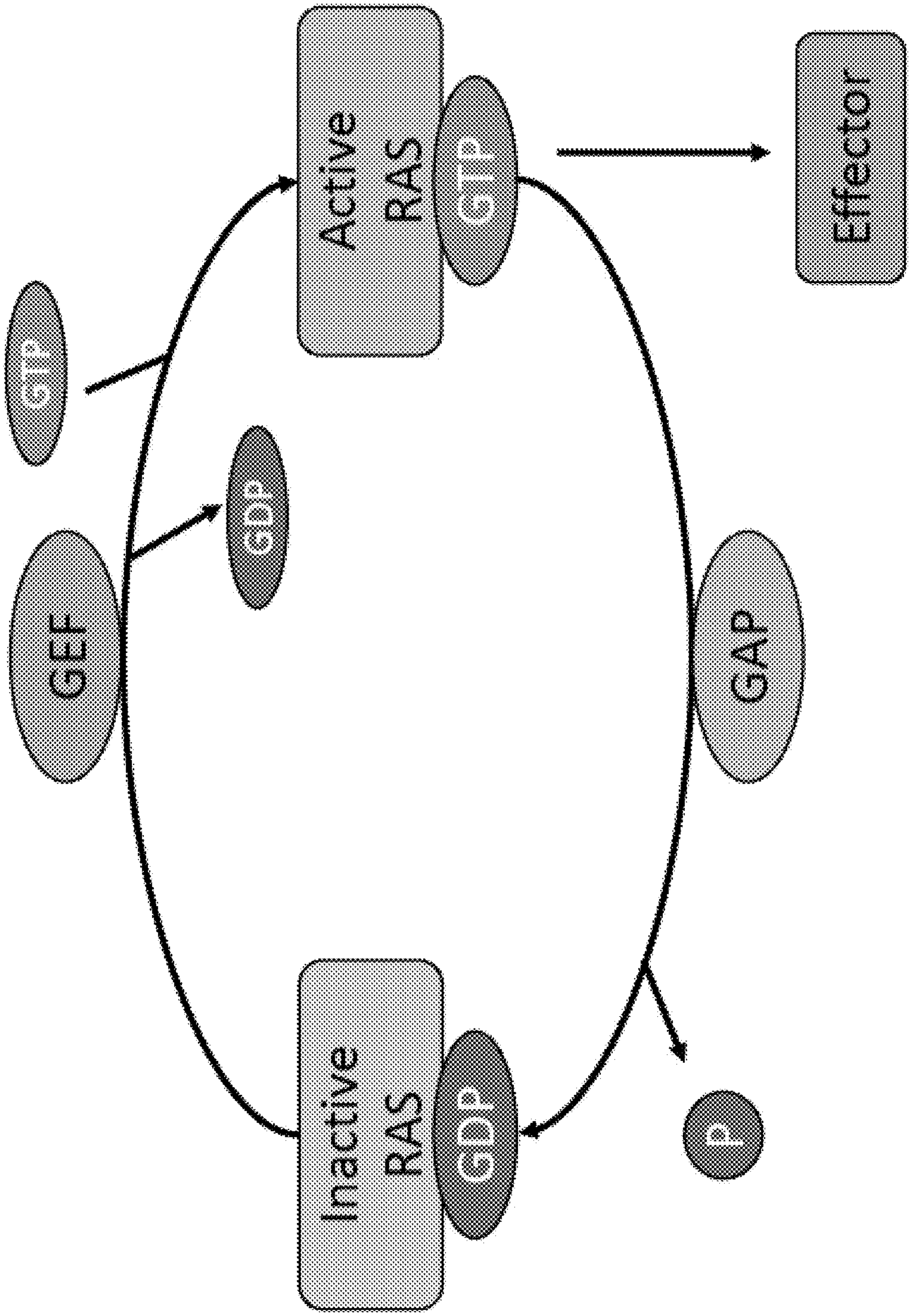
FIG. 73. Activation and Inactivation of RAS. Inactive RAS (GDP-bound) is activated by GEF by displacing GDP. Active RAS (GTP-bound) binds to downstream effectors to activate signaling. GAP molecules facilitate hydrolysis of GTP into GDP. Abbreviations: RAS; rat sarcoma. GDP; guanine nucleotide diphosphate. GTP; guanine nucleotide triphosphate. GAP; GTPase activating proteins. GEF; guanine exchange factors.

The oncoprotein Rat sarcoma GTPase (RAS) cycles between GTP-bound (active) and GDP-bound (inactive) states for activation of downstream effectors, each playing key roles in cell proliferation and survival [1, 2]. This process is highly reliant on GTPase activating proteins (GAPs) and guanine exchange factors (GEFs) for hydrolysis of GTP and nucleotide exchange of GDP to GTP, respectively (FIG. 73) [3, 4]. Upon growth receptor stimulation, activated RAS recruits downstream effectors, including Rapidly Accelerated Fibrosarcoma (RAF) kinase and phosphatidylinositol-3-kinase (PI3K). These effectors subsequently activate signaling pathways responsible for cell growth and survival, including the mitogen-activated kinase to extracellular signal-regulated kinase (ERK) signaling pathway and Ak-thymoma kinase (also known as AKT) to mammalian target of rapamycin (mTOR) pathway, respectively [6, 7]

Thirty percent of all human cancers contain mutations in RAS [1, 14]. Mutant RAS, paired with loss of function in tumor suppressor genes such as TP53 and APC, are sufficient to fully transform cells and drive tumorigenesis [14]. Nearly all RAS mutations occur as point mutations at G12, G13 or Q61, resulting in constitutive activation of RAS [1]. Among the major RAS isoforms (HRAS, NRAS, and KRAS), KRAS is the most frequently mutated isoform among all cancers (85%) followed by NRAS (11%) and HRAS (4%) [14]. RAS mutations are highly enriched specifically in three of the four most lethal cancers in the United States, including pancreatic adenocarcinoma (98%), colorectal adenocarcinoma (52%), and lung adenocarcinoma (32%)[1, 14].

Although numerous studies support the advantages of targeting RAS to treat cancer, it remains an unsolved challenge in the clinic [64, 139-142]. Recent studies have taken advantage of biochemical properties of specific RAS mutants to develop selective small molecule inhibitors specific for highly oncogenic mutant forms of RAS. In particular, small molecules targeting KRAS G12C have been developed and are undergoing clinical trials [15, 16, 143]. Many of these agents have shown clinical success with one molecule receiving FDA accelerated approval earlier this year for treatment of KRAS G12C tumors in non-small cell lung carcinoma [91]. Despite this success, the strategy of selective inhibition has problems of being applicable to only a limited range of cancers integrated with personalized medicine and cannot be used to treat cancers that lack the specific mutation. To address this gap, new approaches are being developed to target RAS more broadly either with proteases that directly cleave RAS or with linkers that target RAS for cellular degradation [127, 136, 144-147].

In line with this alternative strategy, our lab has identified a potent protease that cleaves RAS called the Ras/Rap1-specific endopeptidase (RRSP). RRSP is a small domain of a large toxin secreted by the bacterium *Vibrio vulnificus* during host infection. *V. vulnificus* delivers RRSP into intestinal epithelial cells during host infection, where it targets all RAS isoforms and close homolog Ras-related protein 1 (RAP1). Through RAS inactivation, this bacterium suppresses the host immune response, thereby aiding systemic dissemination of the bacterium [129, 148]. Detailed structural and biochemical studies have shown that RRSP attacks the peptide bond between T32 and D33 in the Switch I region of both RAS and RAP1 [134]. As a result, RAS and RAP1 are unable to undergo GTP-GDP exchange or bind to their downstream effectors [131, 132]. Recently, RRSP engineered as a chimeric toxin for in vivo delivery was shown to significantly reduce breast and colon tumor growth in xenograft mouse models [136].

The potential applicability of RRSP to a broader range of cancers was screened using the standardized National Cancer Institute (NCI) cancer cell panel [137]. Fourteen of 60 cell lines were classified as highly susceptible with cells undergoing cytotoxic effects. However, 38/60 of cell lines showed growth inhibition, but not cytotoxicity. Only 8/60 showed low or no susceptibility with cell growing near normal rates, possibly due to lack of the receptor for the engineered chimeric toxin [136]. The observed wide range of cell fates highlights that the cellular responses to total RAS cleavage has the potential to be quite variable across cancer cell lines. Here, we investigate how RRSP processing affects cell signaling and demonstrate that cleaving total RAS can have a variable impact on cancer cell growth and survival. Specifically, we demonstrate that RRSP can disrupt colorectal cancer (CRC) cell growth through multiple mechanisms, including loss of cell viability, cell cycle arrest, and senescence.

Results

RRSP Cleave and Inhibits Proliferation in RAS Wildtype and KRAS Mutant Cells

RRSP was previously shown to specifically cleave HRAS, NRAS, and KRAS when the proteins were ectopically expressed in HeLa cells and recombinant RRSP was shown to process purified KRAS G12D, G13D, and Q61R in biochemical assays [134]. To get an even broader sense of RRSP effectiveness across different isoforms and mutants of RAS, we tested RRSP against the 'RAS-dependent' mouse embryonic fibroblast (MEF) cell line panel developed by Drosten et al. [6]. These isogenic cell lines have endogenous RAS genetically deleted from their genome and a single allele of a human RAS gene is integrated to rescue growth. For delivery of RRSP into mouse cells, we used the anthrax toxin-based delivery system wherein the anthrax toxin lethal factor N-terminus was fused with RRSP ($LF_N$RRSP) or $LF_N$RRSP with a catalytically inactivating H4030A amino acid substitution (here after referred to as $LF_N$RRSP*). Intracellular delivery of RRSP (previously known as DUF5) by anthrax toxin protective antigen (PA) was previously demonstrated in several mammalian and mouse cell lines [130, 134, 135].

Figures 74A, 74B, 74C, 74D, 74E, 74F:
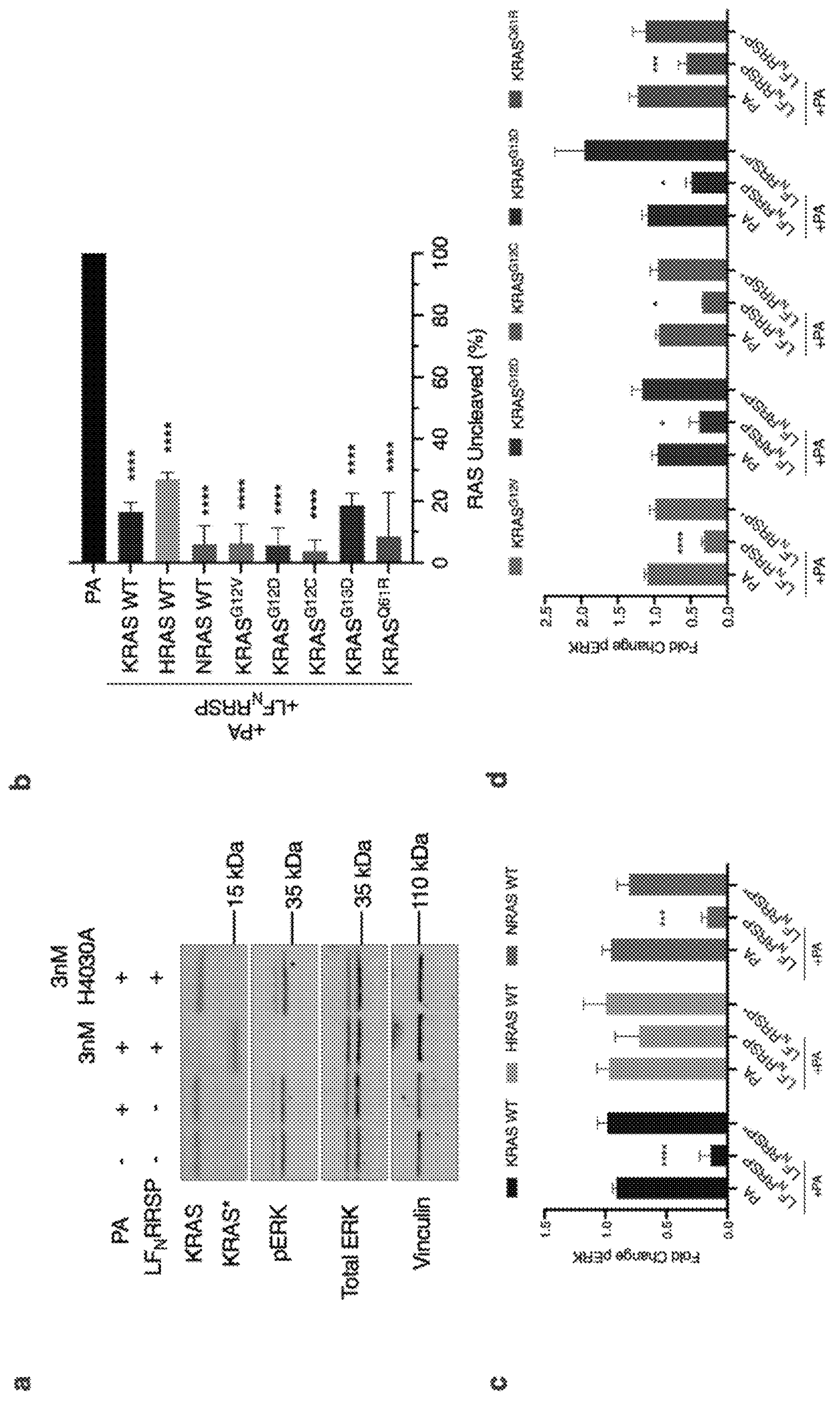
FIG. 74A-74F. $LF_N$RRSP cleaves and inhibits all RAS isoforms and KRAS oncogenic mutants in RAS-dependent MEFs. A) Representative western blot analysis of $LF_N$RRSP cleavage of RAS and inhibition of ERK in KRAS WT RAS-dependent MEFs after 24 h. Vinculin was used as a gel loading control. Protein detection for each immunoblot was analyzed on the same blot. Protein detection for each immunoblot was conducted on the same blot and cropped for each individual protein of interest. (B) Densitometric analysis of total percent RAS in indicated RAS-dependent MEFs following $LF_N$RRSP treatment for 24 h, n=3. (C,D) Densitometric analysis of fold change in pERK compared to PBS control after 24 h for RAS-dependent MEF cell lines indicated; n=3. (E) Brightfield images of KRAS WT RAS-dependent MEFs treated with either PA alone or in combination with $LF_N$RRSP or $LF_N$RRSP* at indicated timepoints. (F) Cell growth over time was monitored with time lapse video microscopy and quantified using Nikon Elements. Values shows relative growth inhibition in RAS-dependent MEFs compared to PA control at 96 h following treatment with either $LF_N$RRSP or $LF_N$RRSP*. Results for all panels are expressed as mean±SEM of three independent experiments (*P<0.05, P<0.01, **P<0.0001 versus PA control as determined through one-way ANOVA followed by Dunnett's multiple comparison test).
Figures 74A, 74B, 74C, 74D, 74E, 74F:
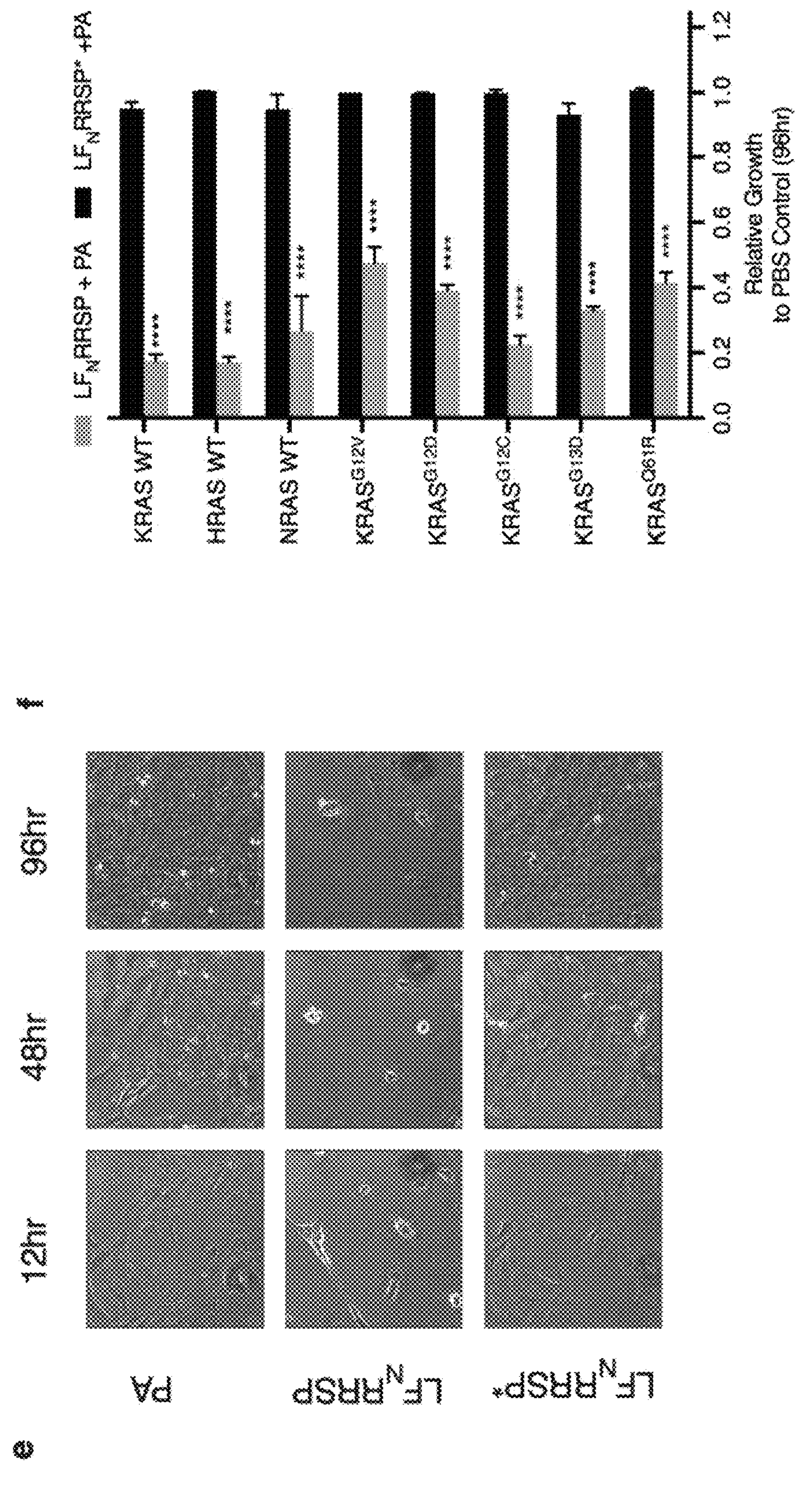
Figures 75A, 75B, 75C, 75D, 75E, 75F, 75G, 75H:
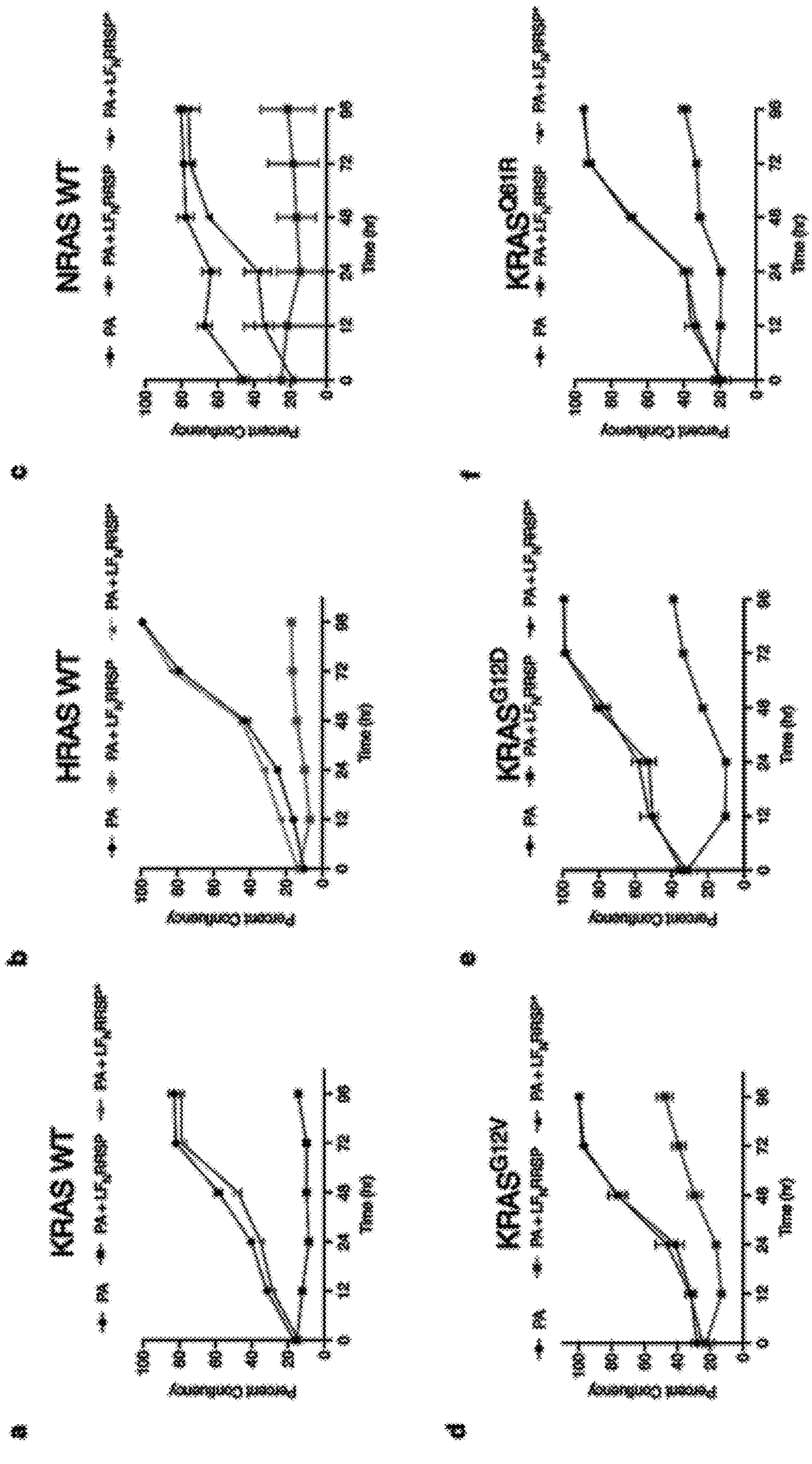
FIG. 75A-75H. Growth inhibition of RAS-dependent MEFs cell lines. (A-H) Growth inhibition observed in of RAS-dependent MEF cell lines at indicted timepoints following treatment with PA alone or in combination with $LF_N$RRSP or $LF_N$RRSP*; n=3. Results are expressed as ±SEM FIG. 76A-76H. RRSP-$DT_B$ growth inhibition in CRC cell lines. (A) Cell line panel of KRAS mutant CRC cells used in this study. (B-E) Cell growth over time was monitored by time lapse video microscopy and cell confluency was quantified using Nikon Elements. Fitted dose response curve of RRSP-$DT_B$ in CRC cell lines show relative growth compared to PBS control after 24 h. Results are displayed as mean±SEM, n=4. (F) Representative western blot analysis of RAS cleavage and ERK inhibition in CRC cell lines treated with either RRSP-$DT_B$ or catalytically inactive mutant (labeled by CI) after 24 h. All concentrations are expressed in nanomolar. In all cell lines, vinculin was used as gel loading control except SW620 cells in which aTubulin was used. Protein detection for each immunoblot was conducted on the same blot and cropped for each individual protein of interest. (G,H) Densitometric analysis of fold change in percent total RAS and pERK compared to PBS control after 24 h in CRC cell lines; n=3. IC50 concentrations for HCT-116 and SW1463 can be found in FIGS. 2B and 2C. For cell lines where IC50 values could not be extrapolated (SW620 and GP5d) RRSP-$DT_B$ was used at 0.1 nM. Results are expressed as means±SEM of three independent experiments (*P<0.05, P<0.01, **P<0.0001 versus PBS control as determined through one-way ANOVA followed by Dunnett's multiple comparison test.
Figures 75A, 75B, 75C, 75D, 75E, 75F, 75G, 75H:
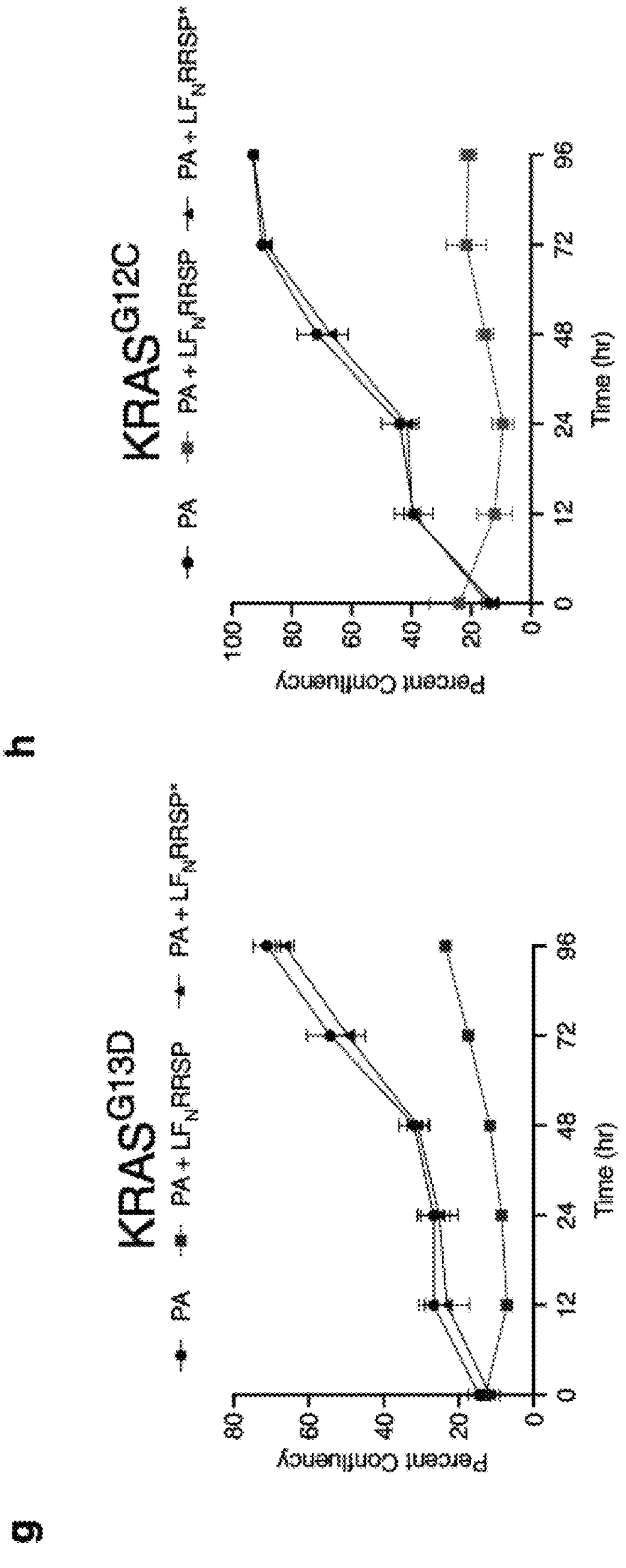

In MEFs expressing human KRAS, HRAS, or NRAS, treatment with 3 nM $LF_N$RRSP dramatically decreased intact full-length RAS levels with increased detection of cleaved RAS. For each isoform, $LF_N$RRSP was found to cleave at least 80% of RAS after 24 h (FIG. 74A). As expected, controls treated with PA alone or in combination with catalytically inactive $LF_N$RRSP* showed no change of intact RAS protein levels (FIG. 74A,B). We observed similar RRSP activity in MEF cell lines expressing oncogenic KRAS, including G12V, G12D, G12C, G13D, and Q61R. Amongst each of the mutant RAS alleles tested, we observed ~25% of total RAS remaining following $LF_N$RRSP treatment, with no significant loss of RAS in cells treated with alone (FIG. 74B). The oncogenic RAS variants with the higher percentage of RAS remaining following $LF_N$RRSP treatment were G13D and Q61R, although these differences were not statistically significant. Further, the total RAS remaining in each $LF_N$RRSP-treated MEF cell line was not statistically significant between groups. In addition to cleavage of RAS, $LF_N$RRSP treated cells showed significant decrease in phosphorylation of ERK when compared to cells treated with PA alone or with the catalytically inactive $LF_N$RRSP* (FIG. 74C, D).

To test the impact of processing of different RAS isoforms on cell proliferation, RRSP-treated cells were tracked using time lapse imaging for four days. At early timepoints following treatment, $LF_N$RRSP-induced a severe cell rounding that was not observed in PA alone and $LF_N$RRSP* control treated cells (FIG. 74E). This phenotype is consistent with previous studies with RRSP and is possibly linked to cleavage of RAP1, which regulates cytoskeletal dynamics [130, 134, 149]. $LF_N$RRSP treated cells showed reduced confluency at both 48 and 96 h (FIG. 74E) and continuous treatment for 96 h resulted in at least at least a 60% reduction in confluency for all RAS-dependent MEF cell lines compared to cells treated with either PA only or $LF_N$RRSP* mutant controls (FIG. 74F, FIG. 75A-H).

Altogether, these results in MEFs demonstrate that RRSP is equally able to cleave all isoforms of RAS and mutant KRAS to inhibit both ERK phosphorylation and cell proliferation in a defined system. Thus, the KRAS mutation does not likely solely account for differences in cancer cell fate upon treatment with RRSP. Instead, the differences more likely depend on processes downstream of RAS processing that could vary in different cell lines.

RRSP Inhibits Proliferation and pERK Activation in CRC Cell Lines

Figures 76A, 76B, 76C, 76D, 76E, 76F, 76G, 76H:
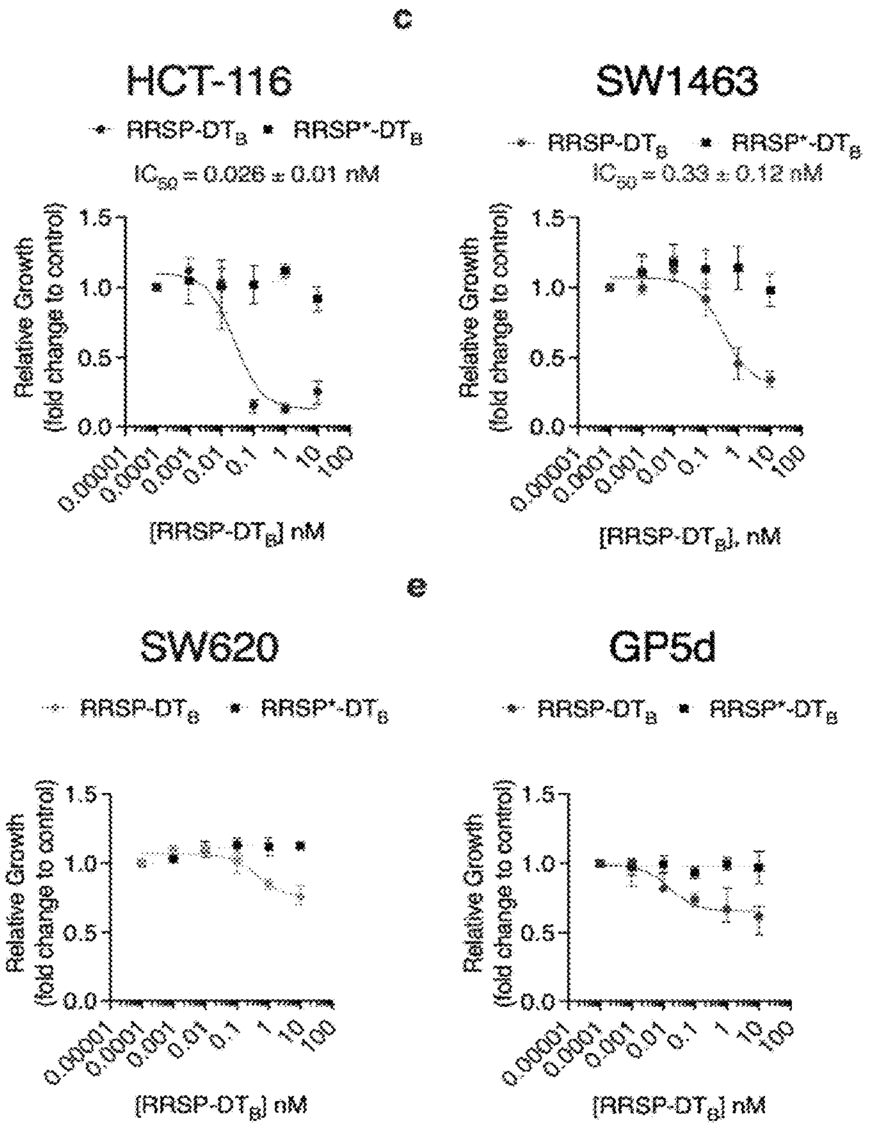
Figures 77A, 77B, 77C, 77D, 77E, 77F, 77G, 77H, 77I, 77J:
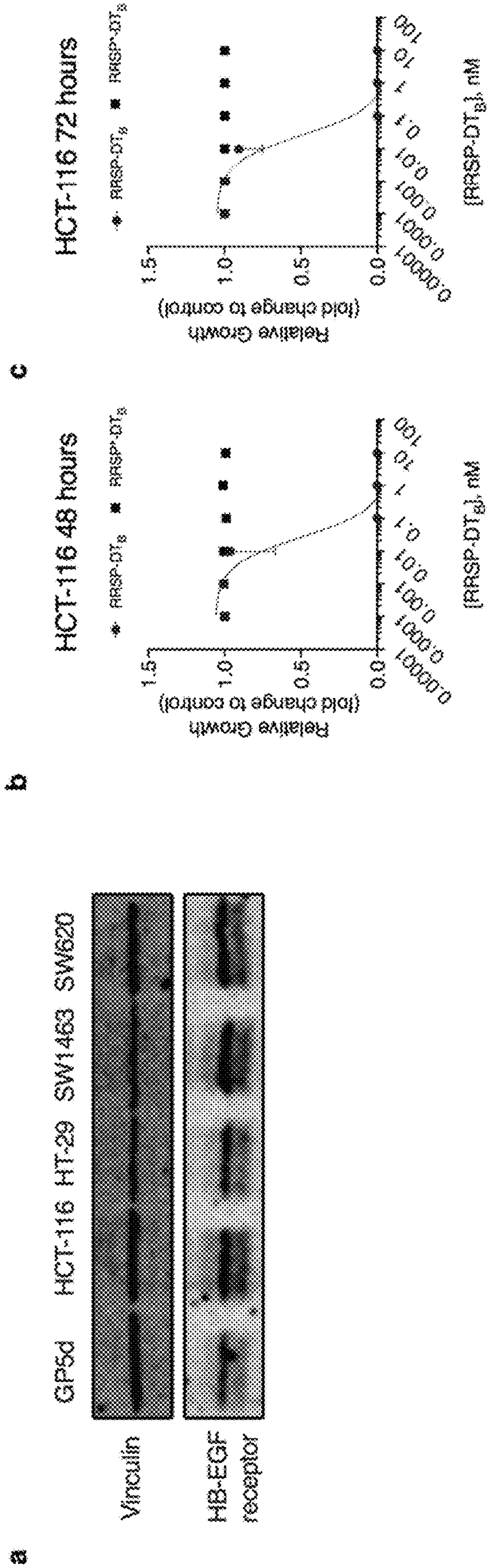
FIG. 77A-77J. Growth inhibition in RRSP-$DT_B$ treated colon cancer cell lines (A). Western blot analysis of HB-EGF receptor (DT receptor) from untreated colon cancer cell line lysates. Vinculin was used as loading control. (B-I) Fitted dose response curve of RRSP-$DT_B$ in colon cancer cell lines after 48 and 72 hours. Results are displayed as mean±SEM, n=4. (J) Representative brightfield images of colon cancer cell lines treated with either RRSP-$DT_B$ or RRSP*-$DT_B$ (0.1 nM) after 24 hours.

To probe the effect of processing of RAS on downstream signaling, we focused on four KRAS mutant CRC cell lines, each harboring different allelic mutations in KRAS (FIG. 76A). Due to problems with variable expression of the anthrax toxin receptor on the selected human cancer cells, we switched to a recently described, highly potent RRSP chimeric toxin wherein RRSP is tethered to the translocation B fragment of diphtheria toxin (RRSP-$DT_B$) [136]. Similar to the anthrax toxin system, RRSP-$DT_B$ binds to a human receptor heparin binding epidermal growth factor-like growth factor (HB-EGF), is endocytosed, and translocated into the cytosol across the vacuolar membrane. Expression of HB-EGF receptor was found to be similar between the selected CRC cell lines (FIG. 77A).

Figures 76A, 76B, 76C, 76D, 76E, 76F, 76G, 76H:
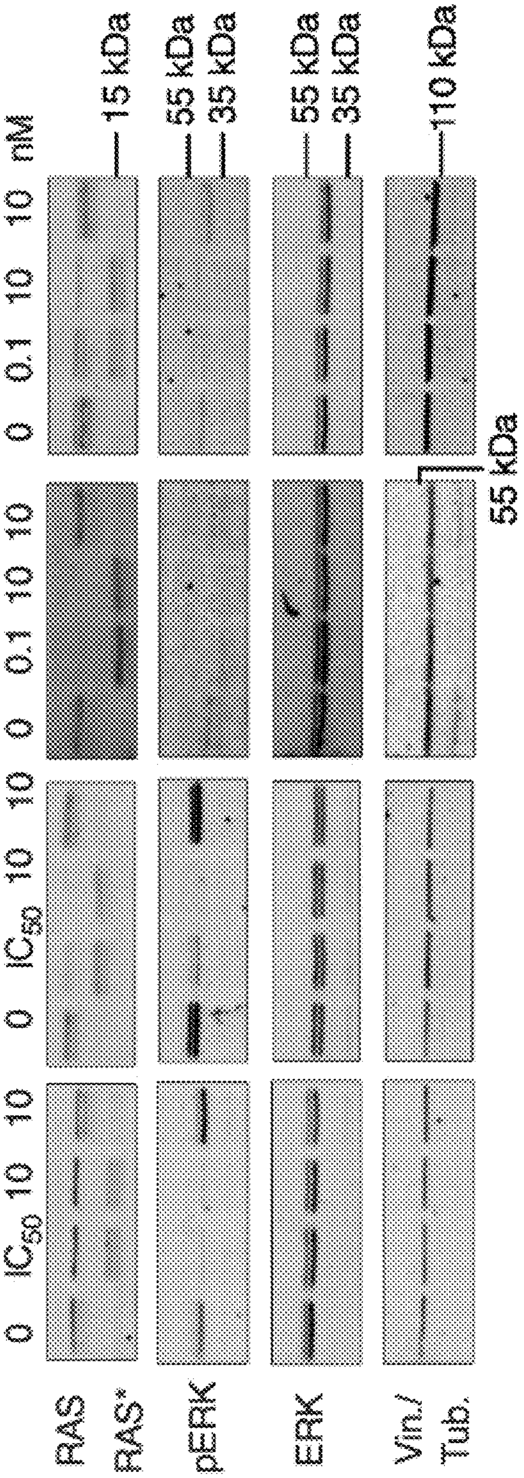
Figures 76A, 76B, 76C, 76D, 76E, 76F, 76G, 76H:
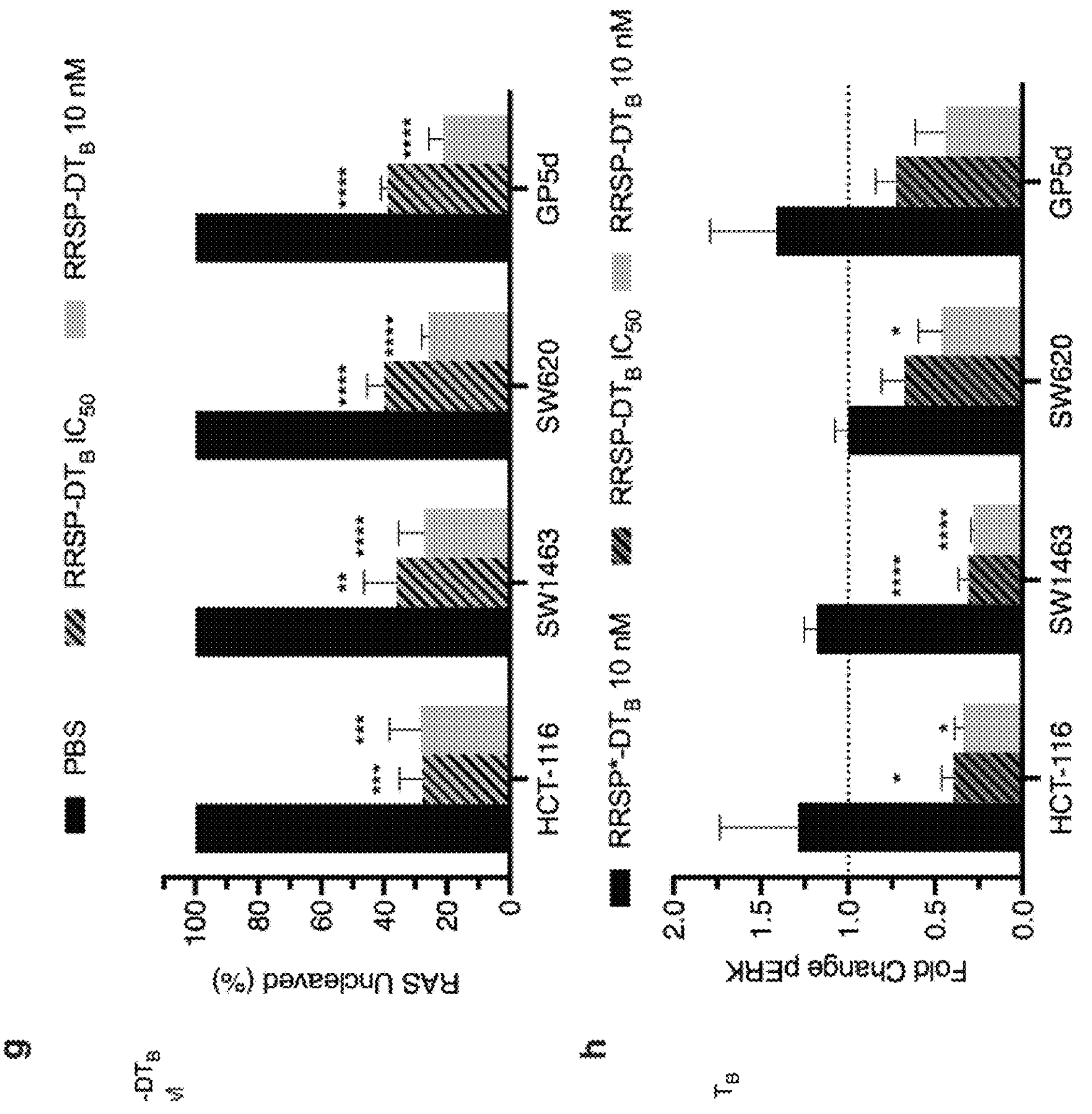
Figures 77A, 77B, 77C, 77D, 77E, 77F, 77G, 77H, 77I, 77J:
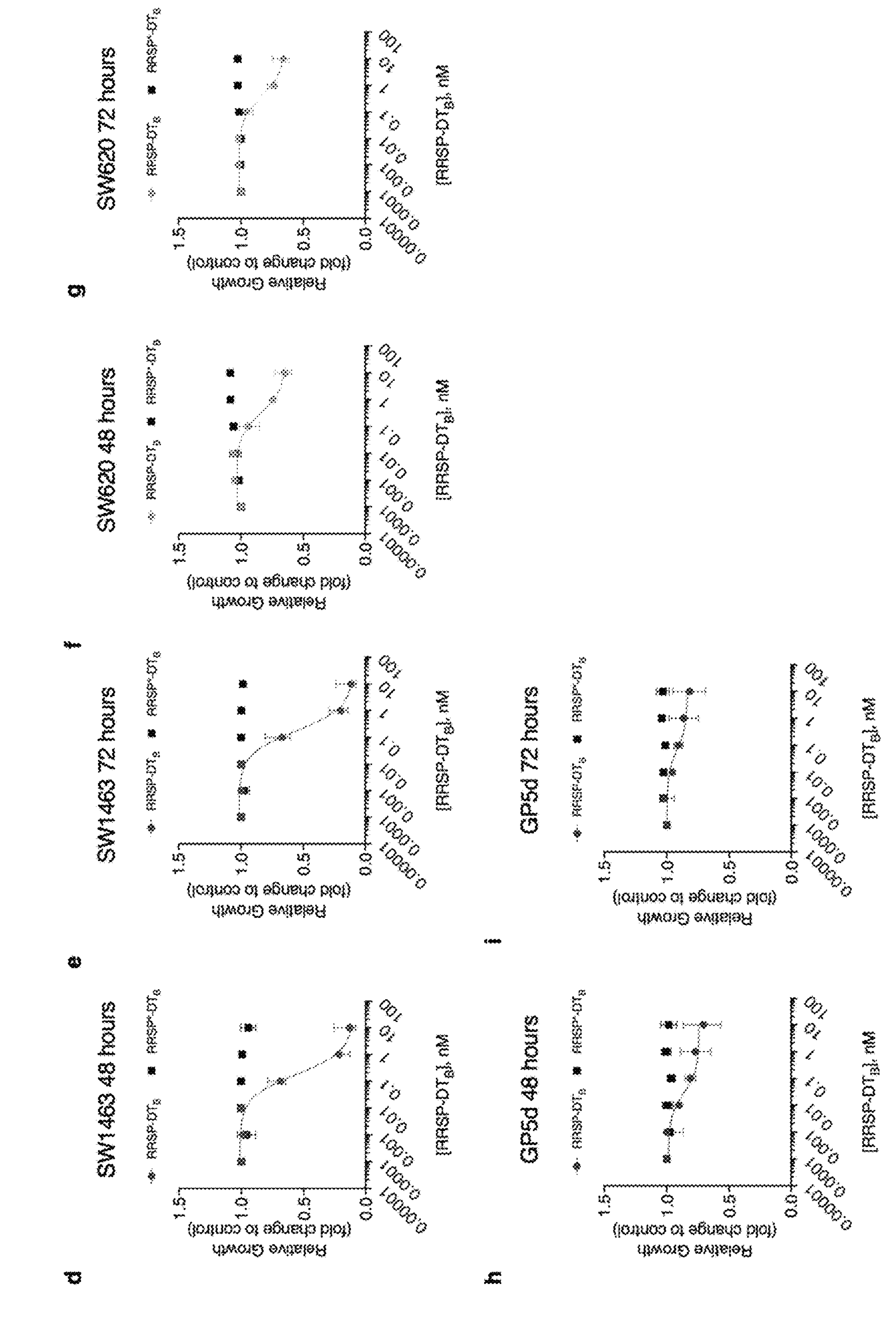
Figures 77A, 77B, 77C, 77D, 77E, 77F, 77G, 77H, 77I, 77J:
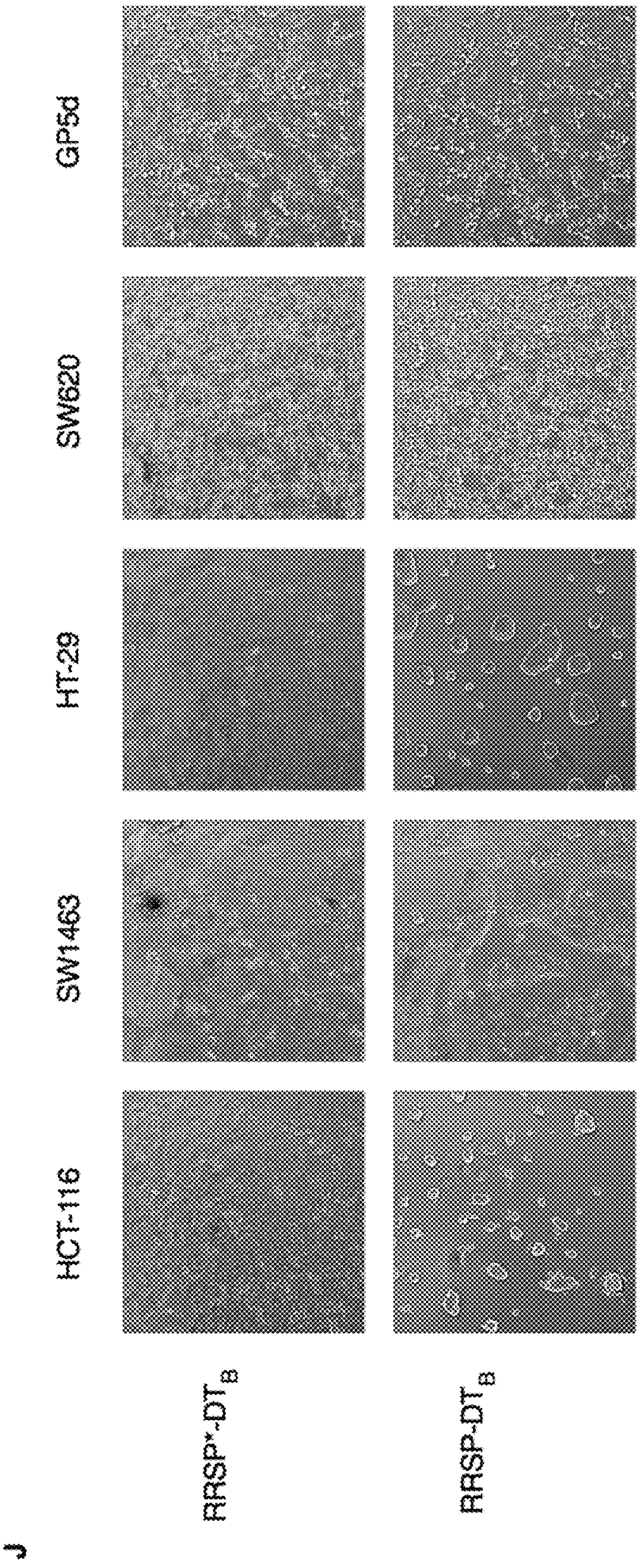

To examine RRSP growth sensitivities between the CRC cell lines, cells were treated with increasing concentration of RRSP-$DT_B$ or with catalytically inactive RRSP-$DT_B$ (RRSP*-$DT_B$) and growth inhibition was monitored. HCT-116 cells showed the greatest impact of RRSP-$DT_B$ on cell confluency and the lowest $IC_{50}$ (FIG. 76B, 77B,C), consistent with prior data using different methods that HCT-116 cells are highly susceptible to RRSP [136]. Cells treated with catalytically inactive RRSP*-$DT_B$ showed no difference, confirming the sensitivity was due to processing of RAS (FIG. 76B, FIG. 77 B,C). SW1463 cells were also highly susceptible to RRSP-$DT_B$ but with a 12-fold higher $IC_{50}$ compared to HCT-116 (FIG. 76C, FIG. 77 D,E). Cell line SW620 was less susceptible to RRSP-$DT_B$ after 24 h with about a 40% growth inhibition compared with control at the highest dose tested of 10 nM (FIG. 76D, FIG. 77F,G). This result using a different method is consistent with prior results, which categorized SW620 as responding to RRSP by growth inhibition, although the percent inhibition here was less due to the earlier time point used for comparison [136]. Cell line GP5d was also less susceptible to RRSP, but also showed growth inhibition when compared to cells treated with the control (FIG. 76 D,E, FIG. 77 H,I). Across all of the cell lines, at least 80% of total RAS was cleaved by RRSP (FIG. 76 F,G). In addition, phosphorylation of ERK was significantly reduced compared to respective RRSP*-$DT_B$ treated samples (FIG. 76 F,H). We did observe some variability in detection of uncleaved RAS between cell lines, which can be attributed in part to cells sensing depleted pools of RAS and therefore upregulating expression. This is best observed in HCT-116 cells treated with RRSP-$DT_B$ where total uncleaved RAS protein levels increase above the levels of Phosphate buffered saline (PBS) control even as cleaved RAS accumulates (FIG. 76 F).

Figures 78A, 78B, 78C, 78D, 78E:
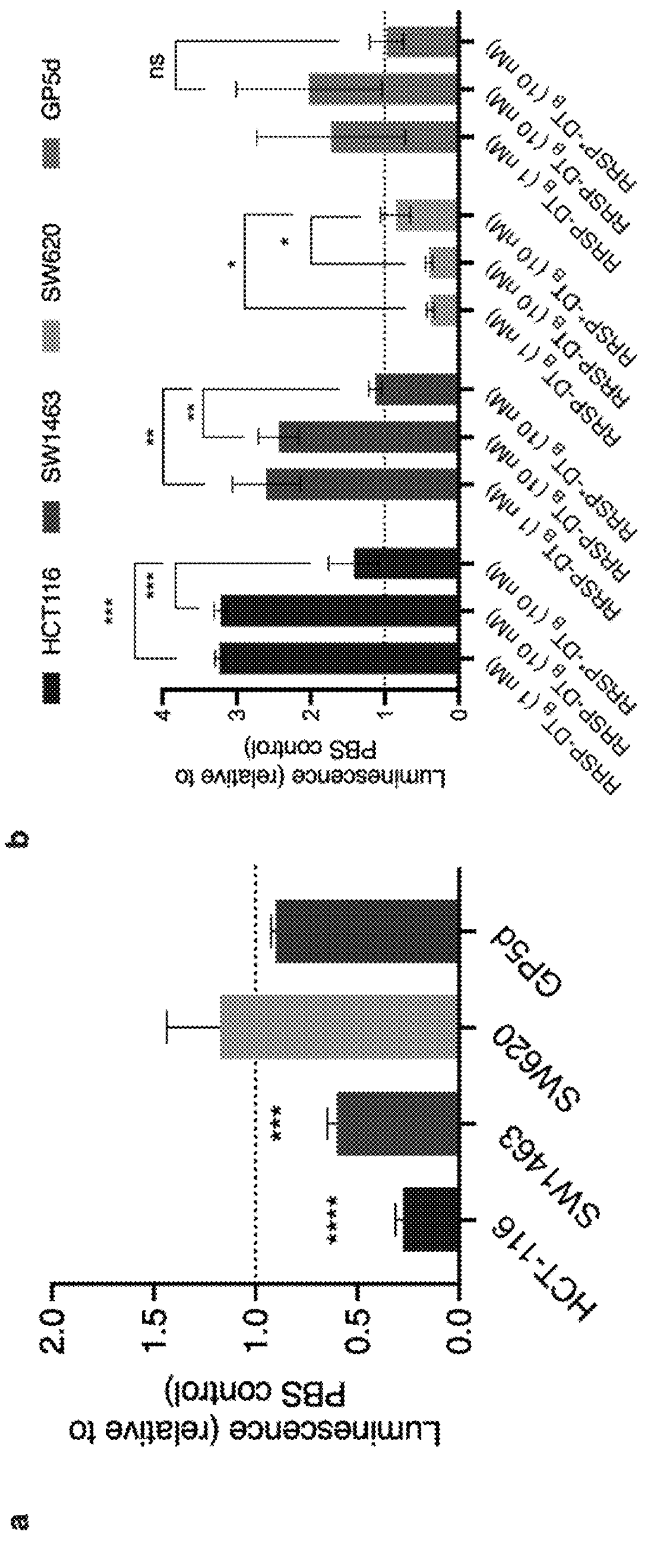
FIG. 78A-78E. RRSP-$DT_B$ decreases cell viability in highly sensitive cell lines but causes irreversible growth inhibition in lower susceptible cell lines (A) Relative cellular metabolic activity quantified using CellTiterGlo assay after 72-h treatment with 10 nM RRSP-$DT_B$ compared to PBS control in CRC cell lines. (B) Relative apoptosis quantified using Caspase-Glo 3/7 assay after 48-h treatment with either 1 or 10 nM RRSP-$DT_B$ compared to PBS control in CRC cell lines. (C) Representative images of crystal violet-stained colonies from RRSP less sensitive cell lines pretreated with 10 nM RRSP-$DT_B$ for 48 h and replated at low seeding density to form colonies over 14 days. (D) Quantitative analysis of crystal-violet stained colonies from less sensitive RRSP cell lines from three independent experiments. Results are expressed as means±SEM of three independent experiments (E) Measured cell senescence activity in RRSP less sensitive cell lines treated with 10 nM RRSP-$DT_B$ for 48 h then incubated with SA-ß Gal Substrate for 1 h at 37° C., n=3. All results described above are expressed as mean±SEM of three independent experiments (*P<0.05, P<0.01, **P<0.0001, ns=not significant versus PBS control as determined through one-way ANOVA followed by Dunnett's multiple comparison test).

The differences in growth following RRSP treatment further impacted long term survival. Using ATP as an indicator of cell viability, the CellTiterGlo Assay can quantitatively measure the presence of metabolically active cells through detection of luminescence signal, even if the cells fail to proliferate. In highly susceptible cell lines HCT-116 and SW1463 cells, treatment with RRSP-$DT_B$ resulted in significantly decreased luminescence compared to mock treated controls after 72 h (FIG. 78A). By contrast, GP5d and SW620 showed no difference in relative ATP levels after 72 h.

Figures 78A, 78B, 78C, 78D, 78E:
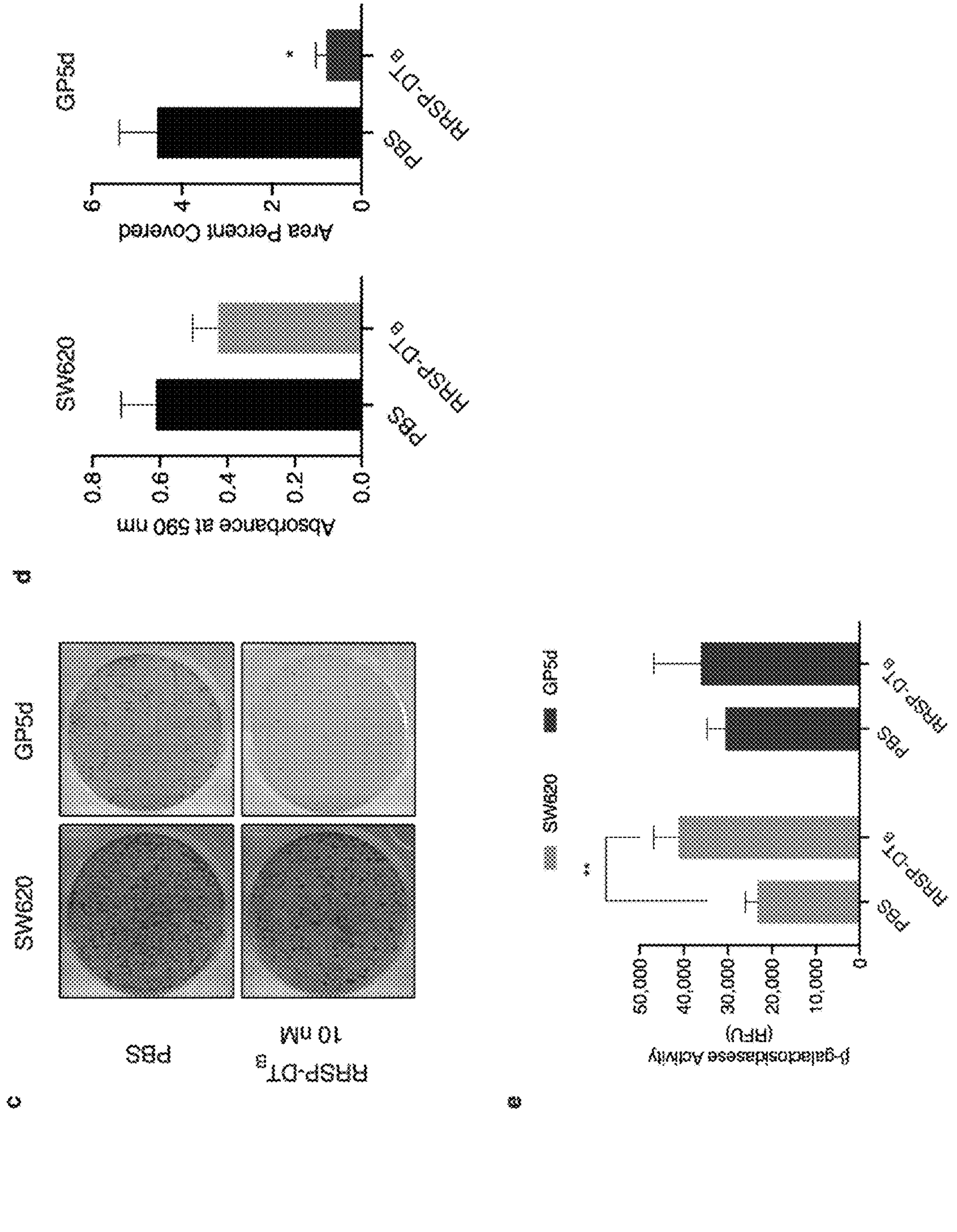

To further understand the survival differences between RRSP-treated cell lines, we used the Caspase-Glo 3/7 Assay, which quantitatively measures caspase-3/7 activity using luminogenic caspase-3/7 substrate to indicate onset of apoptosis. In highly susceptible cell lines HCT-116 and SW1463, treatment with RRSP at both low (1 nM) and high (10 nM) concentrations of RRSP-$DT_B$ significantly increased luminescence compared to mock-treated controls after 48 h, suggesting onset of apoptosis (FIG. 78B). This was not the case for GP5d cells where the signal was highly variable across replicate samples and even decreased in response to RRSP-$DT_B$ treatment. For SW620 cells, we observed RRSP-$DT_B$ treatment significantly decreased luminescence compared to mock-treated control suggesting a suppression of apoptosis. When treated for 48 h and reseeded at low cell densities SW620 and GP5d both showed a decrease in colony formation, suggesting that RRSP can induce a permanent non-proliferative state, even as cells maintain metabolic activity (FIG. 78 C,D). SW620 cells also showed significant increase activity of the enzyme β-galactosidase, a marker of senescence. This would support our earlier observation in which apoptosis was suppressed in RRSP-$DT_B$-treated SW620 cells since senescence is known to counteract apoptosis pathway activation [150]. However, β-galactosidase activity of treated GP5d cells remained unchanged (FIG. 78 E). Altogether, these data demonstrate that RRSP activity results in induction of apoptosis in highly susceptible cell lines while, in less sensitive lines, the cells remain metabolically active, but are unable to proliferate and, in some cases, enter into senescence.

Figure 79:
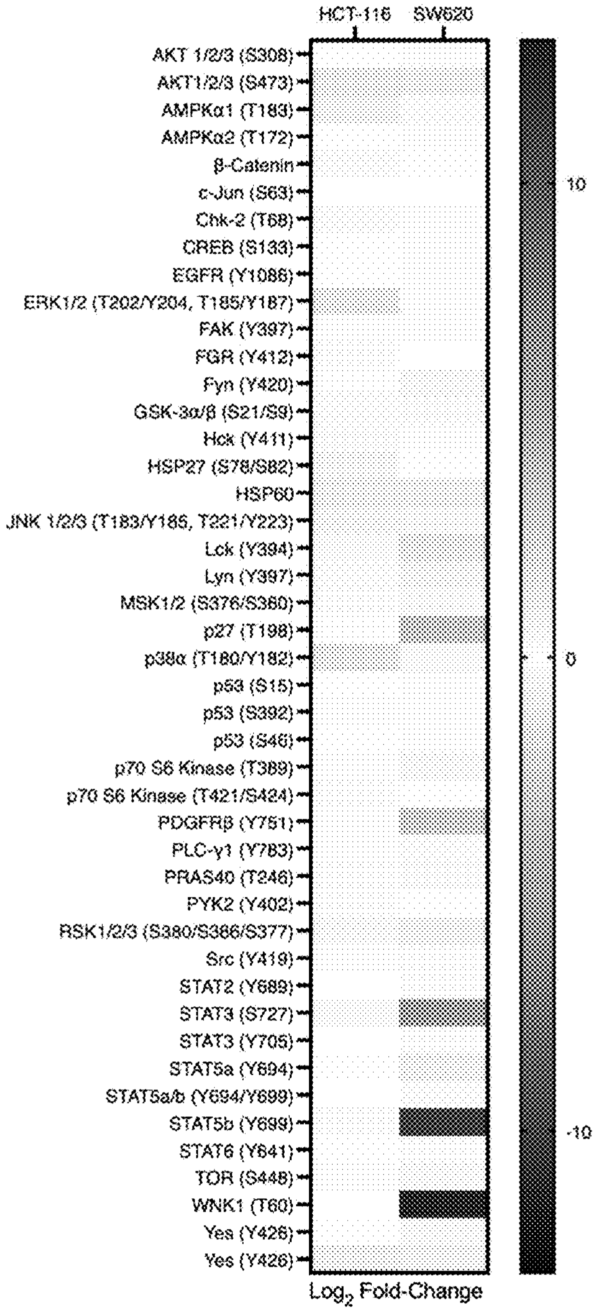
FIG. 79. Heatmap of human phospho-kinase array in HCT-116 and SW620 cells treated RRSP-$DT_B$ treated samples. Densitometric analysis of phospho-kinase array depicted through a heatmap of relative phosphorylated proteins levels in response to 10 nM RRSP-$DT_B$ compared to PBS control in HCT-116 and SW620 cells after 24 hr.
Figures 80A, 80B, 80C, 80D, 80E:
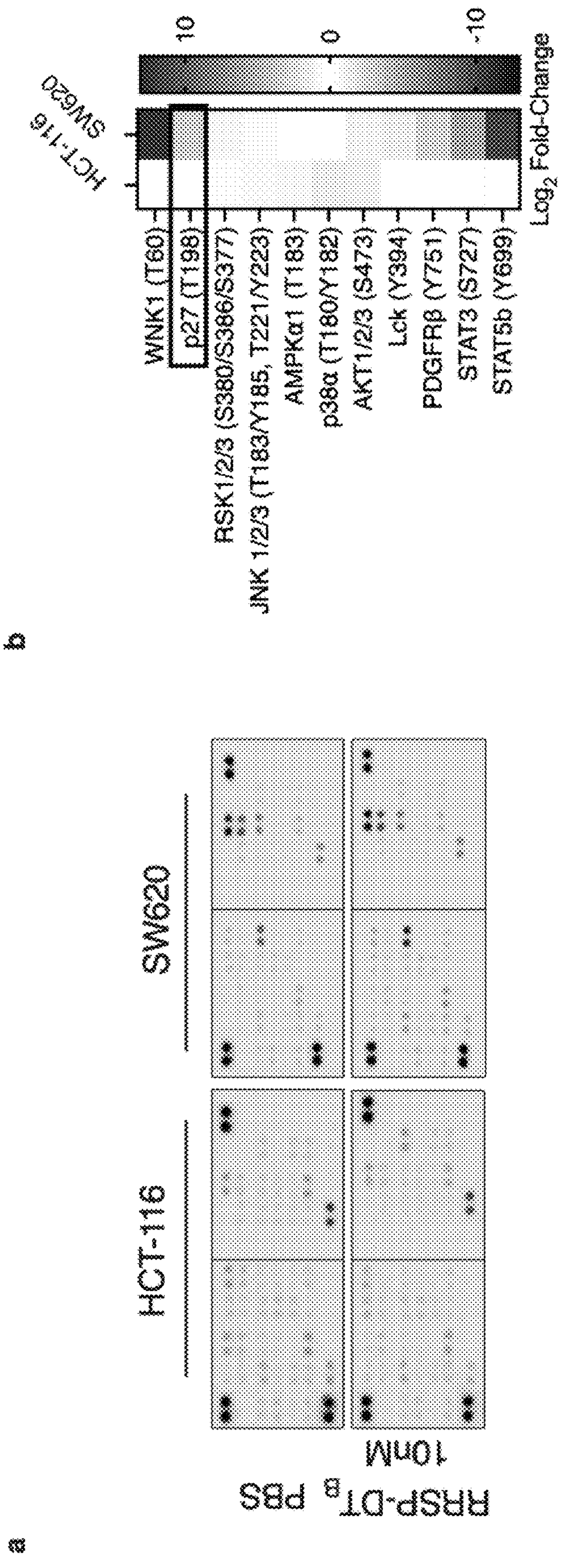
FIG. 80A-80E. RRSP-$DT_B$ cleavage of RAS induces p27 expression in CRC cell lines (A) Human phosphokinase array blots of HCT-116 and SW620 cells treated with either PBS or RRSP-$DT_B$ (10 nM) for 24 h. (B) Densitometric analysis kinase array depicted through a heatmap of relative phosphorylated proteins levels in response to RRSP-$DT_B$ compared to PBS control in HCT-116 and SW620 cells, n=1. (C) Representative western blot images of p27 and phosphor-RB expression in CRC cell lines treated with either RRSP-$DT_B$ or RRSP*-$DT_B$ for 24 h. Protein detection for each immunoblot was conducted on the same blot and cropped for each individual protein of interest. (D, E) Densitometric analysis of fold change in p27 and phospho-RB compared to PBS after 24 h in RRSP-$DT_B$ treated CRC cell lines; n=3. αTubulin was used as gel loading control. Results are expressed as mean±SEM of three independent experiments (*P<0.05, <0.01, **<0.0001 versus PBS control as determined through one-way ANOVA followed by Dunnett's multiple comparison test).
Figures 80A, 80B, 80C, 80D, 80E:
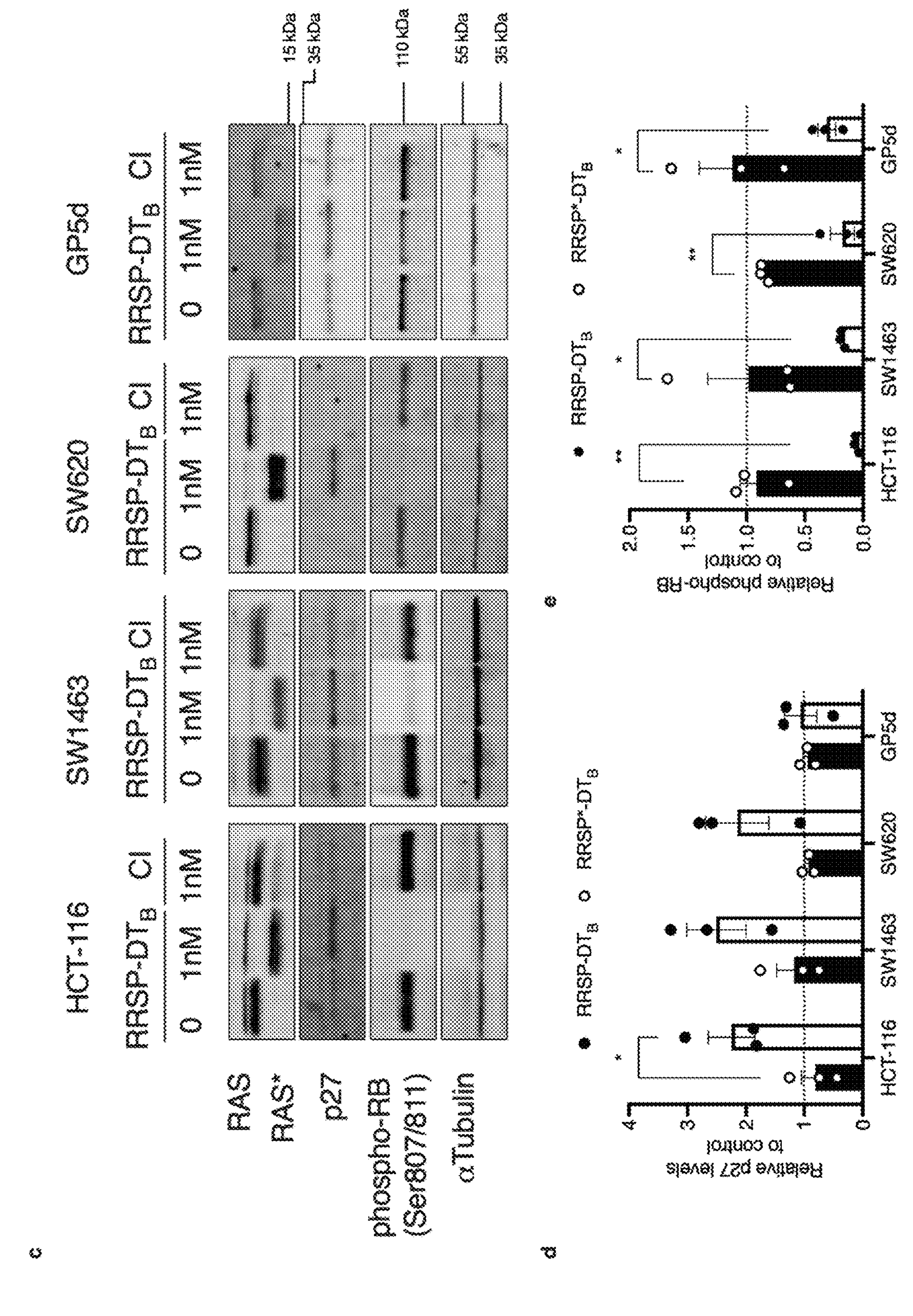

RAS Cleavage Can Induce Upregulation of Cyclin-dependent Kiase Inhibitor p27 Hypophosphorylation of RB We next took advantage of the unique cell line specific effects on cell growth and survival to better understand the underlying mechanisms regulating cell fate following RAS inhibition. Cell lysates from treated or untreated HCT-116 (highly sensitive) and SW620 (less sensitive) were incubated overnight with nitrocellulose membranes containing capture antibodies towards 43 different phosphorylated proteins (FIG. 80A). For RRSP-treated HCT-116 cells, there was increased phosphorylation observed for cell stress proteins such as p38a, p90 ribosomal S6 kinase (RSK1/2/3), and Jun-activated kinase (JNK) (FIG. 79, FIG. 80B). In addition, RRSP treatment increased phosphorylation of several Signal Transducer and Activator of Transcription (STAT) transcription factors. By contrast, the less responsive SW620 cells showed decreased phosphorylation of several STAT proteins (FIG. 79, FIG. 80B,). We also observed a significant fold increase in With No K(lysine)-1 (WNK1) kinase at Thr-60. This kinase is phosphorylated by AKT in HEK293 cells and is best known for regulating ion transport across membranes [151]. However, phosphorylation of Thr-60 has no effect on its kinase activity or its cellular localization [152]. Because RRSP decreases AKT activation (FIG. 80B), it is unlikely that WNK1 Thr-60 phosphorylation is involved in the growth differences we observe between cell lines.

Thus, we focused on the large fold-change difference observed in phosphorylation at Thr-198 of the cyclin-dependent kinase inhibitor p27 (also known as Kip1) (FIG. 80B). While HCT-116 cells showed no significant change in p27 phosphorylation in the screen, SW620 showed a three-fold increase in p27 phosphorylation. RAS is known to regulate critical components involved in cell cycle. RAS activation is directly linked to hyperphosphorylation of retinoblastoma protein (RB), thereby relieving its repression of E2F transcription factors, allowing transcription of G1 promoting genes, and promoting the cell cycle to progress from G1 to S phase [153]. Previous studies have established that phosphorylation of p27 at Thr-198 is critical for stabilizing p27 expression by preventing ubiquitin-dependent degradation [154]. In fact, aberrant RAS activity in cancer cells causes p27 post-translational downregulation through both ERK and AKT [5, 51, 52]. These data support that inhibition of RAS by RRSP could lead to downstream rescue expression of p27 expression in the SW620 cells, thereby slowing reversing the hyper-phosphorylation of RB.

Figures 81A, 81B, 81C:
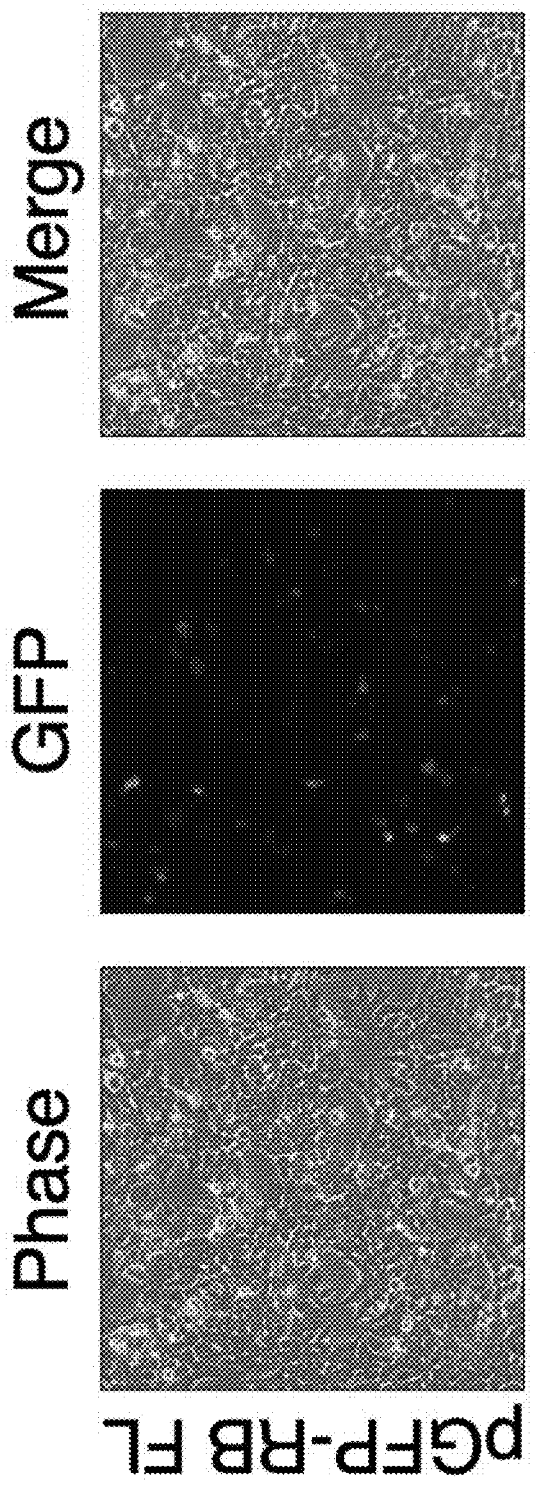
FIG. 81A-81C. Total RB expression in CRC cell lines (A) Representative images of HCT-116 cells transfected with pGFP-RB after 24 hr (B) Western blot analysis of HCT-116 cells transfected with GFP tagged RB following treatment with either PBS, RRSP-$DT_B$ or RRSP*-$DT_B$ after 24 hours. Total RB was detected using anti-GFP primary antibody. αTubulin was used as a gel loading control. (C) Western blot analysis of p21 levels in GP5d cell treated with either PBS, RRSP-$DT_B$ or RRSP*-$DT_B$ after 24 hr.
Figures 81A, 81B, 81C:
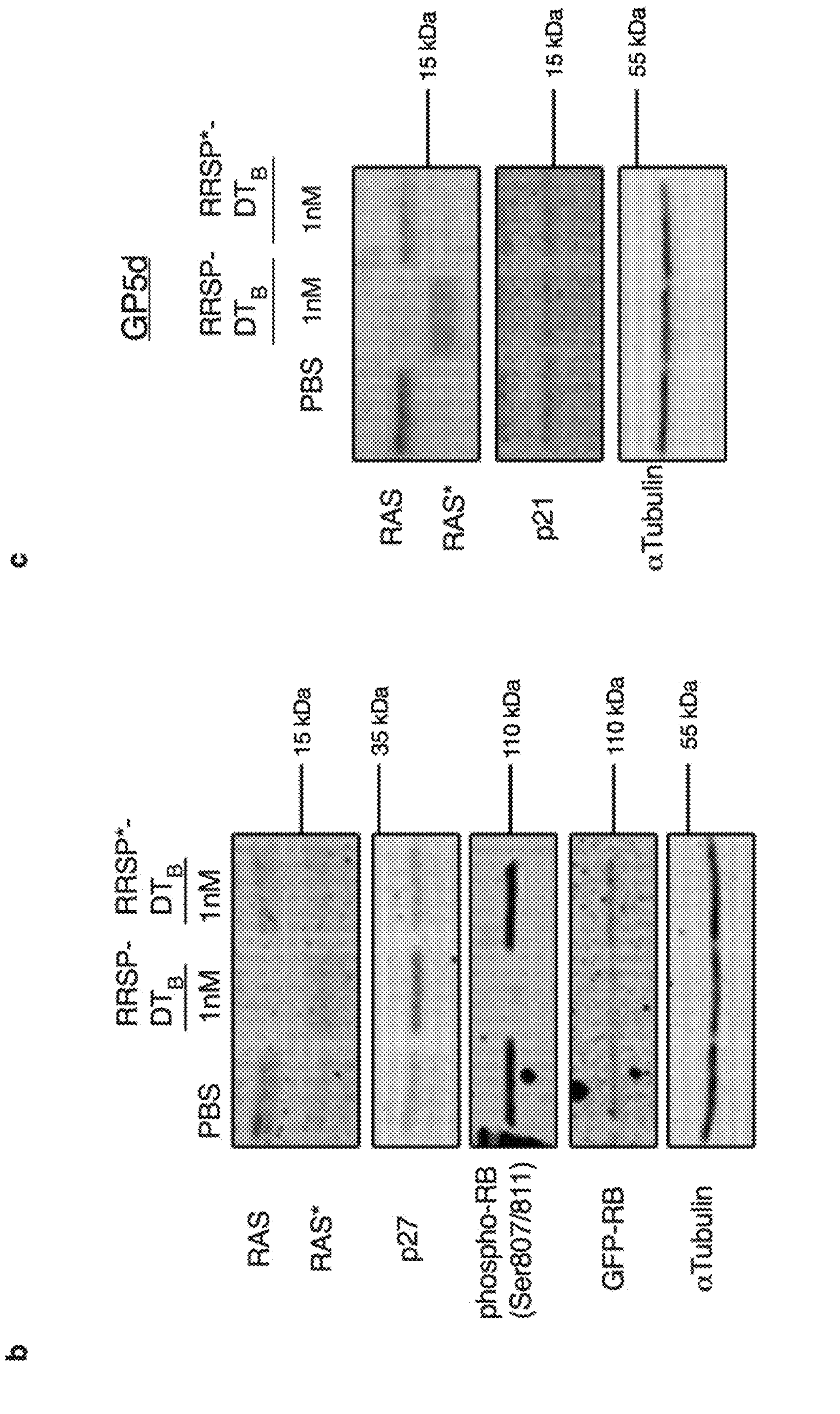

To test this possibility, all four cancer cell lines were treated with a sublethal dose of RRSP-$DT_B$. The treatment increased p27 protein levels in HCT-116, SW620, and SW1463 cells, while in GP5d cells levels remained unchanged (FIG. 80C,D). Concomitant with increased abundance of p27, all cell lines showed a significant decrease in RB phosphorylation at Ser-807/Ser-811 (FIG. 80C,E). Unfortunately, total RB was undetectable using commercially available antibodies. To be confident that RB hypophosphorylation was not due to low RB expression, we transiently expressed green-fluorescent protein (GFP)-tagged RB in HCT-116 cells (FIG. 81A). In GFP-RB expressing cells treated with RRSP-$DT_B$, hypophosphorylation of RB protein compared to PBS and RRSP*-$DT_B$ controls was observed (FIG. 81B). Protein levels of total GFP-RB were decreased upon treatment with RRSP-$DT_B$. This result was expected and is consistent with a role of p27 in degradation of RB protein to promote growth arrest [155].

Unexpectedly, hypo-phosphorylation of RB was also observed in GP5d cells despite showing no change in the expression or phosphorylation of p27 (FIG. 80D,E). The cyclin-dependent kinase inhibitor, p21, also plays a critical role in RB regulation. However, there was also no change in p21 protein levels in RRSP-treated GP5d cells (FIG. 81C).

RRSP Induces G1 Phase Cell Clyde Arrest

Figures 82A, 82B, 82C, 82D:
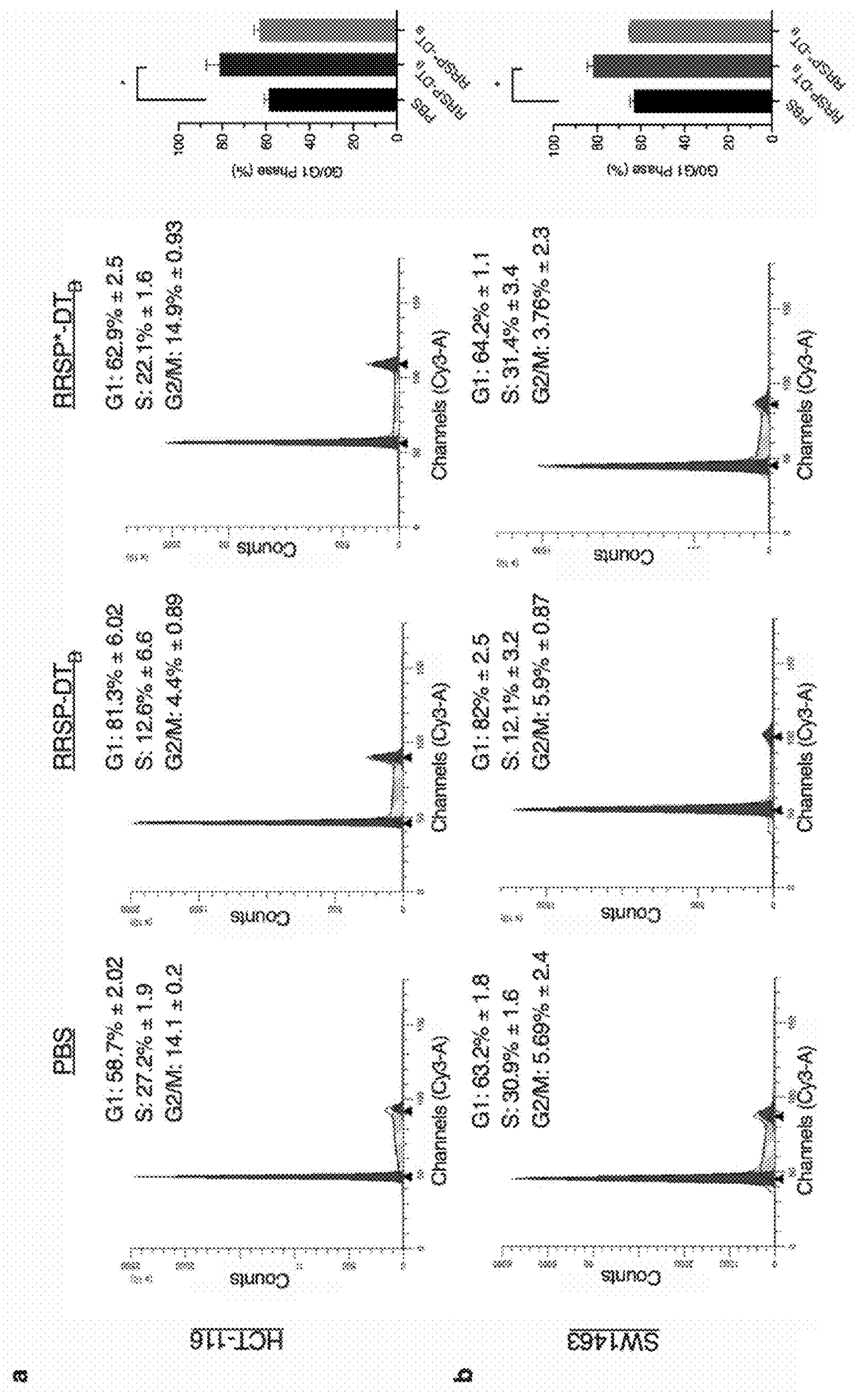
FIG. 82A-82D. RRSP-$DT_B$ induces G1 cell cycle arrest in CRC cell lines (A-D) Cell cycle flow cytometry analysis of CRC cell lines treated with either PBS, RRSP-$DT_B$ or RRSP*-$DT_B$ (1 nM) for 24 h. Percentage of cells in each phase are an average of three independent experiments. Bar graphs depict percentage of cells in G1 phase for each treated sample; n=3. Results are expressed as mean±SEM of three independent experiments (*P<0.05, P<0.01, **P<0.0001 versus PA control as determined through one-way ANOVA followed by Dunnett's multiple comparison test).
Figures 82A, 82B, 82C, 82D:
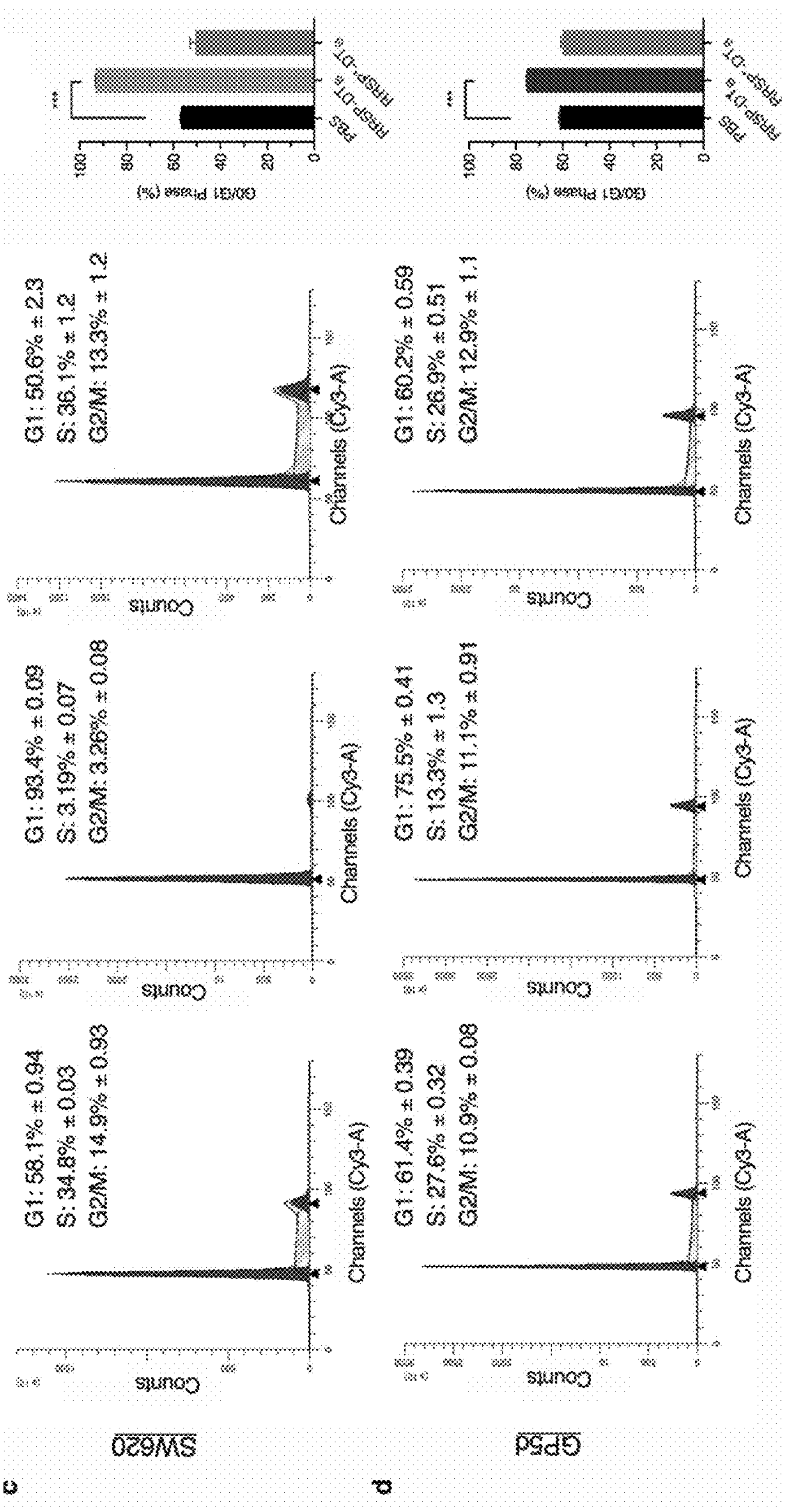
Figures 83A, 83B, 83C, 83D:
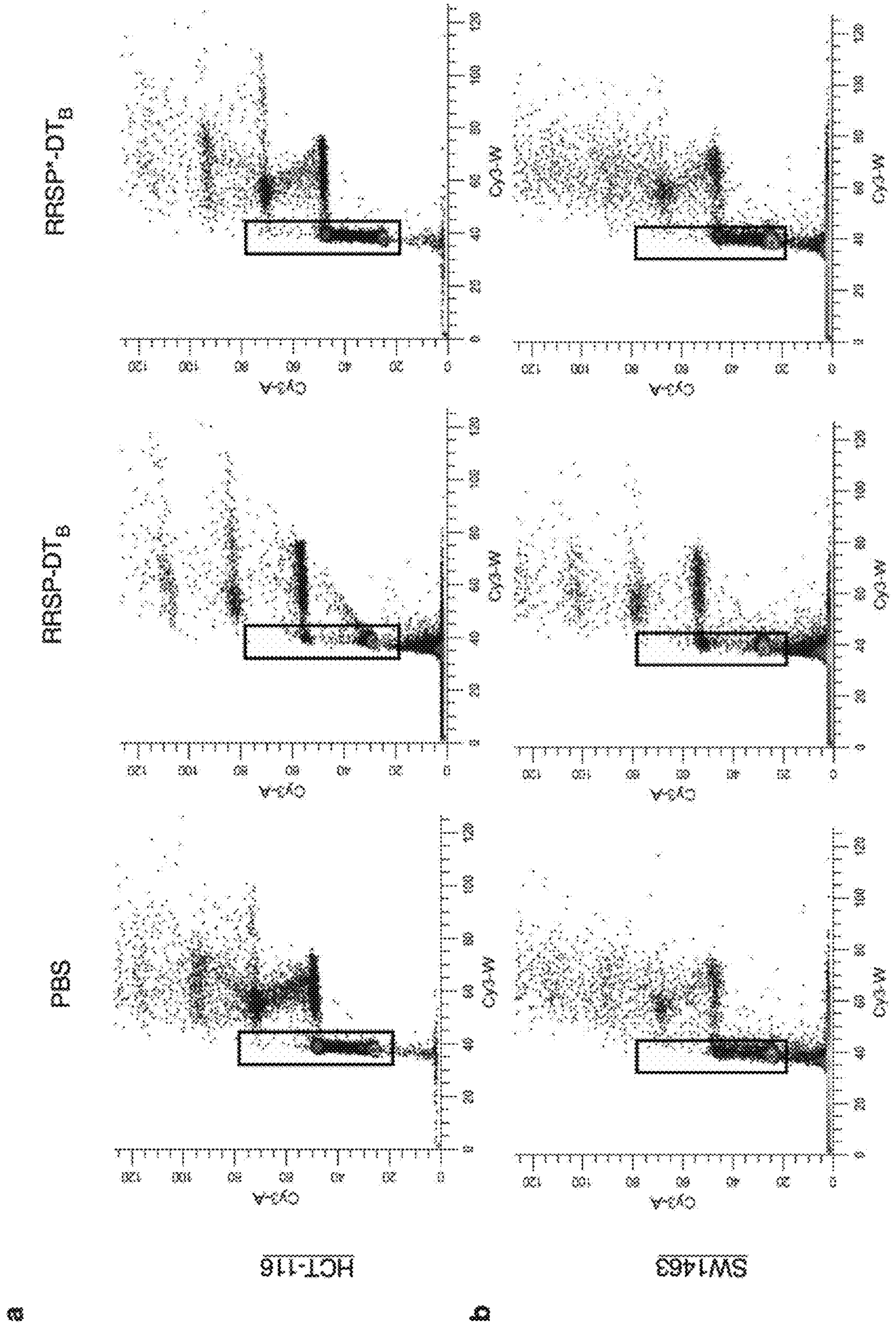
FIG. 83A-83D. Cell cycle analysis of CRC cell lines treated RRSP-$DT_B$ (A-D) Representative flow cytometry plots of CRC cell lines treated with either PBS, RRSP-$DT_B$ or RRSP*-$DT_B$ (1 nM) after 24 hours. Gating parameters were used to only collect single live cell populations.
Figures 83A, 83B, 83C, 83D:
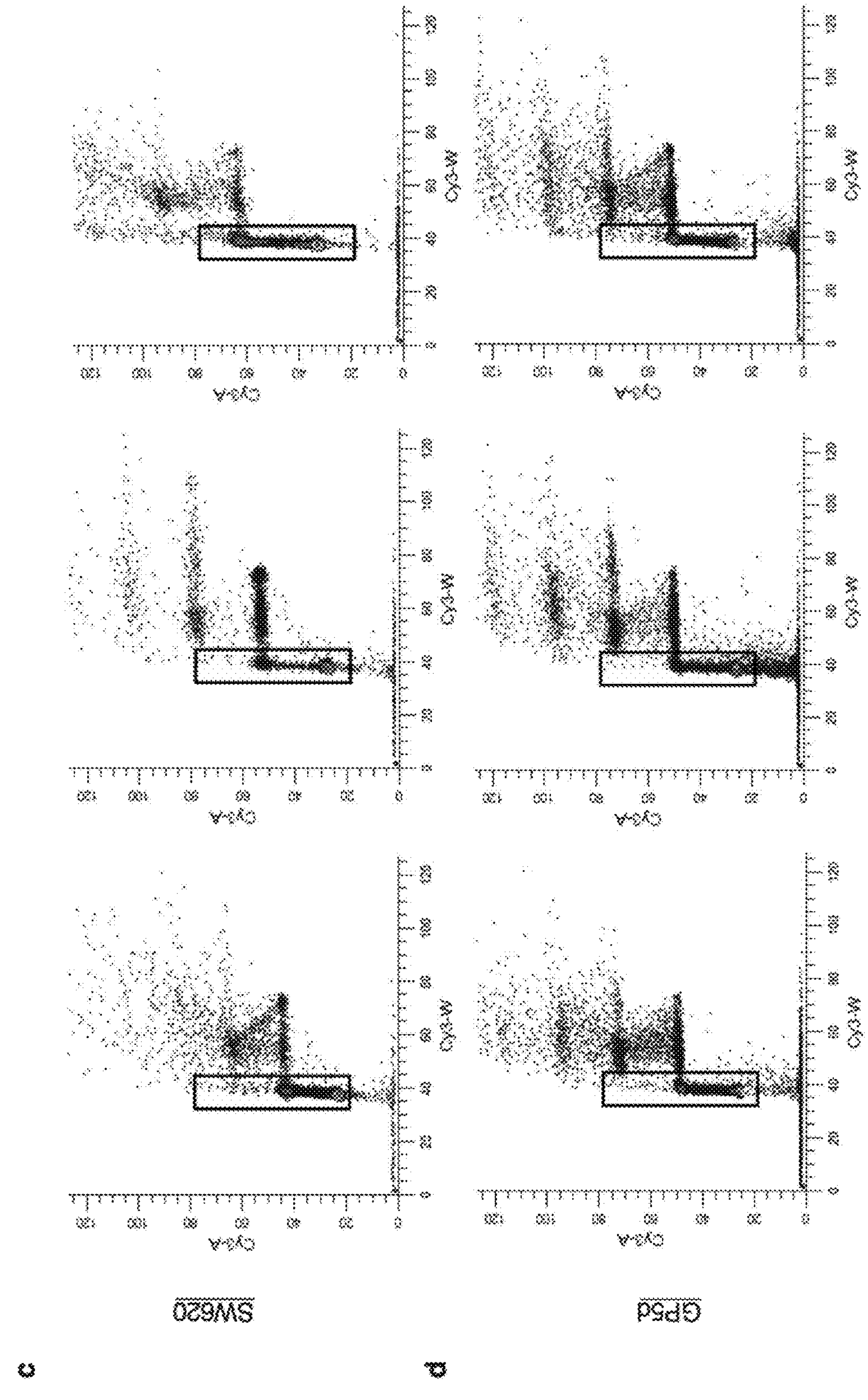
Figures 84A, 84B, 84C, 84D:
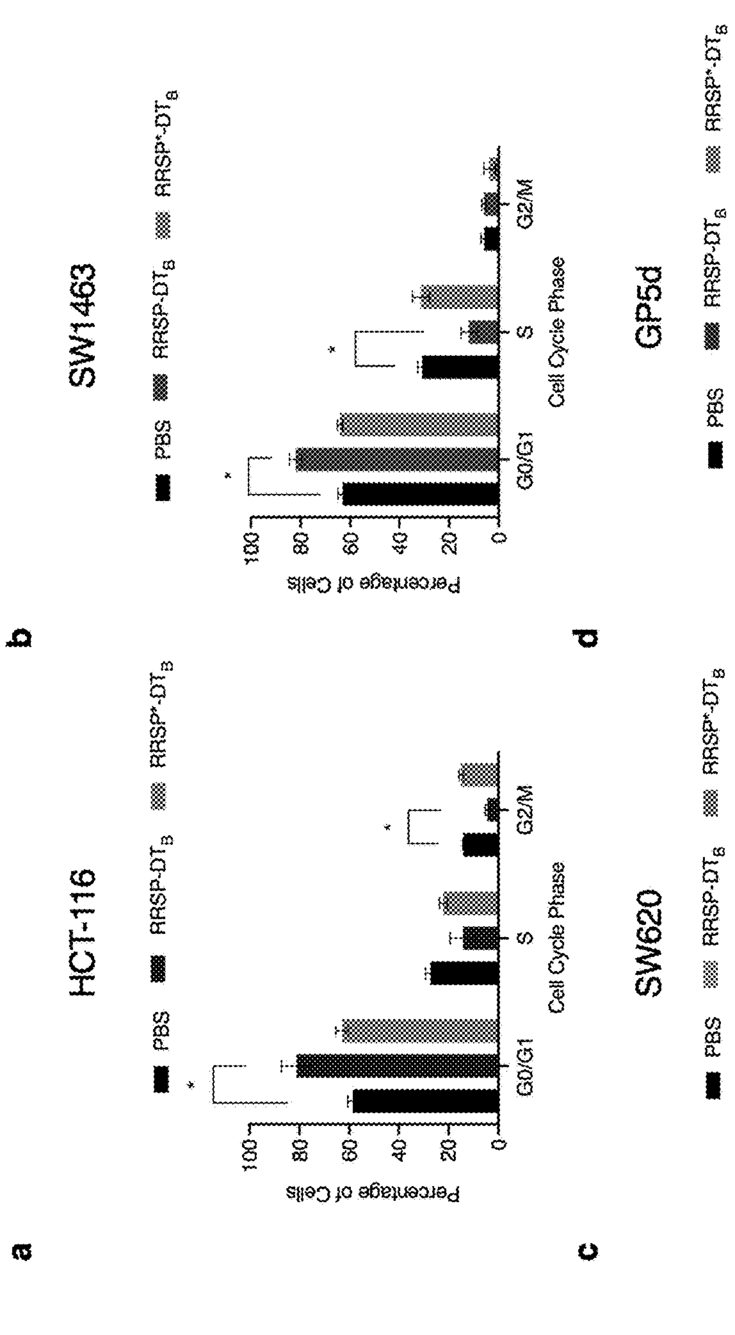
FIG. 84A-84D. Cell cycle analysis of RRSP-$DT_B$ treated CRC cell lines (A-D) Quantitative analysis of cell cycle analysis of CRC cell lines treated with PBS, 1 nM RRSP-$DT_B$ or 1 nM RRSP*-$DT_B$ for 24 hours; n=3. Results are expressed as means±SEM of three independent experiments (*P<0.05, P<0.01, **P<0.0001 versus PA control as determined through one-way ANOVA followed by Dunnett's multiple comparison test).

Elevated p27 protein expression in combination with hypo-phosphorylation of RB suggested that RRSP treatment induces cell cycle arrest. Under normal conditions, p27 regulates G1 checkpoint during the cell cycle by preventing entry into S phase through inhibition of CDK2 [27, 156]. To test if RRSP-$DT_B$ treatment induces cell cycle arrest, cell lines were treated for 24 h and the percentage of cells in G1, S, or G2/M phase was monitored. All cell lines that showed reduced RB phosphorylation had significant population of cells locked in the G1 state compared to PBS and RRSP*-$DT_B$ treated samples (FIG. 82A-D, FIG. 83A-D, FIG. 84A-D). The most dramatic increase in G1 arrest was seen in SW620 cells, where nearly 100% of cells remained in the G0/G1 phase following RRSP-$DT_B$ treatment (FIG. 82C). This G1 cell arrest was dependent on the RAS processing activity of RRSP as the catalytically inactive mutant RRSP*-$DT_B$ did not induce the cell cycle arrest (FIG. 82A-D). Together, these data illustrate that RRSP cleavage of RAS can induce growth inhibition through inducing cell cycle arrest, after which some cell lines progress to cytotoxic death.

BRAF V600E Cells Treated with RRSP Exhibit Growth Inhibition Independent of RAS

Figures 85A, 85B, 85C, 85D, 85E, 85F, 85G:
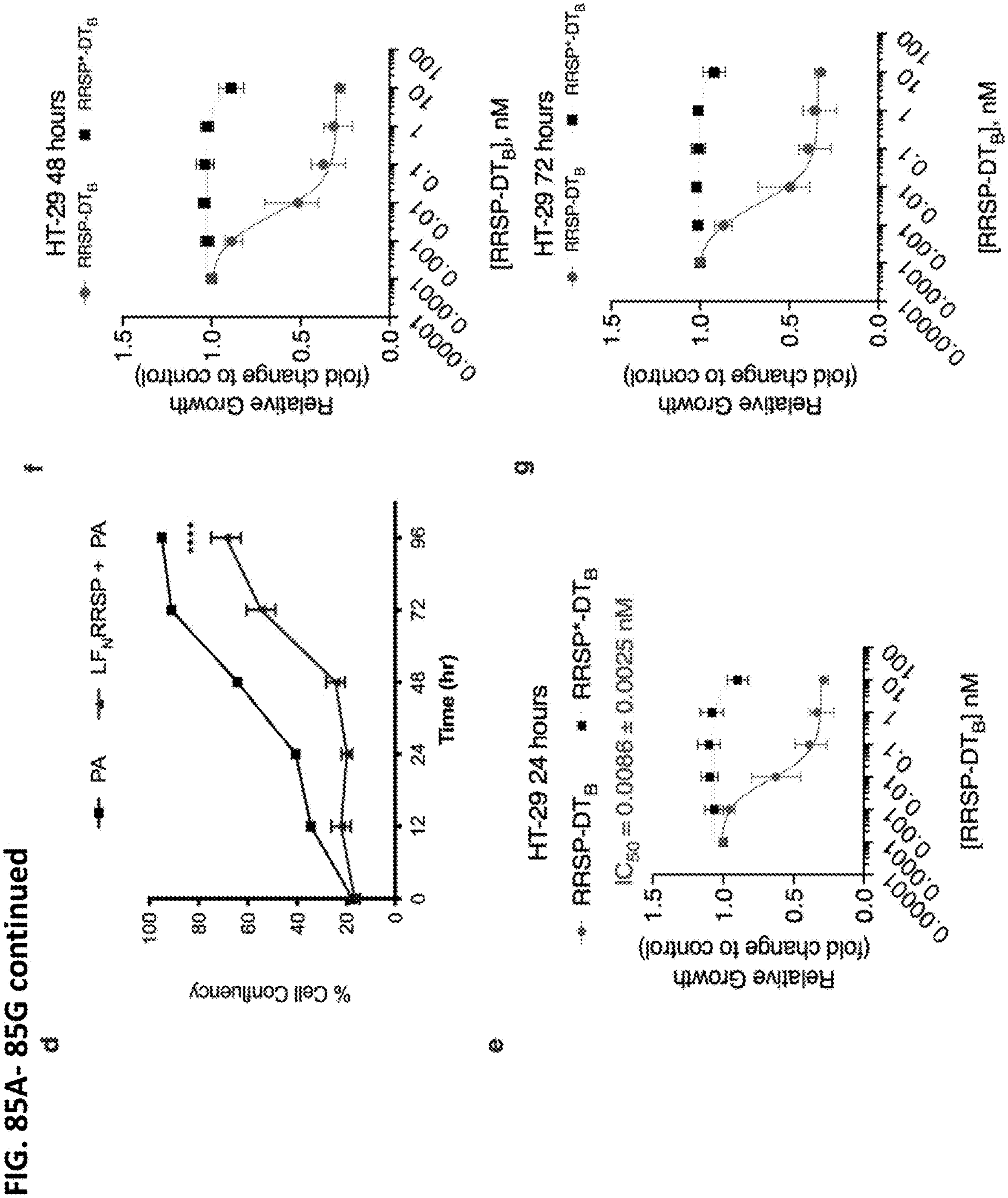
FIG. 85A-85G. RRSP-$DT_B$ growth inhibition in BRAF mutant cell lines (A) BRAF mutant cell lines used in this study. (B, C) Representative western blot analysis of RAS cleavage and ERK activity in BRAF mutant cell lines treated using $LF_N$RRSP or RRSP-$DT_B$ system after 24 hours. Protein detection for each immunoblot was conducted on the same blot and cropped for each individual protein of interest. (D) Cell growth over time in BRAF-dependent MEFs treated with $LF_N$RRSP or PA control was monitored by time lapse video microscopy and cell confluency was quantified using Nikon Elements. (E-G) Cell growth over time was monitored by time lapse video microscopy and cell confluency was quantified using Nikon Elements. Fitted dose response curve of RRSP-$DT_B$ in HT-29 cells show relative growth compared to PBS control at indicated timepoint. Results are displayed as mean±SEM, n=4. Results are expressed as means±SEM of three independent experiments (*P<0.05, P<0.01, **P<0.0001 versus PBS control as determined through one-way ANOVA followed by Dunnett's multiple comparison test).

Previously we have demonstrated the broad antitumor properties of RRSP across several different cancer cell lines from multiple tumor types. Through genetic analysis, we observed a correlation between RRSP susceptibility and mutations in the downstream RAS effector BRAF. From this panel 6/8 of the cell lines classified as "low susceptible" to RRSP-$DT_B$ contained the BRAF V600E activating mutation, suggesting that RRSP is inefficient in KRAS-independent tumors [136]. To test this hypothesis in further detail we tested RRSP against two different cell lines: BRAF-dependent BRAF MEFs and HT-29 cells. Similar to RAS-dependent MEFs, BRAF-dependent MEFs lack endogenous RAS but instead rely on BRAF V600E for proliferation. The CRC cell line, HT-29, lacks mutations in RAS but harbors a point mutation in BRAF V600E (FIG. 85A). For treatment of RAS-dependent BRAF V600E MEFs and HT-29 cells, $LF_N$RRSP and RRSP-$DT_B$ systems were used respectively. MEFs were treated with $LF_N$RRSP in combination with PA while HT-29 cells were treated with RRSP-$DT_B$ for 24 hours before lysates were collected for western blot analysis. In RAS-dependent BRAF V600E MEFs these cells do not express RAS therefore RAS cleavage cannot be examined. Instead, RAP1 expression was used as an indicator of RRSP activity and was found to be decreased in only cells treated with $LF_N$RRSP in combination with PA (data not shown). In HT-29 cells treated with RRSP-$DT_B$, RAS was found to be significantly cleaved at low and high concentrations compared to PBS and RRSP*-$DT_B$ (FIG. 85C). We observed no significant differences in HB-EGF expression in HT-29 cells compared to other KRAS mutant cell lines (FIG. 77A) As expected, when pERK levels were examined we observed no changes in response to RRSP treatment supporting the activity of the BRAF mutation in both cell lines (FIG. 85B,C).

We next investigated the proliferative changes RRSP has on BRAF mutant cells. To examine growth sensitivities BRAF dependent BRAF V600E MEFs were treated with either PA alone or in combination with $LF_N$RRSP/$LF_N$RRSP* and monitored over several time points through time-lapse imaging. For the HT-29 cell line, cells were treated with increasing concentration of RRSP-$DT_B$ or with RRSP*-$DT_B$. Contrary to the predicted outcome, in BRAF dependent MEFs, growth inhibition was observed at early timepoints despite no changes in pERK activity (FIG. 85 B-D). However, inhibition observed was temporary and slowly rebounded at extended timepoints. Interestingly, a similar phenotype was observed in HT-29 cells wherein growth cells were highly susceptible to RRSP treatment (FIG. 85E-G). These data would suggest RRSP can inhibit growth in BRAF mutant cells, albeit to varying degrees with different long-term outcomes on proliferation depending on cell type.

Figures 86A, 86B, 86C, 86D, 86E, 86F, 86G, 86H:
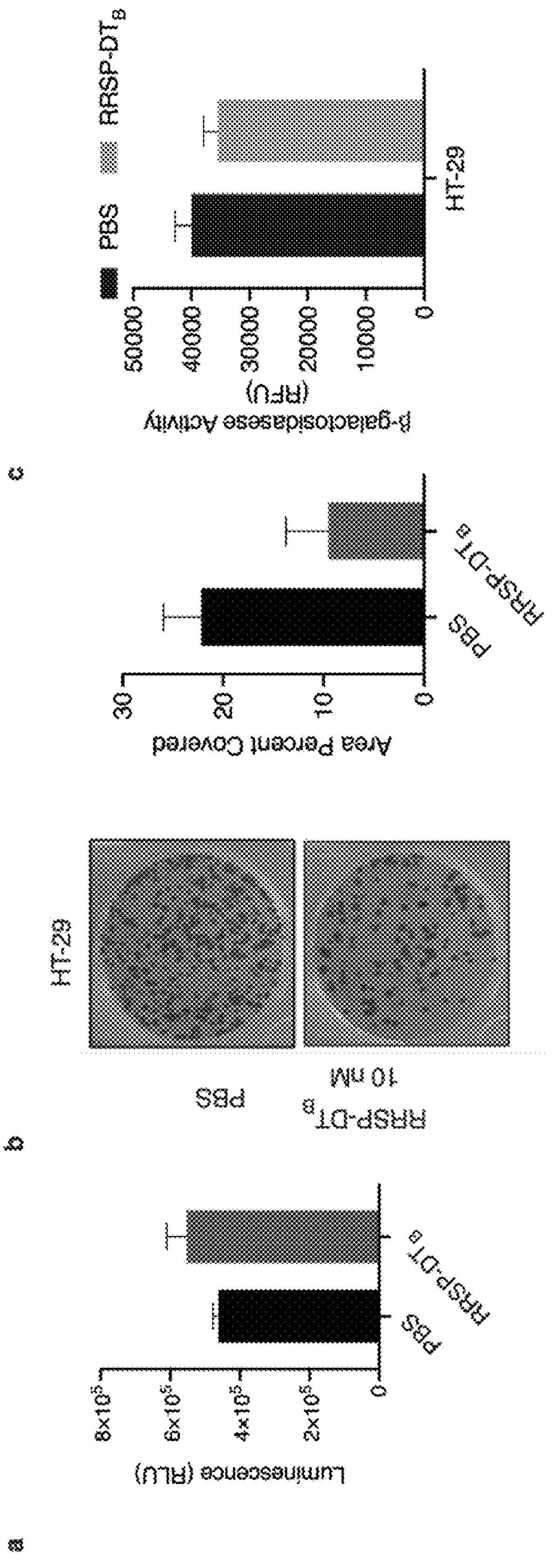
FIG. 86A-86H. RRSP-$DT_B$ effect on survival and cell cycle in HT-29 cells (A) Luminescence in HT-29 cells treated with wither PBS or RRSP-$DT_B$ for 72 hours. (B) Representative images of crystal violet-stained colonies from HT-29 cells pretreated with 10 nM RRSP-$DT_B$ for 48 h and replated at low seeding density to form colonies over 14 days. Quantitative analysis of crystal-violet stained colonies from three independent experiments. Results are expressed as means±SEM of three independent experiments (C) Measured cell senescence activity in HT-29 cells treated with 10 nM RRSP-$DT_B$ for 48 h then incubated with SA-ß Gal Substrate for 1 h at 37° C., n=3. (D) Representative western blot images of p27, RB and phosopho-RB expression in HT-29 cells treated with either RRSP-$DT_B$ or RRSP*-$DT_B$ for 24 h. Protein detection for each immunoblot was conducted on the same blot and cropped for each individual protein of interest. (E,F) Densitometric analysis of fold change in p27 and phospho-RB compared to PBS after 24 h in RRSP-$DT_B$ treated HT-29 cells n=3. αTubulin was used as gel loading control. (G) (above) Representative flow cytometry plots of HT-29 cells treated with wither PBS, RRSP-$DT_B$ or RRSP*-$DT_B$ (1 nM) after 24 h. Gating parameters were used to only collect single live cell populations. (below) Cell cycle flow cytometry analysis of CRC cell lines treated with either PBS, RRSP-$DT_B$ or RRSP*-$DT_B$ (1 nM) for 24 h. (H) Quantitative analysis of cell cycle analysis of HT-29 cell lines treated with PBS, 1 nM RRSP-$DT_B$ or 1 nM RRSP*-$DT_B$ for 24 h; n=3. Results are expressed as means±SEM of three independent experiments. All results described above are expressed as mean±SEM of three independent experiments (*P<0.05, P<0.01, **P<0.0001, ns=not significant versus PBS control as determined through one-way ANOVA followed by Dunnett's multiple comparison test).
Figures 86A, 86B, 86C, 86D, 86E, 86F, 86G, 86H:
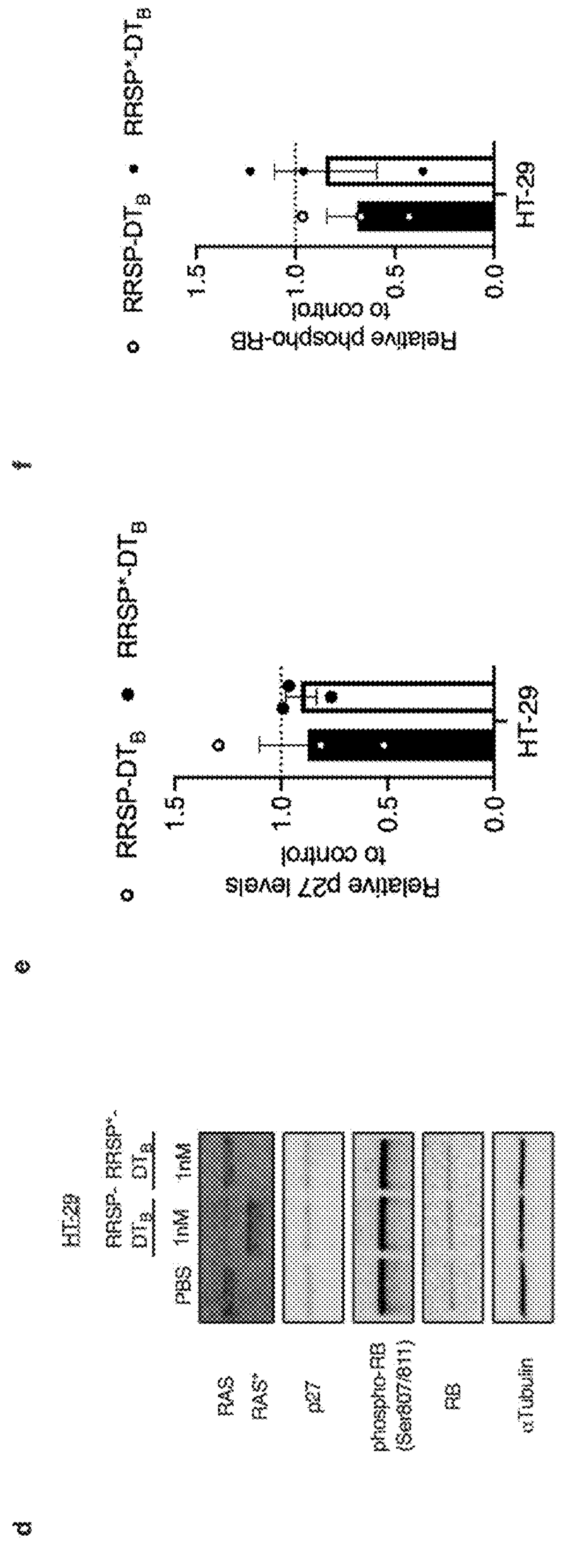
Figures 86A, 86B, 86C, 86D, 86E, 86F, 86G, 86H:
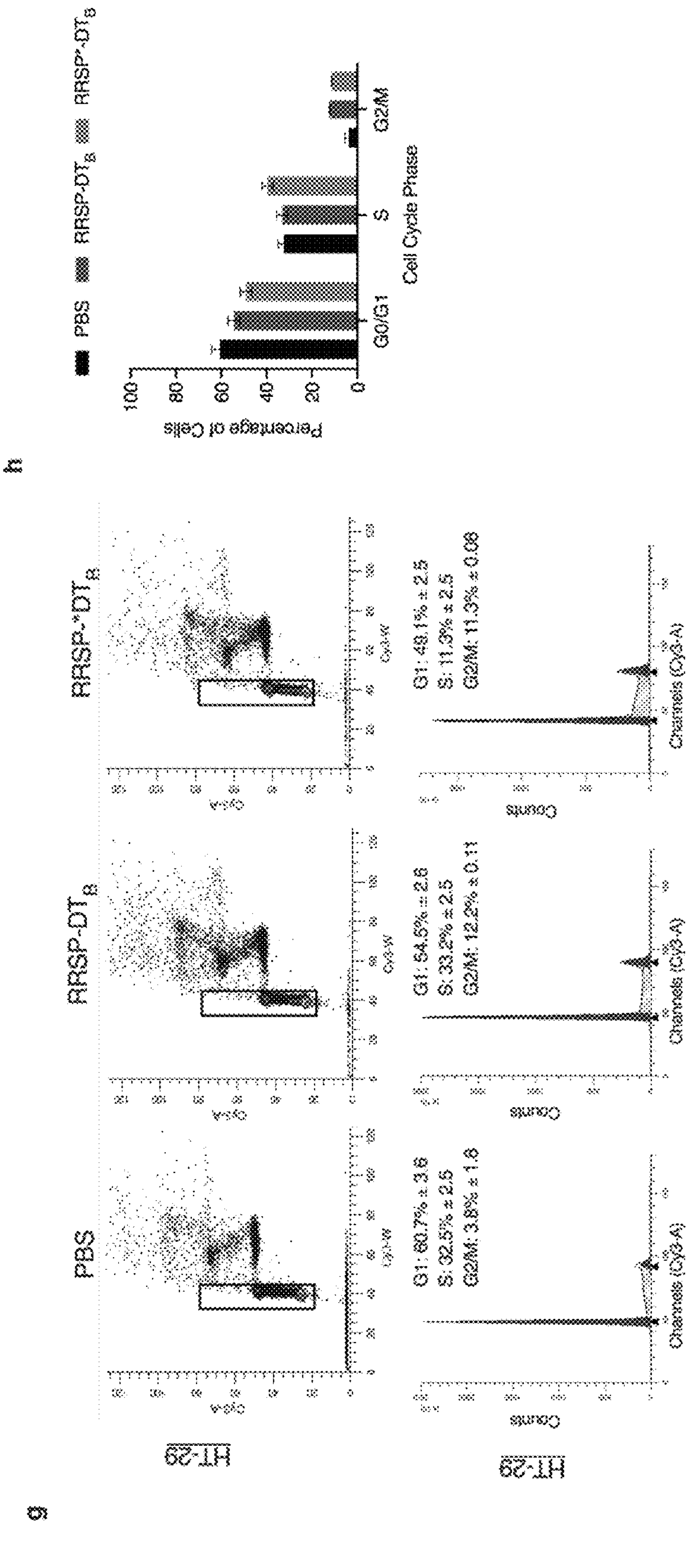

We next investigated the cytotoxic effects RRSP has on BRAF mutant cell lines. Based on the data described above RRSP has no effect on survival in RAS-dependent MEFs. We would expect this phenotype to apply to BRAF dependent MEFS and therefore only HT-29 cells were tested for RRSP cytotoxic effects. We again utilized the CellTiterGlo Assay to quantitatively measure cell survival through the presence of ATP. Contrary to data observed in highly susceptible KRAS mutant CRC cell lines, HT-29 cells showed no adverse survival effects in response to RRSP despite the dramatic growth effects (FIG. 86A). Data from time-lapse imaging can support these findings, where HT-29 cells treated with RRSP-$DT_B$ formed massively rounded colonies that exhibited no obvious signs of cytotoxicity (FIG. 77J). To further understand long-term growth effects following RRSP treatment a colony formation was performed. HT-29 cells were treated with either PBS or RRSP-$DT_B$ for 48 hours followed by reseeding cells at a low cell density for 14 days to examine colony formation. We observed a slight decrease in colony formation compared to PBS control, however, this was deemed statistically insignificant, suggesting that RRSP treatment in these cells may be reversible over time (FIG. 86B). We performed additional analysis for signs of senescence following 48-hour treatment with RRSP-$DT_B$ and observed no changes in β-galactosidase activity (FIG. 86C). Lastly, we examined cell cycle checkpoint molecule p27 and phosphorylation of RB to determine if short-term growth inhibition was due to cell cycle arrest. In HT-29 cells treated with RRSP-$DT_B$ for 24 hours, no changes in p27 or pRB were observed (FIG. 86D-F). In addition, cell cycle analysis using flow cytometry demonstrated no induction of cell cycle arrest ruling out this phenotype for RRSP mediated growth inhibition in HT-29 cells (FIG. 86G-H). Altogether, these results demonstrate that RRSP inhibits growth albeit temporarily in BRAF mutant cells. The mechanism of RRSP-mediated growth inhibition in BRAF mutant cells may be mediated through a cell cycle independent process.

BRAF Dependent ERK Signaling Regulates RAP1a Expression

Figures 87A, 87B:
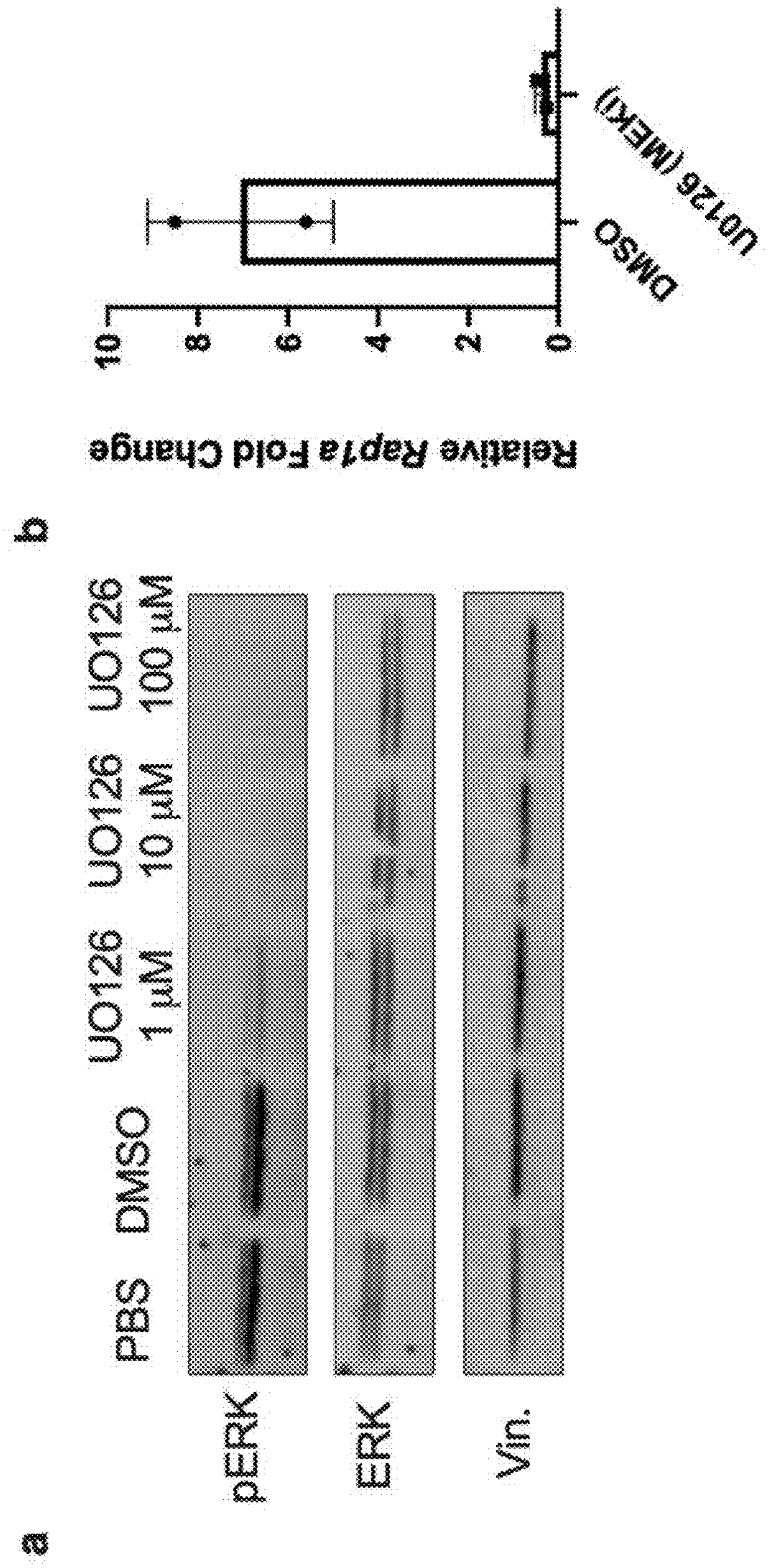
FIG. 87A-87B. MEK/ERK signaling regulates RAP1a expression in MEFs (A) Western blot analysis of pERK expression in BRAF-dependent MEFs following treatment with UO126 MEK inhibitor for 2 h. (B) mRNA transcript expression of RAP1a in BRAF-dependent MEFs treated with UO126 MEK inhibitor (10 μM) for 2 h, n=2.

A critical attribute of BRAF mutant cells is their ability to activate ERK signaling independently of RAS. Therefore, RRSP growth effects in BRAF mutant cells must be independent of RAS and is likely due to inactivation of RAP1. The role of RAP1 is better understood in regulating cell adhesion and migration with some studies highlighting proliferative functions [157]. Our data suggests that temporary growth effects in BRAF dependent MEFs are a result of RAP1 inactivation and that growth rebound is done through ERK driving RAP1 expression. To test this hypothesis BRAF dependent MEFs were treated with either PBS, dimethyl sulfoxide (DMSO), or the MEK inhibitor U0126 for 2 hours, and gene expression of RAP1a was examined. After 2 hours we observed a complete loss of pERK activation in cells treated with UO126 at each concentration (FIG. 87A). When we examined RAP1a expression following UO126 treatment we observed a decrease in RAP1a transcript levels compared to DMSO control (FIG. 87B). Notably, DMSO control increased RAP1a transcript levels after short incubation compared to PBS treated sample (FIG. 87B). These data would suggest that ERK is necessary for RAP1a expression in BRAF dependent MEFs. These data describe for the first time a mechanism by which RAP1a expression is driven through RAS-regulated ERK signaling and could potentially play critical roles in cell growth in MEFs.

Discussion

It has been over 30 years since the discovery of the importance of RAS for driving tumorigenesis in cancer. Lung, pancreatic, and colorectal cancers remain being the most lethal cancers in the United States with high mutation rates in KRAS, the most commonly mutated isoform. Despite the significant amount of research being conducted on RAS, it still remains a challenging target in the field. Small molecules directed to specific RAS mutants, specially KRAS G12C, have shown promising results in clinical trials, but will only benefit a small subset of patients [158]. Our lab has discovered RRSP as a potent, site specific inhibitor of RAS capable of inhibiting all RAS isoforms simultaneously along with downstream activation. RRSP antitumorigenic effects are well demonstrated in vivo with xenograft models for both breast and colon cancers, wherein tumor growth was stunted and, in some cases, showed regression [136]. Evidence for RRSP as a therapeutic inhibitor of RAS is sufficient, however the mechanism by which RRSP mediates growth inhibition has been an outstanding question. In this study, we examined the signaling consequences of cleavage of all RAS in several CRC cell lines and its downstream implications on cell proliferation and survival. The goal of the study was to understand the mechanism of growth inhibition in response to RRSP, in the absence of cytotoxicity.

First, we examined whether RRSP was a suitable inhibitor across RAS variants. Using the isogenic RAS-dependent MEF model, we demonstrated that all three major RAS isoforms and frequently observed KRAS mutants were equivalent substrates for RRSP. Loss of RAS resulted in reduced ERK activation, which as expected, negatively affected proliferation. Most importantly, in this isogenic study, we observed no significant differences in RAS cleavage between wildtype isoforms and KRAS mutants. RAS-dependent MEFs are useful for studying isolated biochemical properties and signaling of specific oncogenic RAS in a cellular context making it an excellent model to study RRSP targeting of mutant RAS. One of the unavoidable disadvantages of this model is the number of integration sites that vary between RAS-dependent MEF cell lines. For some RAS cell lines a single gene integration could not rescue proliferation and required multiple integrations for stable clonal populations. As a result, in the context of RRSP, expression of multiple genes of a single RAS allele may lead to an underestimation of RRSP effectiveness in cleaving RAS.

We next examined RRSP effectiveness in four CRC cell lines, which displayed variations in susceptibility to RRSP. Two of the cell lines with the greatest RRSP growth sensitivity, HCT-116 and SW1463, had dramatically lower metabolic activity and induction of apoptosis compared to controls. Interestingly, GP5d and SW620 retained normal metabolic activity, yet showed significant inability to form colonies following RRSP treatment, mimicking a senescent-like phenotype. This observation is consistent with prior data for SW620 showing a reduction in cellular material stained with sulforhodamine B after 48 h of treatment at 13.5 nM RRSP, but RRSP was not cytotoxic [136]. A logical hypothesis is that GP5d and SW620 cells have elevated pERK activity and therefore are less susceptible to RRSP. However, our data show the opposite in that moderately susceptible cell lines have significant decreases in pERK and RAS following RRSP treatment. This result would suggest that inhibition of pERK activity is not a predictor of susceptibility to RRSP in many cell lines. Similar results have previously demonstrated that varying growth sensitivities to pharmacological inhibition of mitogen-activated protein kinase kinases (MEKs) do not correlate with pERK activity in KRAS and BRAF mutant CRC cell lines [159, 160]. Further investigation of RRSP in the context of KRAS mutants expressing low levels of pERK would elucidate mechanisms regulating cell fate signals between cell lines.

Mechanisms that link RAS and the cell cycle have been well examined. In quiescent cells, p27 is highly expressed in order to inhibit CDKs activity and to suppress RB phosphorylation [27, 156]. Upon mitogen stimulation, RAS activation suppresses p27 protein expression through post-translational modifications that signal for its ubiquitin-mediated degradation [7, 51, 52]. In RAS-driven human cancers, low levels of p27 are frequently observed. We demonstrated that the growth inhibition in HCT-116, SW1463, and SW620 is the result of G1 cell cycle arrest through the upregulation of p27. These data suggest that RAS cleavage in certain CRC cell lines induces p27 upregulation, leading to a cell cycle arrest state that can induce apoptosis at later timepoints. Transient overexpression of p27 is known to then induce cell cycle arrest and later apoptosis [161, 162]. Although in our studies, only the highly susceptible cell lines showed decreases in viability and induction of apoptosis, whereas SW620 retained metabolic activity and undergoes cell cycle arrest. It is important to note that a prolonged cell cycle arrest through p27 induces a persistent cell cycle arrest through induce senescence [163]. We observe this phenotype in SW620 cells in which RRSP treatment induced a senescent-like phenotype.

Unexpectedly, GP5d cells did not show upregulation of p27 or p21, although RB was hypo-phosphorylated, and cells initiated G1 cell cycle arrest. These data reveal there must be other pathways that drive growth inhibition following RAS cleavage. In fact, RRSP from the insect pathogen *Photorhabdus asymbiotica*, which is identical to RRSP, also cleaves RAS and was recently reported to induce G1 cell cycle arrest [134, 162]. The proposed mechanism did not depend on RAS processing, and instead involved RRSP directly binding to CDK1 when it is overexpressed, essentially functioning as a protein trap. Thus, the multi-domain RRSP may possess at least two mechanisms to inhibit the cell cycle, one by restoring p27 downstream of RAS processing and another by directly binding to CDK1. Notably, because low p27 expression levels have been correlated with poor survival in patients with different types of cancer including colon, the ability of RRSP to restore p27 expression and to initiate cell cycle arrest could have important implications for the treatment of tumors with aberrant RAS signaling.

The most unique phenotype from our data was shown in cells with BRAF mutations, which had differing responses on growth inhibition compared to KRAS mutant cell lines. In both BRAF dependent MEFs and HT-29 CRC cell lines RRSP was capable of inhibiting growth, however, growth inhibition seemed to be temporary. Further investigation determined that growth inhibition did not affect survival or cell cycle progression. Thus, these cells still undergo DNA replication but may continue to expand without undergoing cell division. Due to the activating mutation in BRAF, we hypothesized that RRSP-dependent growth inhibition, in this case, may be RAS-independent. In our preliminary data, we demonstrate for the first time RAP1a mRNA expression is regulated by ERK signaling in MEFs. Because RRSP also targets RAP1, a critical regulator of cytokinesis, cleavage of RAP1 could play a role in growth inhibition through disrupting the final stages of cell division. Previous studies have suggested that RAP1 inactivation could lead to growth abnormalities independently of the cell cycle [164]. The role RAP1 plays in proliferation through regulating mitosis-related activity remains to be investigated but could provide an alternative target for therapeutic strategies.

In summary, a critical finding of this study was that processing of RAS does not result in a single easily tractable cell fate in all cancer cells but drives a suite of alternative overlapping outcomes that can include cytotoxicity, inhibition of cell cycle and senescence. The differences are not driven by the nature of KRAS oncogenic mutation as all mutant forms of KRAS were susceptible to RRSP-driven RAS processing in an isogenic system and RAS was processed in all the CRC cell lines. The impact of RAS processing is thus linked to cancer cell differences in signal pathways downstream of RAS. RRSP anti-tumor effects has some translational applicability to RAS-independent BRAF mutant cells with greater implications for understanding the role of RAP1 during proliferation independently of ERK. A limitation of this study is that only five cell lines were assessed, suggesting that the array of variable outcomes could increase as additional cell lines are considered in the future. However, the key finding here is that, despite differences in the mechanisms underlying RRSP susceptibility, all cells tested were ultimately susceptible and all led to reduced cell viability, growth, and/or proliferation. Thus, RAS processing or degradation has great promise as a potential broadly applicable therapy against colon cancer.

Methods

Purification and Intoxication of Cells with $LF_N$-RRSP or RRSP-$DT_B$ in RAS-Less MEFs and Colorectal Cancer Cells 'RAS-dependent' mouse embryonic fibroblast (MEF) cells were provided by the National Cancer Institute RAS Initiative at Frederick National Laboratory for Cancer Research (FNLCR). HCT-116 cells were purchased from the American Type Culture Collection. HT-29 cells were provided from the Marcus Peter lab at Northwestern University. Other colorectal cancer (CRC) cells lines SW1463, GP5d, and SW620 were provided by the FNLCR. Each CRC cell line was validated by the Northwestern University Sequencing Core by Short Tandem Repeat profiling. All cells were cultured at 37° C. and 5% $CO_2$ atmosphere. HCT-116, SW1463, GP5d, SW620 cells were cultured in Dulbecco's Modified Eagle Medium (DMEM)-F12 with Glutamax (Gibco) containing 10% fetal bovine serum (FBS; Gemini Bio) and 1% penicillin/streptomycin (P/S; Invitrogen). HT-29 cells were cultured in RPMI-1640 (Gibco) containing 10% FBS and 1% P/S. All MEF cells, except for HRAS RAS-dependent MEFs, were cultured in DMEM (Gibco) with 10% FBS, 1% P/S, and 4 μg/ml of blasticidin (ThermoFisher Scientific).

HRAS RAS-dependent MEFs was cultured in 2.5 μg/ml of puromycin (ThermoFisher Scientific). Recombinant RRSP-$DT_B$ and RRSP*-$DT_B$ were expressed in *E. coli* BL21(DE3) and purified over a HisTrap FF nickel affinity column as described above. For intoxication in CRC cell lines were seeded in 6-well plates (~70% confluency) overnight, after which medium was replaced with fresh medium containing either RRSP-$DT_B$ or RRSP*-$DT_B$ and incubated at indicated timepoints at 37° C. in the presence of 5% $CO_2$. Recombinant $LF_N$RRSP and $LF_N$RRSP* (previously known as $LF_N$DUF5 and $LF_N$DUF5*) were expressed in *Escherichia coli* BL21(DE3) and purified over a HisTrap FF nickel affinity column followed by Superdex 75 size exclusion chromatography using the ÅKTA protein purifier purification system (GE Healthcare), as described above. For intoxication, MEFs were seeded in 6-well plates at $3\times10^5$ cells per well for 1 h, after which medium was replaced with fresh medium containing with 7 nM Protective antigen (PA) alone (List Labs, #171E) or in the presence of 3 nM $LF_N$RRSP/$LF_N$RRSP$^{H4030A}$ (Also known as $LF_N$RRSP*) and incubated at indicated timepoints at 37° C. in the presence of 5% $CO_2$.

Time-Lapse Video Microscopy

For RAS-dependent MEFs and KPCs ($6\times10^3$ cells per well) were cultured in 96-well clear bottom white plates in corresponding complete growth medium and treated after 4 h with $LF_N$RRSP or RRSP-$DT_B$ respectively. Colorectal cancer cell lines were plated at 80% confluency and cultured in 96-well clear bottom white plates. Complete growth medium with RRSP-$DT_B$ or RRSP*-$DT_B$ was added after overnight cell attachment. All cells were cultured in Nikon Biostation CT and images were taken at indicated timepoints. Cell confluency was quantified using Nikon Elements software. IC50 concentrations were calculated using log(inhibitor) vs. response variable slope (four parameters) function in Graphpad Prism 8.

Cell Viability, Apoptosis, Cell Survival, and Cell Counting Assays

For cell viability assay CRC cell lines were seeded in 96-well clear bottom white plates at ~80% confluency. Complete growth medium with RRSP-$DT_B$ or RRSP*-$DT_B$ was added after overnight cell attachment. After 72 h, CellTiter-Glo (Promega) reagent was added to each well and luminescence was detected using Tecan Safire2 plate reader. For apoptosis assay, CRC cell lines were seeded at 10,000 cells per well in a 96-well clear bottom white plate. Complete growth medium with RRSP-$DT_B$ or RRSP*-$DT_B$ was added overnight after cell attachment. After 48 h, Caspase-Glo 3/7 Assay (Promega) regent was added to each well and luminescence was detected using Tecan Safire2 plate reader. For crystal violet assays, cells were treated as described above and were incubated for 48 h. Following incubation cells were harvested and reseeded at low seeding densities in 6-well plates. Colony formation was monitored over 14 days, during which media was replaced every three days. On day 14 colonies were fixed in crystal violet fixing/staining solution (0.05% (g/vol) crystal violet, 1% formaldehyde, 1% (v/v) methanol in PBS. Open source ColonyArea ImageJ plug-in was used for quantitative analysis of the area % covered by the stained colonies [204]. Due to high background from crystal violet staining in SW620 cells, stained wells were dissolved in 10% acetic acid and destained on rocker for 30 min. Absorbance was measured at 590 nm using Tecan Safire2 plate reader.

Proteome Human Phospho-Kinase Array

CRC cell lines were treated as described and washed in 1×PBS. Cells were solubilized using lysis buffer provided by the vendor (R&D Systems) and rocked for 30 min at 4° C. Suspension was spun for 5 min at 14,000×g and supernatant was collected. Concentration of protein in the collected supernatant fluid determined using the BCA assay (ThermoFisher Scientific, no. 23227). 200 μg of sample lysate was applied to nitrocellulose membranes kinase arrays and incubated overnight at 4° C. Provided detection antibodies were incubated with specified concentrations as suggested by the supplier. Membrane arrays were acquired using Odyssey Infrared Imaging System (LI-COR Biosciences) and quantified by densitometry using NIH ImageJ software. Values from densitometry analysis were normalized to HSP60 control. Normalized value was then converted to $Log_2$ fold change and plotted on heatmap using Graphpad Prism 8.

Flow Cytometry

CRC cell lines were treated as described above. After 24 h of treatment, cells were collected from medium, washed with 1×PBS, and released from well with Trypsin-EDTA (0.25%), phenol red (Invitrogen). Harvested cells were centrifuged at 700×g for 5 min. Cells were washed twice in PBS and spun down at 700 Å~g for 5 min. PBS was removed and cells were resuspended in 600 μL of ice-cold PBS. Cell were permeabilized with addition of 1.4 mL of ice-cold ethanol slowly and incubated overnight at −20° C. Following two washes with PBS (centrifuged at 700 Å~g for 5 min), cells were stained in 200 μL PI staining solution (0.1% Triton X-100, 50 μg propidium iodide (BioLegend), 0.2 mg/mL RNase) for 30 min. Samples were analyzed on BD LSR Fortessa 1 Analyzer. At least 10,000 events were collected for each sample. Single cell populations were viewed and gated on cyanine-3 area (Cy3-A) versus cyanine-3 width (Cy3-W) channels, to eliminate doublet events. ModFit LT Software (Version 5) was used for cell cycle analysis.

Quantitative Reverse Transcription PCR

BRAF V600E dependent MEFs were treated with U0126 MEK inhibitor for 24 hours. After incubation mRNA was harvested using the QIAGEN RNeasy kit (QIAGEN, no. 74014) following the manufacturer's instructions. RNA isolated was measured using a NanoDrop 100 spectrophotometer. Reverse transcription was performed using random hexamers (Roche) and SuperScript III Reverse Transcriptase (Invitrogen, no. 18080044) in the presence of RNaseOUT (Invitrogen, no. 10777019) or RNasin (Promega, no. N2611) under the following conditions: 25° C. for 5 min, 55° C. for 6 min, and 95° C. for 5 min. Remaining RNA was hydrolyzed using 1M NaOH. qPCR was performed using iQ DYBR Green Supermix (Bio-Rad, no. 1708880) on the iQ5 Multicolor Real-Time PCR detection system using RAPla and GAPDH gene specific primers. Relative change in gene expression compared to PBS control was determined using the delta delta CT method [205].

REFERENCES

1. Hobbs, G. A., C. J. Der, and K. L. Rossman, RAS isoforms and mutations in cancer at a glance. J Cell Sci, 2016. 129(7): p. 1287-92.
2. Hunter, J. C., et al., Biochemical and Structural Analysis of Common Cancer-Associated KRAS Mutations. Mol Cancer Res, 2015. 13(9): p. 1325-35.
3. Bos, J. L., H. Rehmann, and A. Wittinghofer, GEFs and GAPs: critical elements in the control of small G proteins. Cell, 2007. 129(5): p. 865-77.
4. Vigil, D., et al., Ras superfamily GEFs and GAPs: validated and tractable targets for cancer therapy? Nat Rev Cancer, 2010. 10(12): p. 842-57.
5. Downward, J., Targeting RAS signalling pathways in cancer therapy. Nat Rev Cancer, 2003. 3(1): p. 11-22.
6. Drosten, M., et al., Genetic analysis of Ras signalling pathways in cell proliferation, migration and survival. EMBO J, 2010. 29(6): p. 1091-104.
7. Kerkhoff, E. and U. R. Rapp, Induction of cell proliferation in quiescent NIH 3T3 cells by oncogenic c-Raf-1. Mol Cell Biol, 1997. 17(5): p. 2576-86.
14. Cox, A. D., et al., Drugging the undruggable RAS: Mission possible? Nat Rev Drug Discov, 2014. 13(11): p. 828-51.
15. Janes, M. R., et al., Targeting KRAS Mutant Cancers with a Covalent G12C-Specific Inhibitor. Cell, 2018. 172(3): p. 578-589 e17.
16. Ostrem, J. M., et al., K-Ras(G12C) inhibitors allosterically control GTP affinity and effector interactions. Nature, 2013. 503(7477): p. 548-51.
64. Chen, J., et al., *Tumor suppression and inhibition of aneuploid cell accumulation in human brain tumor cells by ectopic overexpression of the cyclin-dependent kinase inhibitor p27KIP1*. J Clin Invest, 1996. 97(8): p. 1983-8.
91. Amgen, *FDA Approves LUMAKRAS (Sotorasib), The First And Only Targeted Treatment For patients With KRAS G12C-Mutated Locally Advanced Or Metastatic Non-Small Cell Lung Cancer.* 2021.
127. Bond, M. J., et al., *Targeted Degradation of Oncogenic KRAS(G12C) by VHL-Recruiting PROTACs*. ACS Cent Sci, 2020. 6(8): p. 1367-1375.
128. Satchell, K. J. F., *Multifunctional-autoprocessing repeats-in-toxin (MARTX) Toxins of Vibrios*. Microbiol Spectr, 2015. 3(3).
129. Gavin, H. E. and K. J. F. Satchell, *RRSP and RID Effector Domains Dominate the Virulence Impact of Vibrio vulnificus MARTX Toxin*. J Infect Dis, 2019. 219 (6): p. 889-897.
130. Antic, I., M. Biancucci, and K. J. Satchell, *Cytotoxicity of the Vibrio vulnificus MARTX toxin effector DUF5 is linked to the C2A subdomain*. Proteins, 2014. 82(10): p. 2643-56.

131. Biancucci, M., et al., *The bacterial Ras/Rap1 site-specific endopeptidase RRSP cleaves Ras through an atypical mechanism to disrupt Ras-ERK signaling*. Sci Signal, 2018. 11(550).
132. Biancucci, M., et al., *Substrate Recognition of MARTX Ras/Rap1-Specific Endopeptidase*. Biochemistry, 2017. 56(21): p. 2747-2757.
133. David, M. D., et al., *Pure lipopolysaccharide or synthetic lipid A induces activation of p21Ras in primary macrophages through a pathway dependent on Src family kinases and PI3K*. J Immunol, 2005. 175(12): p. 8236-41.
134. Antic, I., et al., *Site-specific processing of Ras* and *Rap1 Switch I by a MARTX* toxin *effector domain*. Nat Commun, 2015. 6: p. 7396.
135. Loftis, A. R., et al., *Anthrax Protective Antigen Retargeted with Single-Chain Variable Fragments Delivers Enzymes to Pancreatic Cancer Cells*. Chembiochem, 2020. 21(19): p. 2772-2776.
136. Vidimar, V., et al., *An engineered chimeric* toxin *that cleaves activated mutant* and *wild-type RAS inhibits tumor growth*. Proc Natl Acad Sci USA, 2020. 117(29): p. 16938-16948.
137. Chabner, B. A., *NCI-60 Cell Line Screening: A Radical Departure in its Time*. J Natl Cancer Inst, 2016. 108(5).
138. Vania Vidimar, M. P., Caleb Kawun Stubbs, Nana Kwame Ingram, Wenan Qiang, Shanshan Zhang, Demirkan B Gursel, Roman A Melnyk, and Karla J. Satchell, *Proteolytic pan-RAS cleavage leads to tumor regression in patient-derived pancreatic cancer xenografts*. Manuscript in revision, 2022.
139. Collins, M. A., et al., *Metastatic pancreatic cancer is dependent on oncogenic Kras in mice*. PLoS One, 2012. 7(12): p. e49707.
140. Fisher, G. H., et al., *Induction and apoptotic regression of lung adenocarcinomas by regulation of a K-Ras transgene in the presence and absence of tumor suppressor genes. Genes Dev,* 2001. 15(24): p. 3249-62.
141. Kwong, L. N., et al., *Oncogenic NRAS signaling differentially regulates survival and proliferation in melanoma*. Nat Med, 2012. 18(10): p. 1503-10.
142. Ying, H., et al., *Oncogenic Kras maintains pancreatic tumors through regulation of anabolic glucose metabolism*. Cell, 2012. 149(3): p. 656-70.
143. Patricelli, M. P., et al., *Selective Inhibition of Oncogenic KRAS Output with Small Molecules Targeting the Inactive State*. Cancer Discov, 2016. 6(3): p. 316-29.
144. Bery, N., A. Miller, and T. Rabbitts, *A potent KRAS macromolecule degrader specifically targeting tumours with mutant KRAS*. Nat Commun, 2020. 11(1): p. 3233.
145. Chen, Y., et al., *Engineering subtilisin proteases that specifically degrade active RAS*. Commun Biol, 2021. 4(1): p. 299.
146. Lim, S., et al., *Exquisitely Specific anti-KRAS Biodegraders Inform on the Cellular Prevalence of Nucleotide-Loaded States*. ACS Cent Sci, 2021. 7(2): p. 274-291.
147. Roth, S., et al., *Targeting Endogenous K-RAS for Degradation through the Affinity-Directed Protein Missile System*. Cell Chem Biol, 2020. 27(9): p. 1151-1163 e6.
148. Gavin, H. E., N. T. Beubier, and K. J. Satchell, *The Effector Domain Region of the Vibrio vulnificus MARTX* Toxin *Confers Biphasic Epithelial Barrier Disruption* and *Is Essential for Systemic Spread from the Intestine*. PLoS Pathog, 2017. 13(1): p. e1006119.
149. Bos, J. L., *Linking Rap to cell adhesion*. Curr Opin Cell Biol, 2005. 17(2): p. 123-8.
150. Childs, B. G., et al., *Senescence and apoptosis: dueling or complementary cell fates*? EMBO Rep, 2014. 15(11): p. 1139-53.
151. Gallolu Kankanamalage, S., A. S. Karra, and M. H. Cobb, *WNK pathways in cancer signaling networks*. Cell Commun Signal, 2018. 16(1): p. 72.
152. Vitari, A. C., et al., *WNK1, the kinase mutated in an inherited high-blood-pressure syndrome, is a novel PKB (protein kinase B)/Akt substrate*. Biochem J, 2004. 378(Pt 1): p. 257-68.
153. Pruitt, K., R. G. Pestell, and C. J. Der, *Ras inactivation of the retinoblastoma pathway by distinct mechanisms in NIH 3T3 fibroblast and RIE-1 epithelial cells*. J Biol Chem, 2000. 275(52): p. 40916-24.
154. Schiappacassi, M., et al., *Role of T198 modification in the regulation of p27(Kip1) protein stability and function*. PLoS One, 2011. 6(3): p. e17673.
155. Broude, E. V., et al., *p21(Waf1/Cip1/Sdi1) mediates retinoblastoma protein degradation*. Oncogene, 2007. 26(48): p. 6954-8.
156. Hengst, L. and S. I. Reed, *Inhibitors of the Cip/Kip family*. Curr Top Microbiol Immunol, 1998. 227: p. 25-41.
157. Bos, J. L., J. de Rooij, and K. A. Reedquist, *Rap1 signalling: adhering to new models. Nat Rev Mol Cell Biol,* 2001. 2(5): p. 369-77.
158. Goebel, L., et al., *KRasG12C inhibitors in clinical trials: a short historical perspective*. Rsc Medicinal Chemistry, 2020. 11(7): p. 760-770.
159. Solit, D. B., et al., *BRAF mutation predicts sensitivity to MEK inhibition*. Nature, 2006. 439(7074): p. 358-62.
160. Yeh, J. J., et al., *KRAS/BRAF mutation status and ERK1/2 activation as biomarkers for MEK1/2 inhibitor therapy in colorectal cancer*. Mol Cancer Ther, 2009. 8(4): p. 834-43.
161. Schreiber, M., et al., *Comparison of the effectiveness of adenovirus vectors expressing cyclin kinase inhibitors p16INK4A, p18INK4C, p19INK4D, p21(WAF1/CIP1) and p27KIP 1 in inducing cell cycle arrest, apoptosis and inhibition of tumorigenicity*. Oncogene, 1999. 18(9): p. 1663-76.
162. Wang, X., et al., *The Photorhabdus Virulence Cassettes RRSP-Like Effector Interacts With Cyclin-Dependent Kinase 1 and Causes Mitotic Defects in Mammalian Cells. Front Microbiol,* 2020. 11: p. 366.
163. Alexander, K. and P. W. Hinds, *Requirement for p27 (KIP1) in retinoblastoma protein-mediated senescence*. Mol Cell Biol, 2001. 21(11): p. 3616-31.
164. Dao, V. T., et al., *Dynamic changes in Rap1 activity are required for cell retraction and spreading during mitosis*. J Cell Sci, 2009. 122(Pt 16): p. 2996-3004.

Example 8—Proteolytic RAS Cleavage Leads to Tumor Regression in Patient-Derived Pancreatic Cancer Xenografts Reference is, Vidimar V., et al. Proteolytic RAS cleavage leads to tumor regression in patient-derived pancreatic cancer xenografts. Abstract Submission.

Effective RAS inhibition and treatment of pancreatic ductal adenocarcinoma (PDAC) represent major unmet medical needs in oncology. RRSP-$DT_B$ is a novel engineered anticancer biologic that enters cells and cleaves the Switch I of all RAS isoforms. RRSP-$DT_B$ was recently shown to reduce breast and colon tumors in xenograft studies. Here, we investigate the anticancer activity of $RRSPDT_B$ in KRAS-mutant PDAC cell lines and patient-derived xenografts (PDXs). We first demonstrate RRSP-$DT_B$ effectively engages RAS and impacts downstream ERK signaling in multiple KRAS-mutant PDAC cell lines. Ras was cleaved in cells with $IC_{50}$ ranging from 10-280 picomolar and cell proliferation was inhibited at 63-181 picomolar. A modified RRSP-$DT_B$ that lacks catalytic activity was ineffective, demonstrating loss of proliferation is due to protease activity. We next tested RRSP-$DT_B$ by administration to NSG mice bearing KRAS-mutant PDAC PDXs. Treatment led to ≥95% tumor regression after 29 days. Residual tumors exhibited disrupted tissue architecture, increased fibrosis and fewer proliferating cancer cells compared to controls. Levels of phospho-ERK were also significantly lower, indicating in vivo target engagement. Importantly, tumors that started to regrow in the absence of RRSP-$DT_B$ shrank when treatment resumed, indicating resistance to RRSP-$DT_B$ had not developed. A pharmacokinetic (PK) study showed RRSP-$DT_B$ is active in sera of immunocompetent mice for at least one hour, but absent after 16 hours, justifying use of daily dosing. Overall, we report that RRSP-$DT_B$ strongly regresses hard-to-treat KRAS-mutant PDX models of pancreatic cancer, warranting further development of this pan-RAS biologic for the management of RAS-addicted tumors.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A pharmaceutical composition comprising:

(a) a fusion protein, the fusion protein consisting of a *Vibrio vulnificus* Ras/Rap1-specific endopeptidase (RRSP) fragment fused to a carrier protein, wherein the RRSP fragment is selected from:

SEQ ID NO: 1, or a fragment of SEQ ID NO: 1 comprising SEQ ID NO: 2; and (b) a pharmaceutically acceptable vehicle for delivery to a eukaryotic cell.

2. The pharmaceutical composition of claim 1, wherein the carrier protein facilitates transport of the RRSP fragment into proliferating cells.

3. The pharmaceutical composition of claim 1, wherein the carrier protein is a bacterial toxin.

4. The pharmaceutical composition of claim 3, wherein RRSP fragment is fused at its N-terminus to the carrier protein.

5. The pharmaceutical composition of claim 3, wherein the bacterial toxin is anthrax toxin lethal factor N-terminus ($LF_N$).

6. The pharmaceutical composition of claim 5, further comprising anthrax toxin protective antigen (PA) which forms a complex with the fusion protein and the complex is delivered to the cytosol of proliferating cells.

* * * * *